US012448370B2

(12) United States Patent
Yoon et al.

(10) Patent No.: US 12,448,370 B2
(45) Date of Patent: Oct. 21, 2025

(54) HETEROCYCLIC COMPOUND AND ORGANIC LIGHT-EMITTING DEVICE COMPRISING SAME

(71) Applicant: LG CHEM, LTD., Seoul (KR)

(72) Inventors: Jung Min Yoon, Daejeon (KR); Sung Kil Hong, Daejeon (KR); Dong Uk Heo, Daejeon (KR); Miyeon Han, Daejeon (KR); Jae Tak Lee, Daejeon (KR); Heekyung Yun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 804 days.

(21) Appl. No.: 17/784,423

(22) PCT Filed: Dec. 18, 2020

(86) PCT No.: PCT/KR2020/018687

§ 371 (c)(1),
(2) Date: Jun. 10, 2022

(87) PCT Pub. No.: WO2021/167222

PCT Pub. Date: Aug. 26, 2021

(65) Prior Publication Data

US 2023/0053612 A1 Feb. 23, 2023

(30) Foreign Application Priority Data

Feb. 21, 2020 (KR) ........................ 10-2020-0021366

(51) Int. Cl.
*C07D 405/14* (2006.01)
*C07D 401/10* (2006.01)
(Continued)

(52) U.S. Cl.
CPC ......... *C07D 405/14* (2013.01); *C07D 401/10* (2013.01); *C07D 409/14* (2013.01);
(Continued)

(58) Field of Classification Search
CPC ... C07D 401/10; H10K 85/624; H10K 85/654
See application file for complete search history.

(56) References Cited

U.S. PATENT DOCUMENTS

2013/0105767 A1 5/2013 Lin et al.
2019/0378990 A1* 12/2019 Cha ...................... C07D 409/10
(Continued)

FOREIGN PATENT DOCUMENTS

CN 110446702 11/2019
CN 110475769 11/2019
(Continued)

*Primary Examiner* — Vu A Nguyen
(74) *Attorney, Agent, or Firm* — Bryan Cave Leighton Paisner LLP

(57) ABSTRACT

Provided is a heterocyclic compound of Chemical Formula 1:

[Chemical Formula 1]

(Continued)

wherein:

A1 is Chemical Formula 1-1:

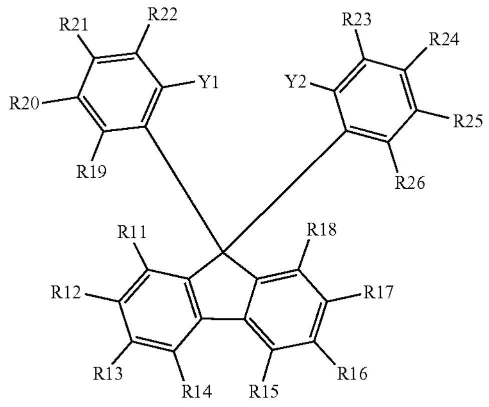

Y1 and Y2 are hydrogen or deuterium, or directly bonded to each other, or linked through —C(R31)(R32)-, —Si(R33)(R34)-, —N(R35)-, —O—, or —S—;

any one of R11 to R26 is linked to L1, and of the remaining, one is linked to L4 of Chemical Formula 1, and the others are each independently hydrogen, deuterium, a cyano group, or a substituted or unsubstituted: alkyl, aryl, or heteroaryl group;

at least two of X1 to X3 are N, and the other is CH;

R1 is a substituted or unsubstituted alkyl group;

L1 to L4 are each independently a direct bond or a substituted or unsubstituted arylene or heteroarylene group; and Ar1 to Ar3 are each independently a substituted or unsubstituted alkyl, aryl, or heteroaryl group; and an organic light-emitting device including the same.

10 Claims, 1 Drawing Sheet

(51) Int. Cl.

| | |
|---|---|
| ***C07D 409/14*** | (2006.01) |
| ***H10K 50/11*** | (2023.01) |
| ***H10K 50/16*** | (2023.01) |
| ***H10K 50/17*** | (2023.01) |
| ***H10K 85/60*** | (2023.01) |

(52) U.S. Cl.

CPC ......... *H10K 85/615* (2023.02); *H10K 85/624* (2023.02); *H10K 85/654* (2023.02); *H10K 85/6574* (2023.02); *H10K 85/6576* (2023.02); *H10K 50/11* (2023.02); *H10K 50/16* (2023.02); *H10K 50/171* (2023.02)

(56) References Cited

U.S. PATENT DOCUMENTS

| | | | | |
|---|---|---|---|---|
| 2020/0048230 | A1 | 2/2020 | Heo et al. | |
| 2020/0227646 | A1 | 7/2020 | Jung et al. | |
| 2020/0227647 | A1 * | 7/2020 | Han | C07D 251/24 |

FOREIGN PATENT DOCUMENTS

| | | | |
|---|---|---|---|
| CN | 110799508 | 2/2020 | |
| KR | 10-2012-0031684 | 4/2012 | |
| KR | 10-2013-0135162 | 12/2013 | |
| KR | 10-2014-0009019 | 1/2014 | |
| KR | 10-2017-0113342 | 10/2017 | |
| KR | 10-2019-0013565 | 2/2019 | |
| WO | WO-2017171376 A1 * | 10/2017 | H10K 50/17 |
| WO | 2018093107 | 5/2018 | |

* cited by examiner

[Figure 1]
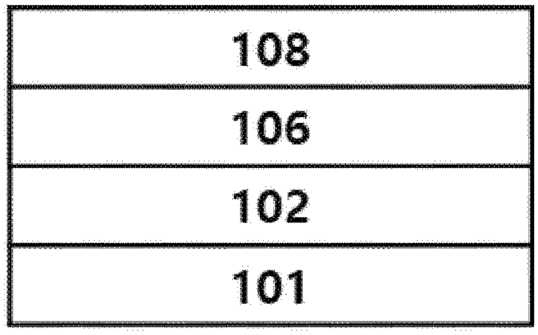
[Figure 2]
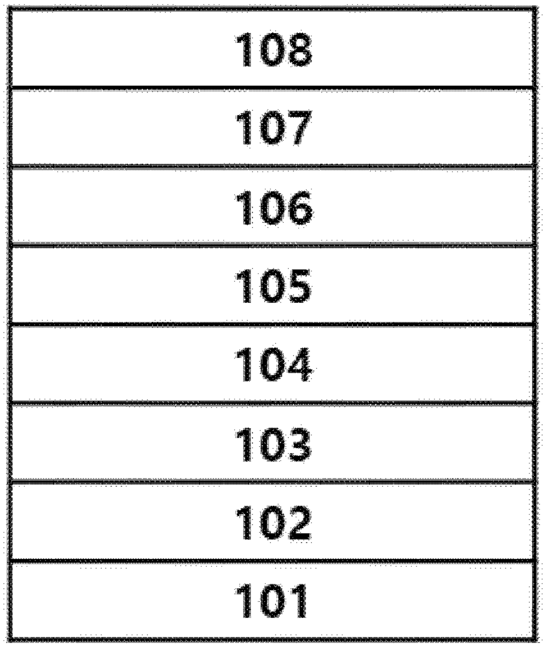

HETEROCYCLIC COMPOUND AND ORGANIC LIGHT-EMITTING DEVICE COMPRISING SAME

CROSS-REFERENCE TO RELATED APPLICATIONS

This application is a National Stage Application of International Application No. PCT/KR2020/018687 filed on Dec. 18, 2020, which claims priority to and the benefit of Korean Patent Application No. 10-2020-0021366 filed in the Korean Intellectual Property Office on Feb. 21, 2020, the entire contents of which are incorporated herein by reference.

TECHNICAL FIELD

The present specification relates to a heterocyclic compound and an organic light emitting device including the same.

BACKGROUND

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer can have a multi-layered structure composed of different materials in many cases in order to improve the efficiency and stability of the organic light emitting device, and can be composed of, for example, a hole injection layer, a hole transport layer, a light emitting layer, an electron transport layer, an electron injection layer, and the like. In such a structure of the organic light emitting device, if a voltage is applied between the two electrodes, holes are injected from the positive electrode into the organic material layer and electrons are injected from the negative electrode into the organic material layer, and when the injected holes and electrons meet each other, an exciton is formed, and light is emitted when the exciton falls down again to a ground state.

There is a continuous need for developing a new material for the aforementioned organic light emitting device.

PRIOR ART DOCUMENT (Patent Document 1) Korean Patent Application Laid-Open No. 10-2013-0135162

BRIEF DESCRIPTION

Technical Problem

The present specification has been made in an effort to provide a heterocyclic compound and an organic light emitting device including the same.

Technical Solution

The present specification provides a heterocyclic compound of the following Chemical Formula 1:

[Chemical Formula 1]

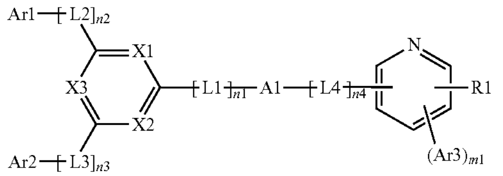

wherein in Chemical Formula 1:

at least two of X1 to X3 are N, and the other is CH;

R1 is a substituted or unsubstituted alkyl group;

L1 to L4 are the same as or different from each other, and are each independently a direct bond, a substituted or unsubstituted arylene group, or a substituted or unsubstituted heteroarylene group;

n1 to n4 are an integer from 0 to 4;

Ar1 to Ar3 are the same as or different from each other, and are each independently a substituted or unsubstituted alkyl group, a substituted or unsubstituted aryl group, or a substituted or unsubstituted heteroaryl group;

m1 is an integer from 0 to 3;

when n1 to n4 and m1 are each 2 or higher, substituents in the parenthesis are the same as or different from each other;

A1 is the following Chemical Formula 1-1:

[Chemical Formula 1-1]

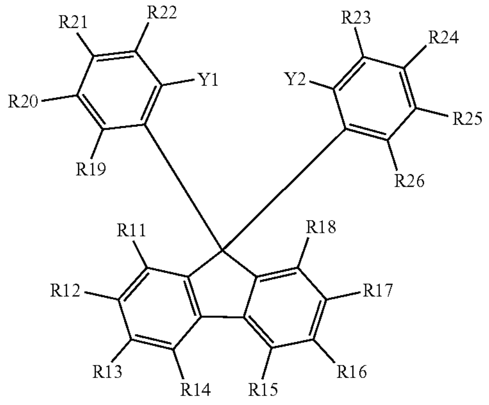

wherein in Chemical Formula 1-1:

Y1 and Y2 are each hydrogen or deuterium, or are directly bonded to each other, or are linked to each other through —C(R31)(R32)-, —Si(R33)(R34)-, —N(R35)-, —O—, or —S—;

any one of R11 to R26 is linked to L1 of Chemical Formula 1, and of the remaining, one is linked to L4 of Chemical Formula 1, and the others are the same as or different from each other, and are each independently hydrogen, deuterium, a cyano group, a substituted or unsubstituted alkyl group, a substituted or unsubstituted aryl group, or a substituted or unsubstituted heteroaryl group; and R31 to R35 are the same as or different from each other, and are each independently hydrogen, deuterium, a cyano group, a substituted or unsubstituted alkyl group, a substituted or unsubstituted aryl group, or a substituted or unsubstituted heteroaryl group.

Further, the present specification provides an organic light emitting device including: a first electrode; a second electrode provided to face the first electrode; and an organic material layer having one or more layers provided between the first electrode and the second electrode, in which one or more layers of the organic material layer include the heterocyclic compound of Chemical Formula 1.

Advantageous Effects

The compound according to an exemplary embodiment of the present specification can be used for an organic light emitting device to lower the driving voltage of the organic light emitting device and improve the light efficiency. Further, the service life characteristics of the device can be improved by the thermal stability of the compound.

BRIEF DESCRIPTION OF DRAWINGS

FIGS. 1 and 2 illustrate an example of an organic light emitting device according to an exemplary embodiment of the present specification.

EXPLANATION OF REFERENCE NUMERALS AND SYMBOLS

101: Substrate
102: Positive electrode
103: Hole injection layer
104, First Hole transport layer
105, Second Hole transport layer
106: Light emitting layer
107: Electron injection and transport layer
108: Negative electrode

DETAILED DESCRIPTION

Hereinafter, the present specification will be described in more detail.

By including a pyridine substituted with an alkyl group (R1), the compound of Chemical Formula 1 can increase the service life and efficiency of a device and decrease the voltage. Specifically, since the polarity of a molecule (dipole moment) can be increased by having pyridine that is an electron depletion structure, the electron mobility during the manufacture of an organic light emitting device including a compound can be smoothly adjusted to improve the efficiency and service life of the organic light emitting device. Further, compared to pyridine that does not include an alkyl group, the electron balance in the device can be adjusted according to the characteristics of each device by introducing pyridine which has an alkyl group, so that the device can have advantages such as high efficiency and low voltage characteristics. When the compound of Chemical Formula 1 is used as a material for an electron transport layer or an electron injection layer, the long service life characteristics of the organic light emitting device are improved due to an increase in the dipole moment in the molecule.

Examples of the substituents in the present specification will be described below, but are not limited thereto.

In the present specification,

means a moiety to be linked.

In the present specification, Cn means n carbon atoms.

In the present specification, "Cn-Cm" means "n to m carbon atoms".

The term "substitution" means that a hydrogen atom bonded to a carbon atom of a compound is changed into another substituent, and a position to be substituted is not limited as long as the position is a position at which the hydrogen atom is substituted, that is, a position at which the substituent can be substituted, and when two or more are substituted, the two or more substituents can be the same as or different from each other.

In the present specification, the term "substituted or unsubstituted" means being substituted with one or two or more substituents selected from the group consisting of deuterium, a halogen group, a cyano group, an alkyl group, an aryl group, and a heteroaryl group including one or more heteroatoms other than carbon, being substituted with a substituent to which two or more substituents among the substituents exemplified above are linked, or having no substituent.

In the present specification, the fact that two or more substituents are linked indicates that hydrogen of any one substituent is linked to another substituent. For example, an isopropyl group and a phenyl group can be linked to each other to become a substituent of

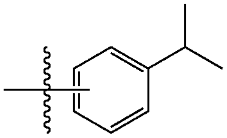

or

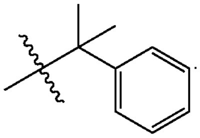

.

In the present specification, the fact that three substituents are linked to one another includes not only a case where (Substituent 1)-(Substituent 2)-(Substituent 3) are consecutively linked to one another, but also a case where (Substituent 2) and (Substituent 3) are linked to (Substituent 1). For example, two phenyl groups and an isopropyl group can be linked to each other to become a substituent of

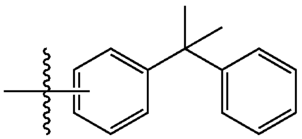

or

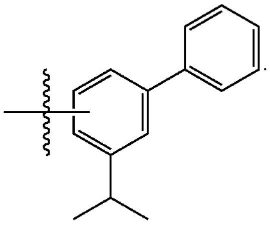

.

The same also applies to the case where four or more substituents are linked to one another.

In the present specification, examples of a halogen group include fluorine, chlorine, bromine or iodine.

In the present specification, an alkyl group can be straight-chained or branched, and the number of carbon atoms thereof is not particularly limited, but is preferably 1 to 30; 1 to 20; 1 to 10; or 1 to 5. Specific examples thereof include methyl, ethyl, propyl, n-propyl, isopropyl, butyl, n-butyl, isobutyl, t-butyl, sec-butyl, 1-methylbutyl, 1-ethylbutyl, pentyl, n-pentyl, isopentyl, neopentyl, t-pentyl, hexyl, n-hexyl, 1-methylpentyl, 2-methylpentyl, 3,3-dimethylbutyl, 2-ethylbutyl, heptyl, n-heptyl, 1-methylhexyl, cyclopentylmethyl, cyclohexylmethyl, octyl, n-octyl, t-octyl, 1-methylheptyl, 2-ethylhexyl, 2-propylpentyl, n-nonyl, 2,2-dimethylheptyl, 1-ethylpropyl, 1,1-dimethylpropyl, isohexyl, 4-methylhexyl, 5-methylhexyl, and the like, but are not limited thereto.

In the present specification, an aryl group means a monovalent aromatic hydrocarbon or a monovalent group of an aromatic hydrocarbon derivative. In the present specification, an aromatic hydrocarbon means a compound in which pi electrons are completely conjugated and which contains a planar ring, and a group derived from an aromatic hydrocarbon means a structure in which an aromatic hydrocarbon or a cyclic aliphatic hydrocarbon is fused with an aromatic hydrocarbon. Further, in the present specification, an aryl group intends to include a monovalent group in which two or more aromatic hydrocarbons or derivatives of an aromatic hydrocarbon are linked to each other. The aryl group is not particularly limited, but preferably has 6 to 50 carbon atoms; 6 to 30 carbon atoms; 6 to 25 carbon atoms; 6 to 20 carbon atoms; 6 to 18 carbon atoms; or 6 to 13 carbon atoms, and the aryl group can be monocyclic or polycyclic. Specific examples of the monocyclic aryl group include a phenyl group, a biphenyl group, a terphenyl group, and the like, but are not limited thereto. Specific examples of the polycyclic aryl group include a naphthyl group, an anthracenyl group, a phenanthryl group, a triphenylene group, a pyrenyl group, a perylenyl group, a chrysenyl group, a fluorenyl group, and the like, but are not limited thereto.

In the present specification, the fluorenyl group can be substituted, and adjacent substituents can be bonded to each other to form a ring.

In the present specification, when it is said that a fluorenyl group can be substituted, the substituted fluorenyl group includes all the compounds in which substituents of a pentagonal ring of fluorene are spiro-bonded to each other to form an aromatic hydrocarbon ring. Examples of the substituted fluorenyl group include 9,9'-spirobifluorene, spiro[cyclopentane-1,9'-fluorene], spiro[benzo[c]fluorene-7,9-fluorene], and the like, but are not limited thereto.

In the present specification, a heterocyclic group includes one or more atoms other than carbon, that is, one or more heteroatoms, and specifically, the heteroatom can include one or more atoms selected from the group consisting of O, N, Si, S, and the like. The number of carbon atoms thereof is not particularly limited, but is preferably 2 to 50; 2 to 30; 2 to 20; 2 to 18; or 2 to 13. Examples of the heterocyclic group include a thiophene group, a furanyl group, a pyrrole group, an imidazole group, a thiazole group, an oxazole group, an oxadiazole group, a pyridine group, a bipyridine group, a pyrimidine group, a triazine group, a triazole group, an acridine group, a pyridazine group, a pyrazine group, a quinoline group, a quinazoline group, a quinoxaline group, a phthalazine group, a pyridopyrimidine group, a pyridopyrazine group, a pyrazinopyrazine group, an isoquinoline group, an indole group, a carbazole group, a benzoxazole group, a benzimidazole group, a benzothiazole group, a benzocarbazole group, a benzothiophene group, a dibenzothiophene group, a benzofuran group, a phenanthrolinyl group, a thiazole group, an isoxazole group, an oxadiazole group, a thiadiazole group, a benzothiazole group, a phenothiazine group, a dibenzofuran group, a dihydrophenothiazine group, a dihydrobenzoisoquinoline group, a chromene group, and the like, but are not limited thereto.

In the present specification, a heterocyclic group can be monocyclic or polycyclic, can be an aromatic ring, an aliphatic ring, or a fused ring of the aromatic ring and the aliphatic ring, and can be selected from the examples of the heterocyclic group.

In the present specification, a heteroaryl group means a monovalent aromatic hetero ring. Here, the monovalent aromatic hetero ring is a monovalent group of an aromatic ring or a derivative of the aromatic ring, and means a group including one or more of 0, N, Si, and S as a heteroatom in the ring. The derivative of the aromatic ring includes both a structure in which an aromatic ring or an aliphatic ring is fused with an aromatic ring. Further, in the present specification, the heteroaryl group intends to include a monovalent group in which an aromatic ring including two or more heteroatoms or derivatives of an aromatic ring including a heteroatom are linked to each other. The number of carbon atoms of the heteroaryl group is preferably 2 to 50; 2 to 30; 2 to 20; 2 to 18; or 2 to 13.

In the present specification, an arylene group means that there are two bonding positions in an aryl group, that is, a divalent group. The above-described description on the aryl group can be applied to the arylene group, except that the arylene groups are each a divalent group.

In the present specification, a heteroarylene group means a group having two bonding positions in a heteroaryl group, that is, a divalent group. The above-described description on the heteroaryl group can be applied to the heteroarylene group, except for a divalent heteroarylene group.

Hereinafter, a heterocyclic compound of the following Chemical Formula 1 will be described in detail.

[Chemical Formula 1]

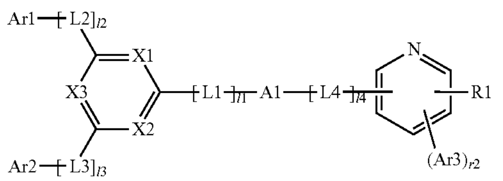

In an exemplary embodiment of the present specification, at least two or more of X1 to X3 are N, and the other is CH.

In an exemplary embodiment of the present specification, X1 and X2 are N, and X3 is CH.

In an exemplary embodiment of the present specification, X1 and X3 are N, and X2 is CH.

In an exemplary embodiment of the present specification, X2 and X3 are N, and X1 is CH.

In an exemplary embodiment of the present specification, X1 to X3 are each N.

In an exemplary embodiment of the present specification, R1 is a substituted or unsubstituted C1-C20 alkyl group.

In an exemplary embodiment of the present specification, R1 is a substituted or unsubstituted C1-C10 alkyl group.

In an exemplary embodiment of the present specification, R1 is a C1-C10 alkyl group.

In an exemplary embodiment of the present specification, R1 is a C1-C6 alkyl group.

In an exemplary embodiment of the present specification, R1 is a methyl group, an ethyl group, a propyl group, an isopropyl group, a butyl group, or a tert-butyl group.

In an exemplary embodiment of the present specification, L1 to L4 are the same as or different from each other, and are each independently a direct bond, a substituted or unsubstituted arylene group, or a substituted or unsubstituted heteroarylene group.

In an exemplary embodiment of the present specification, L1 to L4 are the same as or different from each other, and are each independently a direct bond or a substituted or unsubstituted arylene group.

In an exemplary embodiment of the present specification, L1 to L4 are the same as or different from each other, and are each independently a direct bond or a substituted or unsubstituted C6-C60 arylene group.

In an exemplary embodiment of the present specification, L1 to L4 are the same as or different from each other, and are each independently a direct bond or a substituted or unsubstituted C6-C30 arylene group.

In an exemplary embodiment of the present specification, L1 to L4 are the same as or different from each other, and are each independently a direct bond or a C6-C20 arylene group.

In an exemplary embodiment of the present specification, L1 to L4 are the same as or different from each other, and are each independently a direct bond, a substituted or unsubstituted phenylene group, a substituted or unsubstituted biphenylene group, a substituted or unsubstituted terphenylene group, or a substituted or unsubstituted naphthylene group.

In an exemplary embodiment of the present specification, L1 to L4 are the same as or different from each other, and are each independently a direct bond, a phenylene group, or a biphenylene group.

In an exemplary embodiment of the present specification, L1 is a direct bond.

In an exemplary embodiment of the present specification, L2 and L3 are the same as or different from each other, and are each independently a direct bond or a substituted or unsubstituted C6-C30 arylene group.

In an exemplary embodiment of the present specification, L2 and L3 are the same as or different from each other, and are each independently a direct bond or a C6-C20 arylene group.

In an exemplary embodiment of the present specification, L2 and L3 are the same as or different from each other, and are each independently a direct bond, a substituted or unsubstituted phenylene group, or a substituted or unsubstituted biphenylene group.

In an exemplary embodiment of the present specification, L2 and L3 are the same as or different from each other, and are each independently a direct bond or a phenylene group.

In an exemplary embodiment of the present specification, L4 is a direct bond or a substituted or unsubstituted C6-C30 arylene group.

In an exemplary embodiment of the present specification, L4 is a direct bond or a C6-C20 arylene group.

In an exemplary embodiment of the present specification, L4 is a direct bond, a substituted or unsubstituted phenylene group, or a substituted or unsubstituted biphenylene group.

In an exemplary embodiment of the present specification, L4 is a direct bond, a phenylene group, or a biphenylene group.

In an exemplary embodiment of the present specification, L1 to L4 are the same as or different from each other, and are each independently selected from a direct bond or the following structures:

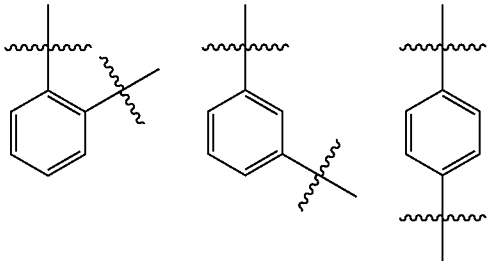

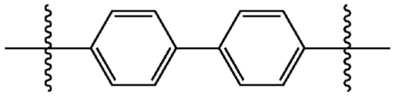

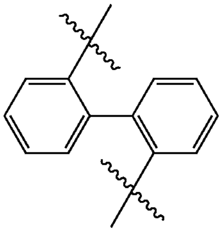

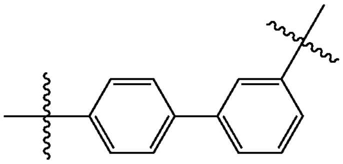

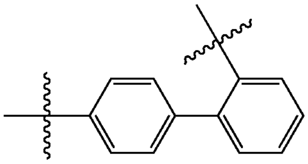

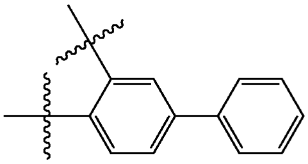

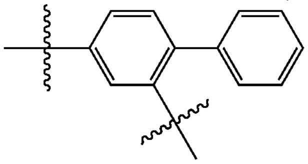

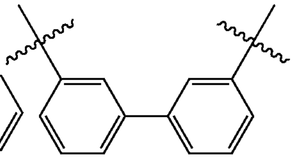

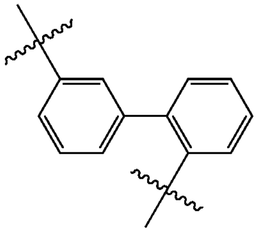

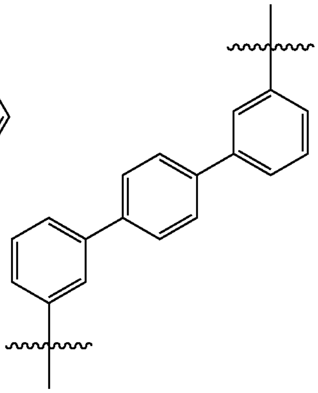

-continued

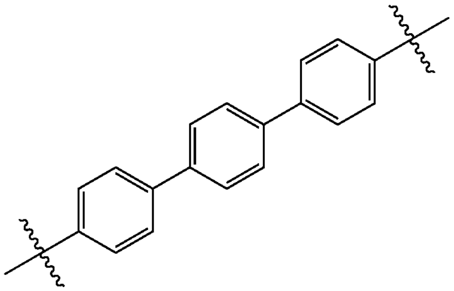

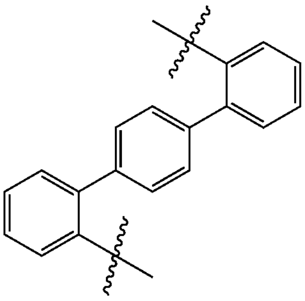

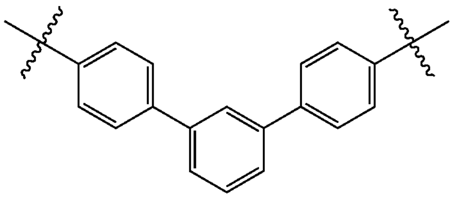

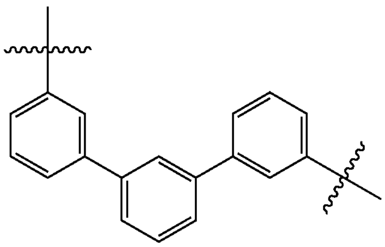

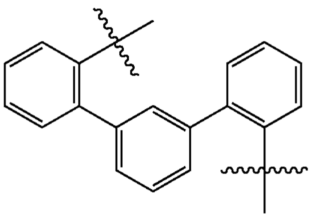

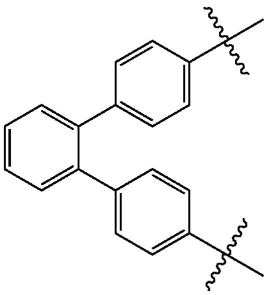

-continued

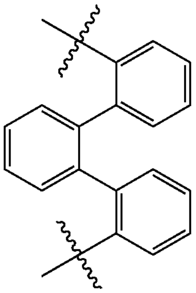

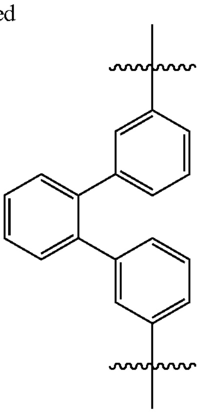

.

In an exemplary embodiment of the present specification, n1 to n4 are an integer from 0 to 4.

When n1 is 2 or higher, a plurality of L1s are the same as or different from each other. When n2 is 2 or higher, a plurality of L2s are the same as or different from each other. When n3 is 2 or higher, a plurality of L3s are the same as or different from each other. When n4 is 2 or higher, a plurality of L4s are the same as or different from each other.

In an exemplary embodiment of the present specification, n1 to n4 are an integer from 0 to 2.

In an exemplary embodiment of the present specification, n1 is 0.

In an exemplary embodiment of the present specification, n4 is 0 or 1.

In an exemplary embodiment of the present specification, n1+n4 is 1 or higher.

In an exemplary embodiment of the present specification, L1 and L4 are not simultaneously a direct bond.

In an exemplary embodiment of the present specification, n1+n4 is 2 or higher.

In an exemplary embodiment of the present specification, n2 and n3 are 0 or 1.

In an exemplary embodiment of the present specification, n2 and n3 are 0.

In an exemplary embodiment of the present specification, Ar1 to Ar3 are the same as or different from each other, and are each independently a substituted or unsubstituted alkyl group, a substituted or unsubstituted aryl group, or a substituted or unsubstituted heteroaryl group.

In an exemplary embodiment of the present specification, Ar1 to Ar3 are the same as or different from each other, and are each independently a substituted or unsubstituted C1-C20 alkyl group or a substituted or unsubstituted C6-C60 aryl group.

In an exemplary embodiment of the present specification, Ar1 to Ar3 are the same as or different from each other, and are each independently a substituted or unsubstituted C1-C10 alkyl group or a substituted or unsubstituted C6-C30 aryl group.

In an exemplary embodiment of the present specification, Ar1 to Ar3 are the same as or different from each other, and are each independently a C1-C6 alkyl group or a C6-C20 aryl group.

In an exemplary embodiment of the present specification, Ar1 and Ar2 are the same as or different from each other, and are each independently a substituted or unsubstituted C6-C30 aryl group.

In an exemplary embodiment of the present specification, Ar1 and Ar2 are the same as or different from each other, and are each independently a C6-C20 aryl group which is unsubstituted or substituted with a C1-C6 alkyl group.

In an exemplary embodiment of the present specification, Ar1 and Ar2 are the same as or different from each other, and are each independently a C6-C20 aryl group.

In an exemplary embodiment of the present specification, Ar3 is a substituted or unsubstituted C1-C10 alkyl group or a substituted or unsubstituted C6-C30 aryl group.

In an exemplary embodiment of the present specification, Ar3 is a C1-C6 alkyl group or a C6-C20 aryl group.

In an exemplary embodiment of the present specification, Ar1 to Ar3 are the same as or different from each other, and are each independently a substituted or unsubstituted methyl group, a substituted or unsubstituted ethyl group, a substituted or unsubstituted propyl group, a substituted or unsubstituted isopropyl group, a substituted or unsubstituted butyl group, a substituted or unsubstituted tert-butyl group, a substituted or unsubstituted phenyl group, a substituted or unsubstituted biphenyl group, or a substituted or unsubstituted naphthyl group.

In an exemplary embodiment of the present specification, Ar1 and Ar2 are the same as or different from each other, and are each independently a substituted or unsubstituted phenyl group, a substituted or unsubstituted biphenyl group, or a substituted or unsubstituted naphthyl group.

In an exemplary embodiment of the present specification, Ar1 and Ar2 are the same as or different from each other, and are each independently a phenyl group which is unsubstituted or substituted with a methyl group; a biphenyl group; or a naphthyl group.

In an exemplary embodiment of the present specification, Ar3 is a substituted or unsubstituted methyl group, a substituted or unsubstituted ethyl group, a substituted or unsubstituted propyl group, a substituted or unsubstituted isopropyl group, a substituted or unsubstituted butyl group, a substituted or unsubstituted tert-butyl group, a substituted or unsubstituted phenyl group, a substituted or unsubstituted biphenyl group, or a substituted or unsubstituted naphthyl group.

In an exemplary embodiment of the present specification, Ar3 is a substituted or unsubstituted methyl group, a substituted or unsubstituted isopropyl group, a substituted or unsubstituted phenyl group, a substituted or unsubstituted biphenyl group, or a substituted or unsubstituted naphthyl group.

In an exemplary embodiment of the present specification, Ar3 is a methyl group or a phenyl group.

In an exemplary embodiment of the present specification, Ar3 is a methyl group.

In an exemplary embodiment of the present specification, when m1 is an integer from 0 to 3, and when m1 is 2 or higher, a plurality of Ar3s are the same as or different from each other.

In an exemplary embodiment of the present specification, m1 is an integer from 0 to 2.

In an exemplary embodiment of the present specification, m1 is 0 or 1.

In an exemplary embodiment of the present specification, A1 is the following Chemical Formula 1-1:

[Chemical Formula 1-1]

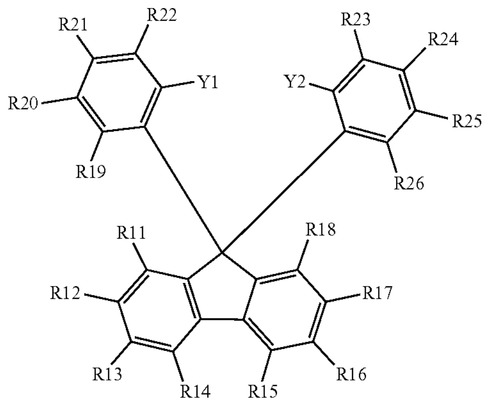

wherein in Chemical Formula 1-1:

Y1 and Y2 are each hydrogen or deuterium, or are directly bonded to each other, or linked to each other through —C(R31)(R32)-, —Si(R33)(R34)-, —N(R35)-, —O—, or —S—;

any one of R11 to R26 is linked to L1 of Chemical Formula 1, and of the remaining, one is linked to L4 of Chemical Formula 1, and the others are the same as or different from each other, and are each independently hydrogen, deuterium, a cyano group, a substituted or unsubstituted alkyl group, a substituted or unsubstituted aryl group, or a substituted or unsubstituted heteroaryl group; and R31 to R35 are the same as or different from each other, and are each independently hydrogen, deuterium, a cyano group, a substituted or unsubstituted alkyl group, a substituted or unsubstituted aryl group, or a substituted or unsubstituted heteroaryl group.

In an exemplary embodiment of the present specification, Y1 and Y2 are each hydrogen or deuterium, or are directly bonded to each other, or are linked to each other through —O— or —S—.

In an exemplary embodiment of the present specification, Y1 and Y2 are each hydrogen or deuterium.

In an exemplary embodiment of the present specification, Y1 and Y2 are directly bonded to each other, or are linked to each other through —O— or —S—.

In an exemplary embodiment of the present specification, the others among R11 to R26 which are not linked to L1 and L4 of Chemical Formula 1 are the same as or different from each other, and are each independently hydrogen, deuterium, a cyano group, a substituted or unsubstituted C1-C10 alkyl group, a substituted or unsubstituted C6-C30 aryl group, or a substituted or unsubstituted C2-C30 heteroaryl group.

In an exemplary embodiment of the present specification, the others among R11 to R26 which are not linked to L1 and L4 of Chemical Formula 1 are the same as or different from each other, and are each independently hydrogen, deuterium, or a C6-C20 aryl group.

In an exemplary embodiment of the present specification, the others among R11 to R26 which are not linked to L1 and L4 of Chemical Formula 1 are the same as or different from each other, and are each independently hydrogen, deuterium, or a phenyl group.

In an exemplary embodiment of the present specification, the others among R11 to R26 which are not linked to L1 and L4 of Chemical Formula 1 are the same as or different from each other, and are each independently hydrogen or deuterium.

In an exemplary embodiment of the present specification, R31 to R35 are the same as or different from each other, and are each independently hydrogen, deuterium, a cyano group, a substituted or unsubstituted C1-C10 alkyl group, a substituted or unsubstituted C6-C30 aryl group, or a substituted or unsubstituted C2-C30 heteroaryl group.

In an exemplary embodiment of the present specification, R31 to R35 are the same as or different from each other, and are each independently a methyl group or a phenyl group.

In an exemplary embodiment of the present specification, R11 is linked to L1 of Chemical Formula 1. In another exemplary embodiment, R12 is linked to L1 of Chemical Formula 1. In still another exemplary embodiment, R13 is linked to L1 of Chemical Formula 1. In yet another exemplary embodiment, R14 is linked to L1 of Chemical Formula 1. In yet another exemplary embodiment, R15 is linked to L1 of Chemical Formula 1. In yet another exemplary embodiment, R16 is linked to L1 of Chemical Formula 1. In yet another exemplary embodiment, R17 is linked to L1 of Chemical Formula 1. In yet another exemplary embodiment, R18 is linked to L1 of Chemical Formula 1. In yet another exemplary embodiment, R19 is linked to L1 of Chemical Formula 1. In yet another exemplary embodiment, R20 is linked to L1 of Chemical Formula 1. In yet another exemplary embodiment, R21 is linked to L1 of Chemical Formula 1. In yet another exemplary embodiment, R22 is linked to L1 of Chemical Formula 1. In yet another exemplary embodiment, R23 is linked to L1 of Chemical Formula L1. In yet another exemplary embodiment, R24 is linked to L1 of Chemical Formula 1. In yet another exemplary embodiment, R25 is linked to L1 of Chemical Formula 1. In yet another exemplary embodiment, R26 is linked to L1 of Chemical Formula 1.

In an exemplary embodiment of the present specification, R11 is linked to L4 of Chemical Formula 1. In another exemplary embodiment, R12 is linked to L4 of Chemical Formula 1. In still another exemplary embodiment, R13 is linked to L4 of Chemical Formula 1. In yet another exemplary embodiment, R14 is linked to L4 of Chemical Formula 1. In yet another exemplary embodiment, R15 is linked to L4 of Chemical Formula 1. In yet another exemplary embodiment, R16 is linked to L4 of Chemical Formula 1. In yet another exemplary embodiment, R17 is linked to L4 of Chemical Formula 1. In yet another exemplary embodiment, R18 is linked to L4 of Chemical Formula 1. In yet another exemplary embodiment, R19 is linked to L4 of Chemical Formula 1. In yet another exemplary embodiment, R20 is linked to L4 of Chemical Formula 1. In yet another exemplary embodiment, R21 is linked to L4 of Chemical Formula 1. In yet another exemplary embodiment, R22 is linked to L4 of Chemical Formula 1. In yet another exemplary embodiment, R23 is linked to L4 of Chemical Formula 1. In yet another exemplary embodiment, R24 is linked to L4 of Chemical Formula 1. In yet another exemplary embodiment, R25 is linked to L4 of Chemical Formula 1. In yet another exemplary embodiment, R26 is linked to L4 of Chemical Formula 1.

In an exemplary embodiment of the present specification, Chemical Formula 1-1 is any one of the following Chemical Formulae A11 to A13:

[Chemical Formula A11]

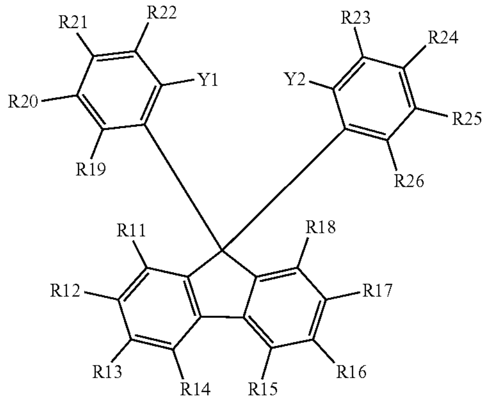

[Chemical Formula A12]

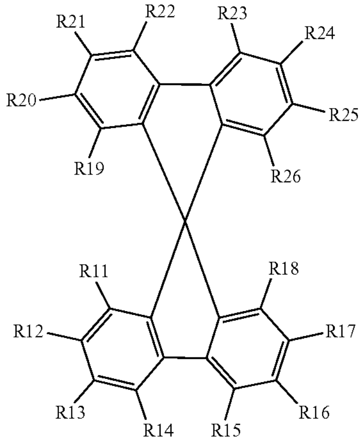

[Chemical Formula A13]

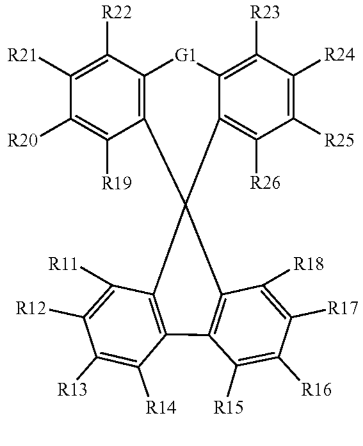

wherein in Chemical Formulae A11 to A13, the definitions of R11 to R26 are the same as those defined in Chemical Formula 1-1;

Y1 and Y2 are each hydrogen or deuterium;

G1 is C(R31)(R32), Si(R33)(R34), N(R35), 0, or S; and

R31 to R35 are the same as or different from each other, and are each independently hydrogen, deuterium, a cyano group, a substituted or unsubstituted alkyl group, a substituted or unsubstituted aryl group, or a substituted or unsubstituted heteroaryl group.

In an exemplary embodiment of the present specification, A1 is a divalent group selected from among the following structures:

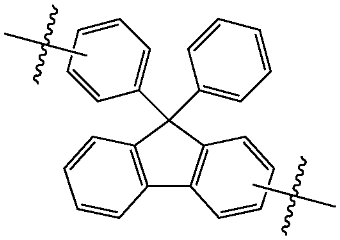

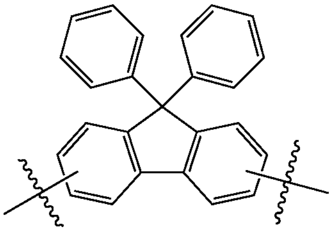

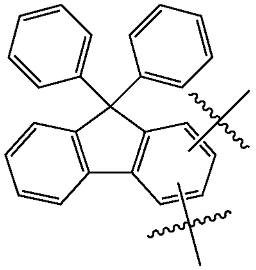

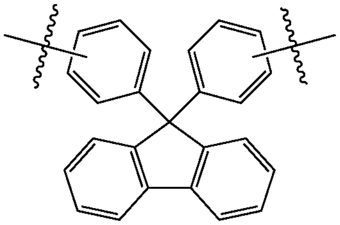

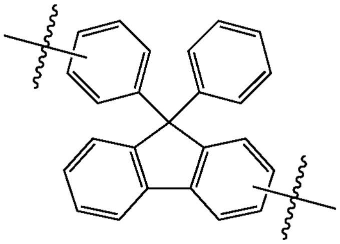

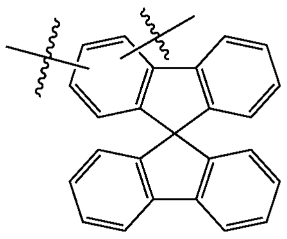

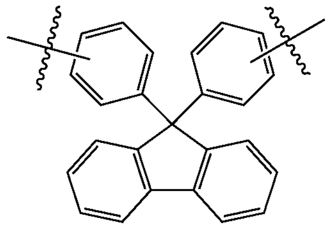

-continued

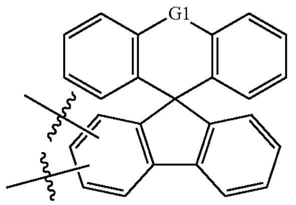

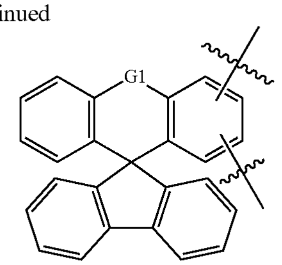

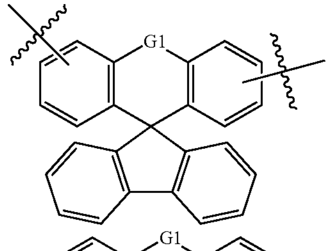

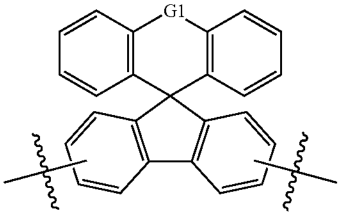

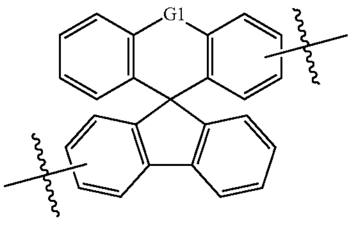

wherein in the structures:

G1 is C(R31)(R32), Si(R33)(R34), N(R35), 0, or S;

the structures are unsubstituted or substituted with deuterium, a cyano group, an alkyl group, an aryl group, or a heteroaryl group: and

is a position which is linked to L1 or L4 of Chemical Formula 1.

In an exemplary embodiment of the present specification, the structure of A1 is unsubstituted or substituted with deuterium, a cyano group, a C1-C10 alkyl group, a C6-C30 aryl group, or a C2-C30 heteroaryl group.

In an exemplary embodiment of the present specification, the structure of A1 is unsubstituted or substituted with a C6-C20 aryl group.

In an exemplary embodiment of the present specification, the structure of A1 does not have any substituent.

In an exemplary embodiment of the present specification, R1 is a C1-C6 alkyl group, L1 to L4 are the same as or different from each other, and are each independently a direct bond, or a C6-C20 arylene group; Ar1 to Ar3 are the same as or different from each other, and are each independently a C1-C6 alkyl group or a C6-C20 aryl group; Y1 and Y2 are each hydrogen or deuterium, or are directly bonded to each other, or are linked to each other through —O— or —S—, and the others among R11 to R26 which are not linked to L1 and L4 of Chemical Formula 1 are the same as or different from each other, and are each independently hydrogen or deuterium.

In an exemplary embodiment of the present specification, the heterocyclic compound of Chemical Formula 1 is any one compound selected from among the following compounds:

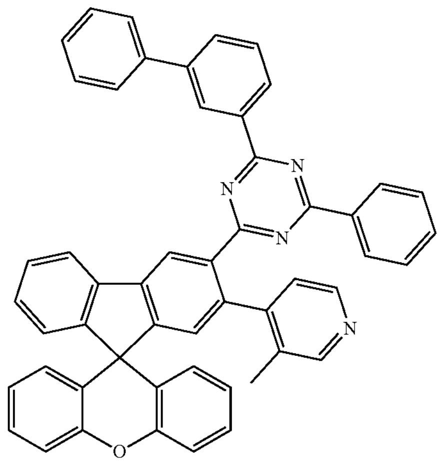

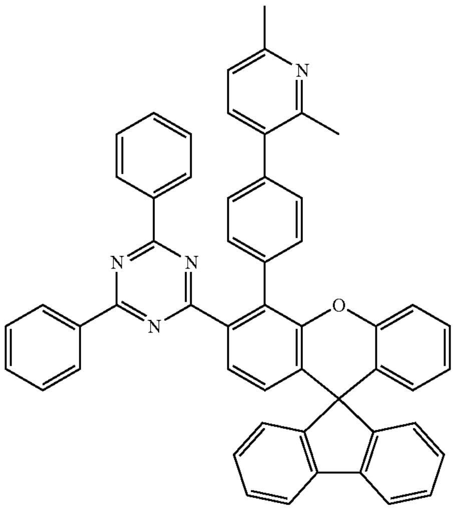

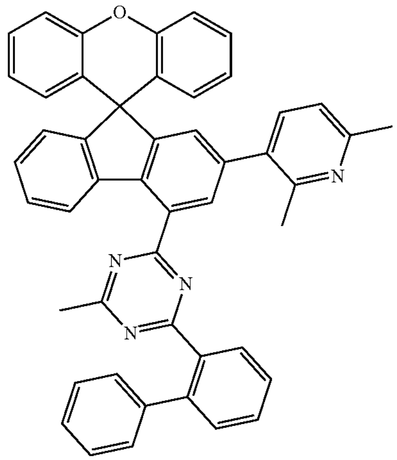

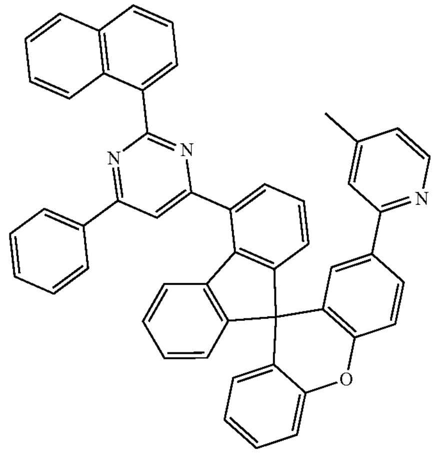

-continued
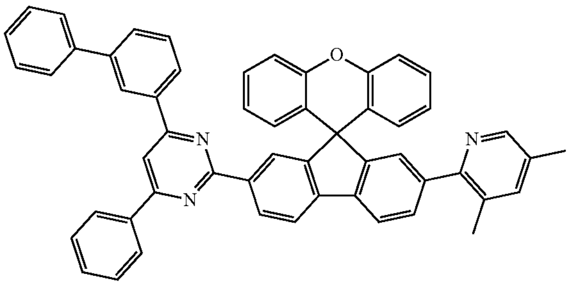
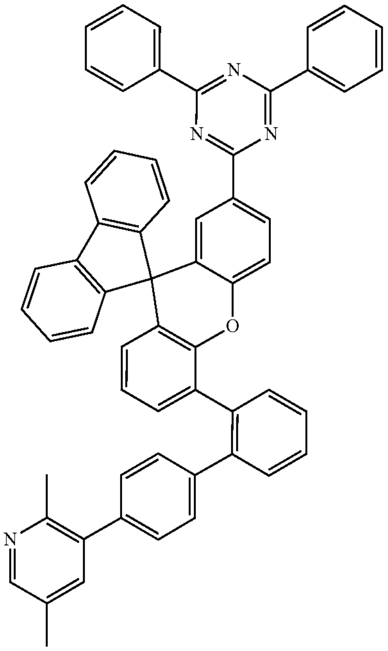
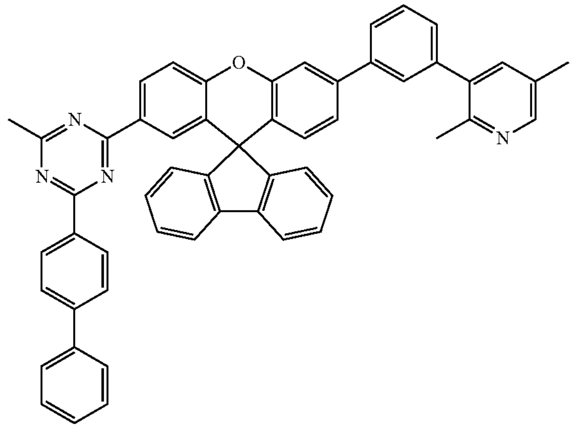
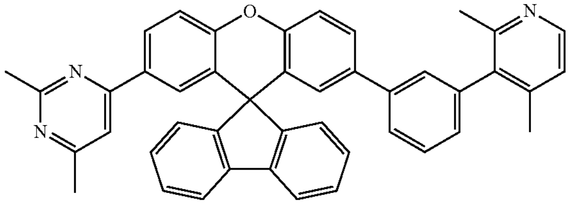
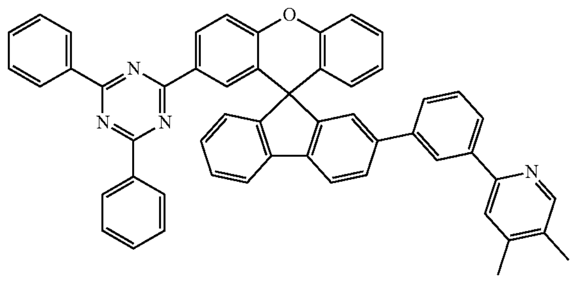
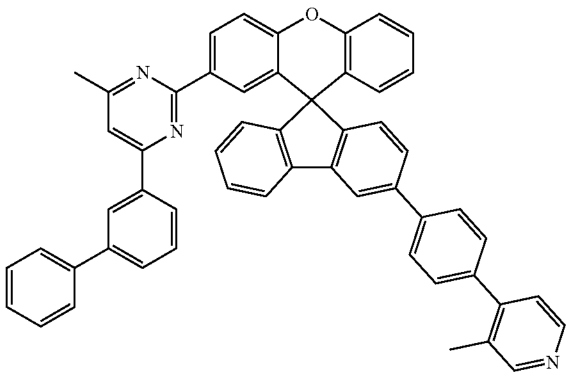

-continued
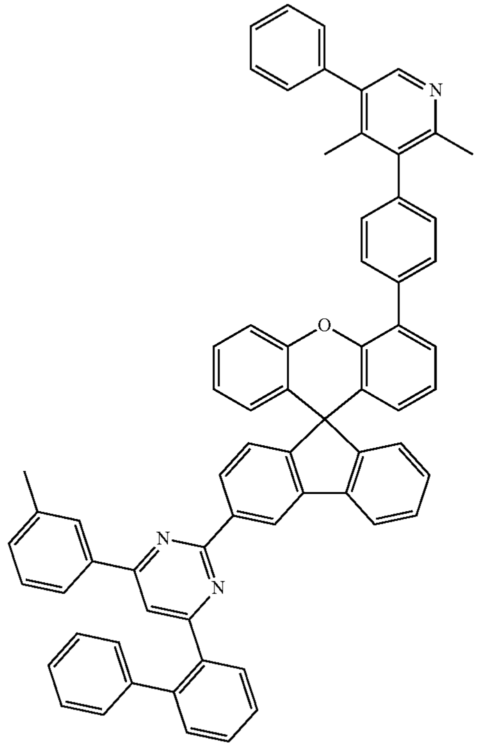
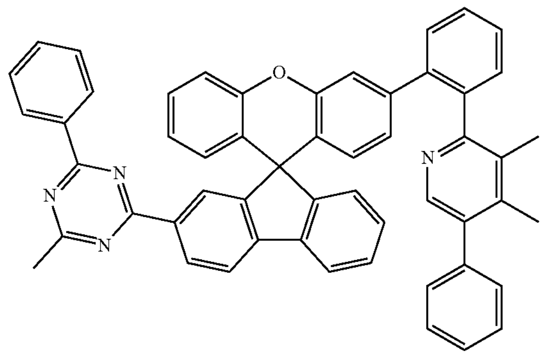
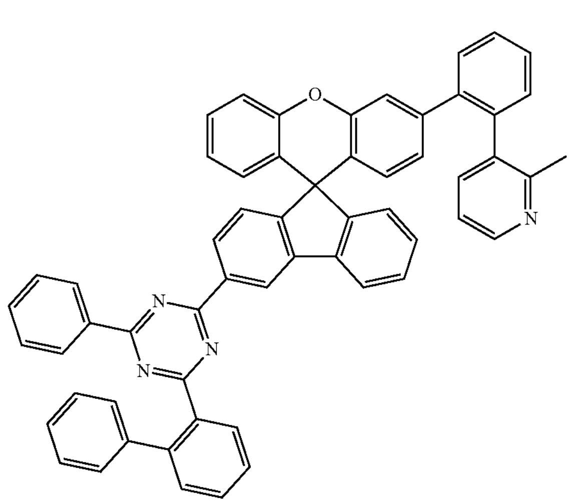
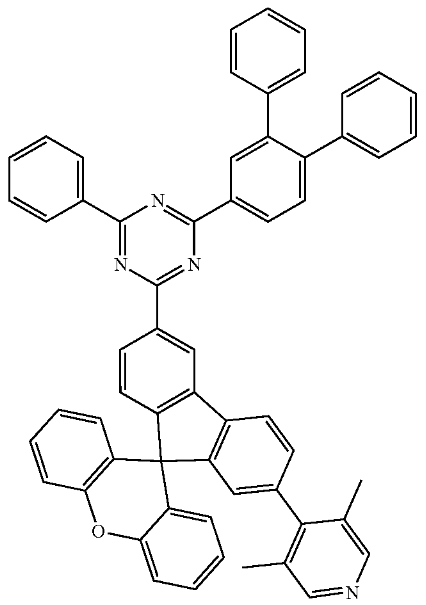

-continued
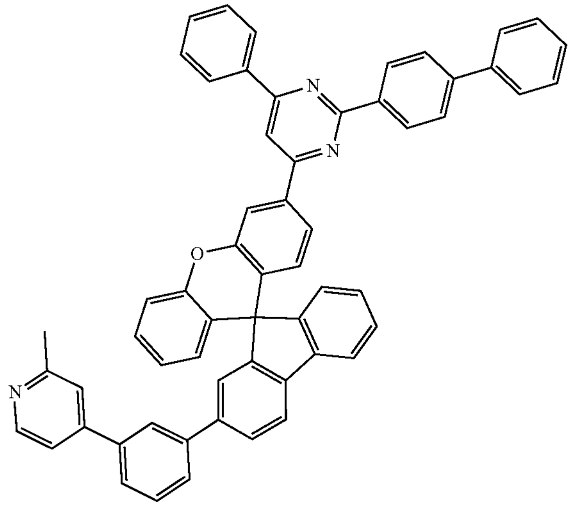
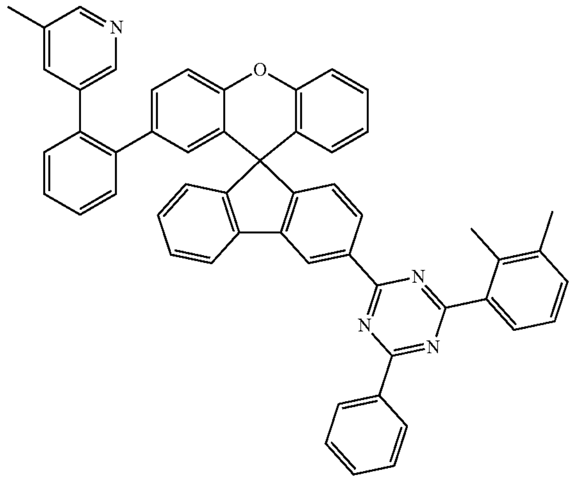
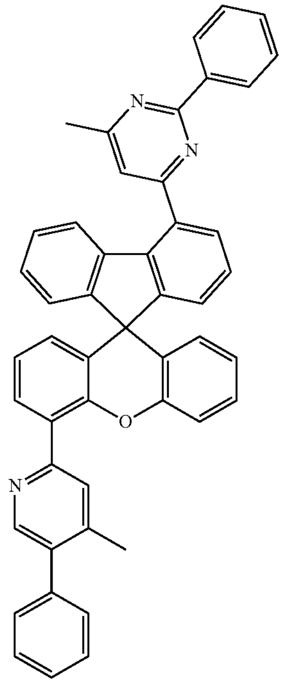
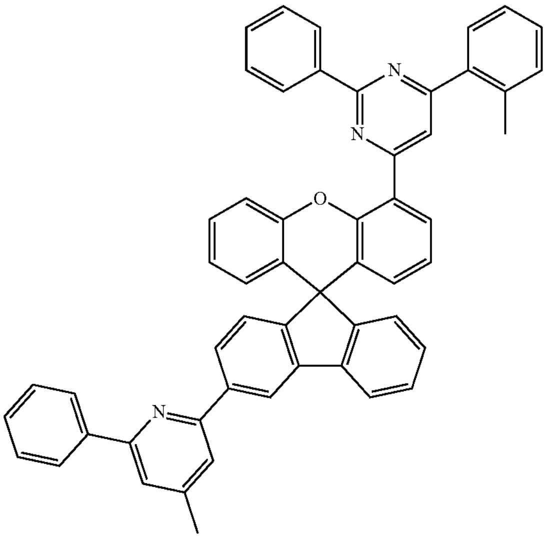
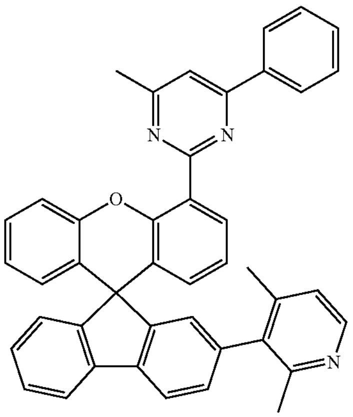

-continued
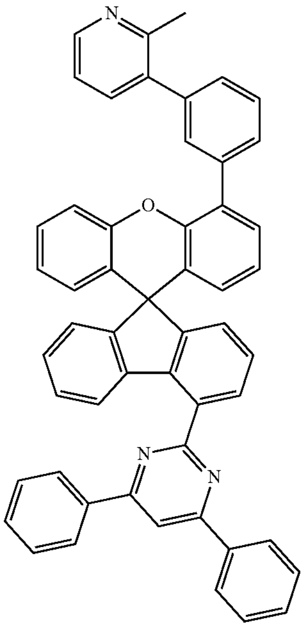
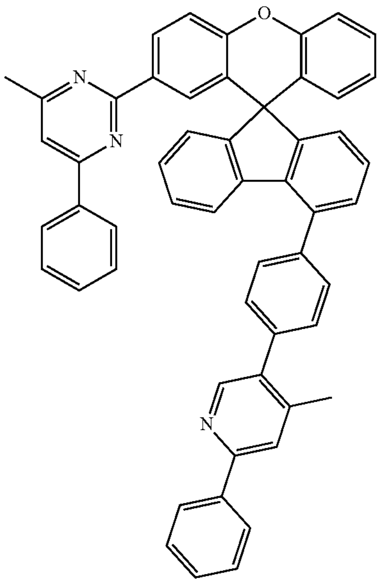
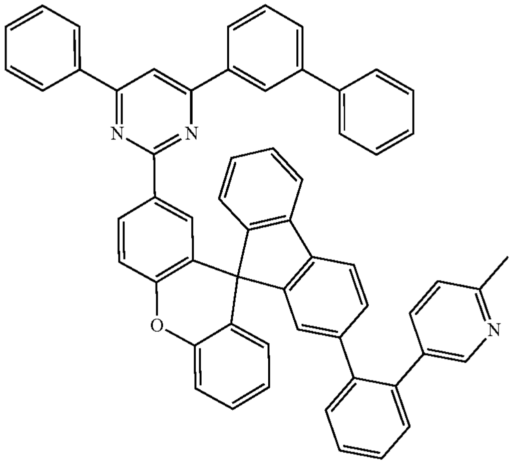
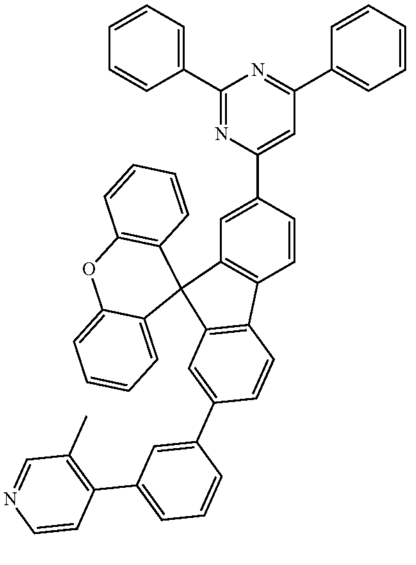
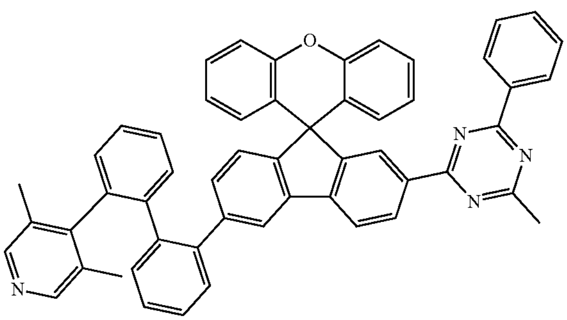

-continued
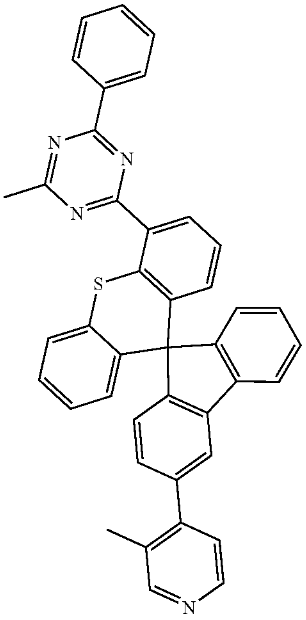
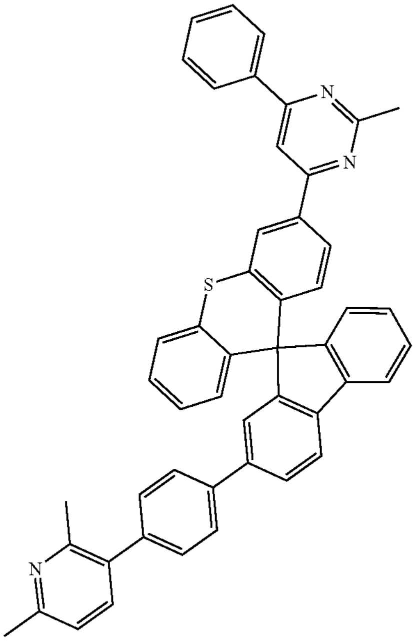
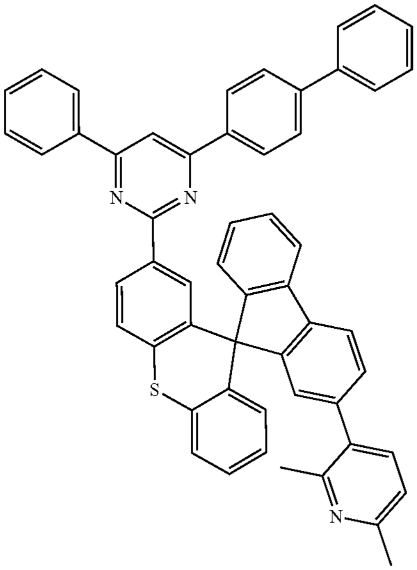
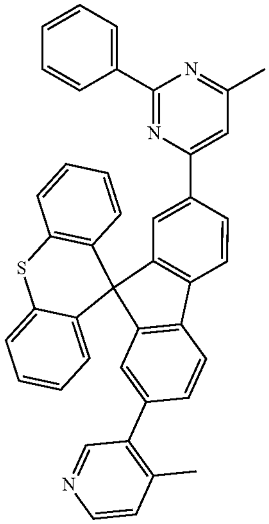
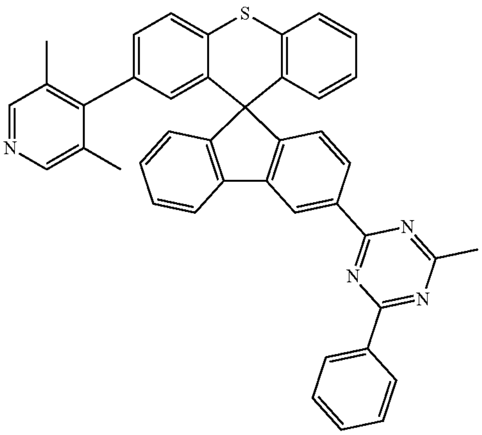
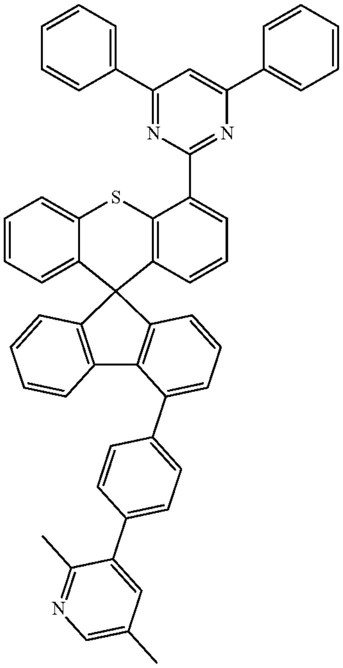

-continued
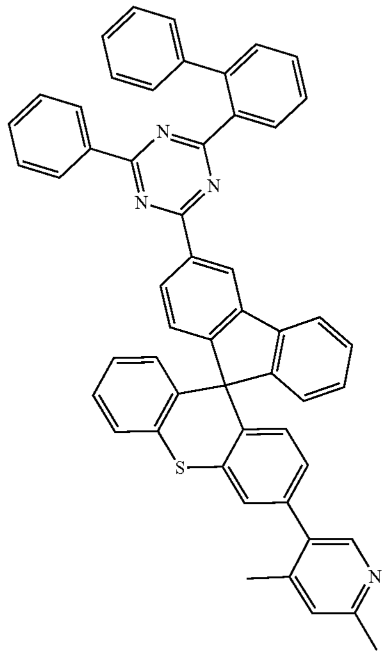
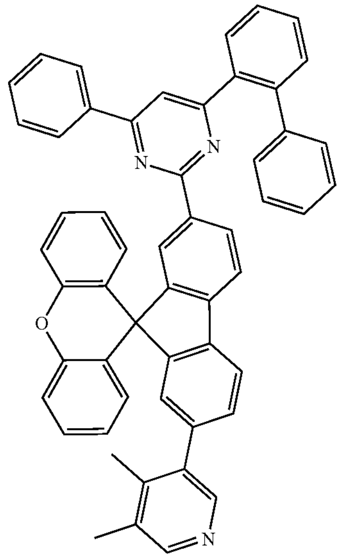
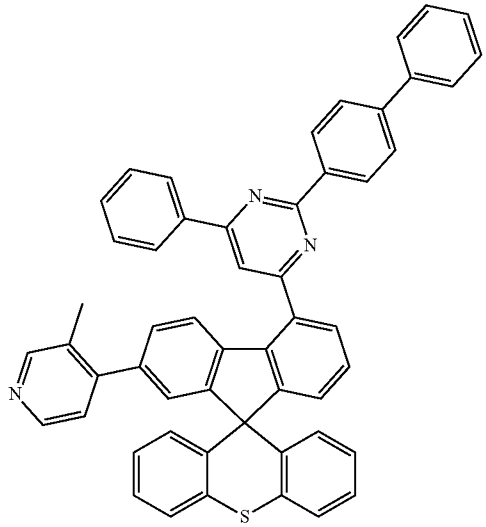
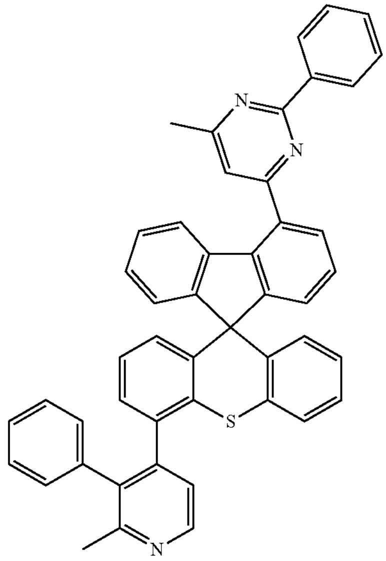

-continued
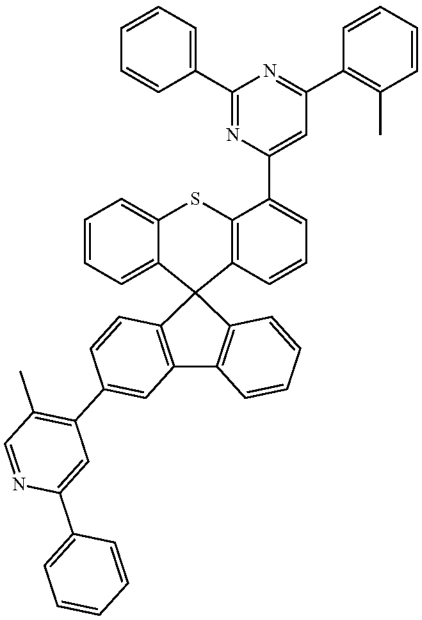
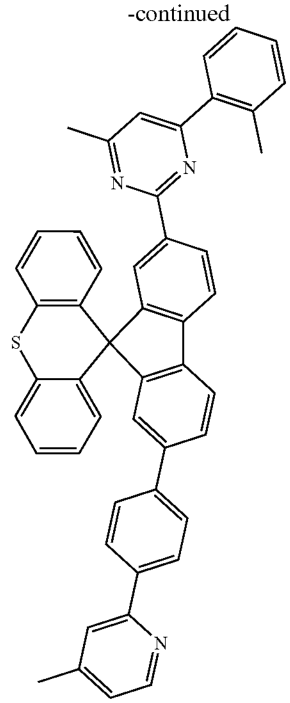
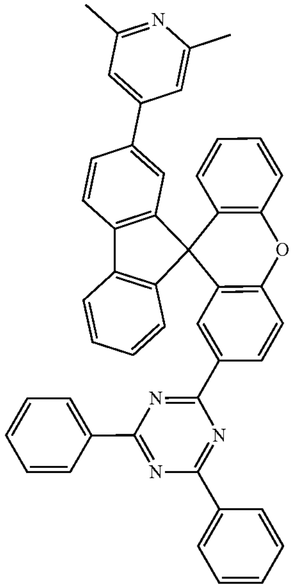
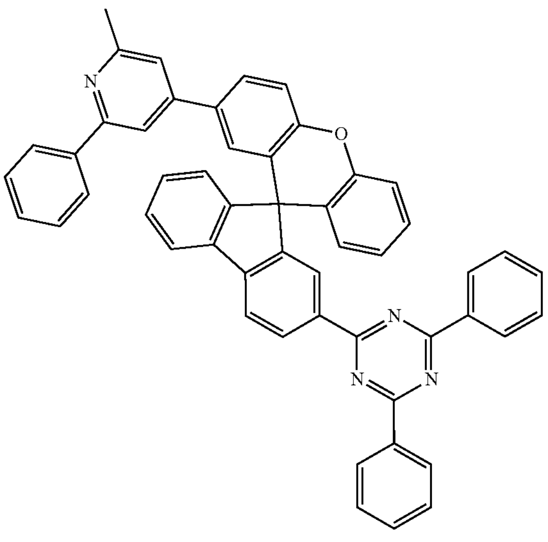
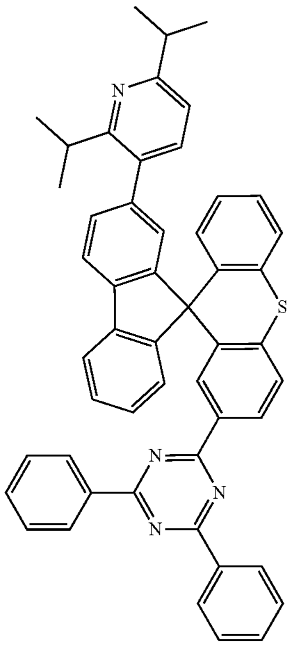

-continued
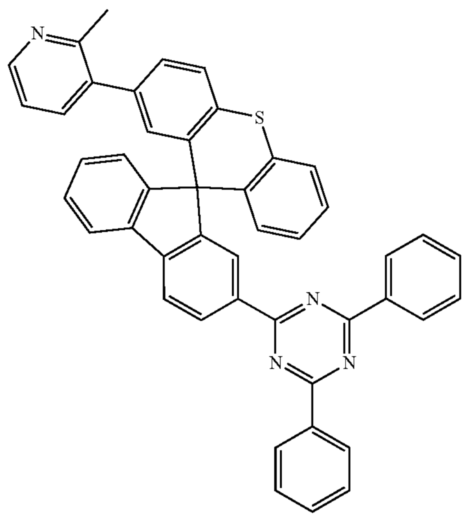
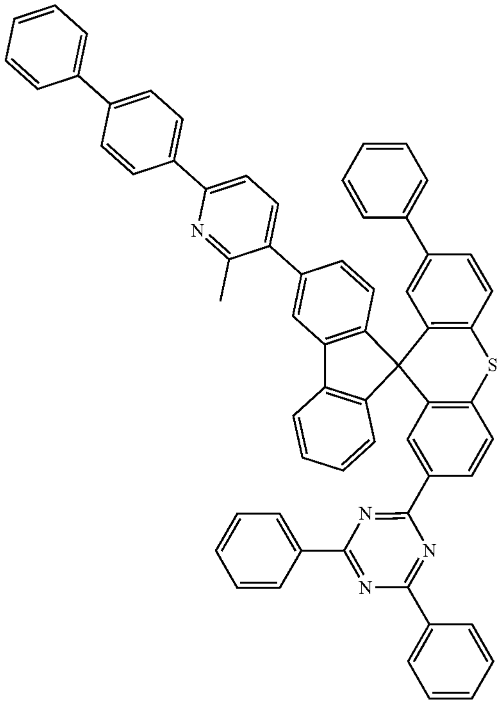
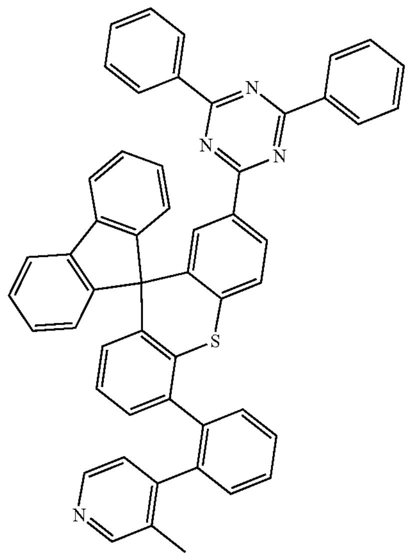
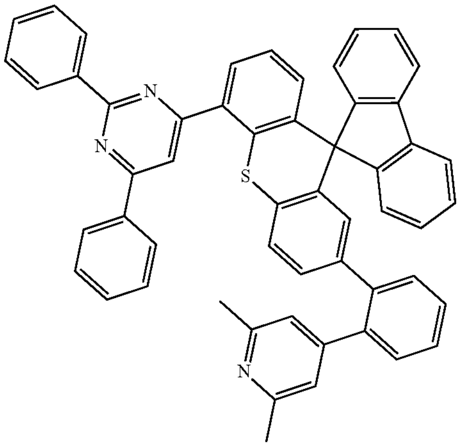

-continued
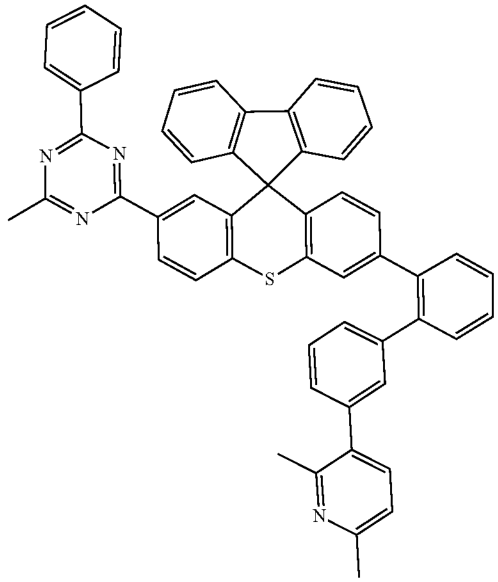
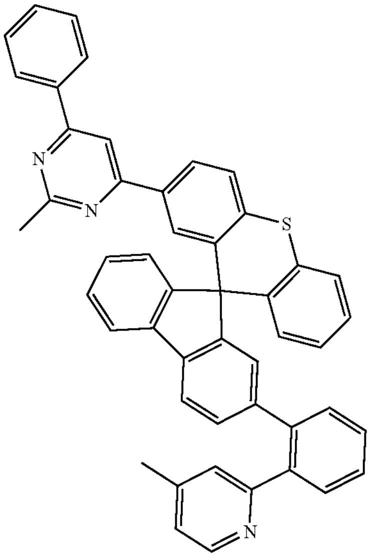
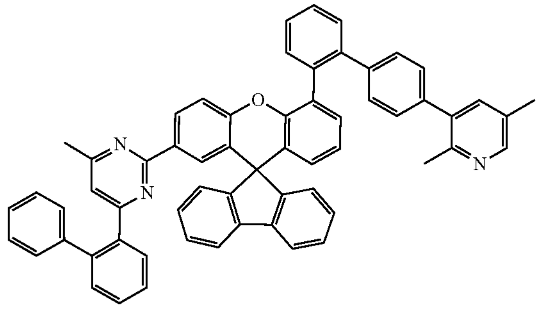
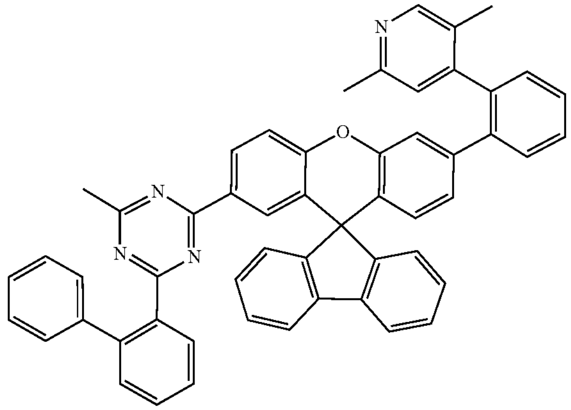
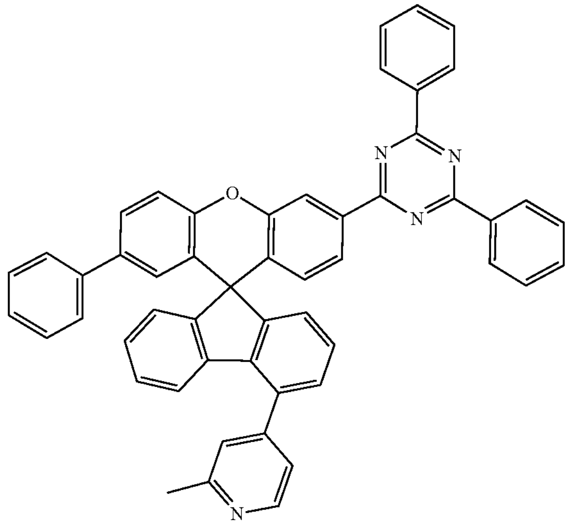
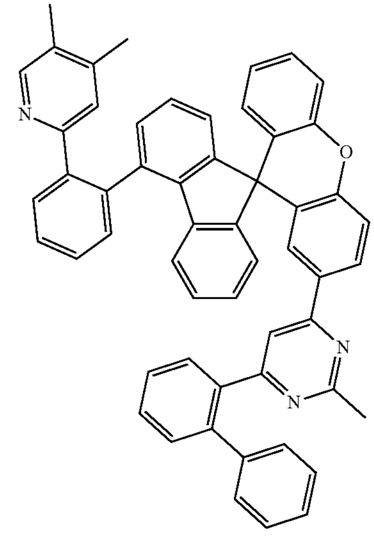

-continued
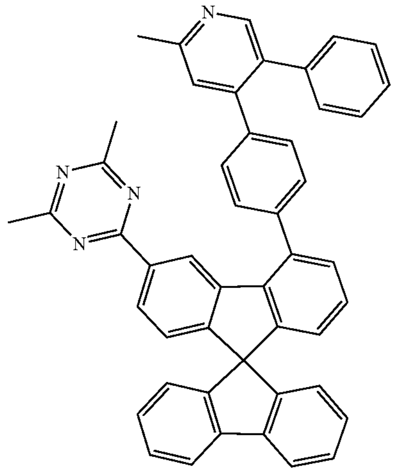
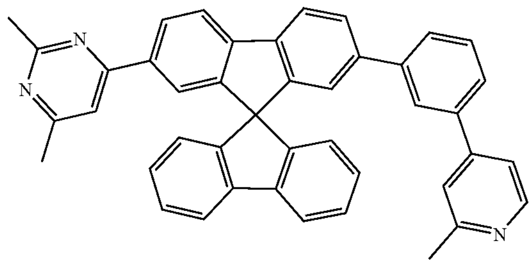
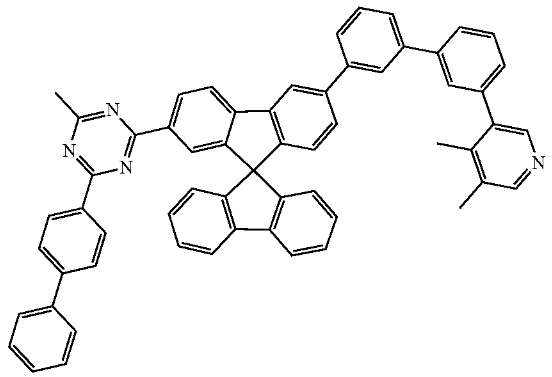
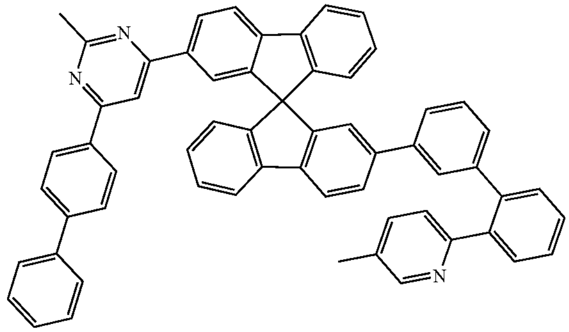
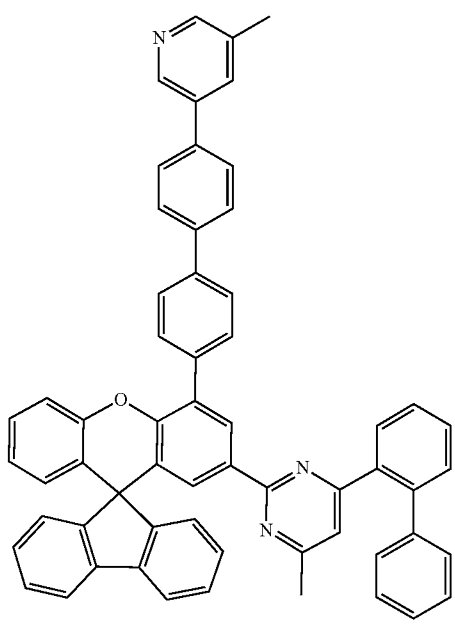
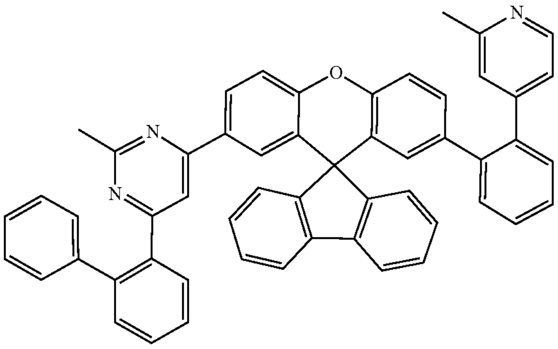

-continued
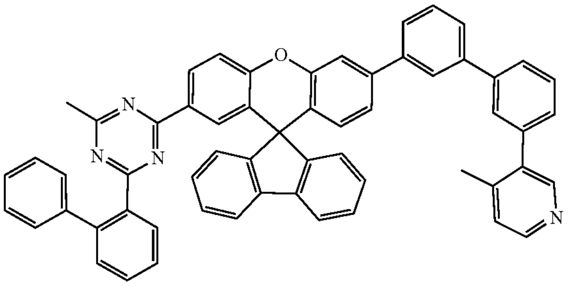
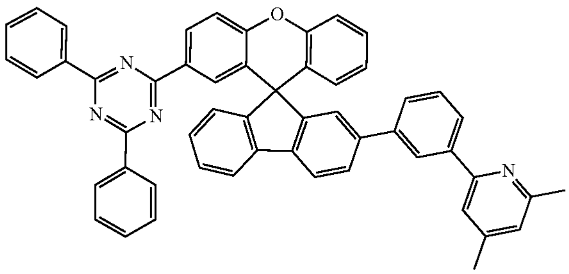
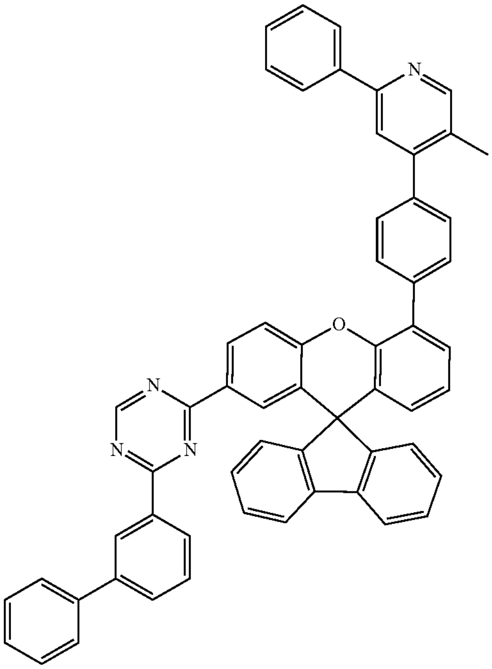
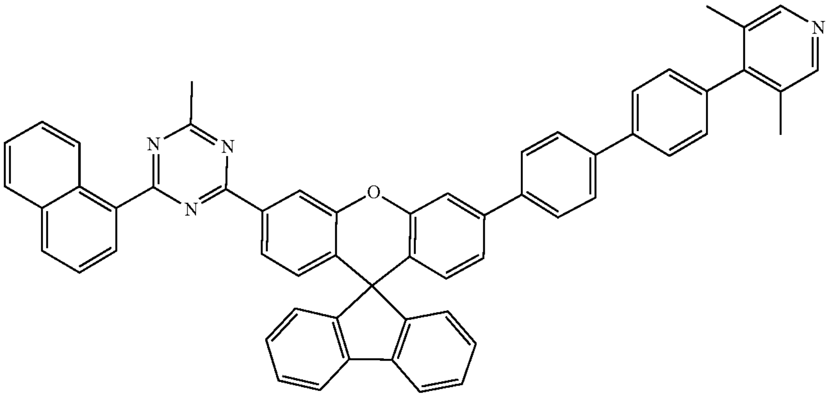

-continued
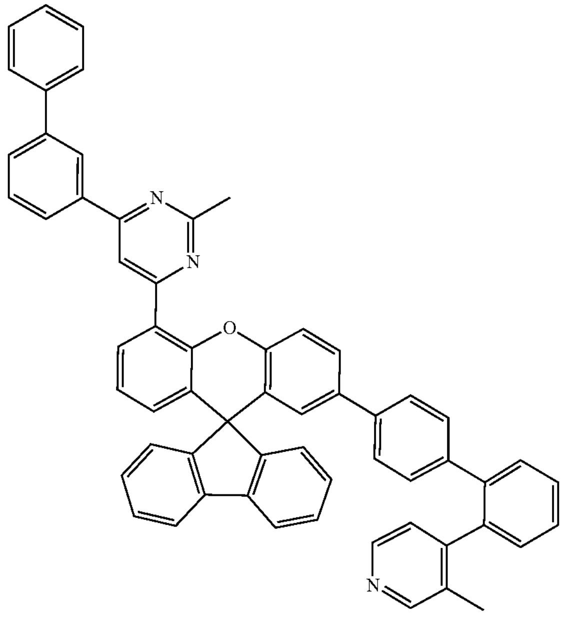
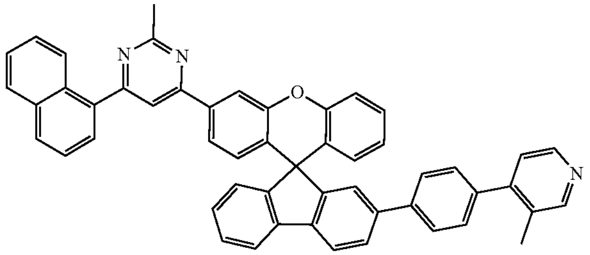
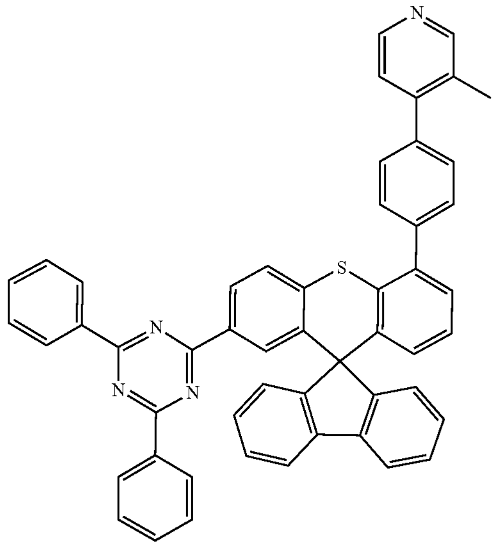
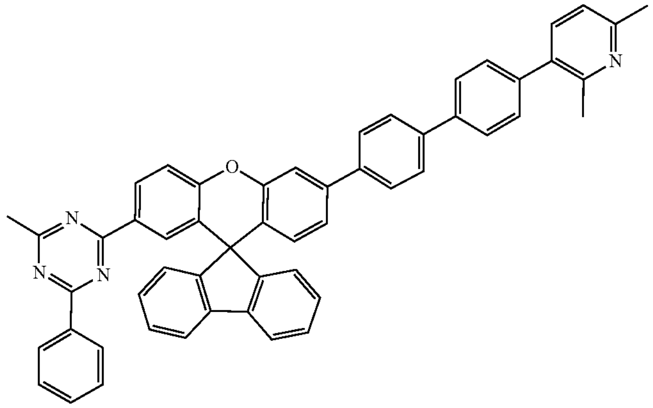
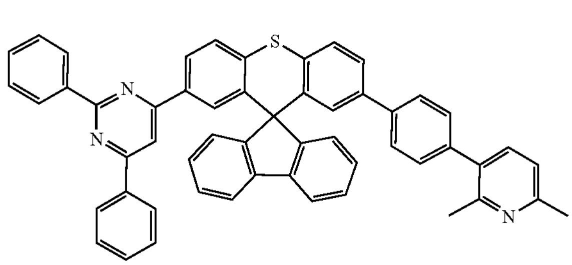
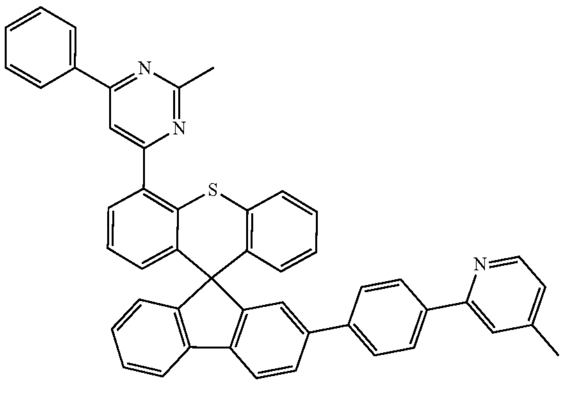

-continued
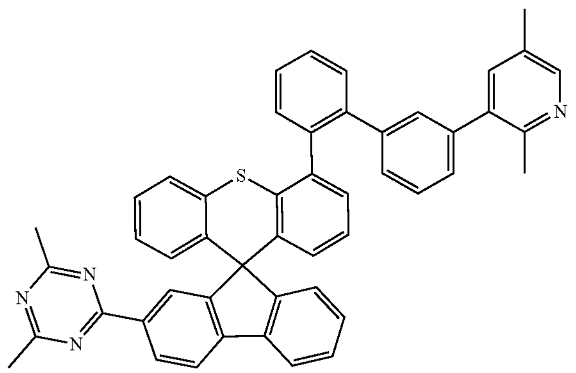
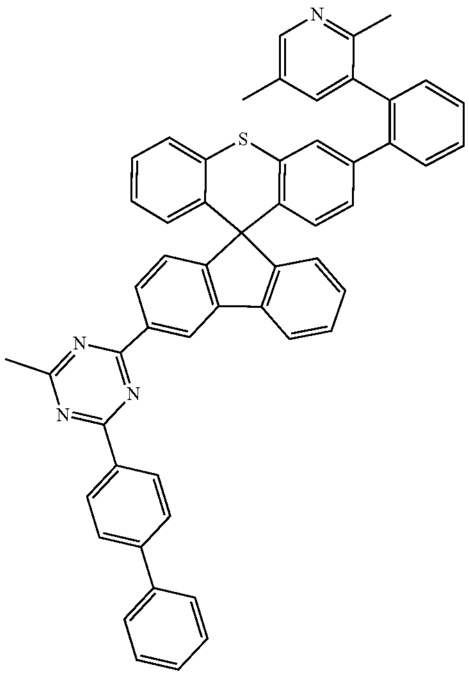
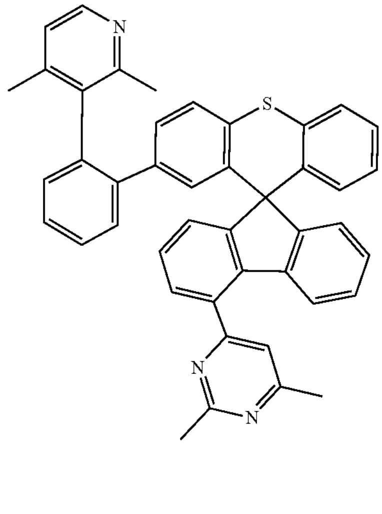
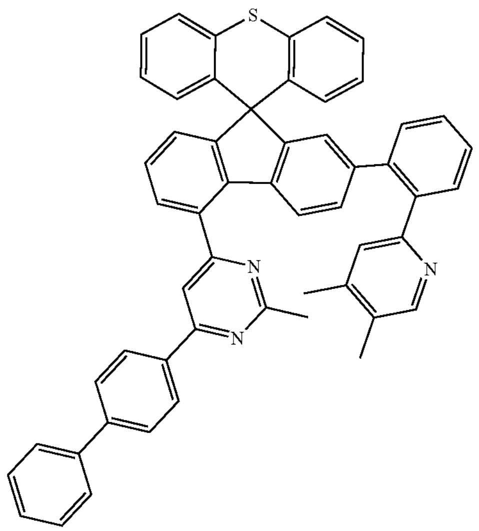

-continued
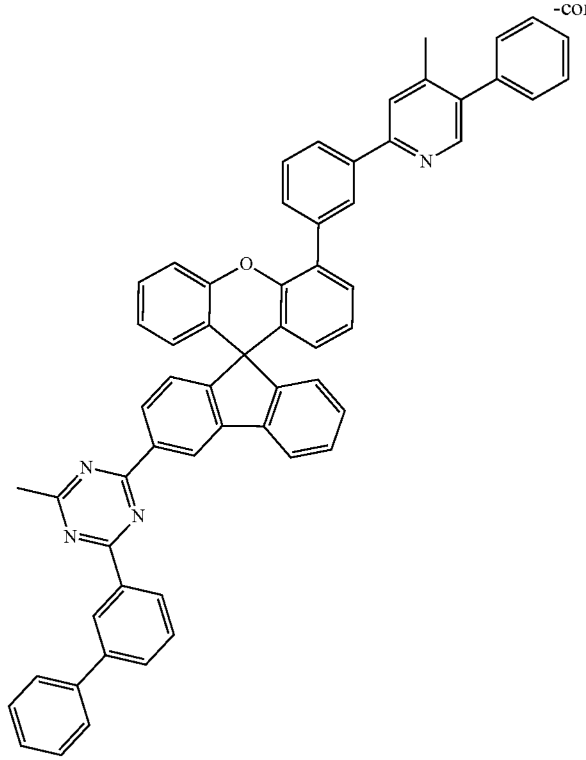
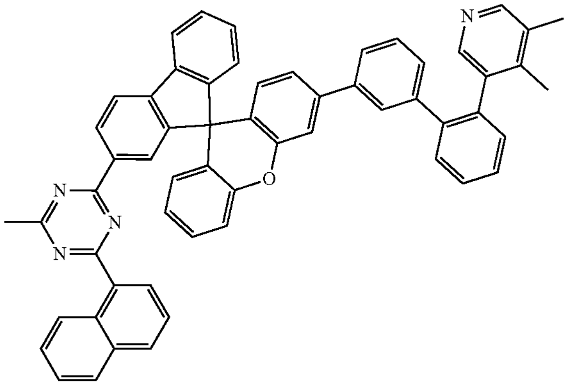
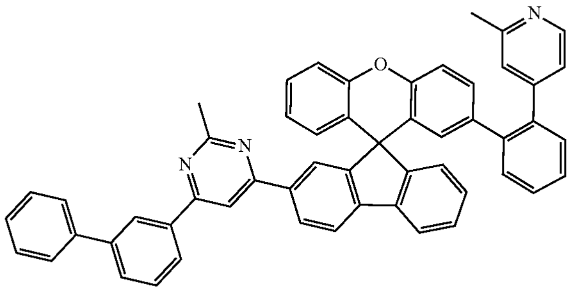
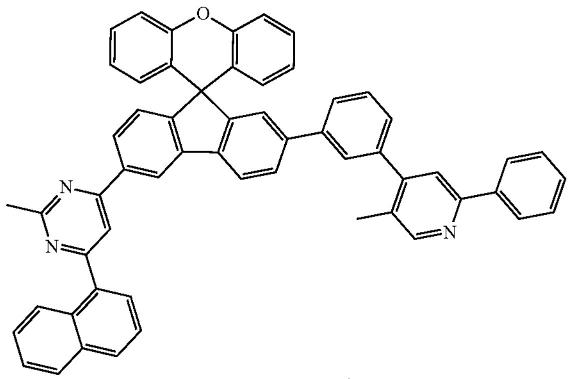
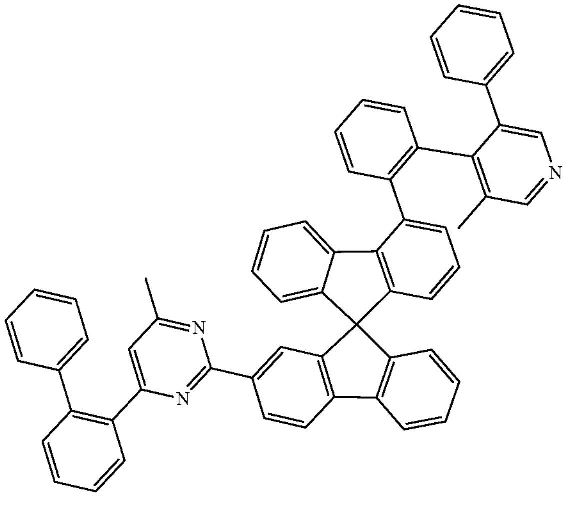
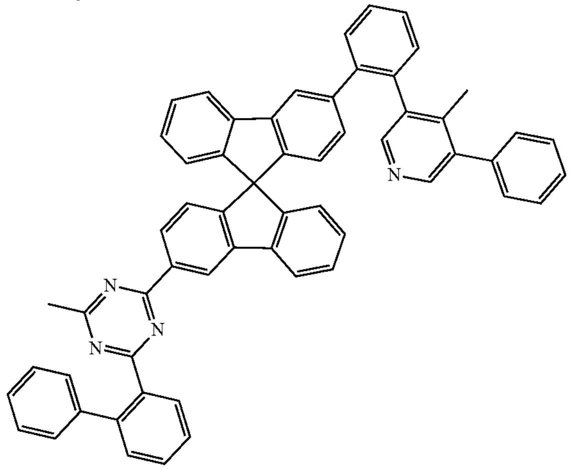

-continued
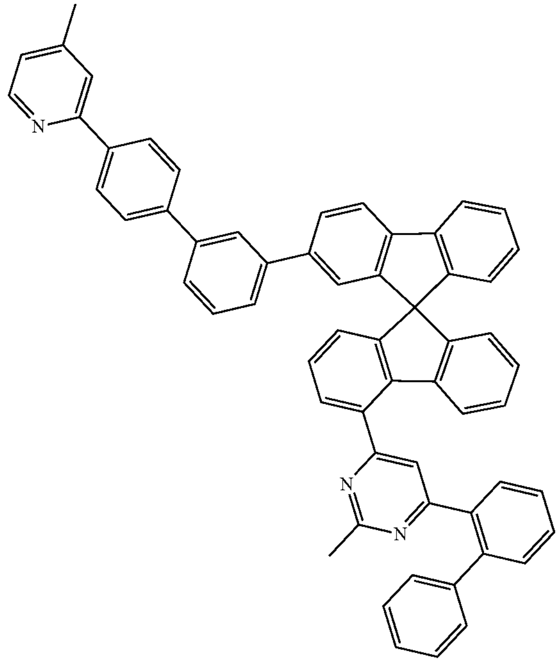
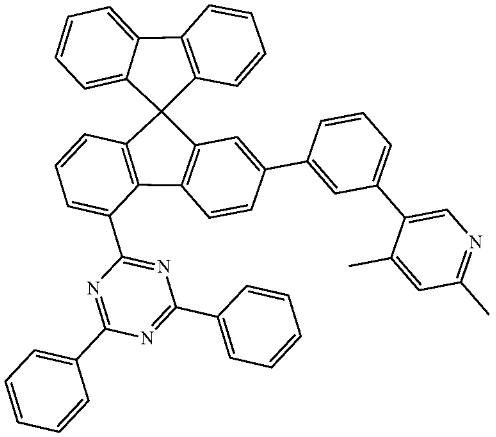
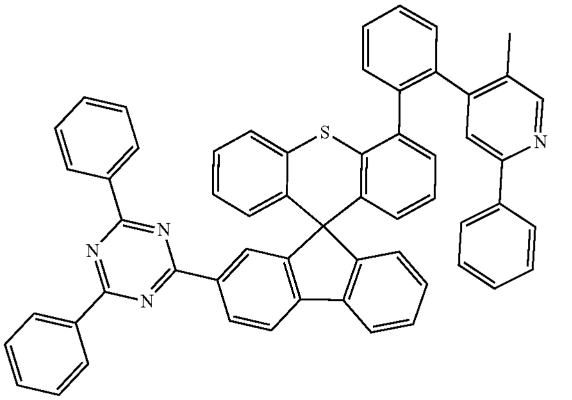
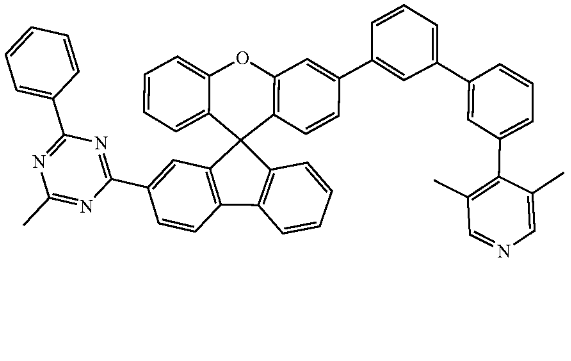
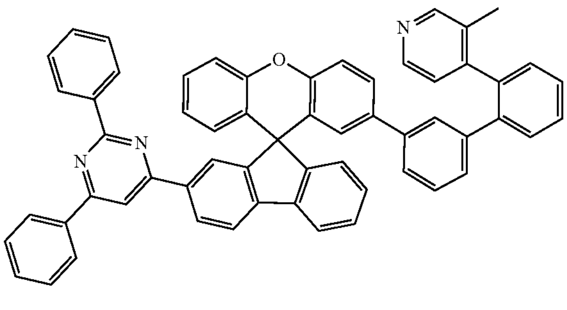
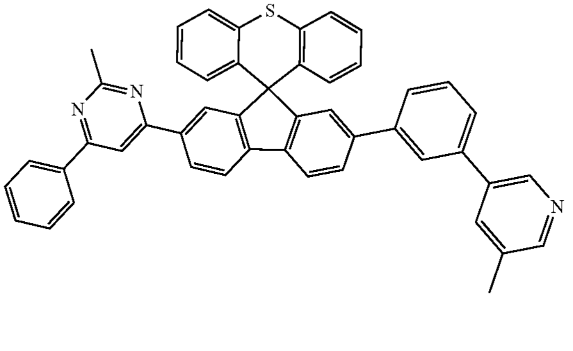

-continued
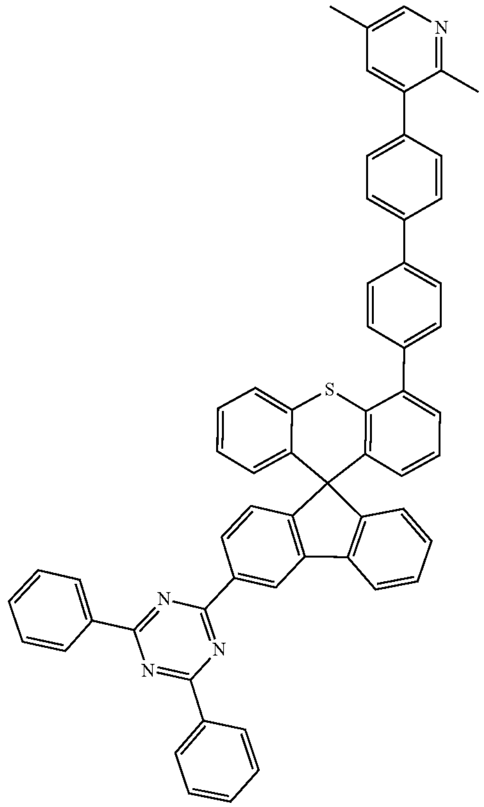
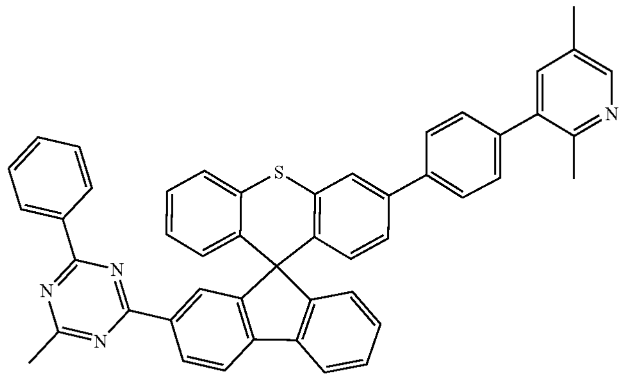
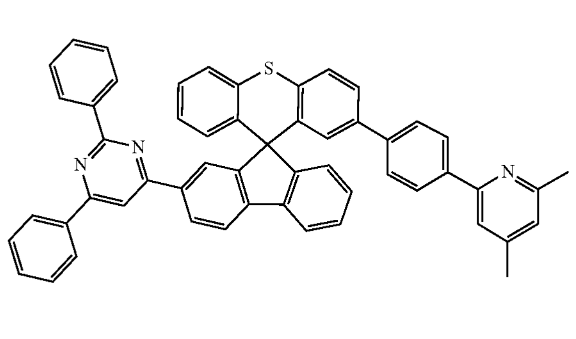
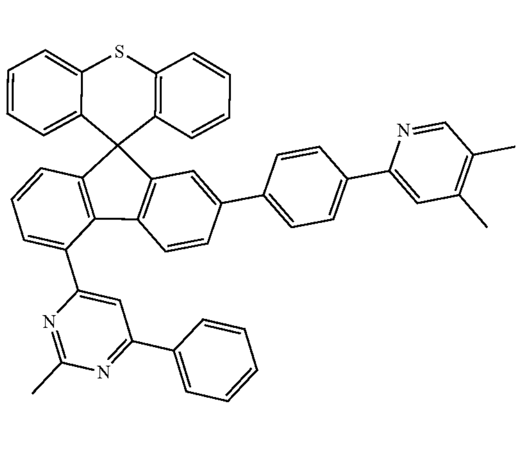

-continued
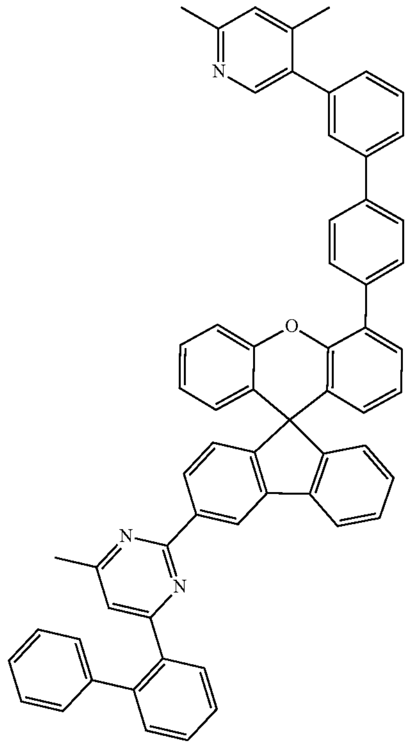
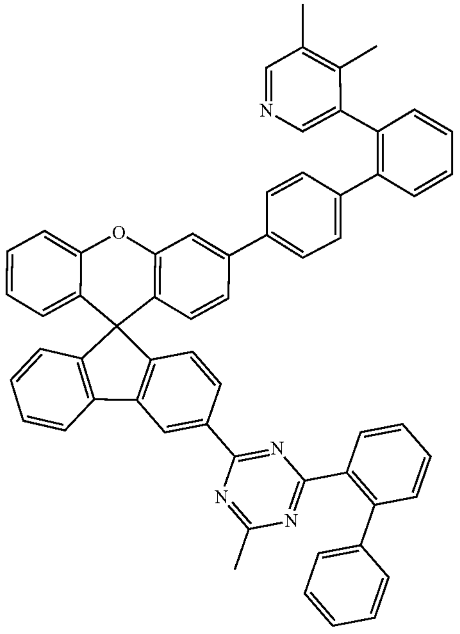
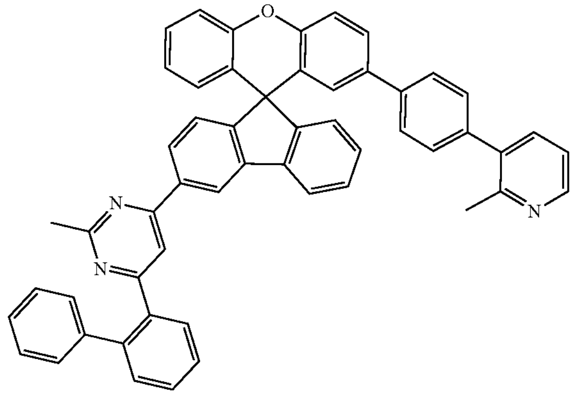
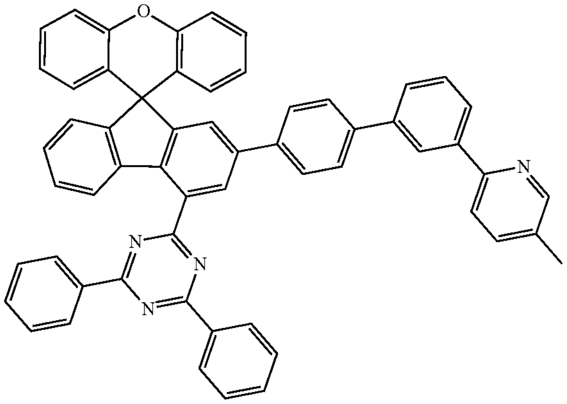
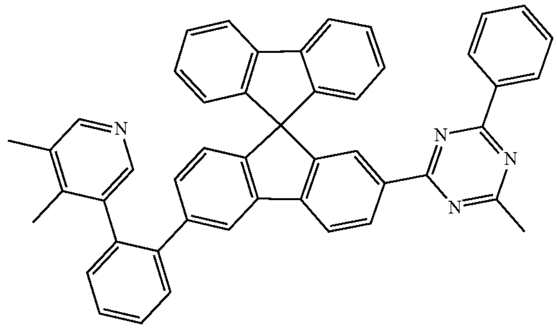
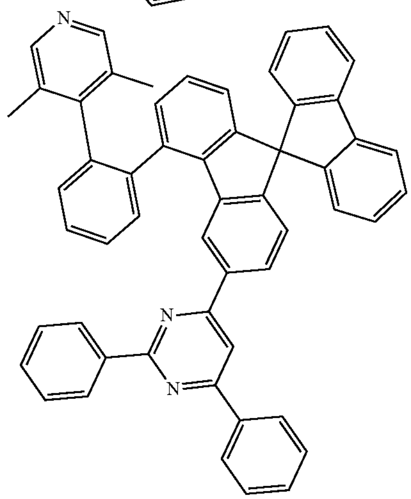

-continued
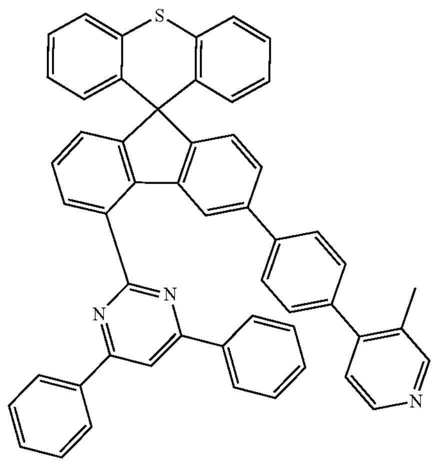
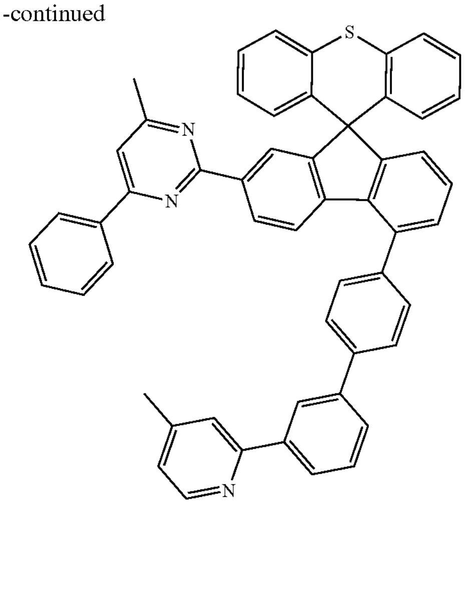
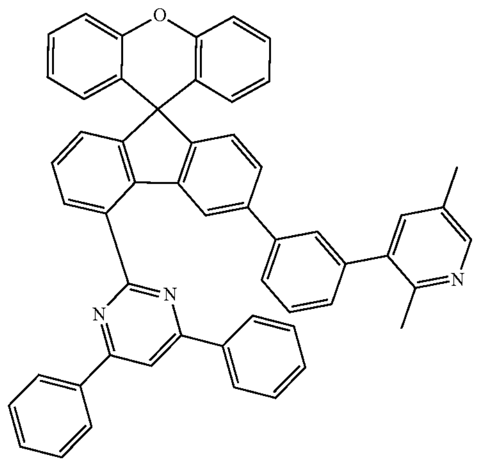
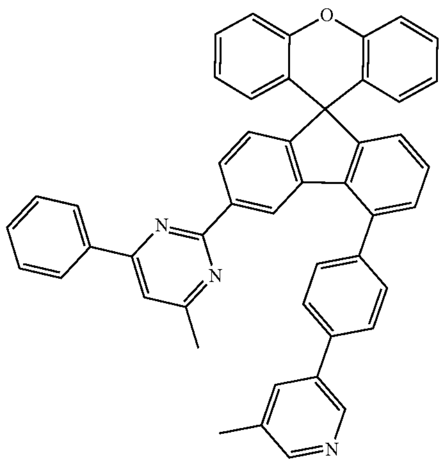
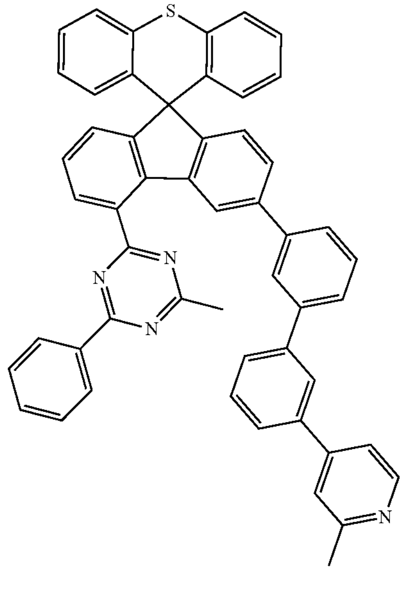
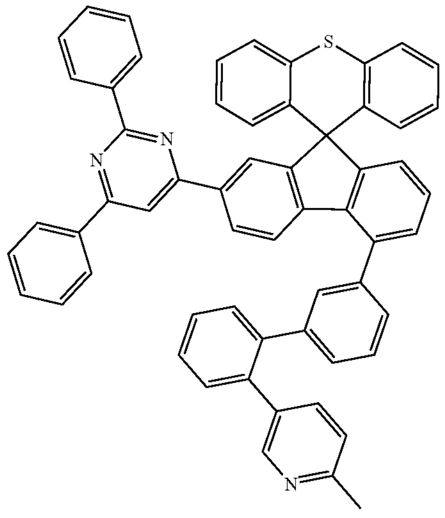

-continued
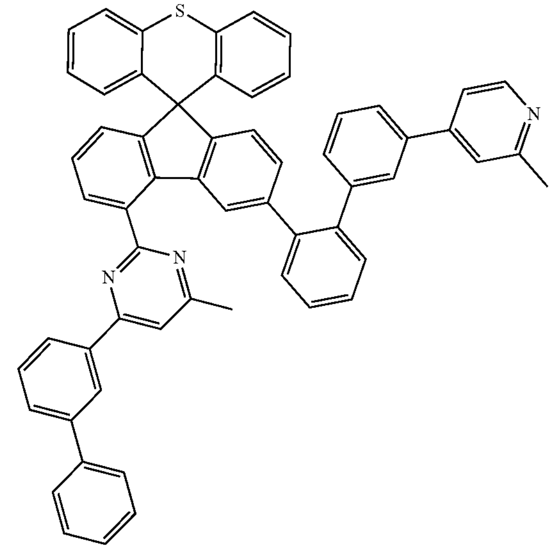
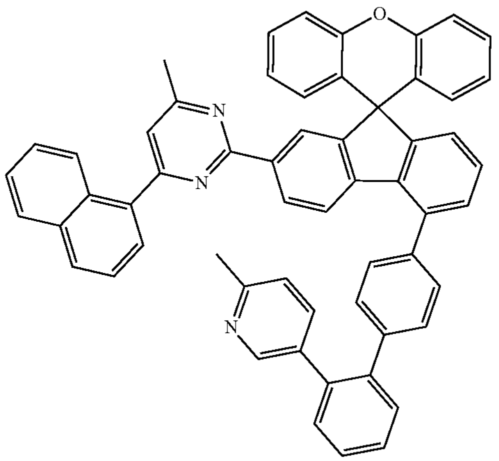
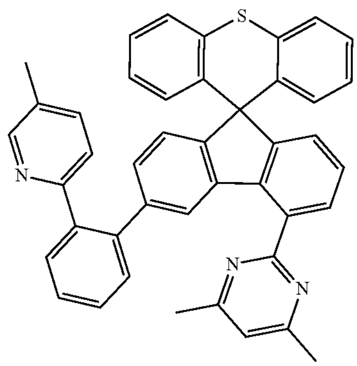
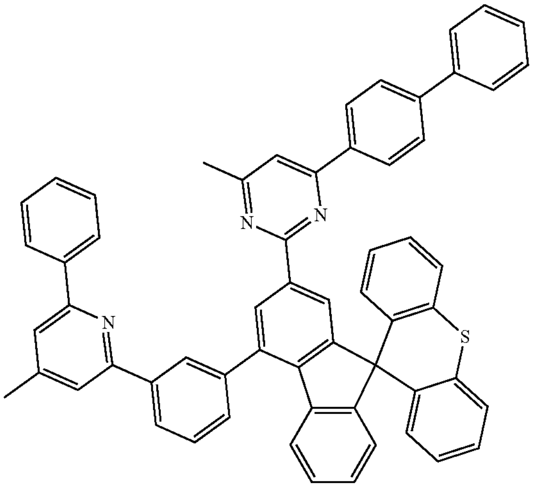
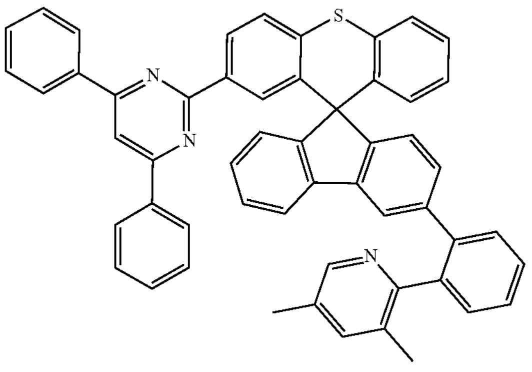
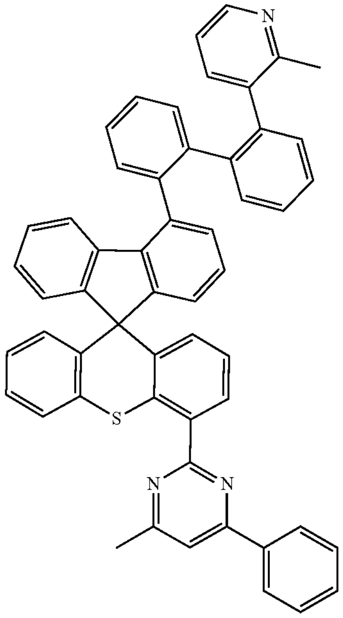

-continued
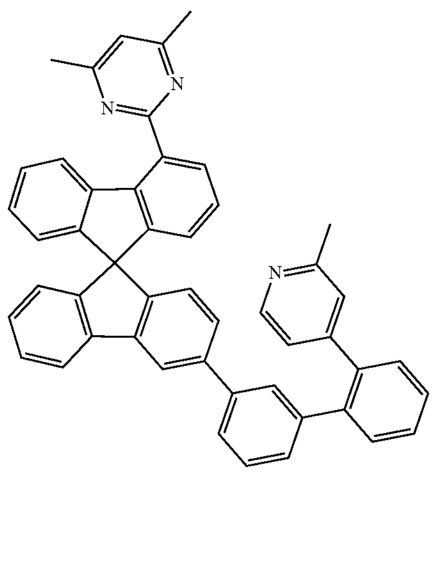
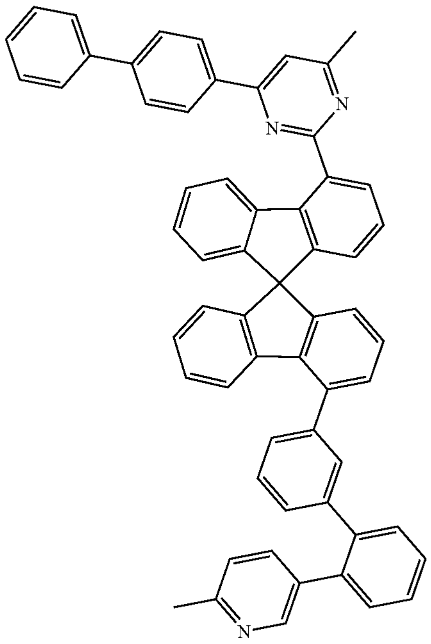
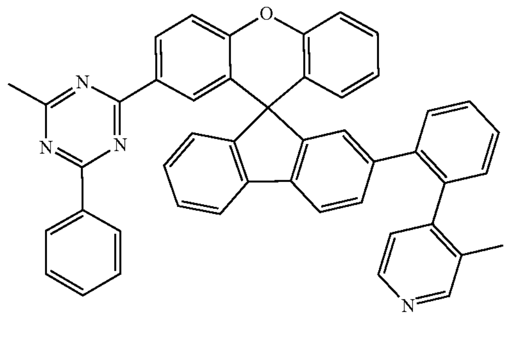
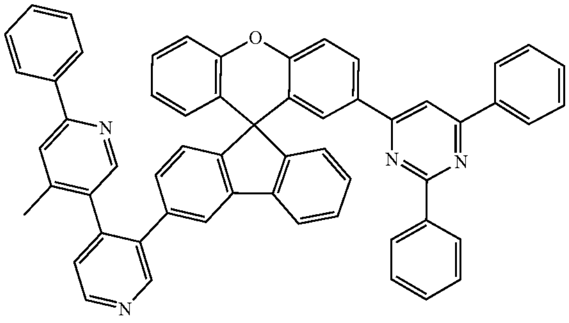
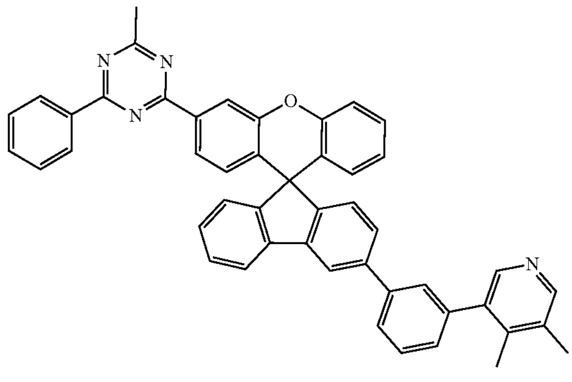
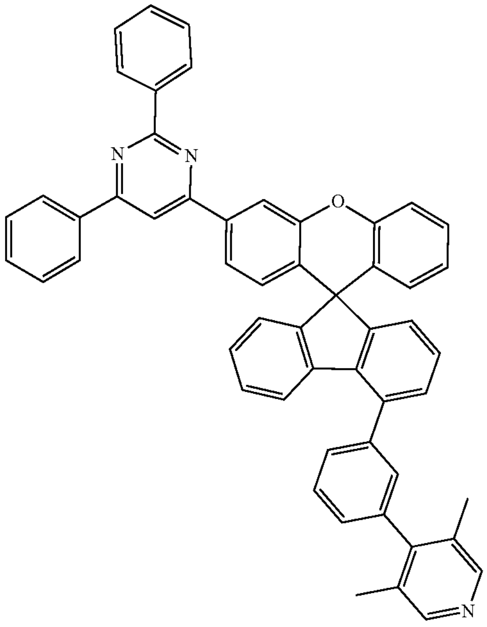

-continued
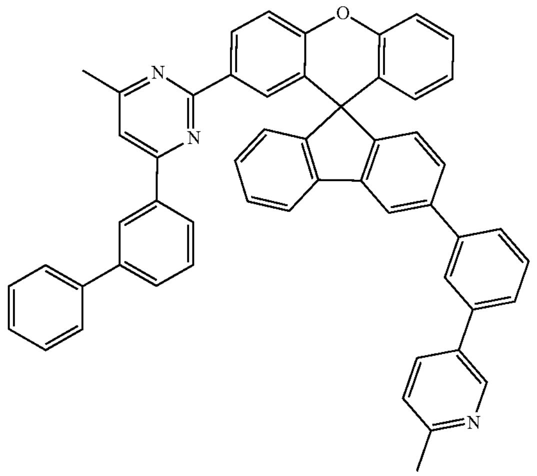
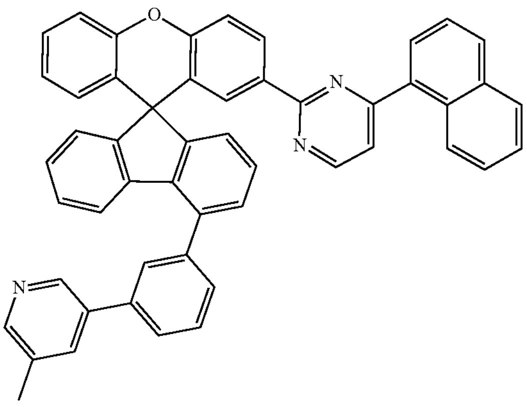
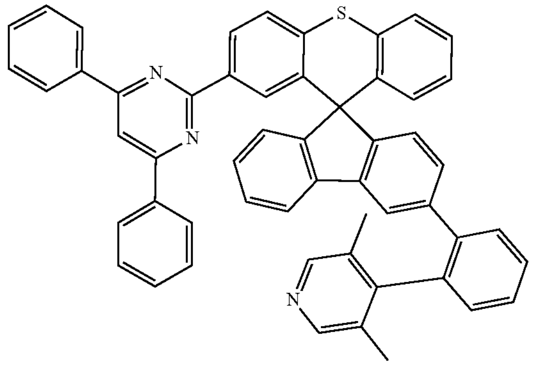
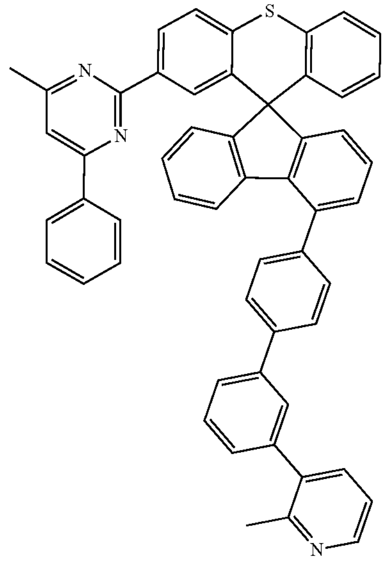
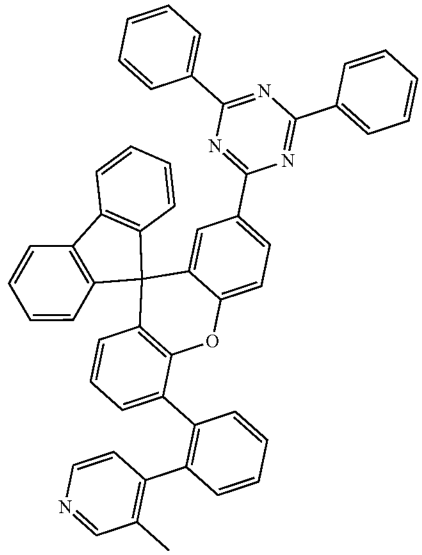
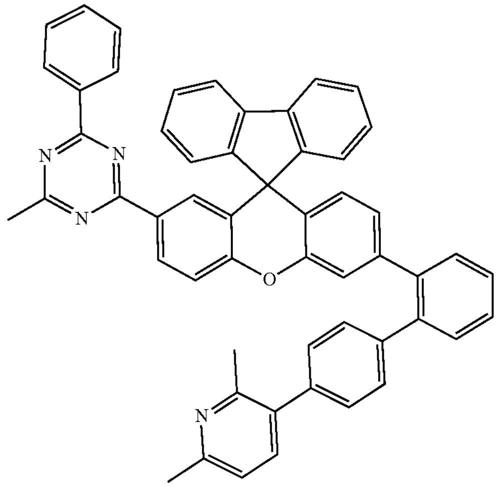

-continued
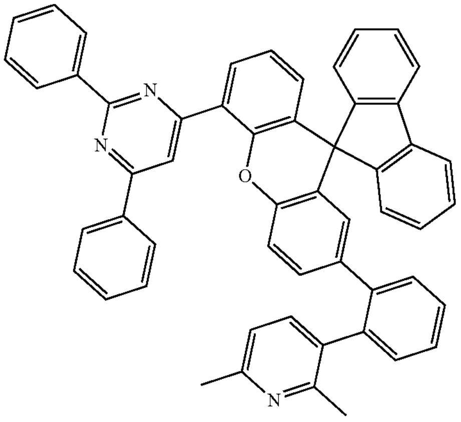
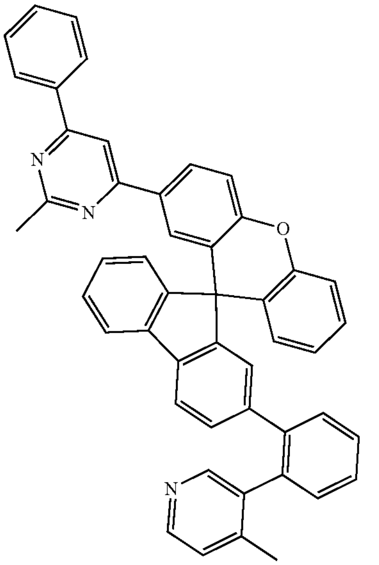
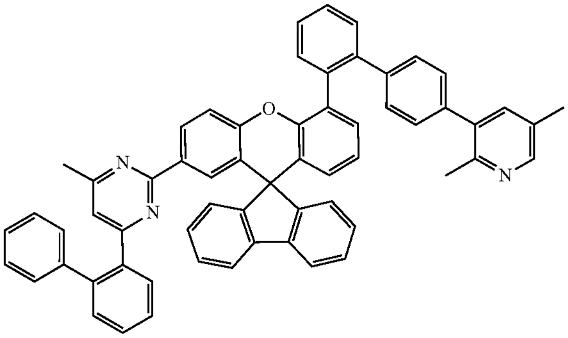
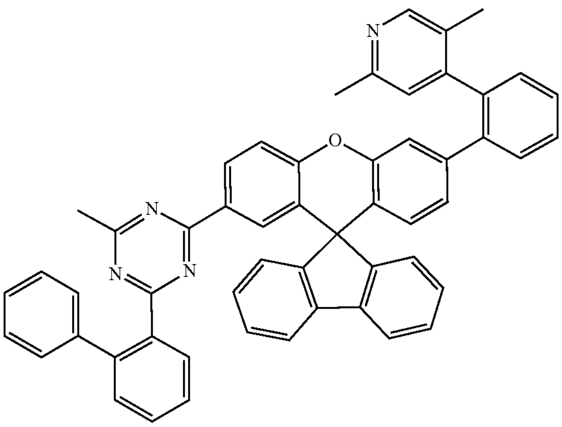
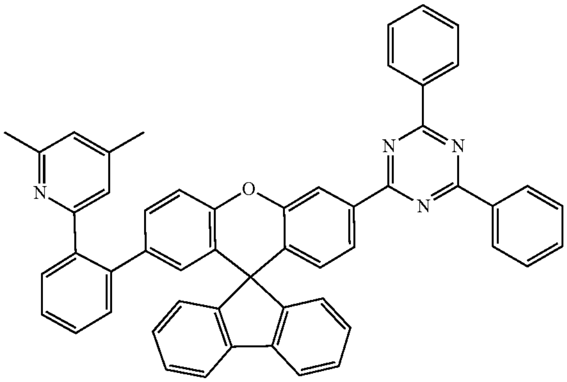
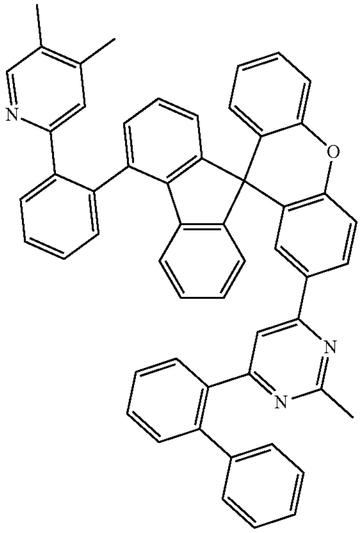

-continued
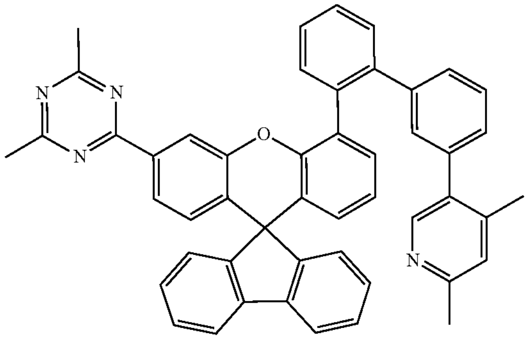
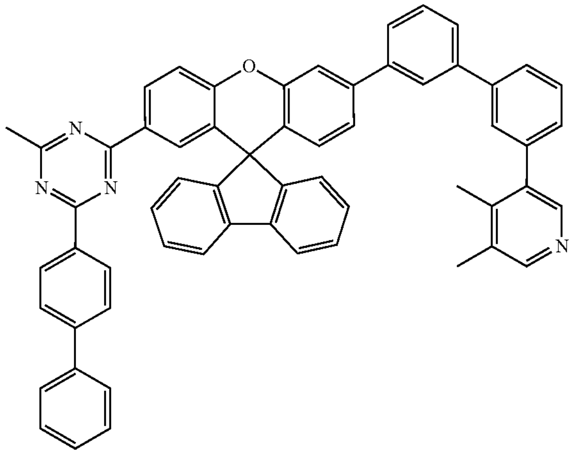
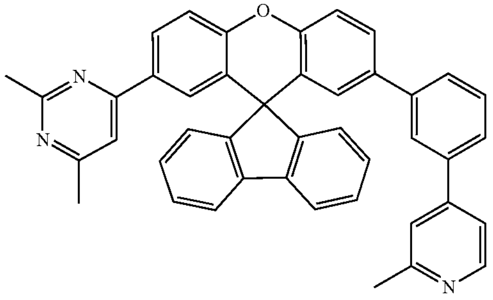
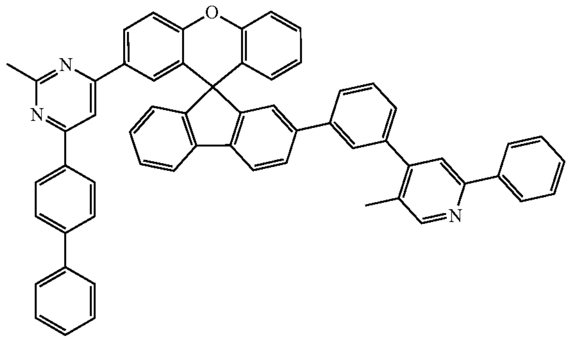
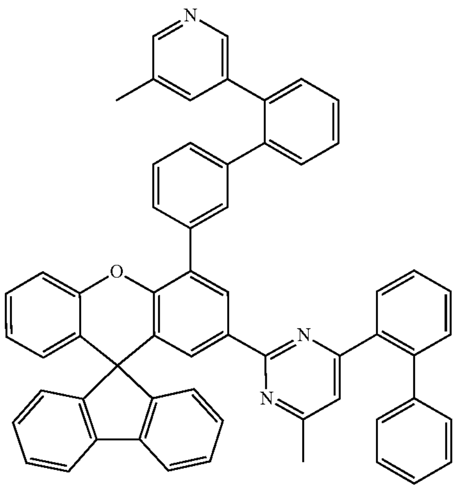
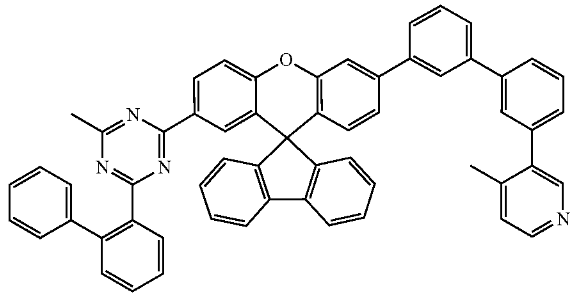
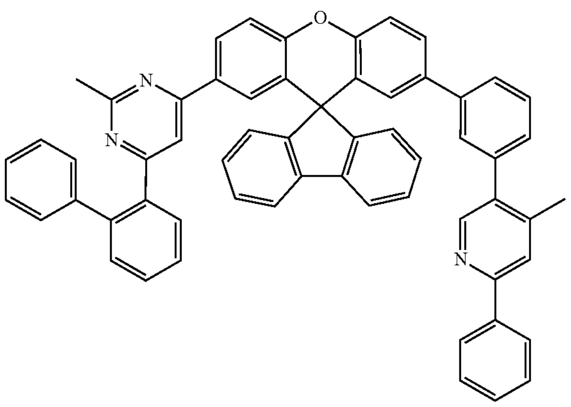
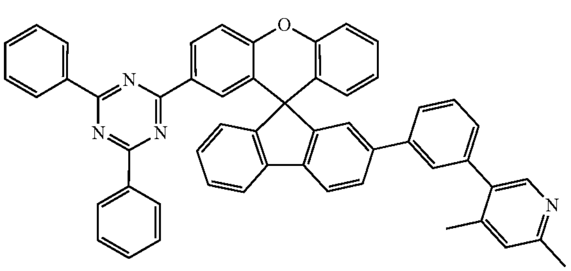

-continued
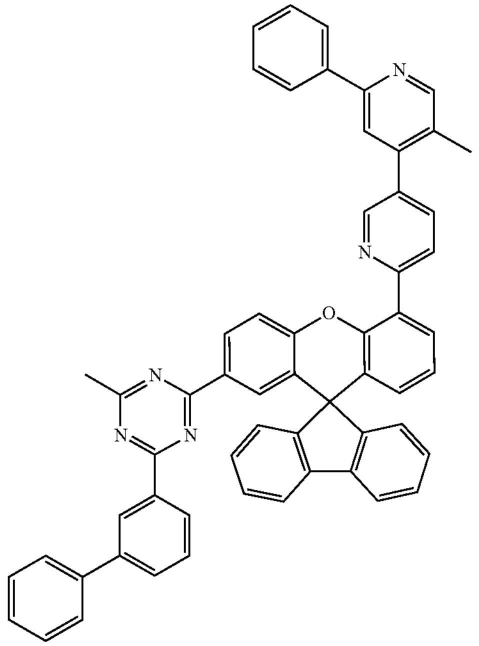
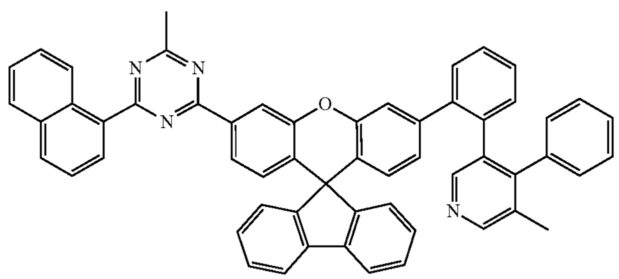
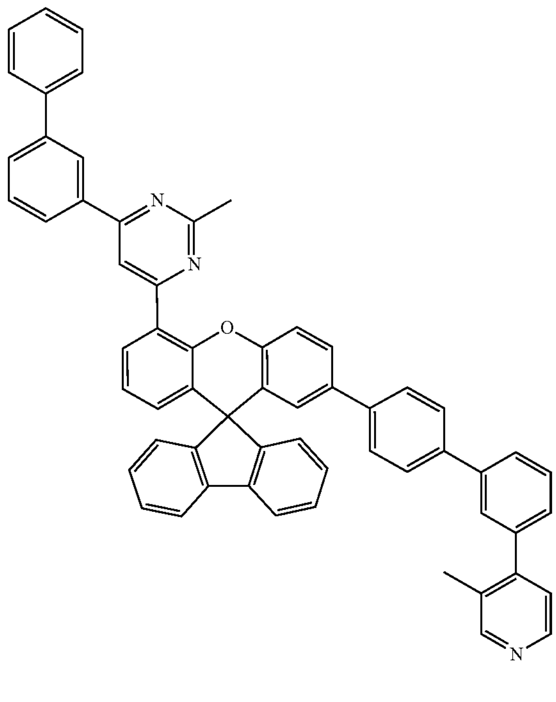
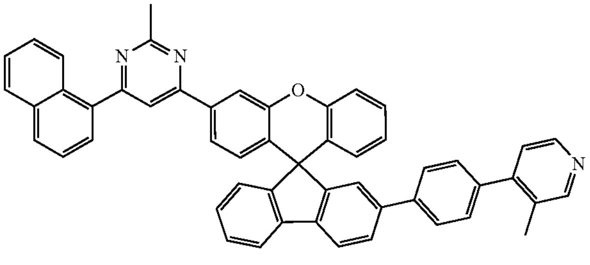

-continued
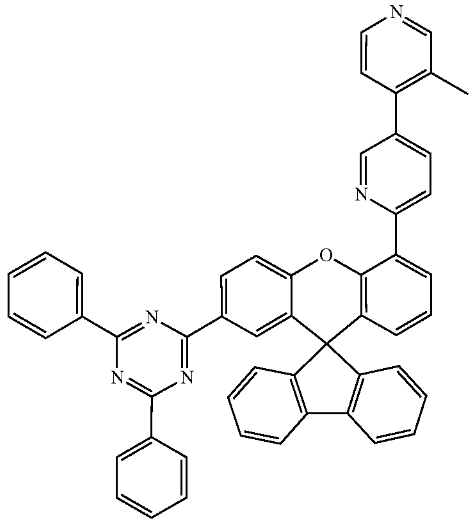
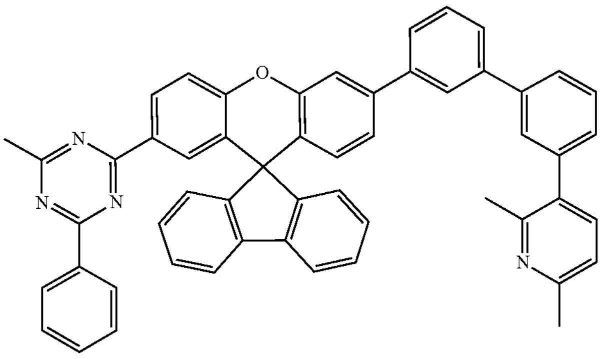
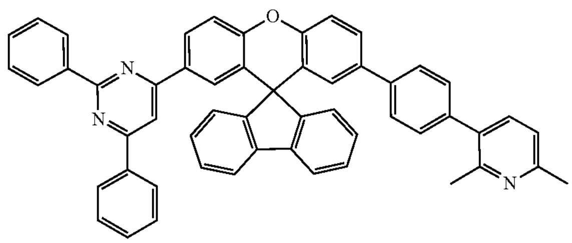
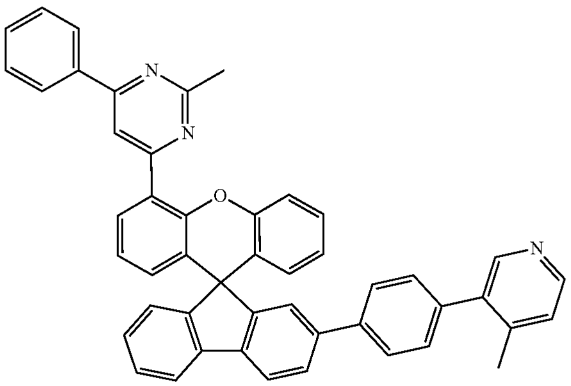
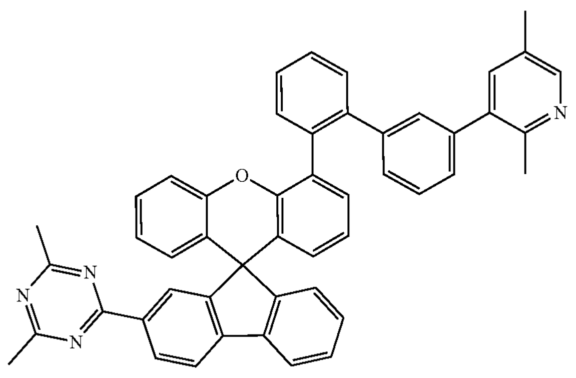
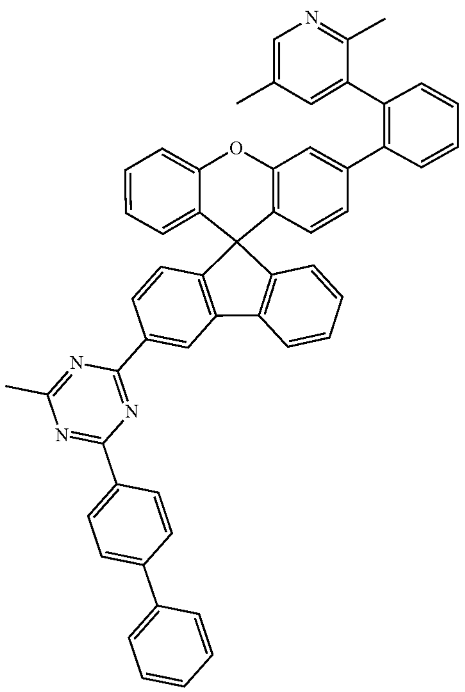

-continued
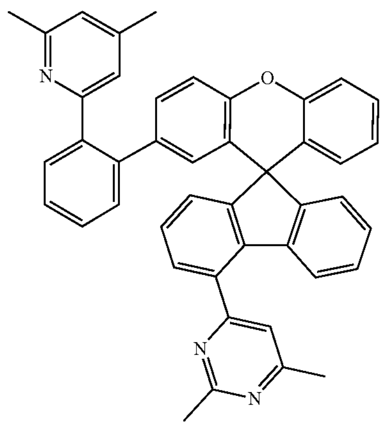
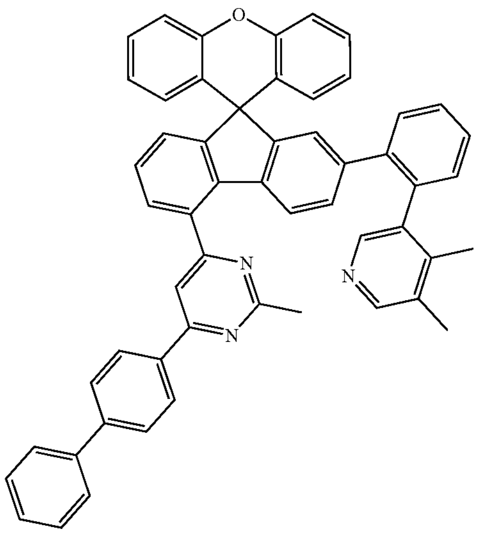
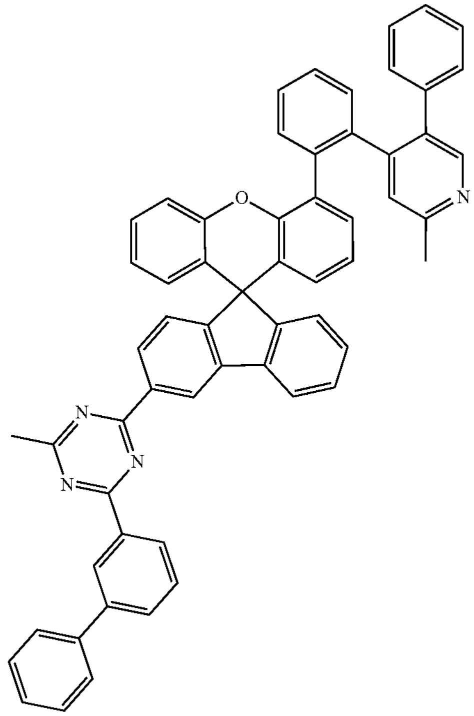
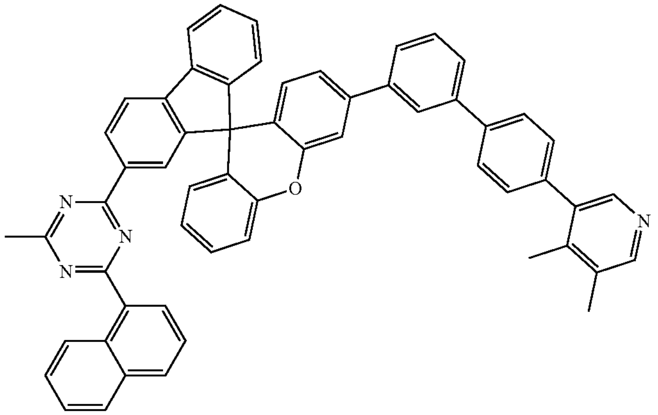
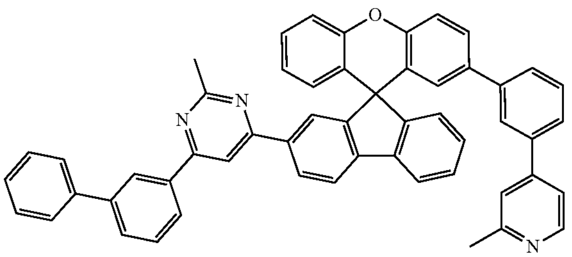
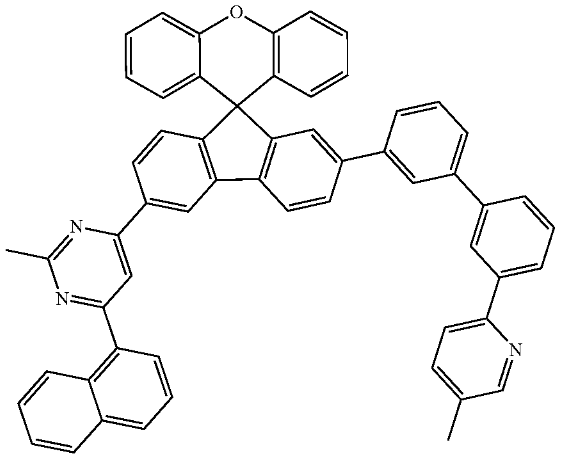

-continued
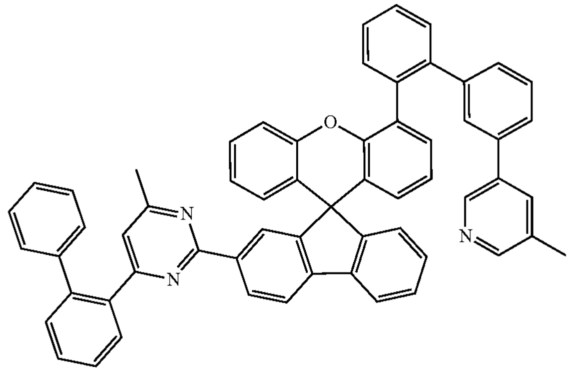
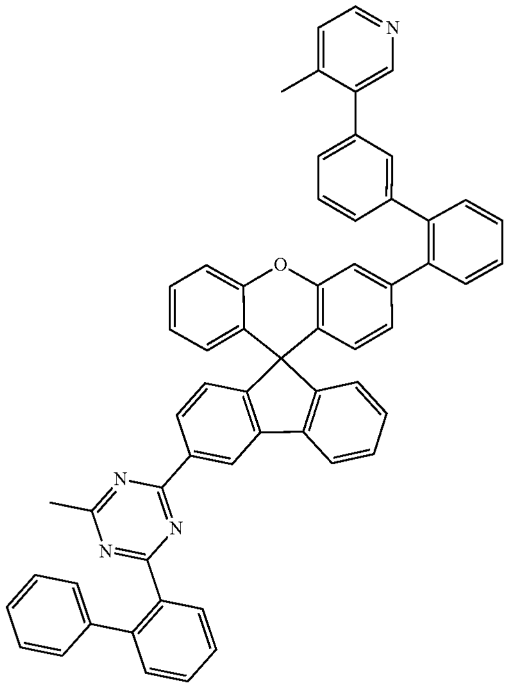
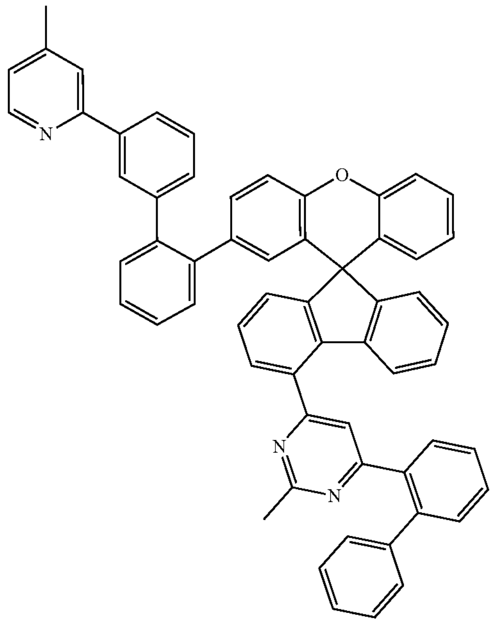
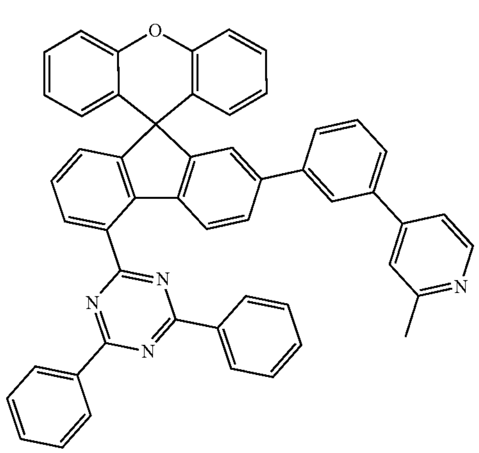

-continued
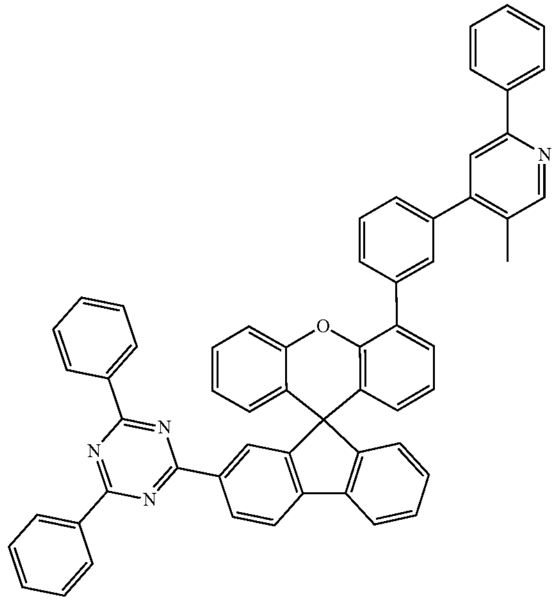
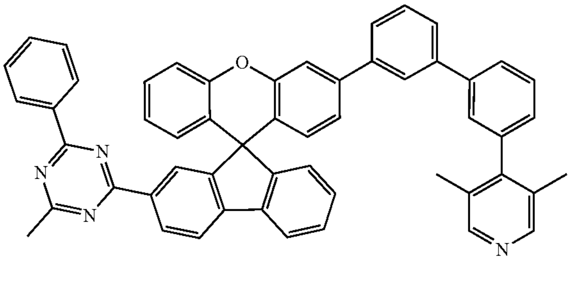
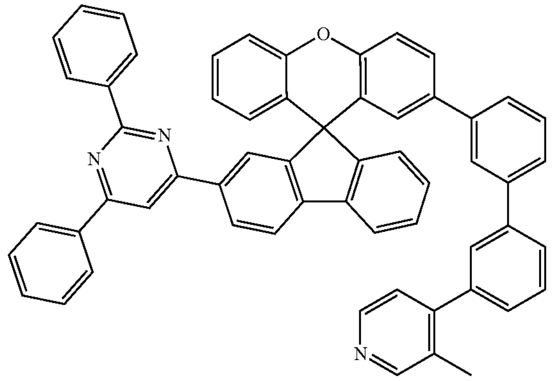
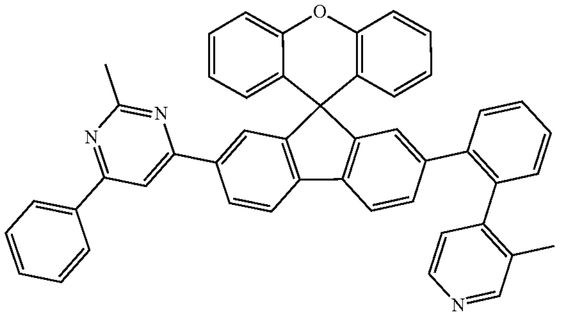
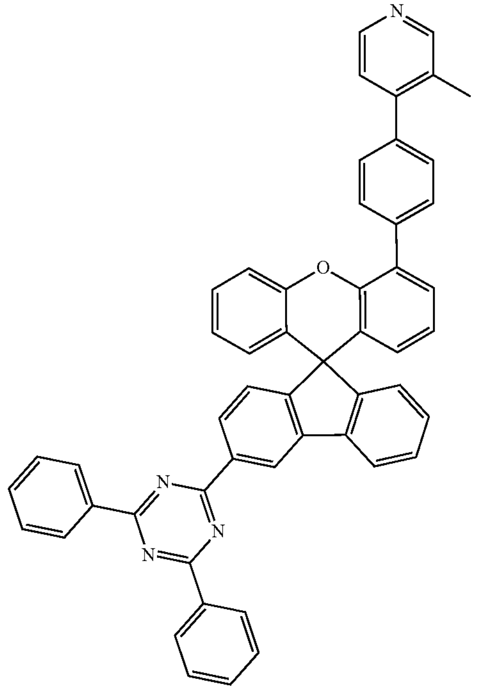
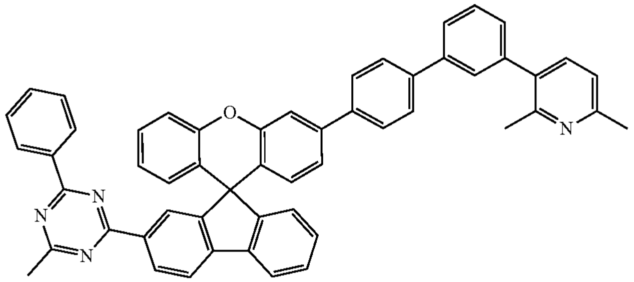

-continued
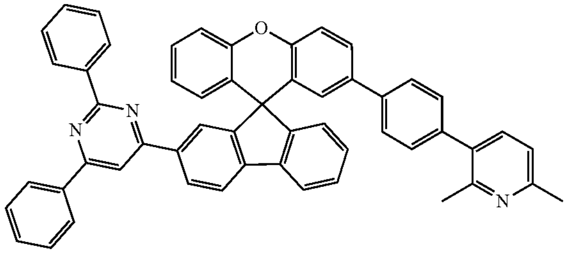
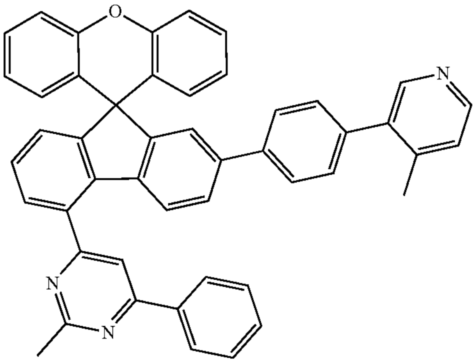
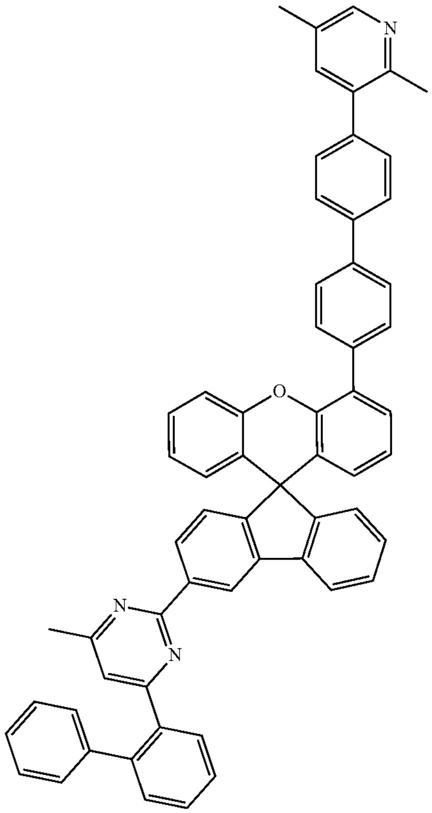
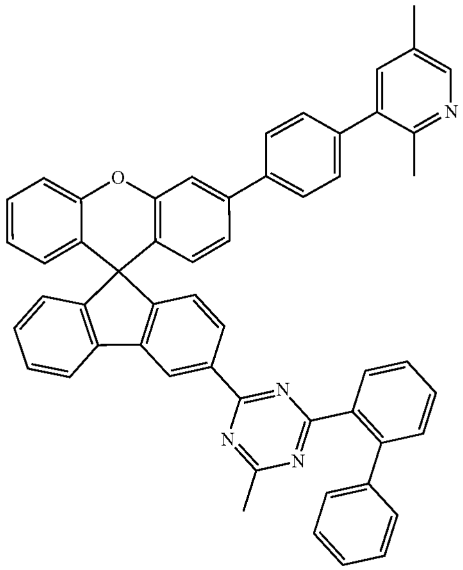
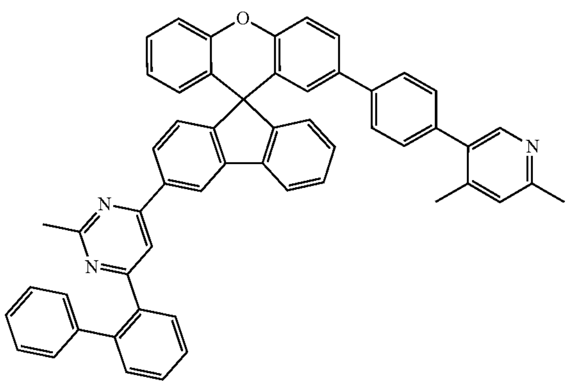
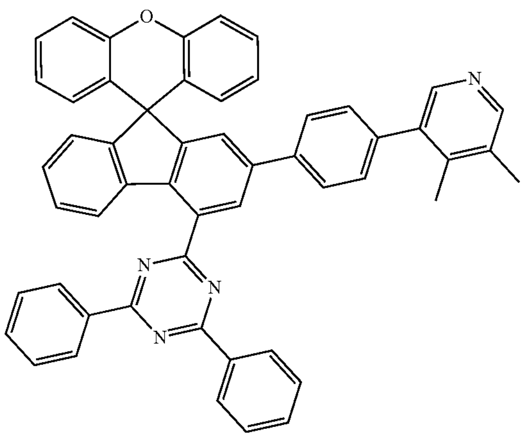

-continued
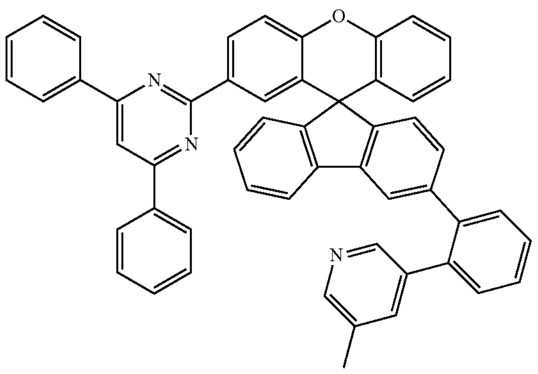
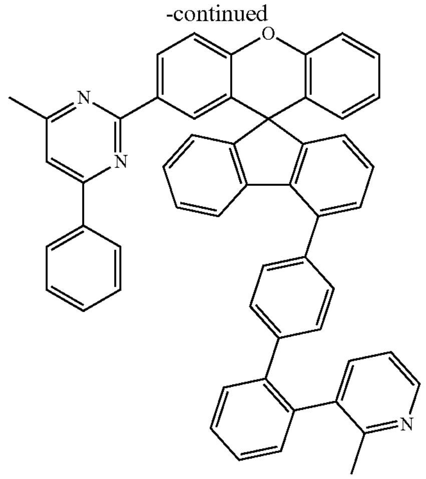
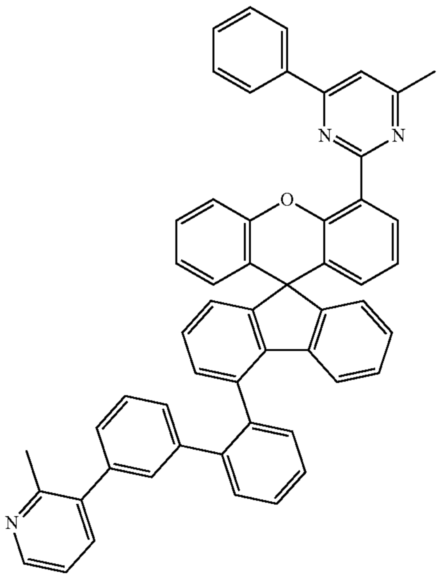
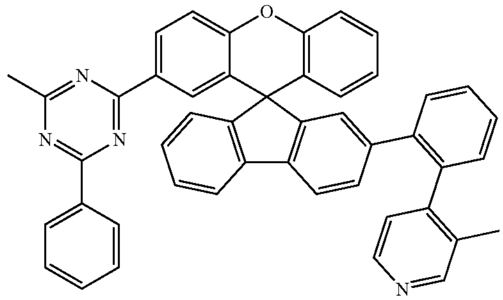
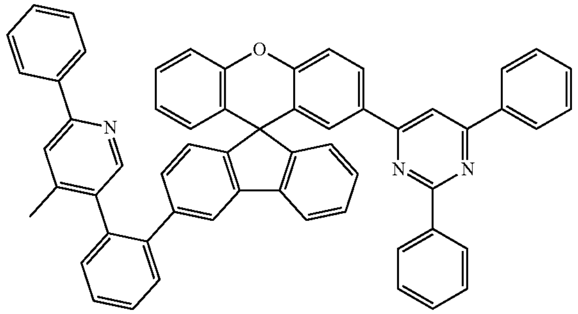
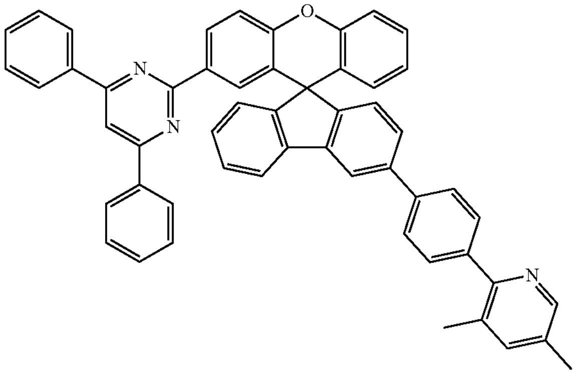
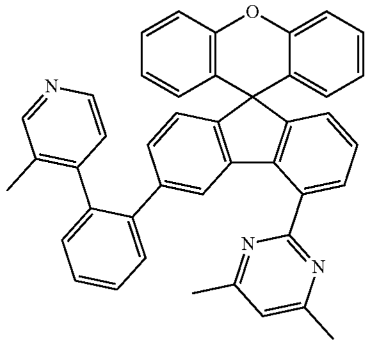

-continued
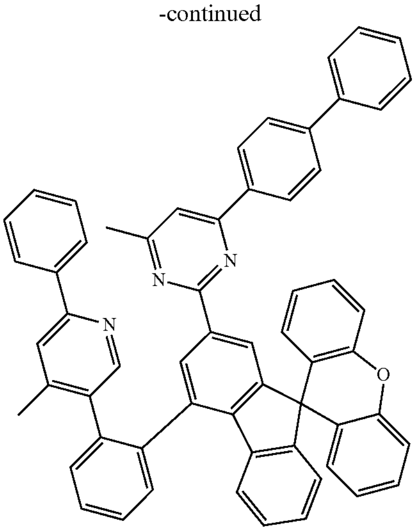
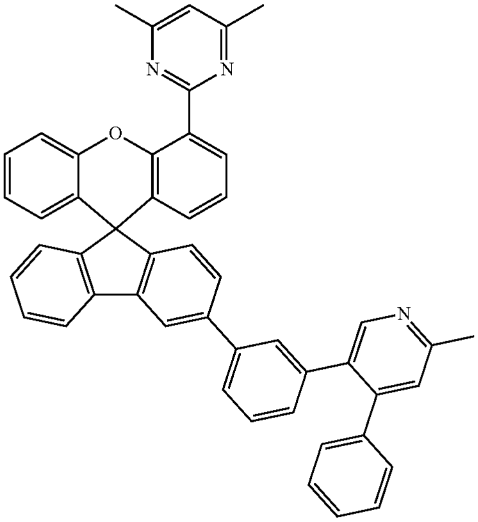
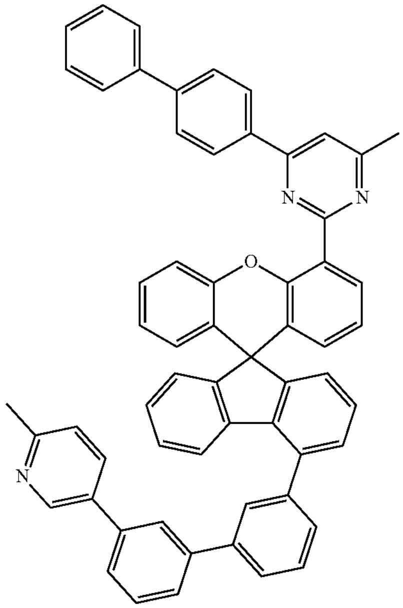
-continued
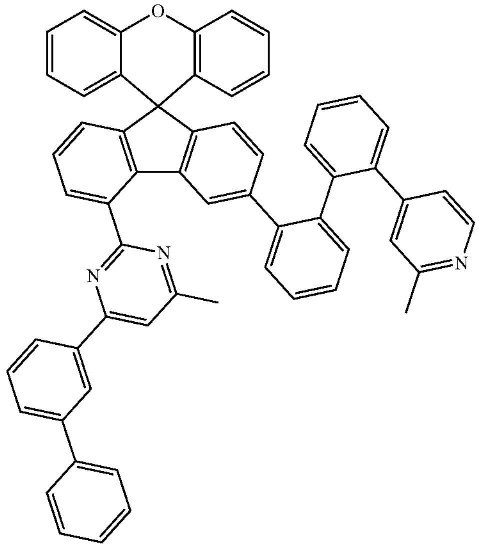
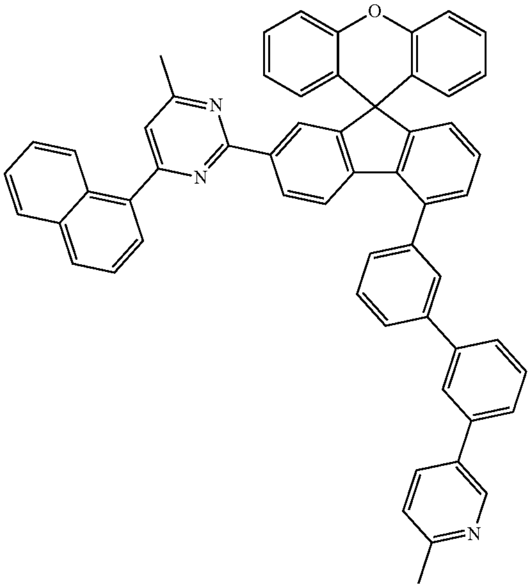
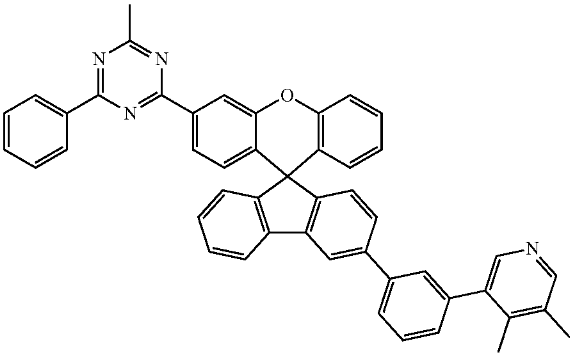

-continued
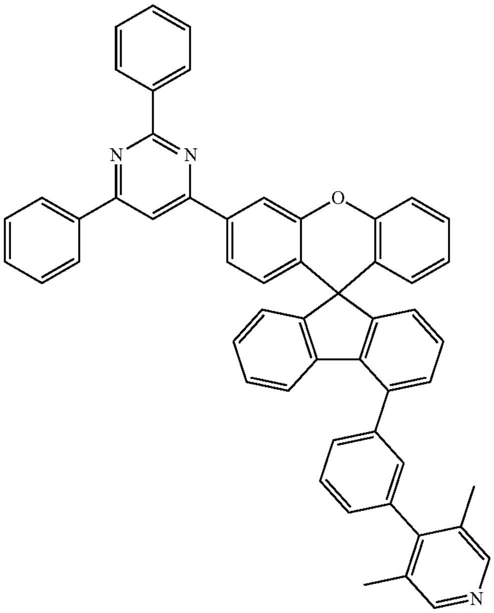
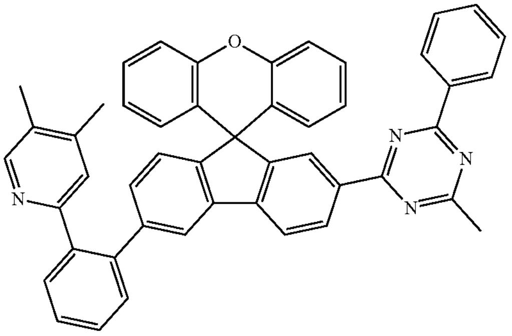
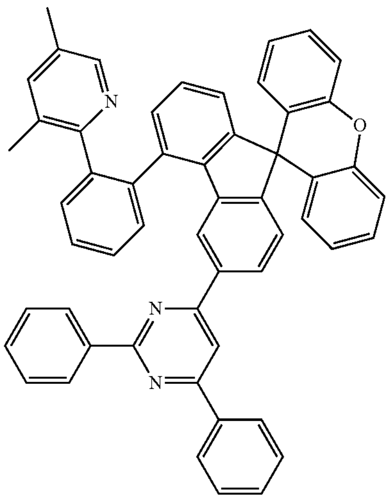
-continued
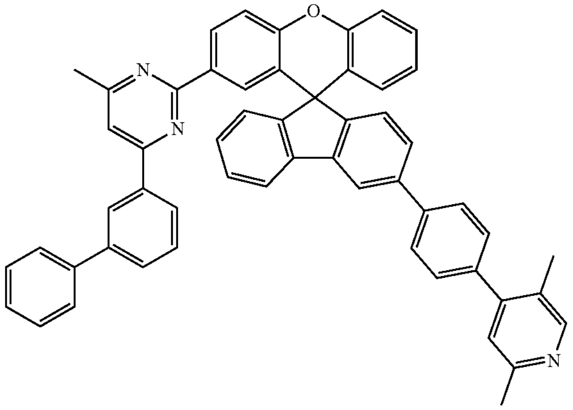
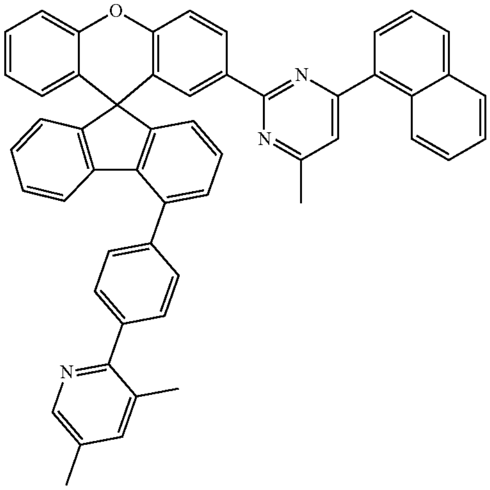
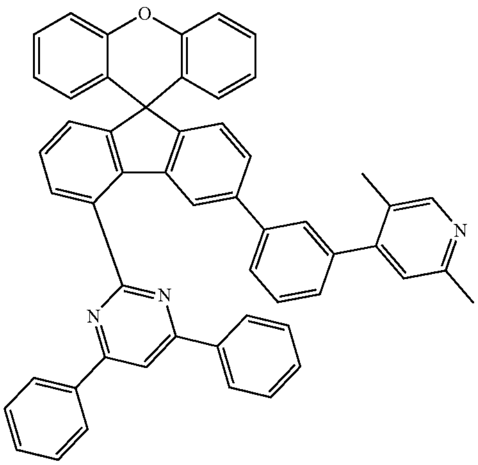

-continued
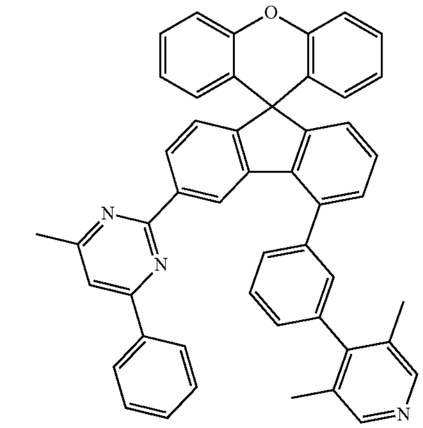
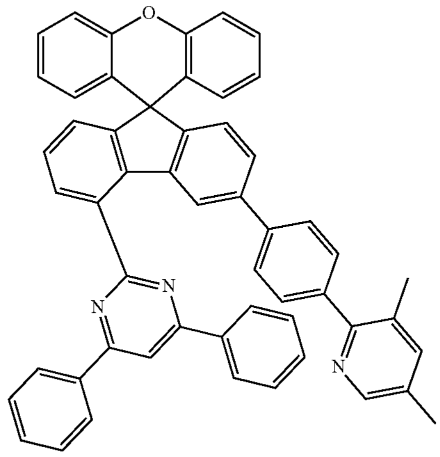
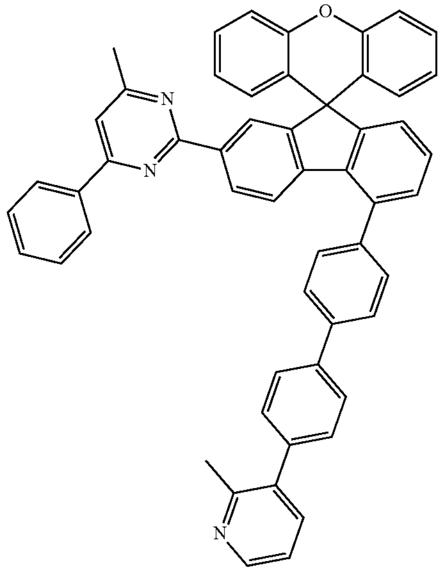
-continued
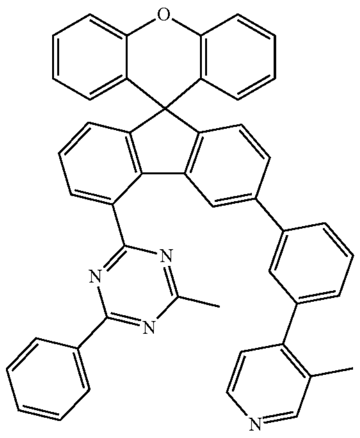
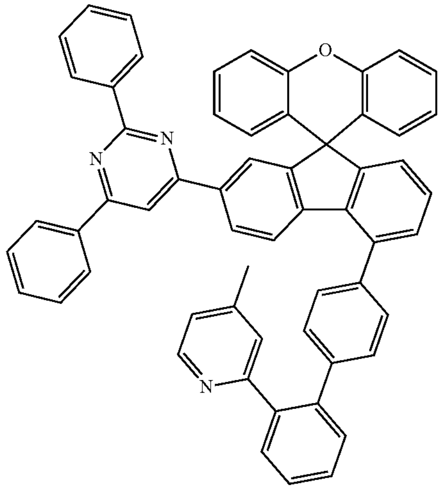
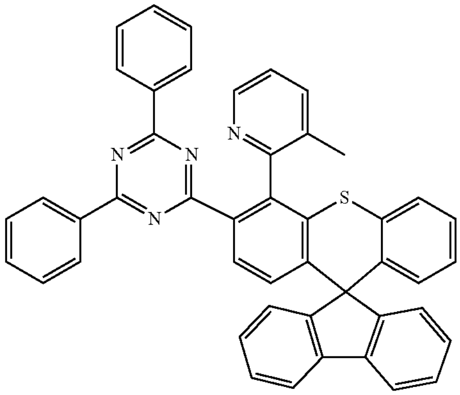

-continued
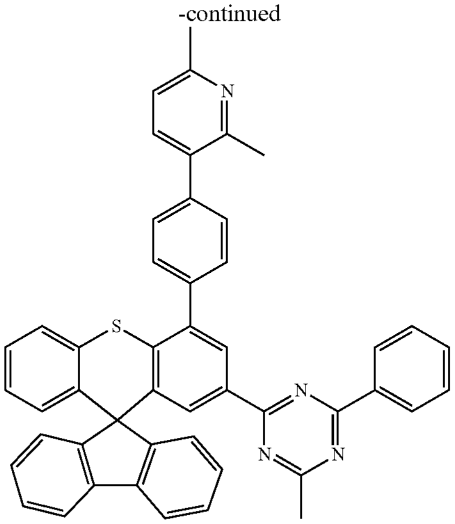
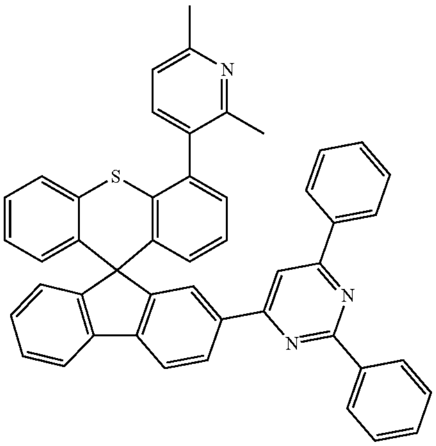
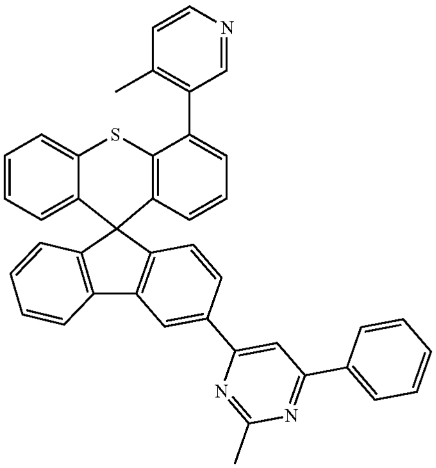
-continued
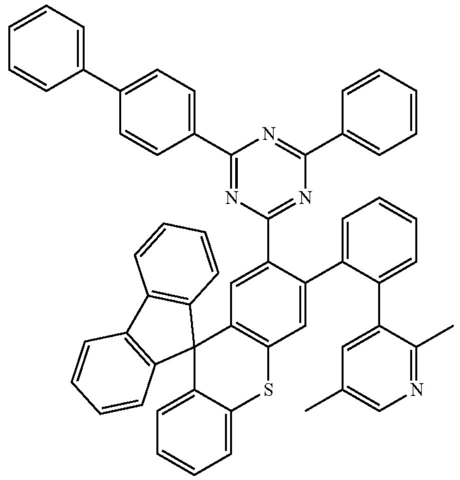
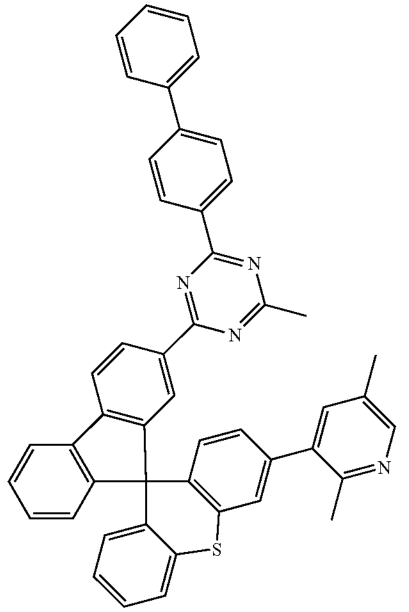
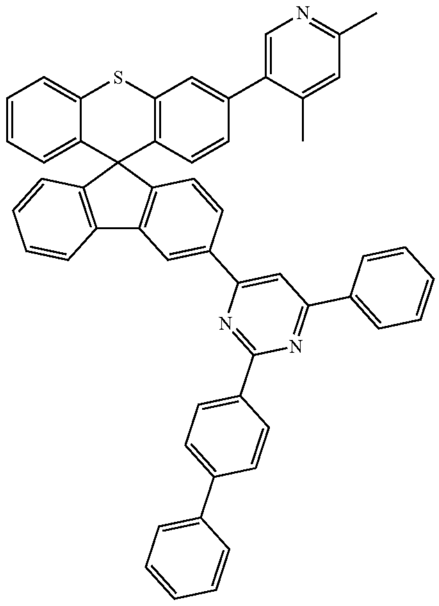

-continued
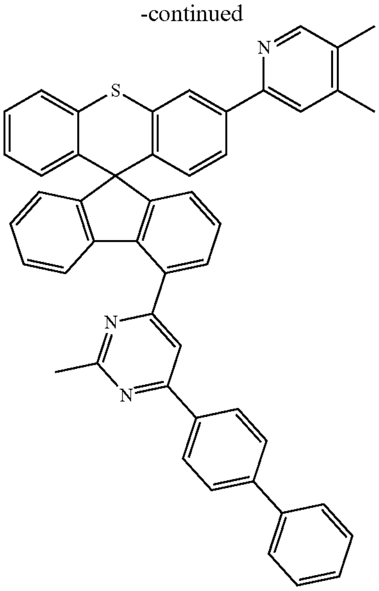
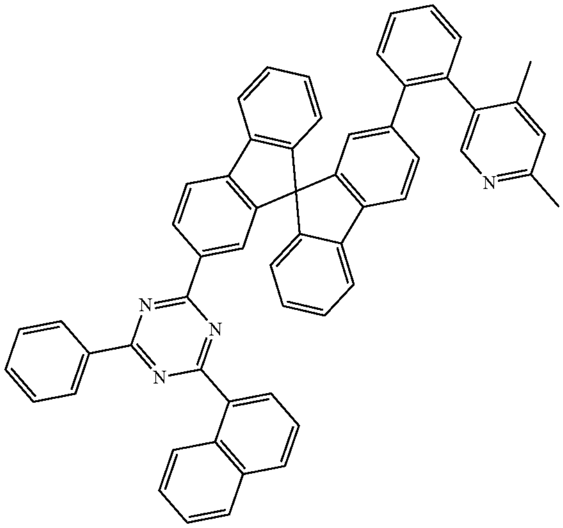
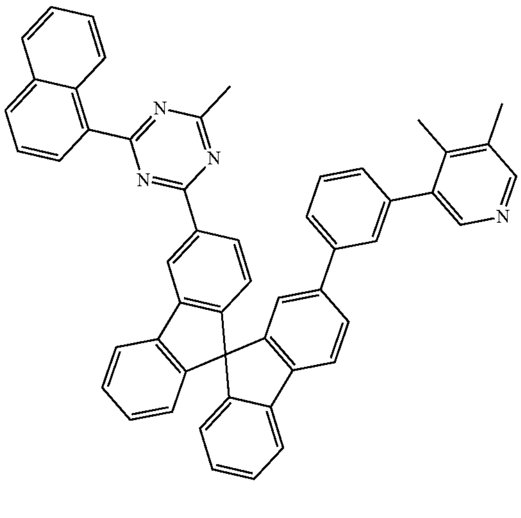
-continued
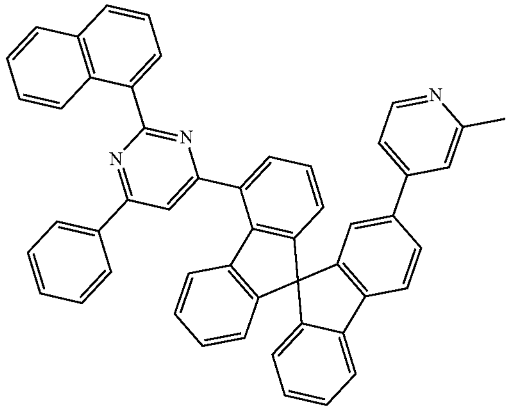
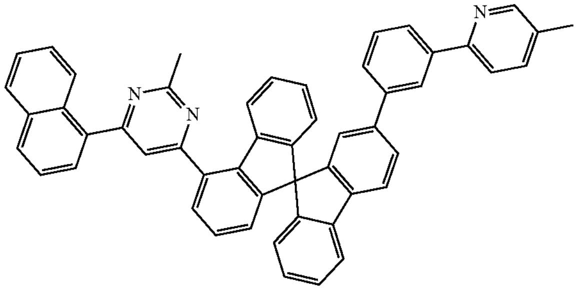
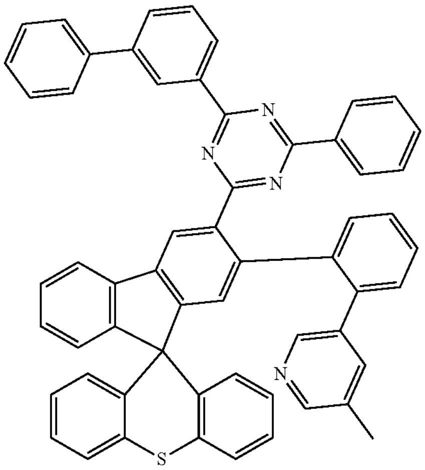
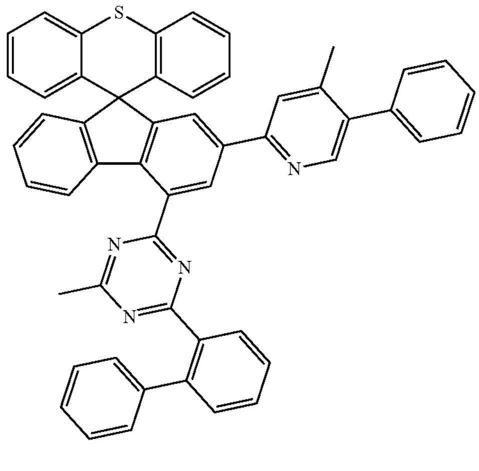

-continued
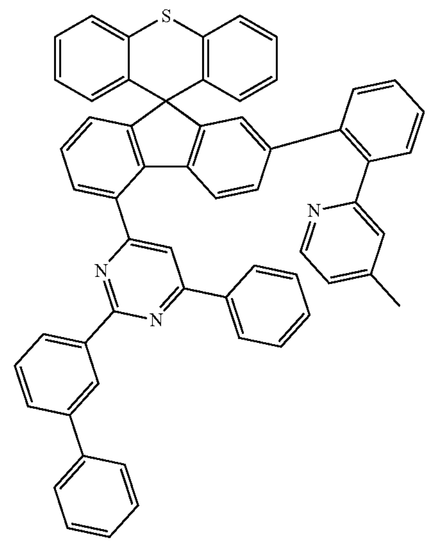
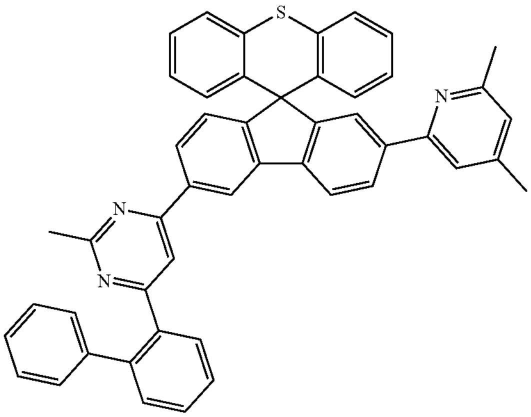
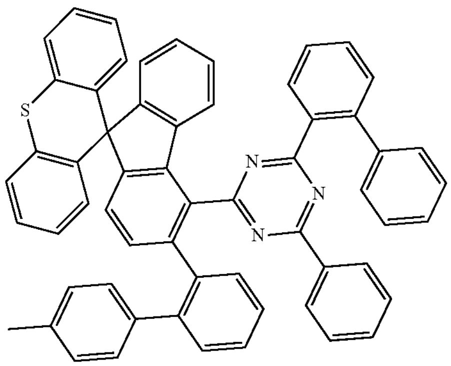
-continued
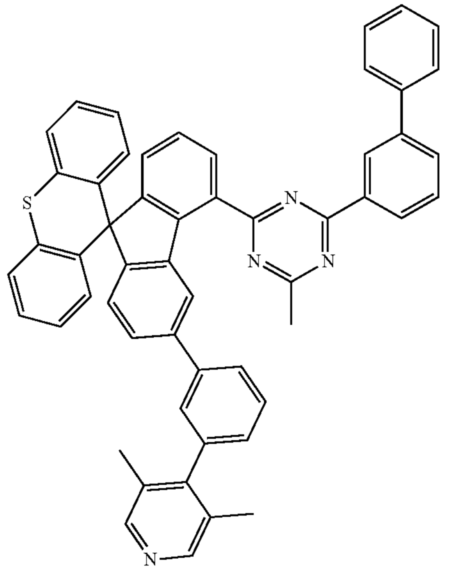
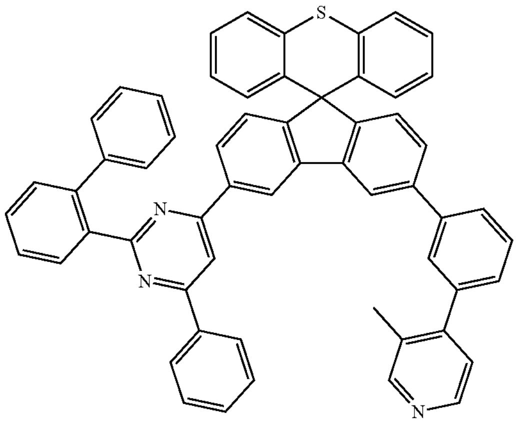
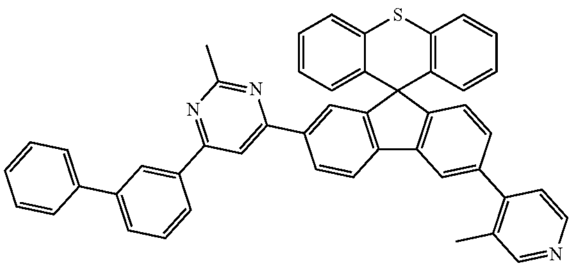

-continued
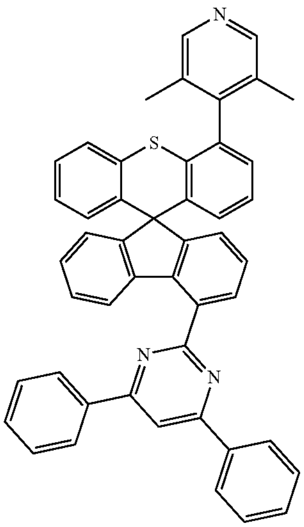
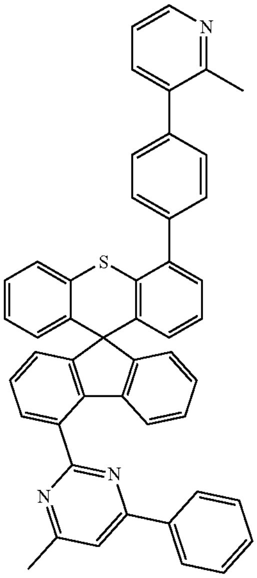
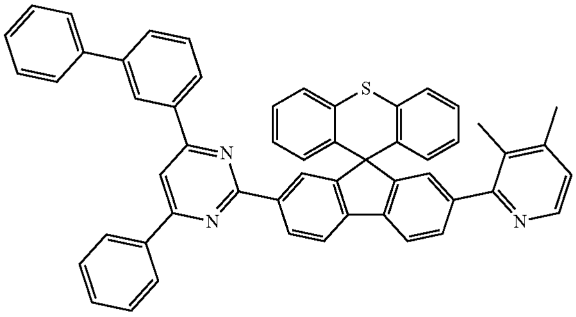
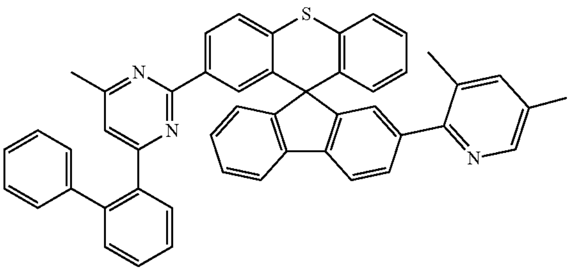
-continued
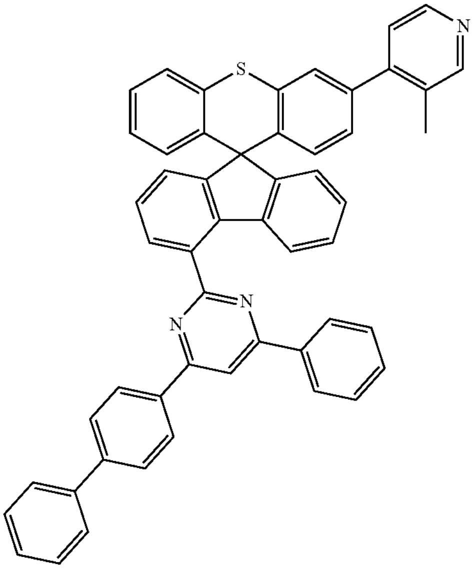
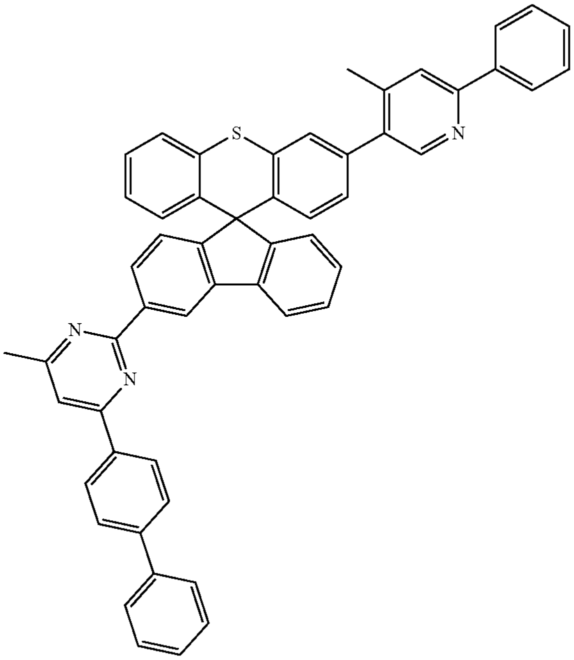
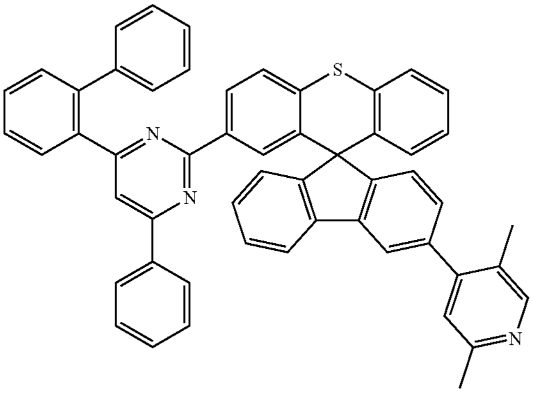

-continued
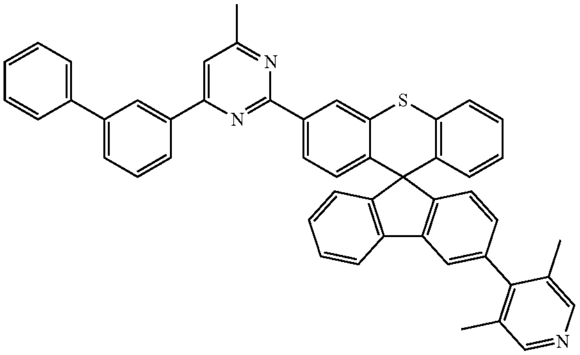
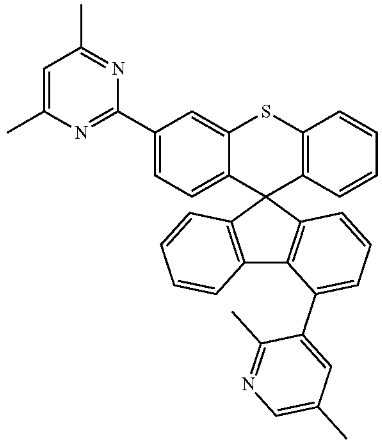
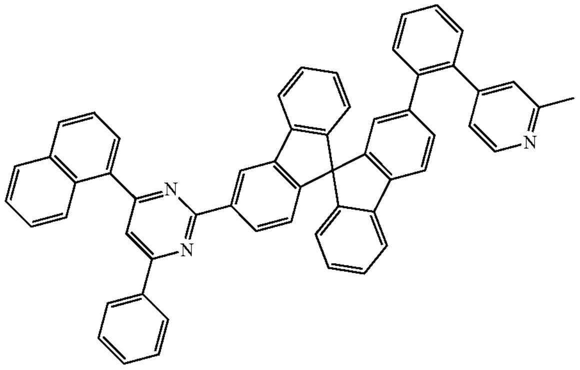
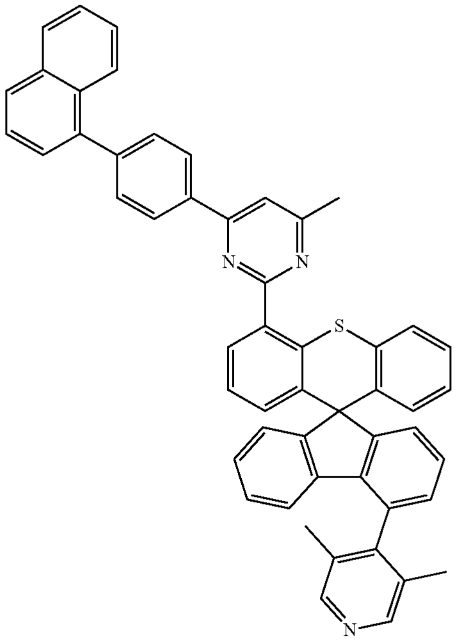
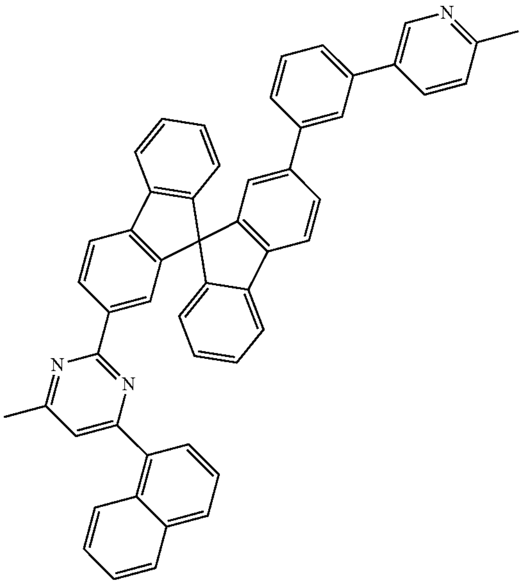
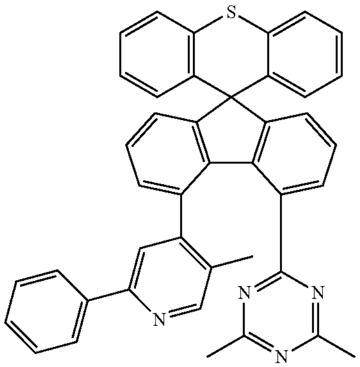
-continued -continued
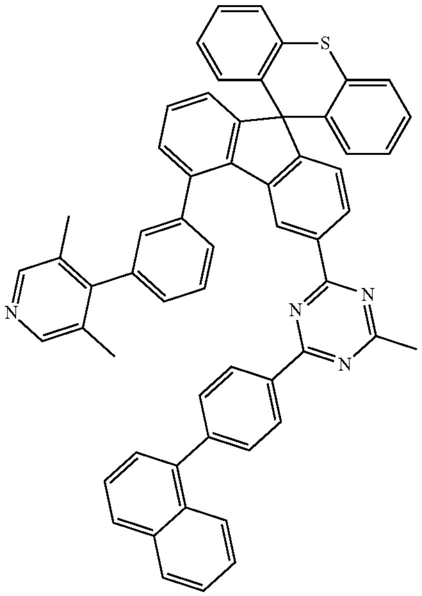
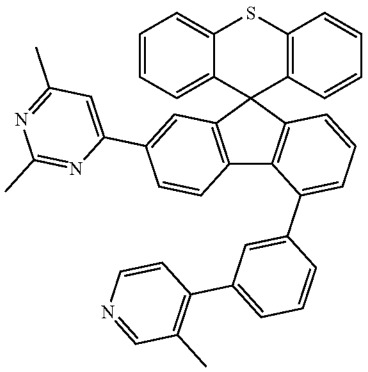
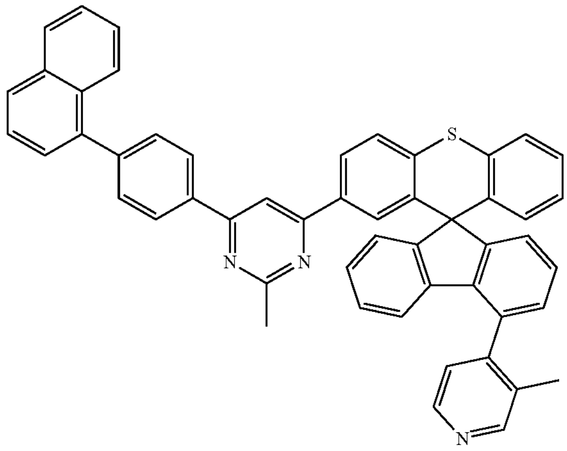
-continued
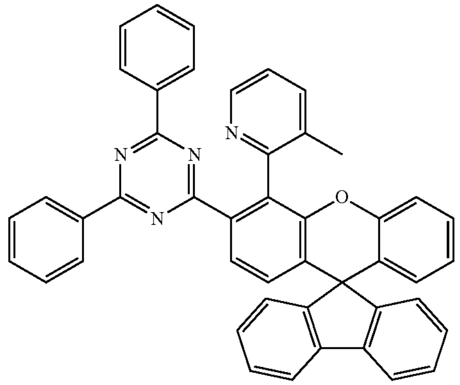
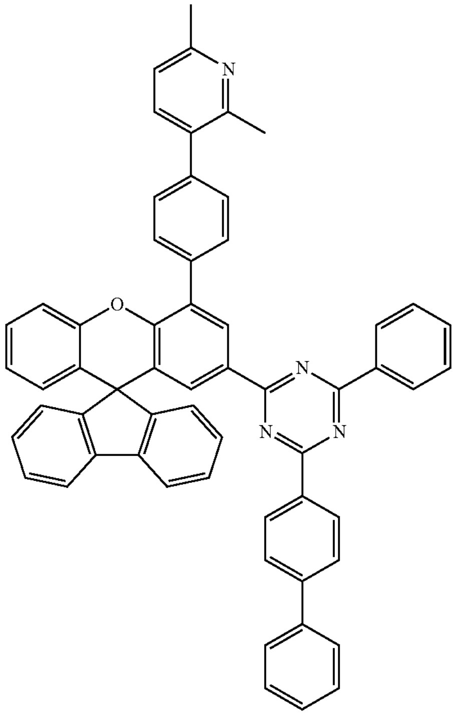
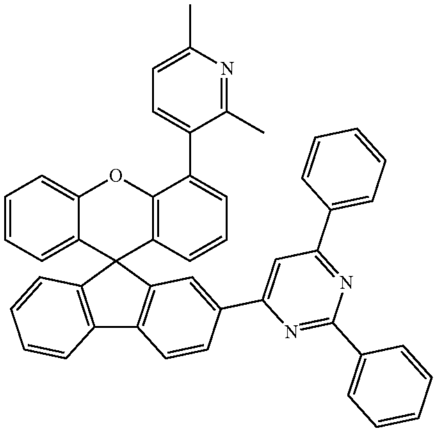

-continued
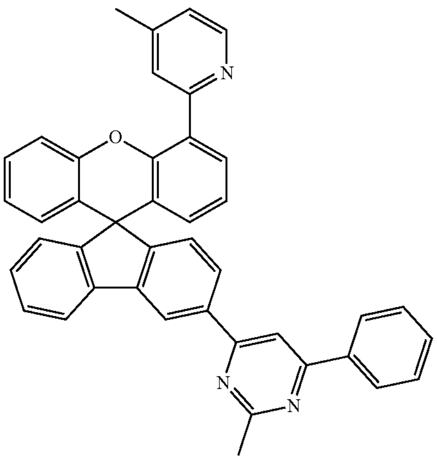
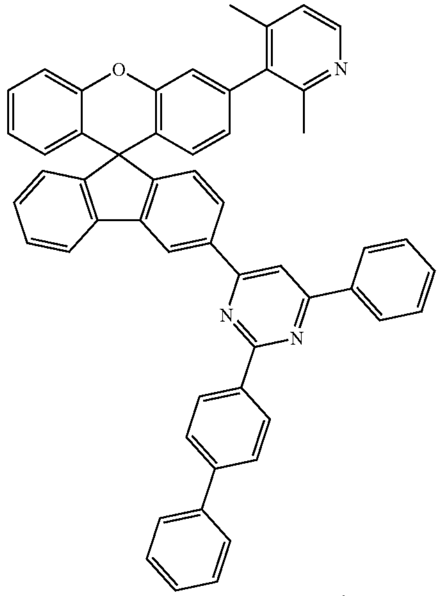
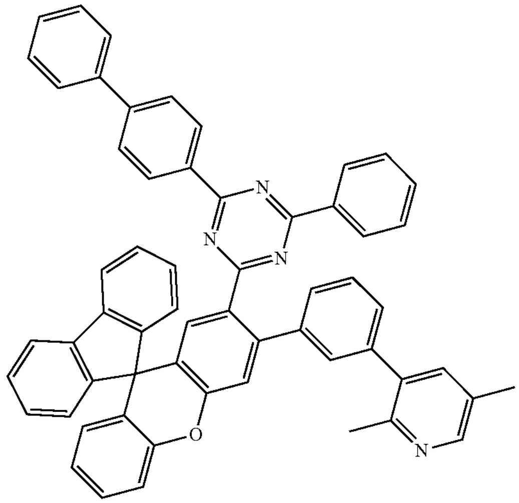
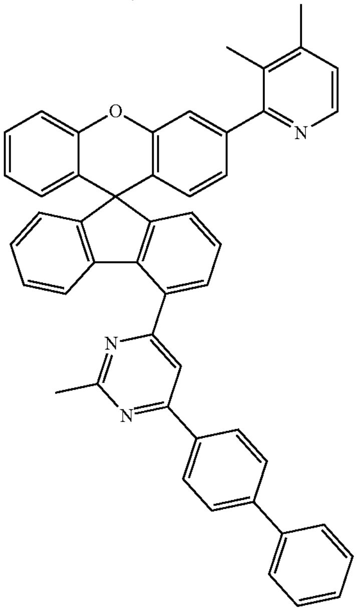
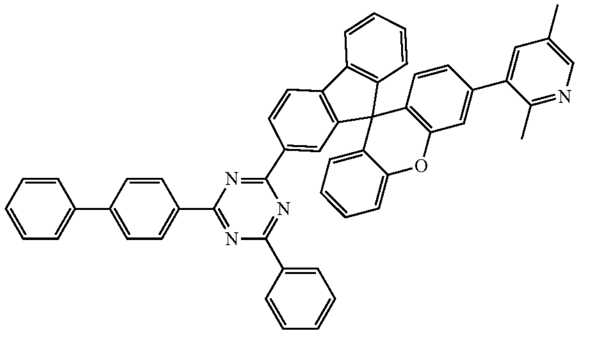
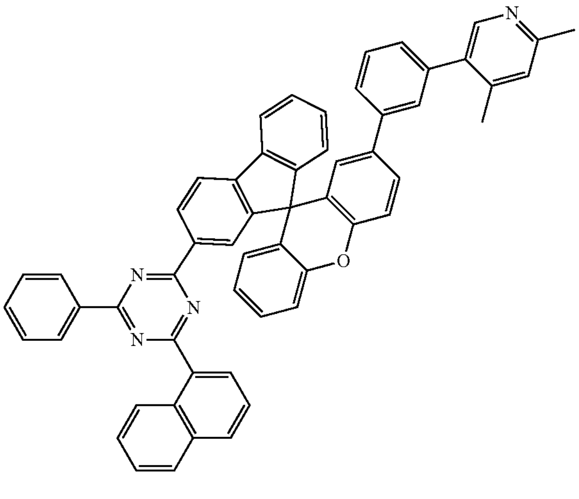

-continued
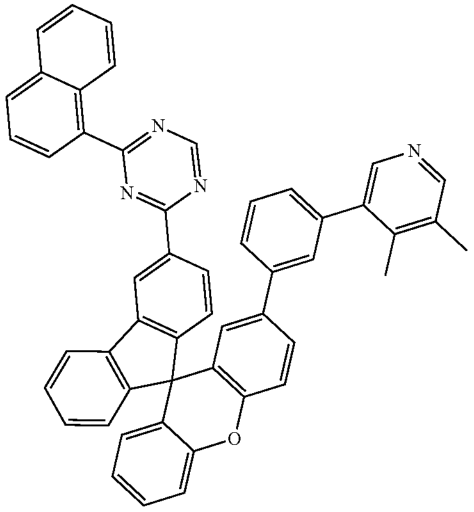
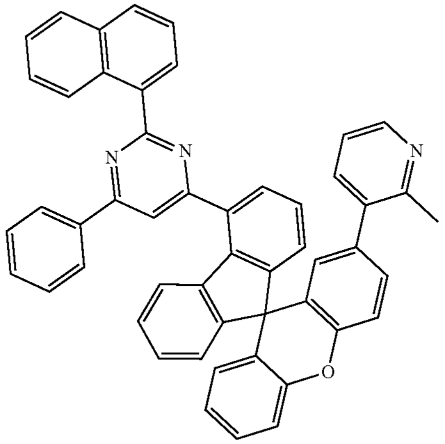
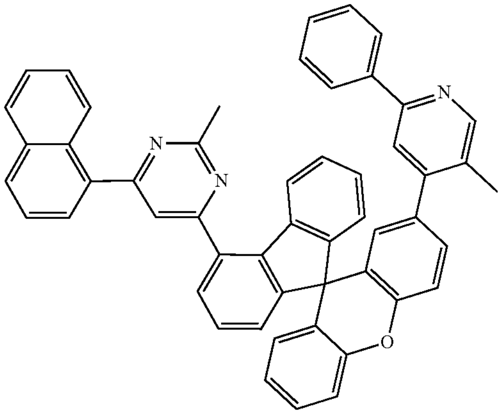
-continued
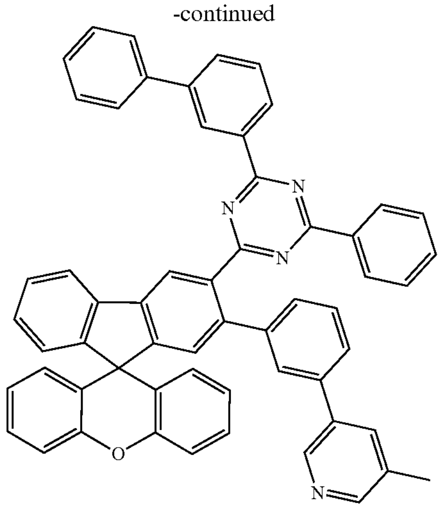
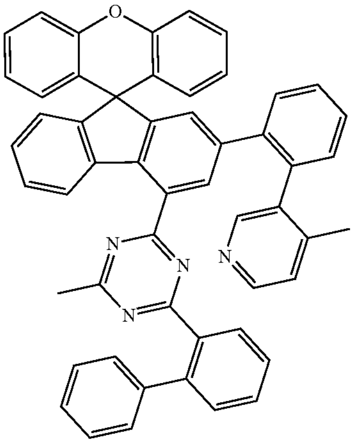
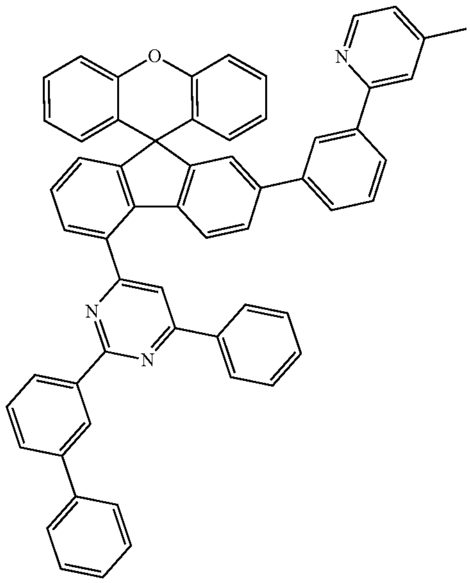

-continued
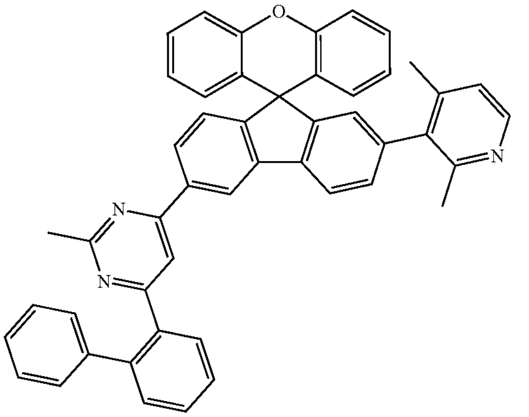
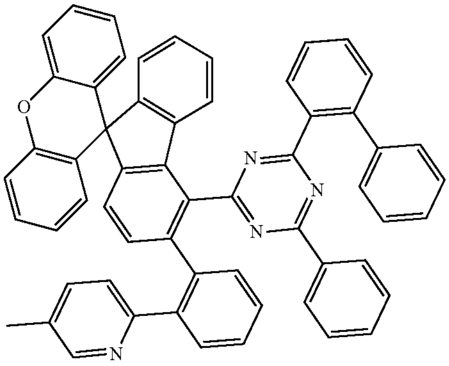
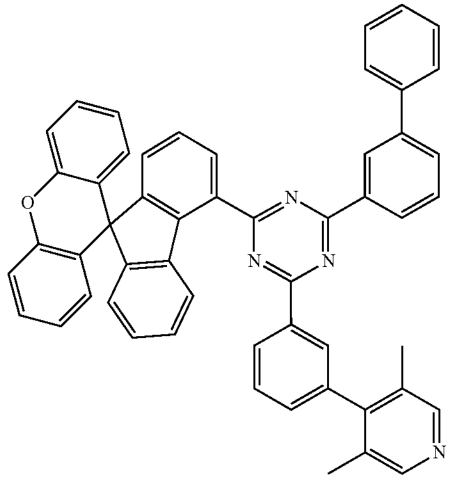
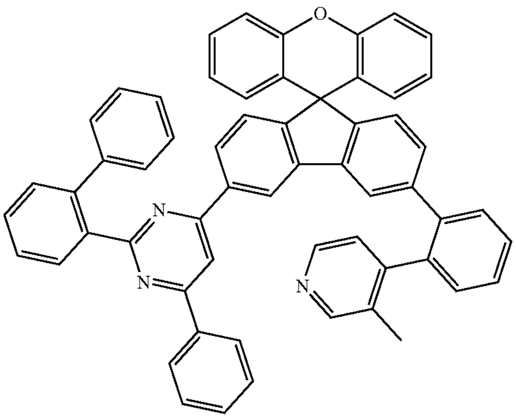
-continued
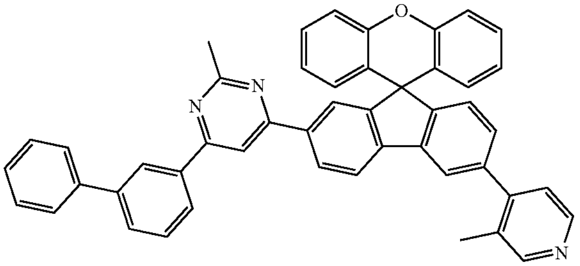
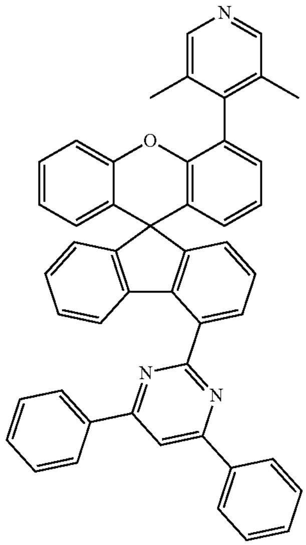
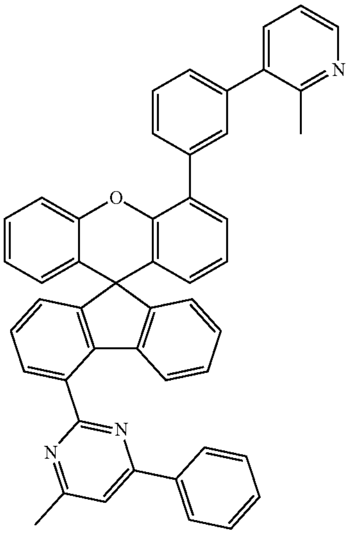
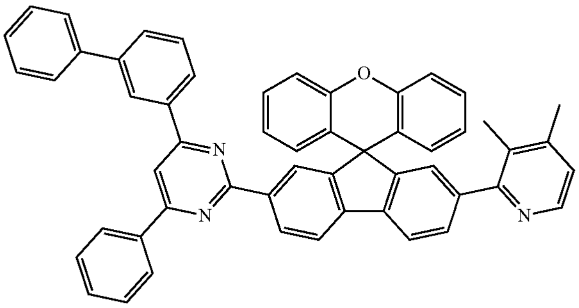

-continued
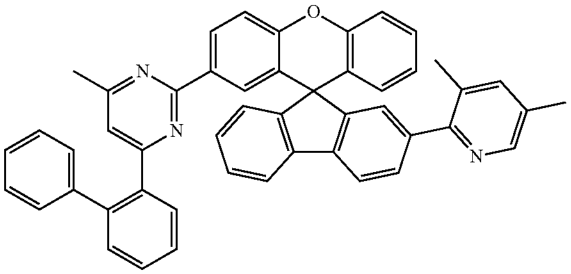
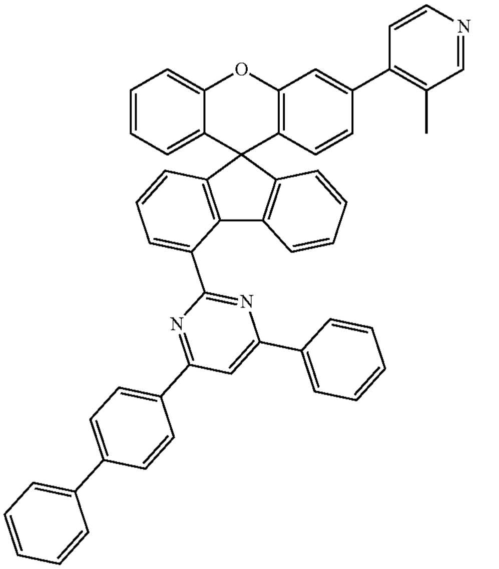
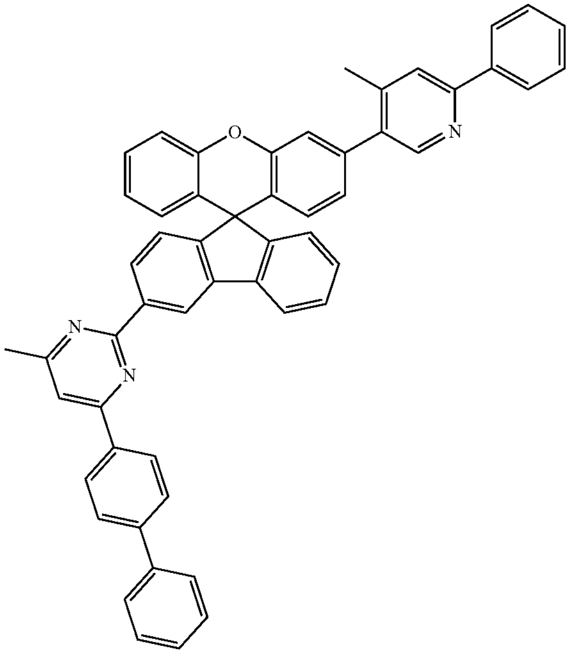
-continued
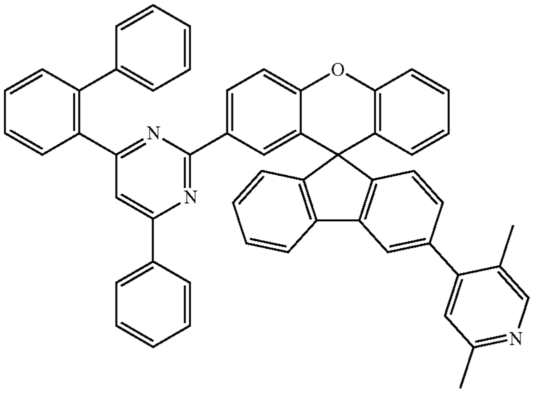
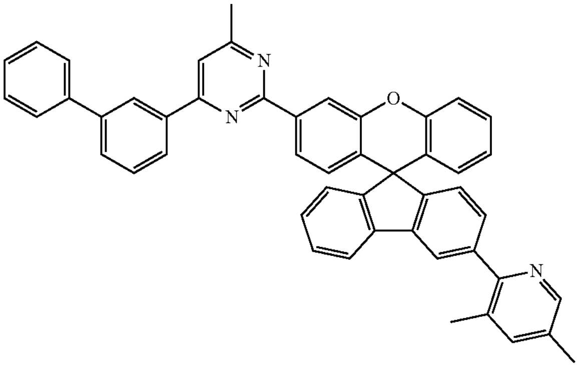
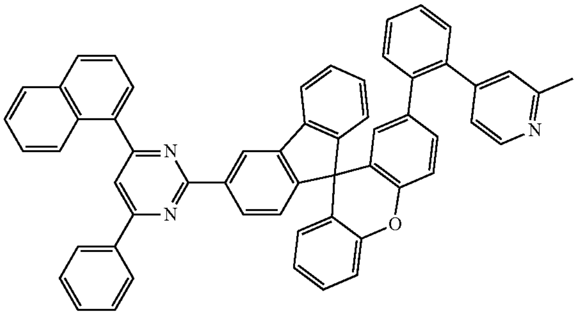
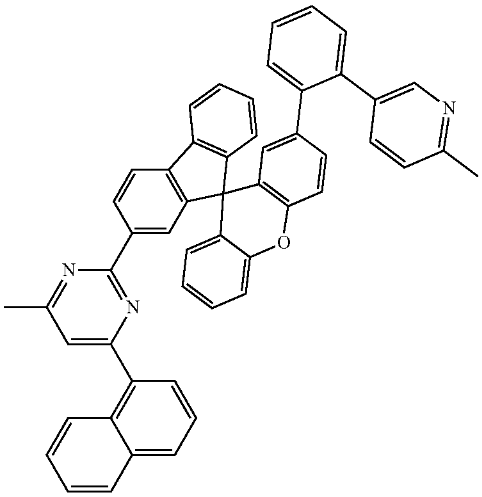

-continued
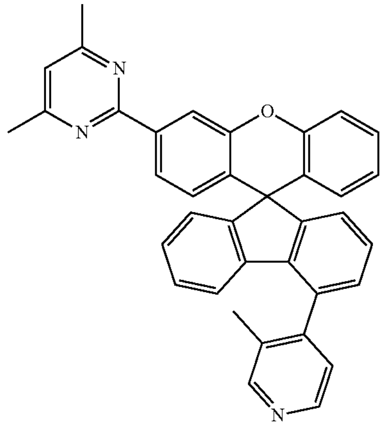
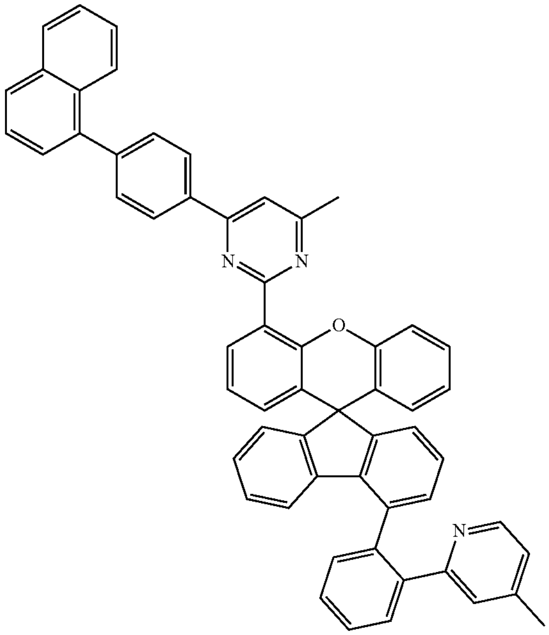
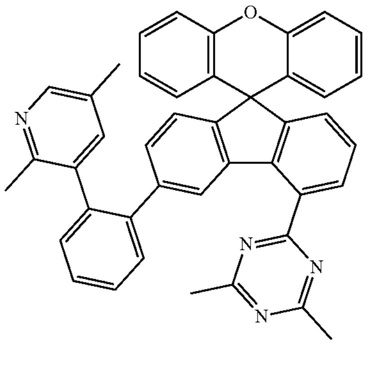
-continued
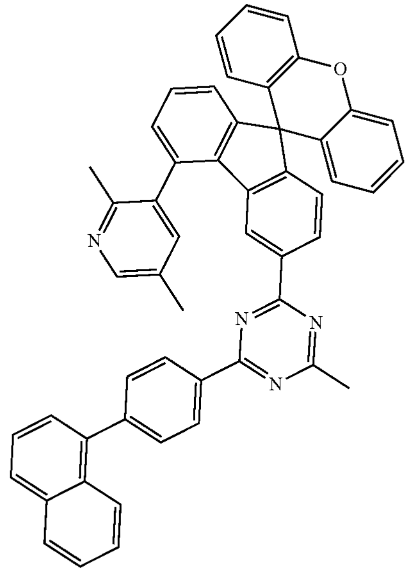
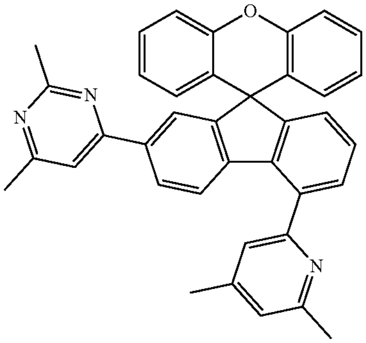
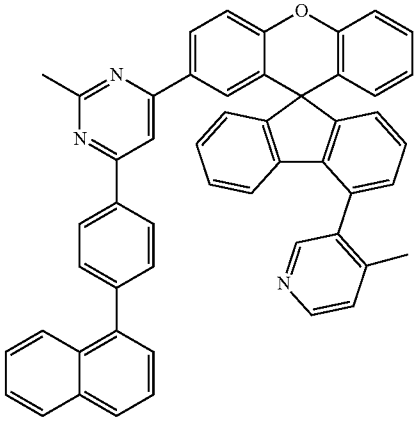

-continued
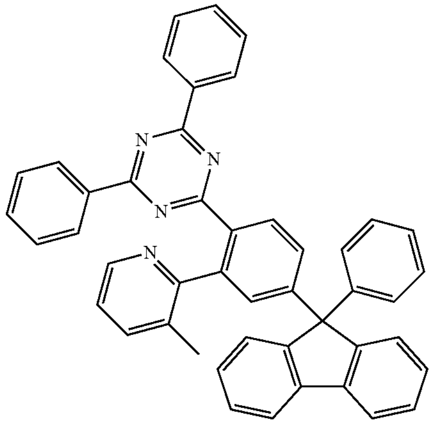
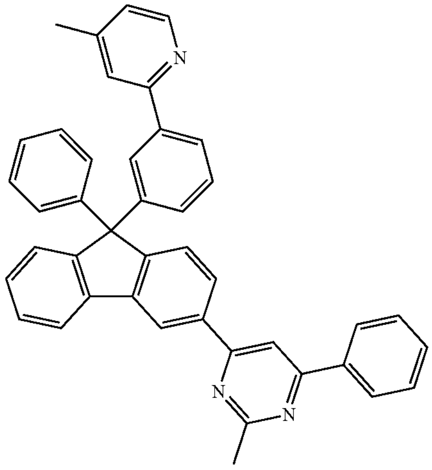
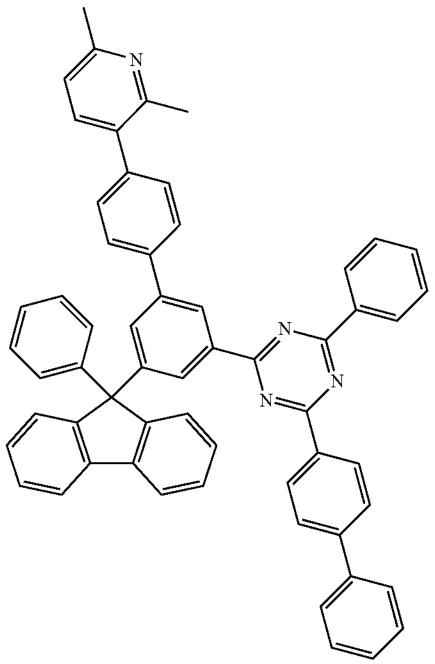
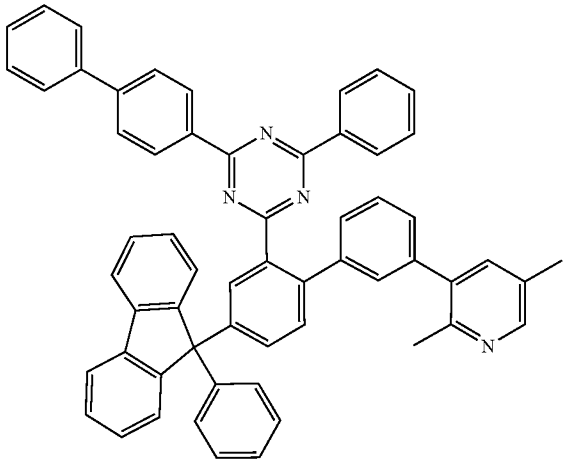
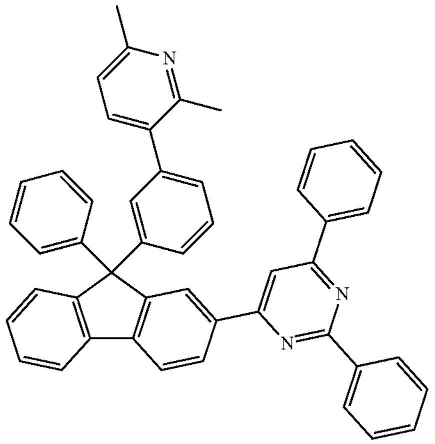
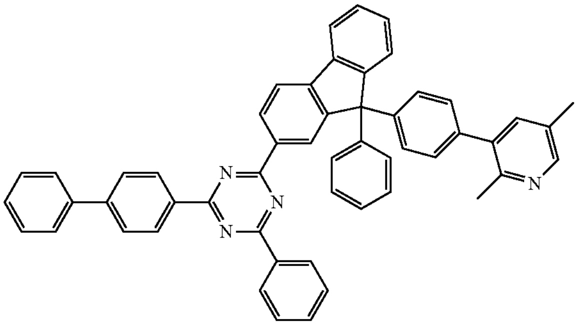
-continued -continued
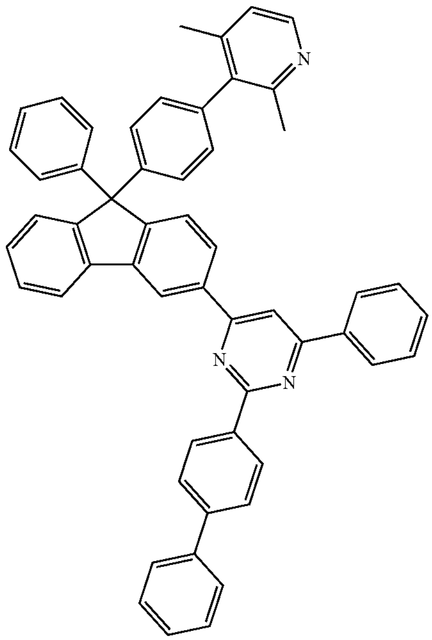
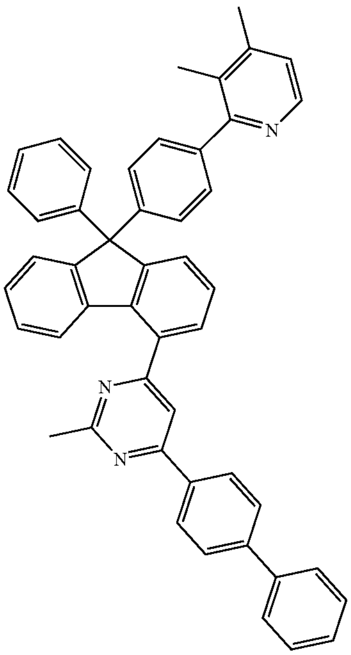
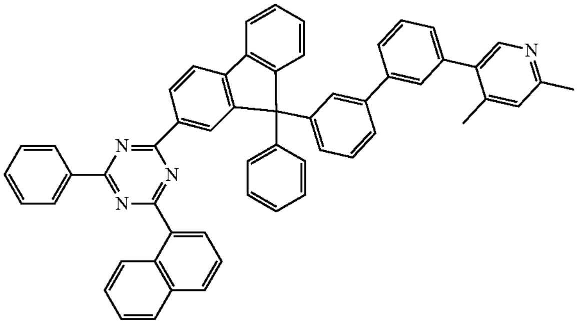
-continued
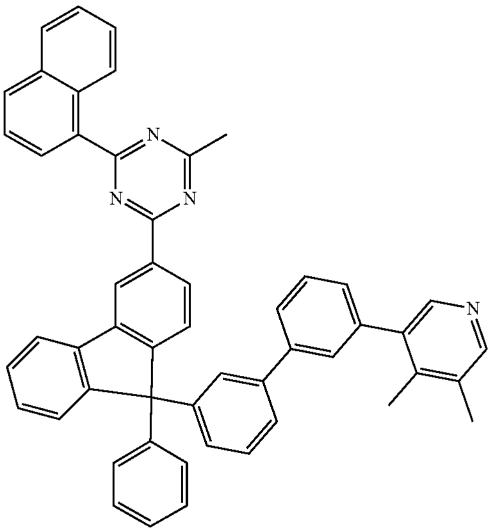
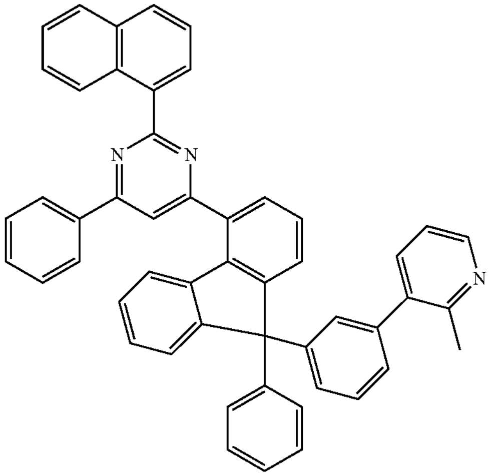
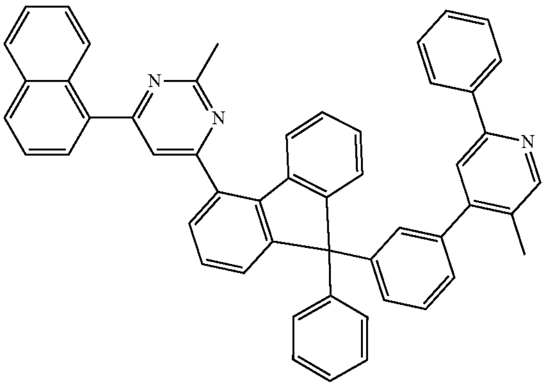

-continued
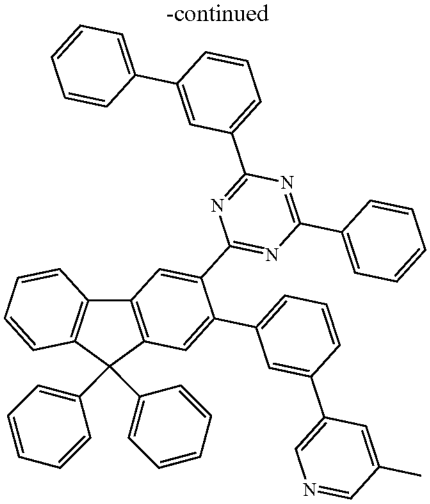
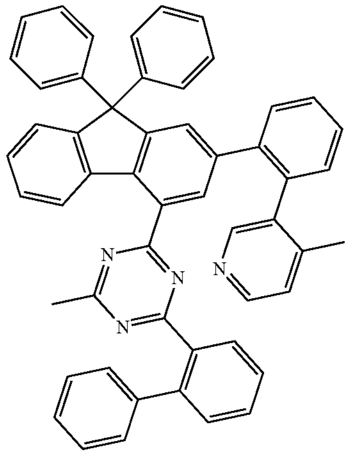
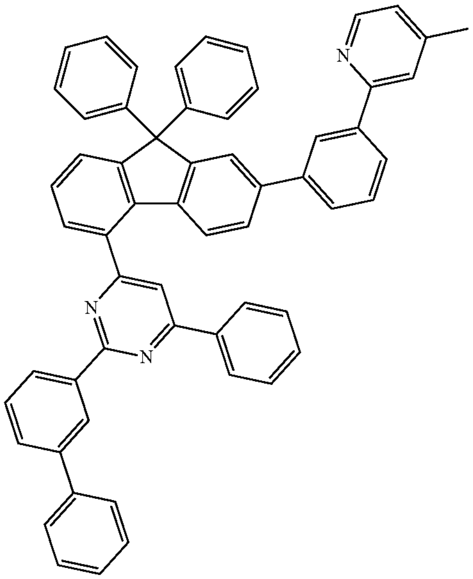
-continued
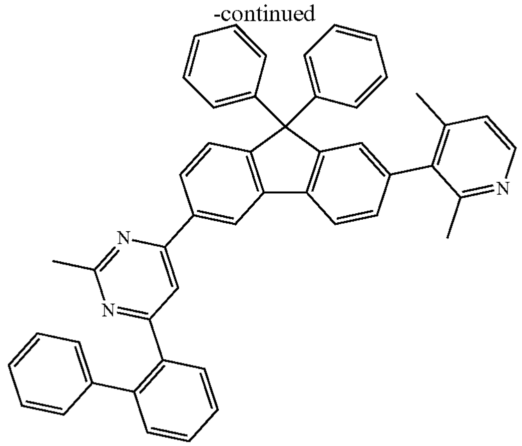
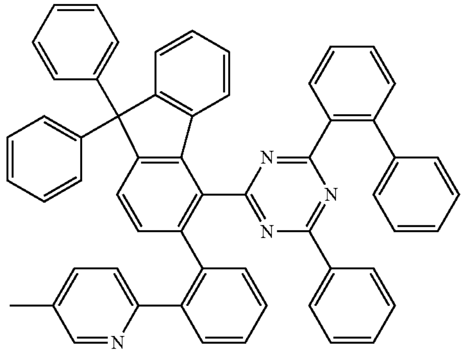
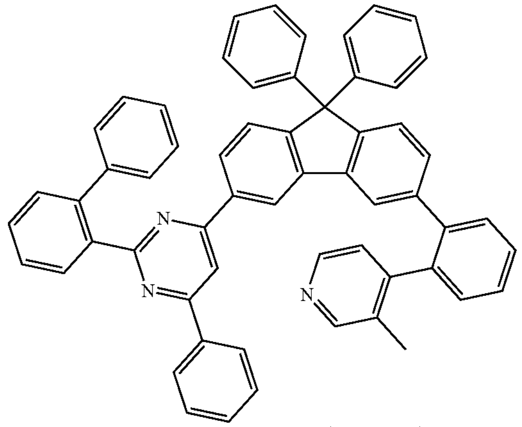
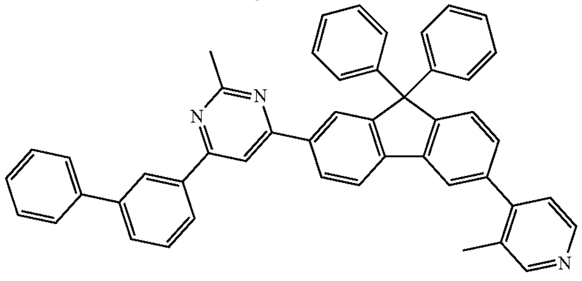

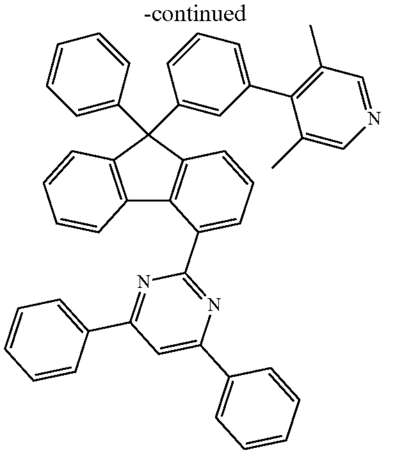
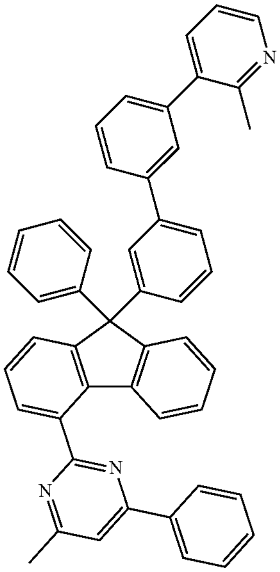
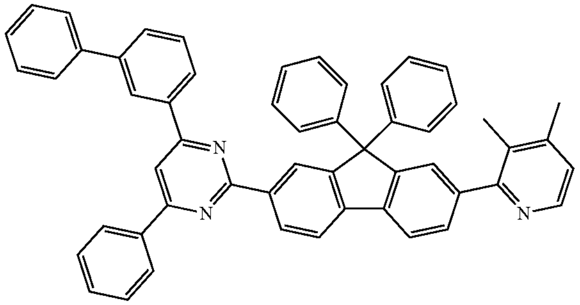
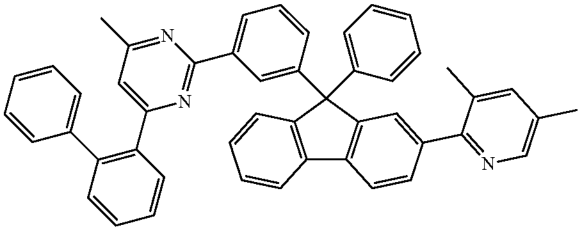
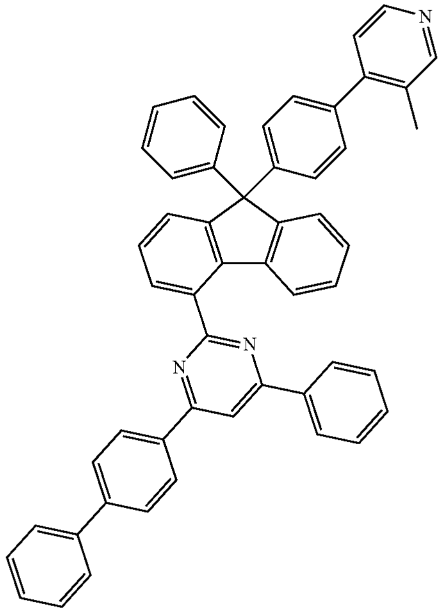
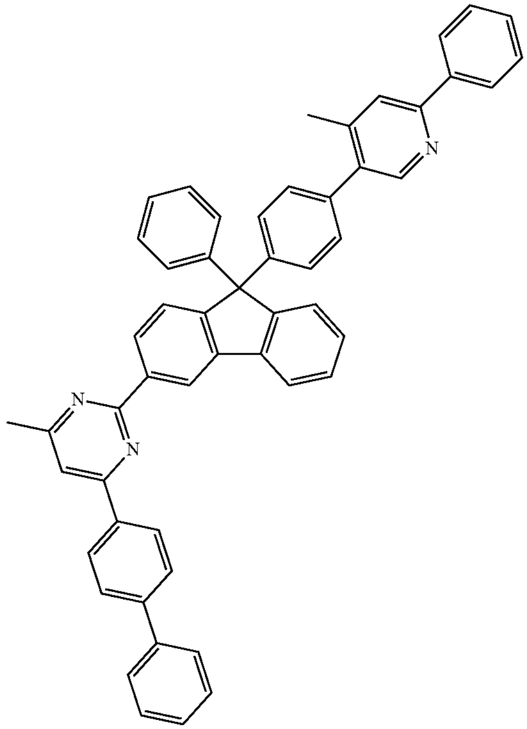

-continued
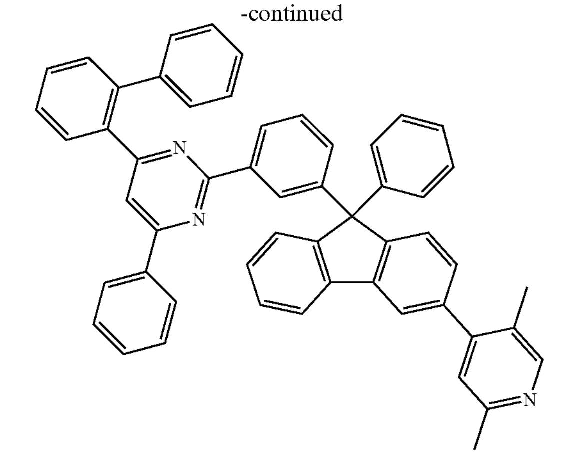
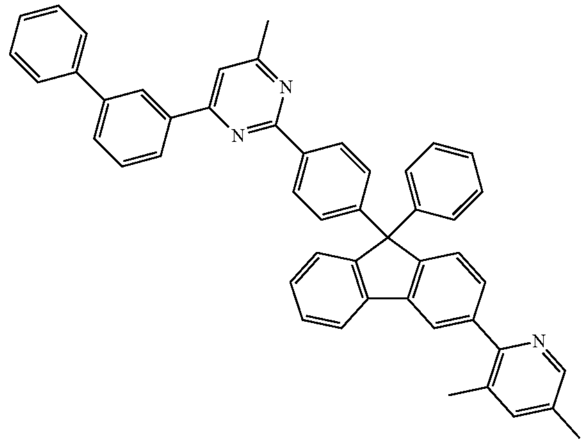
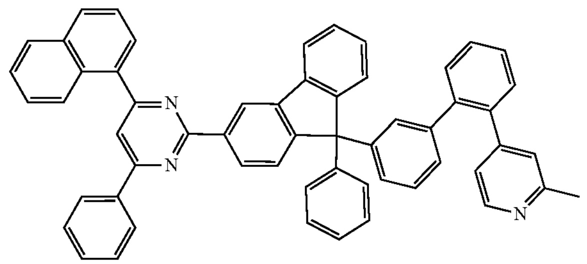
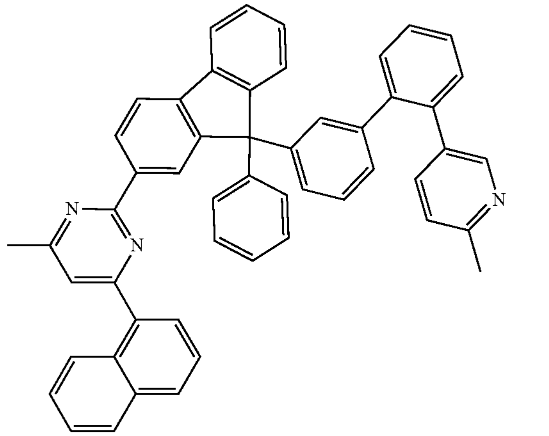
-continued
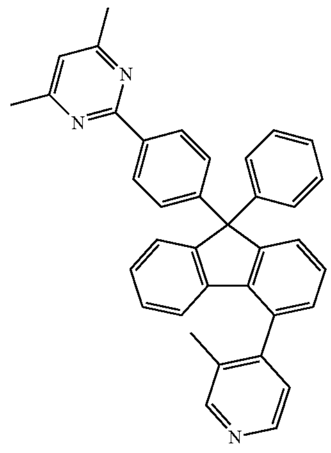
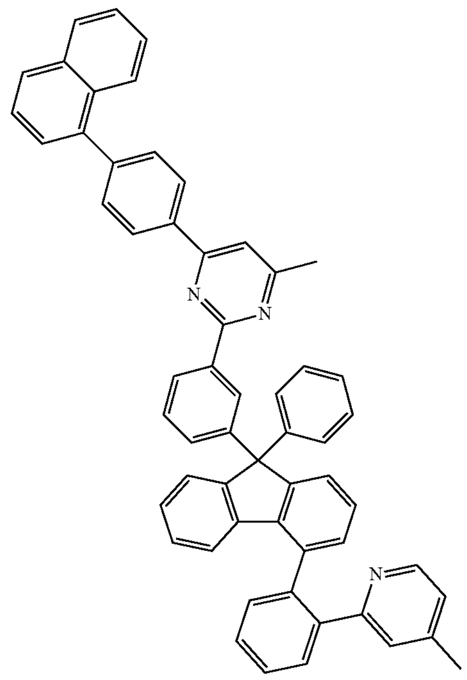
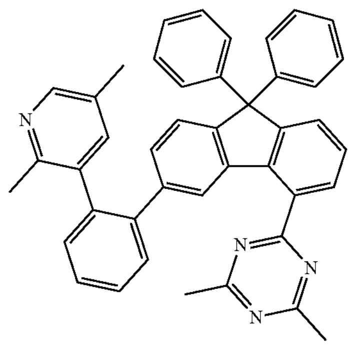

-continued
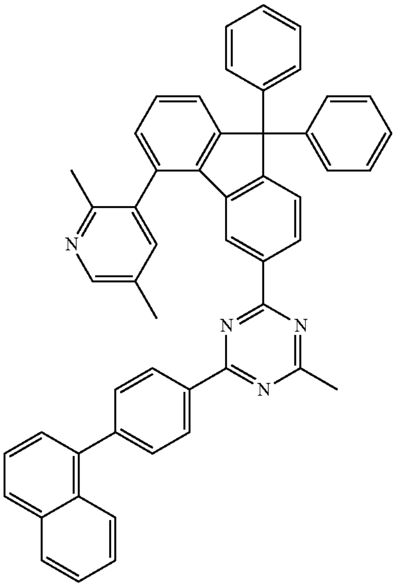
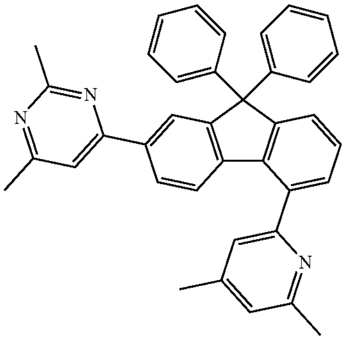
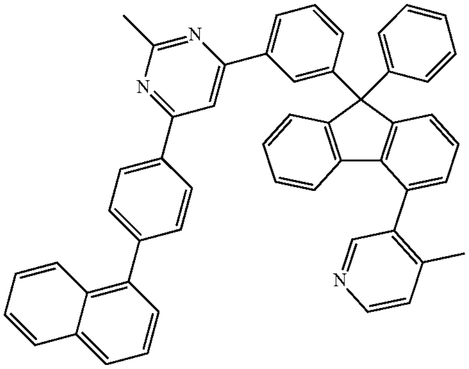
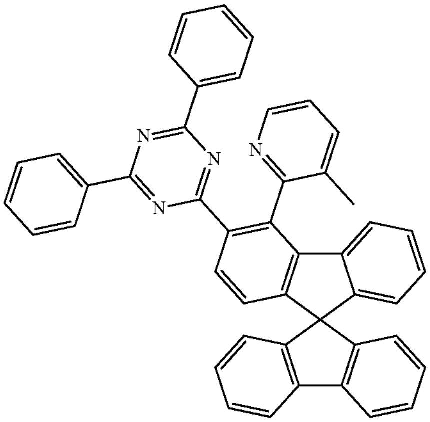
-continued
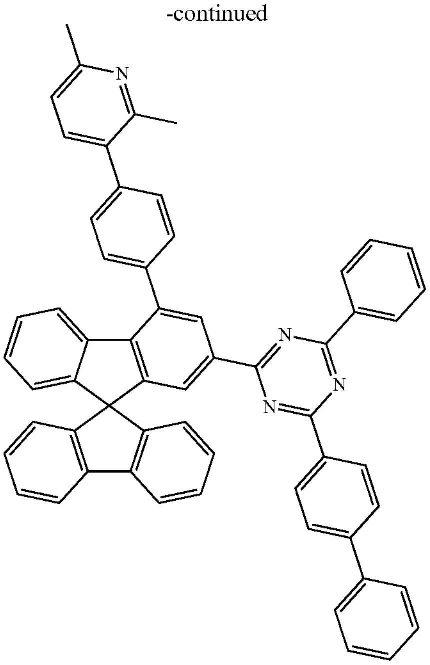
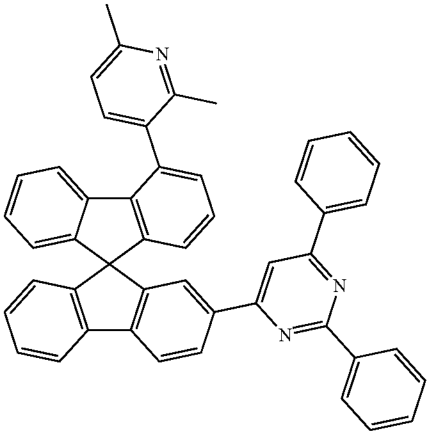
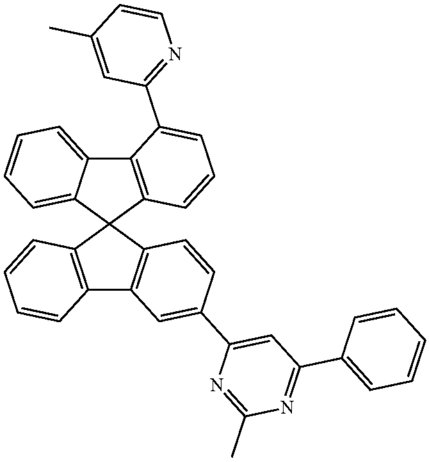

-continued
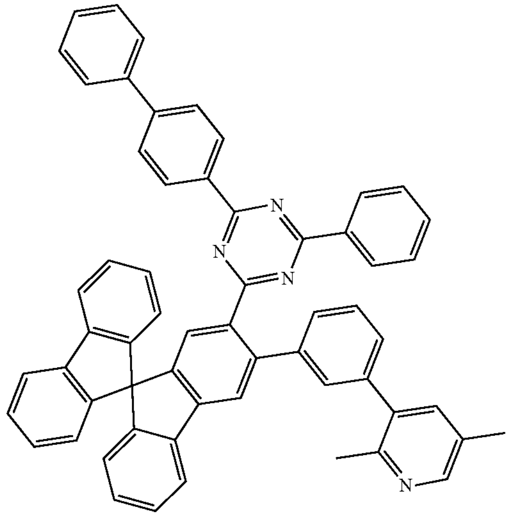
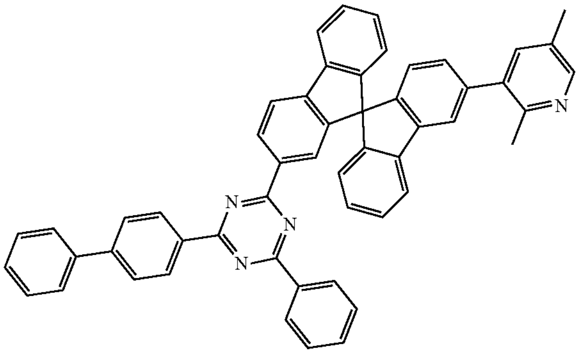
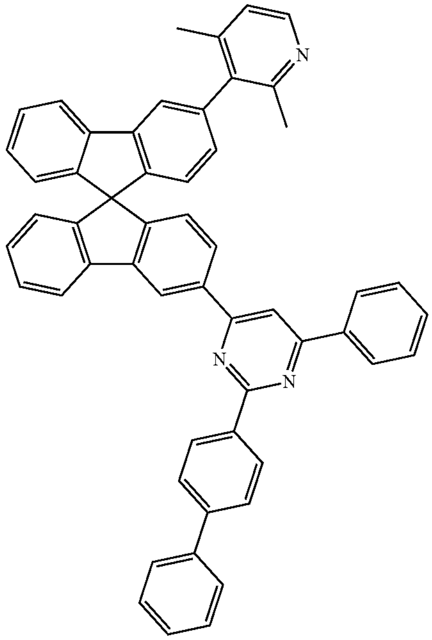
-continued
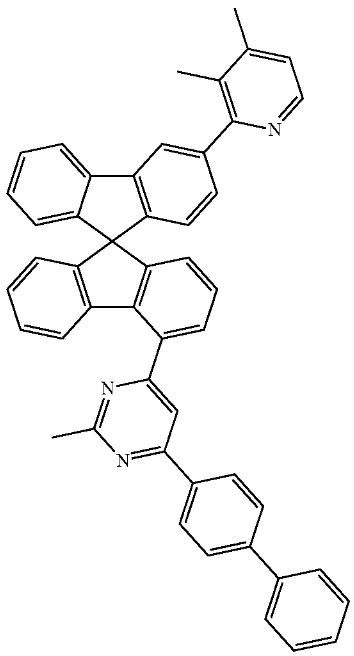
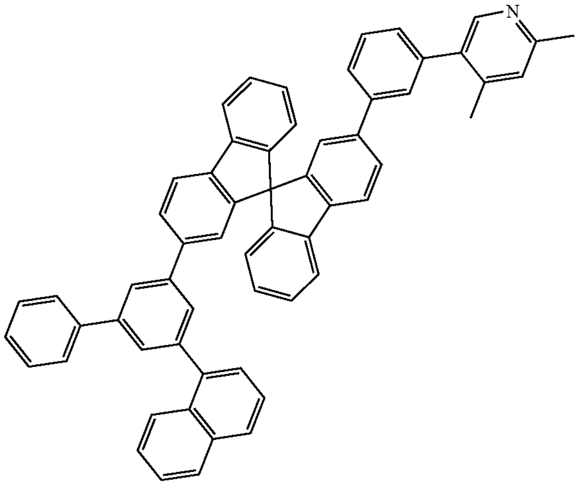
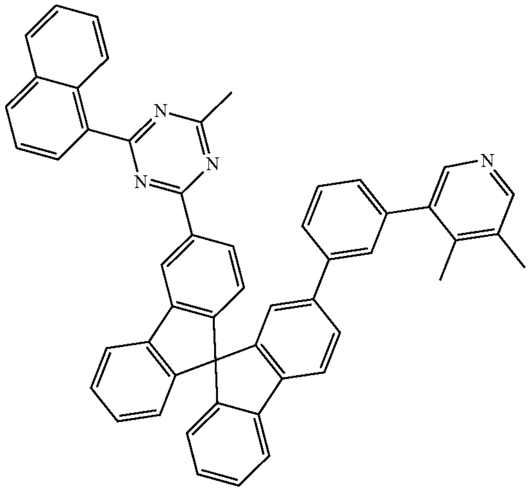

-continued
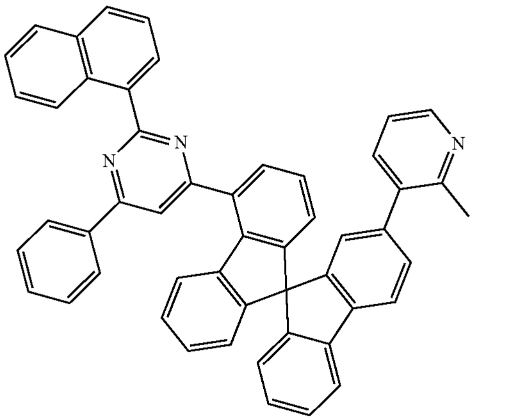
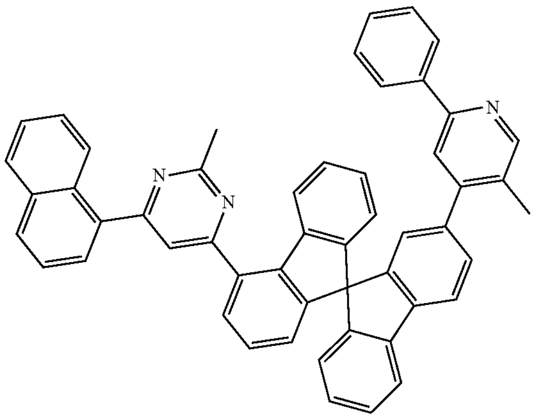
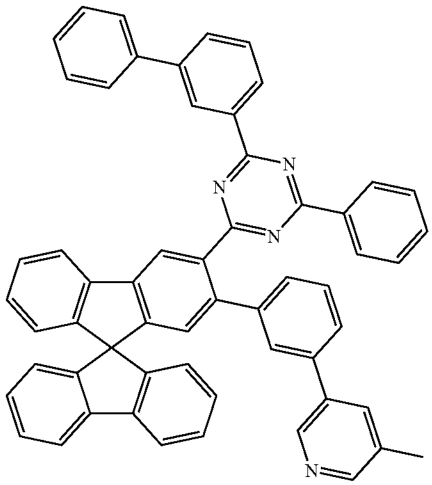
-continued
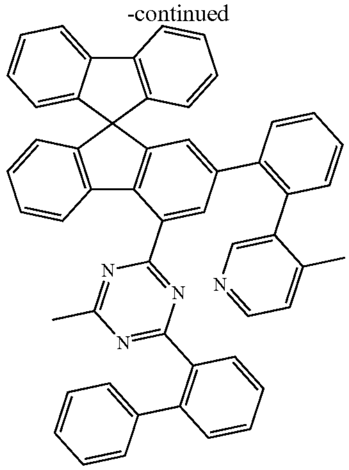
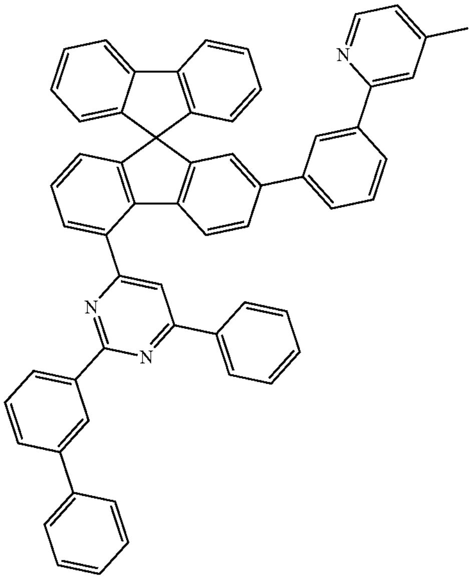
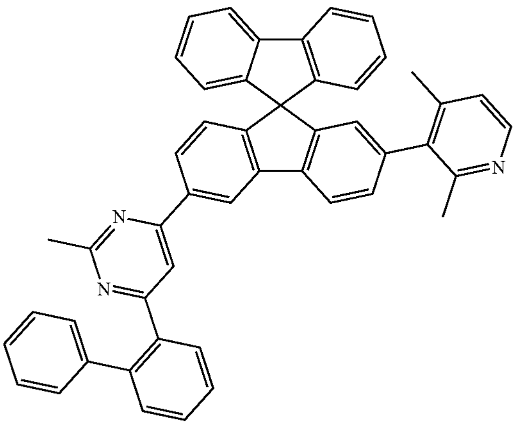

-continued
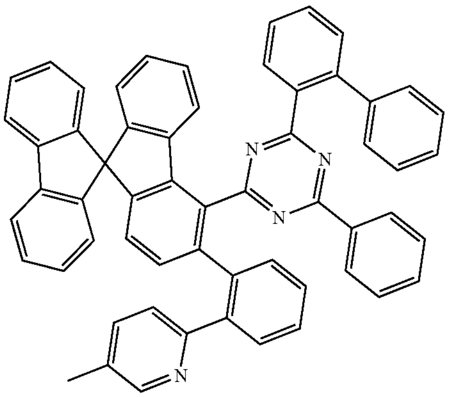
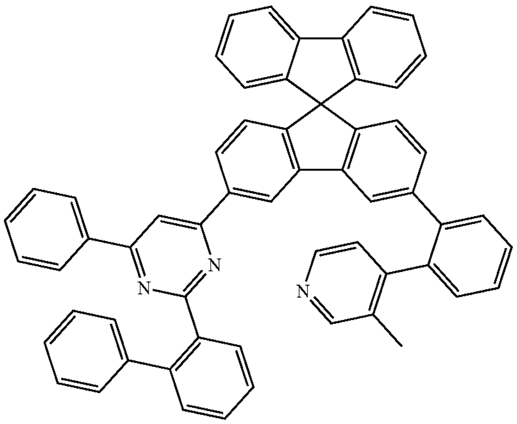
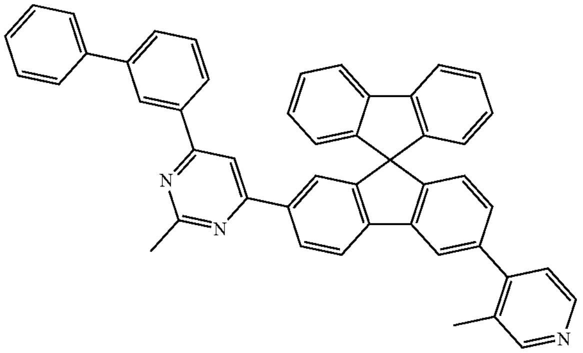
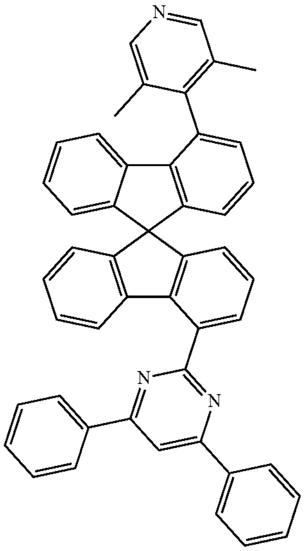
-continued
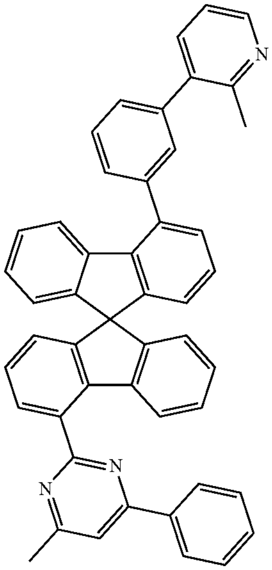
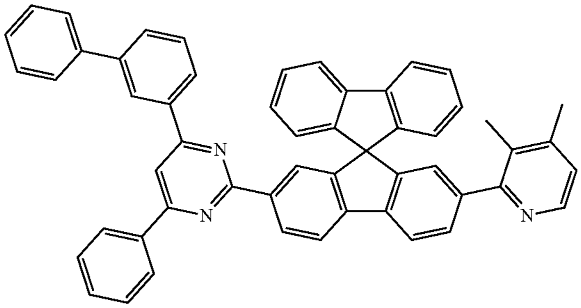
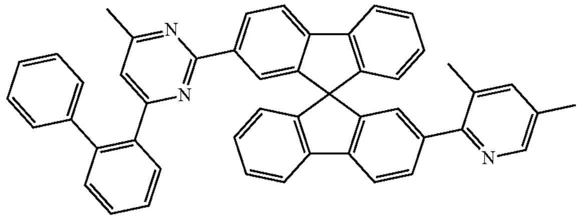
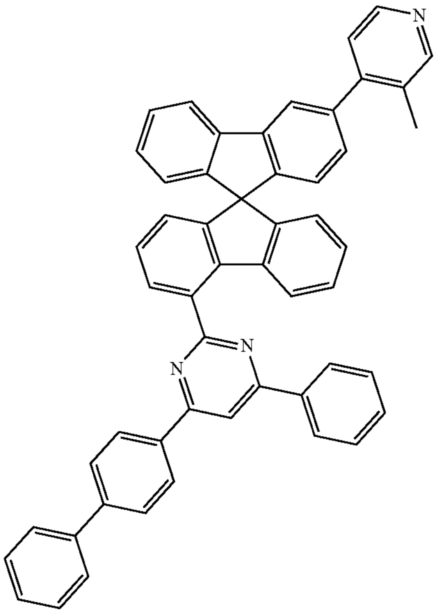

-continued
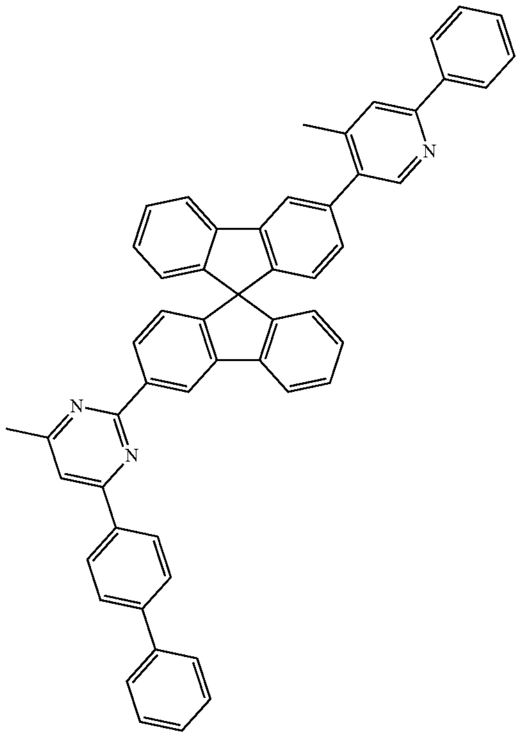
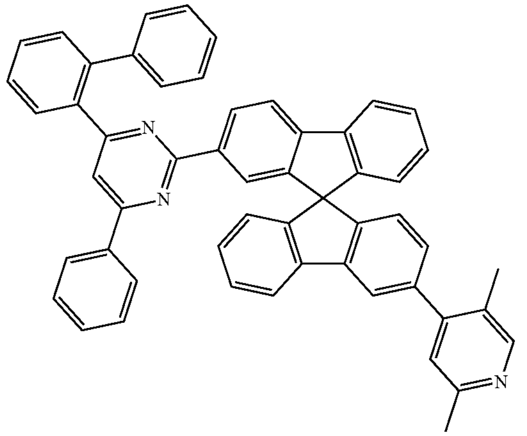
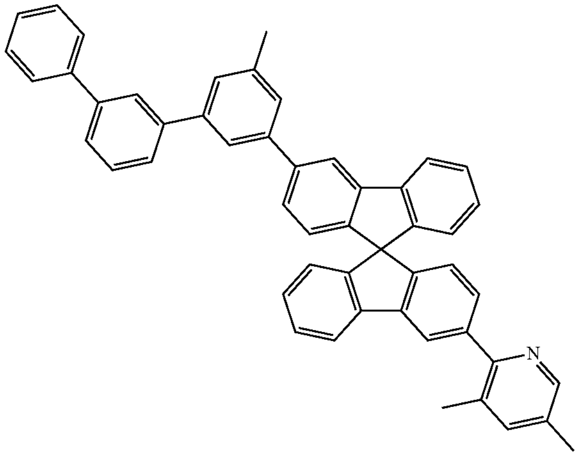
-continued
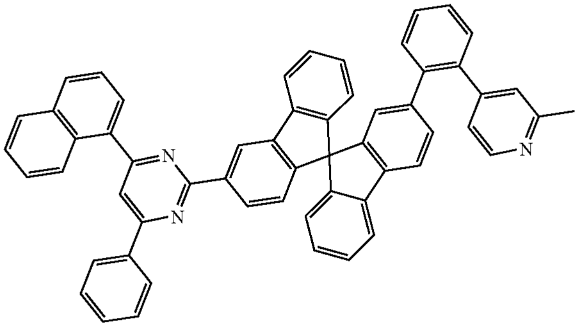
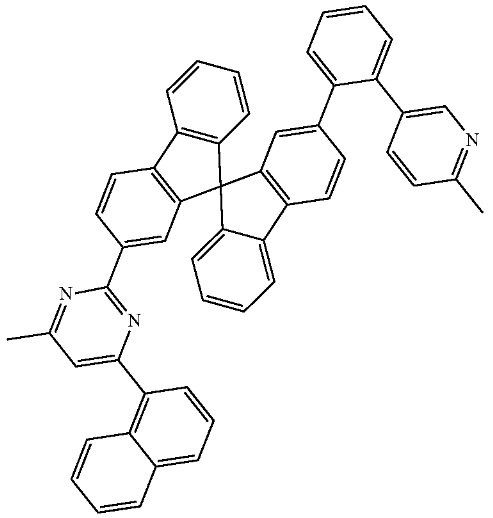
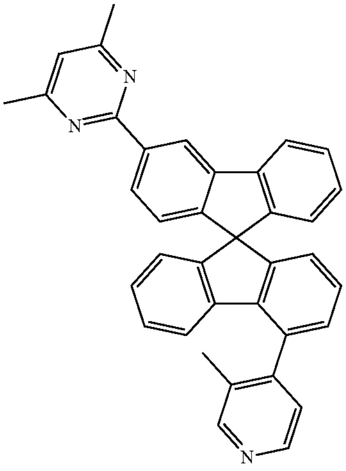

-continued
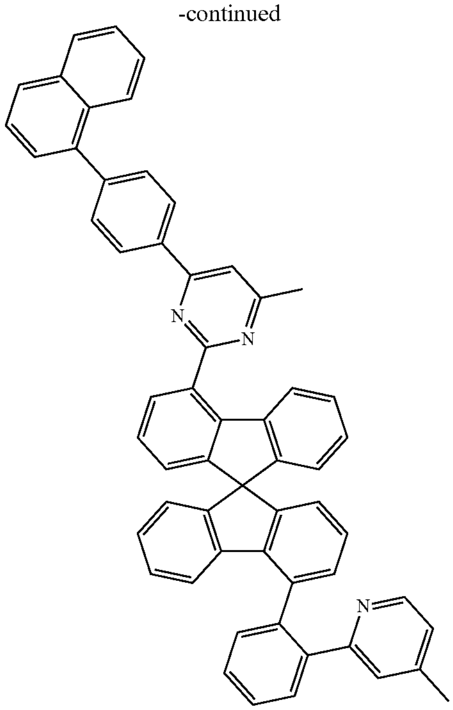
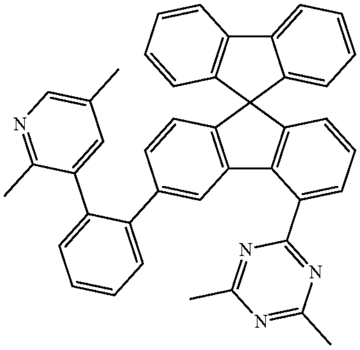
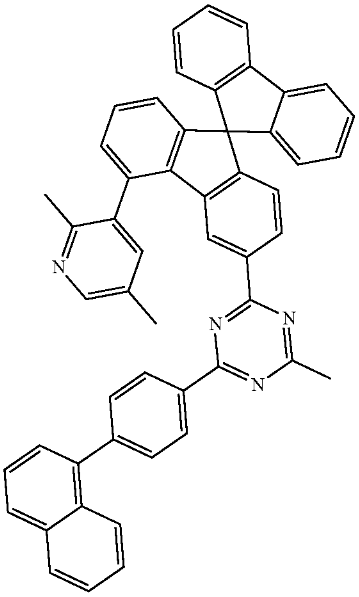
-continued
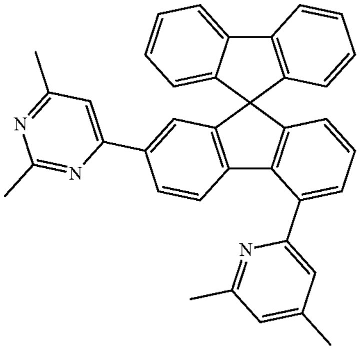
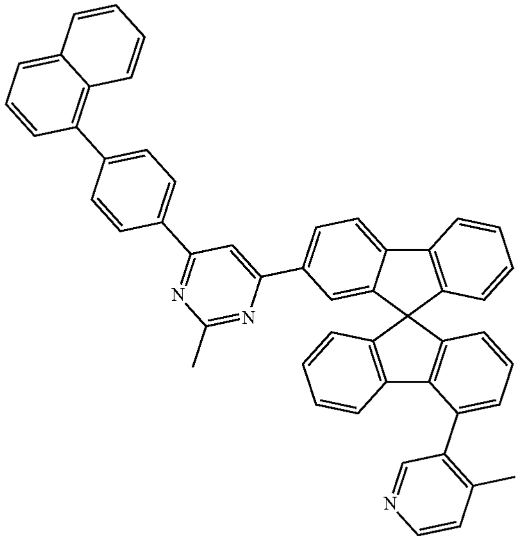

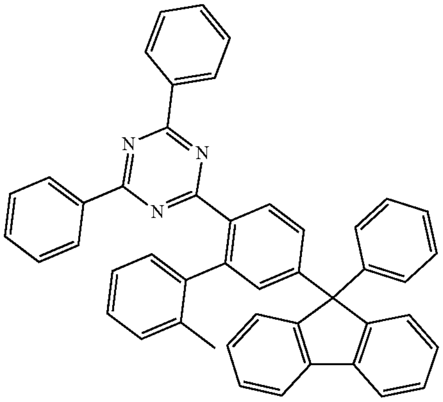
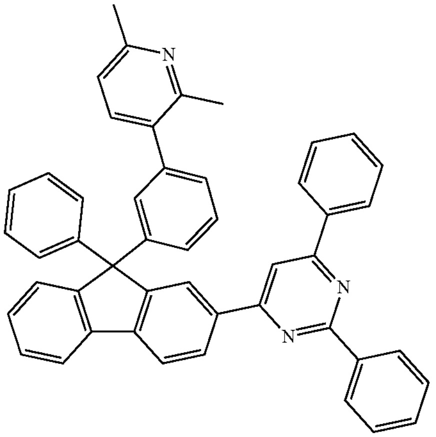
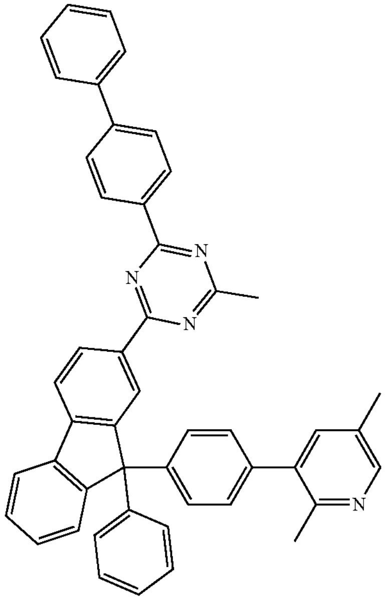
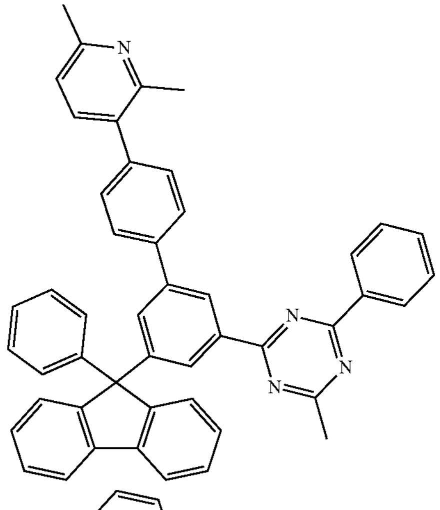
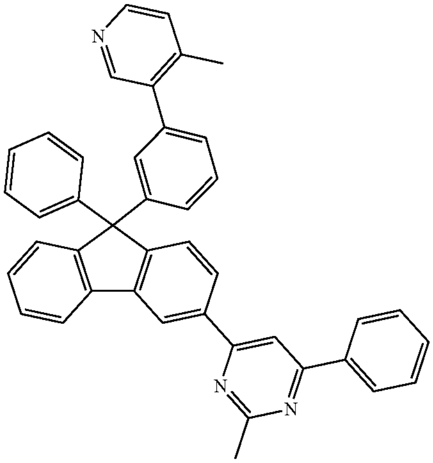
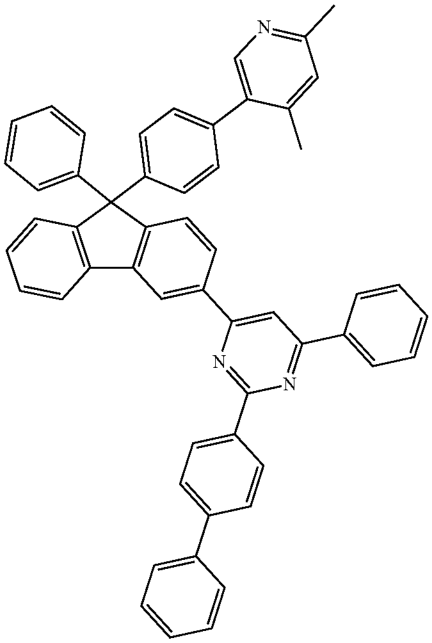

-continued
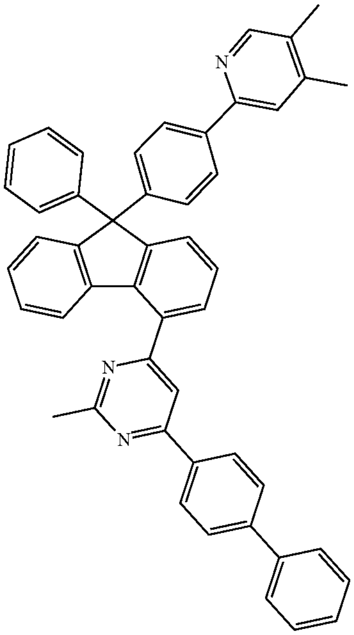
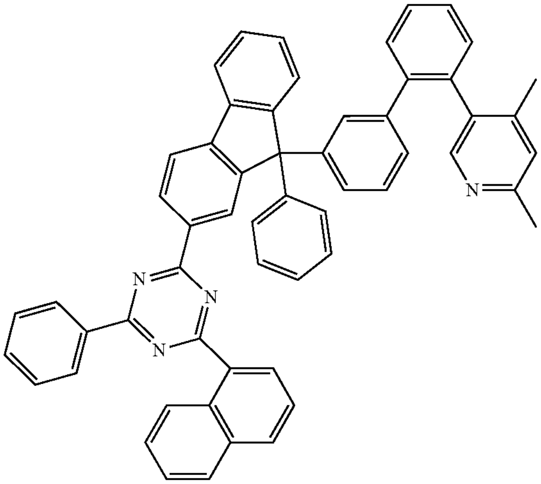
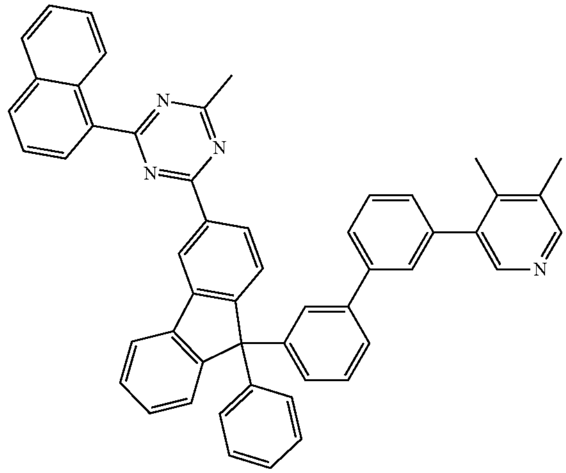
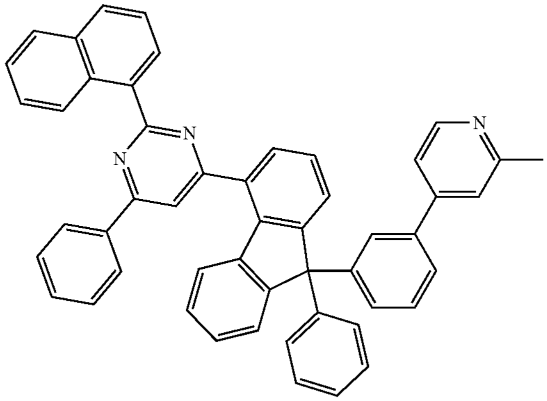
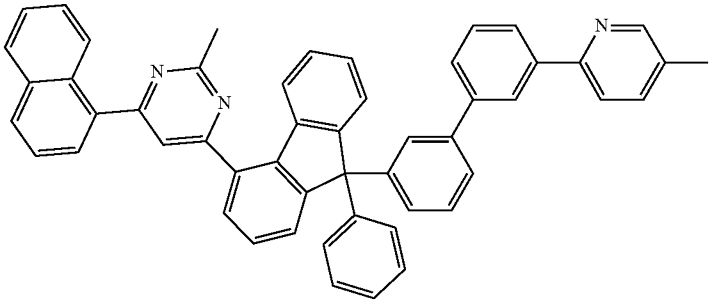

-continued
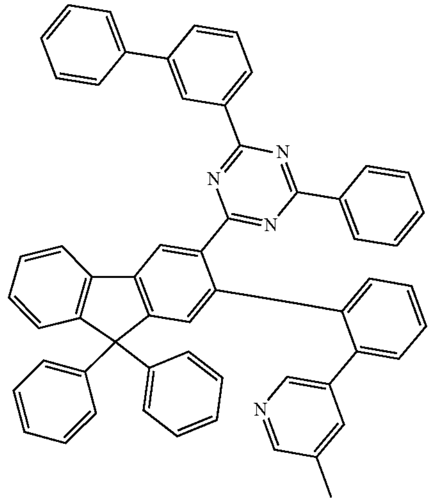
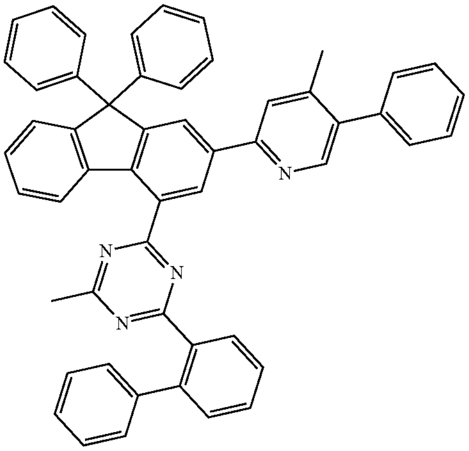
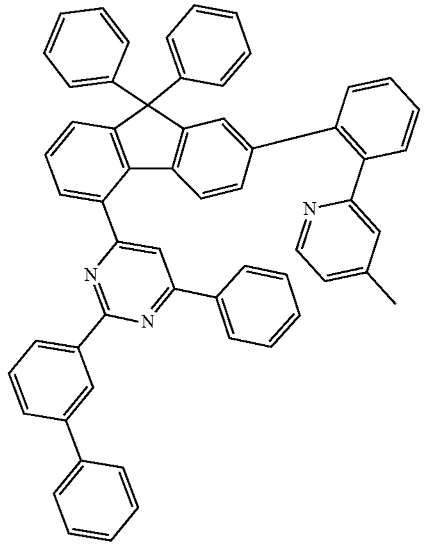
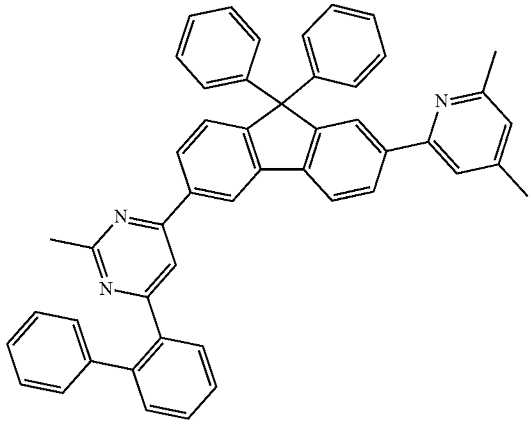
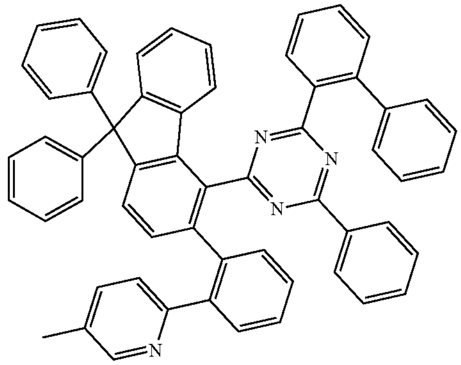
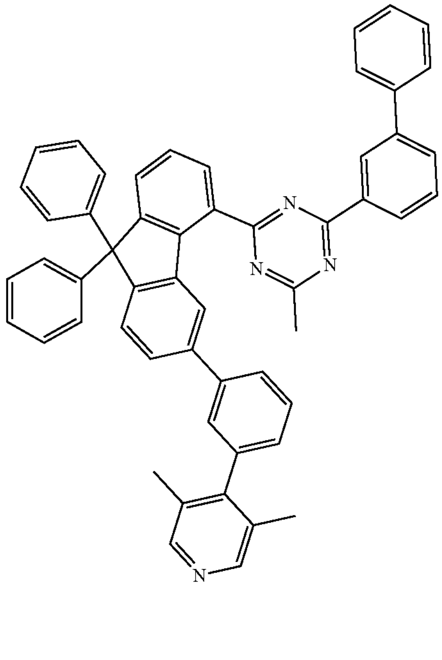

-continued
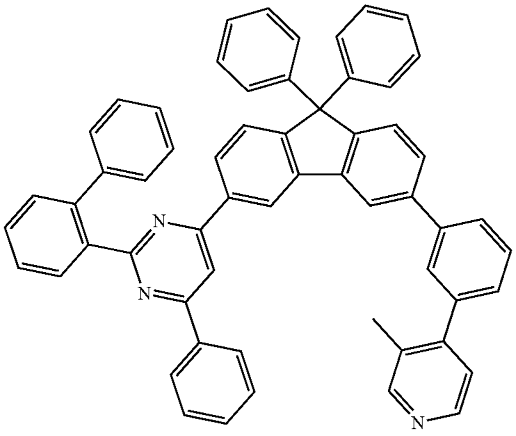
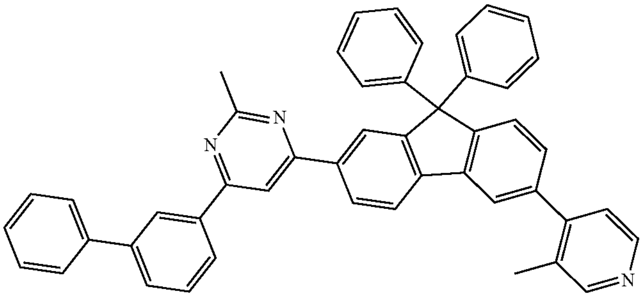
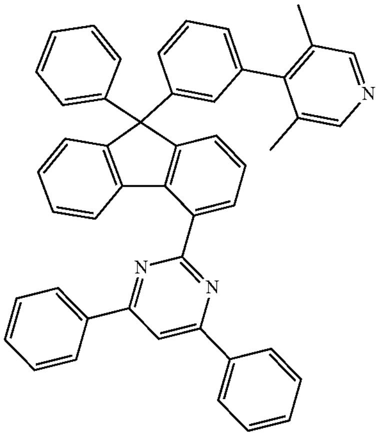
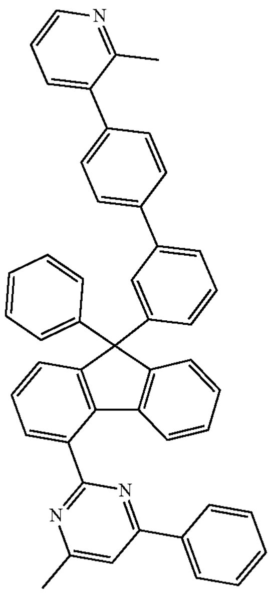
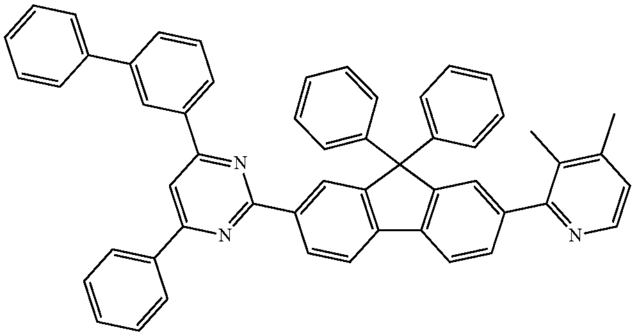

-continued
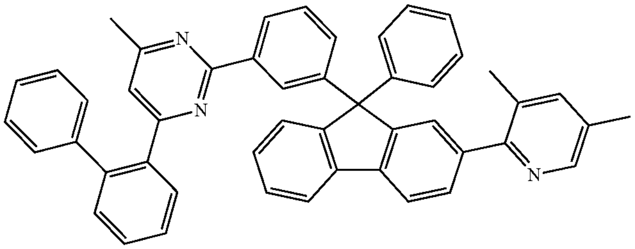
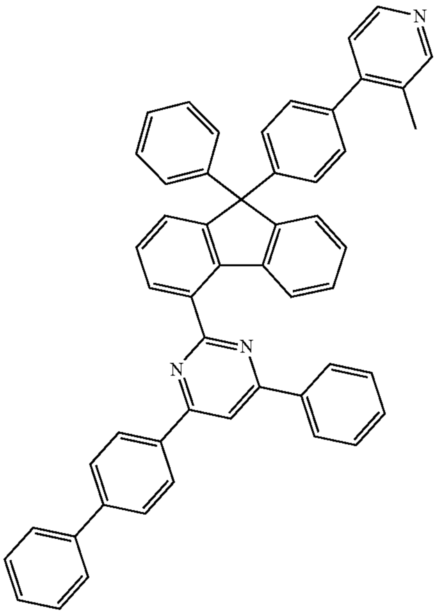
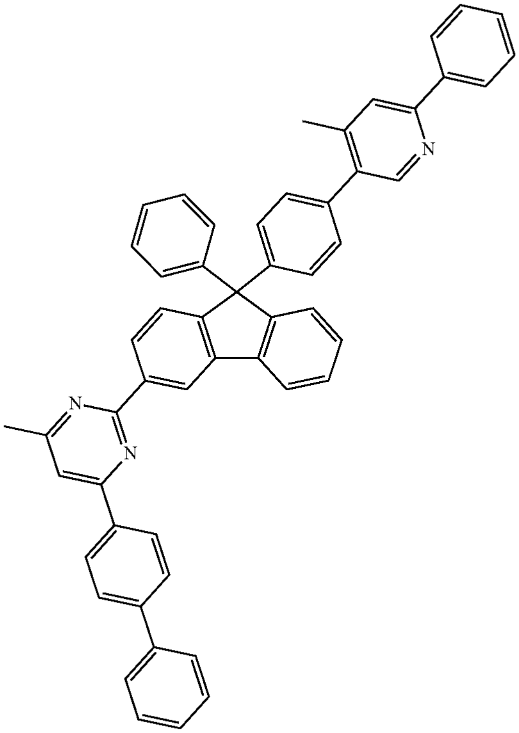
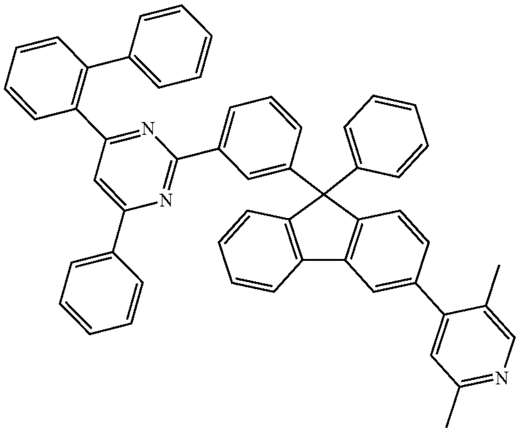

-continued
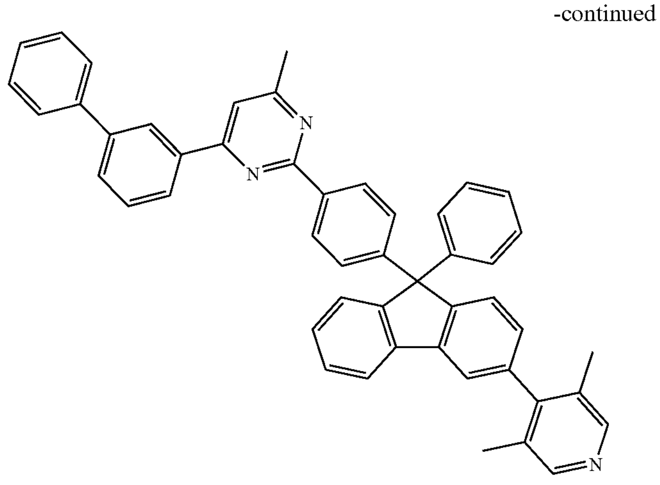
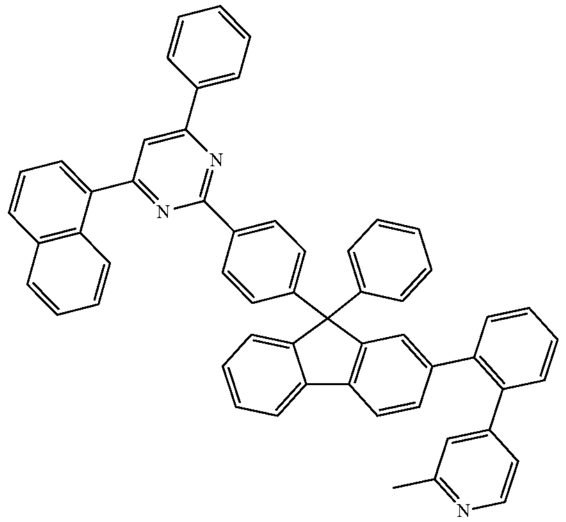
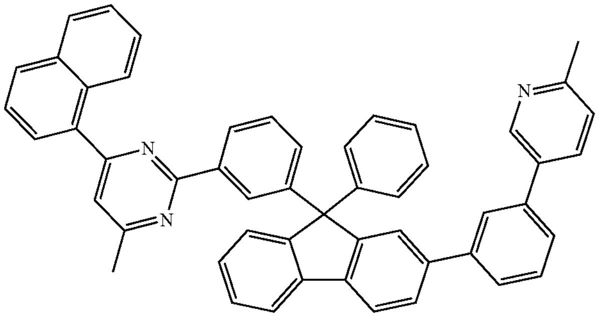
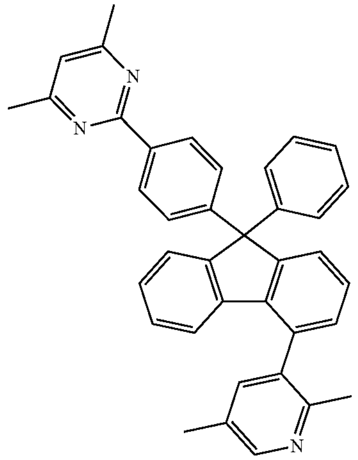
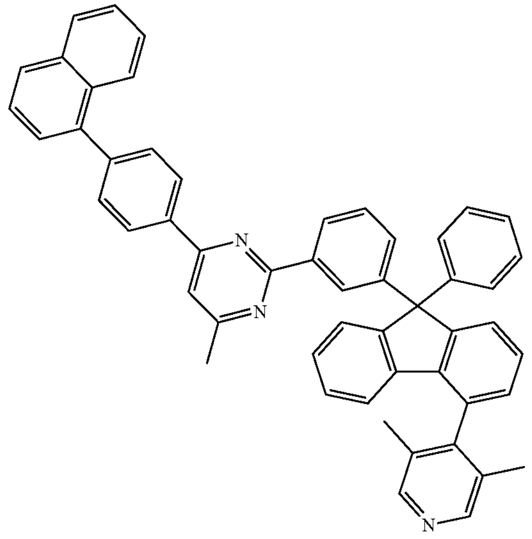

-continued
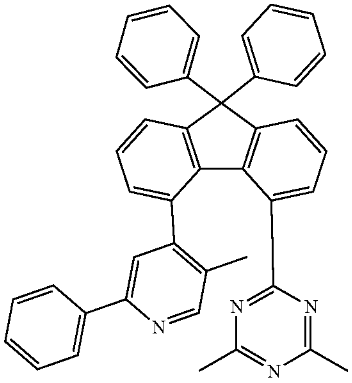
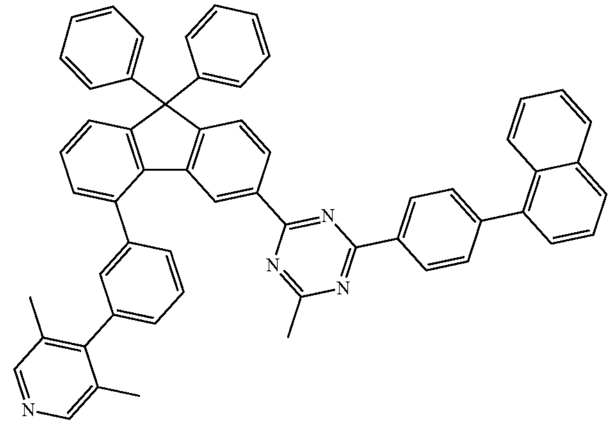
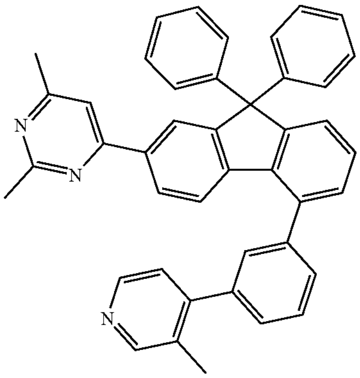
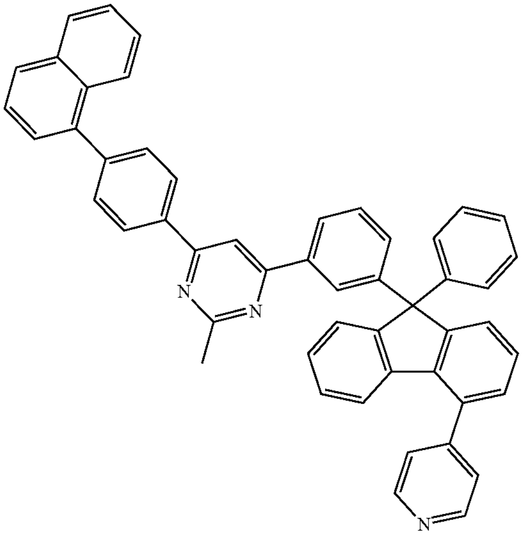
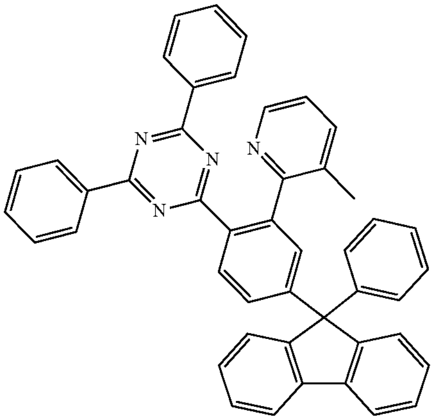
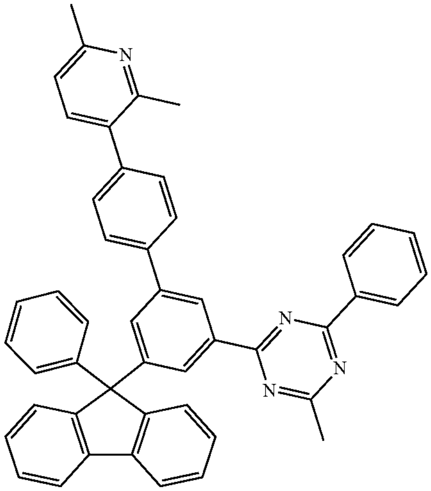

-continued
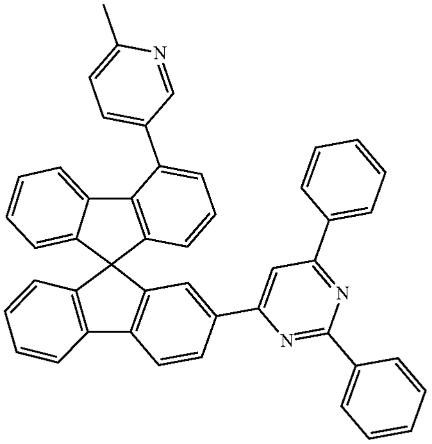
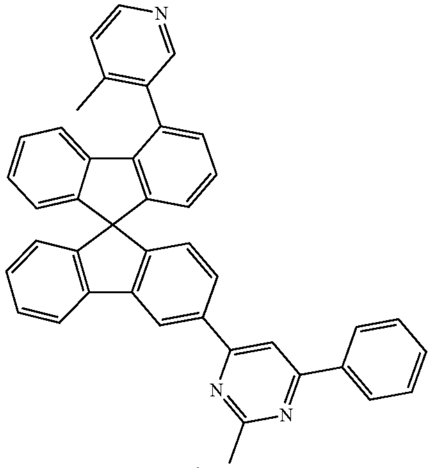
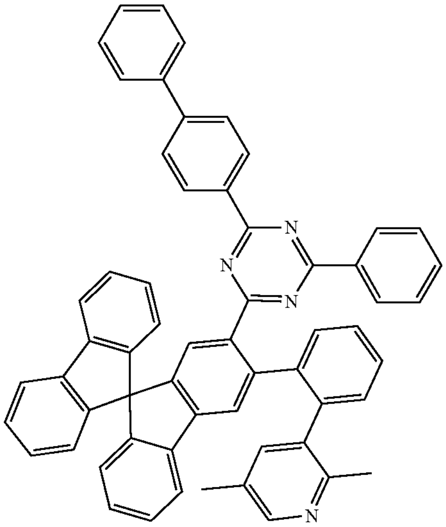
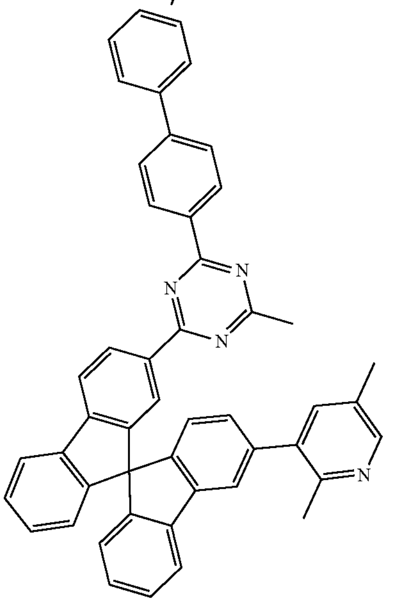
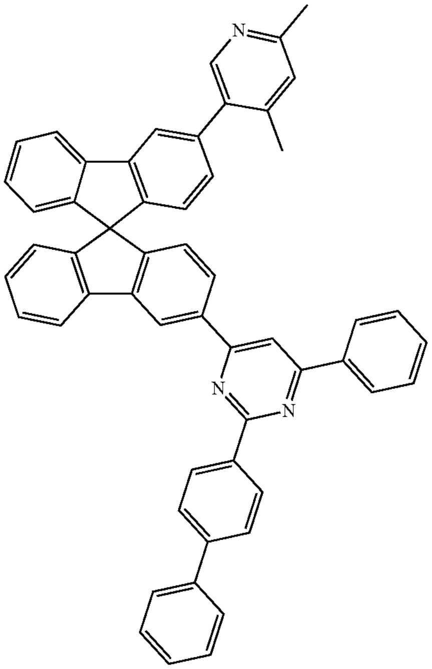
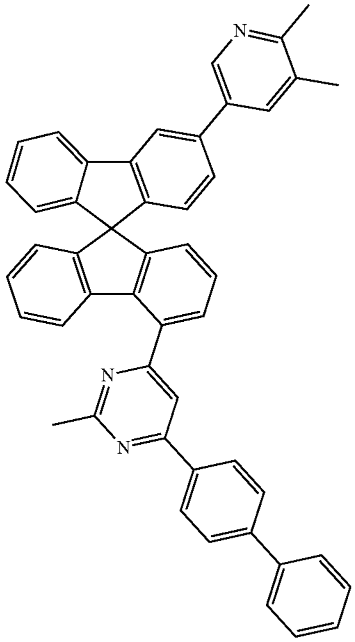

-continued
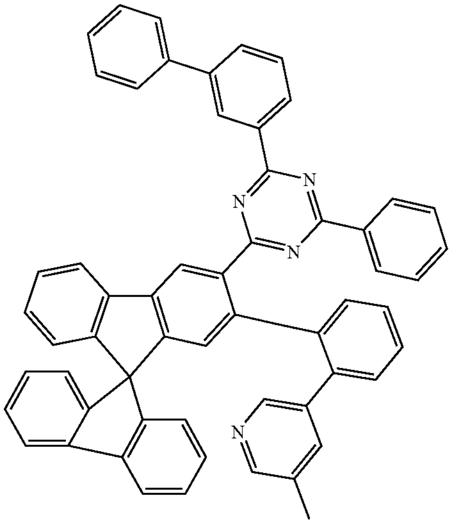
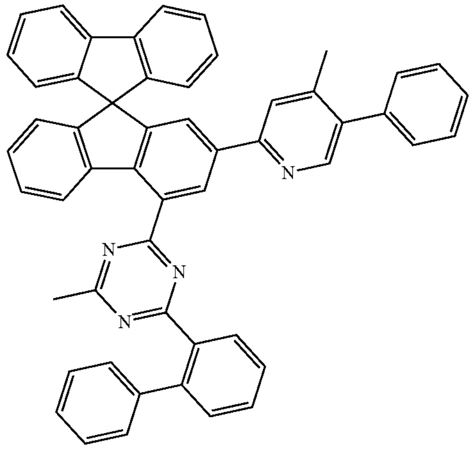
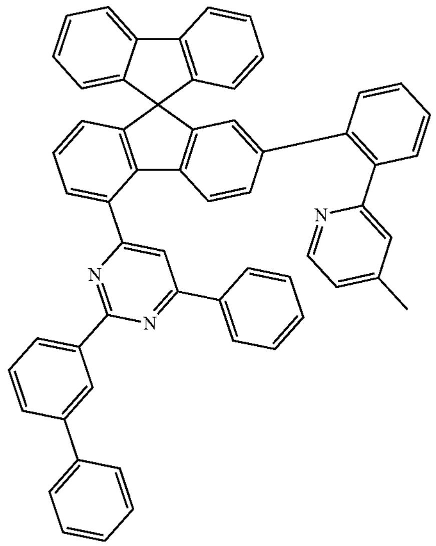
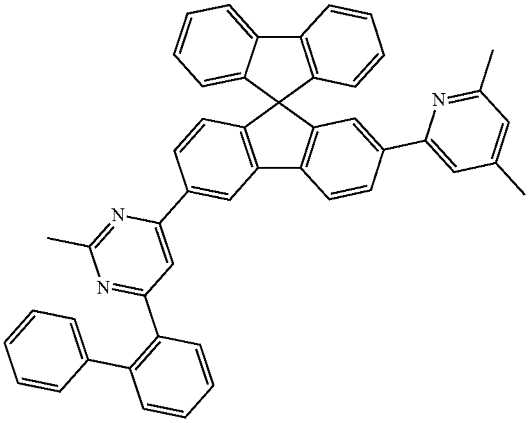
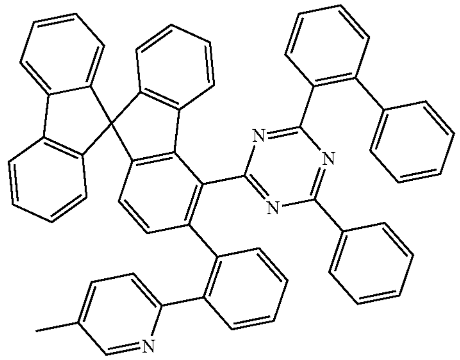
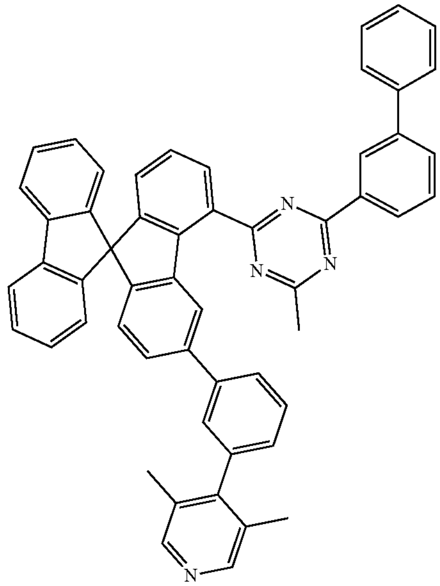

-continued
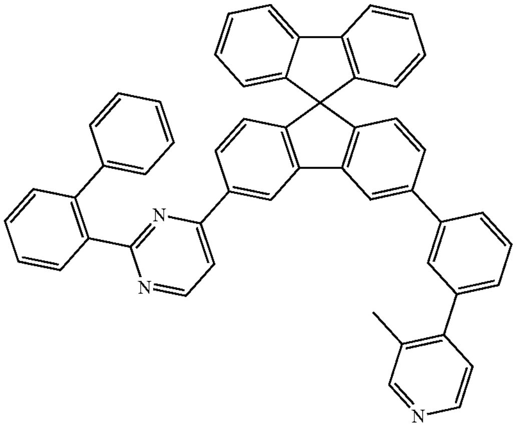
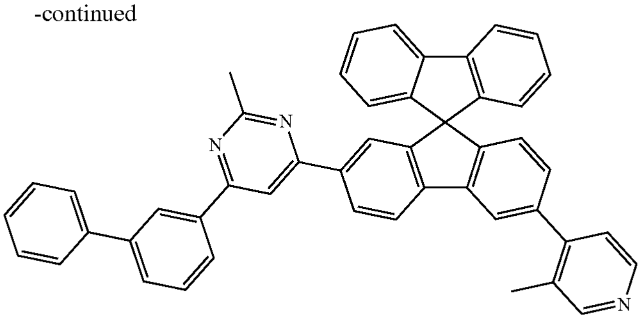
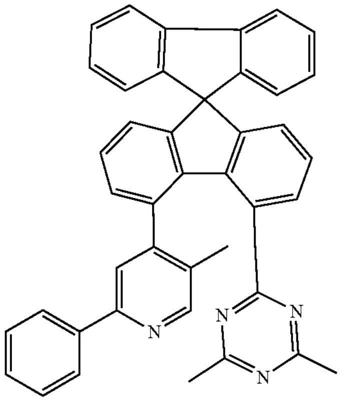
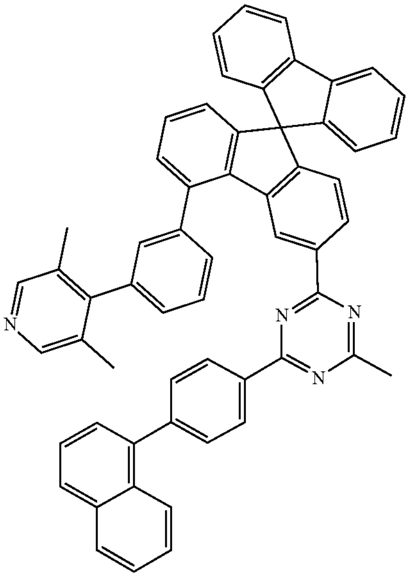
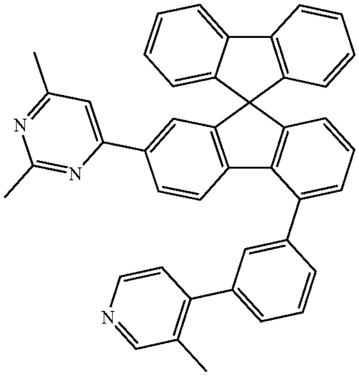
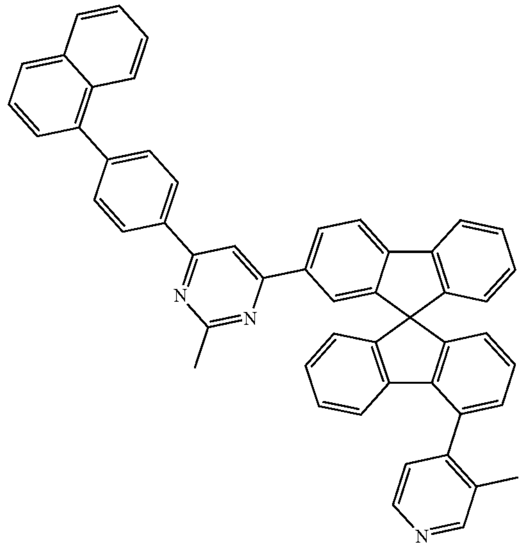

-continued
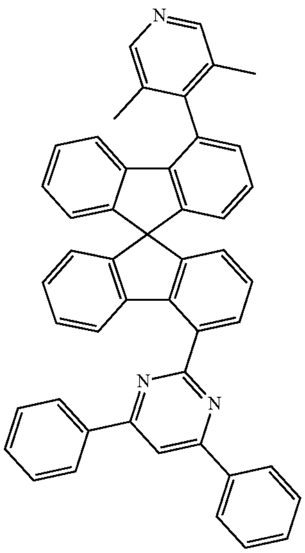
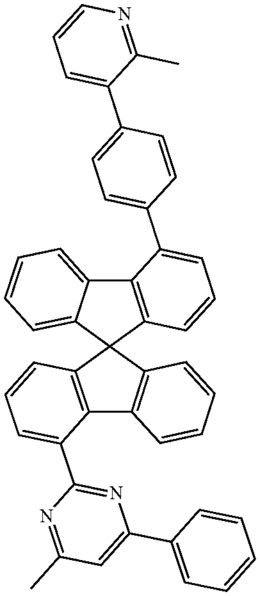
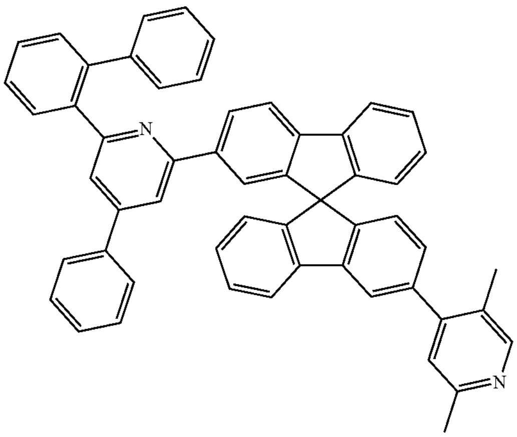
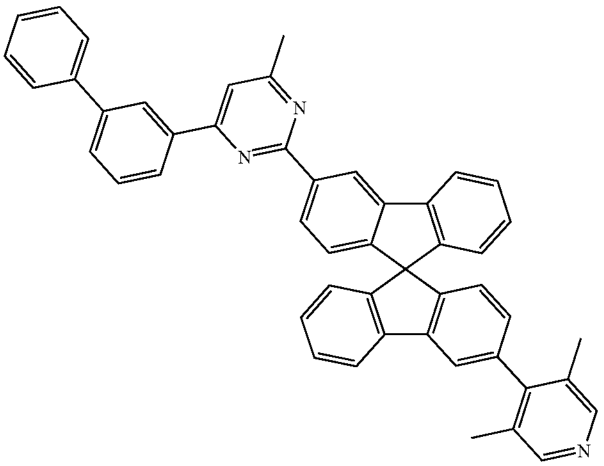

-continued
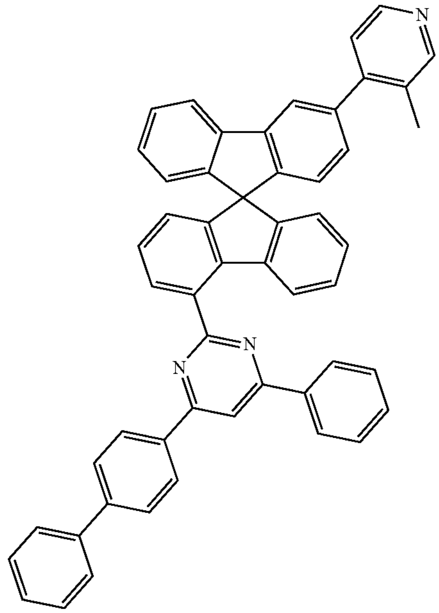
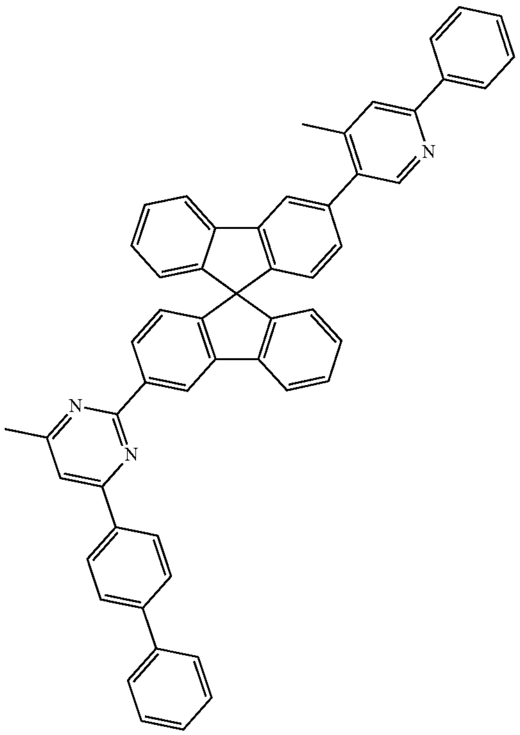
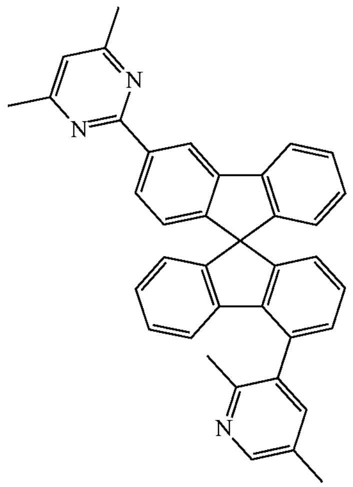
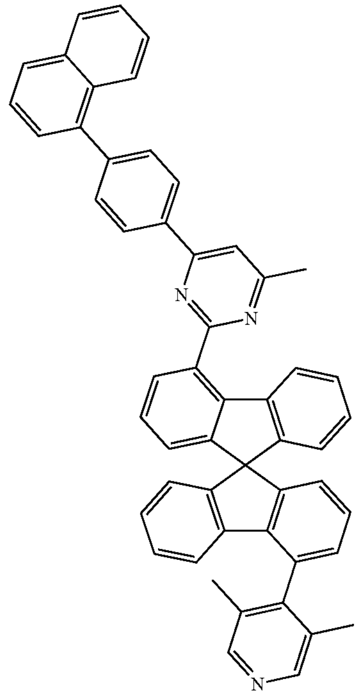

-continued
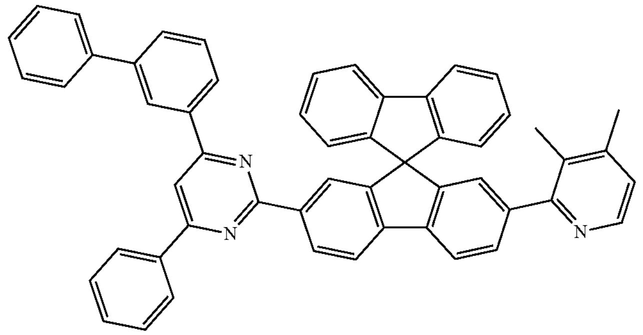
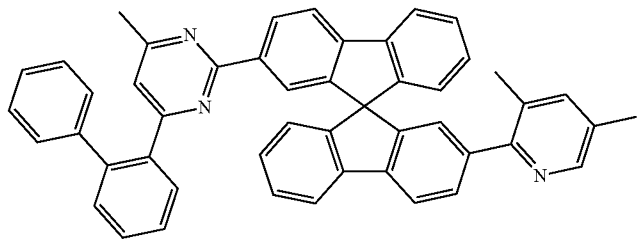
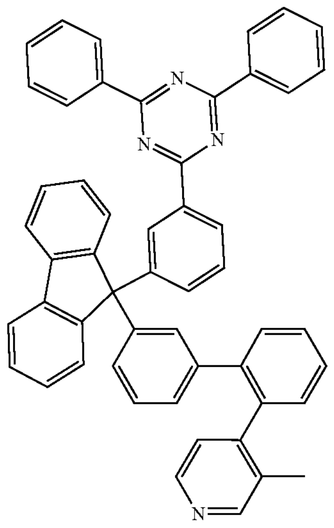
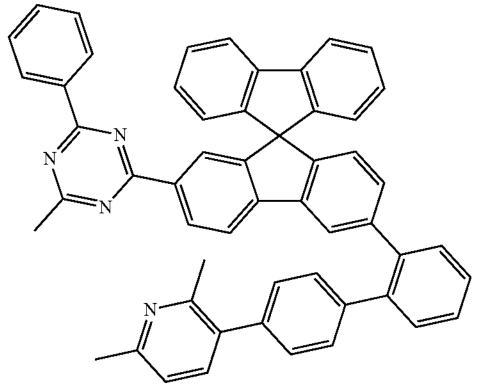
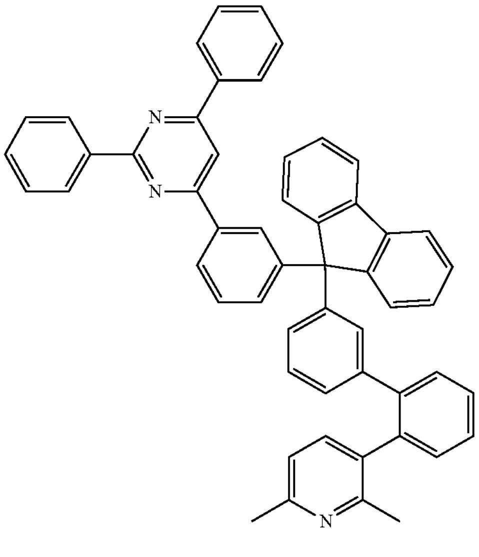

-continued
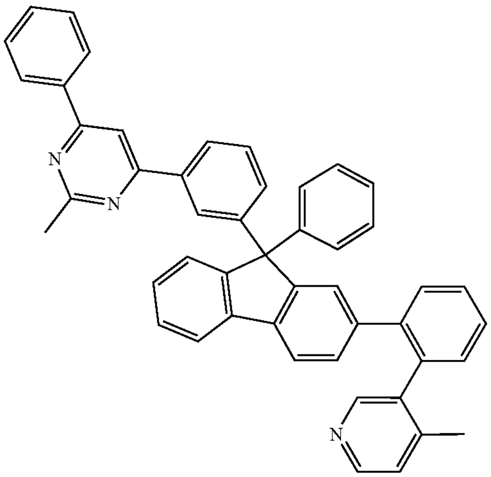
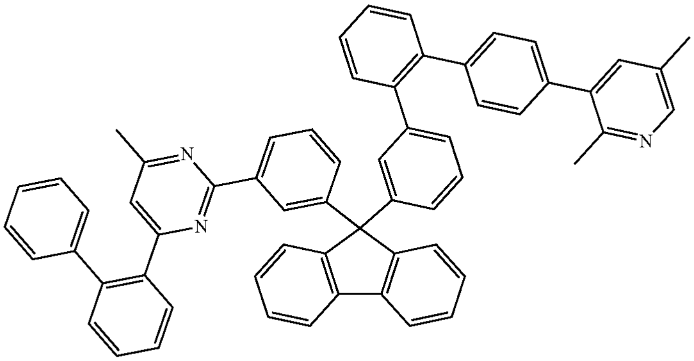
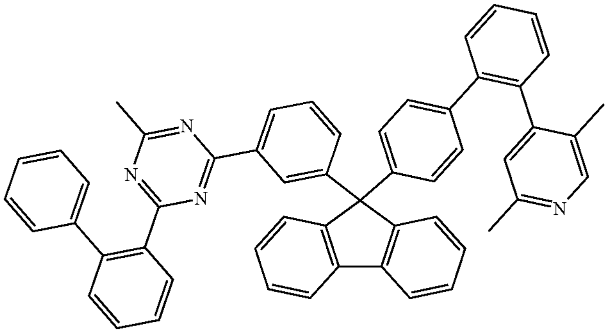
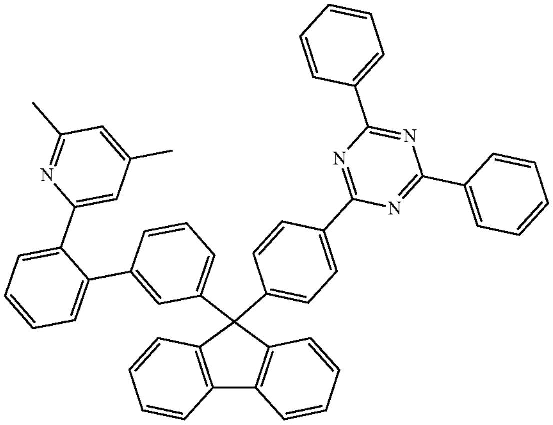
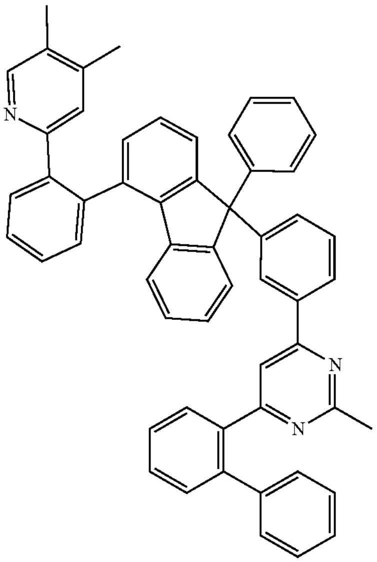
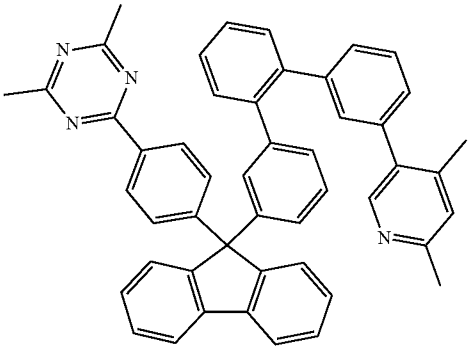

-continued
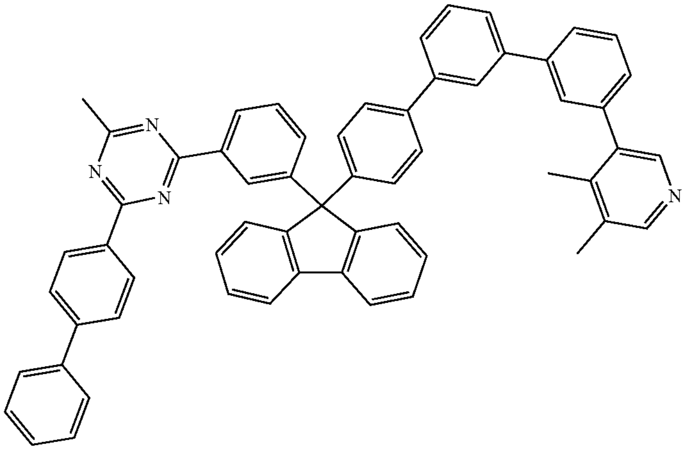
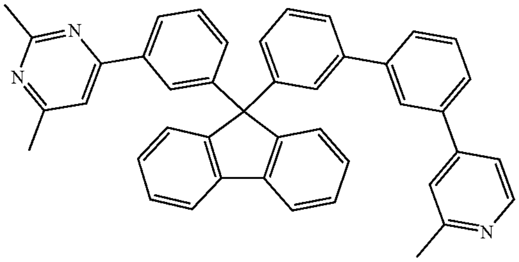
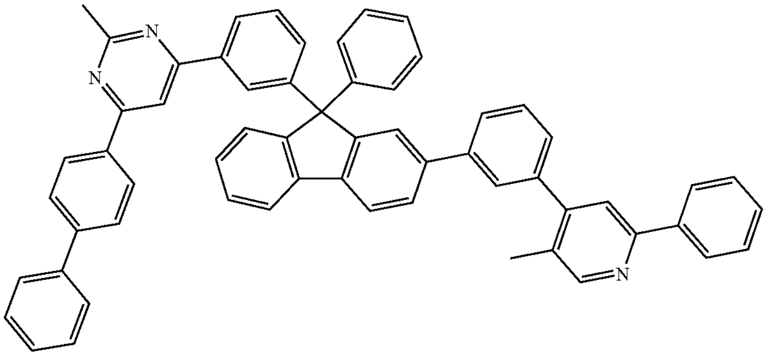
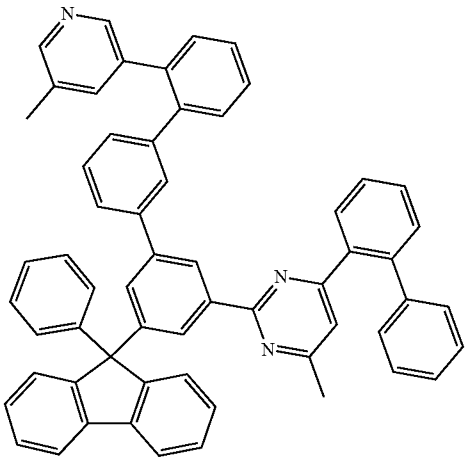

-continued
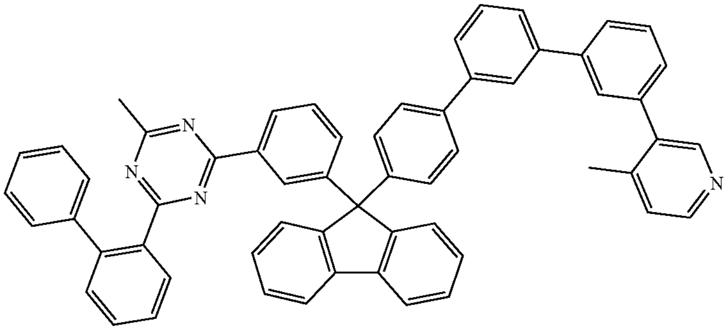
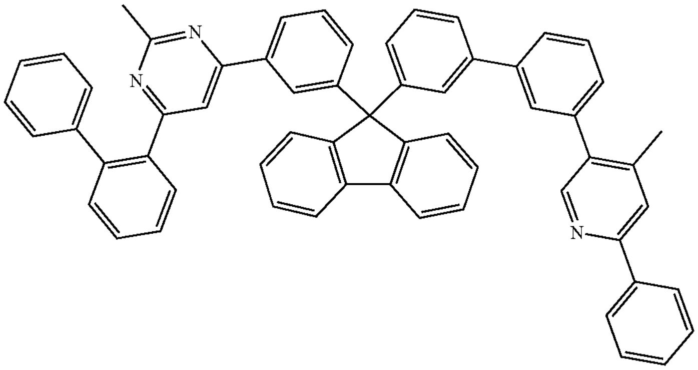
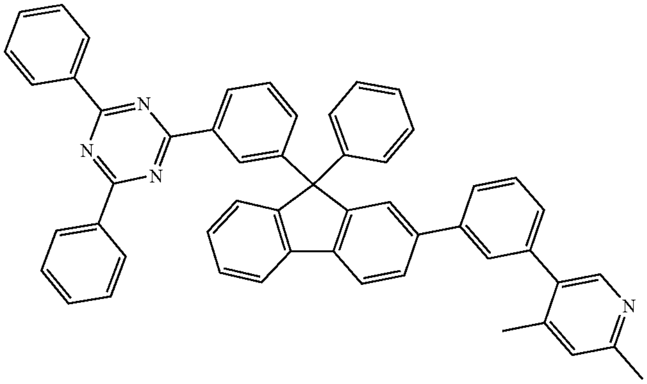
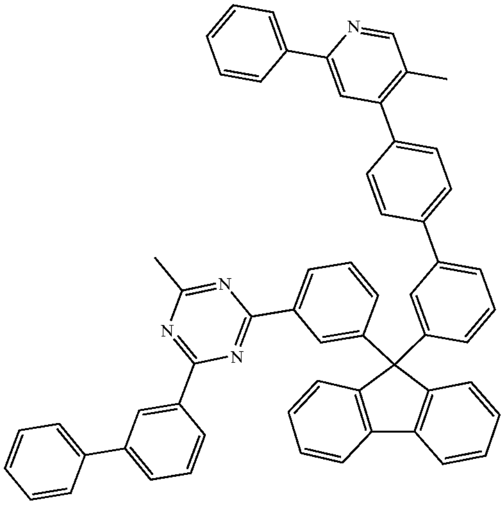
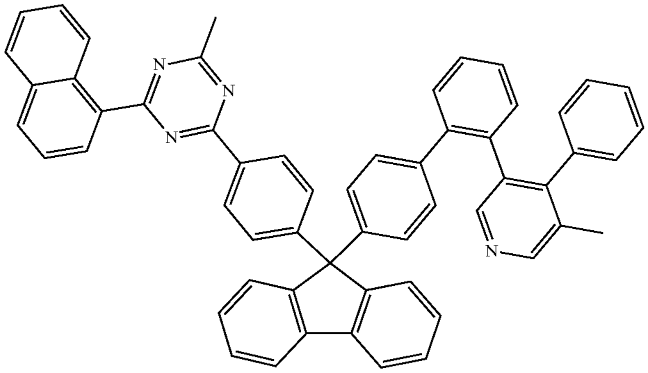

-continued
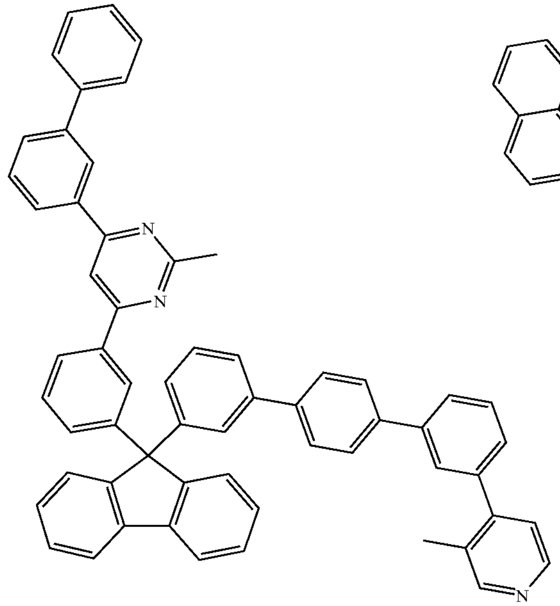
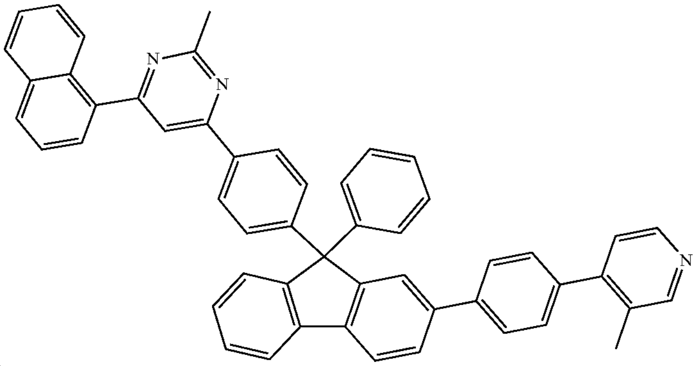
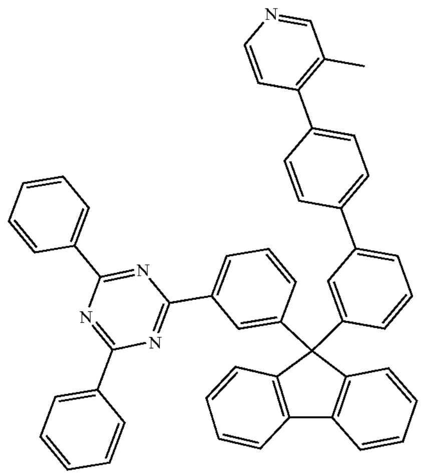
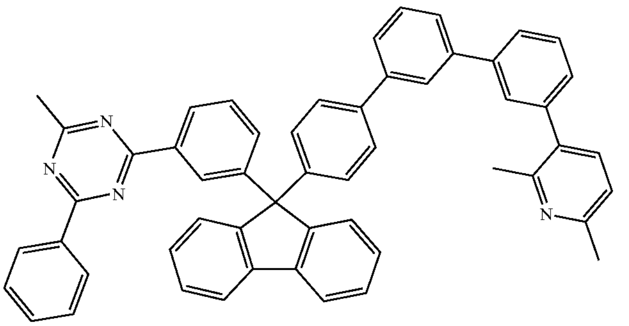
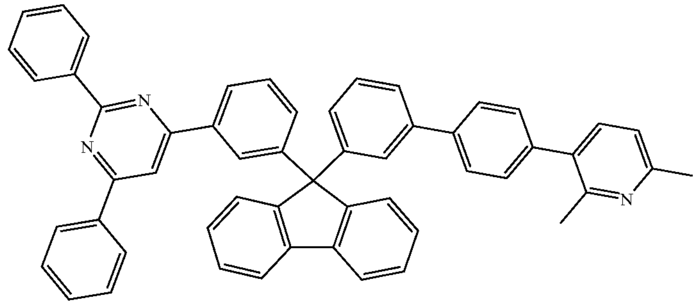

-continued
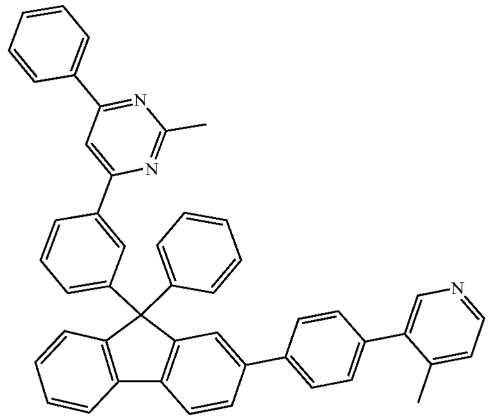
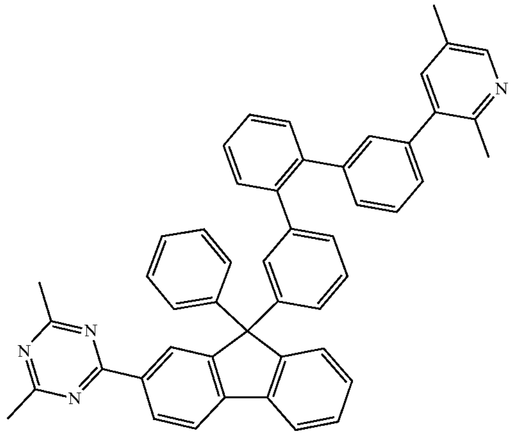
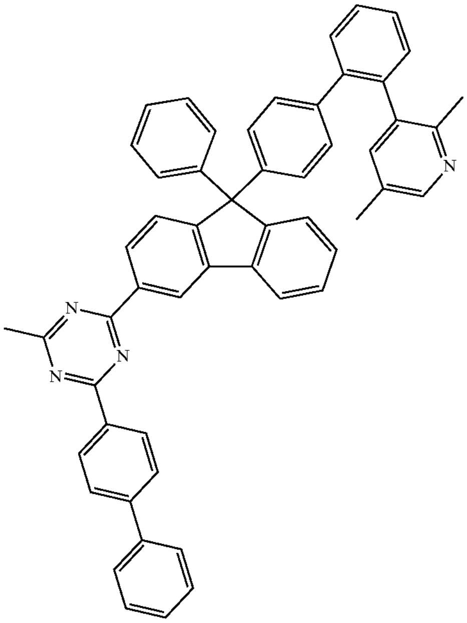
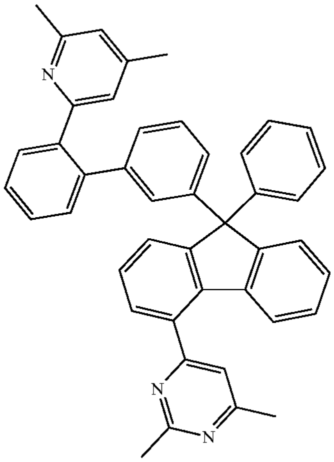

-continued
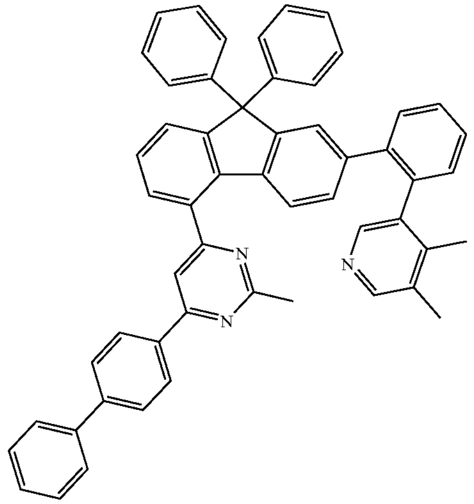
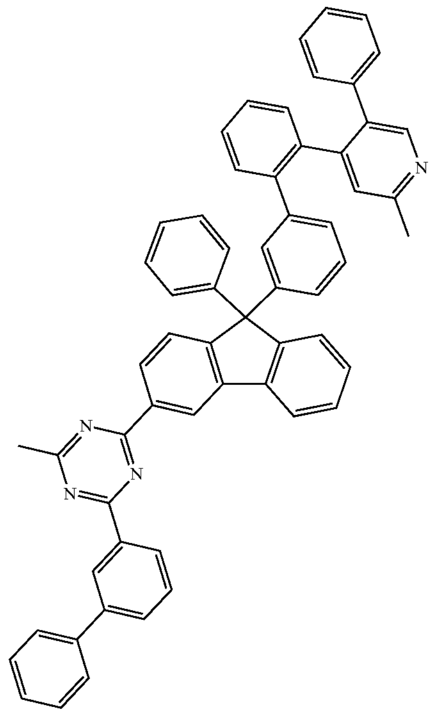
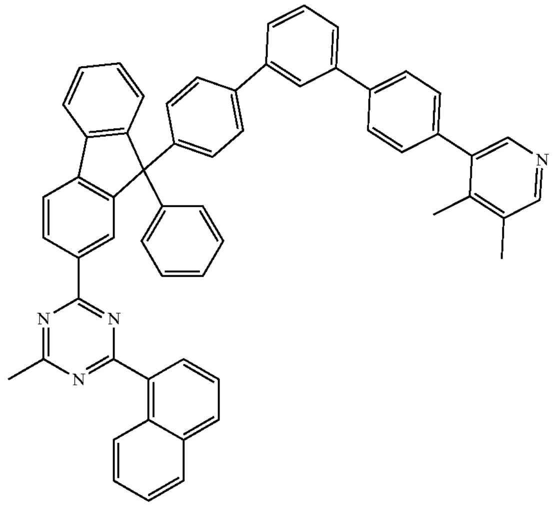
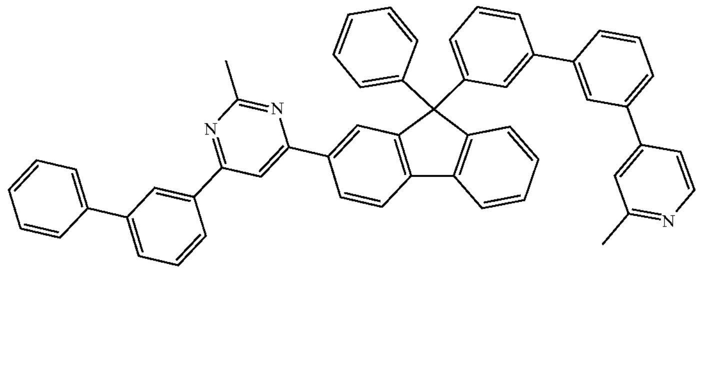

-continued
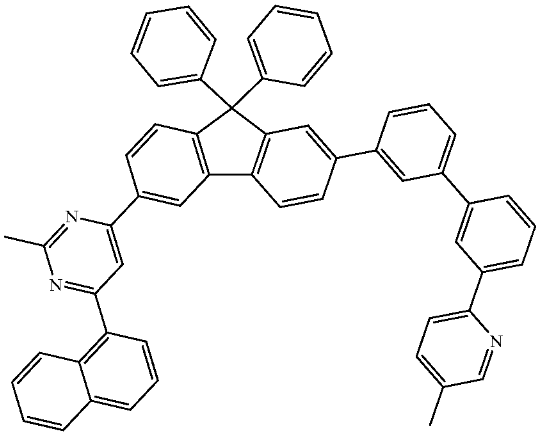
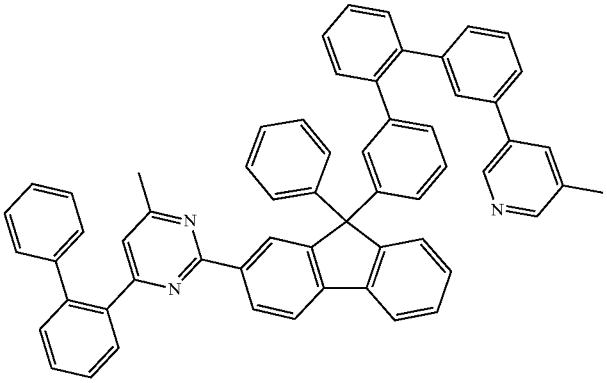
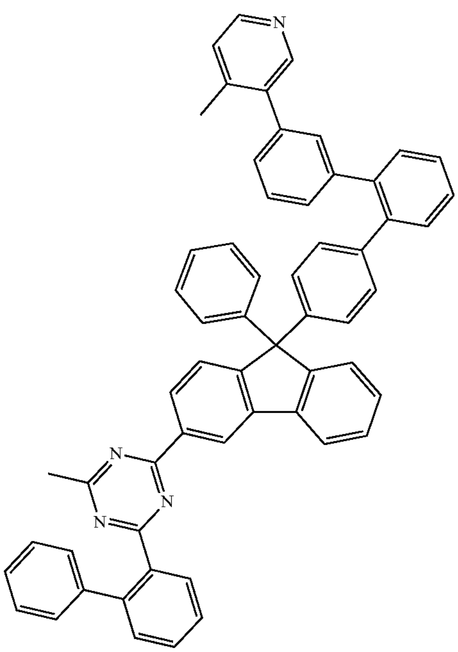
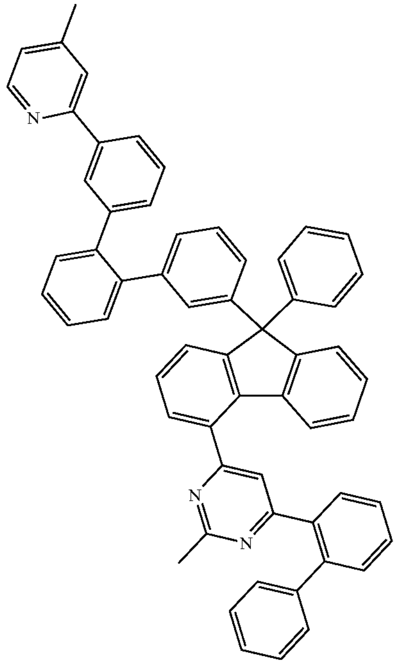
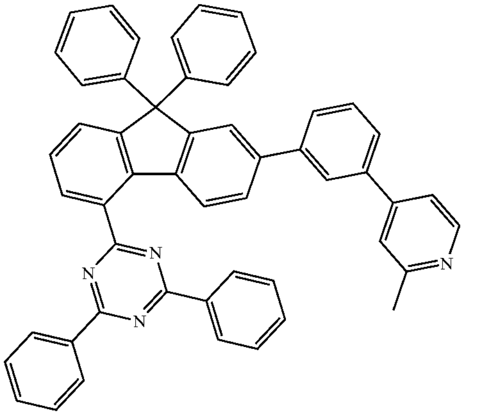
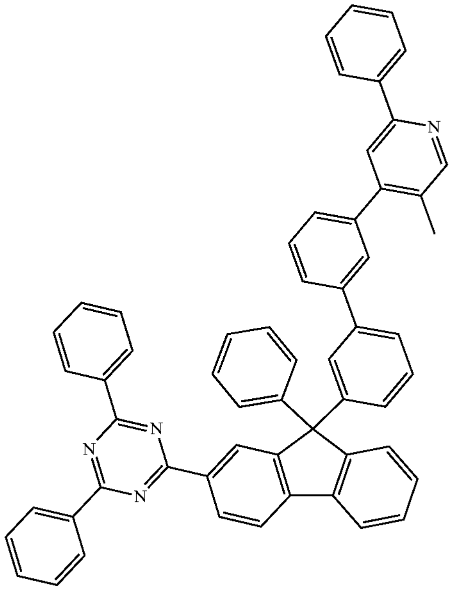

-continued
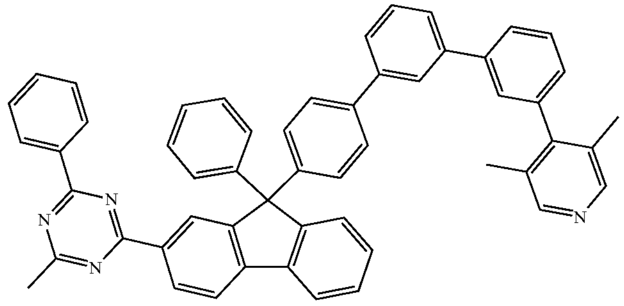
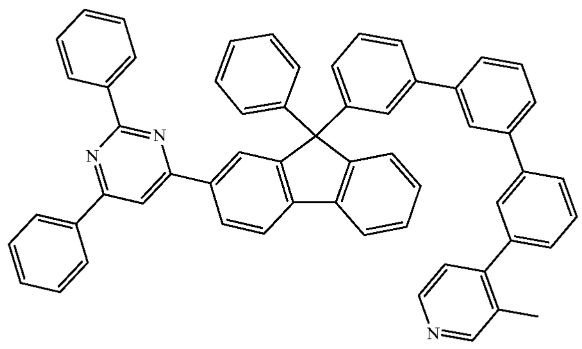
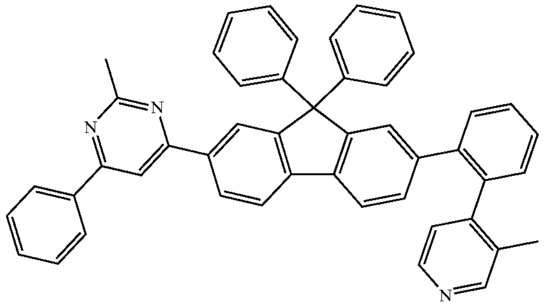
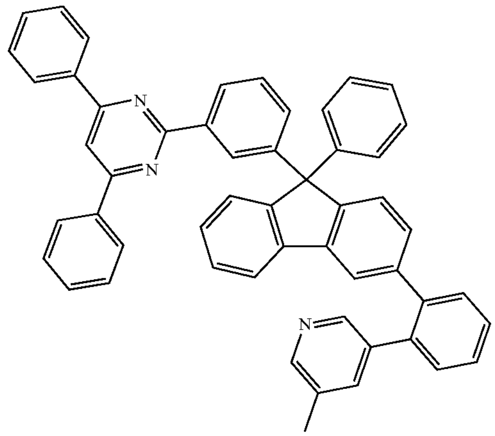
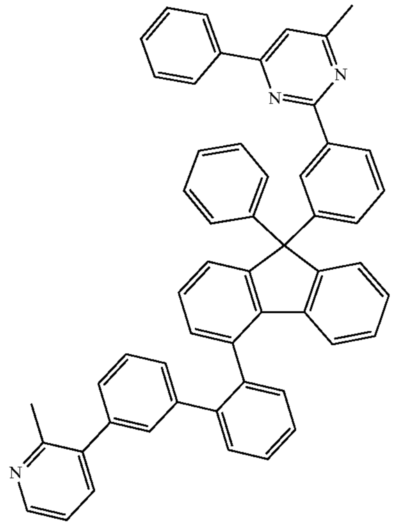

-continued
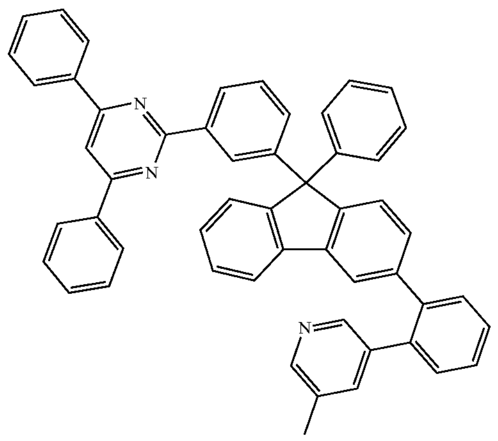
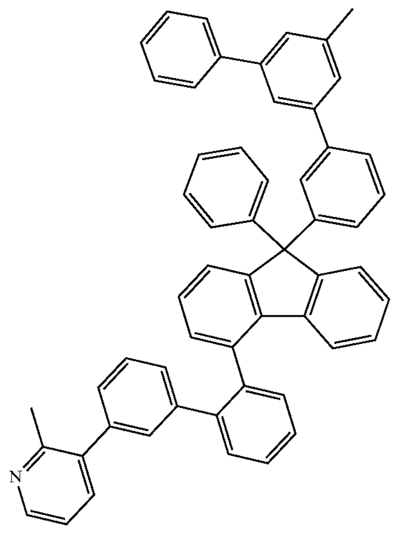
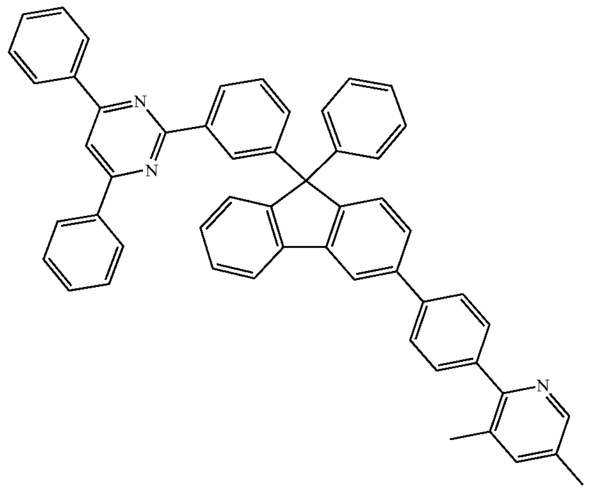
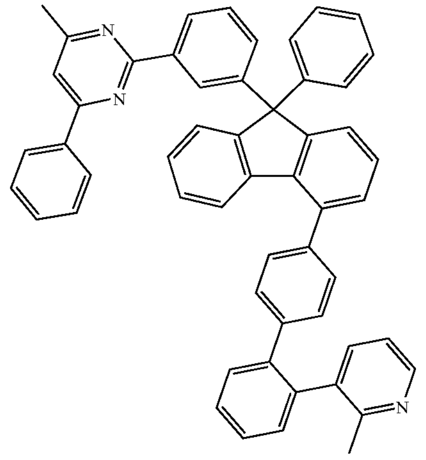
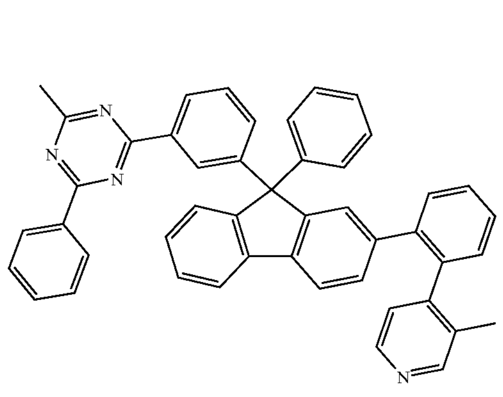
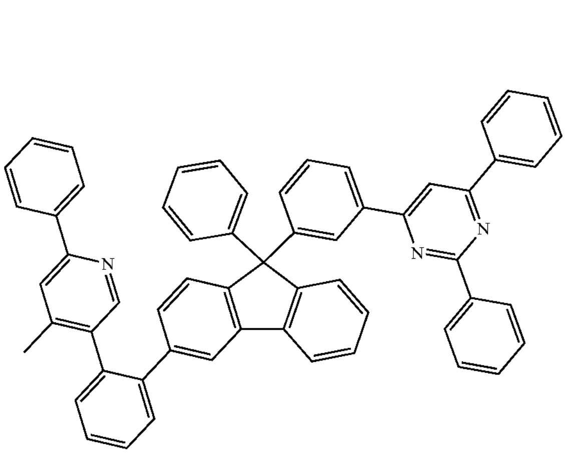

-continued
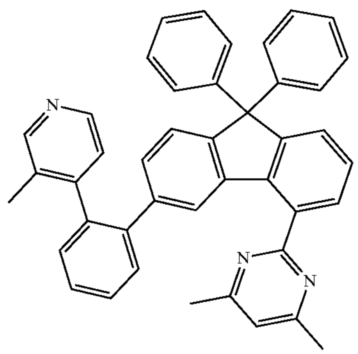
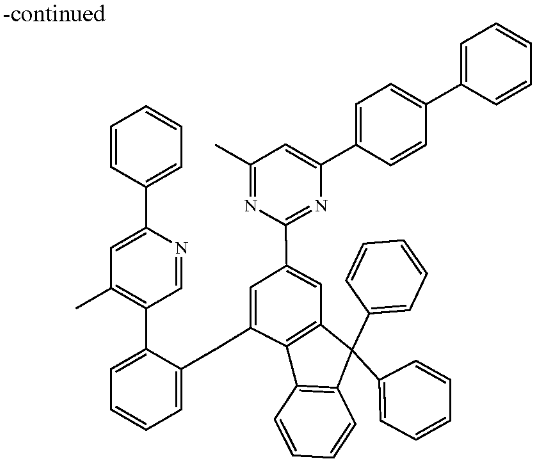
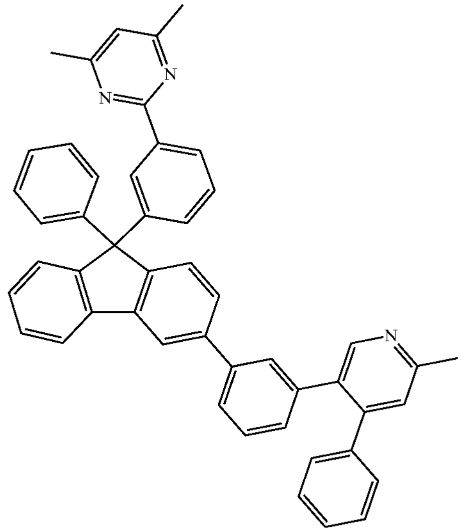
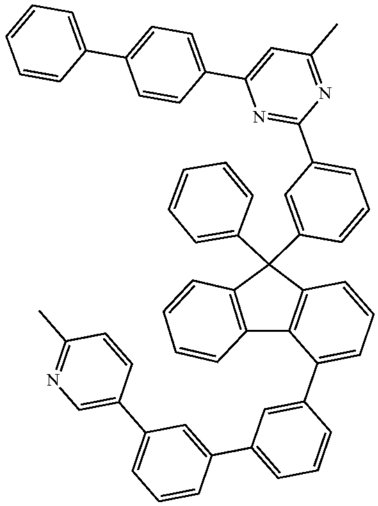
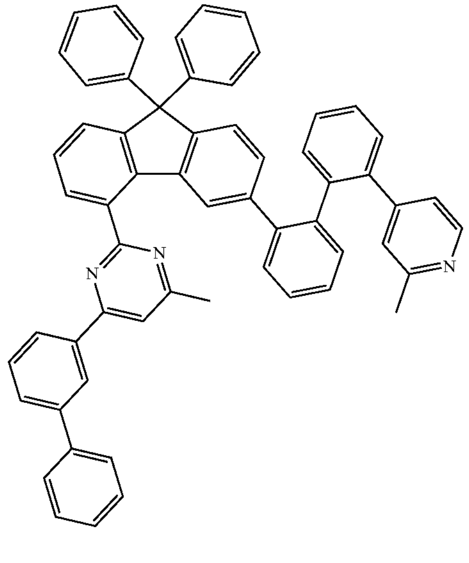
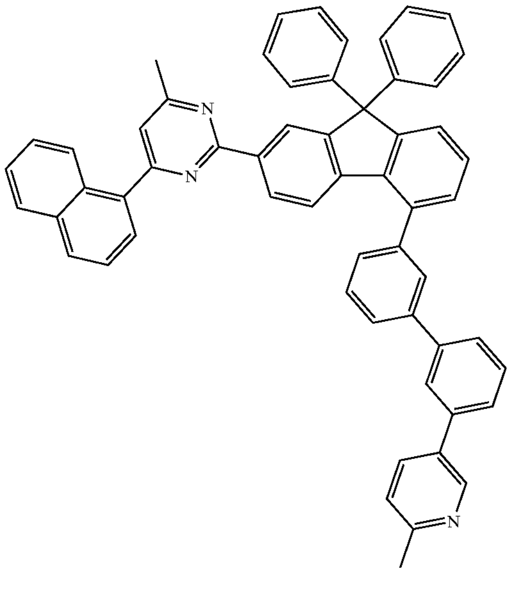

-continued
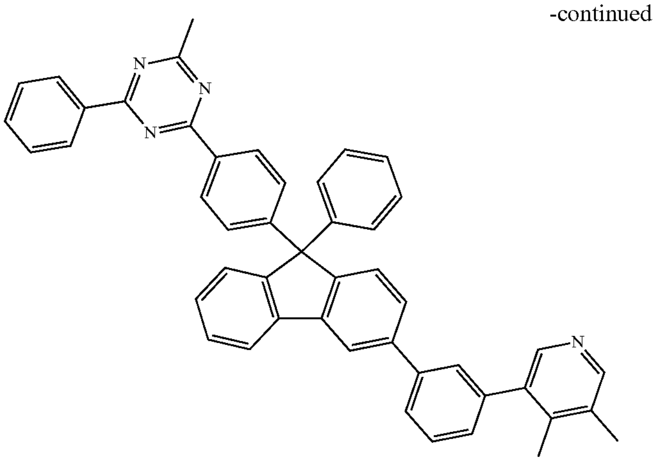
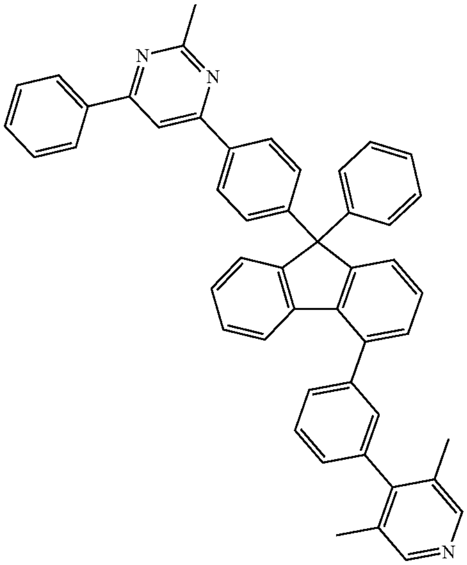
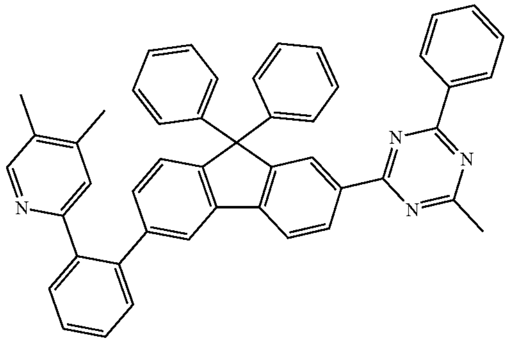
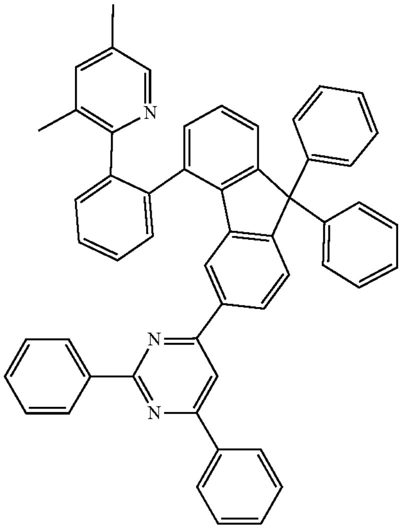
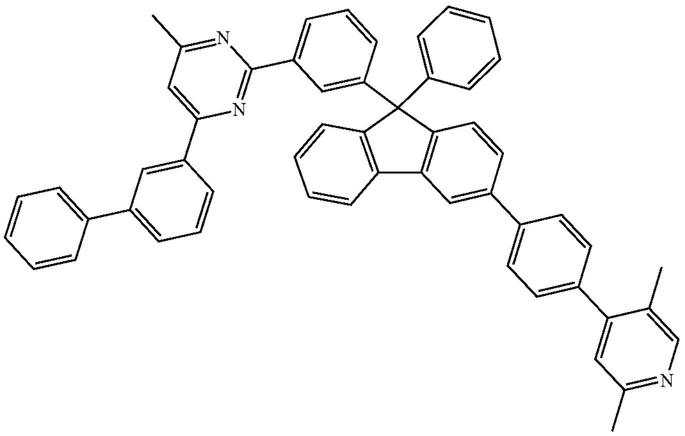

-continued
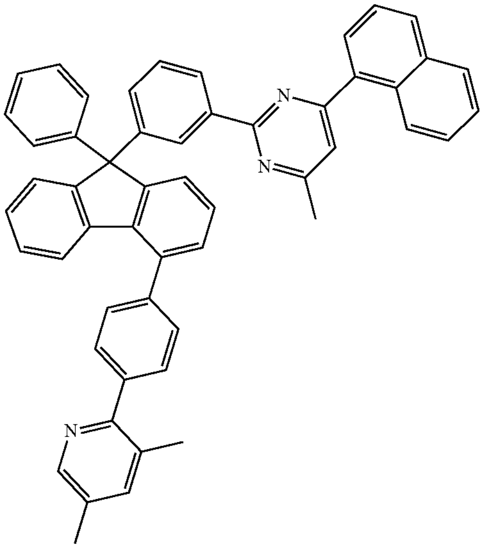
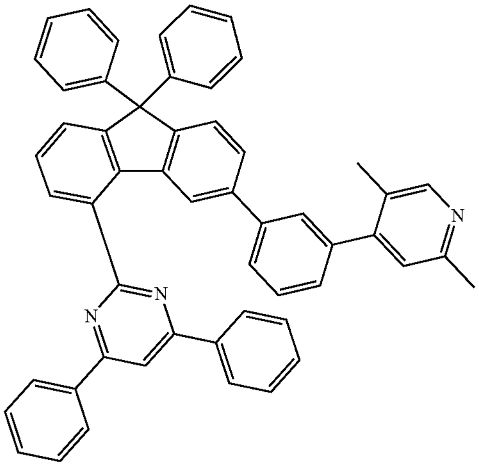
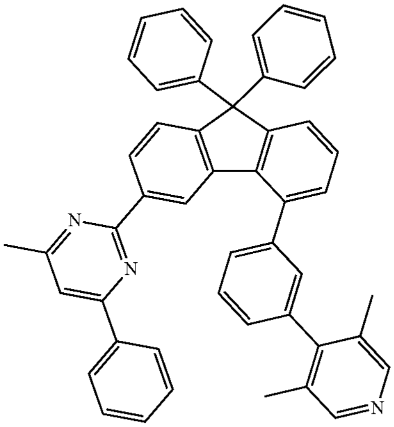
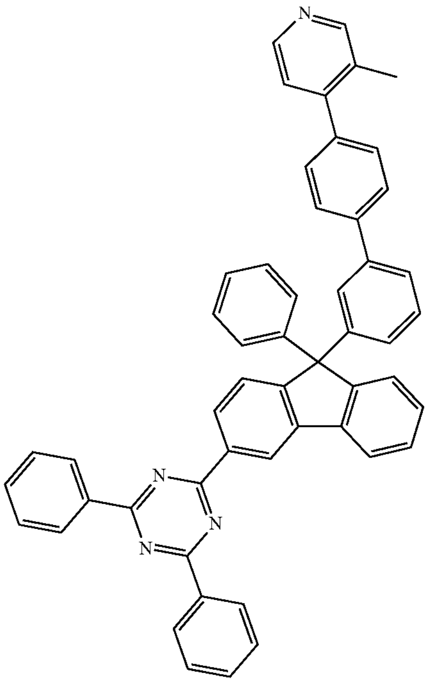
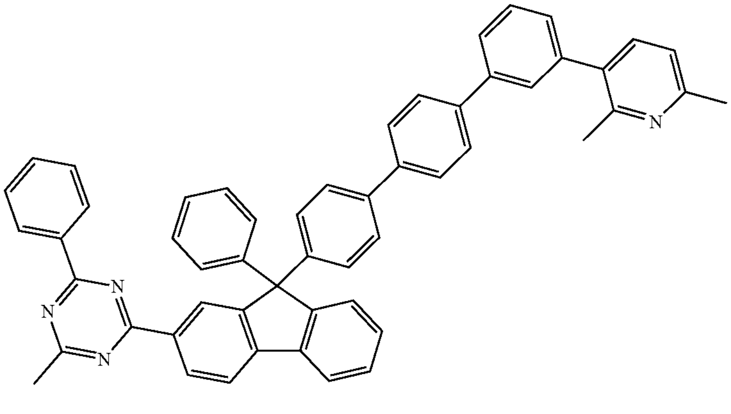

-continued
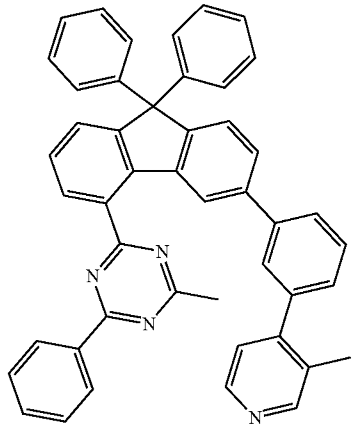
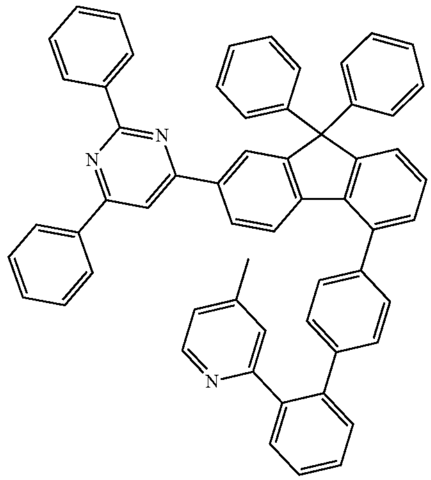
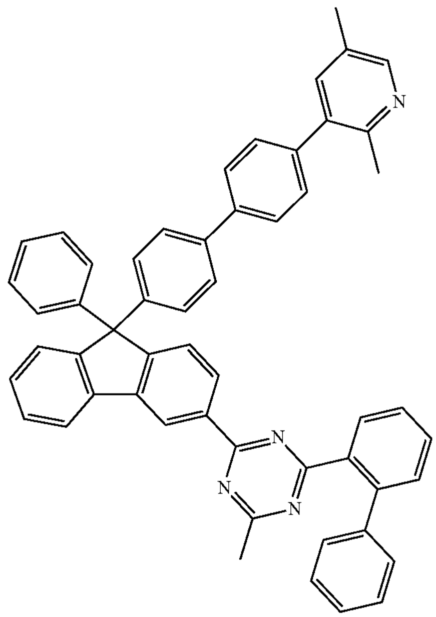
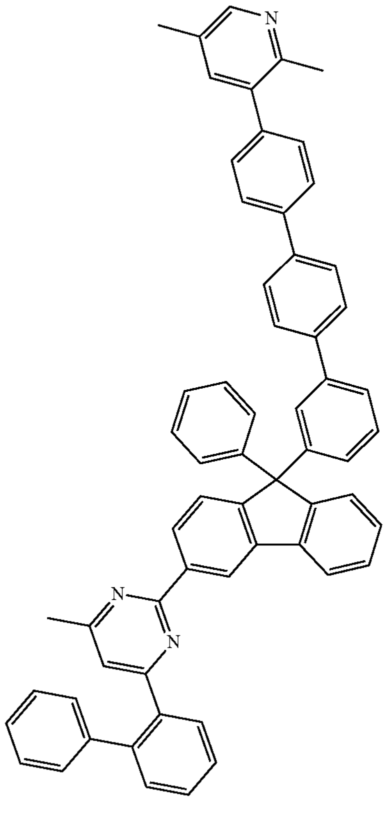

-continued
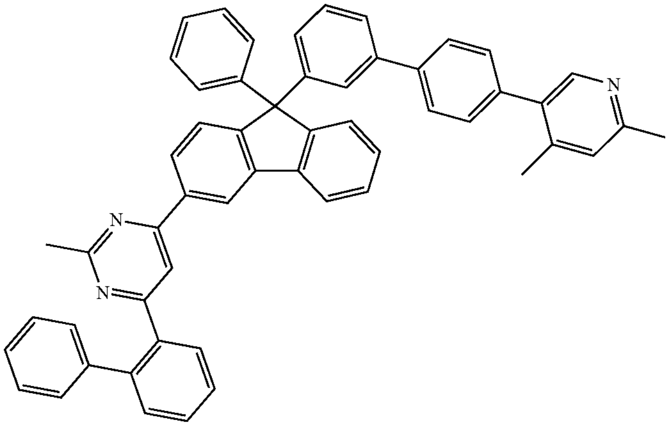
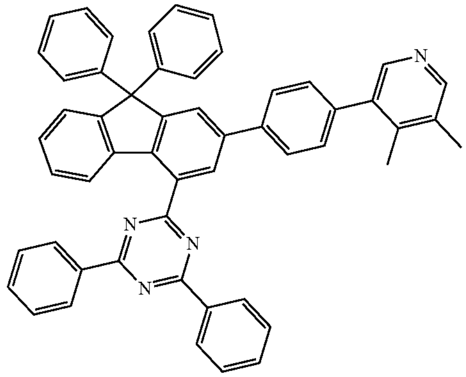
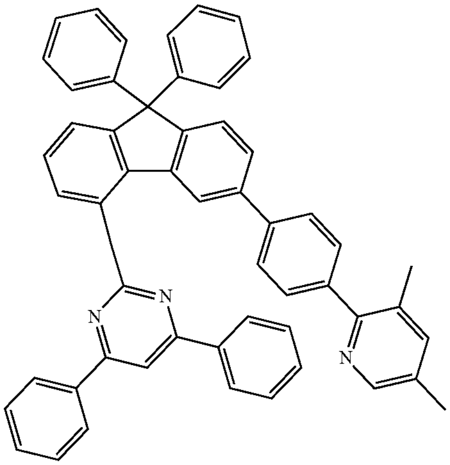
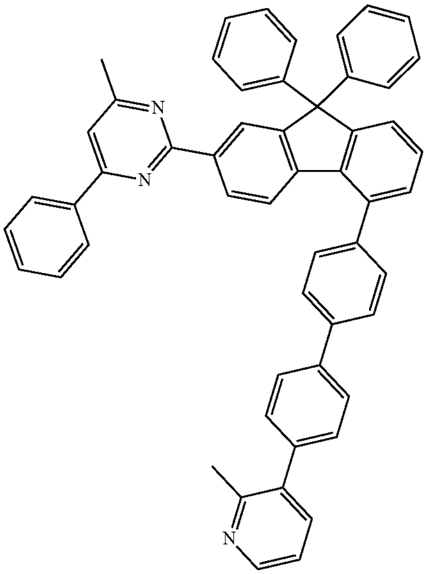
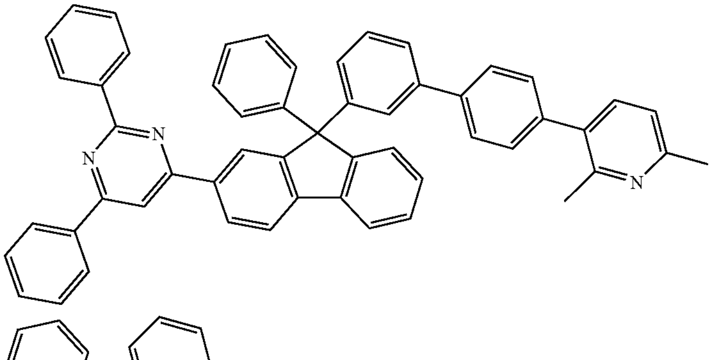
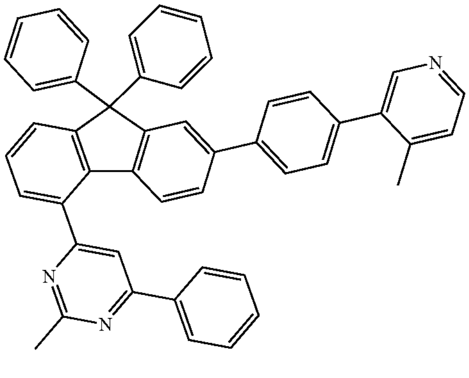

-continued
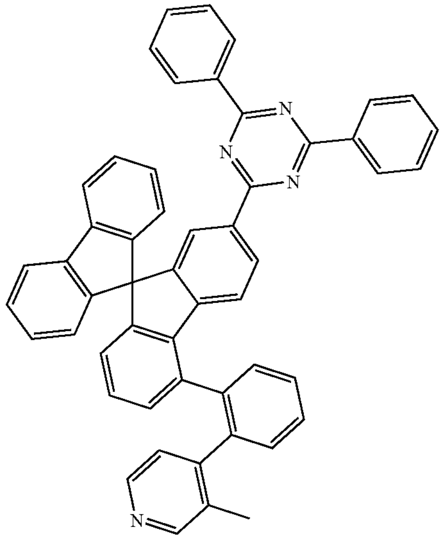
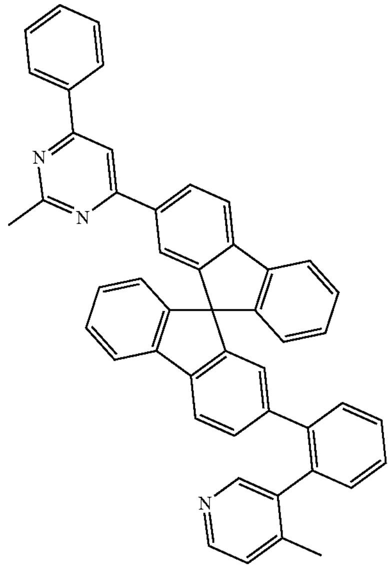
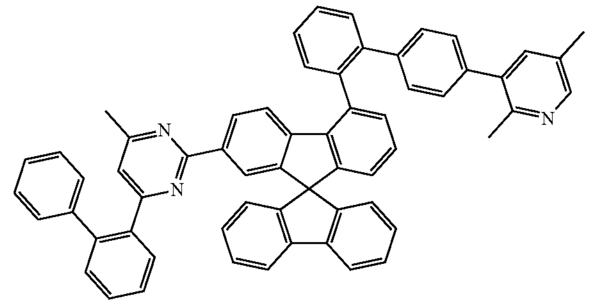
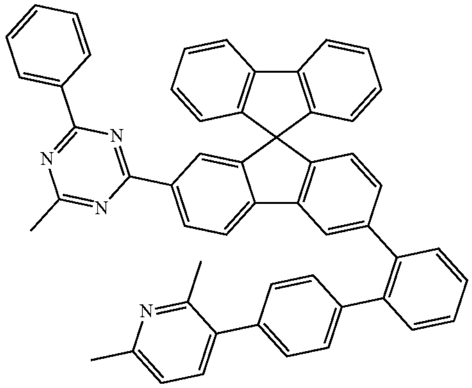
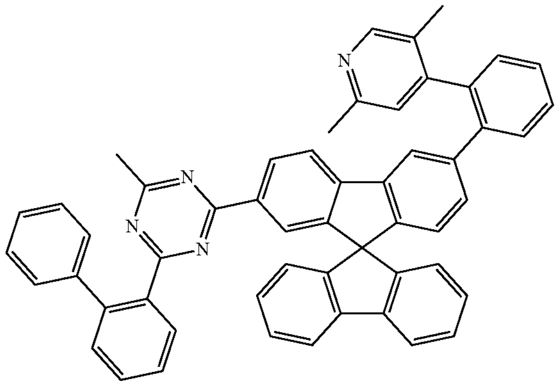
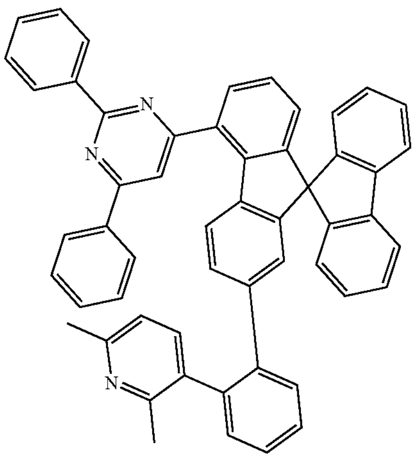
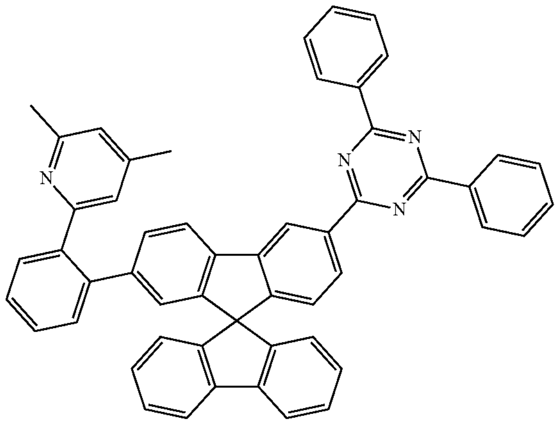

-continued
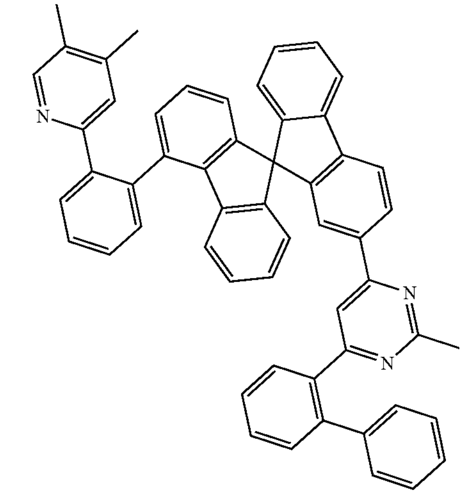
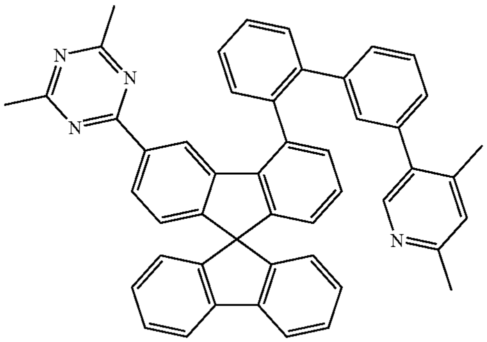
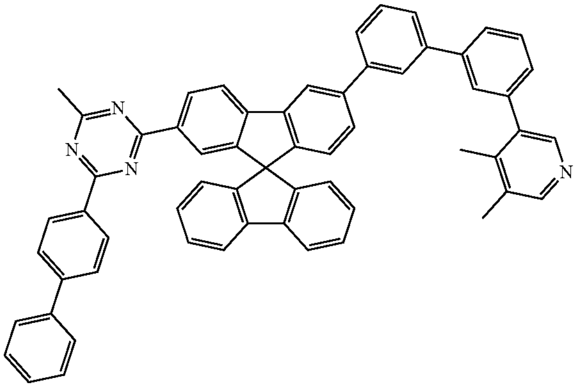
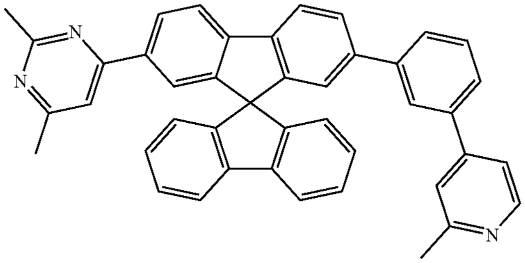
-continued
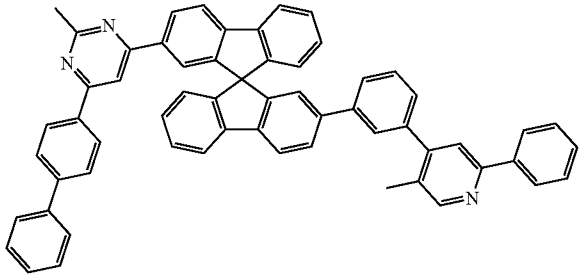
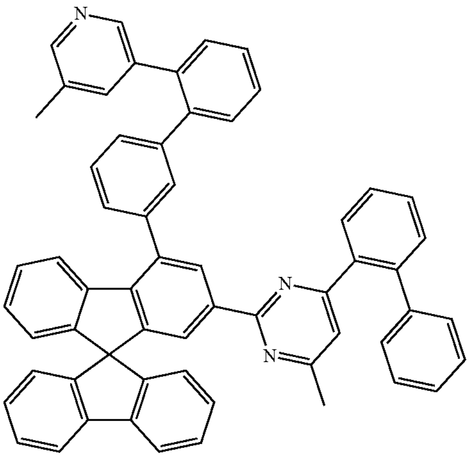
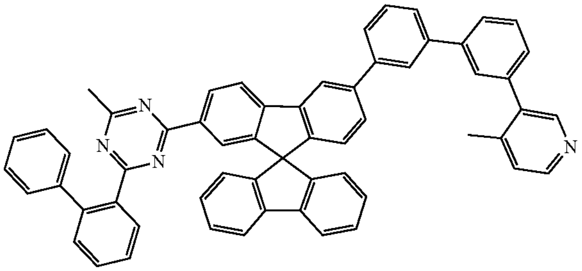
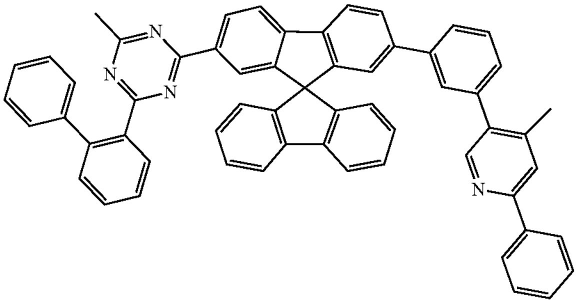
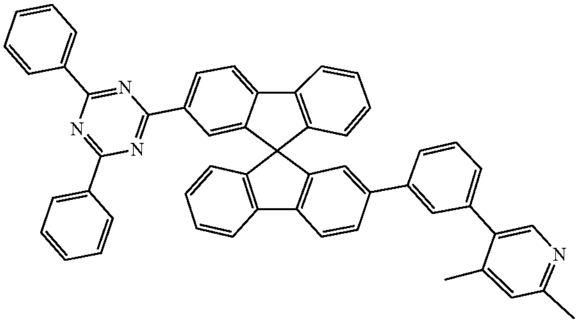

-continued
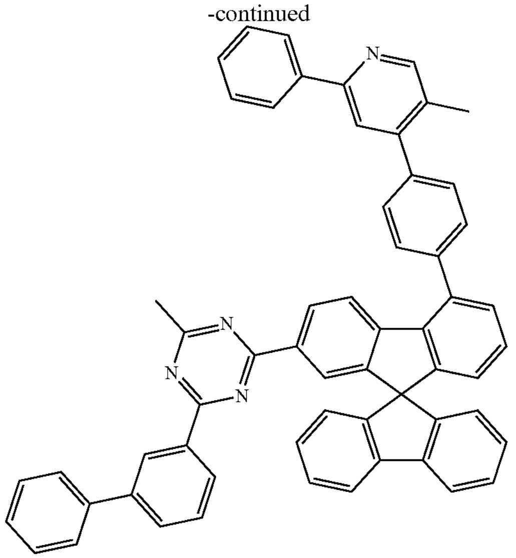
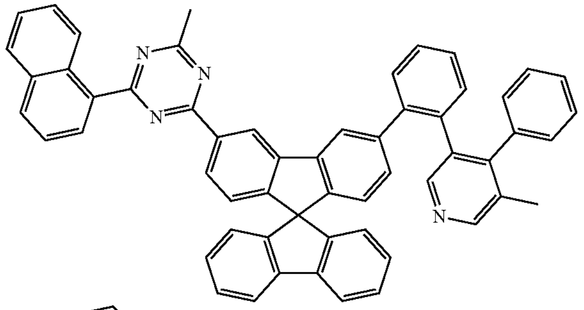
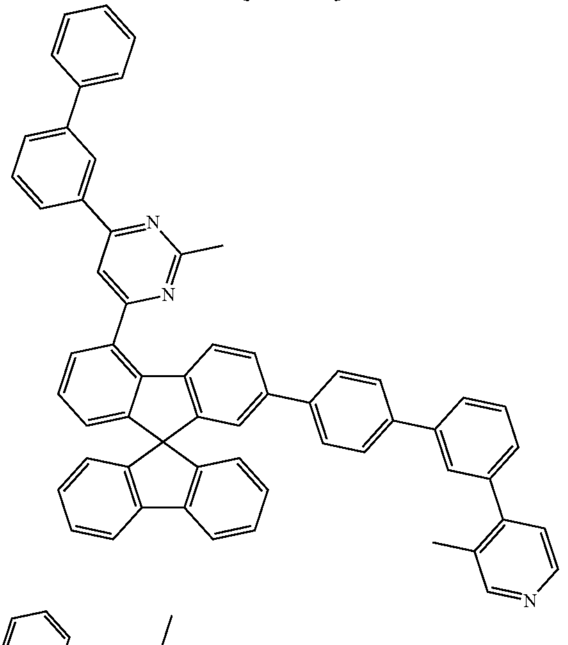
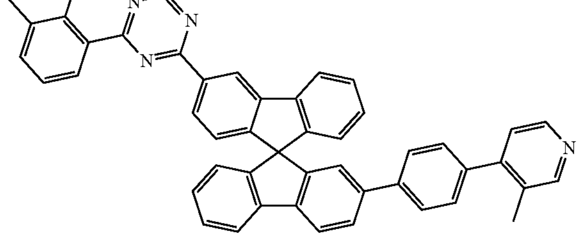
-continued
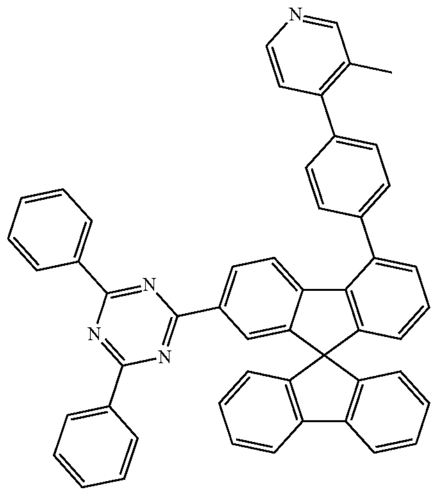
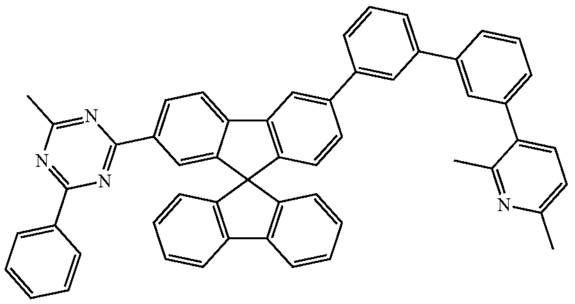
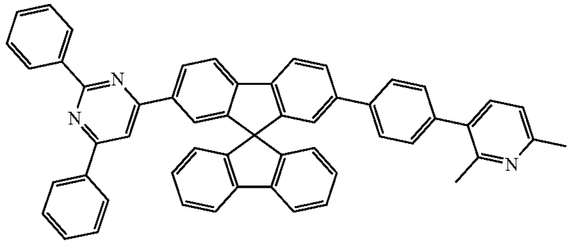
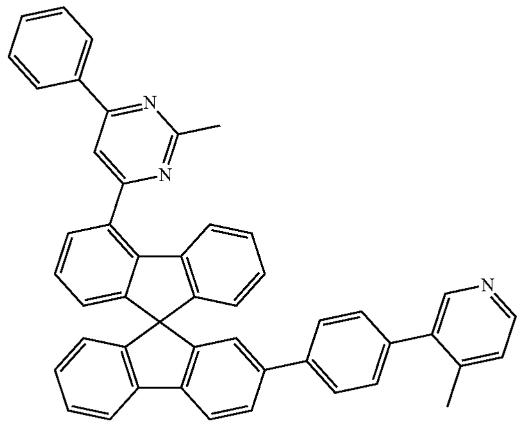

-continued
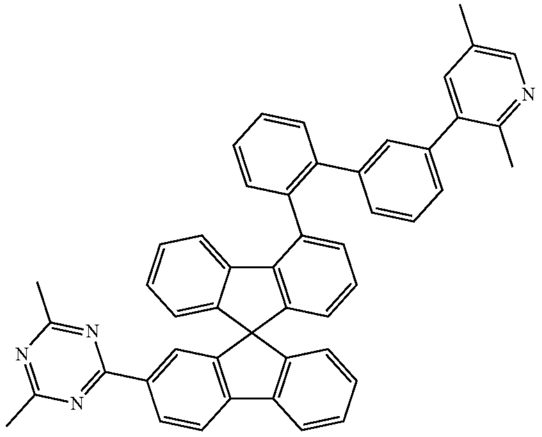
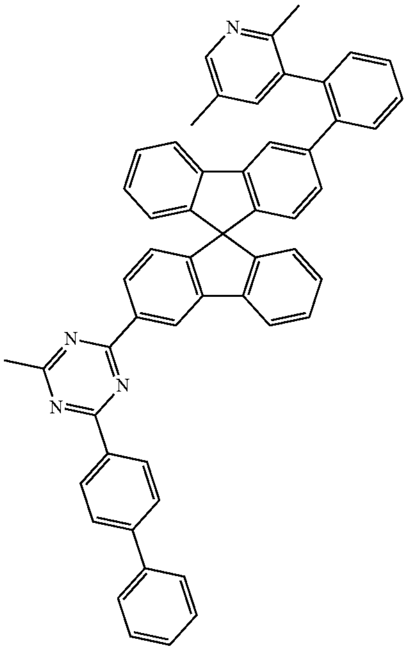
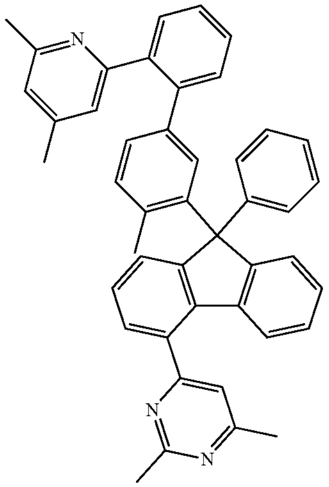
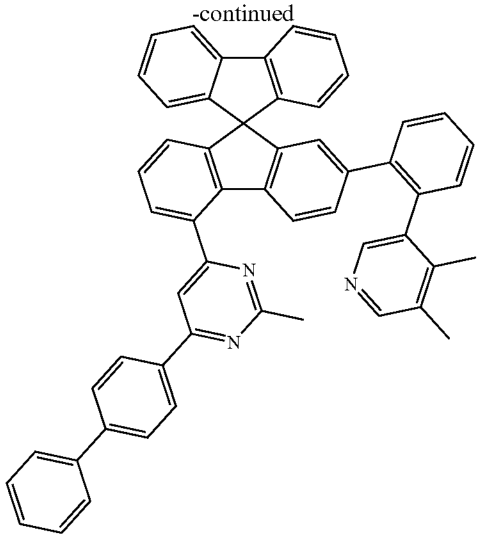
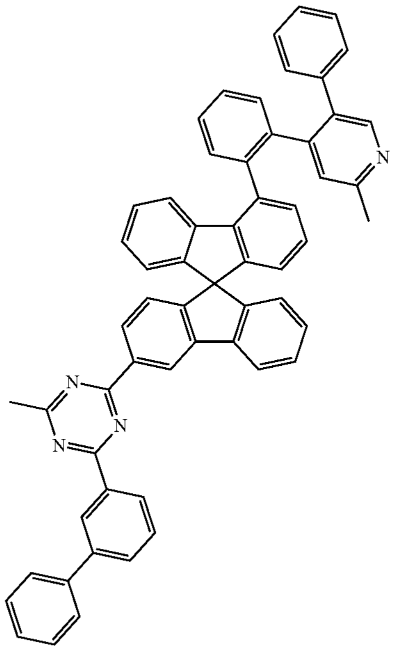
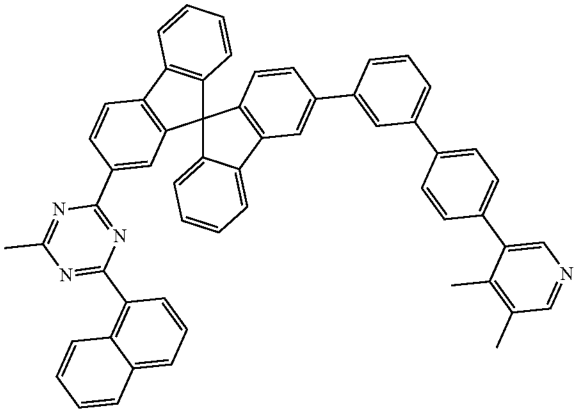
-continued -continued
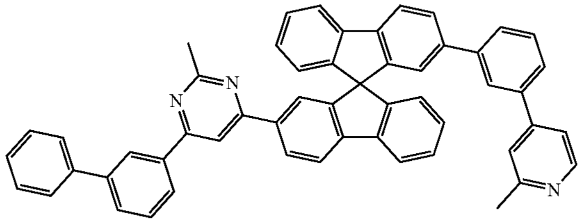
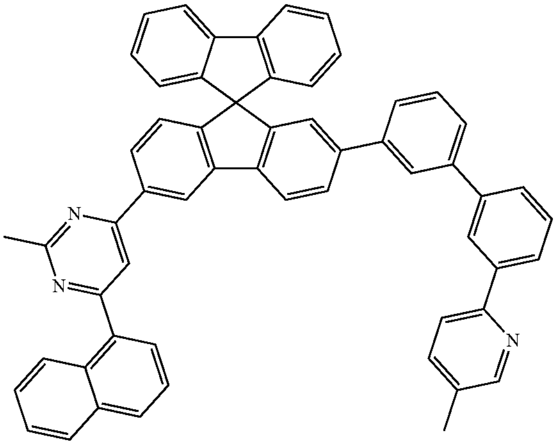
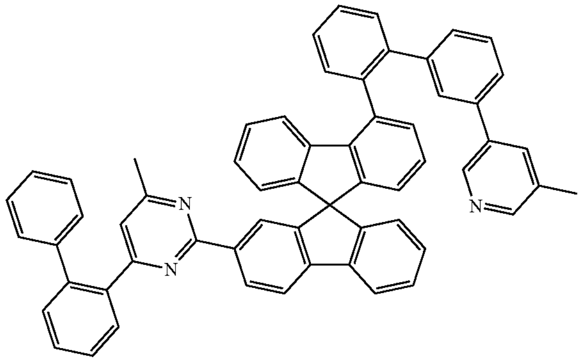
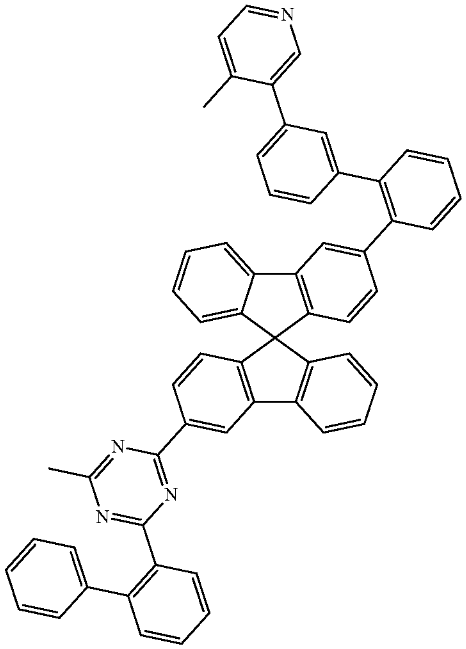
-continued
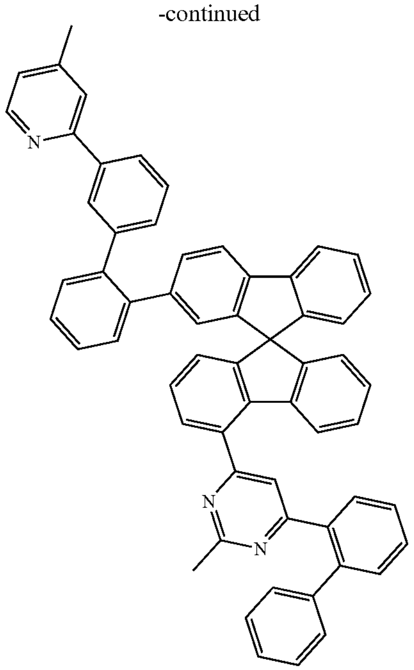
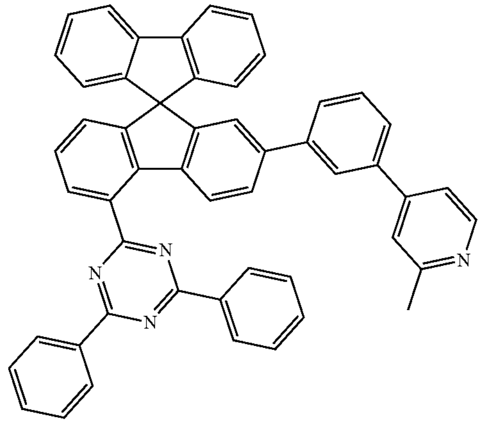
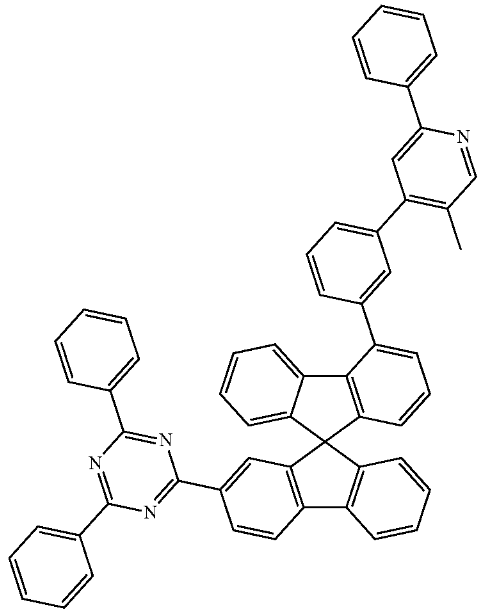

-continued
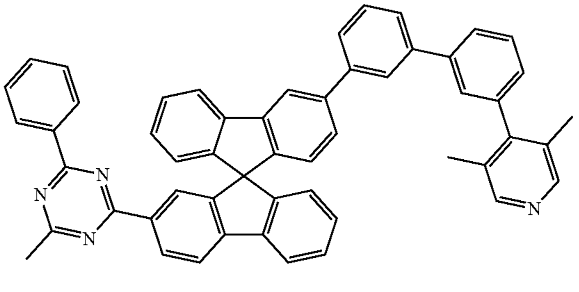
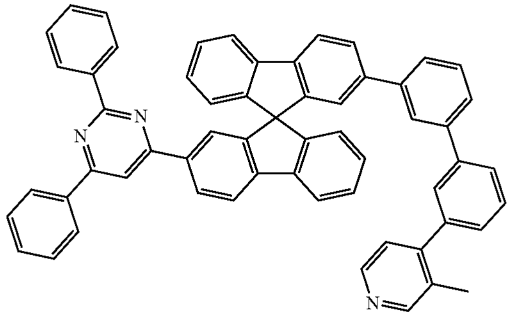
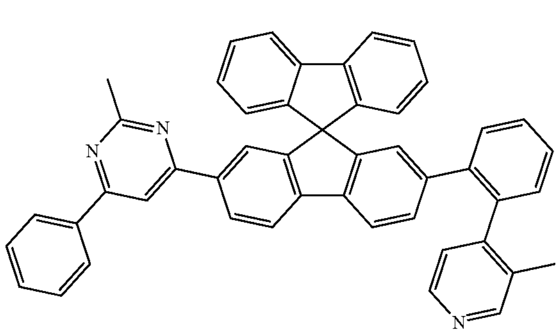
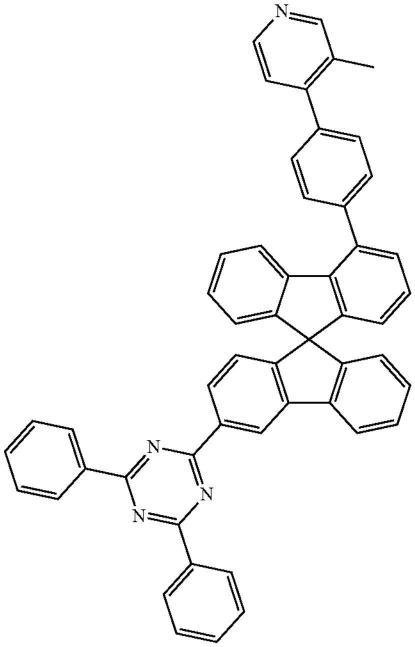
-continued
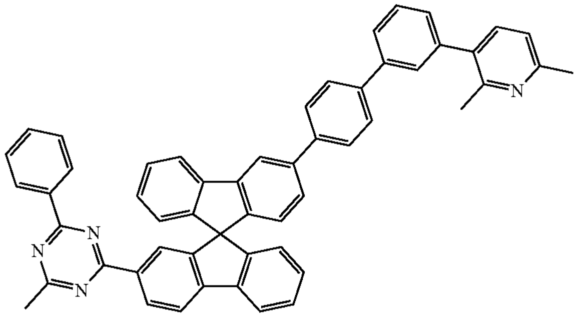
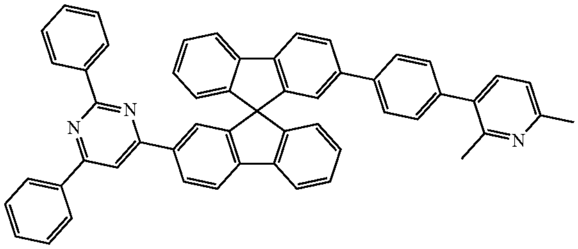
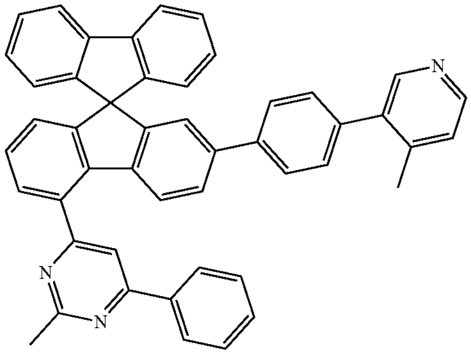
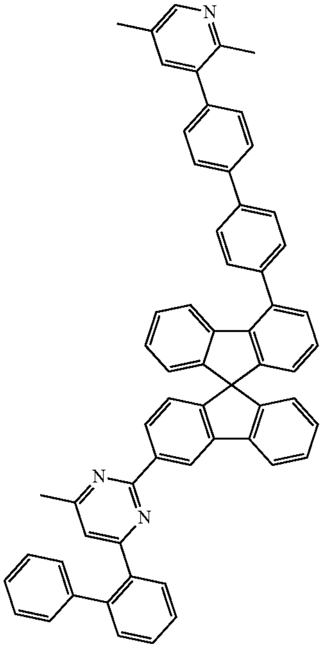

-continued
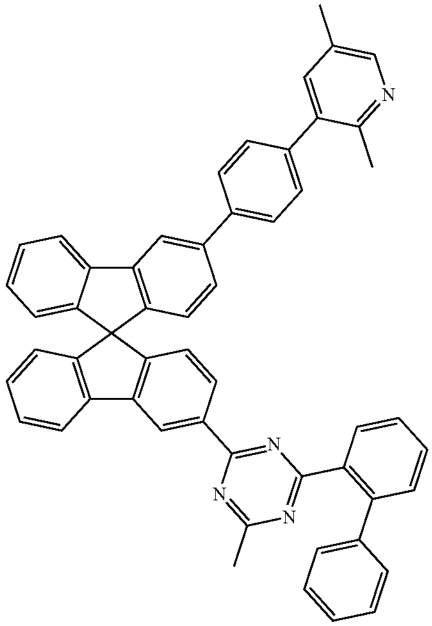
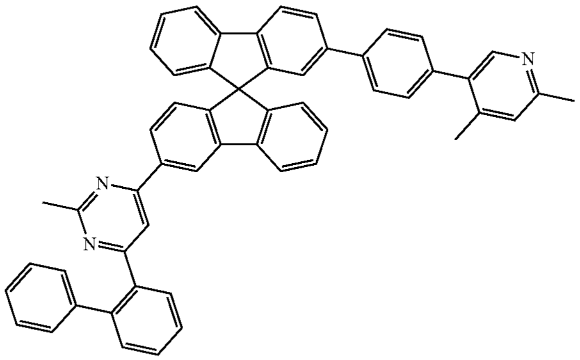
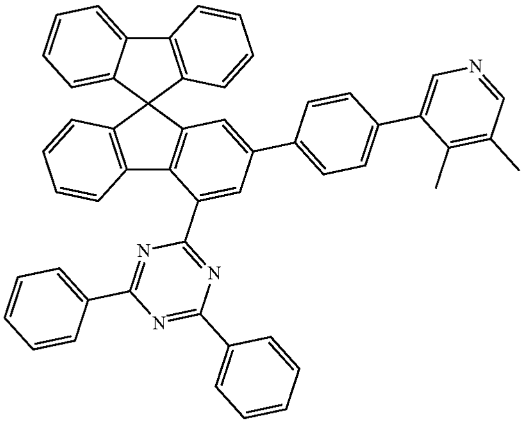
-continued
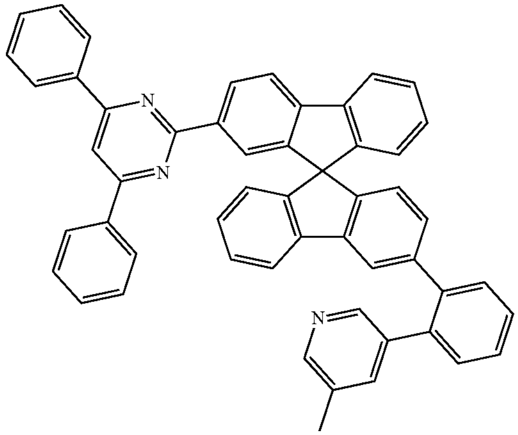
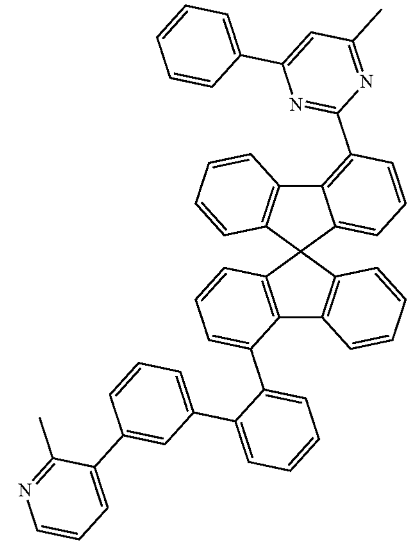
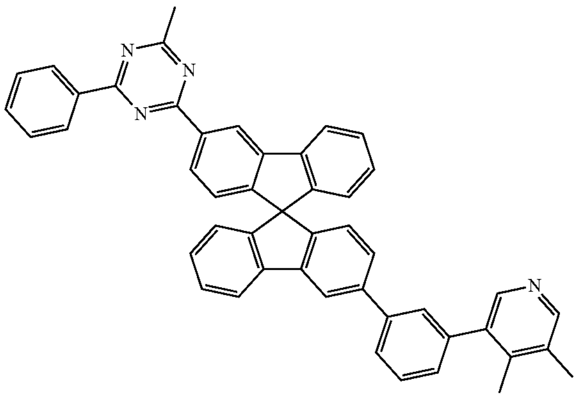

-continued
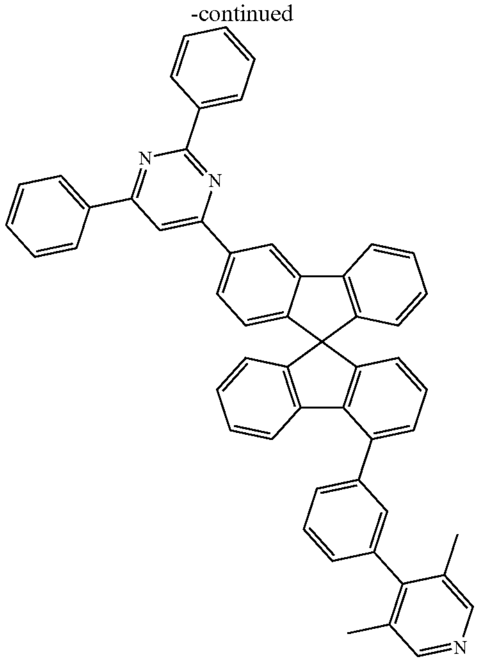
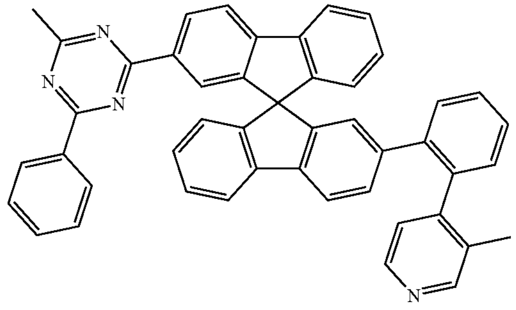
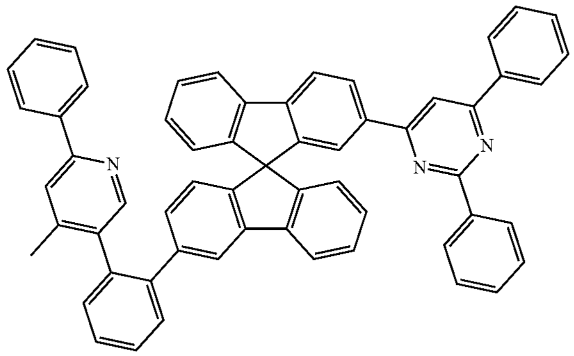
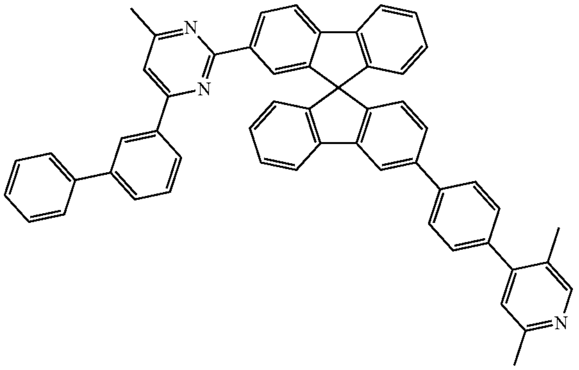
-continued
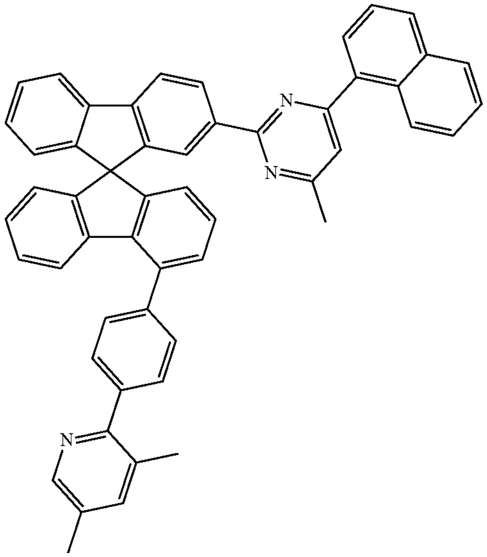
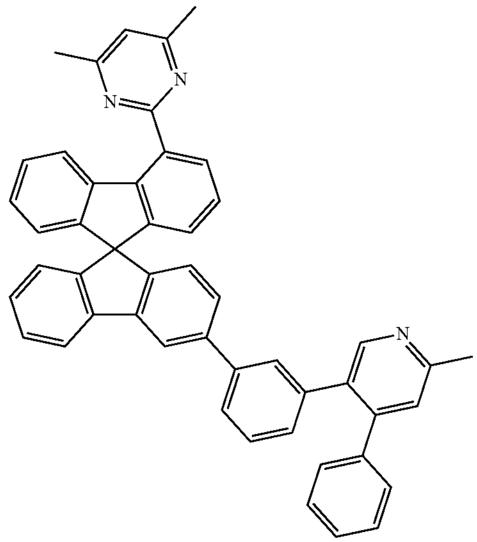
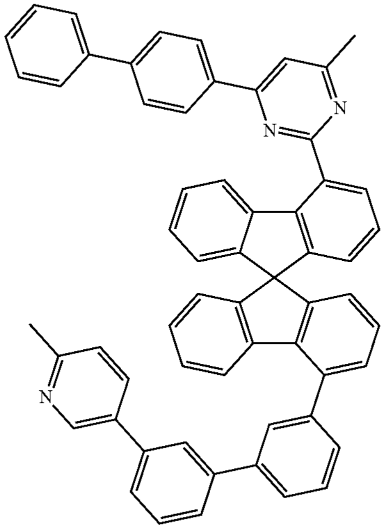

-continued
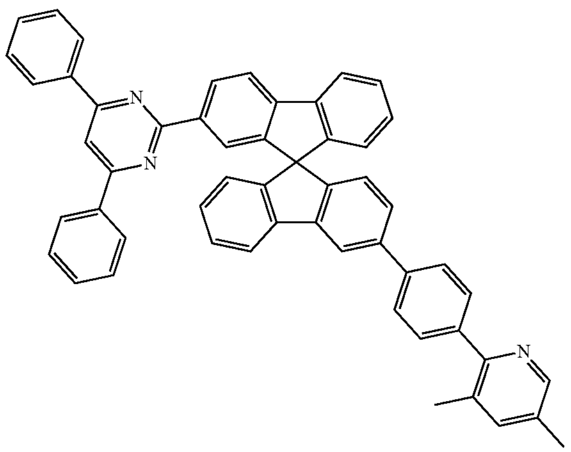
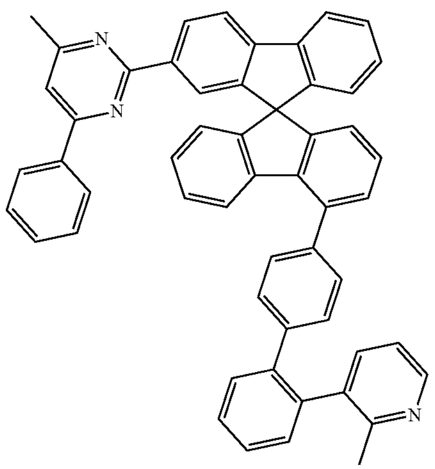
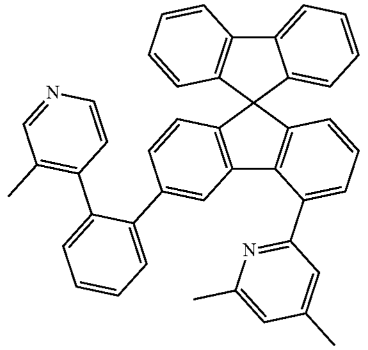
-continued
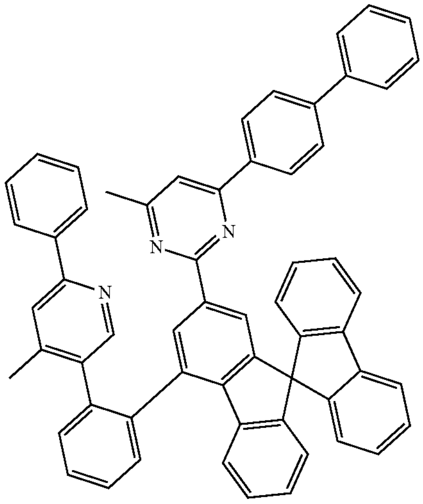
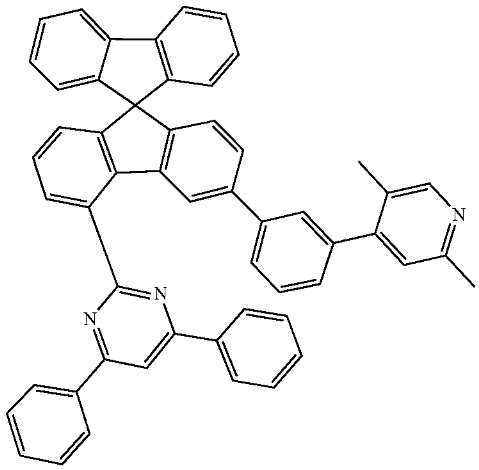
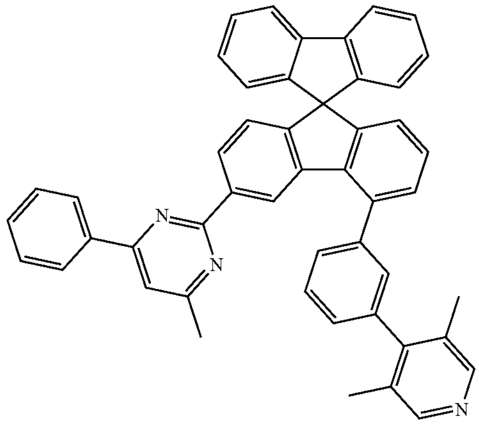

-continued
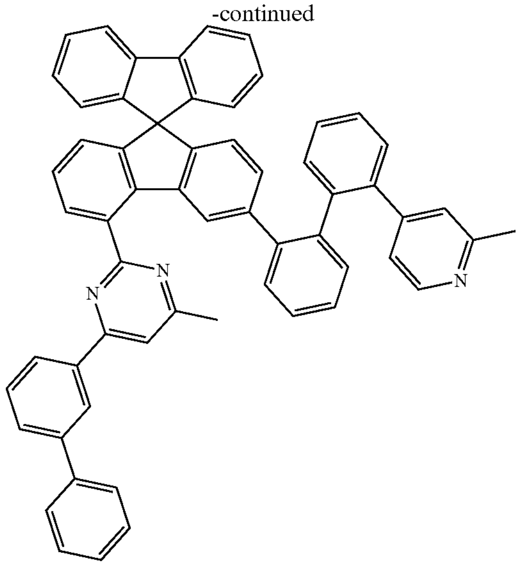
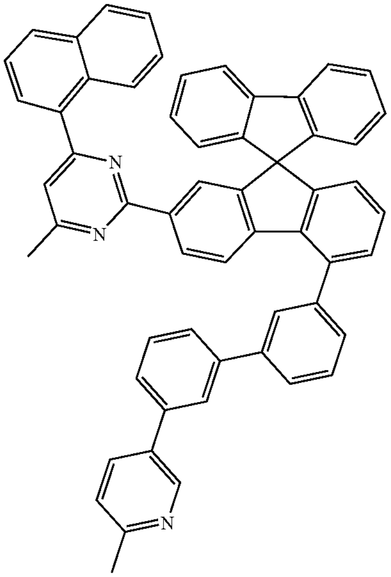
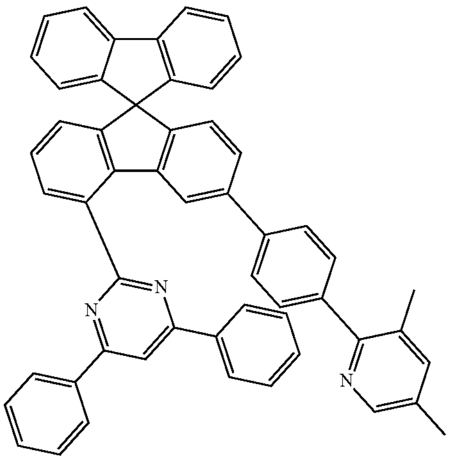
-continued
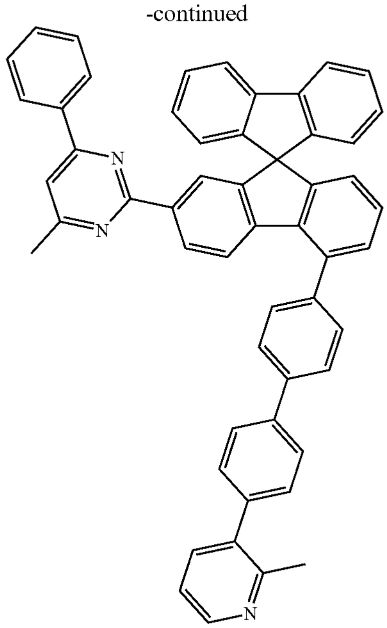
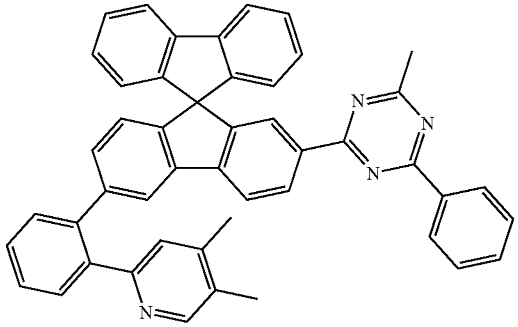
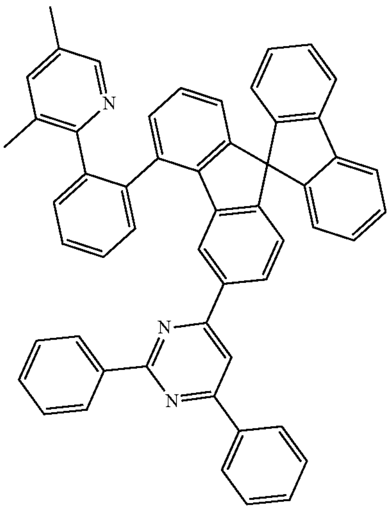

-continued
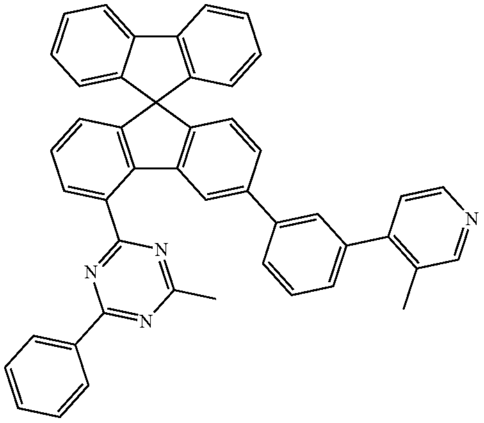
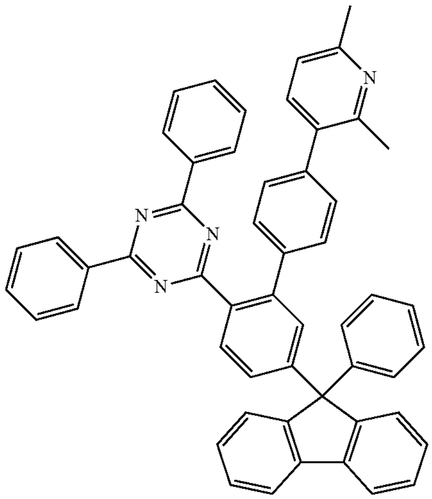
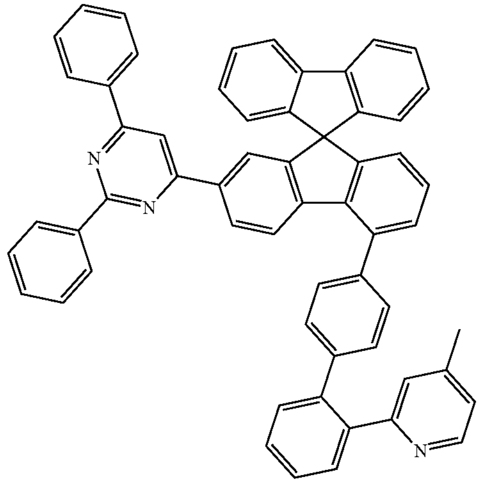
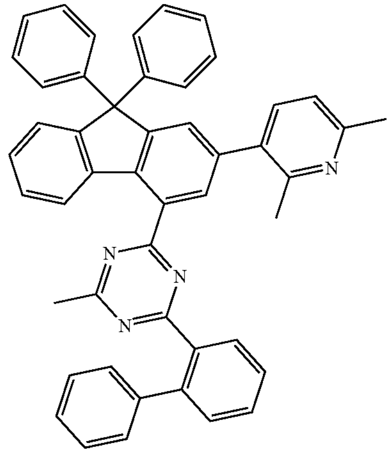
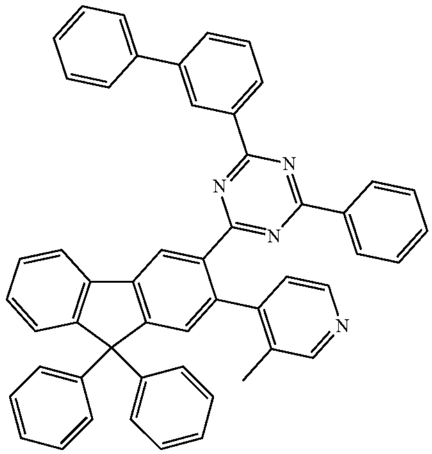
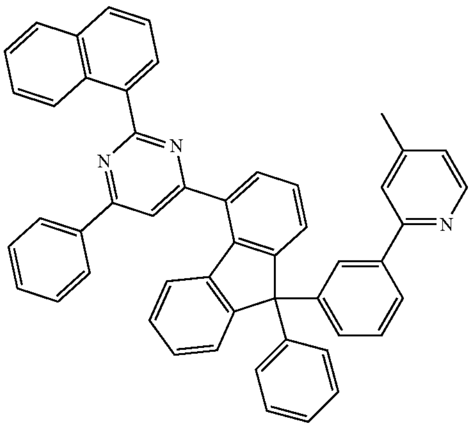
-continued -continued
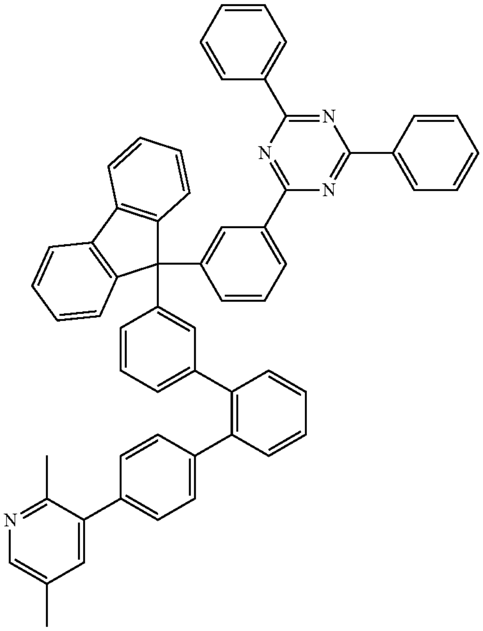
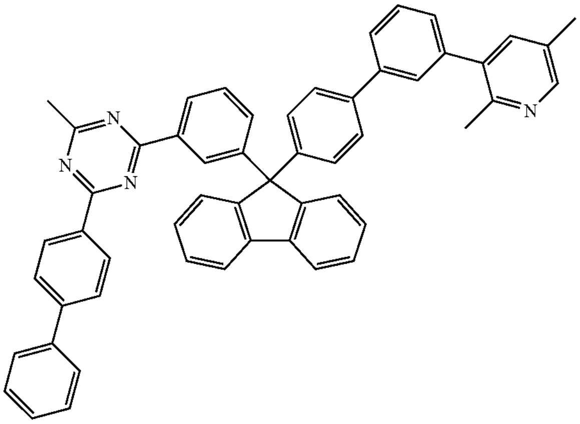
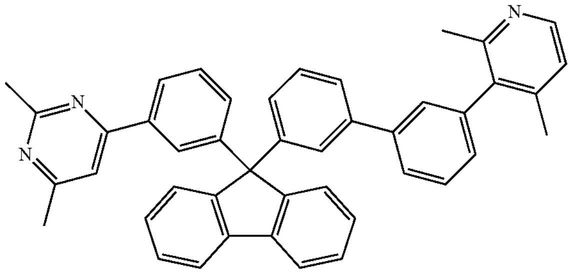
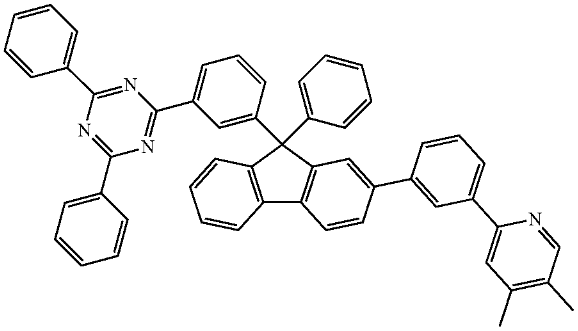
-continued
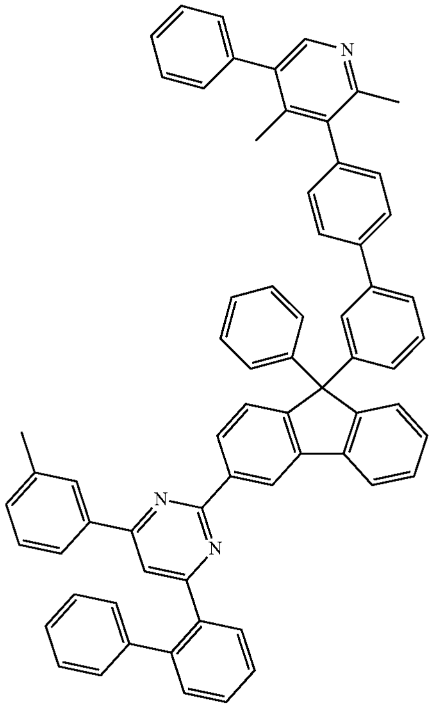
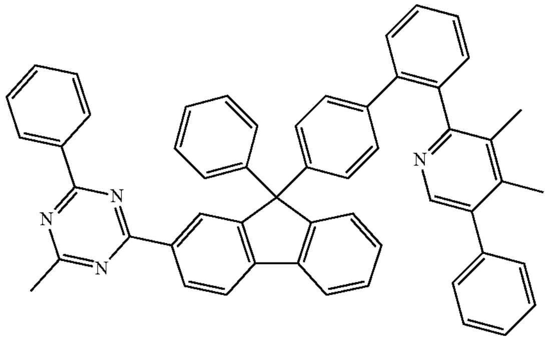
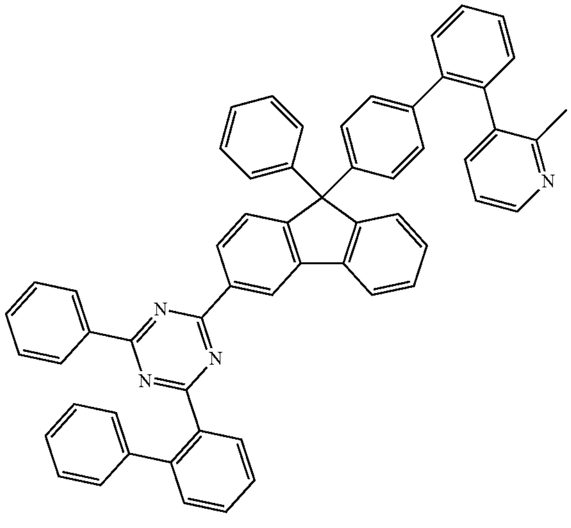

-continued
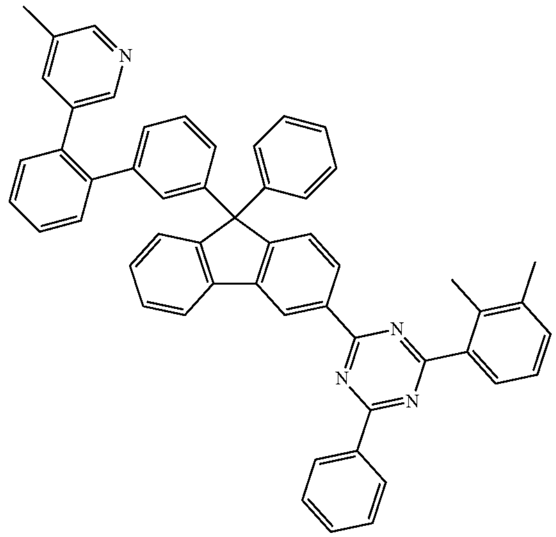
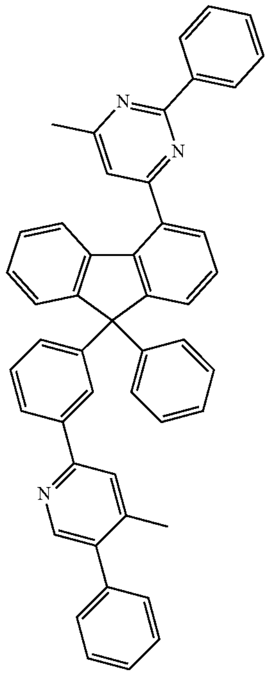
-continued
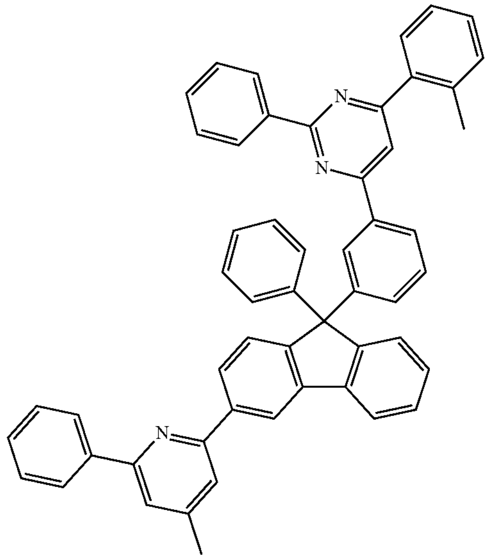
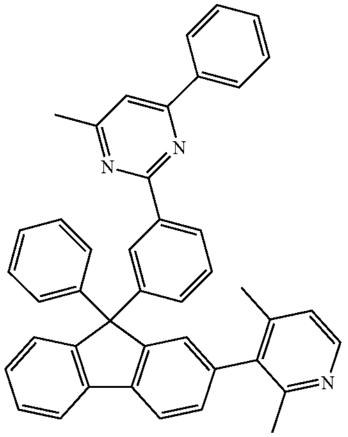
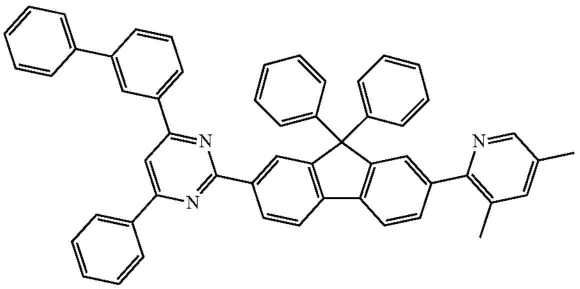

-continued
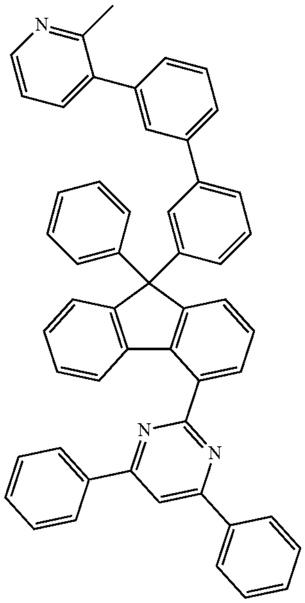
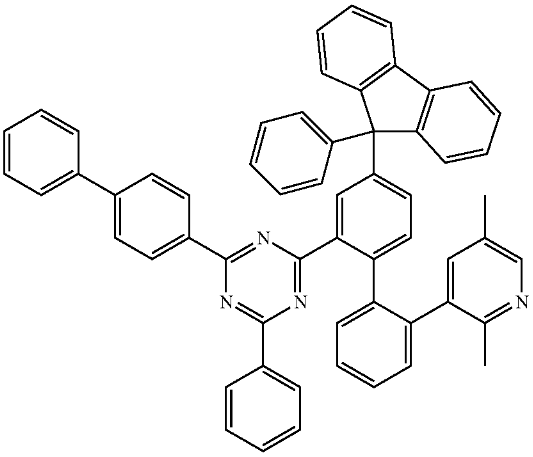
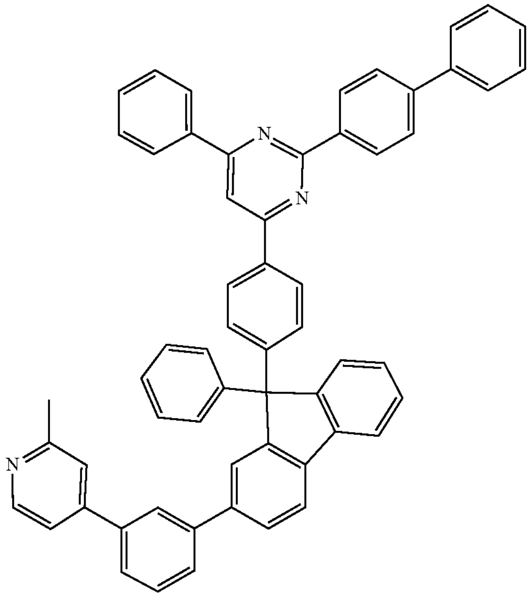
-continued
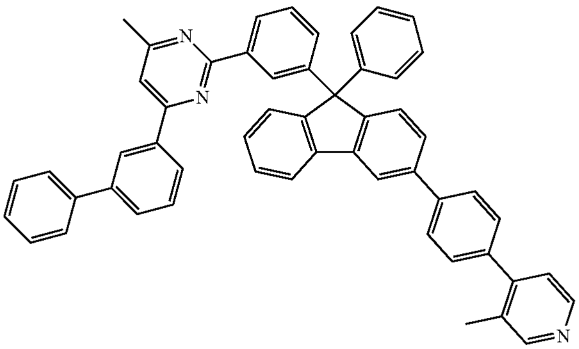
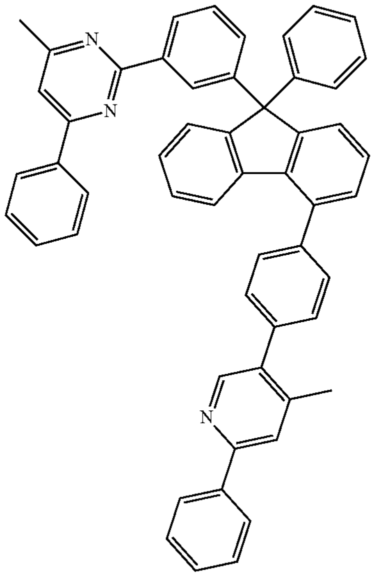
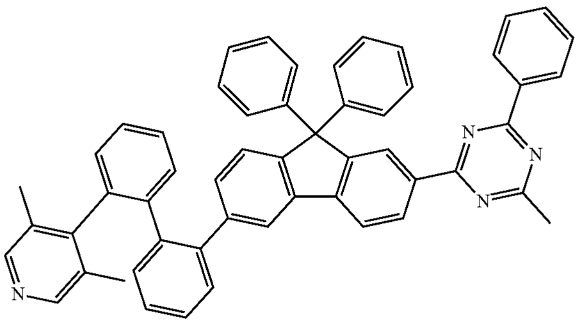

-continued
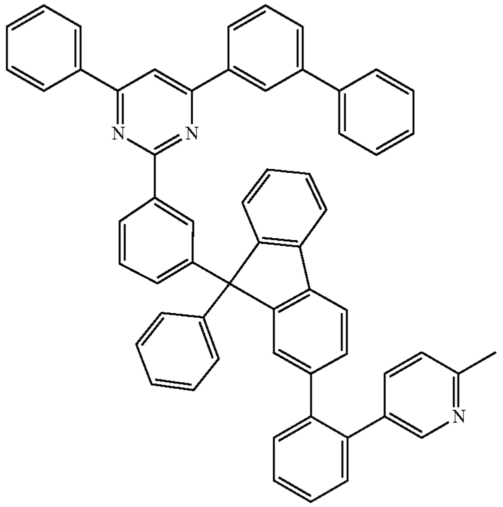
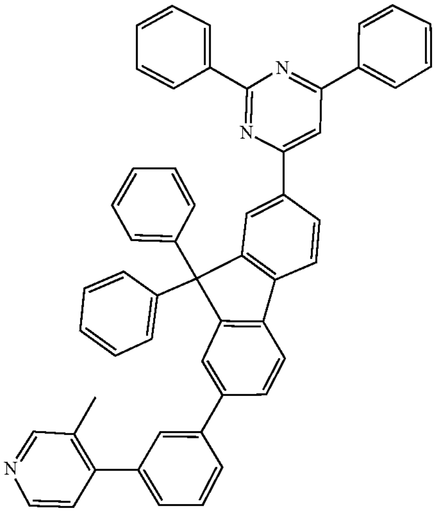
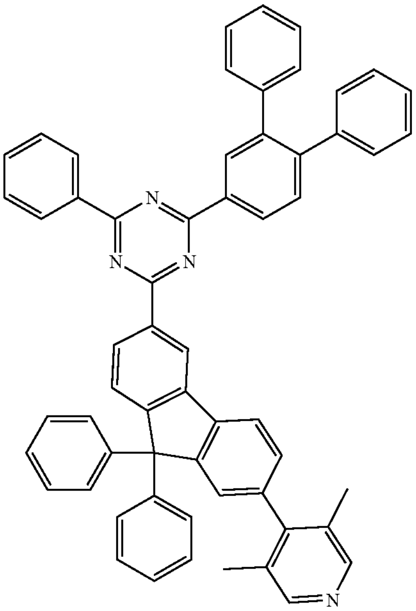
-continued
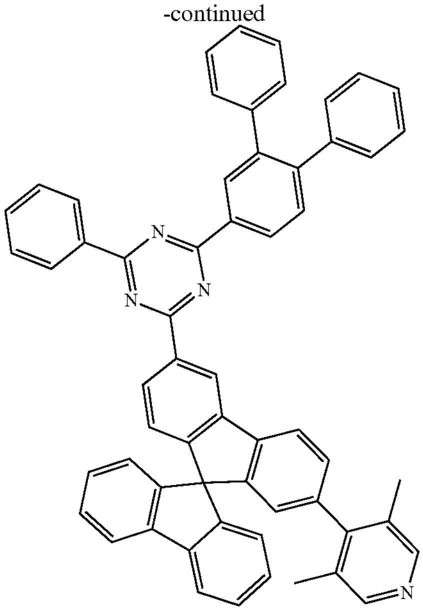
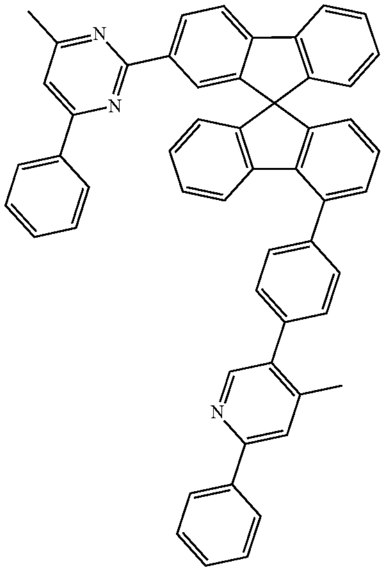
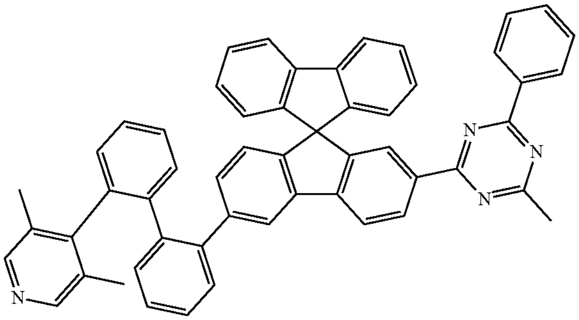

-continued
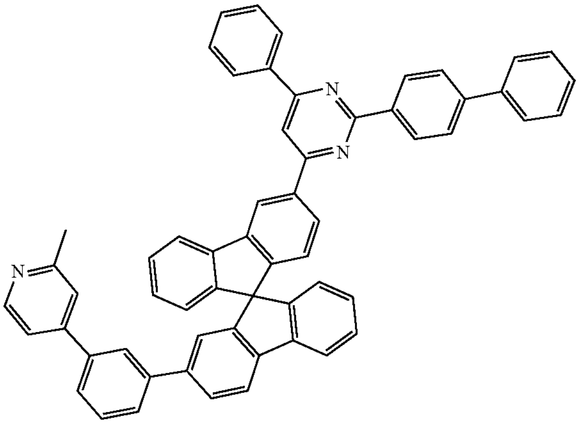
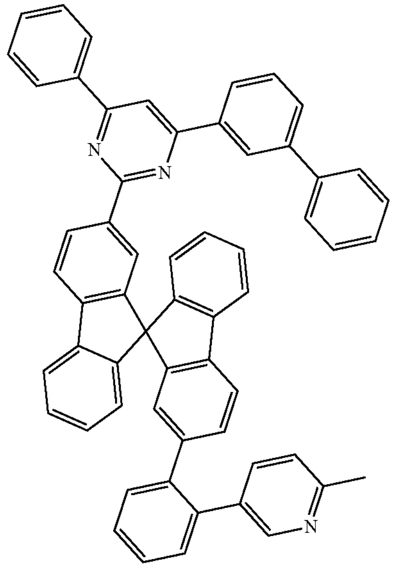
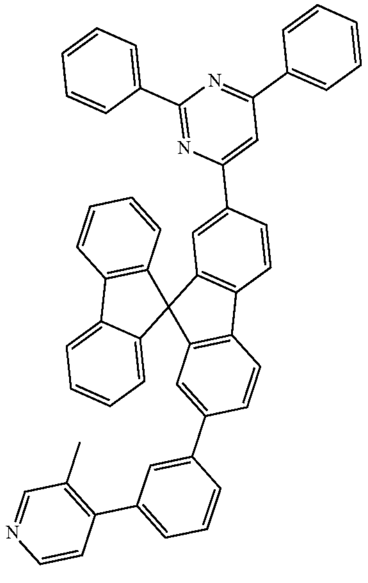
-continued
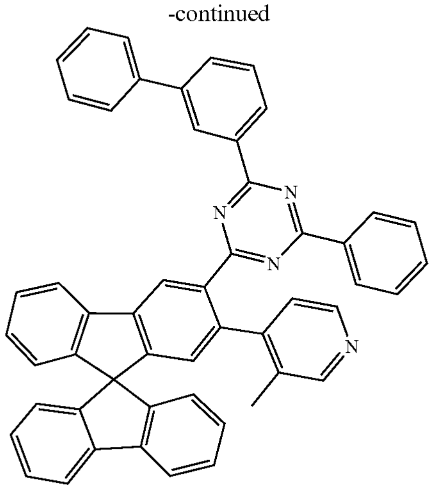
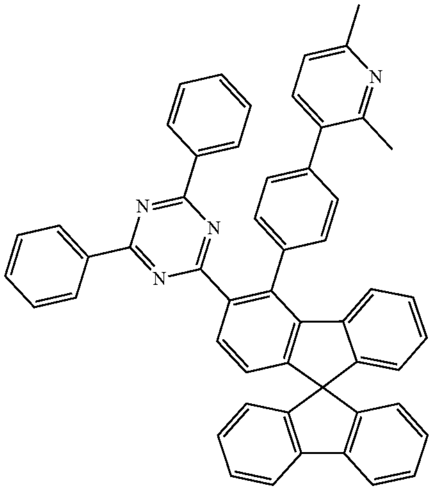
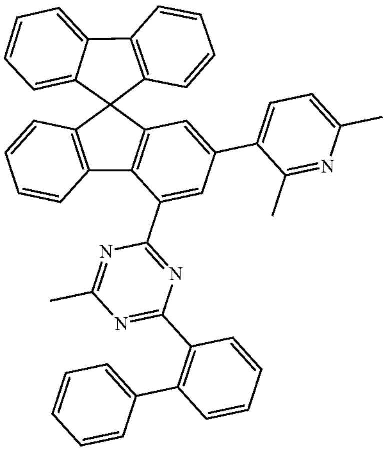

-continued
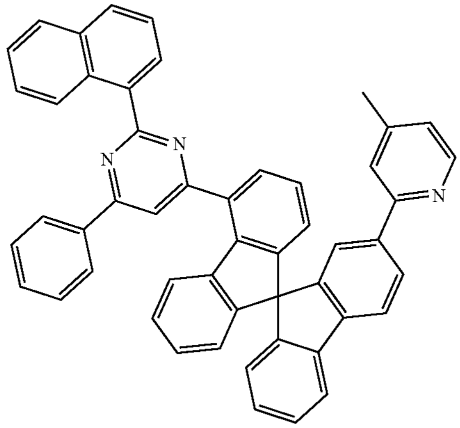
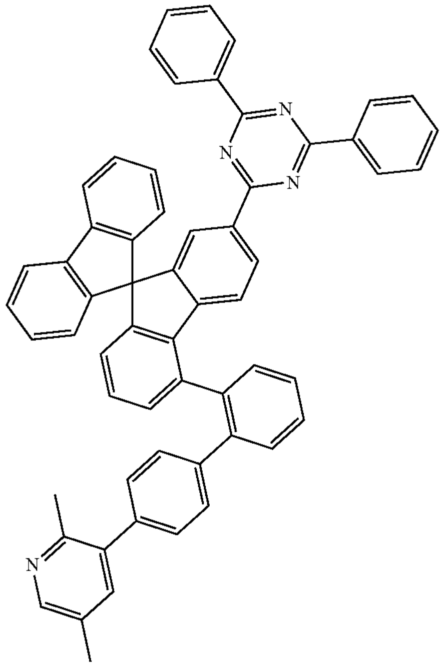
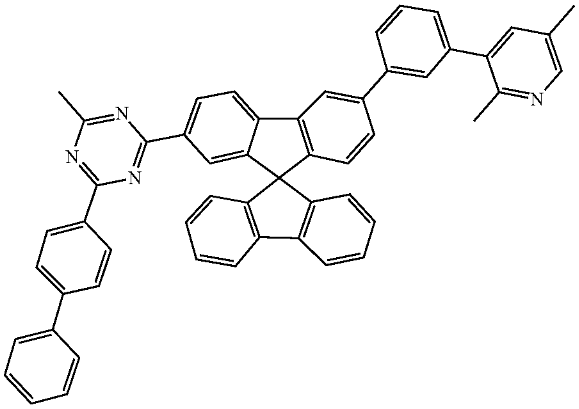
-continued
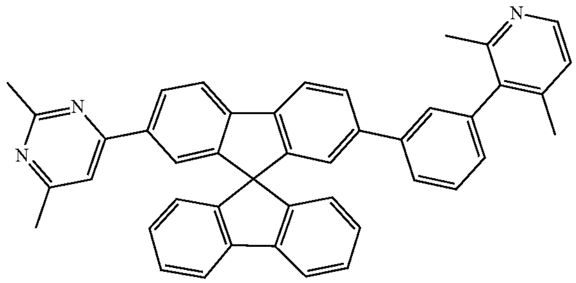
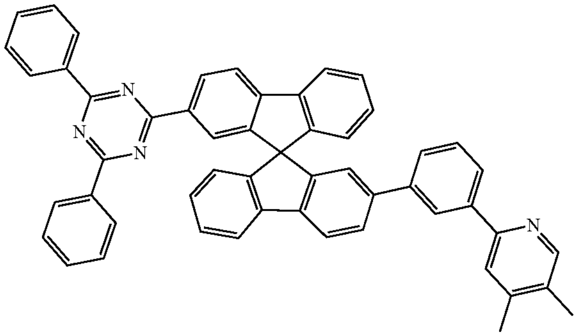
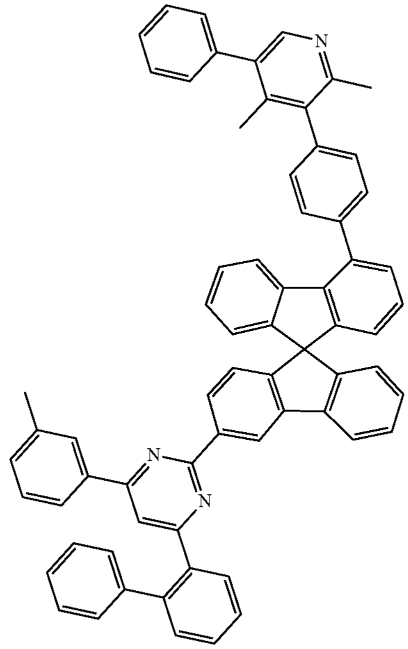
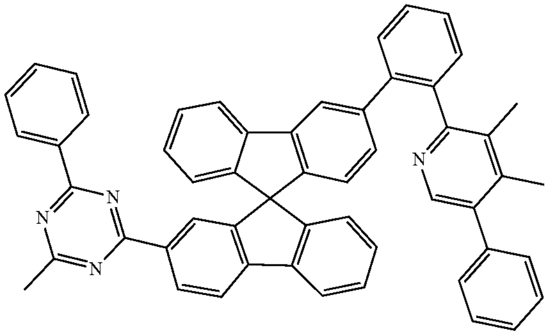

-continued
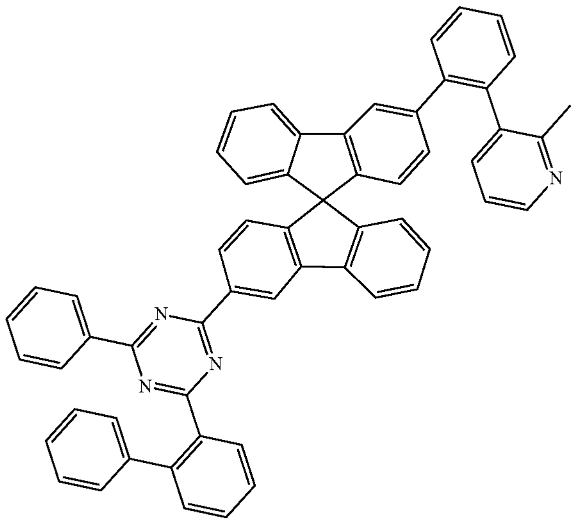
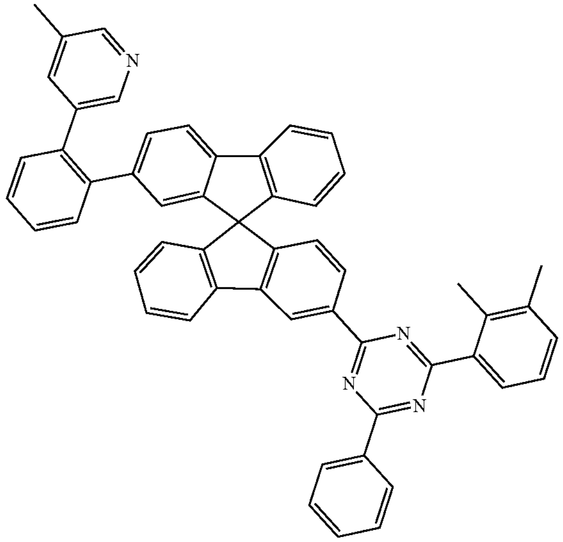
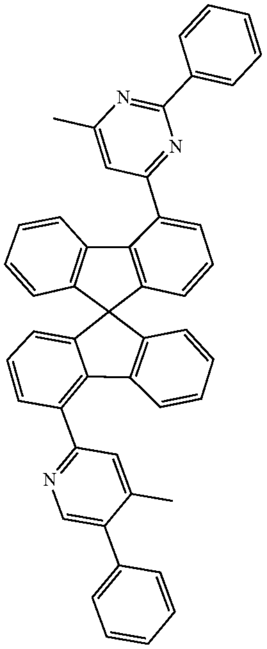
-continued
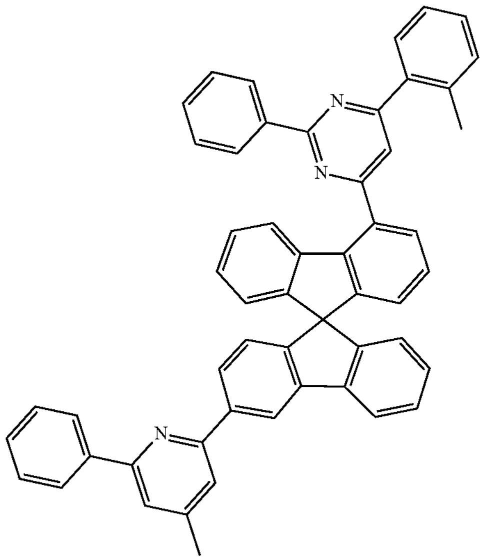
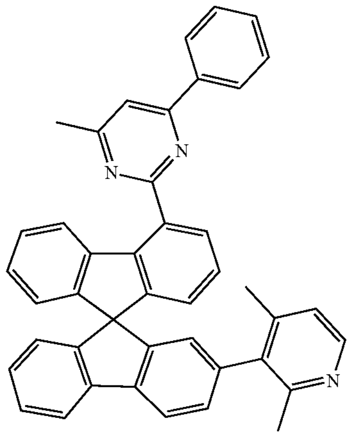
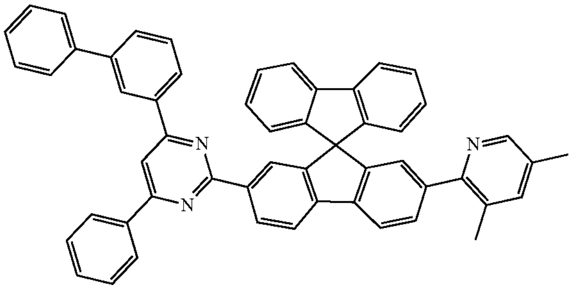

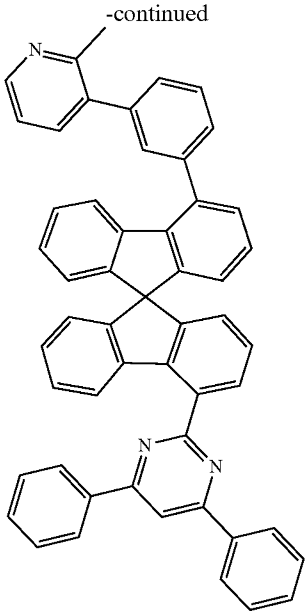
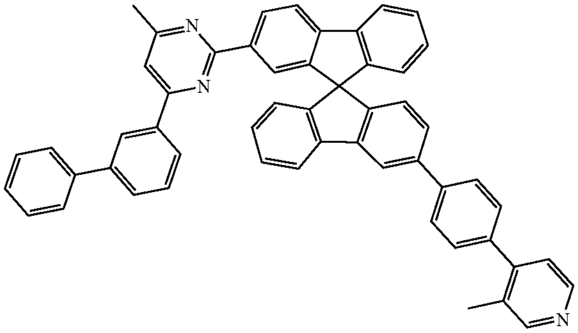
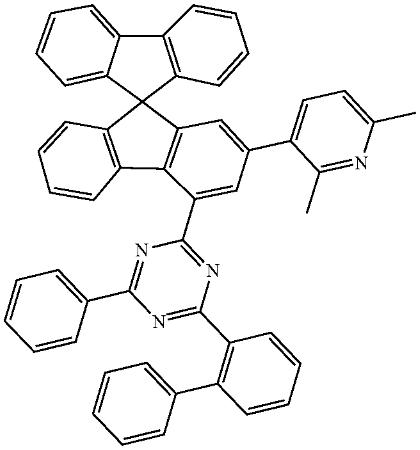
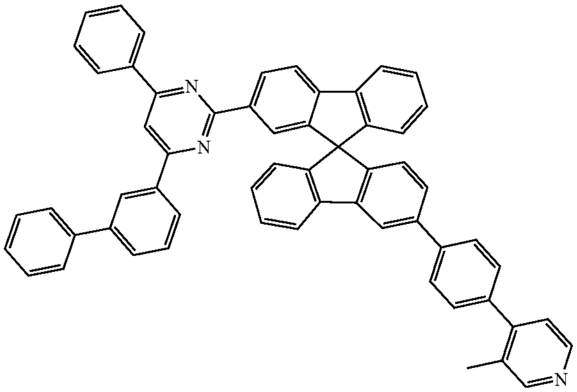
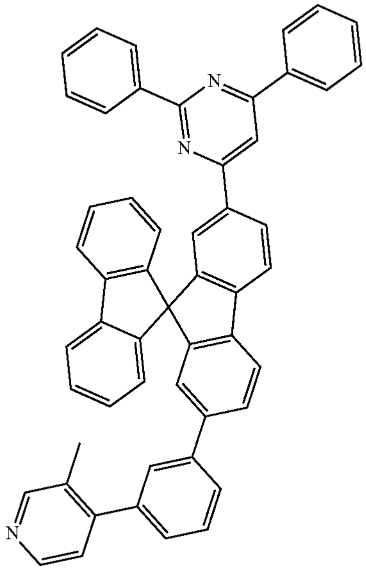
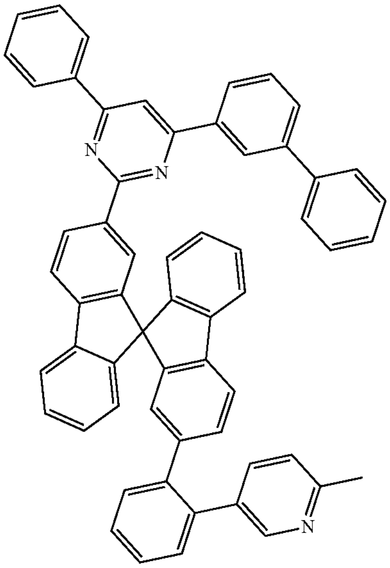

-continued
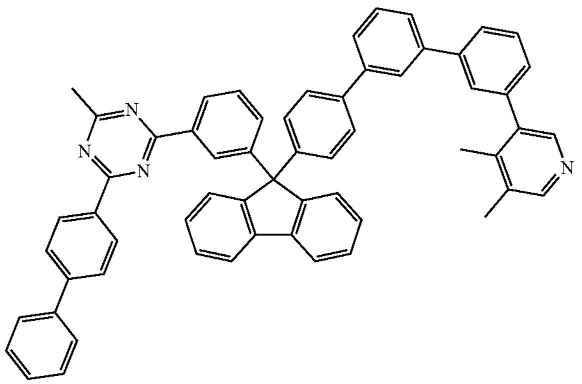
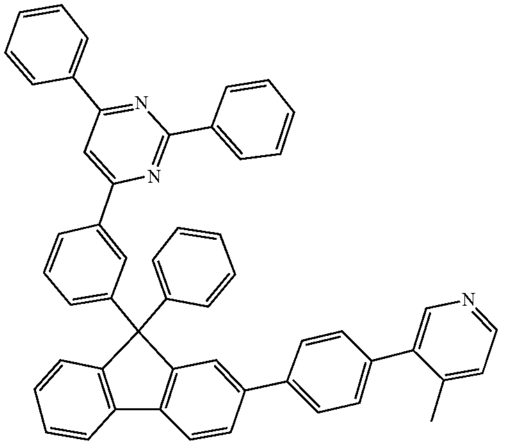
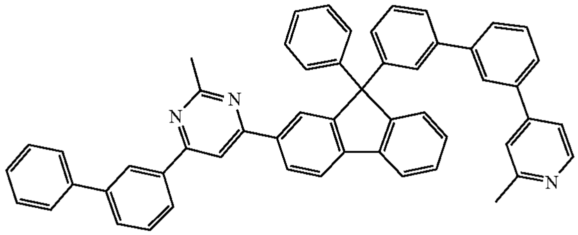
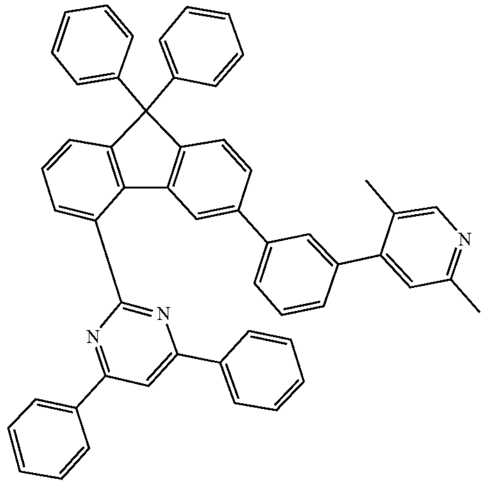
-continued
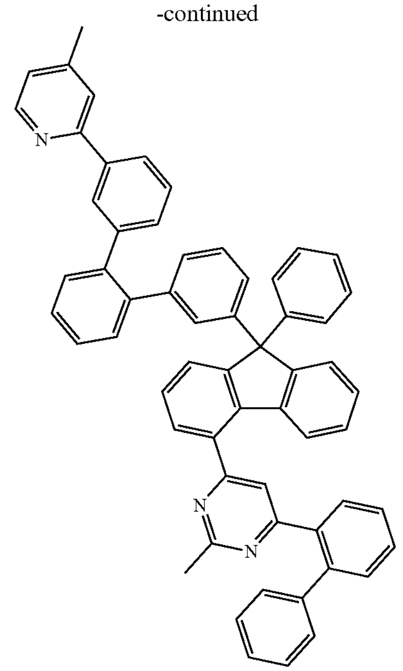
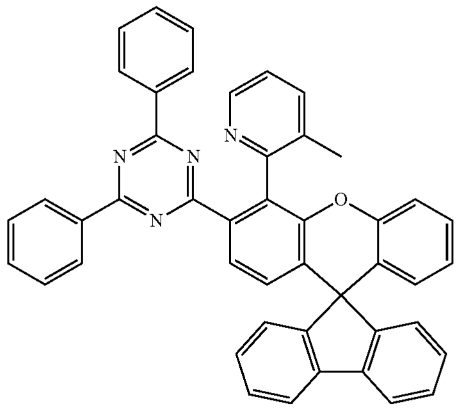
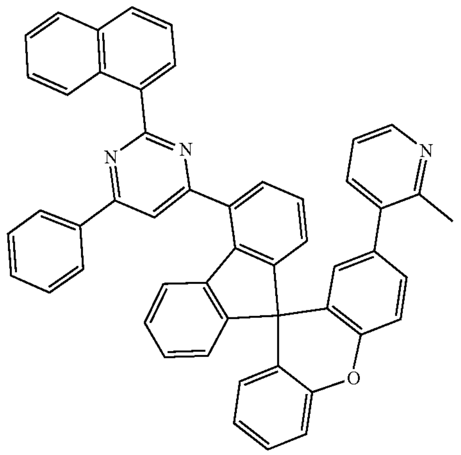

-continued
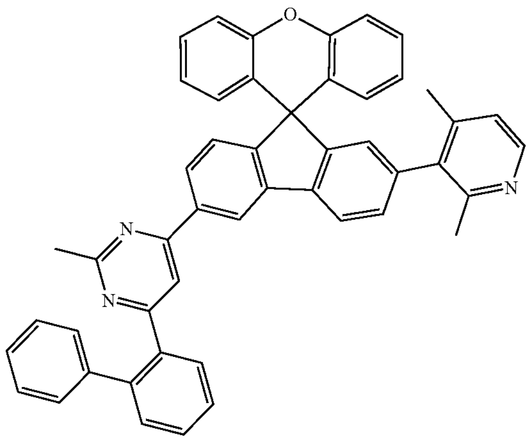
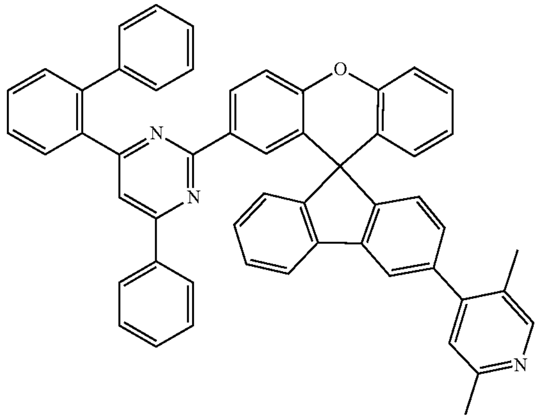
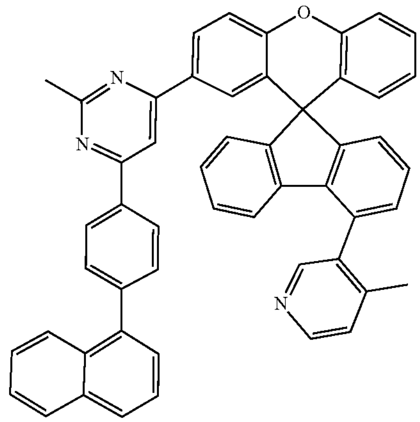
-continued
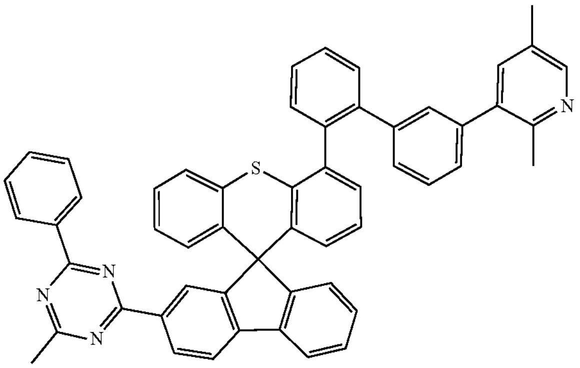
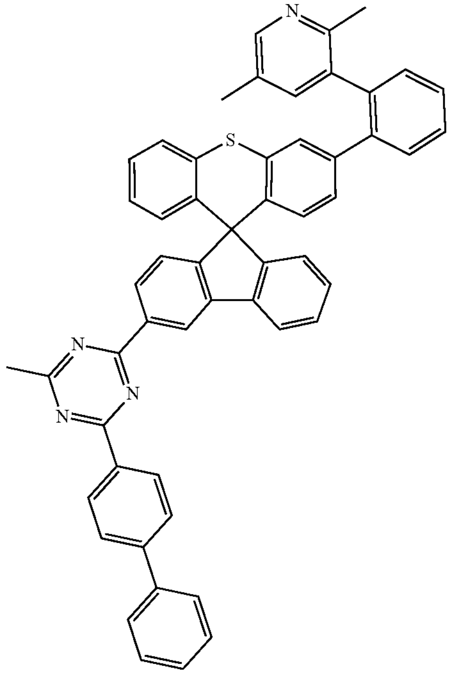
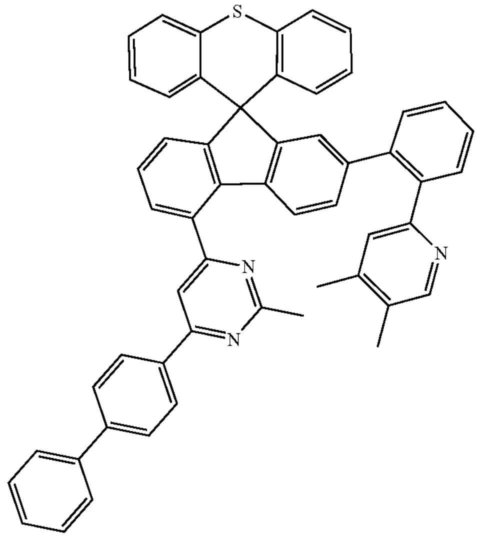

-continued

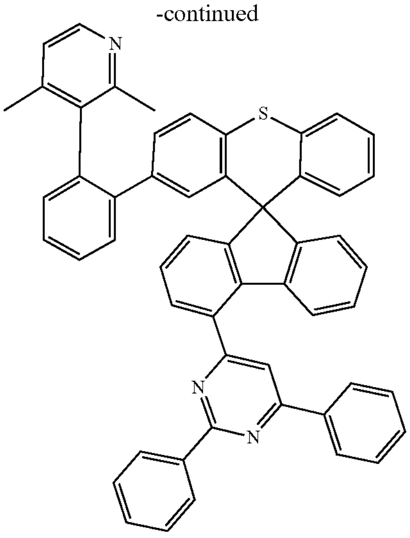

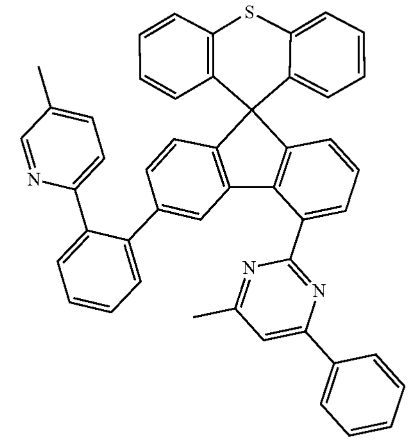

-continued

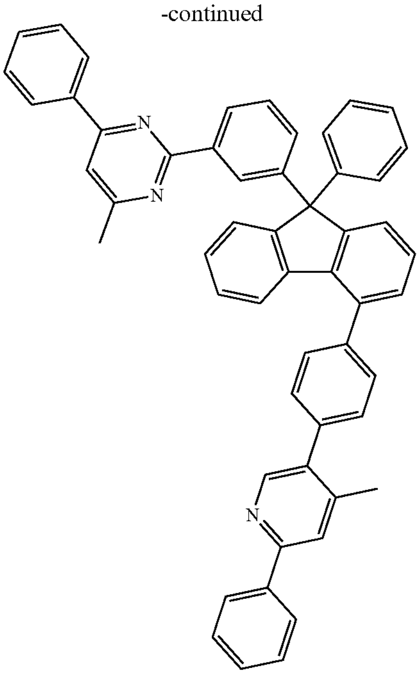

The compound according to an exemplary embodiment of the present specification can be prepared by a preparation method described below. If necessary, a substituent can be added or excluded, and a position of the substituent can be changed. Further, a starting material, a reactant, reaction conditions, and the like can be changed based on the technology known in the art.

For example, a core structure of the compound of Chemical Formula 1 can be prepared as in the following General Formula 1. The substituents can be bonded by a method known in the art, and the type or position of the substituent or the number of substituents can be changed according to the technology known in the art. The substituent can be bonded as in the following General Formula 1, but the bonding method is not limited thereto.

[General Formula 1]

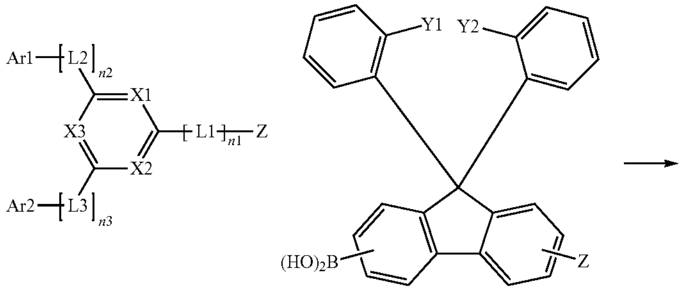

Z = halogen (Br, Cl, I)

-continued

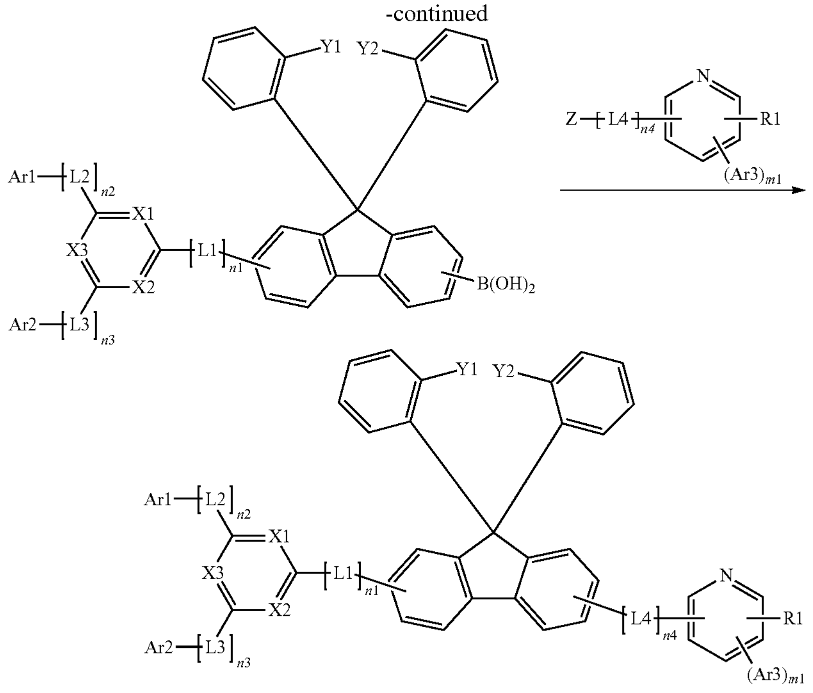

In General Formula 1, the definitions of X1 to X3, R1, L1 to L4, n1 to n4, Ar1 to Ar3, m1, Y1, and Y2 are the same as those defined in Chemical Formula 1. It is preferred that the reaction is carried out as a Suzuki coupling reaction in the presence of a palladium catalyst and a base, and a reactor for the Suzuki coupling reaction can be changed as known in the art. The preparation method can be further embodied in the Preparation Example to be described below.

The present specification provides an organic light emitting device including the above-described compound.

The present specification provides an organic light emitting device including: a first electrode; a second electrode provided to face the first electrode; and an organic material layer having one or more layers provided between the first electrode and the second electrode, in which one or more layers of the organic material layer include the compound of Chemical Formula 1.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element can be further included.

In the present specification, the 'layer' has a meaning compatible with a 'film' usually used in the art, and means a coating covering a target region. The size of the 'layer' is not limited, and the sizes of the respective 'layers' can be the same as or different from one another. In an exemplary embodiment, the size of the 'layer' can be the same as that of the entire device, can correspond to the size of a specific functional region, and can also be as small as a single sub-pixel.

In the present specification, when a specific A material is included in a B layer, this means both i) the fact that one or more A materials are included in one B layer and ii) the fact that the B layer is composed of one or more layers, and the A material is included in one or more layers of the multi-layered B layer.

In the present specification, when a specific A material is included in a C layer or a D layer, this means all of i) the fact that the A material is included in one or more layers of the C layer having one or more layers, ii) the fact that the A material is included in one or more layers of the D layer having one or more layers, and iii) the fact that the A material is included in each of the C layer having one or more layers and the D layer having one or more layers.

The organic material layer of the organic light emitting device of the present specification can also be composed of a single-layered structure, but can be composed of a multi-layered structure in which an organic material layer having two or more layers is stacked. For example, the organic material layer can have a structure including a hole injection layer, a hole transport layer, a light emitting layer, an electron transport layer, an electron injection layer, an electron blocking layer, a hole blocking layer, and the like. However, the structure of the organic light emitting device is not limited thereto, and can include a fewer number of organic material layers.

In an exemplary embodiment of the present specification, the organic material layer includes a light emitting layer, and the light emitting layer includes the heterocyclic compound of Chemical Formula 1.

In an exemplary embodiment of the present specification, the organic material layer includes an electron injection layer, an electron transport layer, an electron injection and transport layer, or a hole blocking layer, and the electron injection layer, the electron transport layer, the electron injection and transport layer, or the hole blocking layer includes the heterocyclic compound of Chemical Formula 1.

In an exemplary embodiment of the present specification, the electron injection layer, the electron transport layer, the electron injection and transport layer, or the hole blocking layer includes one or two or more n-type dopants selected from alkali metals and alkaline earth metals. Specifically, the electron injection layer, the electron transport layer, the electron injection and transport layer, or the hole blocking layer including the compound of Chemical Formula 1 includes one or two or more n-type dopants selected from alkali metals and alkaline earth metals.

When the organic alkali metal compound or the organic alkaline earth metal compound is used as an n-type dopant, the stability for holes can be secured from the light emitting layer, so that the service life of the organic light emitting device can be improved. In addition, for the electron mobility of the electron transport layer, the balance of holes and electrons in the light emitting layer can be maximized by controlling the ratio of the organic alkali metal compound or the organic alkaline earth metal compound, thereby increasing the light emitting efficiency.

In the present specification, LiQ is more preferred as the n-type dopant used in the electron injection layer, the electron transport layer, the electron injection and transport layer, or the hole blocking layer.

The electron injection layer, the electron transport layer, the electron injection and transport layer, or the hole blocking layer can include a heterocyclic compound of Chemical Formula 1 and the n-type dopant at a weight ratio of 1:9 to 9:1. Preferably, the electron injection layer, the electron transport layer, the electron injection and transport layer, or the hole blocking layer can include the heterocyclic compound of Chemical Formula 1 and the n-type dopant at a weight ratio of 2:8 to 8:2, and more preferably at a weight ratio of 3:7 to 7:3. In an exemplary embodiment of the present specification, the organic light emitting device further includes one or two or more layers selected from the group consisting of a hole injection layer, a hole transport layer, a light emitting layer, an electron transport layer, an electron injection layer, a hole blocking layer, and an electron blocking layer.

In an exemplary embodiment of the present specification, the organic light emitting device includes: a first electrode; a second electrode provided to face the first electrode; a light emitting layer provided between the first electrode and the second electrode; and an organic material layer having one or more layers provided between the light emitting layer and the first electrode, or between the light emitting layer and the second electrode.

In an exemplary embodiment of the present specification, the organic material layer having one or more layers further includes one or more layers selected from the group consisting of a hole injection layer, a hole transport layer, a light emitting layer, an electron transport layer, an electron injection layer, a hole blocking layer, and an electron blocking layer.

In an exemplary embodiment of the present specification, the first electrode is a positive electrode, and the second electrode is a negative electrode.

In an exemplary embodiment of the present specification, the first electrode is a negative electrode, and the second electrode is a positive electrode.

In an exemplary embodiment of the present specification, the organic light emitting device can be a normal type organic light emitting device in which a positive electrode, an organic material layer having one or more layers, and a negative electrode are sequentially stacked on a substrate.

In an exemplary embodiment of the present specification, the organic light emitting device can be an inverted type organic light emitting device in which a negative electrode, an organic material layer having one or more layers, and a positive electrode are sequentially stacked on a substrate.

For example, the structure of the organic light emitting device according to an exemplary embodiment of the present specification is exemplified in FIGS. 1 and 2. FIGS. 1 and 2 exemplify an organic light emitting device, and the organic light emitting device is not limited thereto.

FIG. 1 exemplifies the structure of an organic light emitting device in which a positive electrode 102, a light emitting layer 106, and a negative electrode 108 are sequentially stacked on a substrate 101. The compound of Chemical Formula 1 is included in the light emitting layer.

FIG. 2 exemplifies a structure of an organic light emitting device in which a positive electrode 102, a hole injection layer 103, a first hole transport layer 104, a second hole transport layer 105, a light emitting layer 106, an electron injection and transport layer 107, and a negative electrode 108 are sequentially stacked on a substrate 101. According to an exemplary embodiment of the present specification, the compound of Chemical Formula 1 is included in an electron injection and transport layer 107.

The organic light emitting device of the present specification can be manufactured by materials and methods known in the art, except that the light emitting layer includes the compound.

When the organic light emitting device includes a plurality of organic material layers, the organic material layers can be formed of the same material or different materials.

For example, the organic light emitting device of the present specification can be manufactured by sequentially stacking a first electrode, an organic material layer, and a second electrode on a substrate. In this case, the organic light emitting device of the present specification can be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which can be used as a negative electrode, thereon, by using a physical vapor deposition (PVD) method such as sputtering or e-beam evaporation. In addition to the method described above, an organic light emitting device can be manufactured by sequentially depositing a negative electrode material, an organic material layer, and a positive electrode material on a substrate.

Further, the compound of Chemical Formula 1 can be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device can also be made by sequentially depositing a negative electrode material, an organic material layer, and a positive electrode material on a substrate. However, the manufacturing method is not limited thereto.

As the positive electrode material, materials having a high work function are usually preferred so as to facilitate the injection of holes into an organic material layer. Examples thereof include: a metal, such as vanadium, chromium, copper, zinc, and gold, or an alloy thereof; a metal oxide, such as zinc oxide, indium oxide, indium tin oxide (ITO), and indium zinc oxide (IZO); a combination of a metal and an oxide, such as ZnO:Al or $SnO_2$:Sb; a conductive polymer, such as poly(3-methylthiophene), poly[3,4-(ethylene-1,2-dioxy)thiophene] (PEDOT), polypyrrole, and polyaniline; and the like, but are not limited thereto.

As the negative electrode material, materials having a low work function are usually preferred so as to facilitate the injection of electrons into an organic material layer. Examples thereof include: a metal, such as magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al; and the like, but are not limited thereto.

The light emitting layer can include a host material and a dopant material. Examples of the host material include a fused aromatic ring derivative, or a hetero ring-containing compound, and the like. Specific examples of the fused aromatic ring derivative include anthracene derivatives, pyrene derivatives, naphthalene derivatives, pentacene derivatives, phenanthrene compounds, fluoranthene compounds, and the like, and specific examples of the hetero ring-containing compound include dibenzofuran derivatives, ladder-type furan compounds, pyrimidine derivatives, and the like, but the examples are not limited thereto.

In an exemplary embodiment of the present specification, an anthracene derivative substituted with deuterium can be used as a host material for the light emitting layer.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamine group, and examples thereof include pyrene, anthracene, chrysene, periflanthene, and the like having an arylamine group. Further, the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamine group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The hole injection layer is a layer which accepts holes from an electrode. It is preferred that hole injection material has an ability to transport holes, and has an effect of accepting holes from a positive electrode and an excellent hole injection effect for a light emitting layer or a light emitting material. Further, the hole injection material is preferably a material which is excellent in ability to prevent excitons produced from a light emitting layer from moving to an electron injection layer or an electron injection material. In addition, the hole injection material is preferably a material which is excellent in ability to form a thin film. In addition, the highest occupied molecular orbital (HOMO) of the hole injection material is preferably a value between the work function of the positive electrode material and the HOMO of the neighboring organic material layer. Specific examples of the hole injection material include: metal porphyrin, oligothiophene, and arylamine-based organic materials; hexanitrile hexaazatriphenylene-based organic materials; quinacridone-based organic materials; perylene-based organic materials; polythiophene-based conductive polymers such as anthraquinone and polyaniline; and the like, but are not limited thereto.

The hole transport layer is a layer which accepts holes from a hole injection layer and transports the holes to a light emitting layer. A hole transport material is preferably a material having high hole mobility which can accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto. Further, the hole transport layer can have a multi-layered structure. For example, the hole transport layer can include a first hole transport layer and a second hole transport layer.

The electron transport layer is a layer which accepts electrons from an electron injection layer and transports the electrons to a light emitting layer. An electron transport material is preferably a material having high electron mobility which can proficiently accept electrons from a negative electrode and transfer the electrons to a light emitting layer. Specific examples thereof include: Al complexes of 8-hydroxyquinoline; complexes including $Alq_3$; organic radical compounds; hydroxyflavone-metal complexes; and the like, but are not limited thereto. An electron transport layer can be used with any desired negative electrode material, as used according to the related art. In particular, an appropriate negative electrode material is a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which accepts electrons from an electrode. It is preferred that an electron injection material is excellent in ability to transport electrons and has an effect of accepting electrons from the second electrode and an excellent electron injection effect for a light emitting layer or a light emitting material. Further, the electron injection material is preferably a material which prevents excitons produced from a light emitting layer from moving to a hole injection layer and is excellent in ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, metal complex compounds, nitrogen-containing 5-membered ring derivatives, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The electron injection and transport layer means a layer which simultaneously injects and transports electrons.

The electron blocking layer is a layer which can improve the service life and efficiency of a device by preventing electrons injected from an electron injection layer from passing through a light emitting layer and entering a hole injection layer. A publicly-known material can be used without limitation, and the electron blocking layer can be formed between a light emitting layer and a hole injection layer, or between a light emitting layer and a hole injection and transport layer.

The hole blocking layer is a layer which blocks holes from reaching a negative electrode, and can be generally formed under the same conditions as those of the electron injection layer. Specific examples thereof include oxadiazole derivatives or triazole derivatives, phenanthroline derivatives, aluminum complexes, and the like, but are not limited thereto.

The organic light emitting device according to the present specification can be a top emission type, a bottom emission type, or a dual emission type according to the materials to be used.

EXAMPLES

Hereinafter, the present specification will be described in detail with reference to Examples, Comparative Examples, and the like for specifically describing the present specification. However, the Examples and the Comparative Examples according to the present specification can be modified in various forms, and it is not interpreted that the scope of the present specification is limited to the Examples and the Comparative Examples described below in detail. The Examples and the Comparative Examples of the present specification are provided to more completely explain the present specification to a person with ordinary skill in the art.

Synthesis Example 1

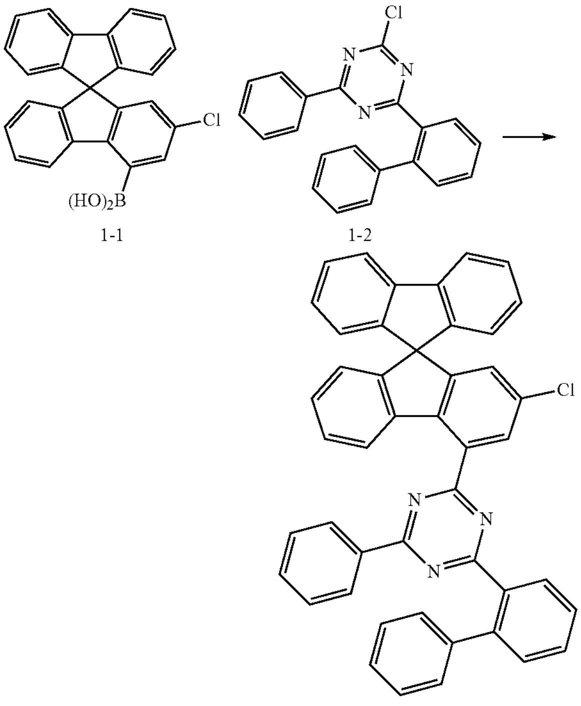

1-1 1-2 1-3

Compound 1-1 (11.8 g, 30 mmol) and Compound 1-2 (11.3 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 1-3. (14.2 g, yield 72%, MS: [M+H]+=659).

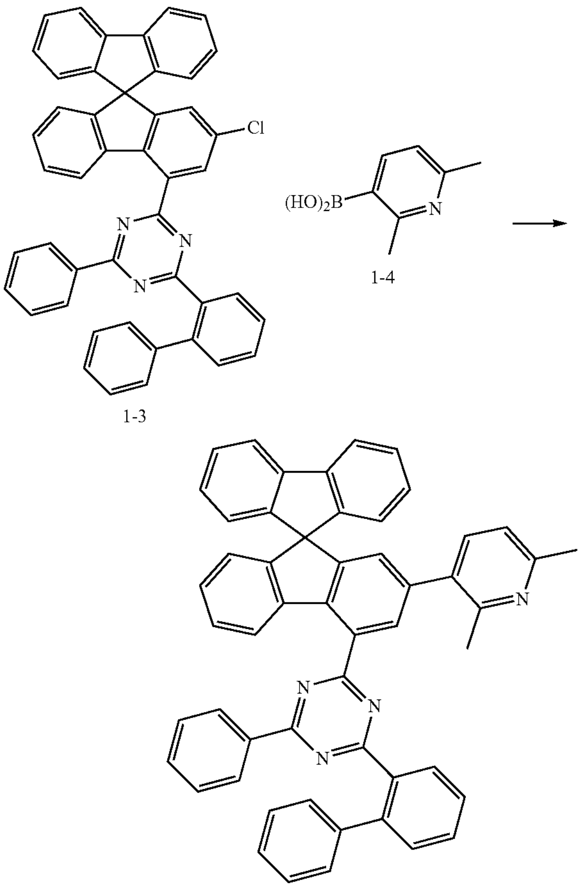

1-3 1-4 1

Compound 1-3 (19.7 g, 30 mmol) and Compound 1-4 (5.0 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 1. (9.4 g, yield 43%, MS: [M+H]+ =729).

Synthesis Example 2

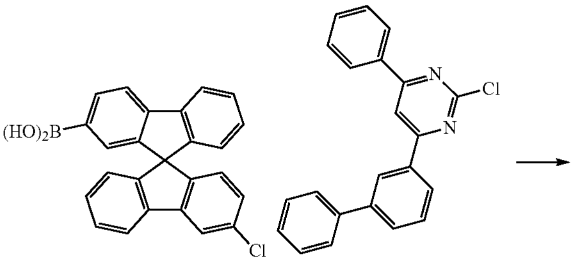

2-1 2-2

-continued

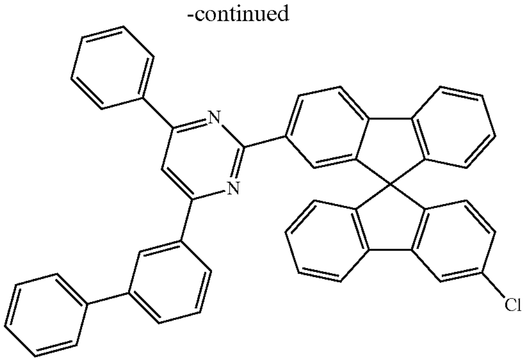

2-3

Compound 2-1 (11.8 g, 30 mmol) and Compound 2-2 (11.3 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 2-3. (14.8 g, yield 75%, MS: [M+H]+=658).

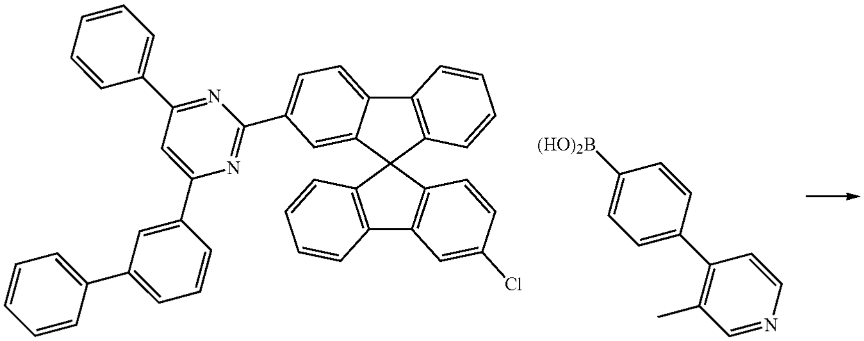

2-3 2-4

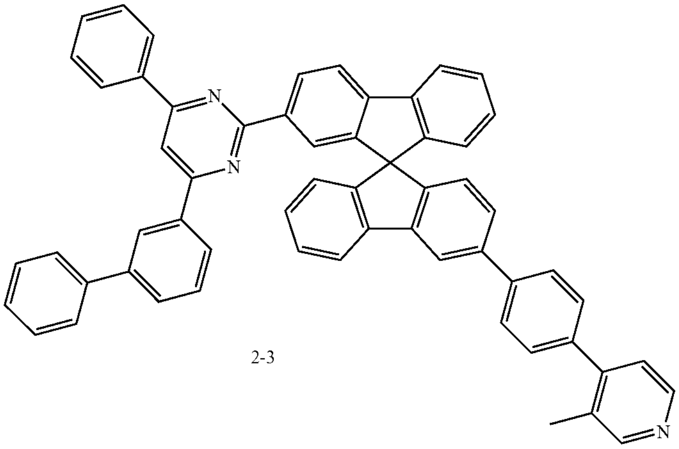

2-3

2

Compound 2-3 (19.7 g, 30 mmol) and Compound 2-4 (7.0 g, 33 mmol) were introduced into tetrahydrofuran (300 mL). After 2 M $K_2CO_3$ (100 mL) and $Pd(PtBu_3)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 2. (12.3 g, yield 52%, MS: [M+H]+=790).

Synthesis Example 3

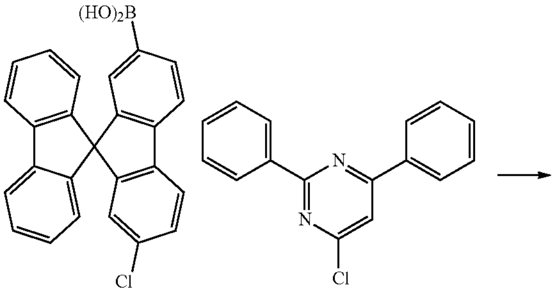

3-1 3-2

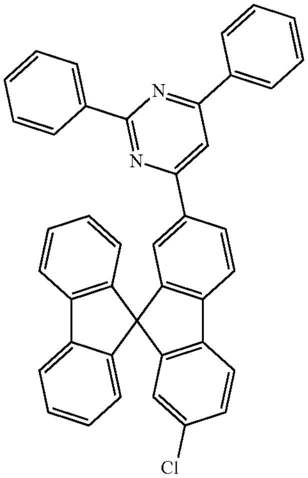

3-3

Compound 3-1 (11.8 g, 30 mmol) and Compound 3-2 (8.8 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 3-3. (14.2 g, yield 80%, MS: [M+H]+=591).

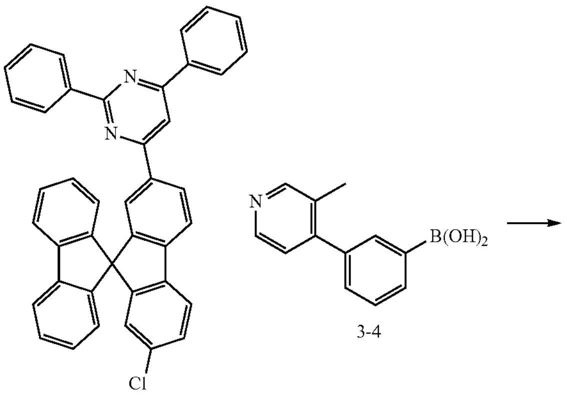

3-3 3-4

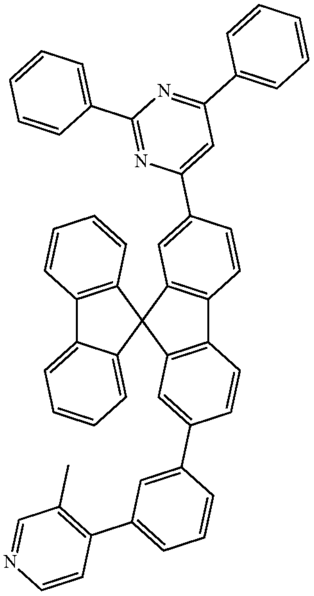

3

Compound 3-3 (17.7 g, 30 mmol) and Compound 3-4 (6.6 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 3. (11.4 g, yield 53%, MS: [M+H]+=714).

Synthesis Example 4

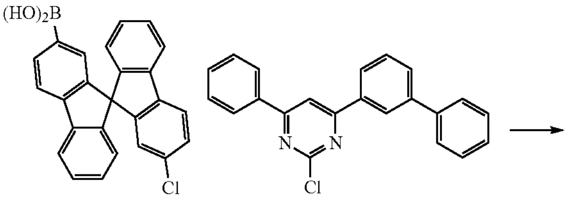

4-1 4-2

-continued

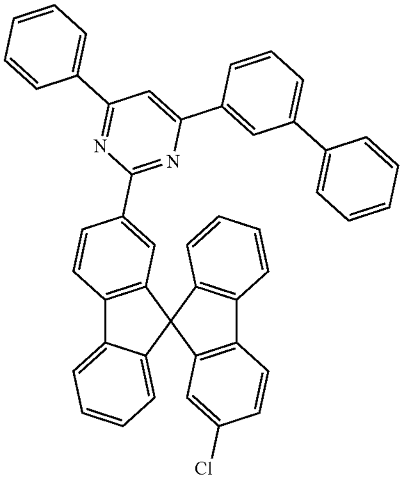

4-3

Compound 4-1 (11.8 g, 30 mmol) and Compound 4-2 (11.3 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 4-3. (16.0 g, yield 81%, MS: [M+H]+=658).

-continued

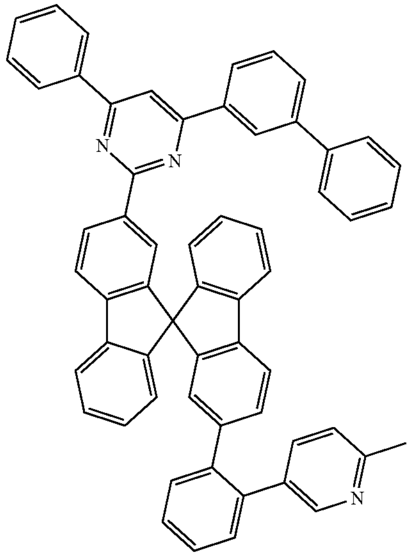

4

Compound 4-3 (19.7 g, 30 mmol) and Compound 4-4 (7.0 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 4. (12.1 g, yield 51%, MS: [M+H]+=790).

Synthesis Example 5

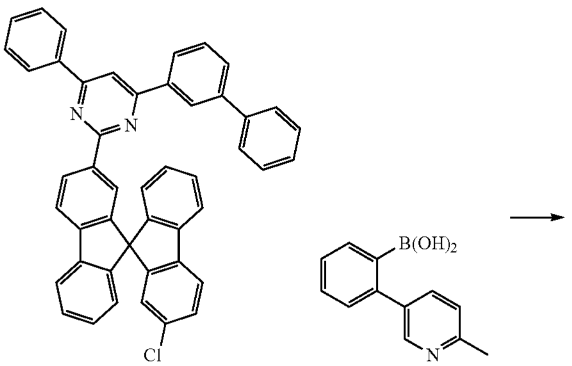

4-3 4-4

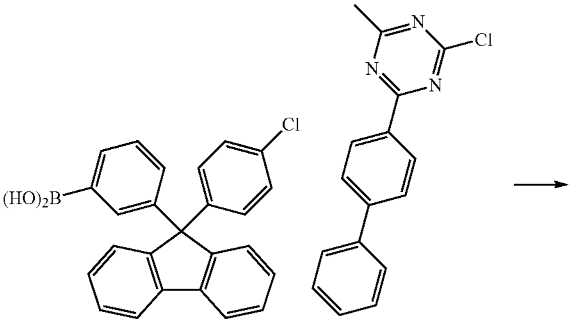

5-1 5-2

-continued

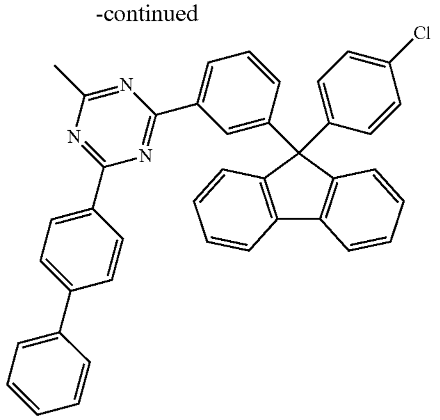

5-3

Compound 5-1 (11.9 g, 30 mmol) and Compound 5-2 (9.3 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 5-3. (11.7 g, yield 65%, MS: [M+H]+=599).

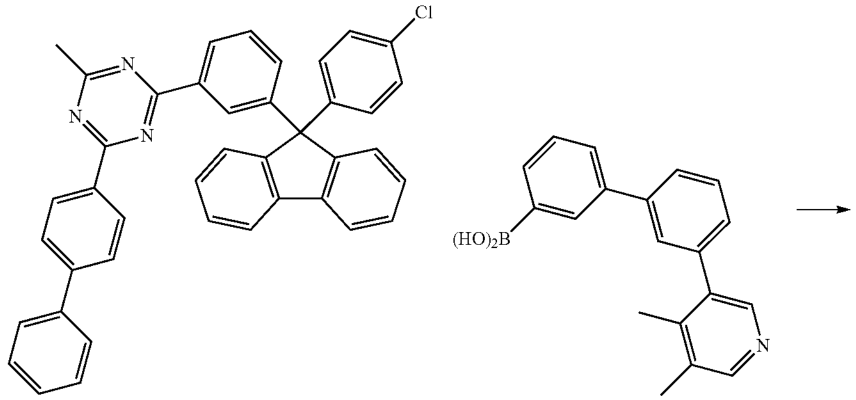

5-3 5-4

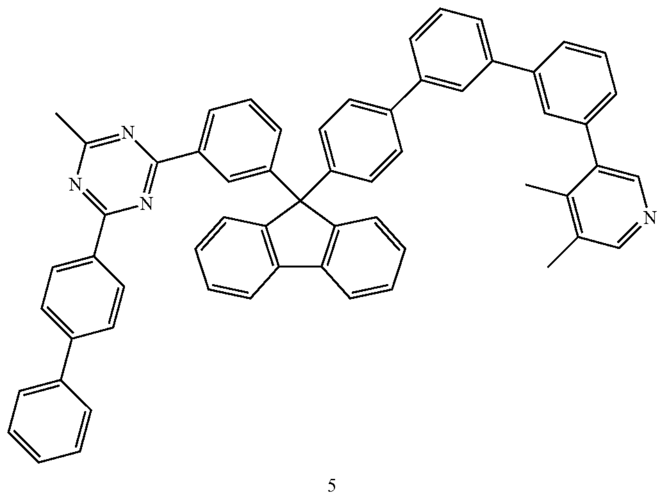

5

Compound 5-3 (17.9 g, 30 mmol) and Compound 5-4 (10.0 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 5. (11.8 g, yield 48%, MS: [M+H]+=822).

Synthesis Example 6

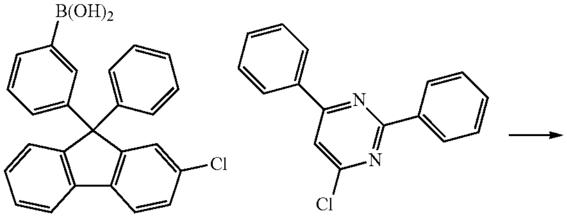

6-1 6-2

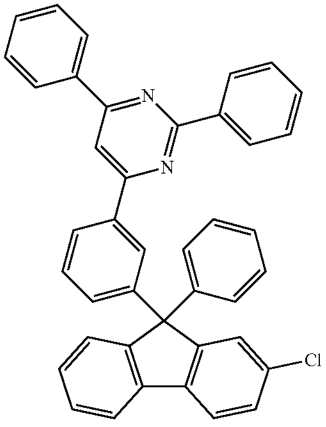

6-3

Compound 6-1 (11.9 g, 30 mmol) and Compound 6-2 (8.8 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 6-3. (13.5 g, yield 77%, MS: [M+H]+=584).

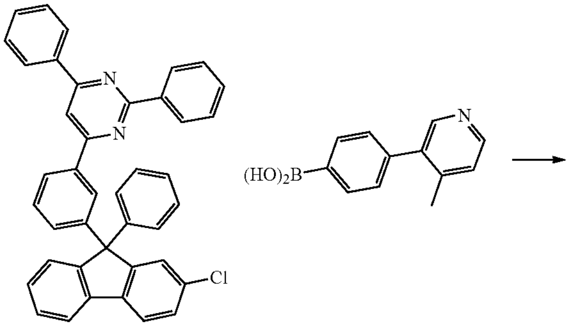

6.3 6.4

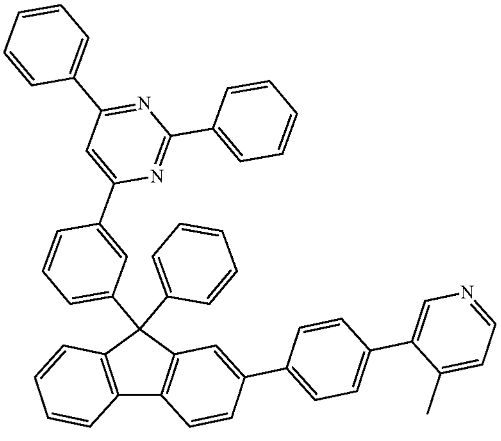

6

Compound 6-3 (17.5 g, 30 mmol) and Compound 6-4 (7.0 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 6. (9.4 g, yield 44%, MS: [M+H]+=716).

Synthesis Example 7

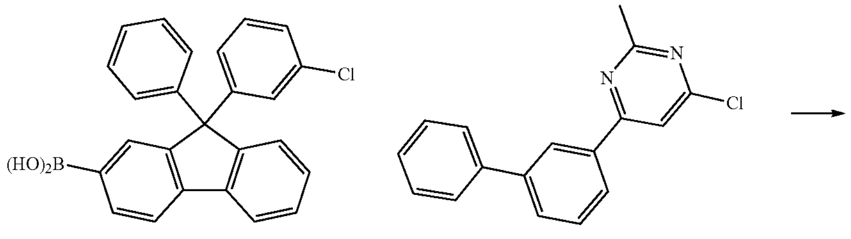

7-1 7-2

-continued

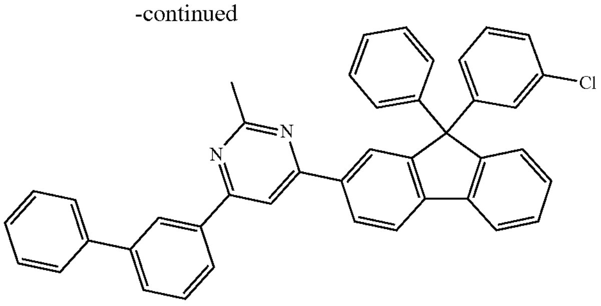

7-3

Compound 7-1 (11.9 g, 30 mmol) and Compound 7-2 (9.3 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 7-3. (14.5 g, yield 81%, MS: [M+H]+=598).

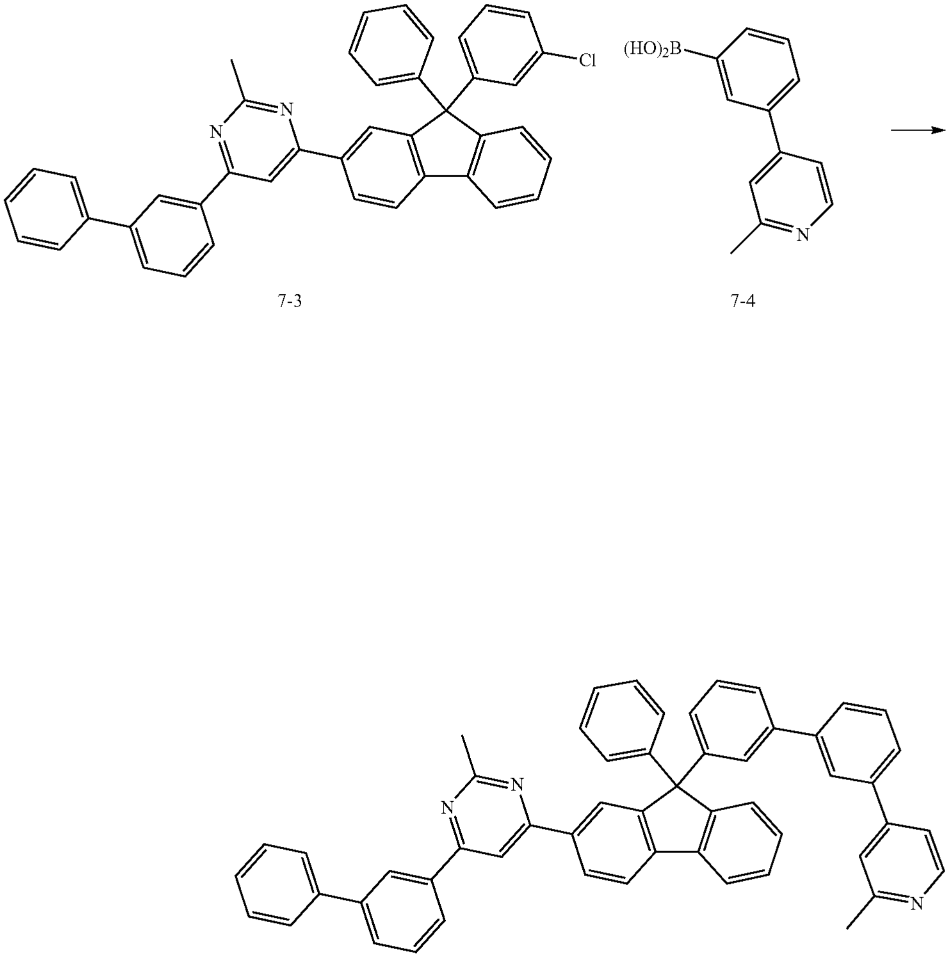

7-3 7-4

7

Compound 7-3 (17.8 g, 30 mmol) and Compound 7-4 (7.0 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 7. (9.6 g, yield 44%, MS: [M+H]+=730).

Synthesis Example 8

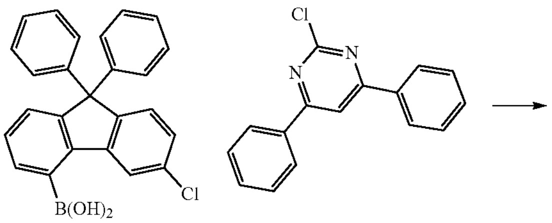

8-1 8-2

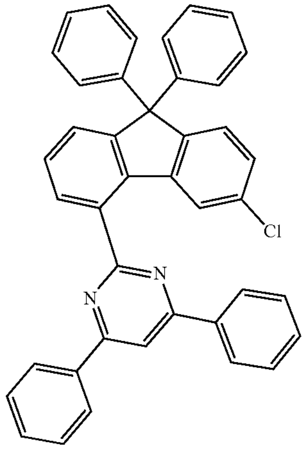

8-3

Compound 8-1 (11.9 g, 30 mmol) and Compound 8-2 (8.8 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 8-3. (12.4 g, yield 71%, MS: [M+H]+=584).

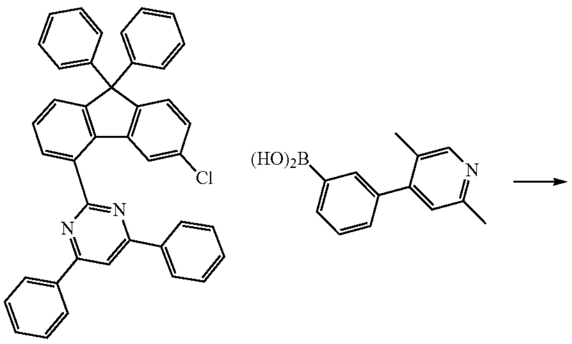

8-3 8-4

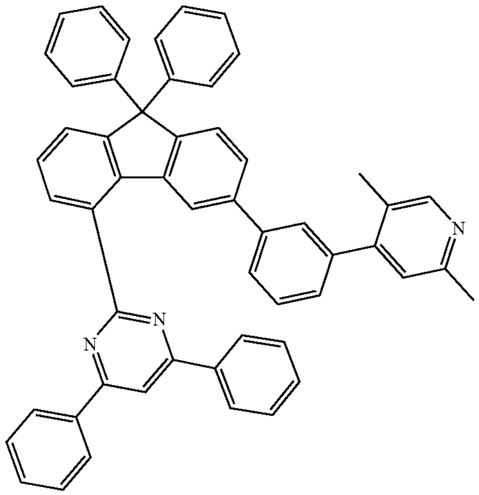

8

Compound 8-3 (17.5 g, 30 mmol) and Compound 8-4 (7.5 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 8. (9.9 g, yield 45%, MS: [M+H]+=730).

Synthesis Example 9

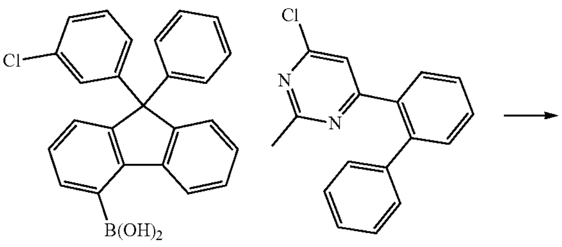

9-1 9-2

-continued

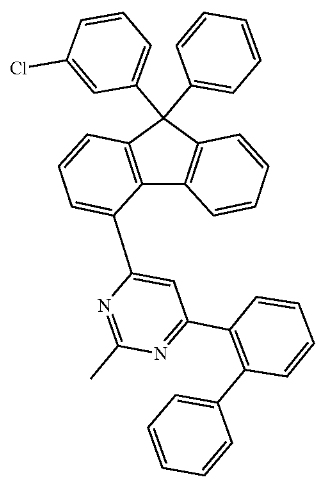

9-3

Compound 9-1 (11.9 g, 30 mmol) and Compound 9-2 (9.3 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 9-3. (11.6 g, yield 65%, MS: [M+H]+=598).

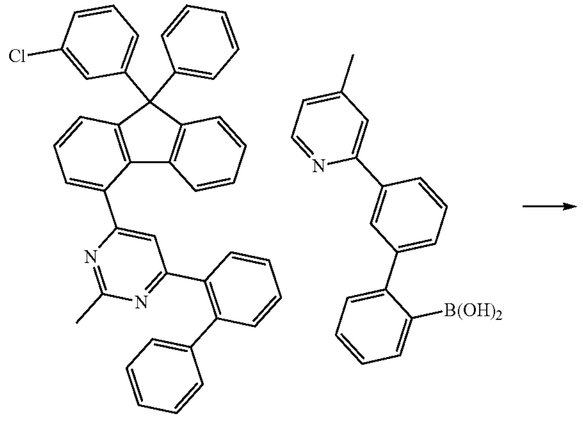

9-3 9-4

-continued

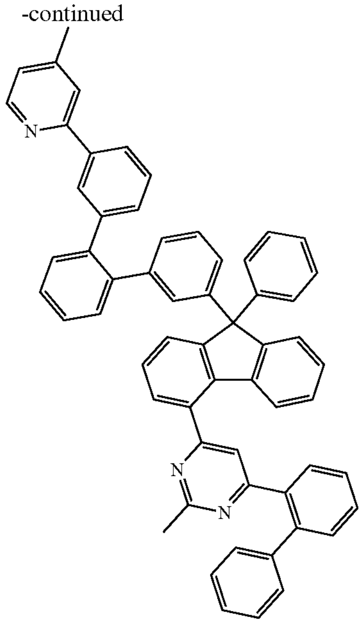

9

Compound 9-3 (17.9 g, 30 mmol) and Compound 9-4 (9.5 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 9. (12.1 g, yield 50 MS: [M+H]+=807).

Synthesis Example 10

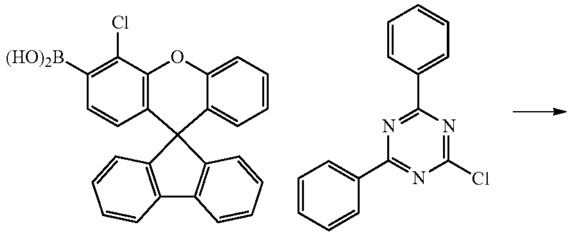

10-1 10-2

-continued

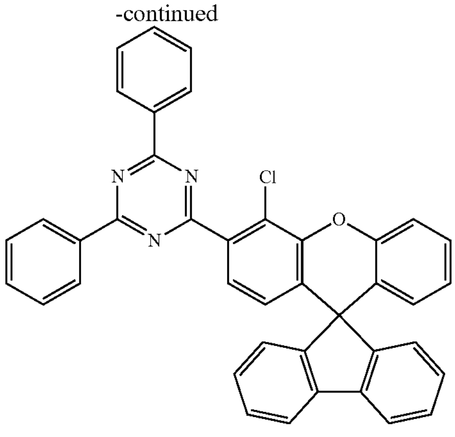

10-3

Compound 10-1 (12.3 g, 30 mmol) and Compound 10-2 (8.8 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 10-3. (15.3 g, yield 85%, MS: [M+H]+=599).

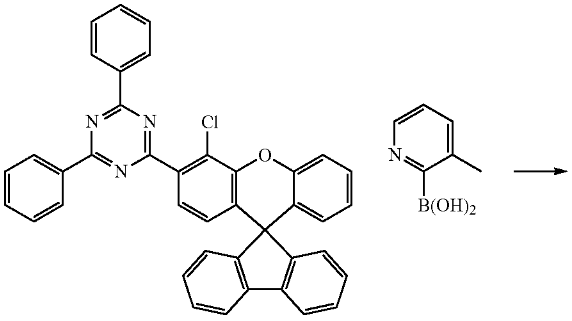

10-3 10-4

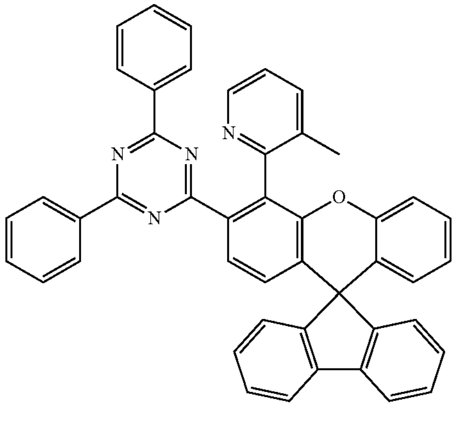

10

Compound 10-3 (17.9 g, 30 mmol) and Compound 10-4 (4.5 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 10. (10.2 g, yield 52%, MS: [M+H]+=655).

Synthesis Example 11

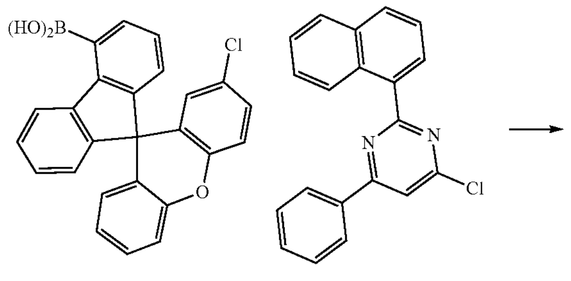

11-1 11-2

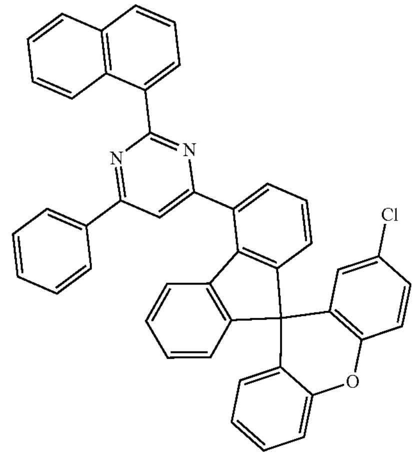

11-3

Compound 11-1 (12.3 g, 30 mmol) and Compound 11-2 (10.5 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 11-3. (14.4 g, yield 74%, MS: [M+H]+=648).

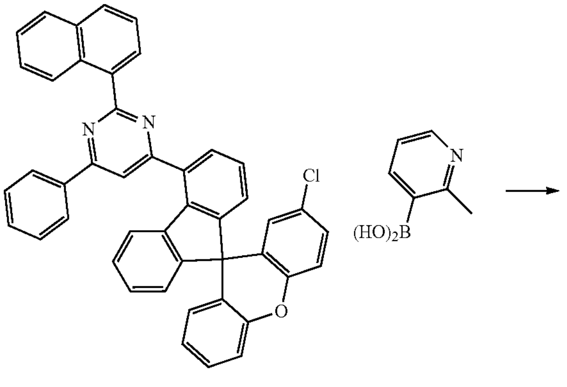

11-3 11-4

-continued

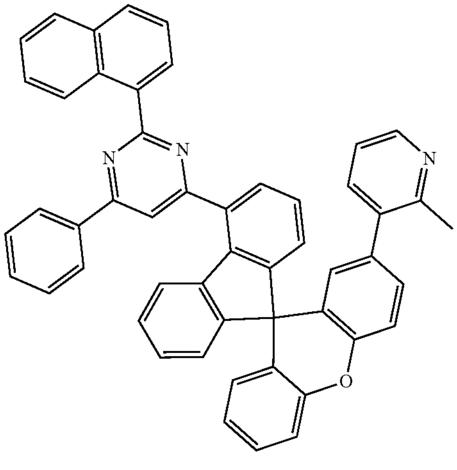

11

Compound 11-3 (19.4 g, 30 mmol) and Compound 11-4 (4.5 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 11. (8.9 g, yield 42%, MS: [M+H]+=704).

Synthesis Example 12

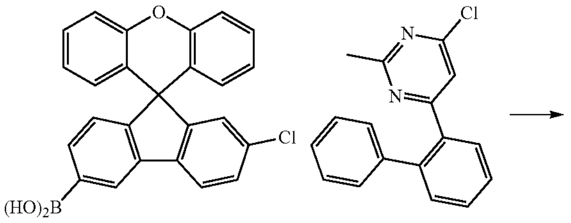

12-1 12-2

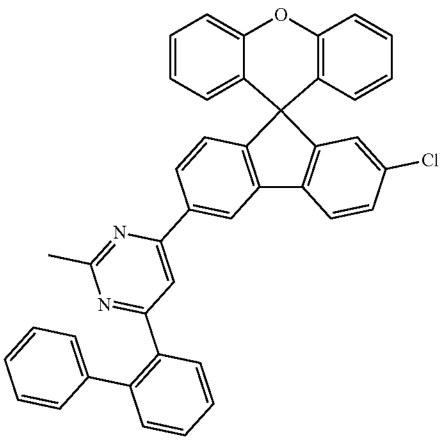

12-3

Compound 12-1 (12.3 g, 30 mmol) and Compound 12-2 (9.3 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 12-3. (14.1 g, yield 77%, MS: [M+H]+=612).

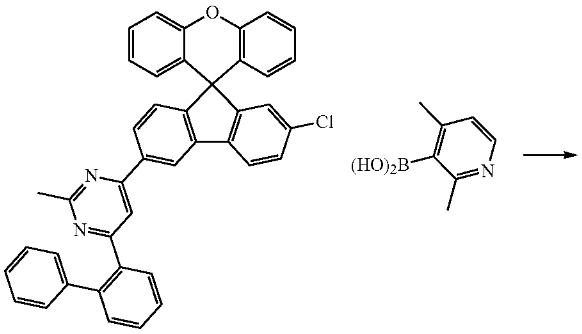

12-3 12-4

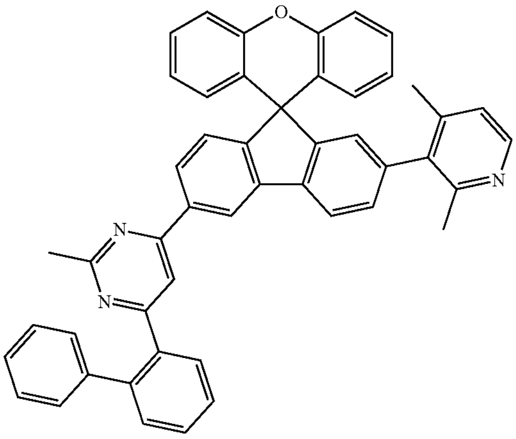

12

Compound 12-3 (18.3 g, 30 mmol) and Compound 12-4 (5.0 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 12. (9.0 g, yield 44%, MS: [M+H]+=682).

Synthesis Example 13

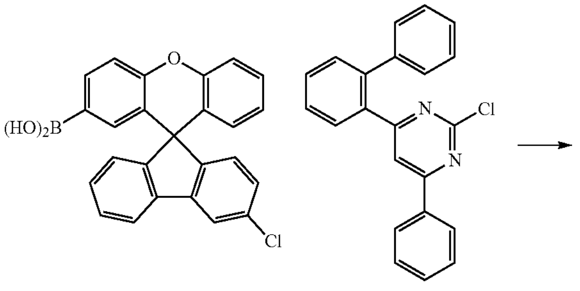

13-1 13-2

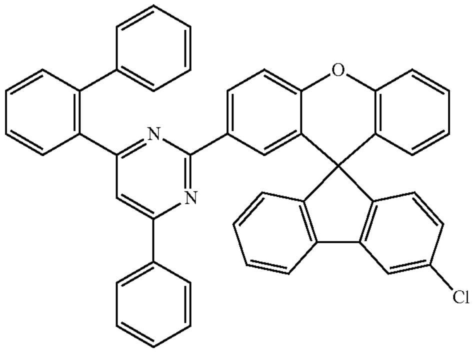

13-3

Compound 13-1 (12.3 g, 30 mmol) and Compound 13-2 (11.3 mol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 13-3. (15.3 g, yield 76%, MS: [M+H]+=674).

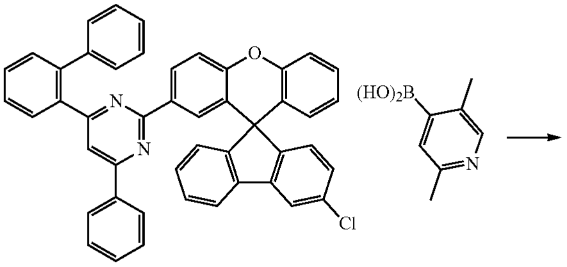

13-3 13-4

-continued

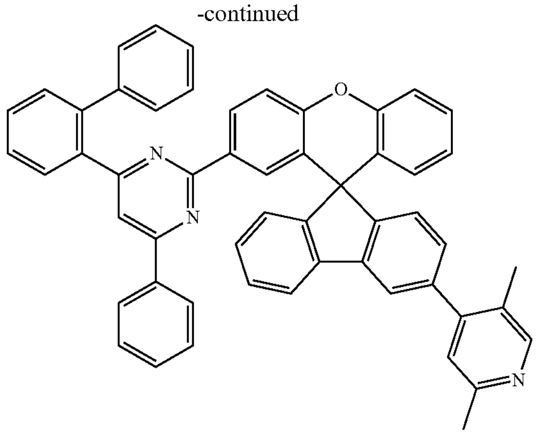

13

Compound 13-3 (20.2 g, 30 mmol) and Compound 13-4 (5.0 g, 33 mmol) were introduced into tetrahydrofuran (300 mL). After 2 M $K_2CO_3$ (100 mL) and $Pd(PtBu_3)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 13. (11.0 g, yield 50%, MS: [M+H]+=735).

Synthesis Example 14

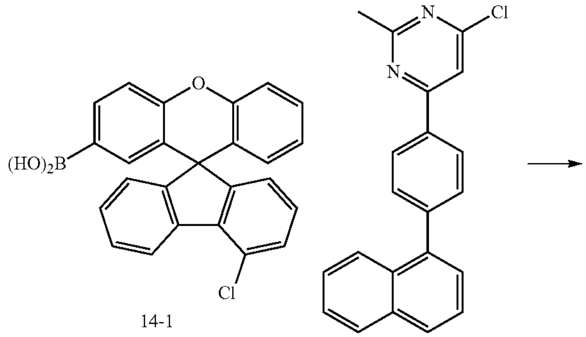

14-1 14-2

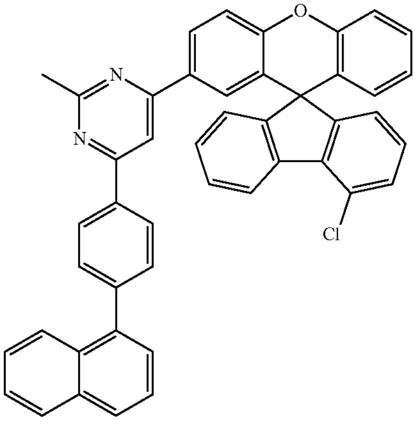

14-3

Compound 14-1 (12.3 g, 30 mmol) and Compound 14-2 (10.9 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 14-3. (15.3 g, yield 77%, MS: [M+H]+=662).

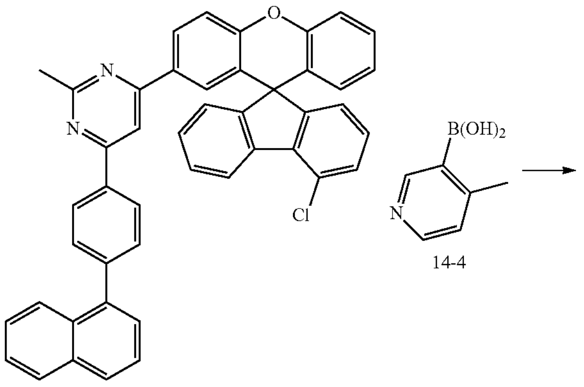

14-3

14-4

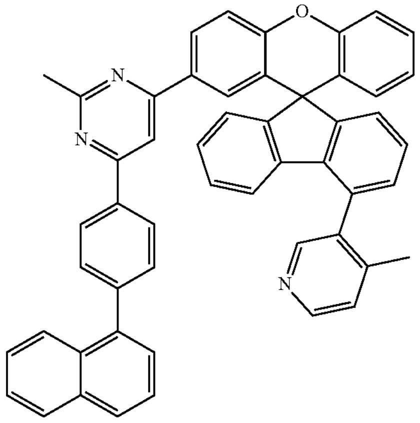

14

Compound 14-3 (19.8 g, 30 mmol) and Compound 14-4 (4.5 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 14. (11.0 g, yield 51%, MS: [M+H]+=718).

Synthesis Example 15

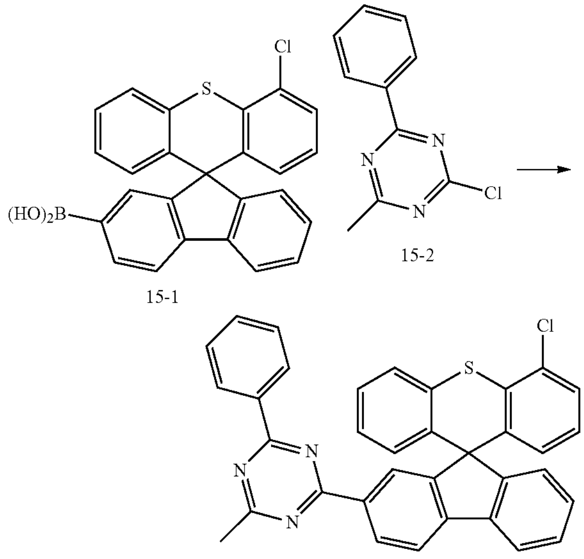

15-1

15-2

15-3

Compound 15-1 (12.8 g, 30 mmol) and Compound 15-2 (6.8 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 15-3. (13.3 g, yield 80%, MS: [M+H]+=553).

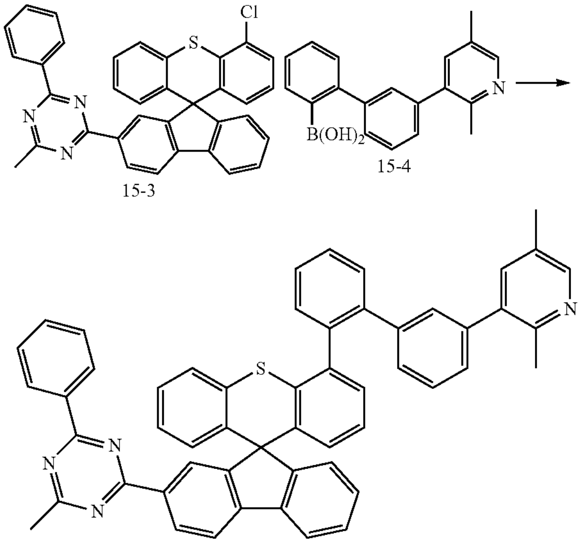

15-3

15-4

15

Compound 15-3 (16.6 g, 30 mmol) and Compound 15-4 (10.0 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 15. (13.9 g, yield 60%, MS: [M+H]+=775).

Synthesis Example 16

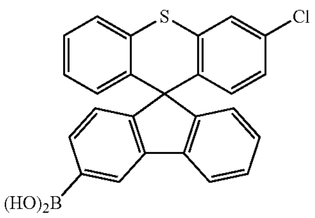

16-1

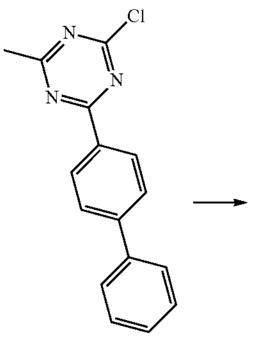

16-2

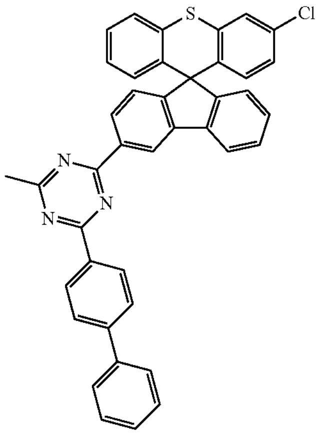

16-3

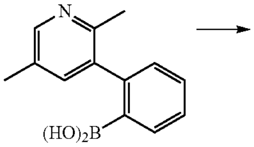

16-4

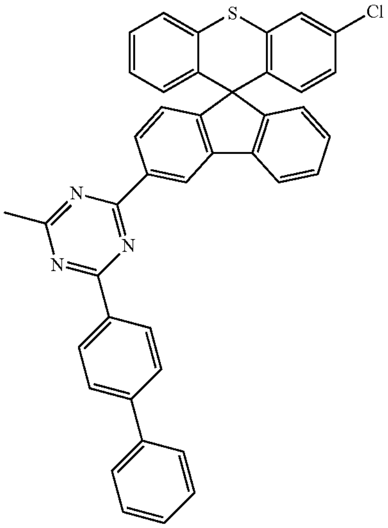

16-3

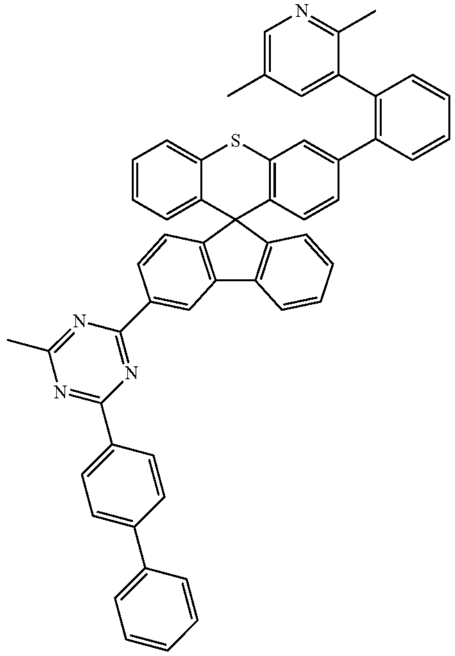

16

Compound 16-1 (12.8 g, 30 mmol) and Compound 16-2 (9.8 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 16-3. (11.7 g, yield 62%, MS: [M+H]+=629).

Compound 16-3 (18.8 g, 30 mmol) and Compound 16-4 (7.0 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 16. (13.5 g, yield 58%, MS: [M+H]+=775).

Synthesis Example 17

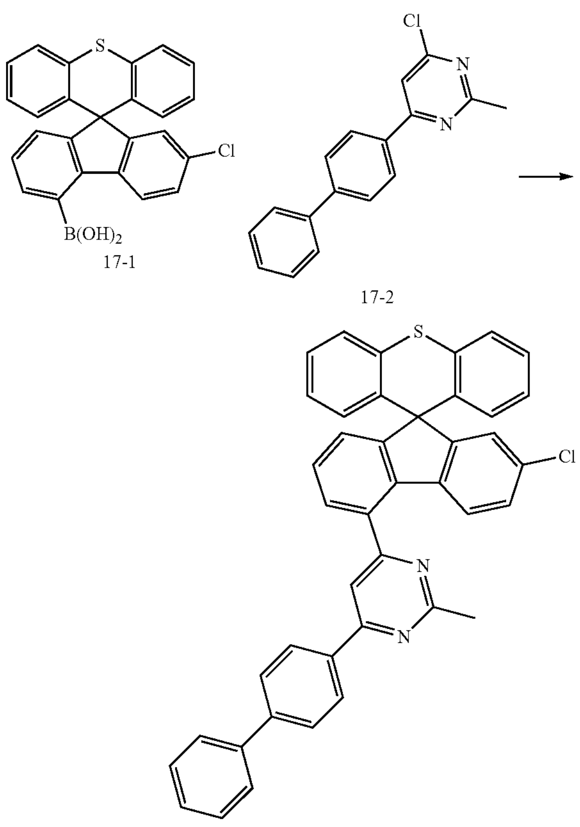

17-1 17-2 17-3

Compound 17-1 (12.8 g, 30 mmol) and Compound 17-2 (9.3 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 17-3. (12.8 g, yield 68%, MS: [M+H]+=628).

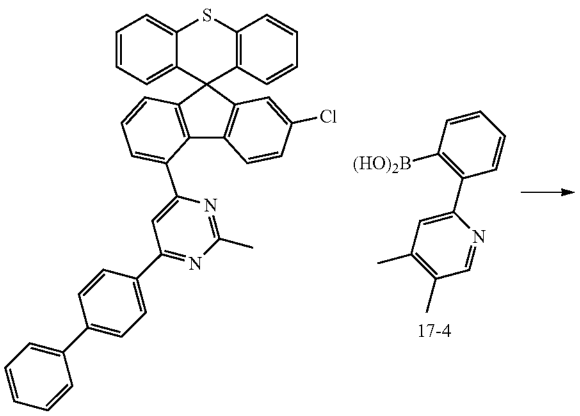

17-3 17-4

-continued

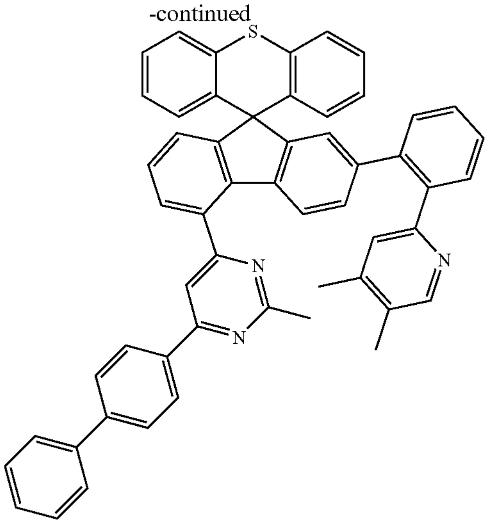

17

Compound 17-3 (18.8 g, 30 mmol) and Compound 17-4 (7.0 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 17. (9.8 g, yield 42%, MS: [M+H]+=775).

Synthesis Example 18

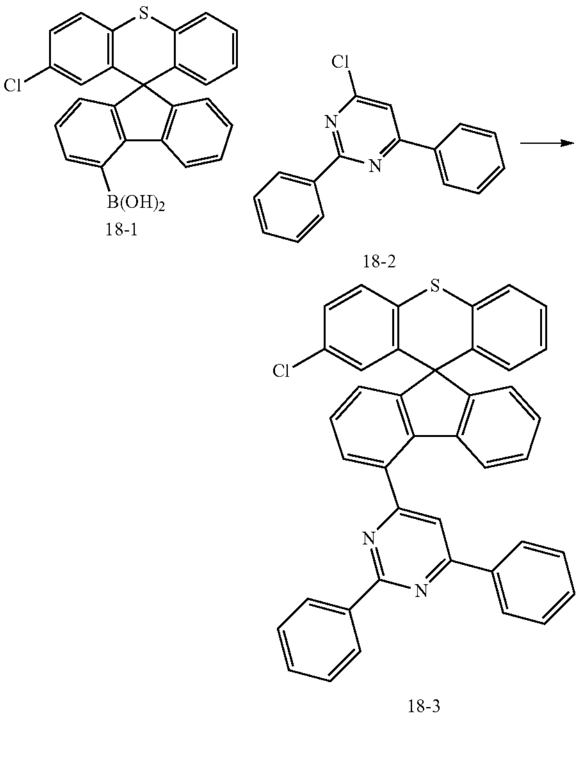

18-1 18-2 18-3

Compound 18-1 (12.8 g, 30 mmol) and Compound 18-2 (8.8 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 18-3. (12.9 g, yield 70%, MS: [M+H]+=614).

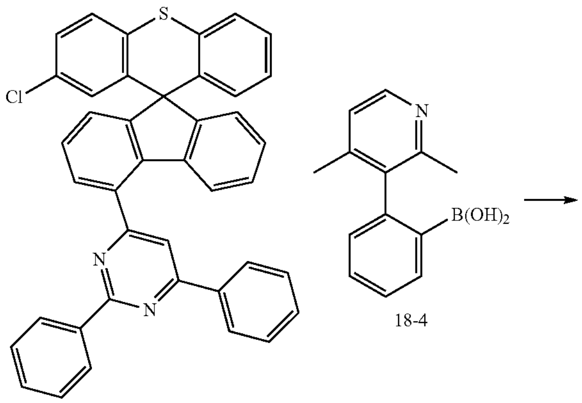

18-3 18-4

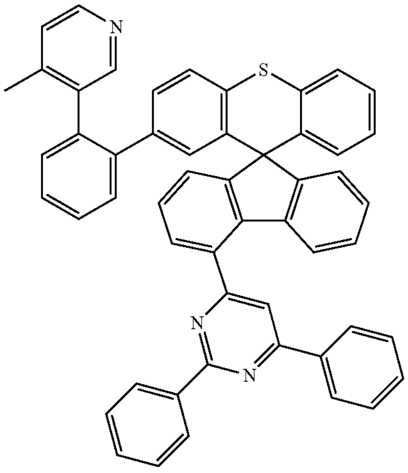

18

Compound 18-3 (18.4 g, 30 mmol) and Compound 18-4 (7.5 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 18. (9.8 g, yield 43%, MS: [M+H]+=760).

Synthesis Example 19

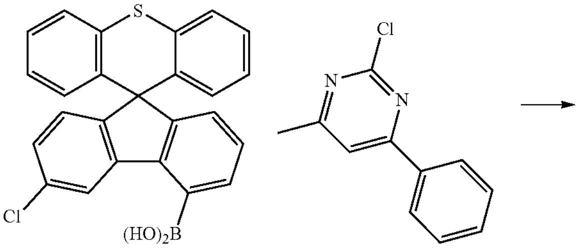

19-1 19-2

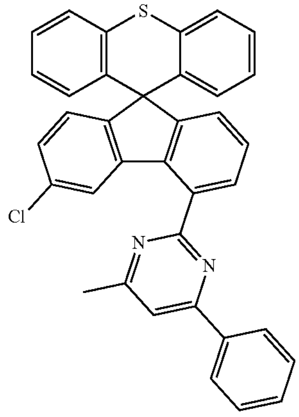

19-3

Compound 19-1 (12.8 g, 30 mmol) and Compound 19-2 (6.8 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 19-3. (11.7 g, yield 71%, MS: [M+H]+=552).

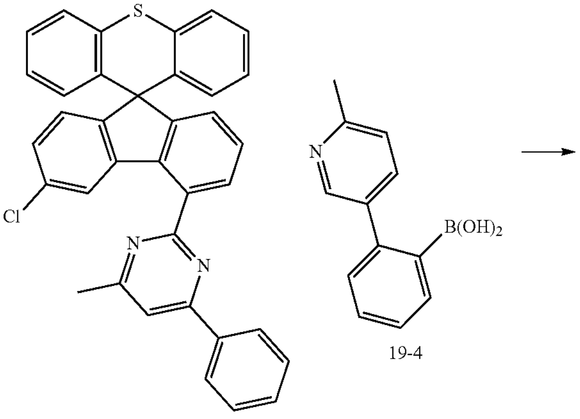

19-3 19-4

-continued

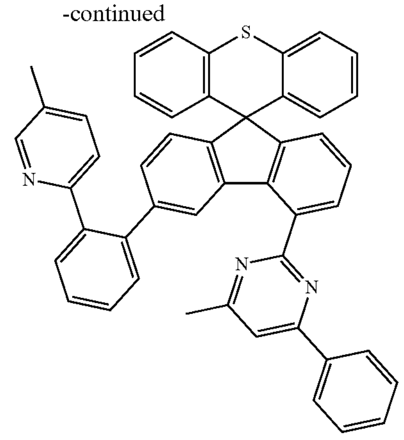

19

Compound 19-3 (16.5 g, 30 mmol) and Compound 19-4 (7.0 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 19. (8.8 g, yield 43%, MS: [M+H]+=684).

Synthesis Example 20

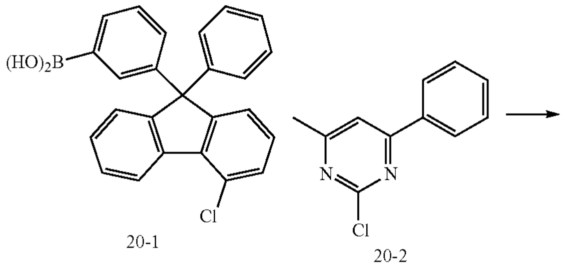

20-1 20-2

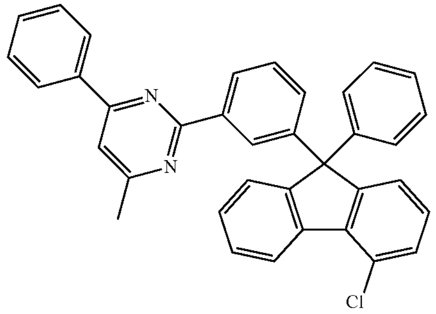

20-3

Compound 20-1 (11.9 g, 30 mmol) and Compound 20-2 (6.8 g, 33 mmol) were introduced into tetrahydrofuran (300 mL). After 2 M $K_2CO_3$ (100 mL), $Pd(dba)_2$ (0.6 g), and $PCy_3$ (0.6 g) were introduced thereinto, the resulting mixture was stirred and refluxed for 5 hours. The mixture was cooled to room temperature, and then a solid produced by filtering the mixture was recrystallized with chloroform and ethanol, thereby preparing Compound 20-3. (11.4 g, yield 73%, MS: [M+H]+=522).

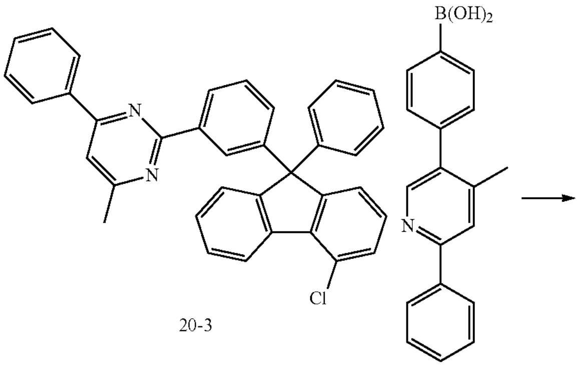

20-3 20-4

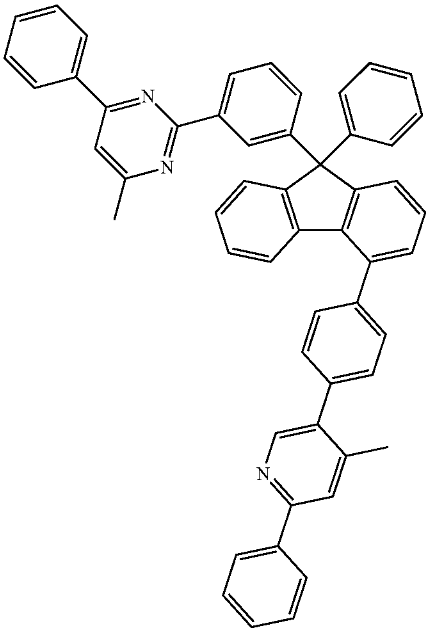

20

Compound 20-3 (15.6 g, 30 mmol) and Compound 20-4 (9.5 g, 33 mmol) were introduced into tetrahydrofuran (300 mL). After 2 M $K_2CO_3$ (100 mL) and $Pd(PtBus)_2$ (0.9 g) were introduced thereinto, the resulting mixture was stirred and refluxed for 5 hours. The mixture was cooled to room temperature, and then a solid produced by filtering the mixture was recrystallized twice with ethyl acetate, thereby preparing Compound 20. (11.4 g, yield 52%, MS: [M+H]+=730).

Experimental Example 1

A glass substrate thinly coated with indium tin oxide (ITO) to have a thickness of 1000 Å was put into distilled water in which a detergent was dissolved, and ultrasonically washed. In this case, a product manufactured by the Fischer Co., was used as the detergent, and distilled water twice filtered using a filter manufactured by Millipore Co., was used as the distilled water. After the ITO was washed for 30 minutes, ultrasonic washing was repeated twice by using distilled water for 10 minutes. After the washing using distilled water was completed, ultrasonic washing was conducted by using isopropyl alcohol, acetone, and methanol solvents, and the resulting product was dried and then transported to a plasma washing machine. The substrate was cleaned by using oxygen plasma for 5 minutes, and then was transported to a vacuum deposition machine.

The following HI-A compound was thermally vacuum-deposited to have a thickness of 600 Å on the ITO transparent electrode thus prepared, thereby forming a hole injection layer. The following HAT compound and the following HT-A compound were sequentially vacuum-deposited to have a thickness of 50 Å and 60 Å, respectively, on the hole injection layer, thereby forming a first hole transport layer and a second hole transport layer.

Subsequently, the following BH compound and BD compound were vacuum-deposited at a weight ratio of 25:1 to have a film thickness of 200 Å on the second hole transport layer, thereby forming a light emitting layer.

Compound 1 prepared in Synthesis Example 1 and the following LiQ compound were vacuum-deposited at a weight ratio of 1:1 on the light emitting layer, thereby forming an electron injection and transport layer having a thickness of 350 Å. Lithium fluoride (LiF) and aluminum were sequentially deposited to have a thickness of 10 Å and 1000 Å, respectively, on the electron injection and transport layer, thereby forming a negative electrode.

In the aforementioned procedure, the deposition rate of the organic material was maintained at 0.4 to 0.9 Å/sec, the deposition rates of lithium fluoride and aluminum of the negative electrode were maintained at 0.3 Å/sec and at 2 Å/sec, respectively, and the degree of vacuum during the deposition was maintained at $1\times10^{-7}$ to $5\times10^{-5}$ torr, thereby manufacturing an organic light emitting device.

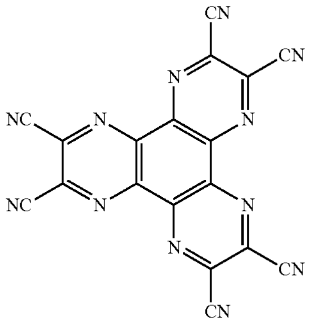

HAT

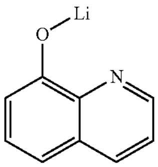

LiQ

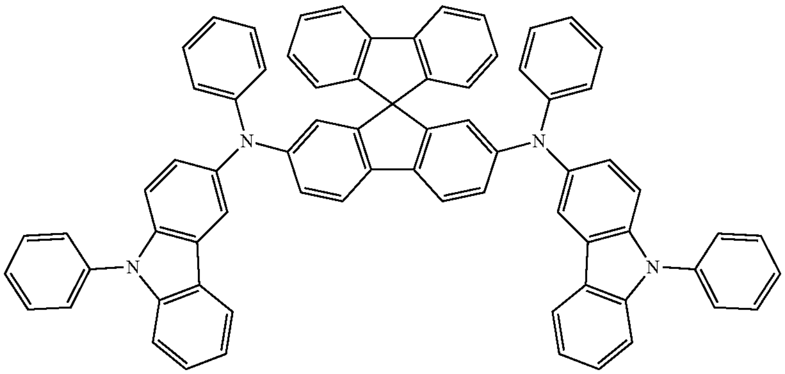

HI-A

-continued
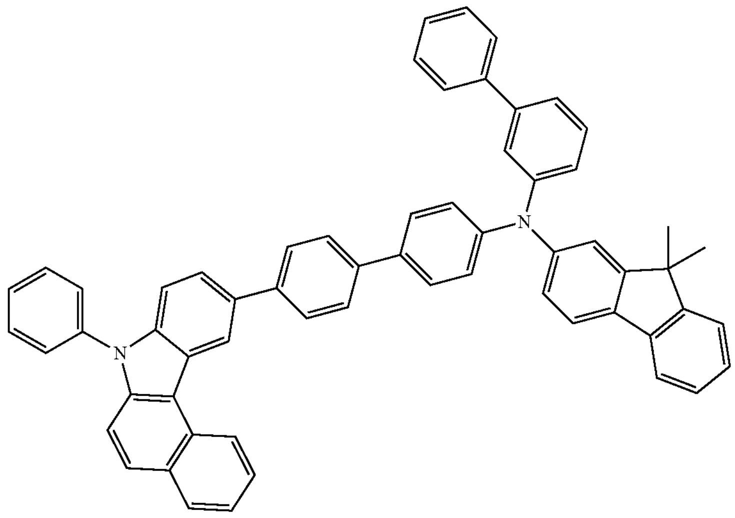
HT-A
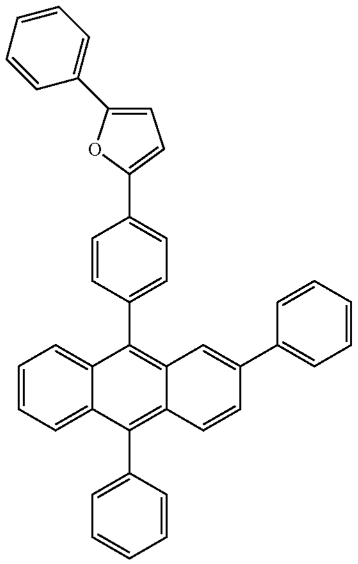
BH
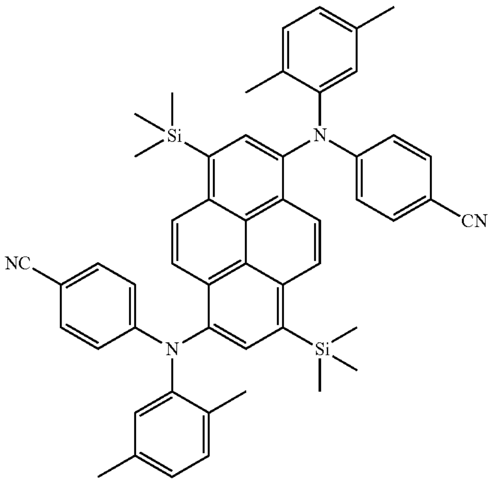
BD

Experimental Examples 2 to 20 and Comparative Examples 1 to 4
Organic light emitting devices were manufactured in the same manner as in Experimental Example 1, except that the compounds in the following Table 1 were used instead of Compound 1.
1
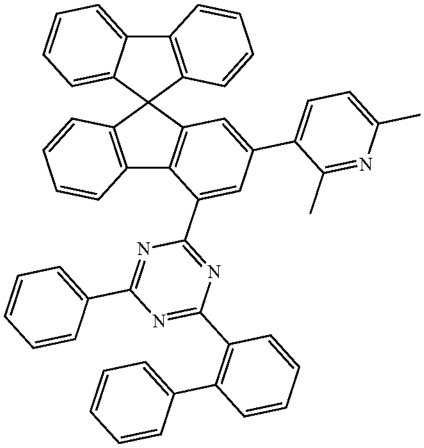
2
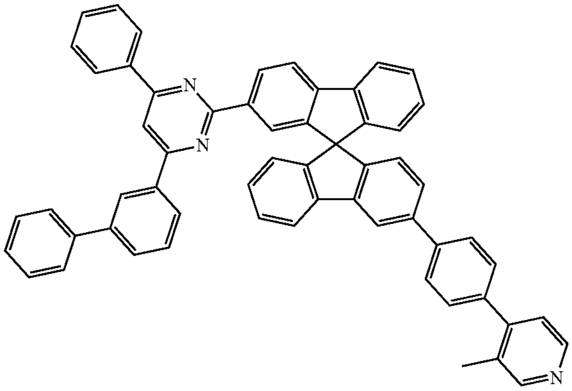
3
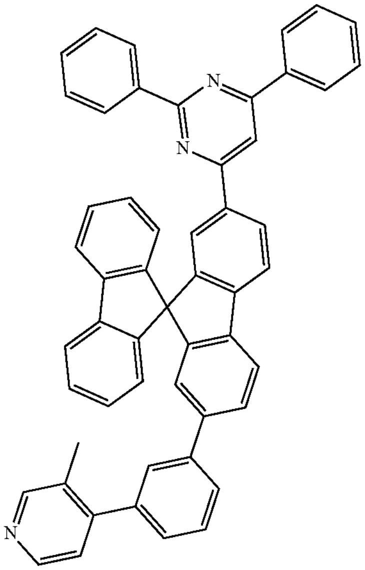
-continued
4
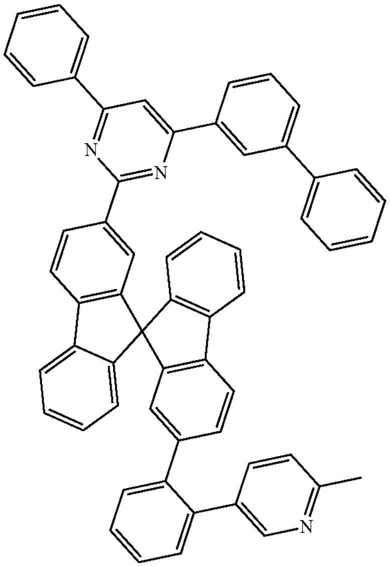
5
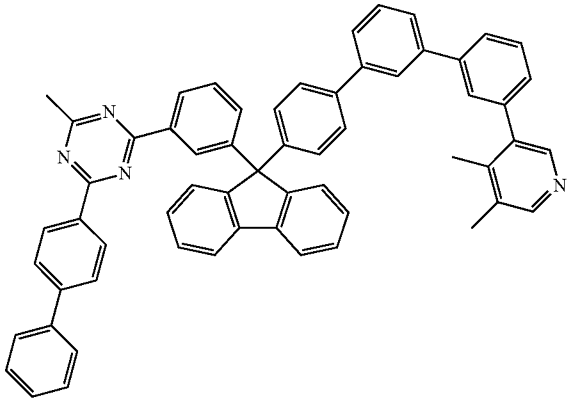
6
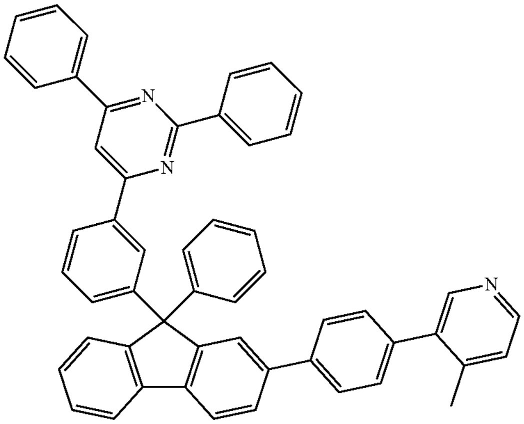

7
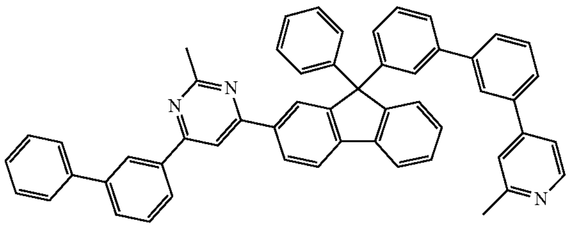
8
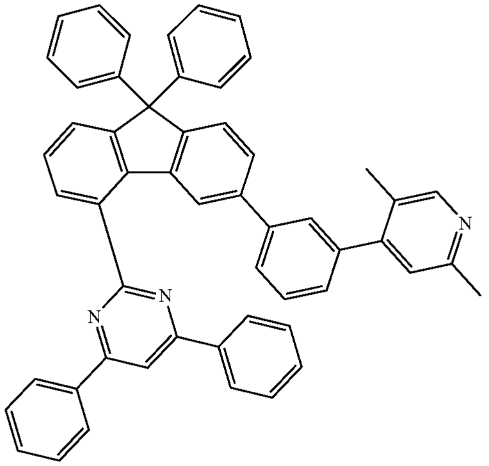
9
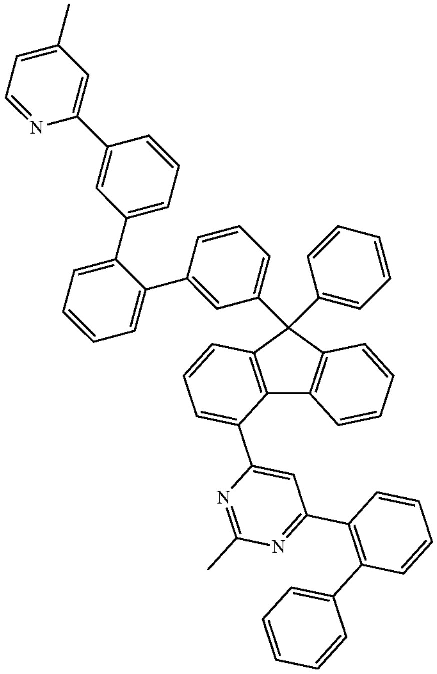
10
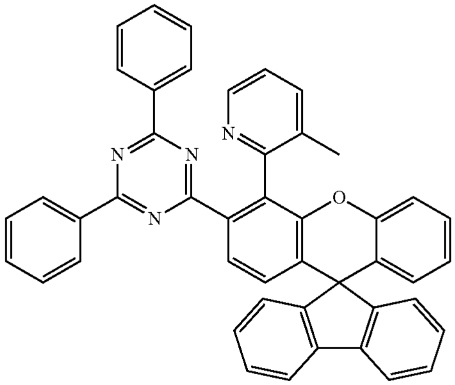
11
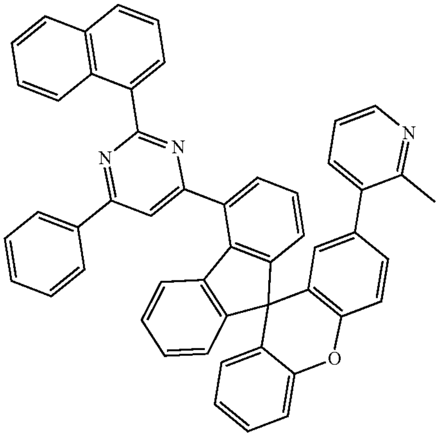
12
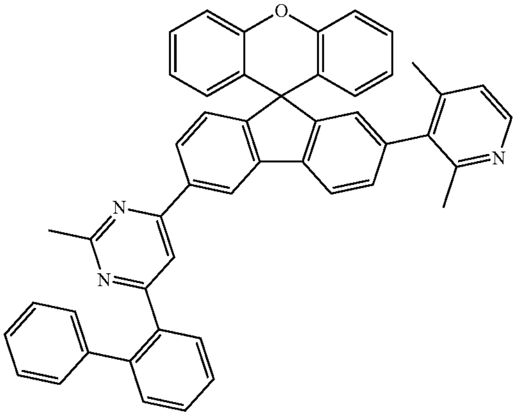

13
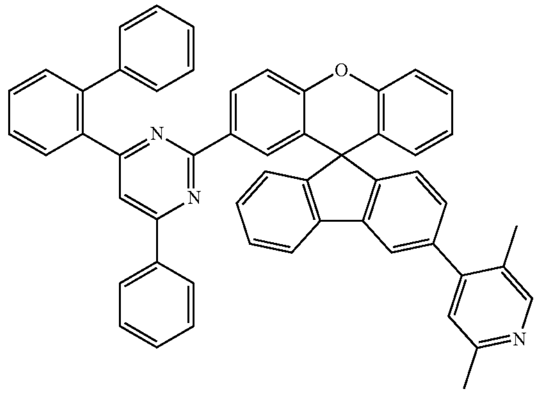
14
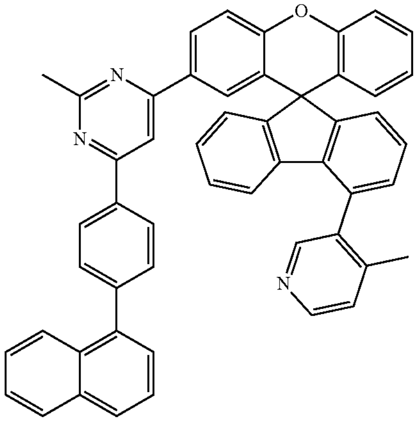
15
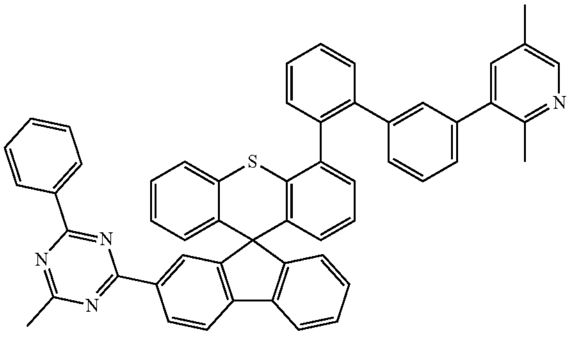
16
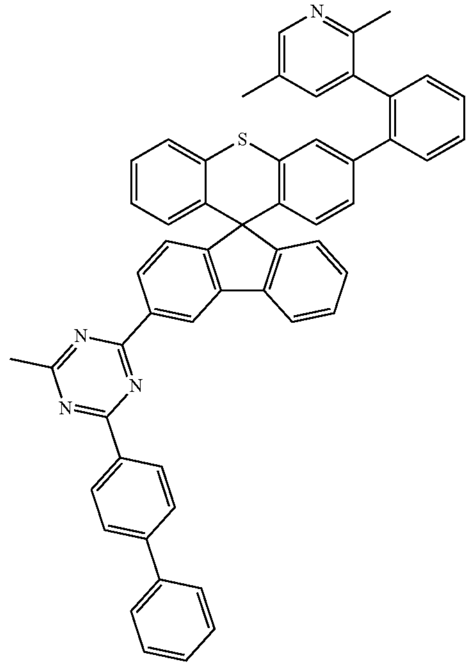
17
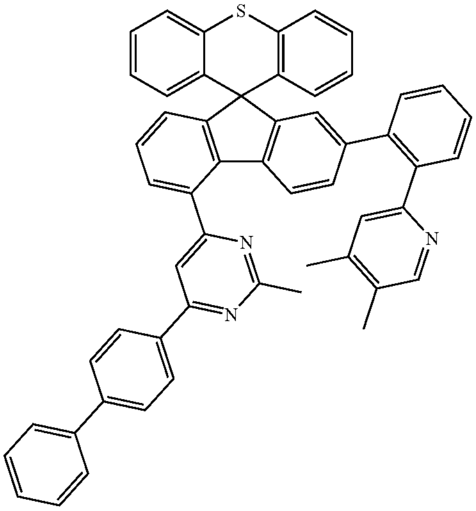
18
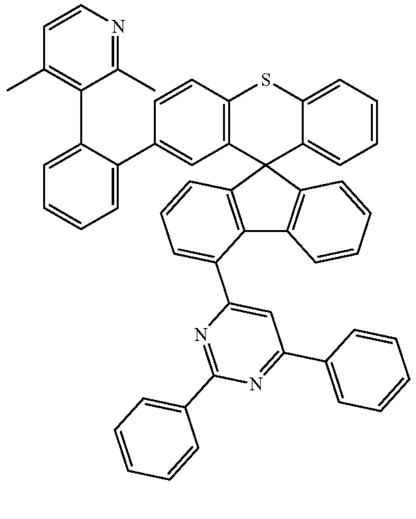

-continued

19

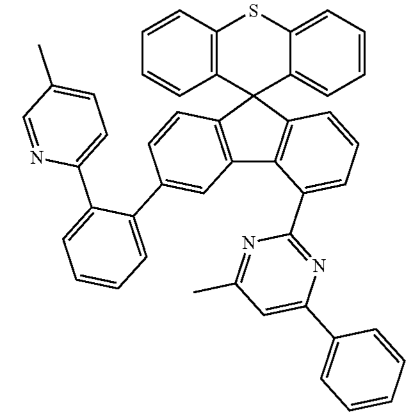

20

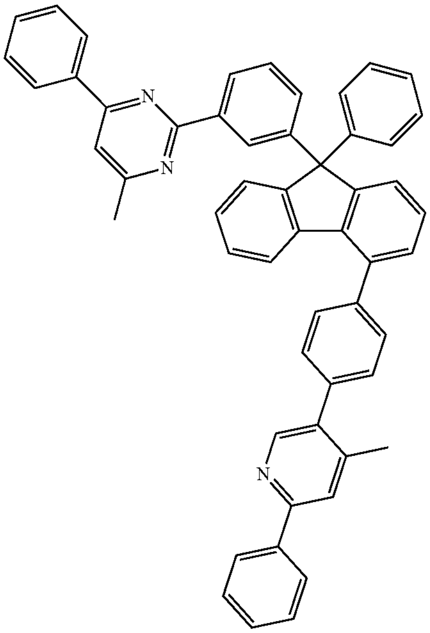

A

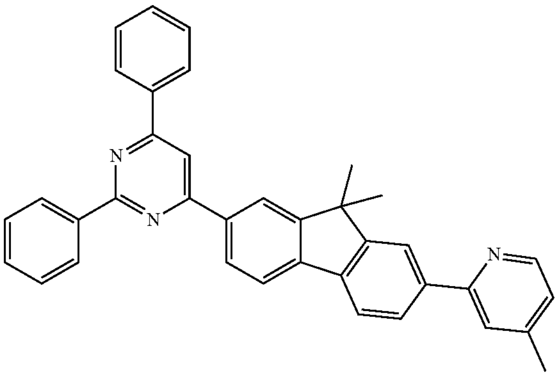

-continued

B

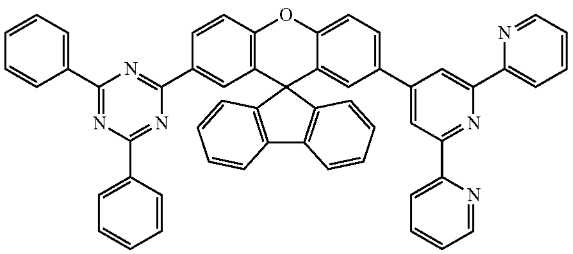

C

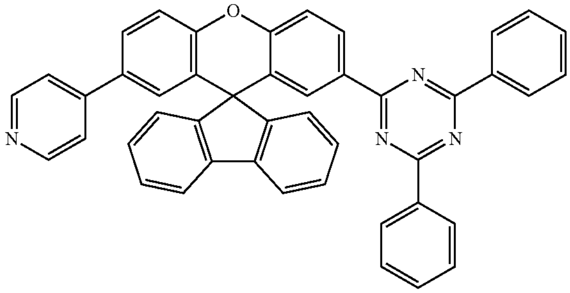

D

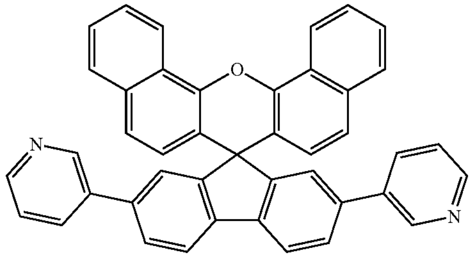

For the organic light emitting devices manufactured by Experimental Examples 1 to 20 and Comparative Examples 1 to 4, the driving voltage and the efficiency were measured at a current density of 10 mA/cm$^2$, and a time (T96) for reaching a 96% value compared to the initial luminance was measured at a current density of 20 mA/cm$^2$. The results are shown in the following Table 1.

TABLE 1

| Classification | Compound | Voltage (V) | Current efficiency (cd/A) | Life Time T96 at 20 mA/cm$^2$ |
|---|---|---|---|---|
| Experimental Example 1 | Compound 1 | 3.52 | 5.38 | 75 |
| Experimental Example 2 | Compound 2 | 3.63 | 5.71 | 50 |
| Experimental Example 3 | Compound 3 | 3.62 | 5.65 | 55 |
| Experimental Example 4 | Compound 4 | 3.70 | 5.60 | 80 |
| Experimental Example 5 | Compound 5 | 3.62 | 5.40 | 75 |
| Experimental Example 6 | Compound 6 | 3.83 | 5.63 | 75 |
| Experimental Example 7 | Compound 7 | 3.80 | 5.66 | 60 |
| Experimental Example 8 | Compound 8 | 3.80 | 5.61 | 60 |
| Experimental Example 9 | Compound 9 | 3.78 | 5.61 | 75 |
| Experimental Example 10 | Compound 10 | 3.90 | 5.45 | 75 |

TABLE 1-continued

| Classification | Compound | Voltage (V) | Current efficiency (cd/A) | Life Time T96 at 20 mA/cm$^2$ |
|---|---|---|---|---|
| Experimental Example 11 | Compound 11 | 3.80 | 5.60 | 70 |
| Experimental Example 12 | Compound 12 | 4.00 | 5.61 | 65 |
| Experimental Example 13 | Compound 13 | 3.90 | 5.55 | 65 |
| Experimental Example 14 | Compound 14 | 3.75 | 5.54 | 75 |
| Experimental Example 15 | Compound 15 | 3.63 | 5.40 | 60 |
| Experimental Example 16 | Compound 16 | 3.62 | 5.42 | 65 |
| Experimental Example 17 | Compound 17 | 3.75 | 5.60 | 80 |
| Experimental Example 18 | Compound 18 | 3.62 | 5.61 | 75 |
| Experimental Example 19 | Compound 19 | 3.83 | 5.50 | 80 |
| Experimental Example 20 | Compound 20 | 3.80 | 5.62 | 80 |
| Comparative Example 1 | Compound A | 4.30 | 5.52 | 30 |
| Comparative Example 2 | Compound B | 5.00 | 3.50 | 80 |
| Comparative Example 3 | Compound C | 4.80 | 4.00 | 50 |
| Comparative Example 4 | Compound D | 4.82 | 3.26 | 40 |

As can be confirmed from the experimental data in Table 1, it was confirmed that an organic light emitting device using the compound of Chemical Formula 1 according to the present invention exhibits excellent characteristics in terms of efficiency, driving voltage, and/or stability. Compared to the device of Comparative Example 1 including Compound A in which A1 of Chemical Formula 1 is dimethylfluorene, the devices of Experimental Examples 1 to 20 including the compound of Chemical Formula 1 of the present invention are remarkably excellent in low voltage and long service life characteristics.

Compared to the device of Comparative Example 2 including Compound B in which a methyl group is not linked to pyridine and a heteroaryl group is linked to pyridine, the devices of Experimental Examples 1 to 20 including the compound of Chemical Formula 1 of the present invention are remarkably excellent in low voltage and high efficiency characteristics.

Compared to the device of Comparative Example 3 including Compound C in which a substituent is not linked to pyridine, the devices of Experimental Examples 1 to 20 including the compound of Chemical Formula 1 of the present invention are remarkably excellent in low voltage, high efficiency, and long service life characteristics.

Compared to the device of Comparative Example 4 including Compound D which does not include triazine or pyrimidine, the devices of Experimental Examples 1 to 20 including the compound of Chemical Formula 1 of the present invention are remarkably excellent in low voltage, high efficiency, and long service life characteristics.

The invention claimed is:

1. A heterocyclic compound of Chemical Formula 1:

[Chemical Formula 1]

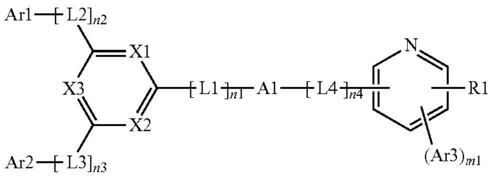

wherein in Chemical Formula 1:

at least two of X1 to X3 are N, and the other is CH;

R1 is a substituted or unsubstituted alkyl group;

L1 to L4 are the same as or different from each other, and are each independently a direct bond, a substituted or unsubstituted arylene group, or a substituted or unsubstituted heteroarylene group;

n1 to n4 are an integer from 0 to 4;

Ar1 to Ar3 are the same as or different from each other, and are each independently a substituted or unsubstituted alkyl group, a substituted or unsubstituted aryl group, or a substituted or unsubstituted heteroaryl group;

m1 is an integer from 0 to 3;

when n1 to n4 and m1 are each 2 or higher, substituents in the parenthesis are the same as or different from each other;

A1 is Chemical Formula 1-1,

[Chemical Formula 1-1]

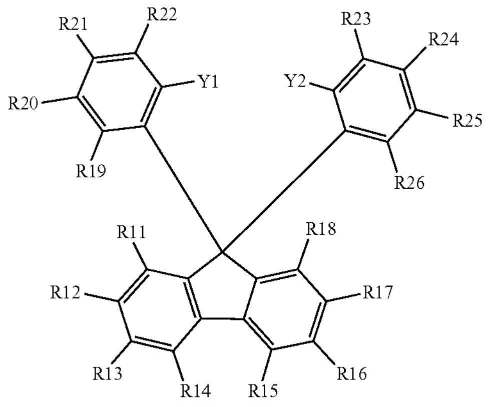

wherein in Chemical Formula 1-1:

Y1 and Y2 are each hydrogen or deuterium, or are directly bonded to each other, or are linked to each other through —C(R31)(R32)-, —Si(R33)(R34)-, —N(R35)-, —O—, or —S—;

any one of R11 to R26 is linked to L1 of Chemical Formula 1, and of the remaining, one is linked to L4 of Chemical Formula 1, and the others are the same as or different from each other, and are each independently hydrogen, deuterium, a cyano group, a substituted or unsubstituted alkyl group, a substituted or unsubstituted aryl group, or a substituted or unsubstituted heteroaryl group; and R31 to R35 are the same as or different from each other, and are each independently hydrogen, deuterium, a cyano group, a substituted or unsubstituted alkyl group, a substituted or unsubstituted aryl group, or a substituted or unsubstituted heteroaryl group.

2. The heterocyclic compound of claim 1, wherein Chemical Formula 1-1 is any one of the following Chemical Formulae A11 to A13:

[Chemical Formula A11]

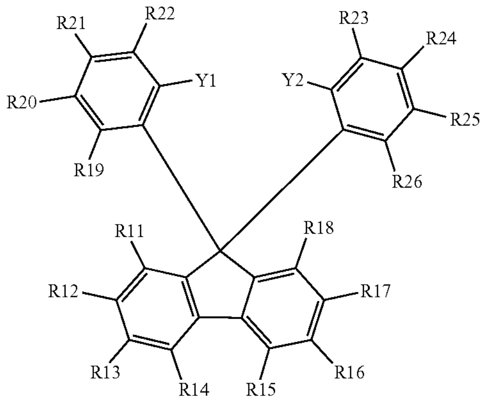

[Chemical Formula A12]

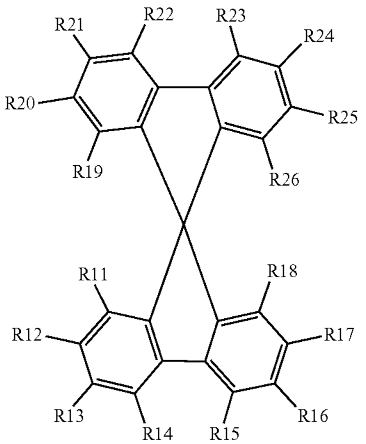

[Chemical Formula A13]

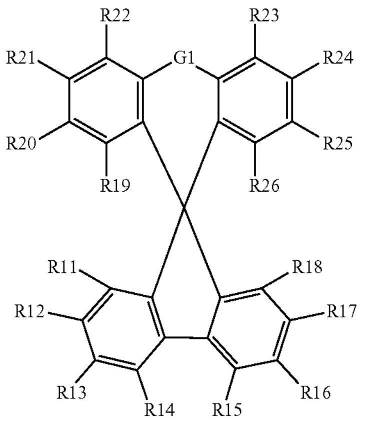

wherein in Chemical Formulae A11 to A13, the definitions of R11 to R26 are the same as those defined in Chemical Formula 1-1;

Y1 and Y2 are each hydrogen or deuterium;

G1 is C(R31)(R32), Si(R33)(R34), N(R35), O; or S; and

R31 to R35 are the same as or different from each other, and are each independently hydrogen, deuterium, a cyano group, a substituted or unsubstituted alkyl group, a substituted or unsubstituted aryl group, or a substituted or unsubstituted heteroaryl group.

3. The heterocyclic compound of claim 1, wherein A1 is a divalent group selected from among the following structures:

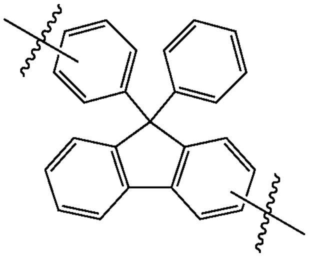

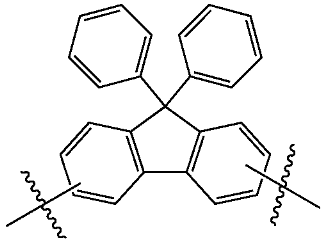

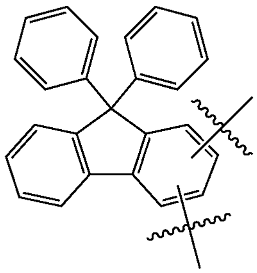

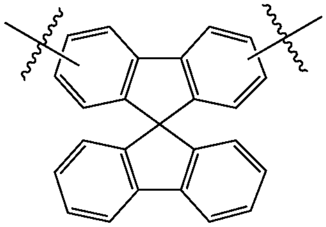

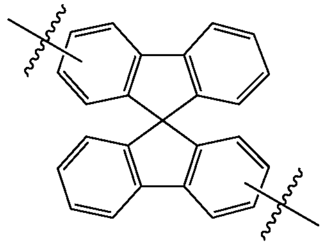

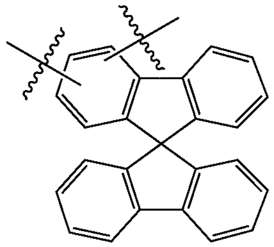

-continued

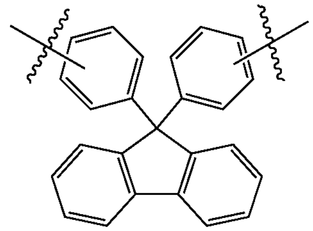

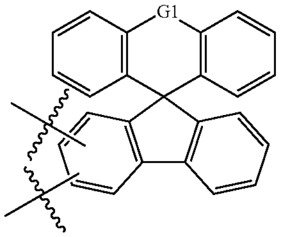

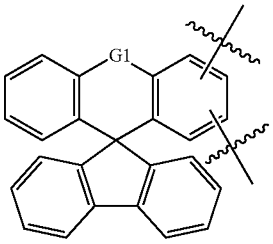

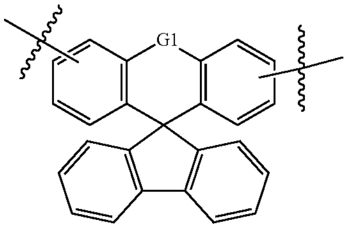

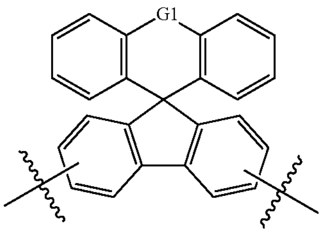

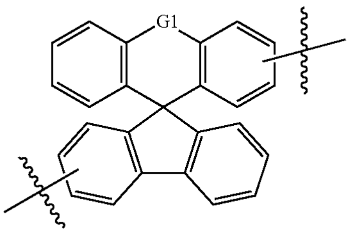

wherein in the structures:

G1 is C(R31)(R32), Si(R33)(R34), N(R35), O, or S, R31 to R35 are the same as or different from each other, and are each independently hydrogen, deuterium, a cyano group, a substituted or unsubstituted alkyl group, a substituted or unsubstituted aryl group, or a substituted or unsubstituted heteroaryl group;

the structures are unsubstituted or substituted with deuterium, a cyano group, an alkyl group, an aryl group, or a heteroaryl group; and

is a position which is linked to L1 or L4 of Chemical Formula 1.

4. The heterocyclic compound of claim 1, wherein L1 to L4 are the same as or different from each other, and are each independently selected from a direct bond or the following structures:

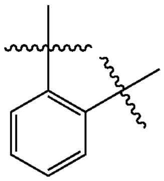

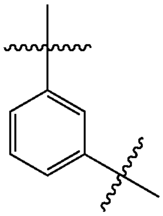

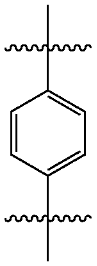

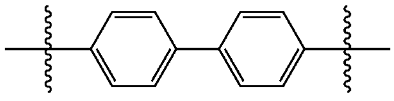

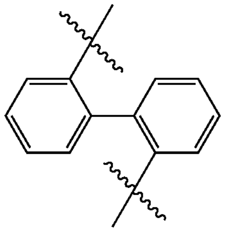

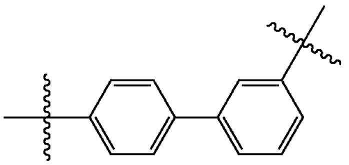

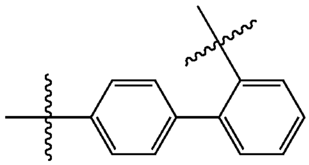

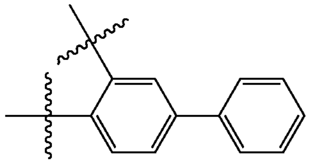

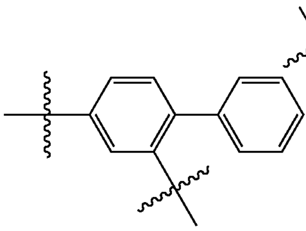

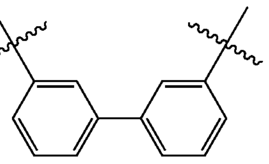

-continued

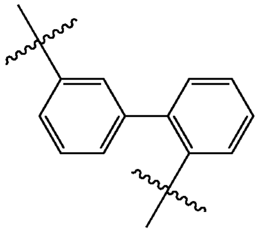

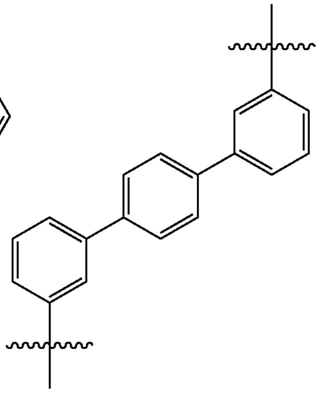

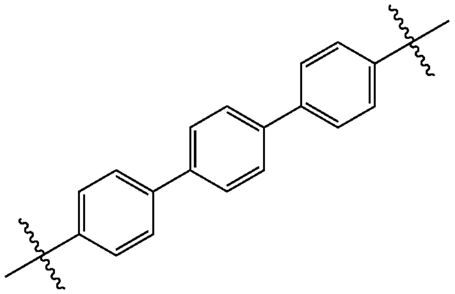

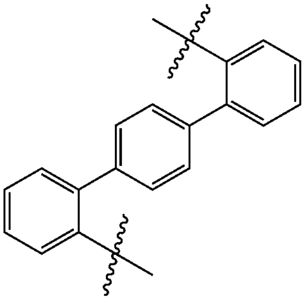

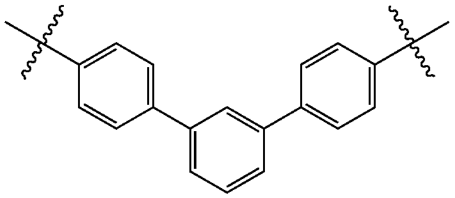

-continued

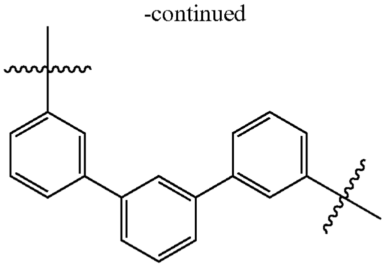

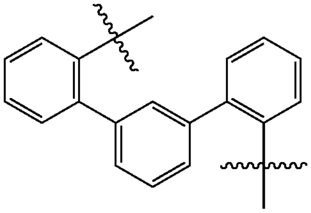

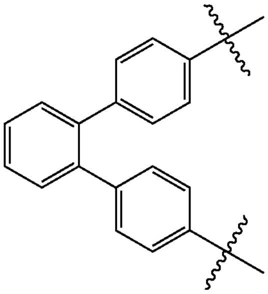

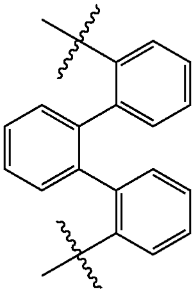

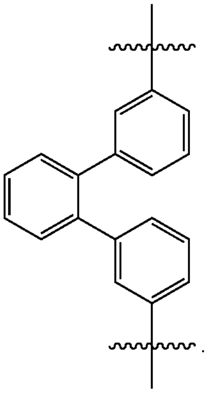

5. The heterocyclic compound of claim 1, wherein;

R1 is a C1-C6 alkyl group;

L1 to L4 are the same as or different from each other, and are each independently a direct bond or a C6-C20 arylene group;

Ar1 to Ar3 are the same as or different from each other, and are each independently a C1-C6 alkyl group or a C6-C20 aryl group;

Y1 and Y2 are each hydrogen or deuterium, or are directly bonded to each other, or are linked to each other through —O— or —S—; and the others among R11 to R26 which are not linked to L1 and L4 of Chemical Formula 1 are the same as or different from each other, and are each independently hydrogen or deuterium.

6. The heterocyclic compound of claim 1, wherein the heterocyclic compound of Chemical Formula 1 is any one compound selected from among the following compounds:

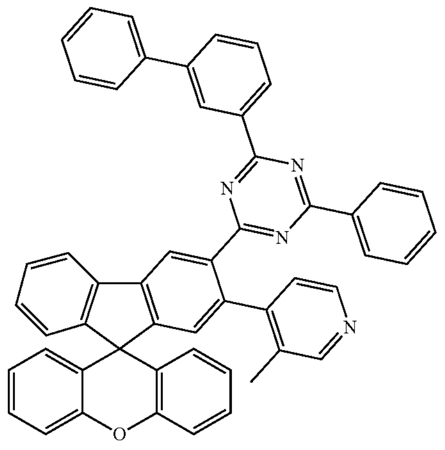
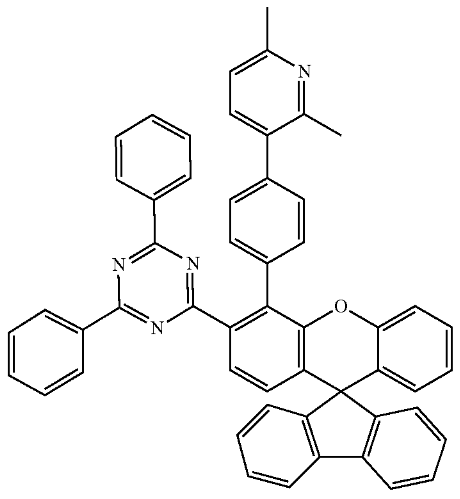
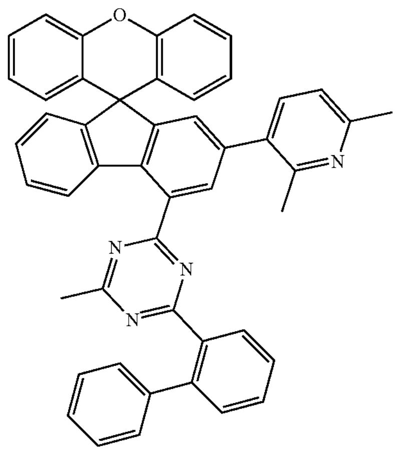
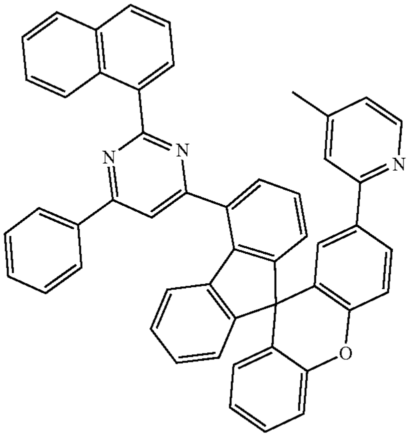
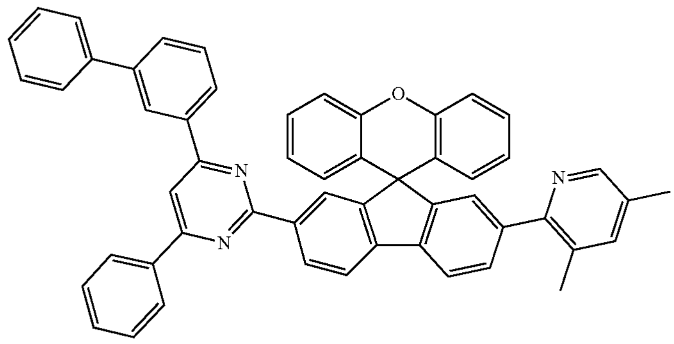
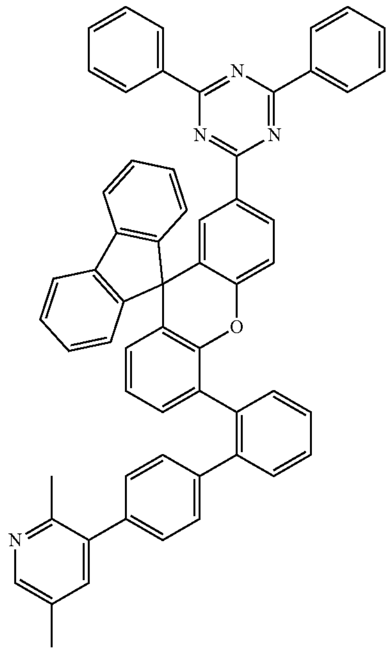

-continued
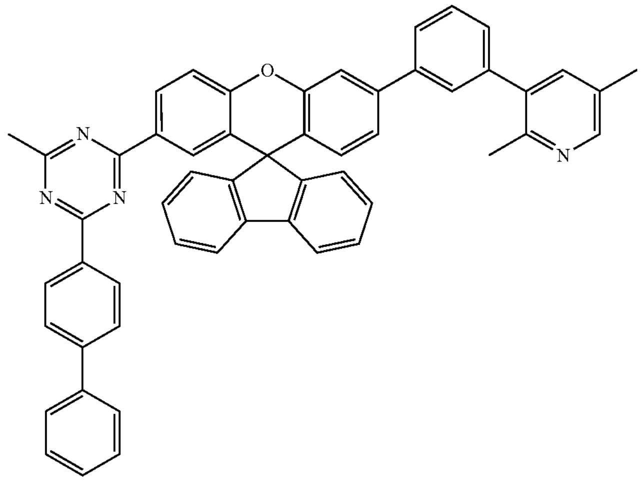
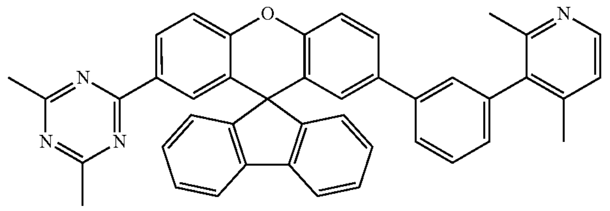
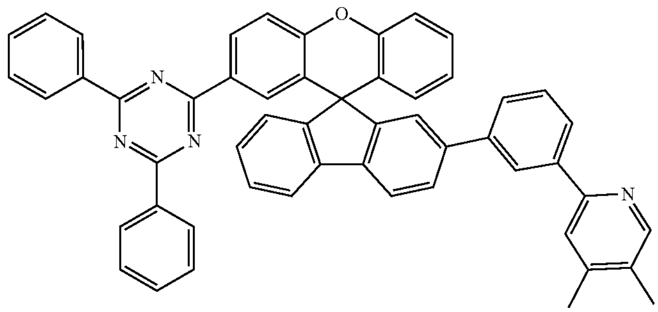
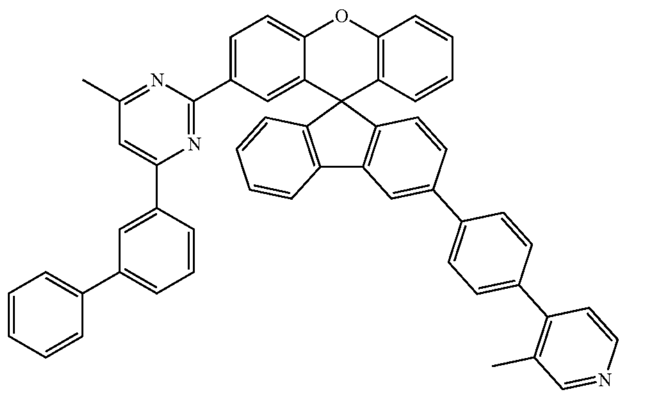

-continued
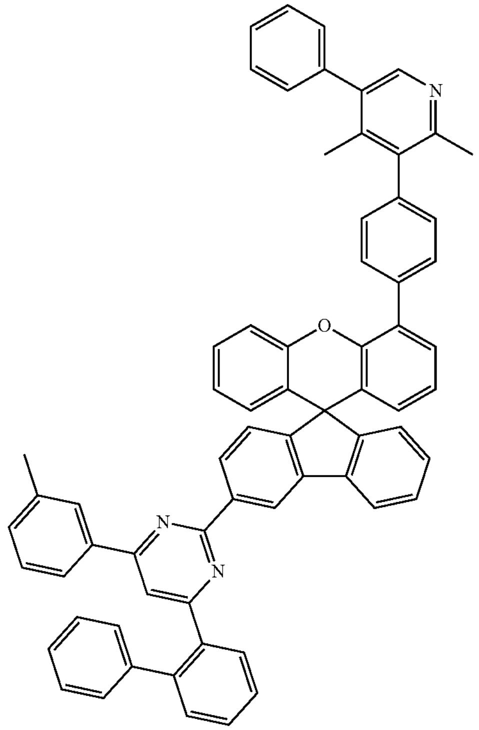
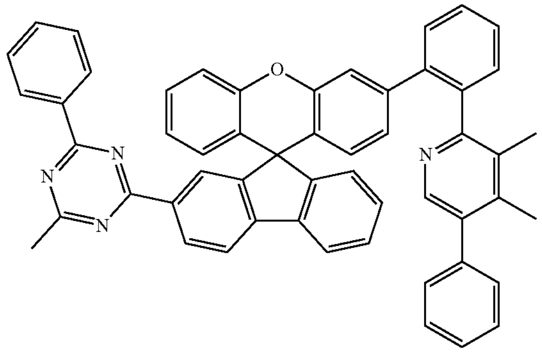
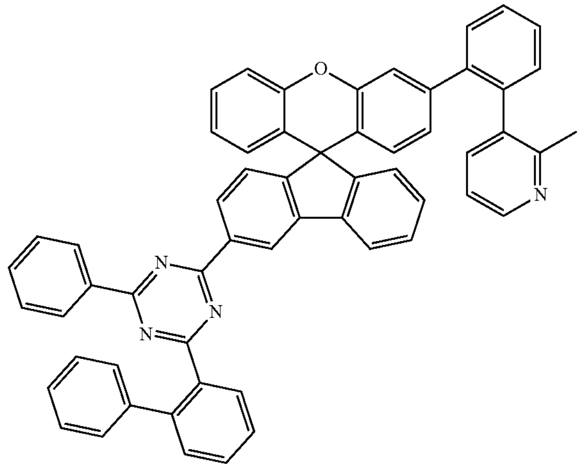
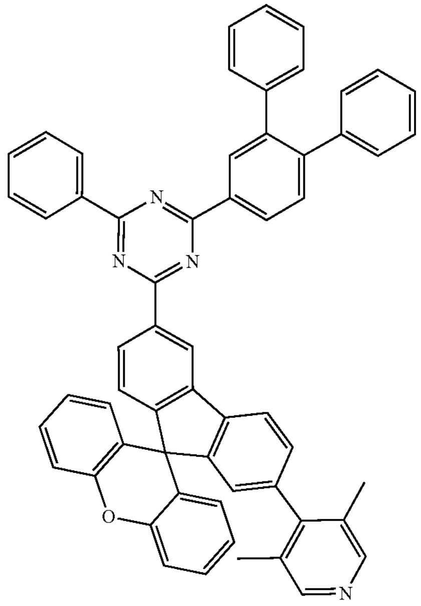

-continued
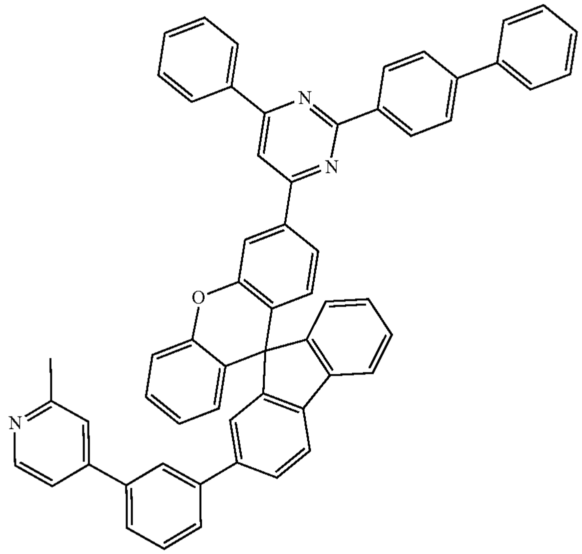
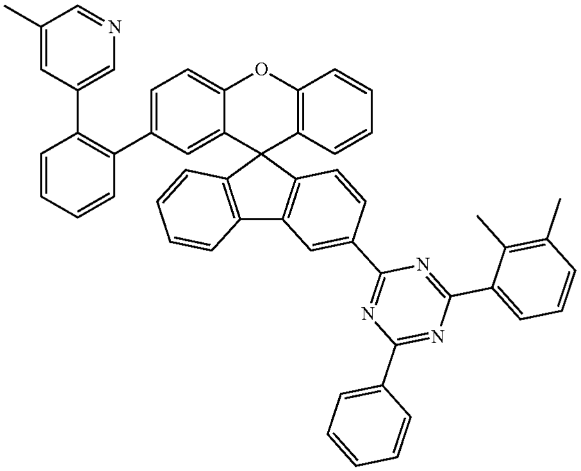
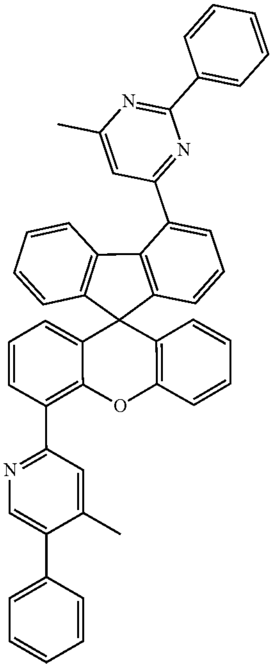
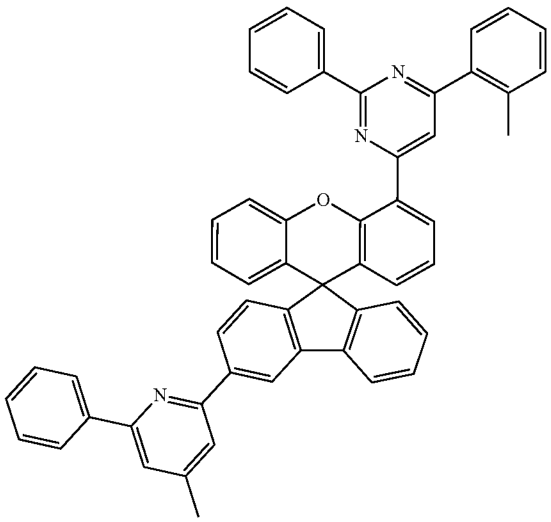
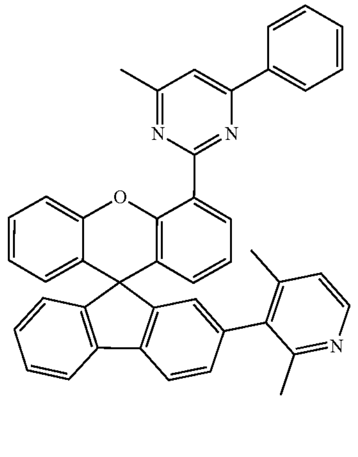

-continued
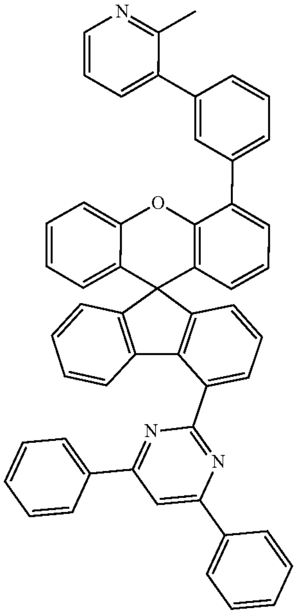
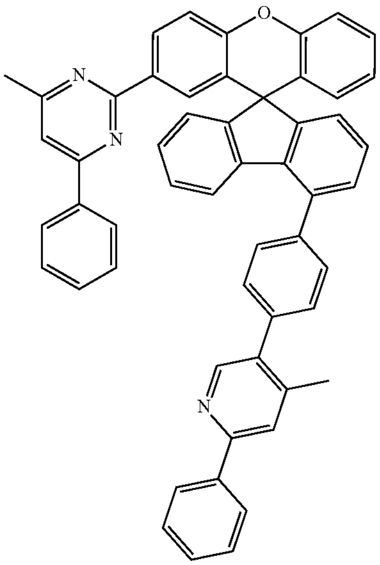
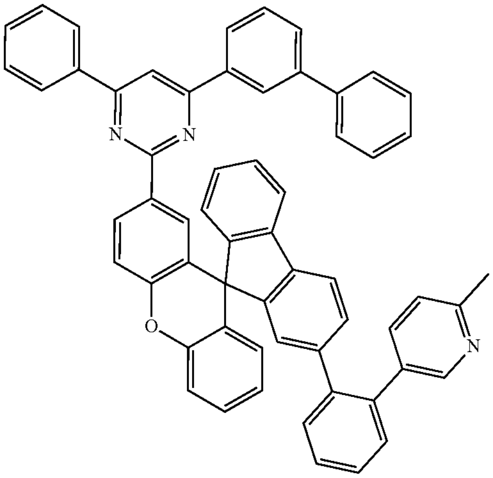
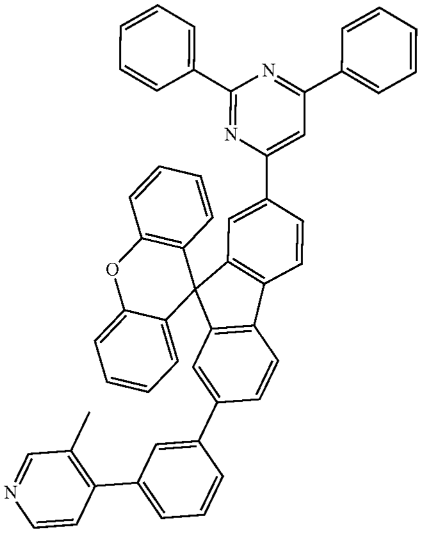

-continued
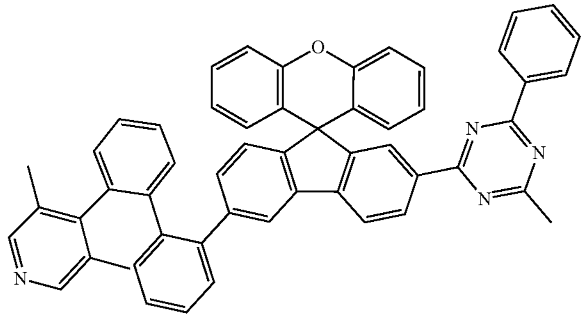
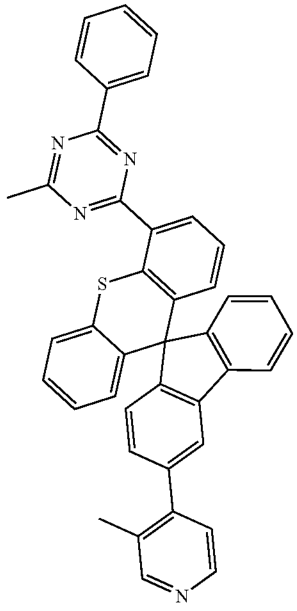
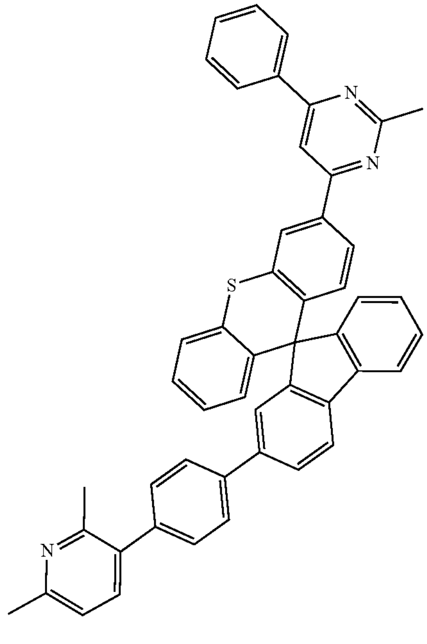
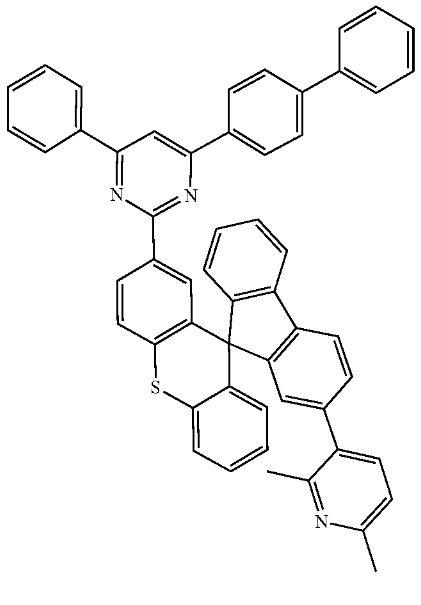

-continued
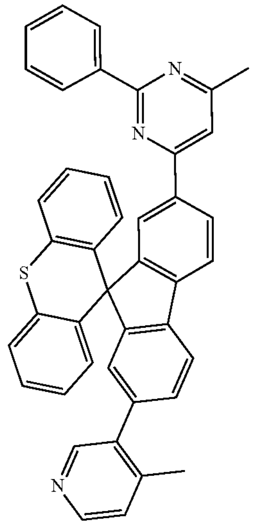
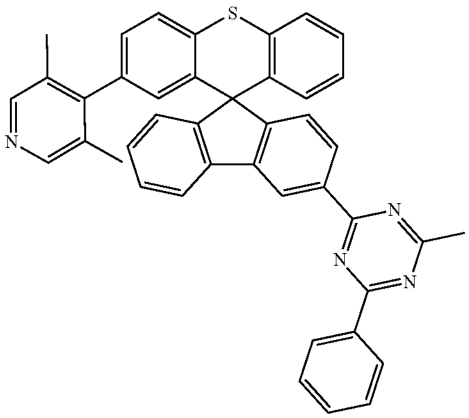
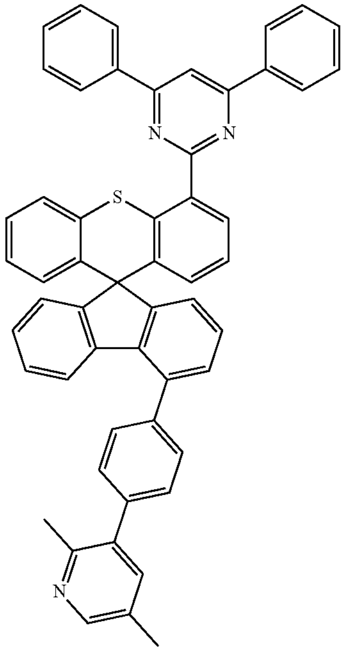
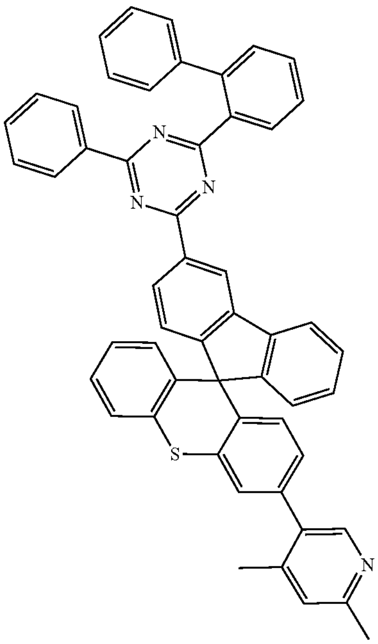
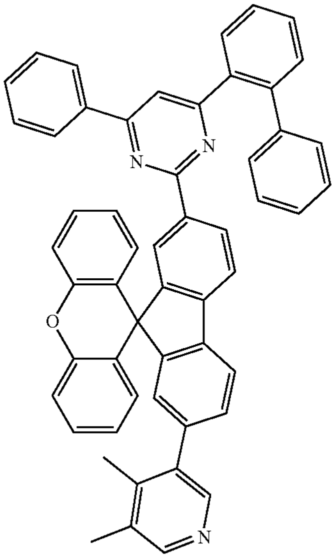

-continued
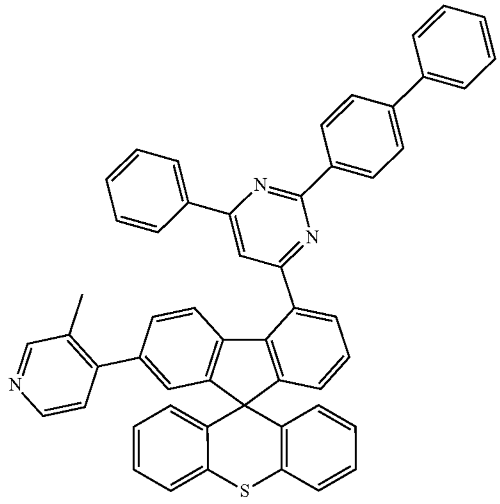
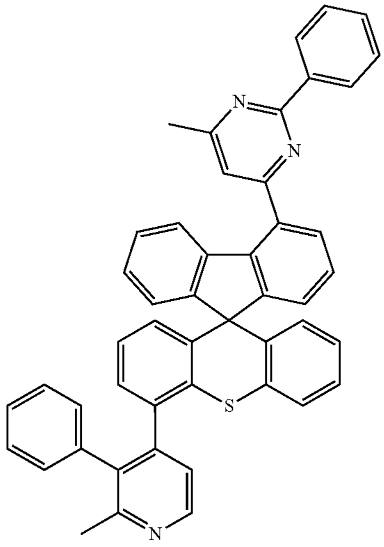
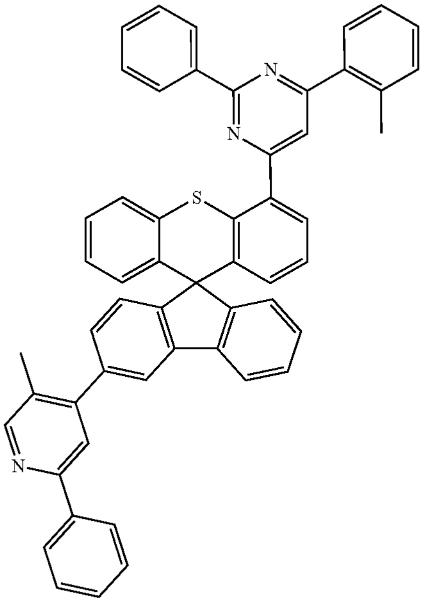
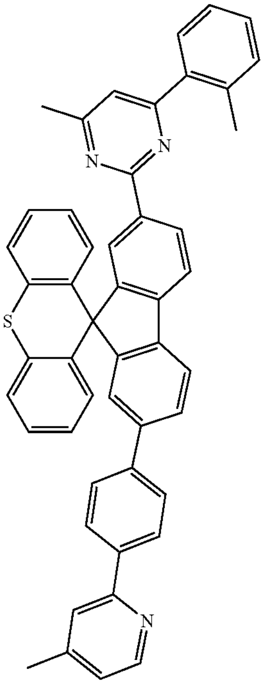

-continued
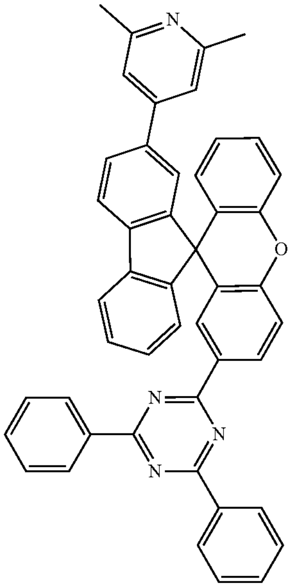
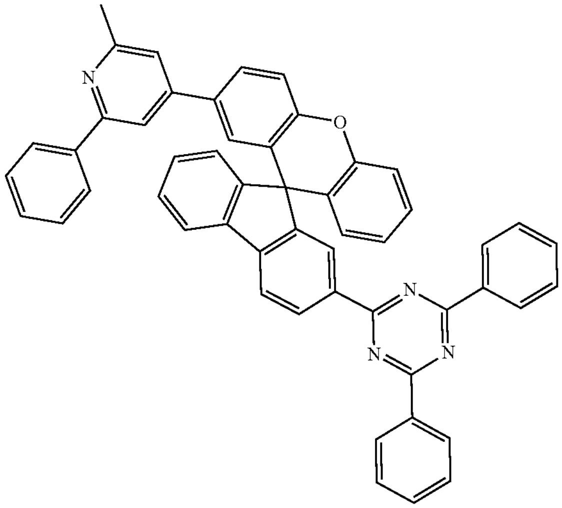
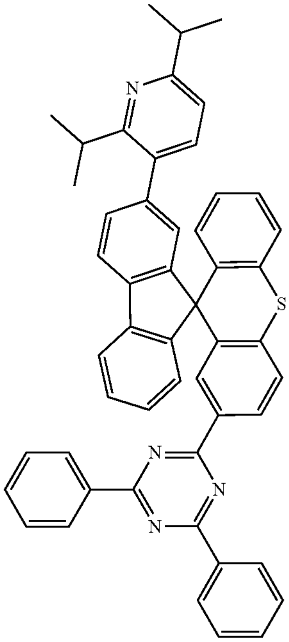
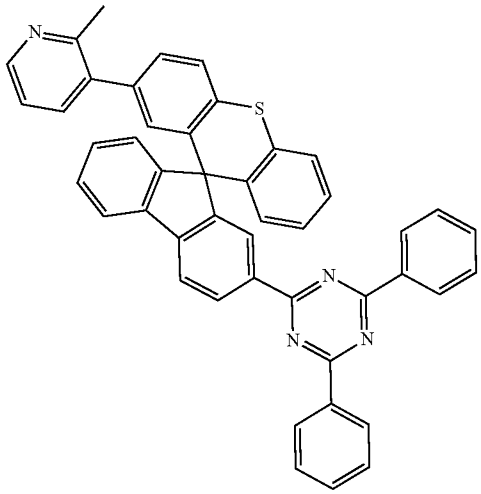

-continued
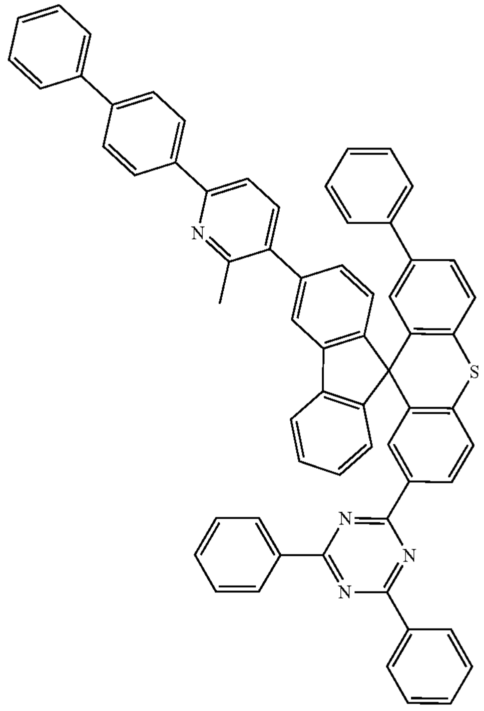
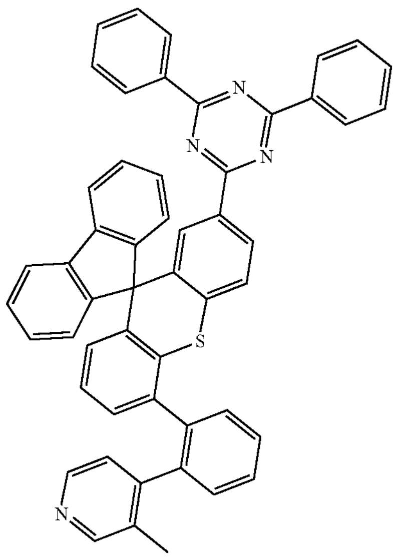
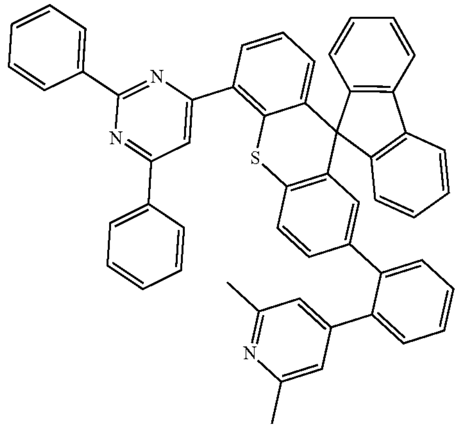
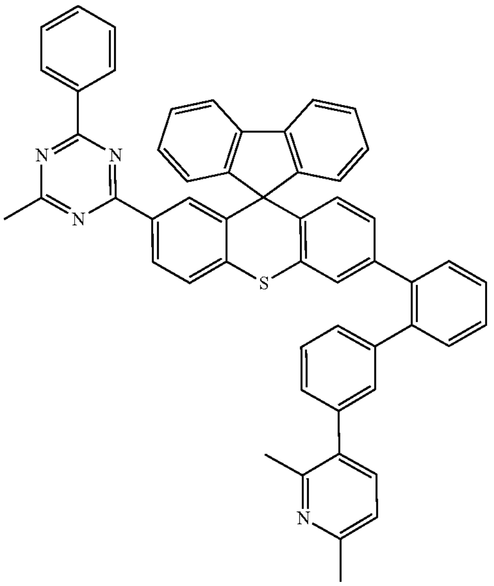

-continued
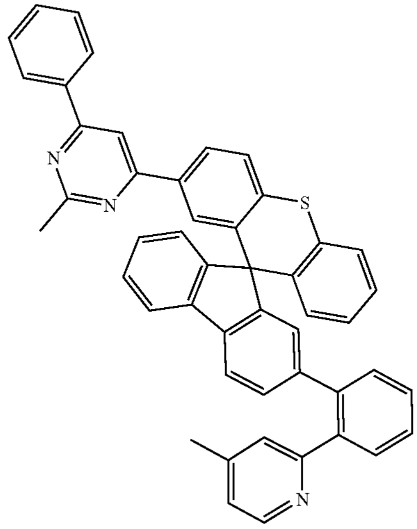
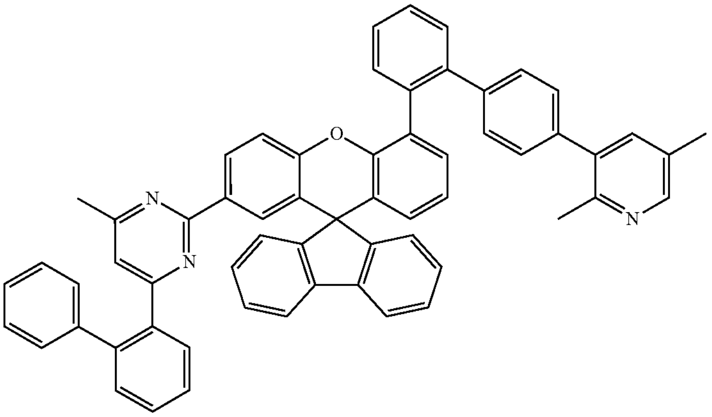
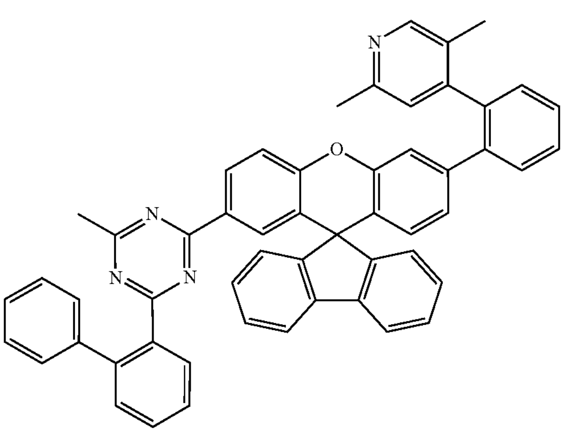
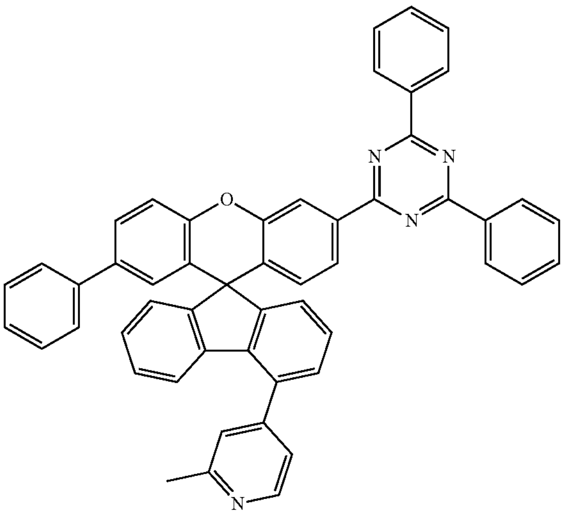
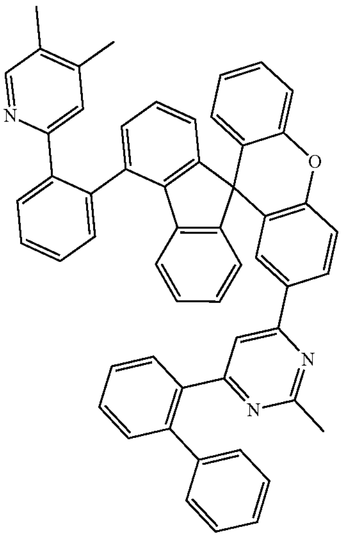
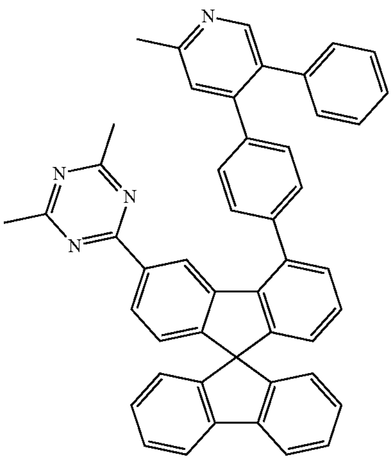

-continued
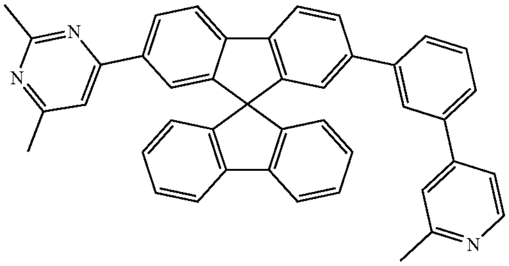
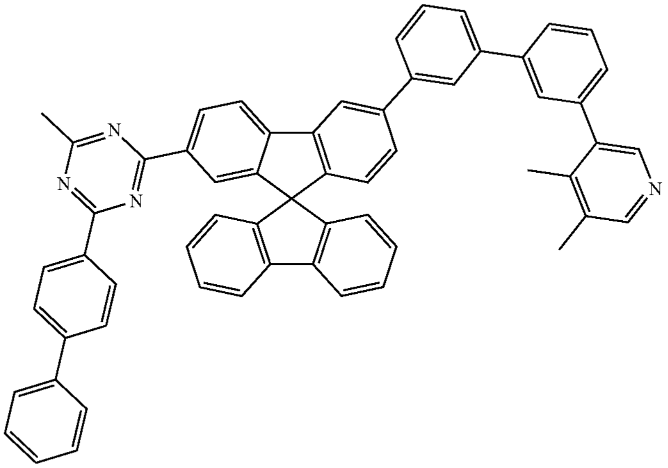
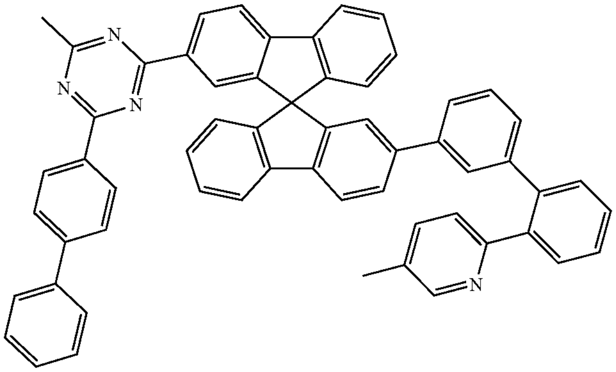
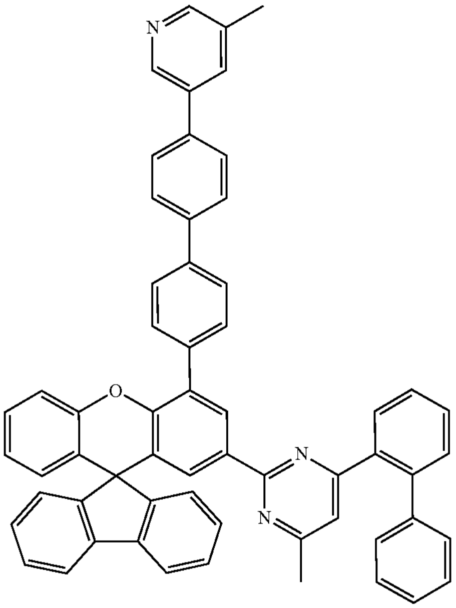
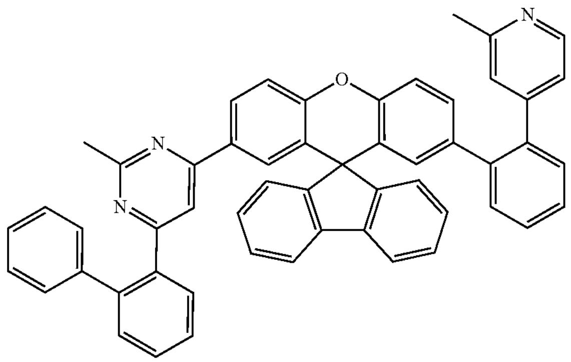

-continued
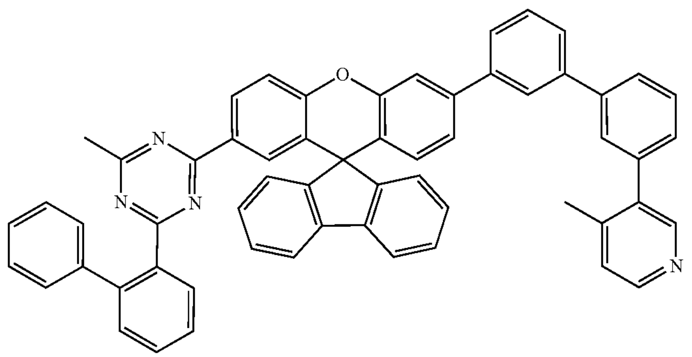
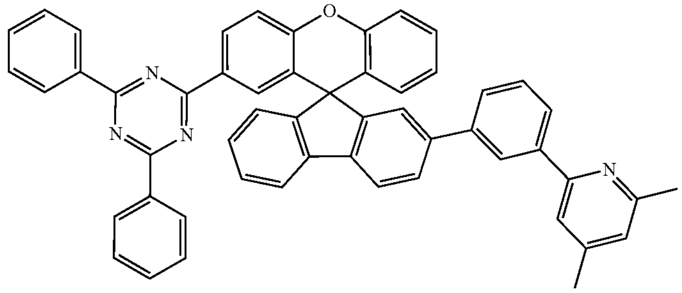
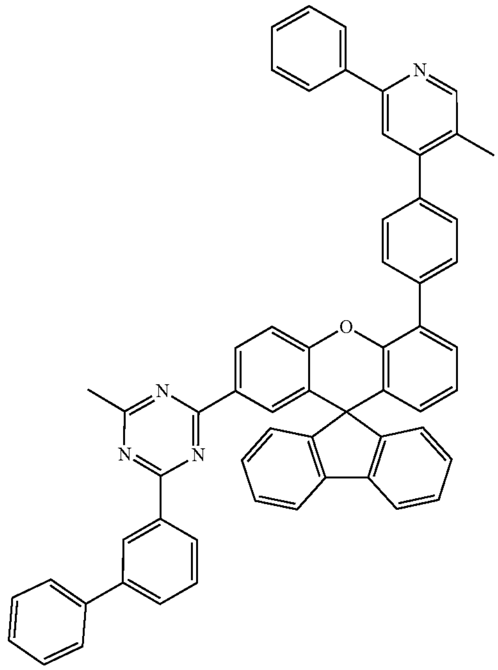
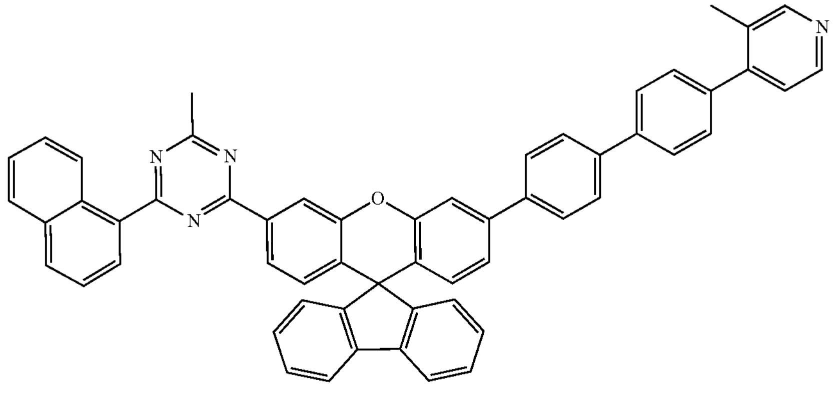

-continued
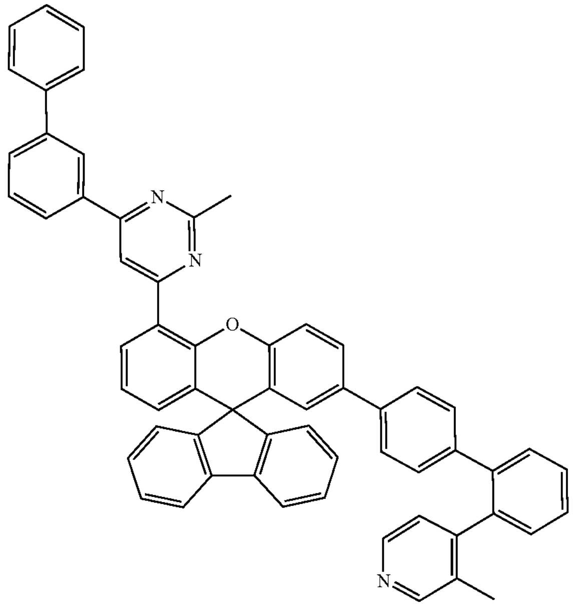
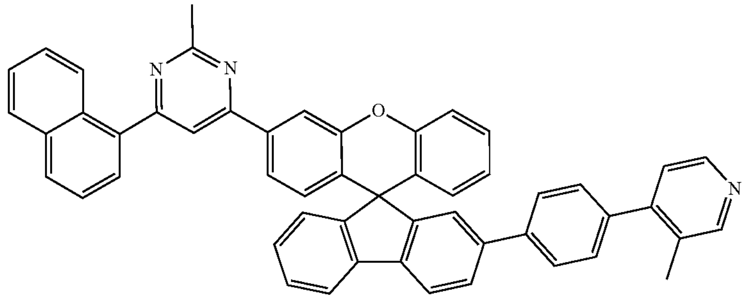
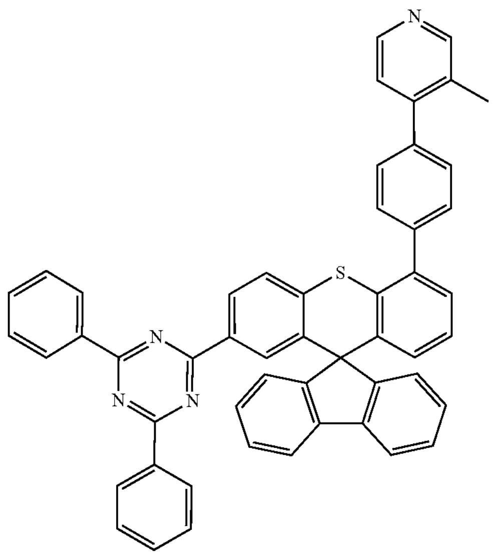

-continued
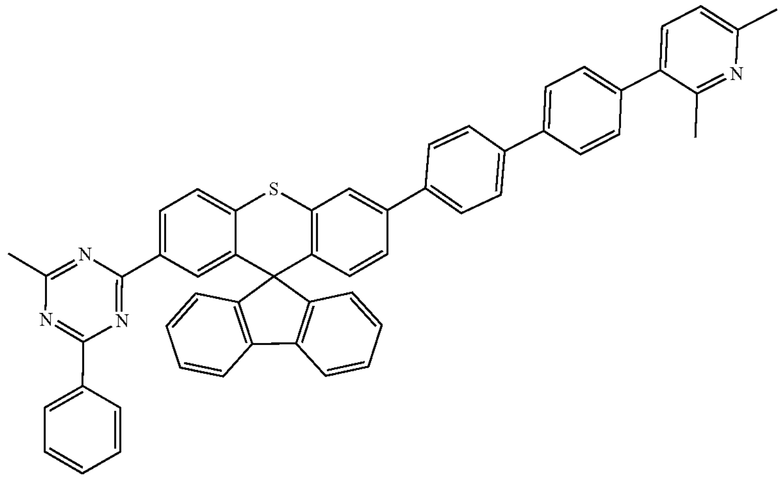
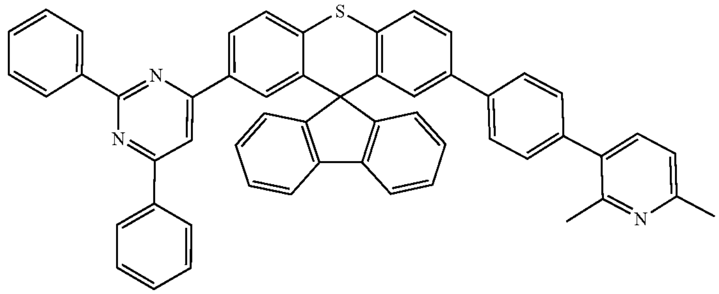
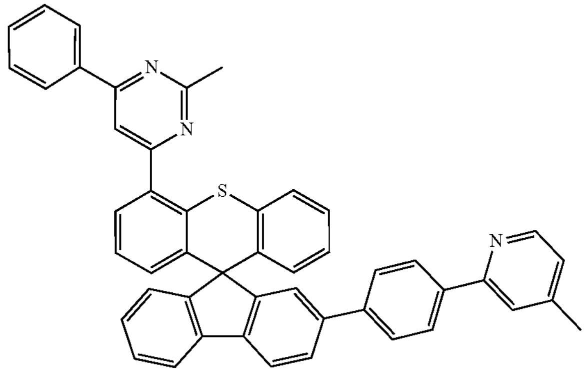
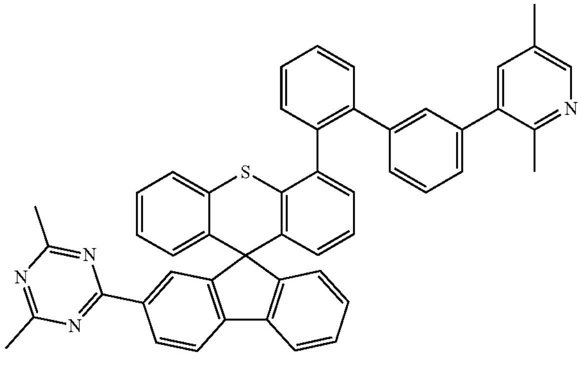

-continued
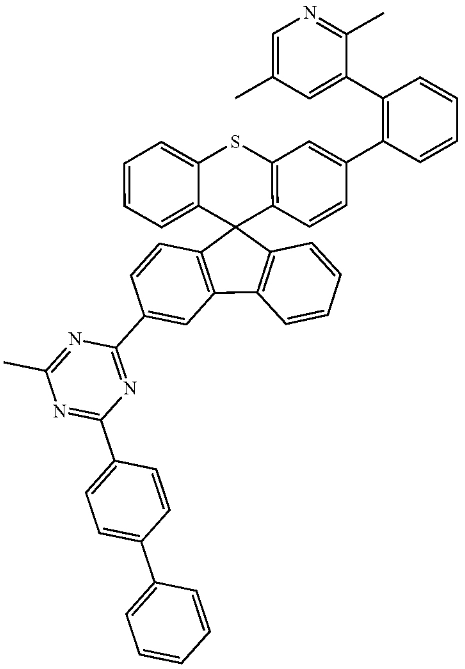
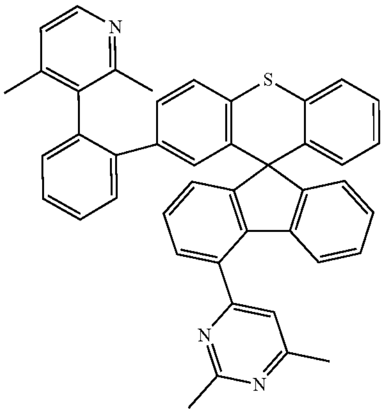
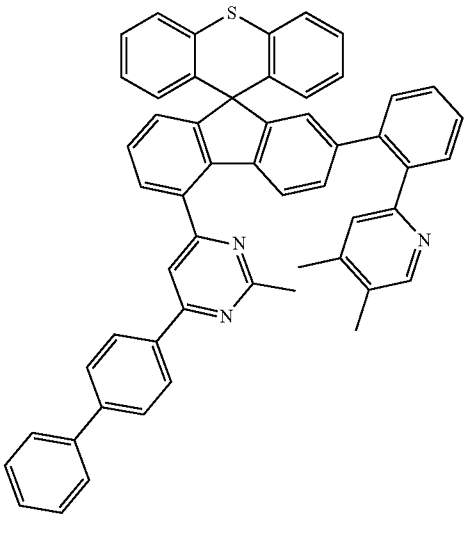
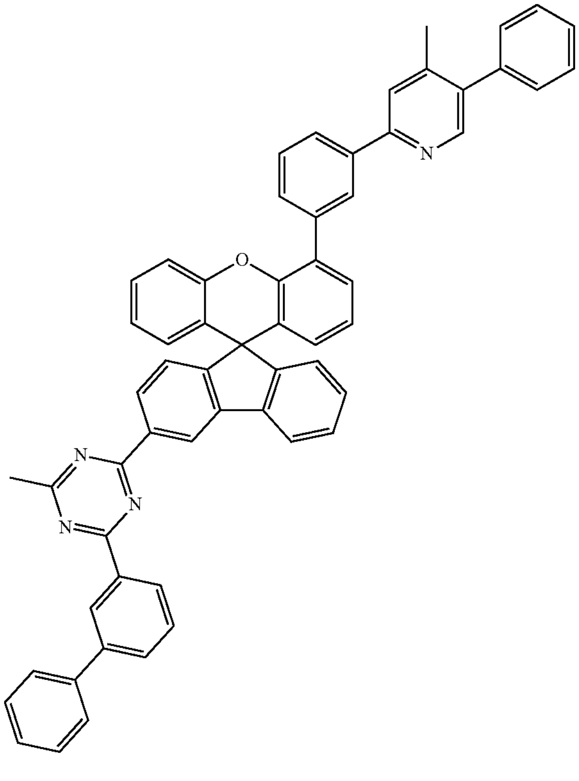

-continued
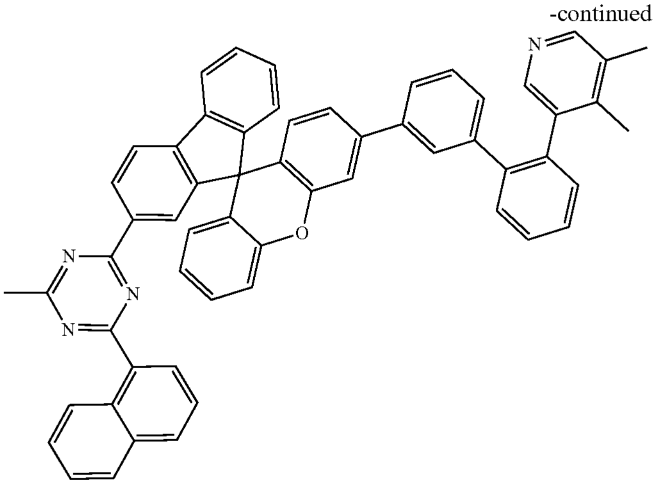
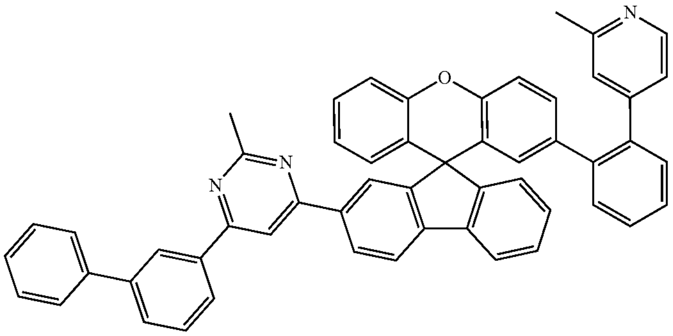
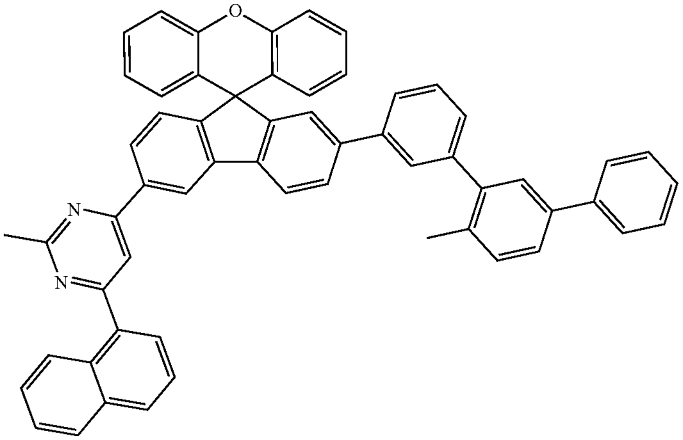
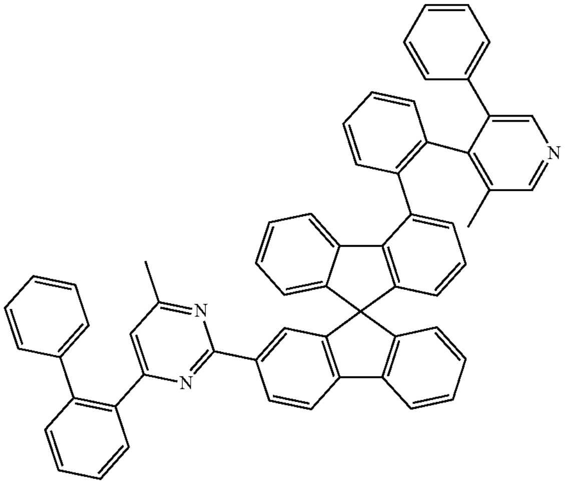

-continued
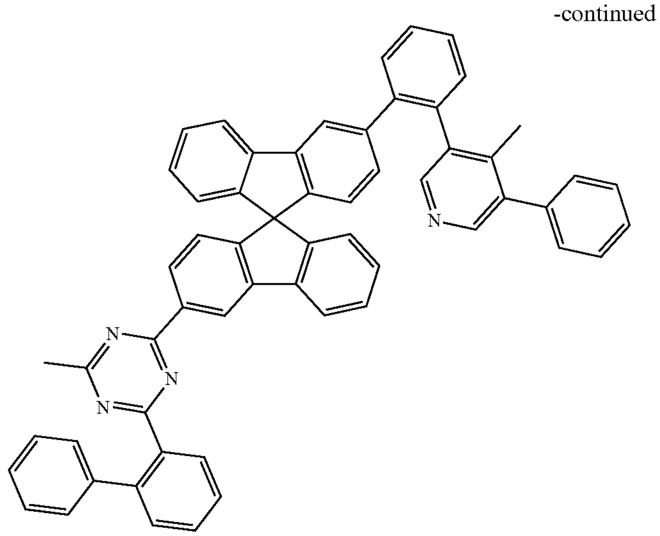
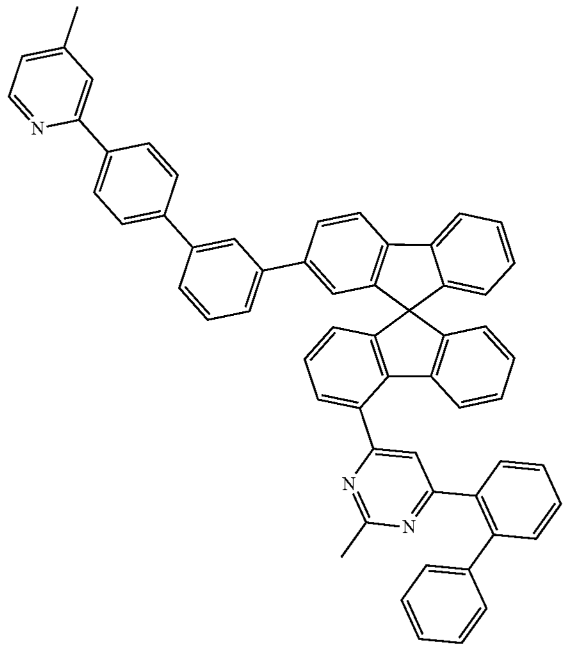
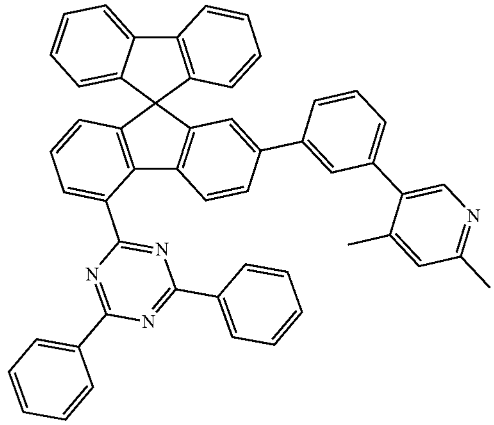
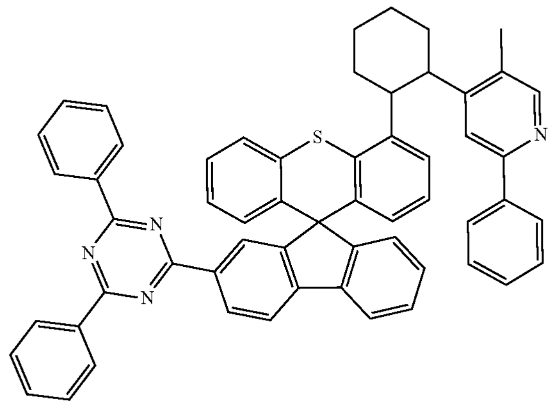

-continued
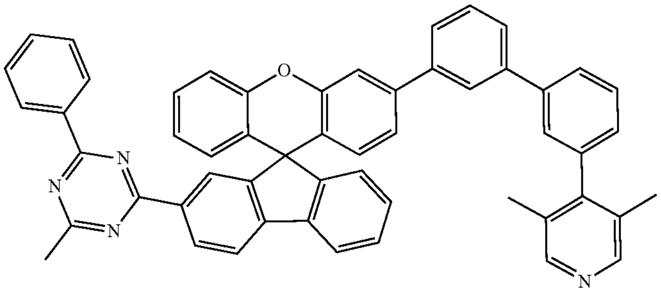
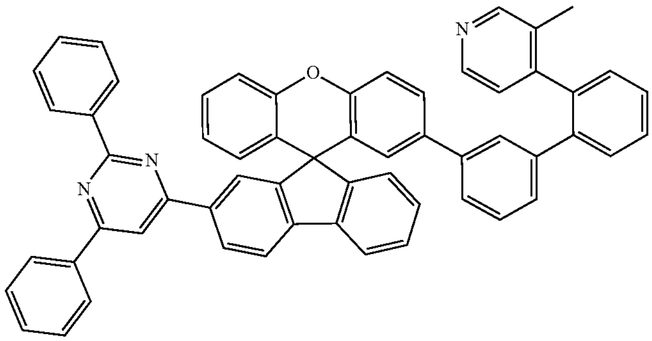
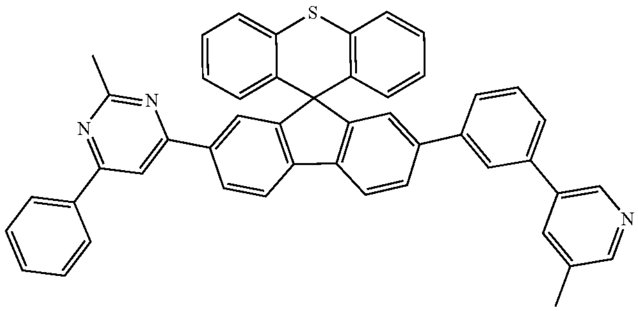
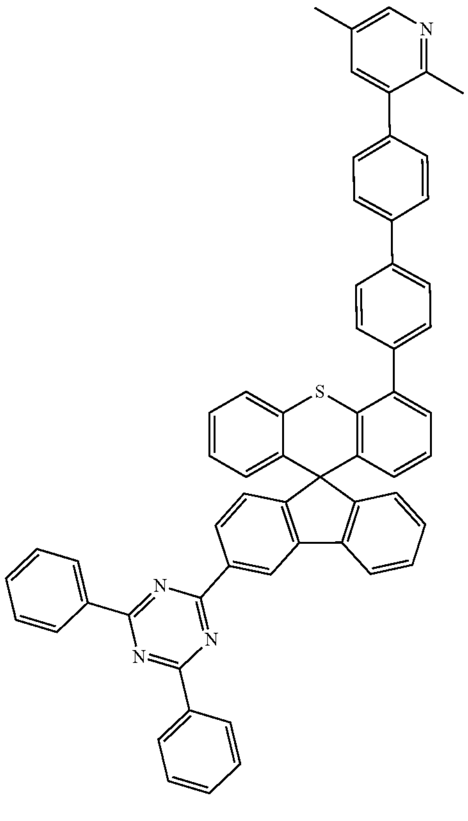

-continued
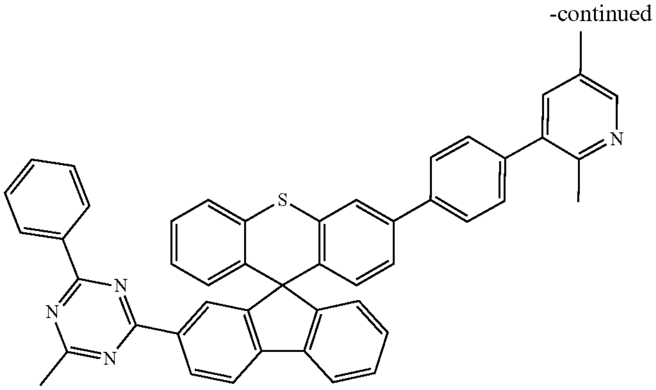
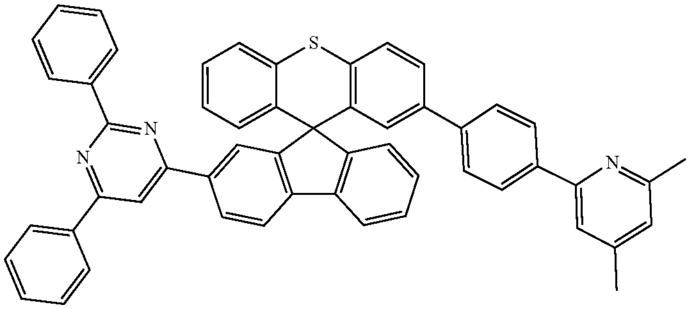
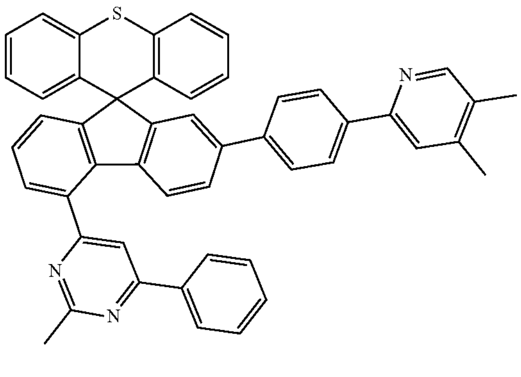
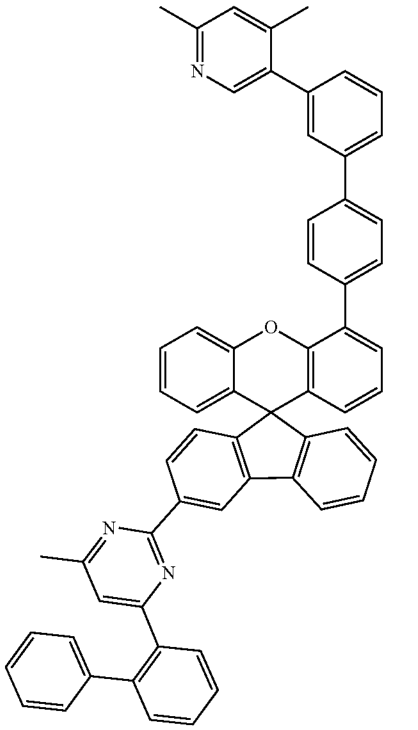

-continued
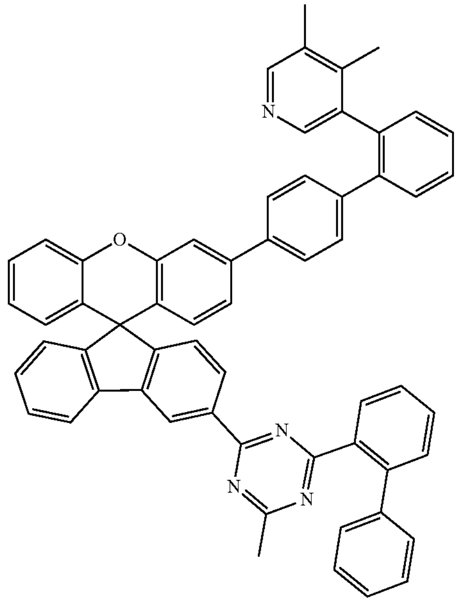
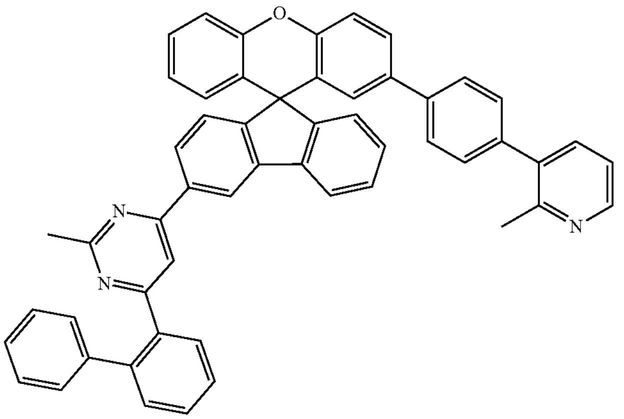
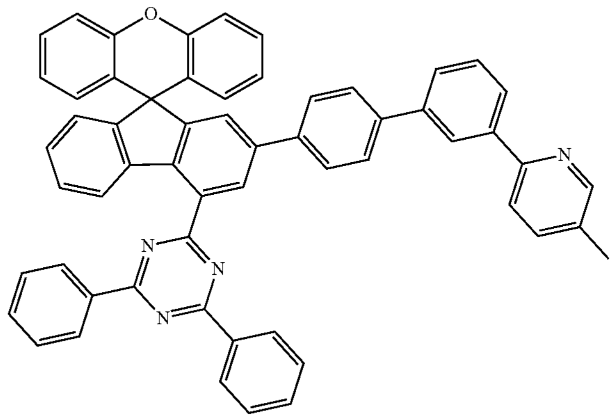
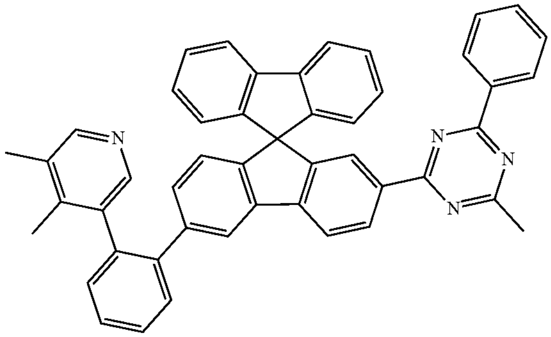
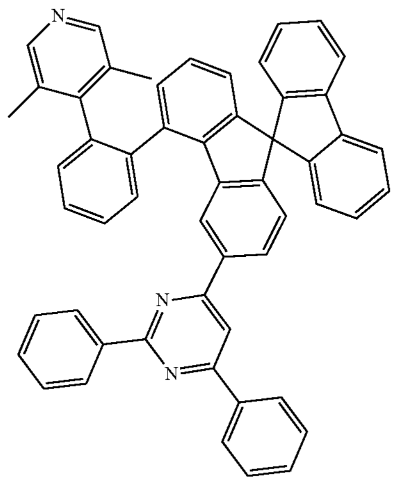
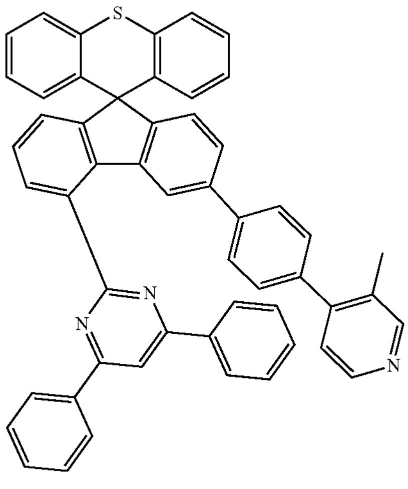

-continued
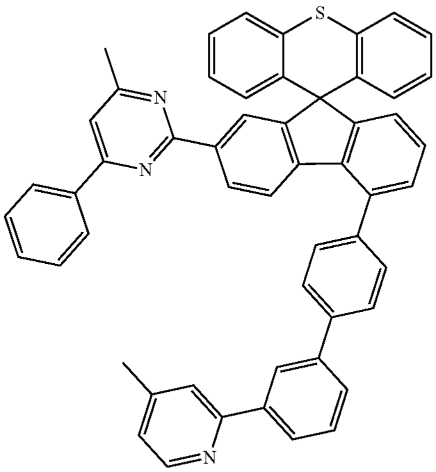
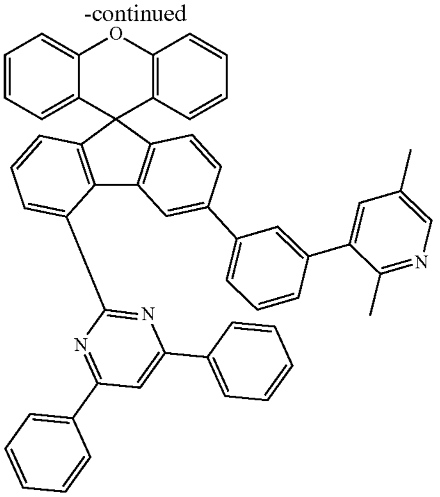
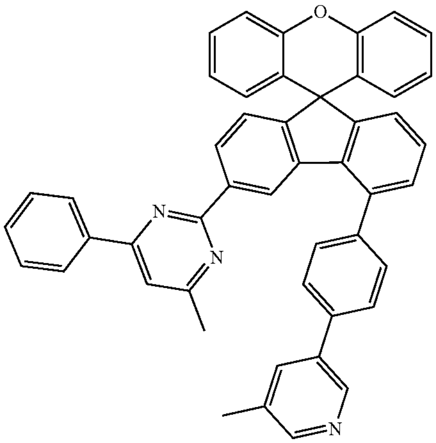
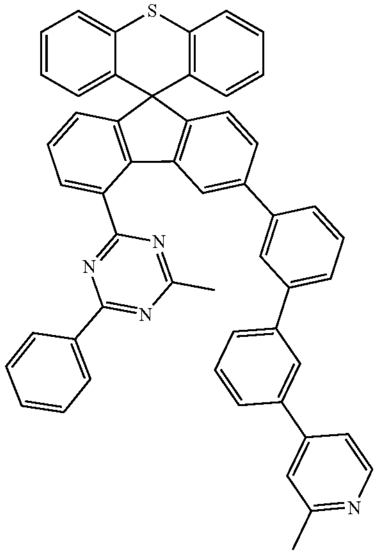
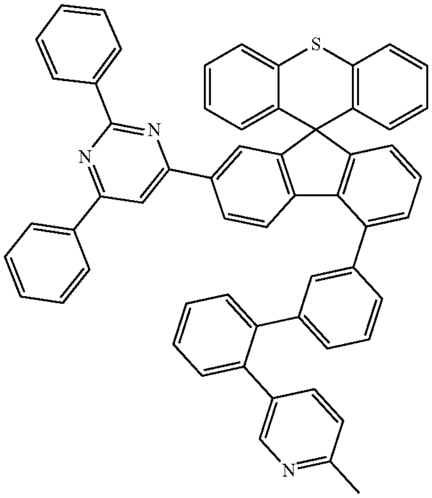
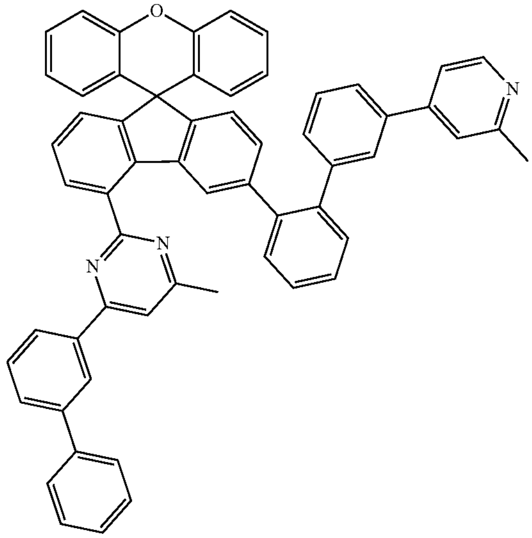

-continued
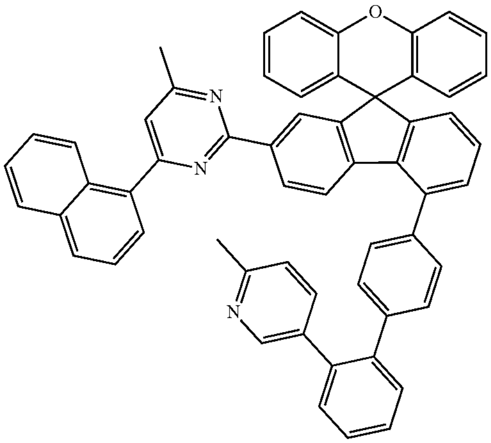
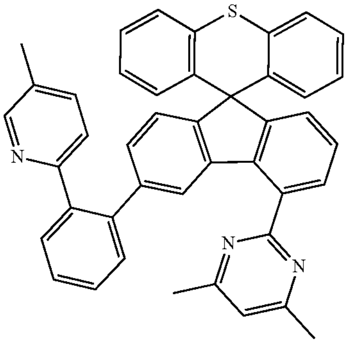
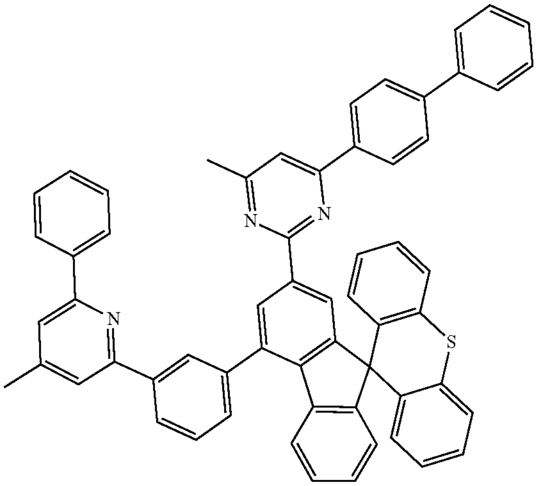
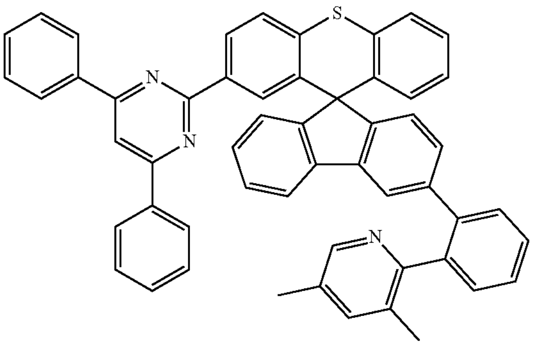
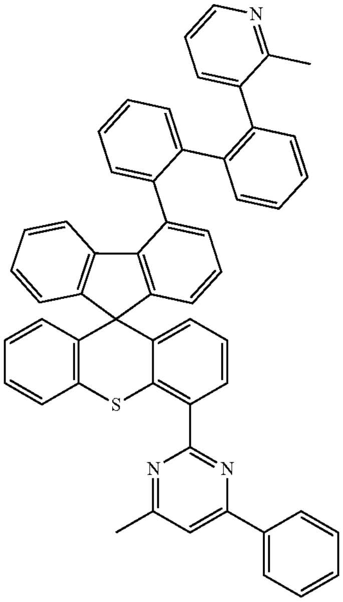
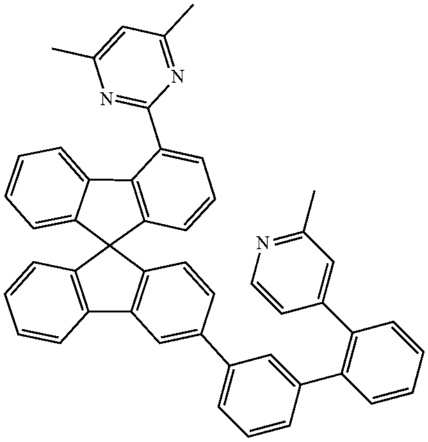

-continued
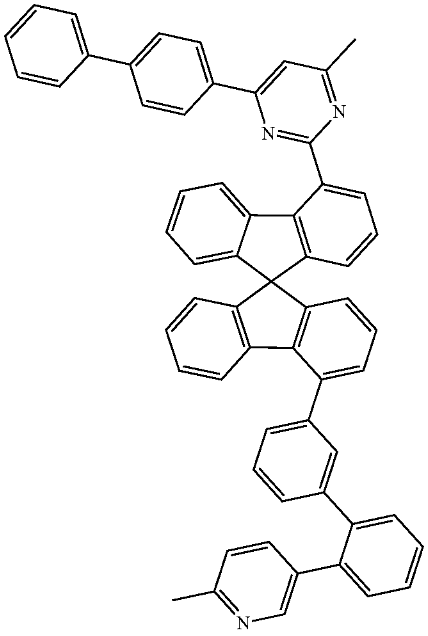
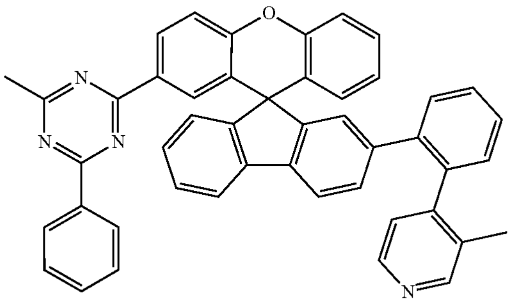
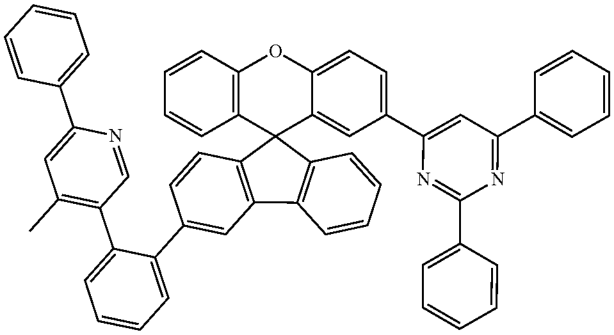
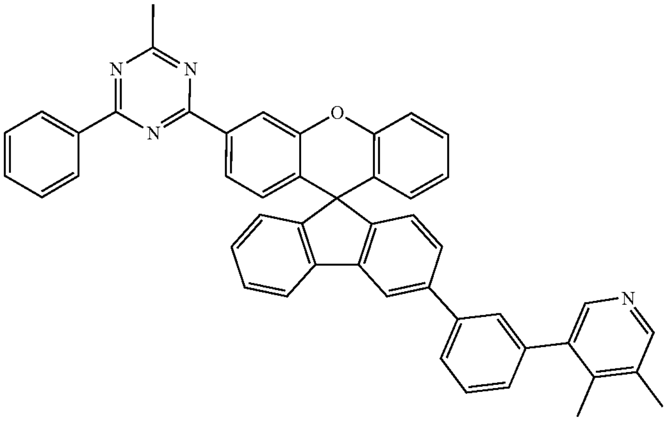

-continued
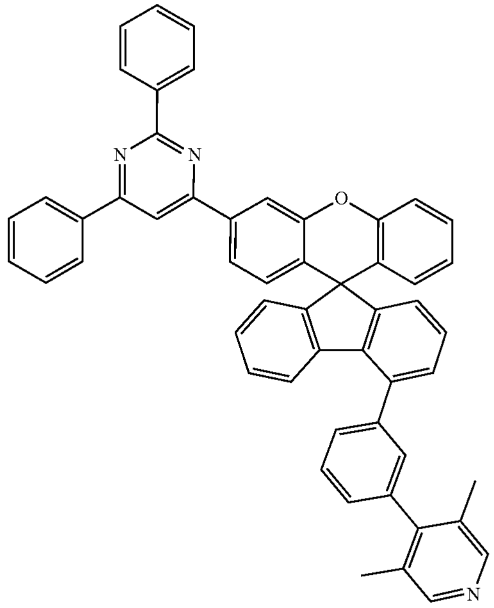
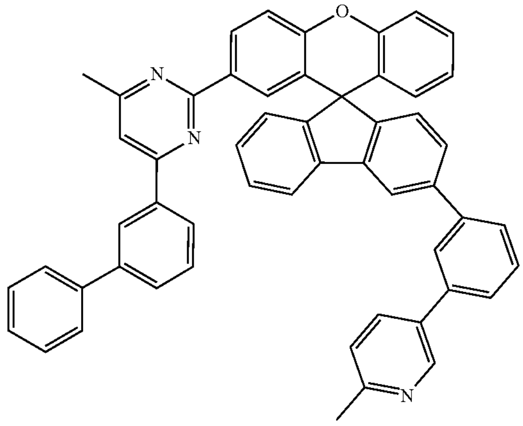
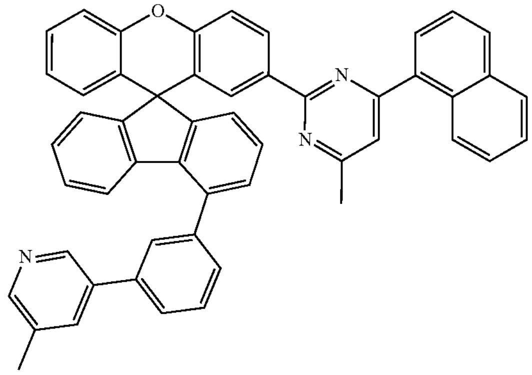
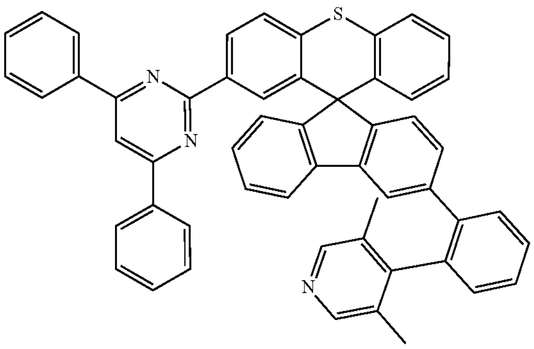
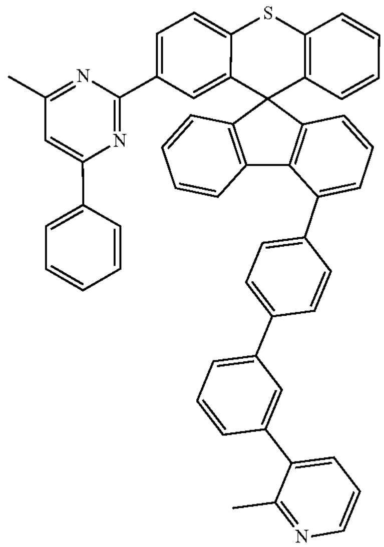
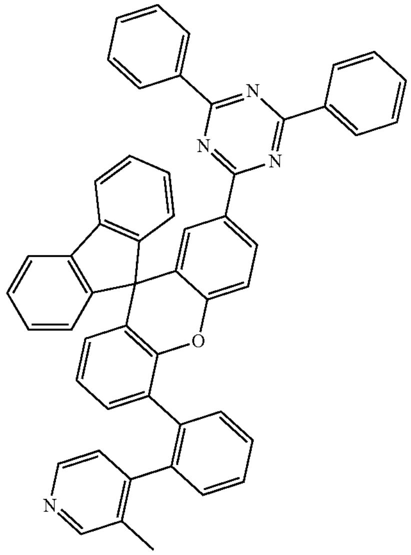

-continued
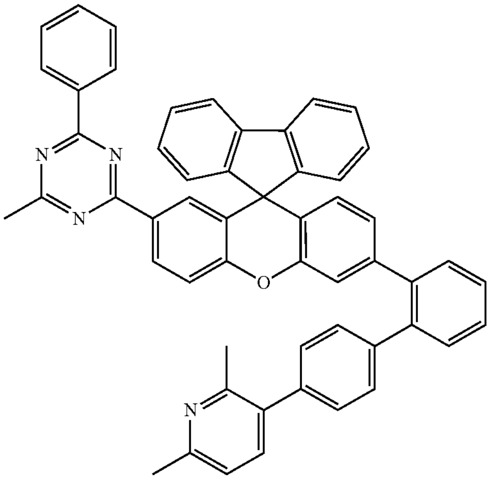
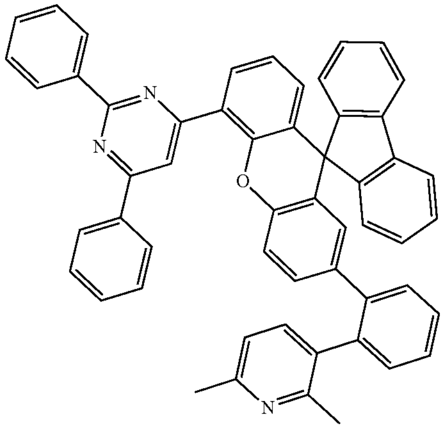
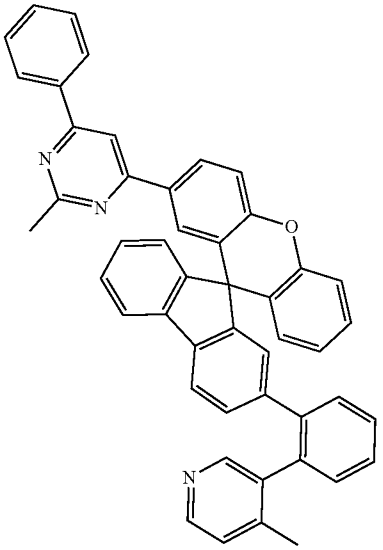
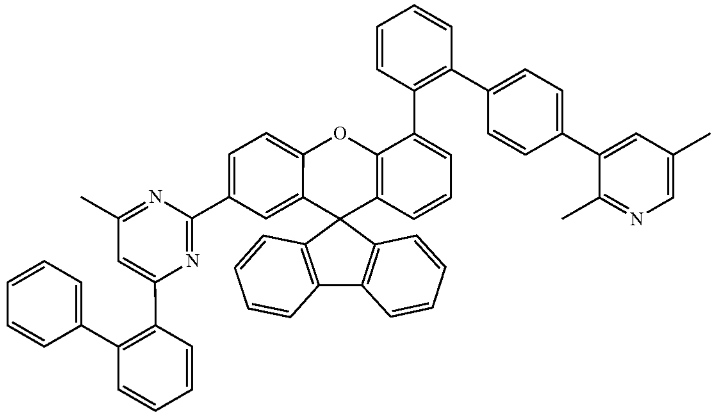
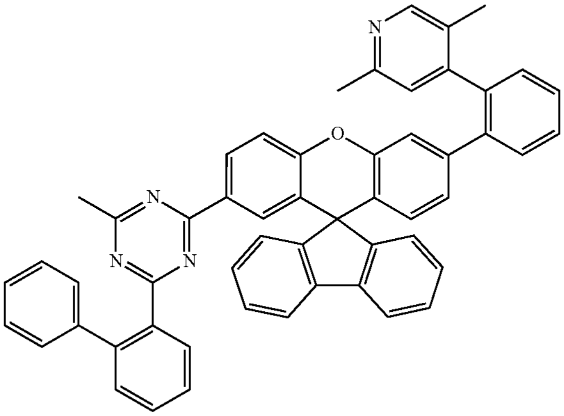
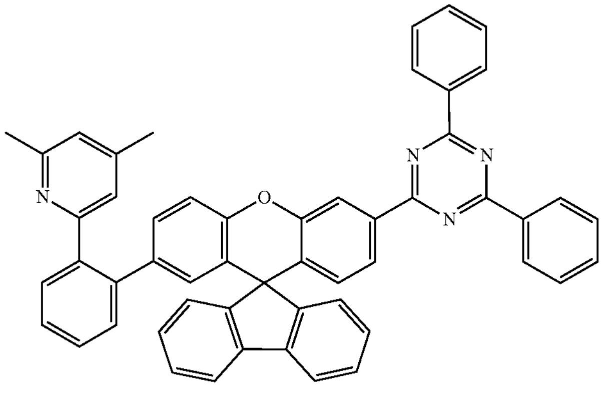

-continued
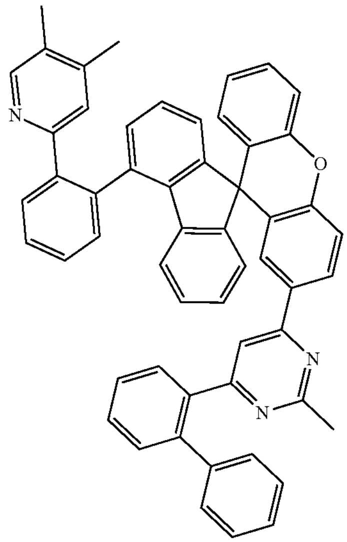
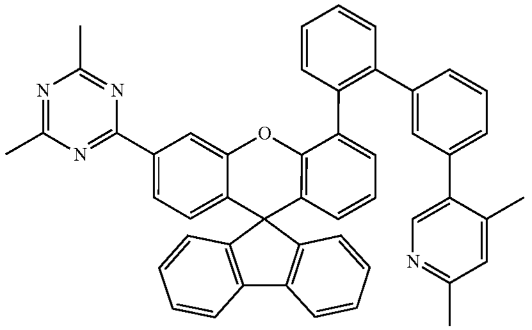
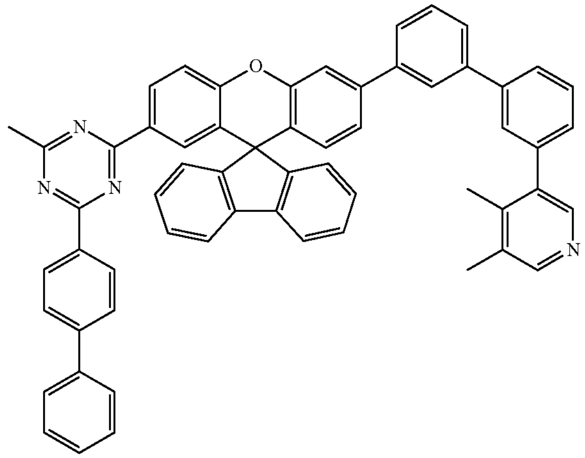
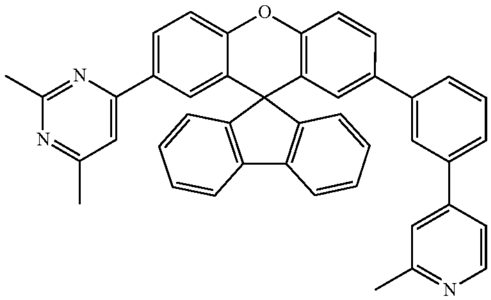
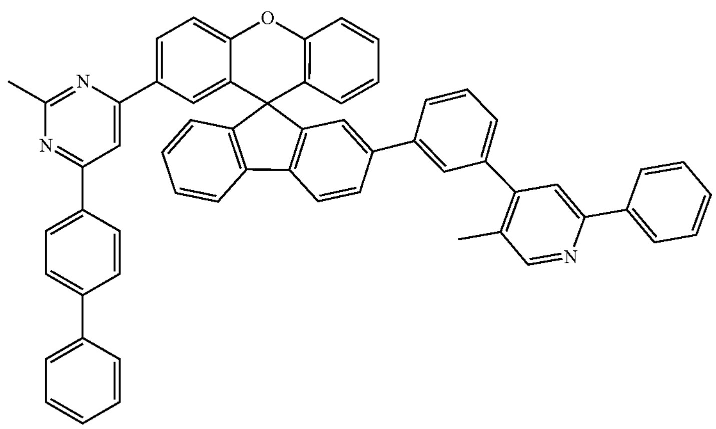
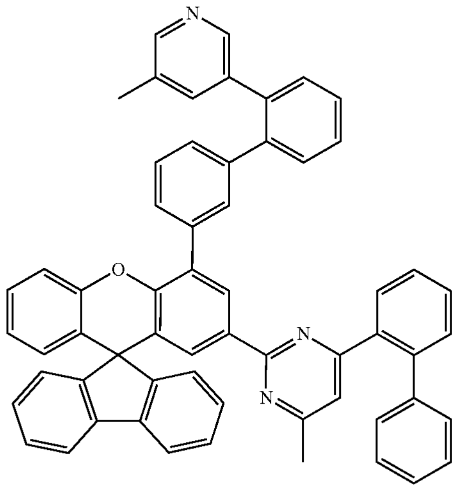

-continued
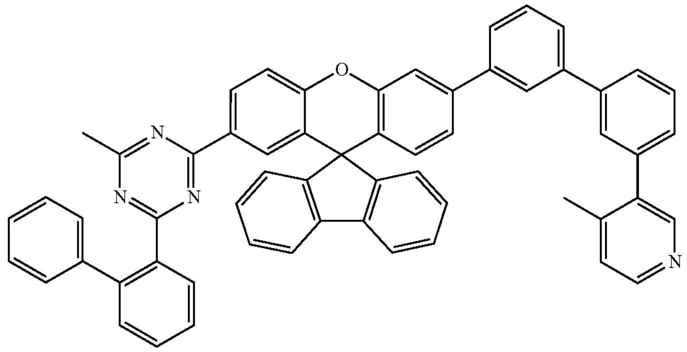
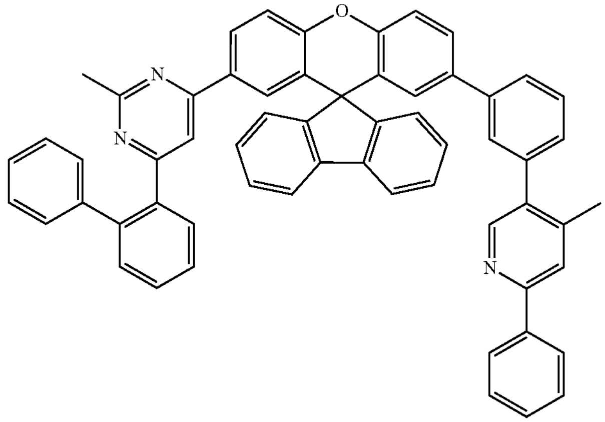
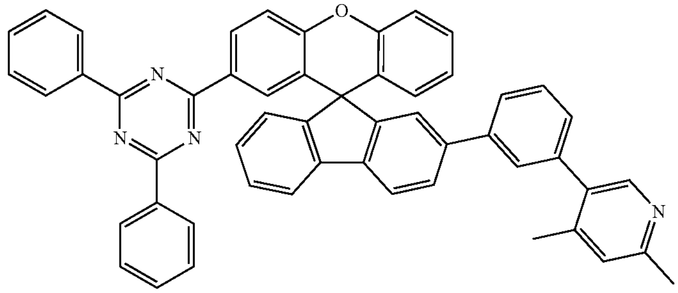

-continued
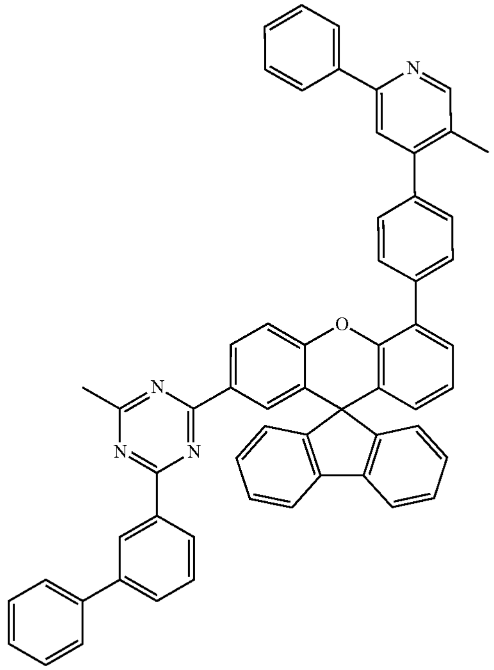
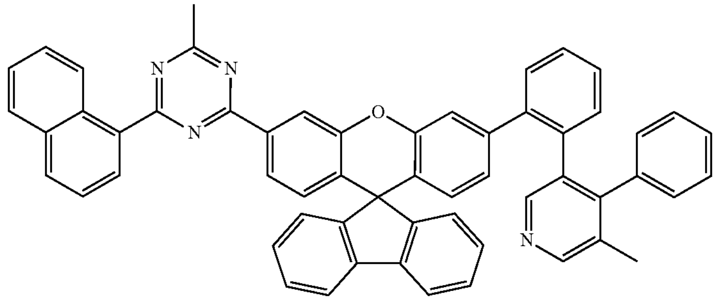
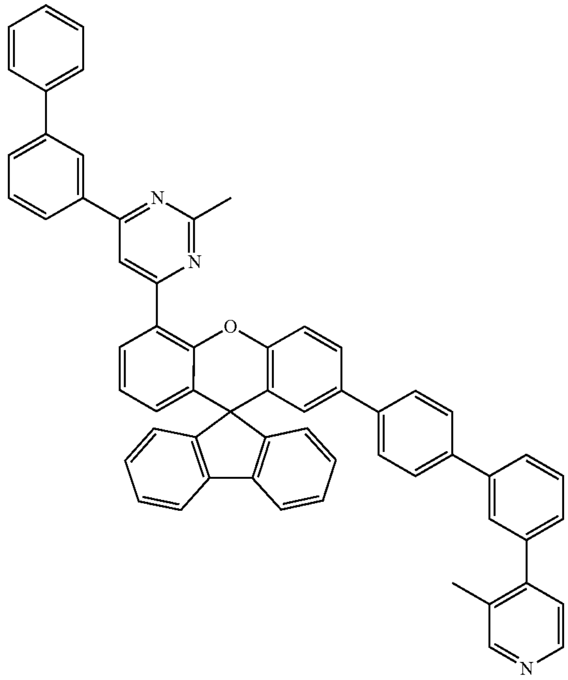

-continued
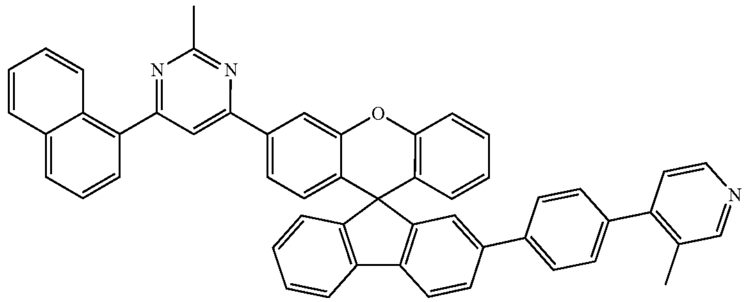
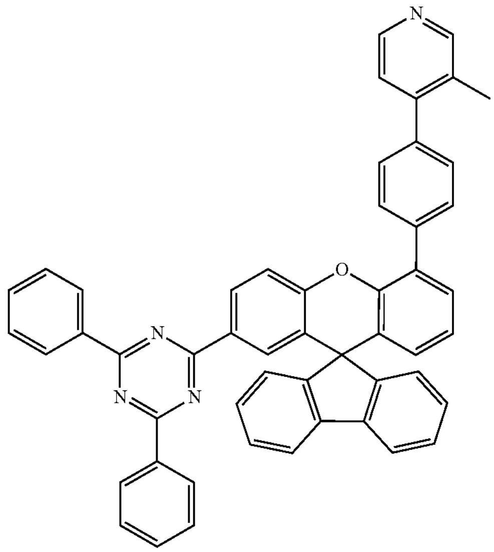
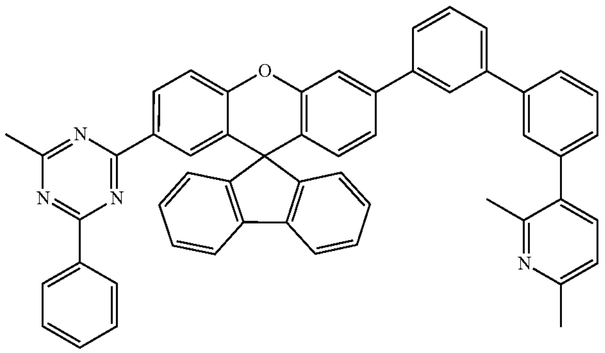
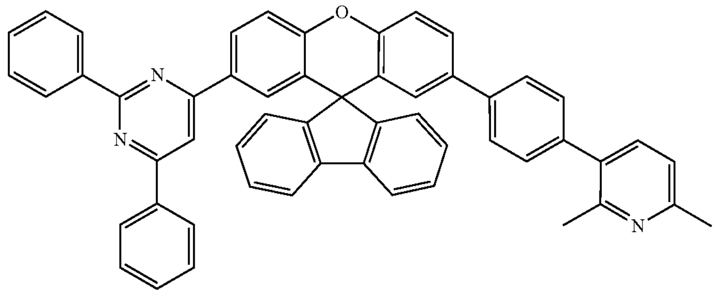
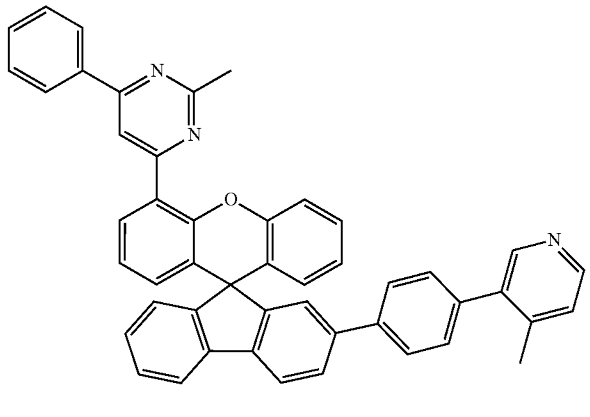

-continued
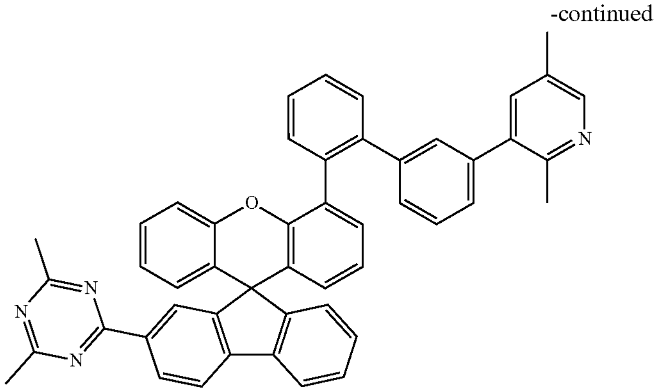
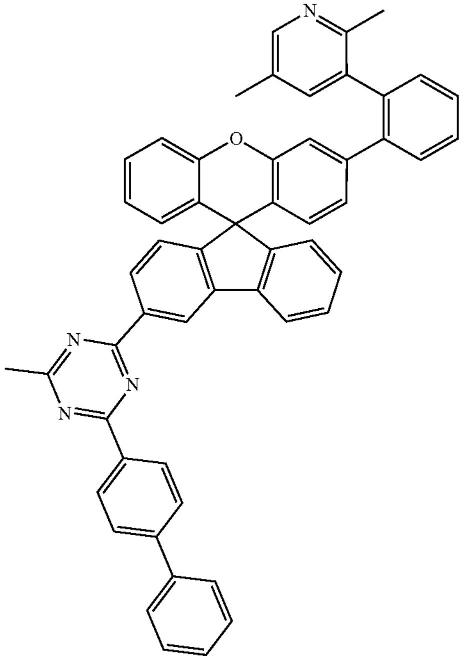
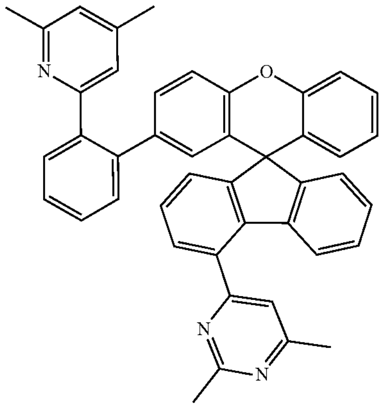
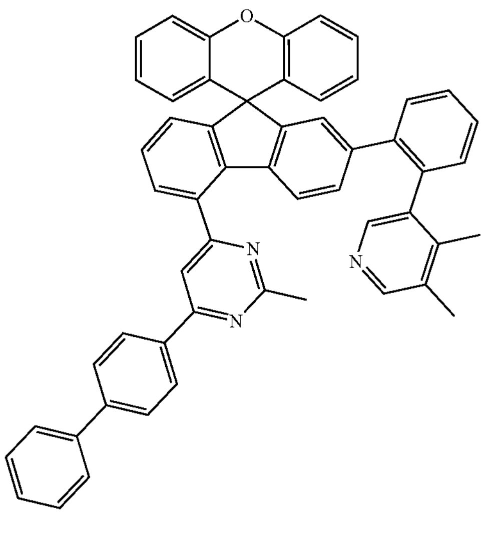
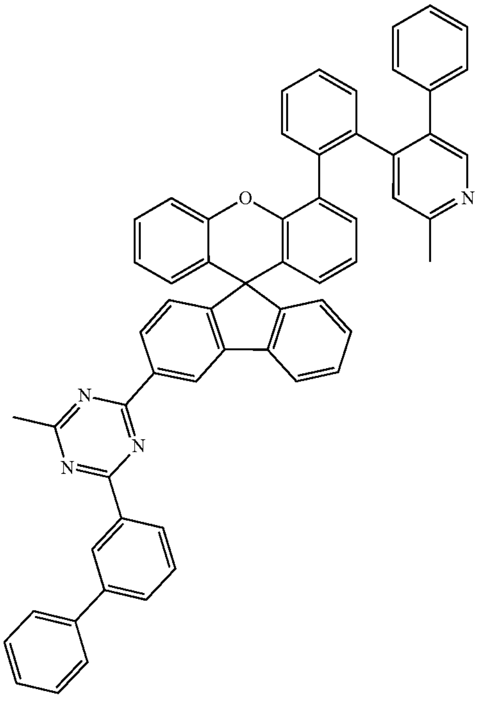

-continued
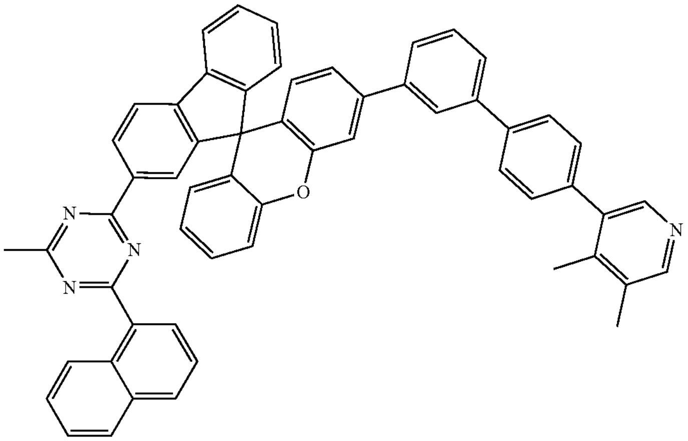
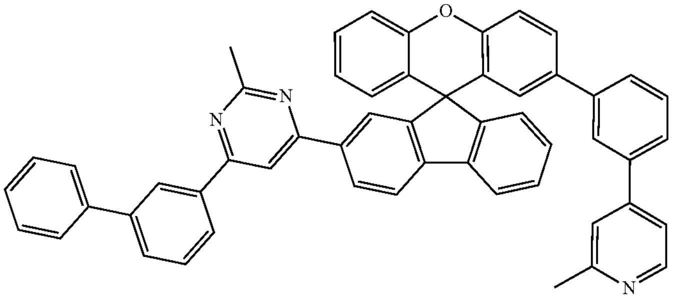
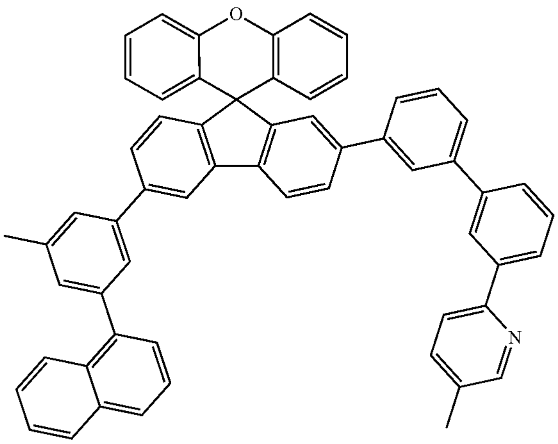
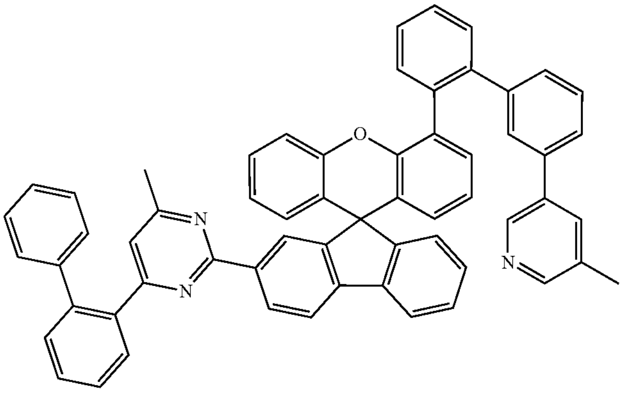

-continued
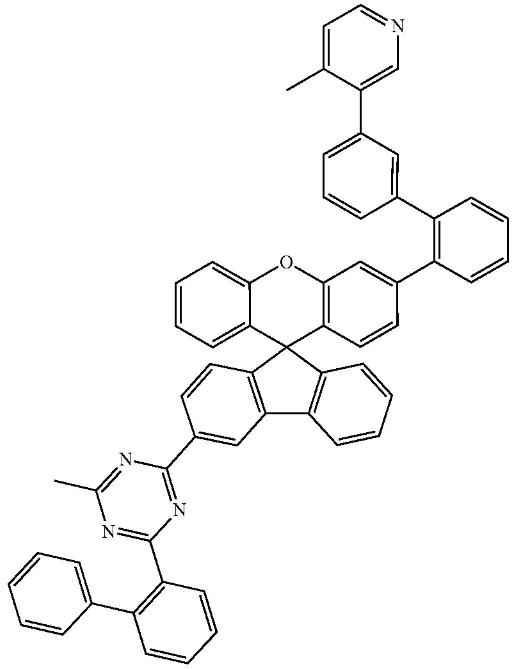
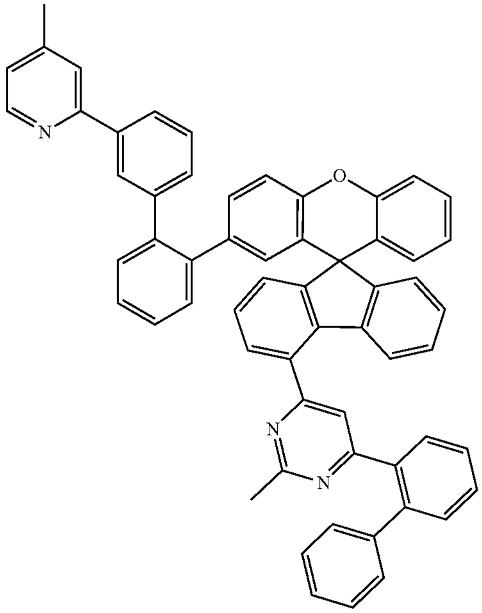
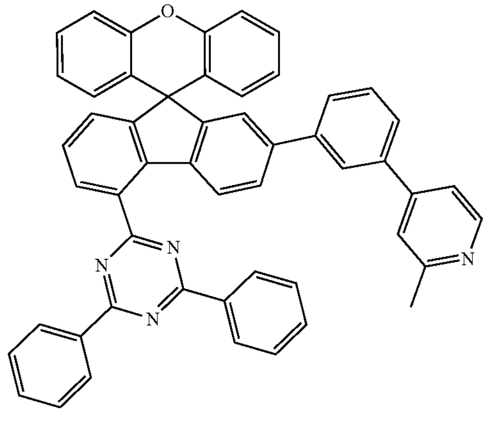
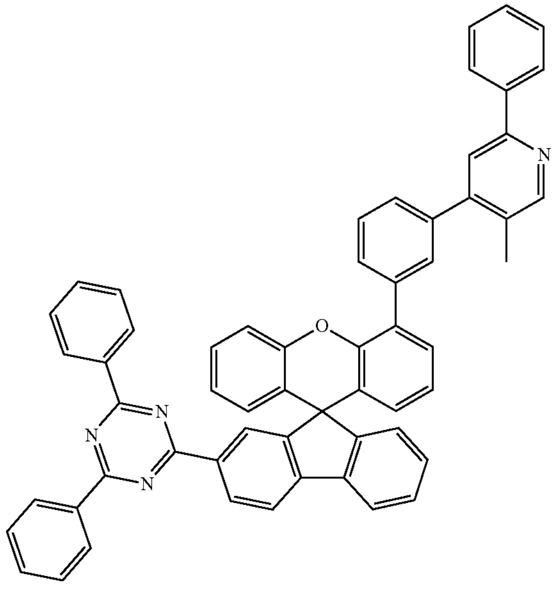
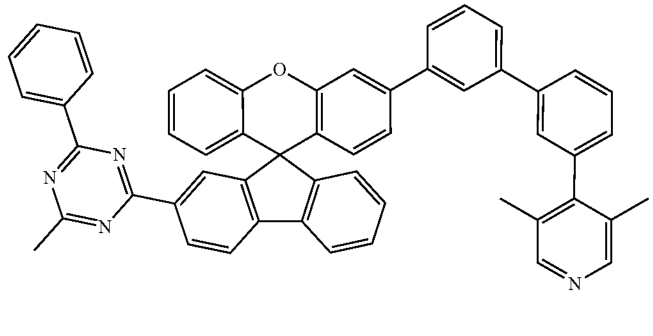

-continued
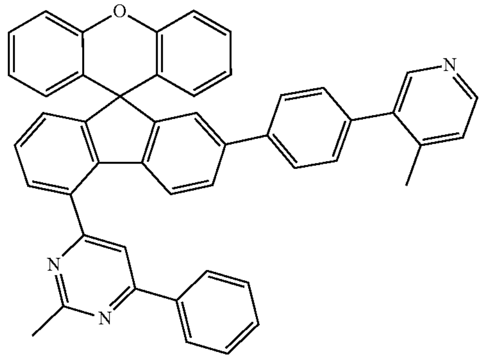
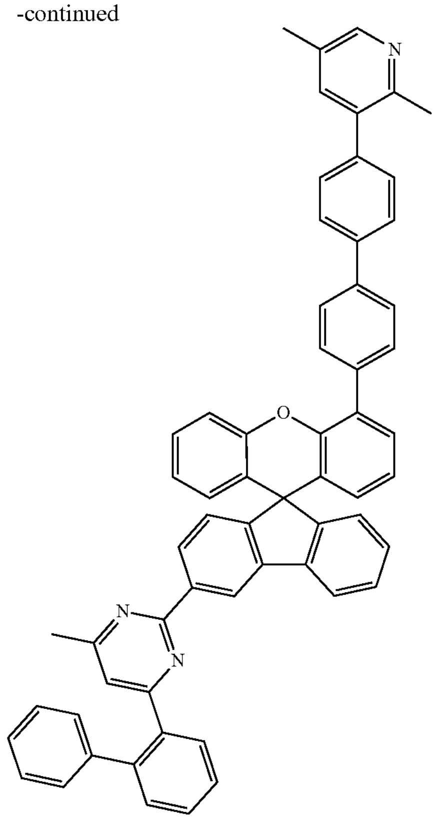
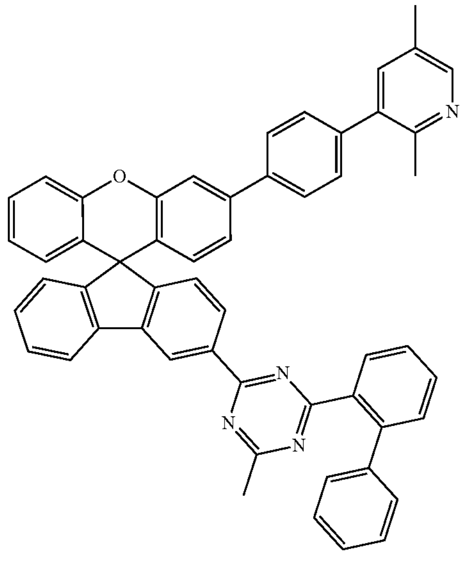
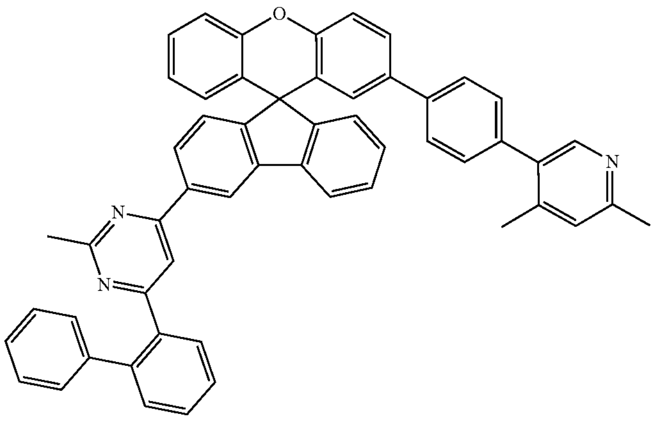

-continued
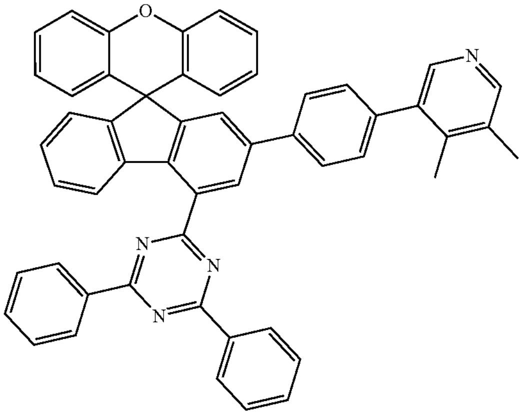
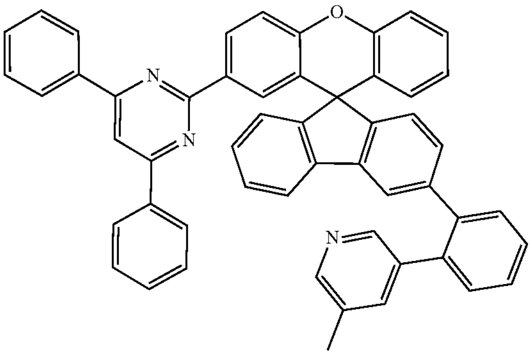
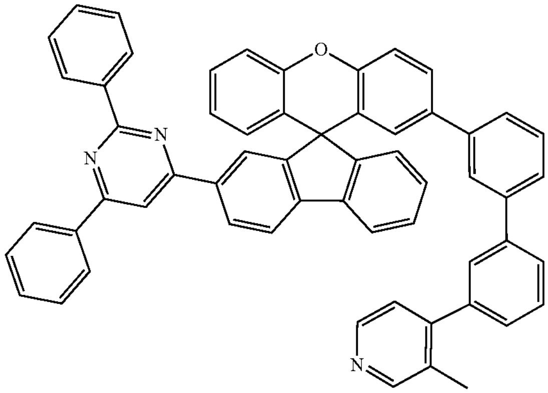
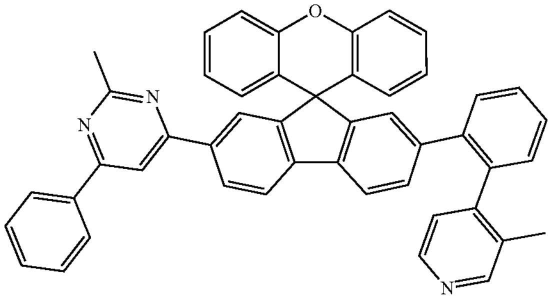
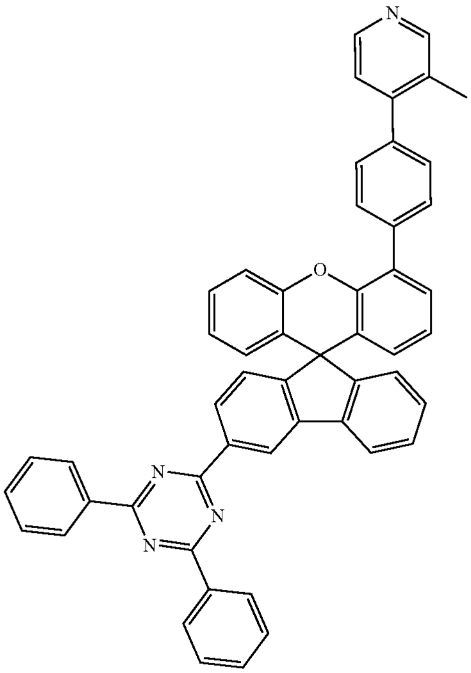

-continued
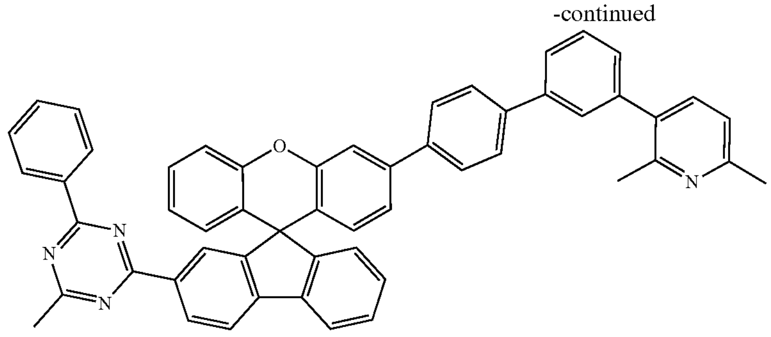
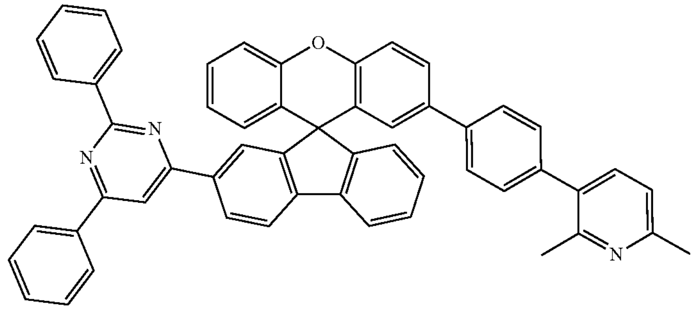
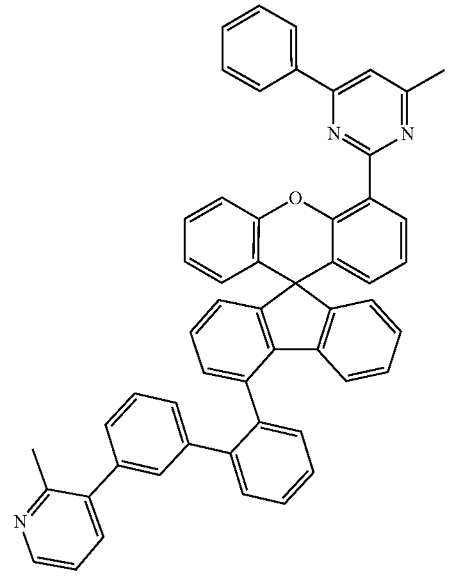
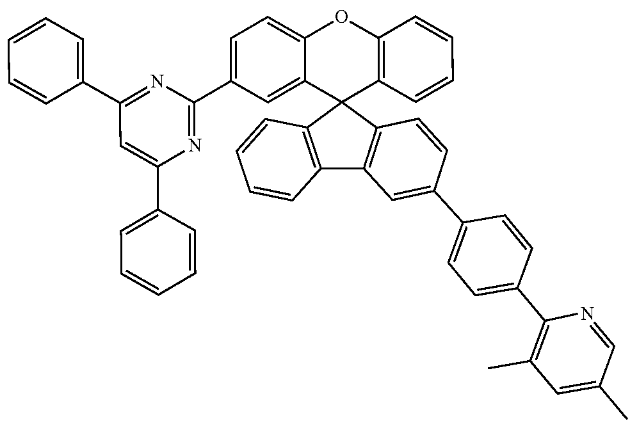
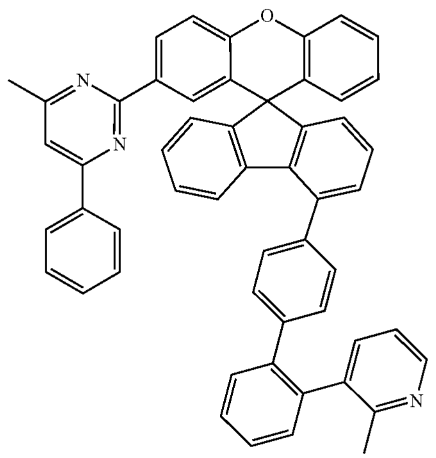
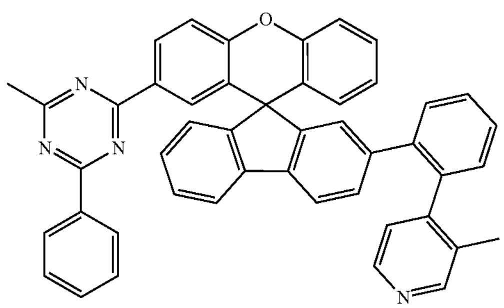

-continued
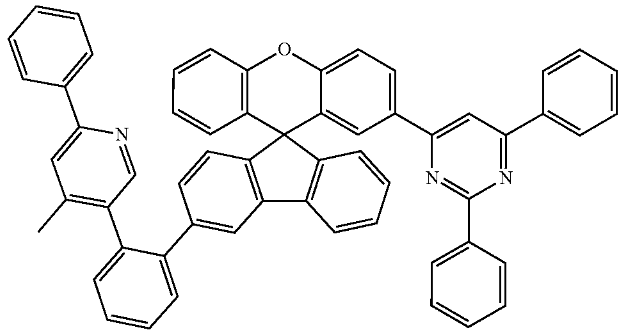
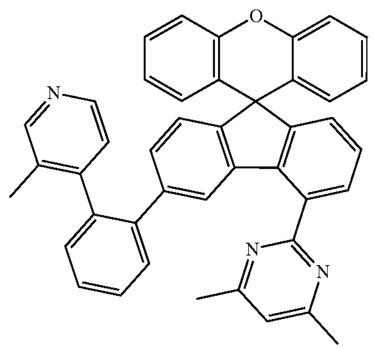
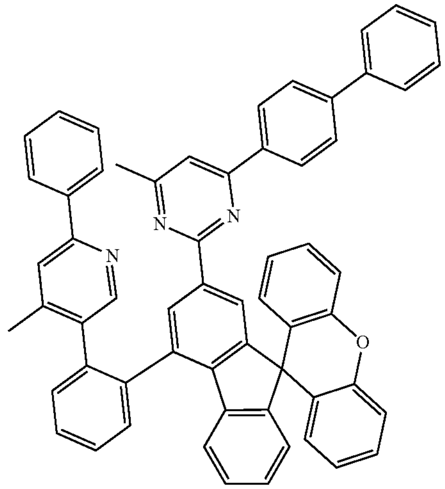
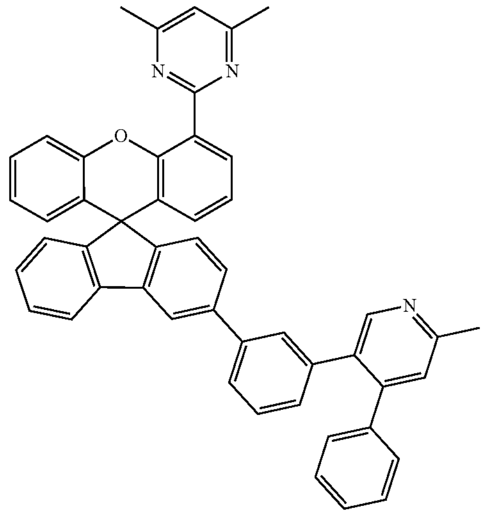
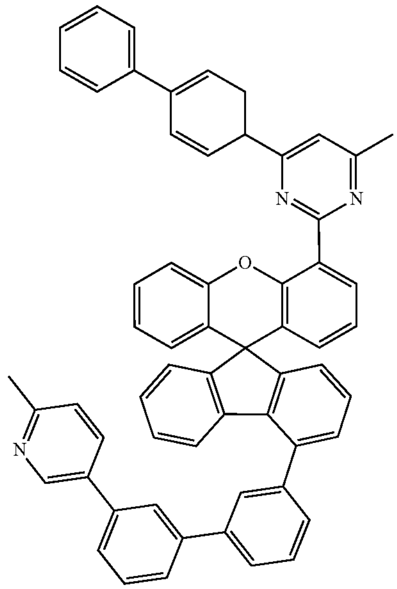
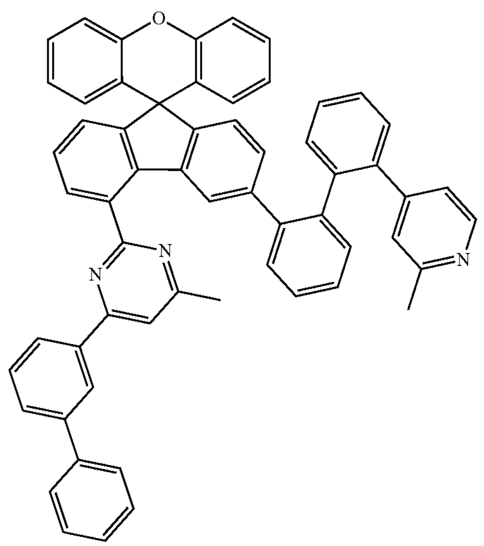

-continued
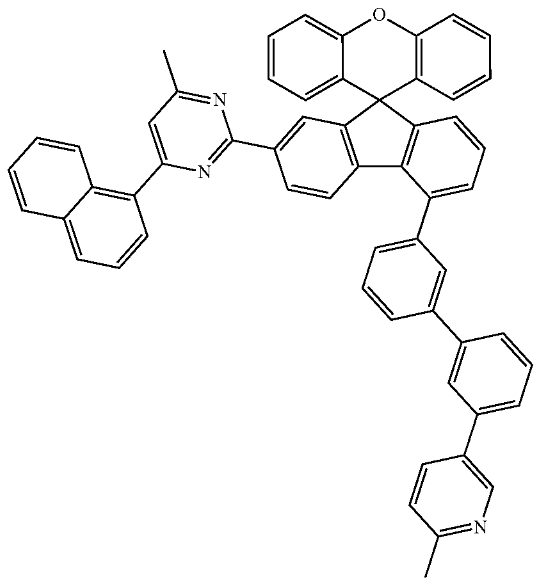
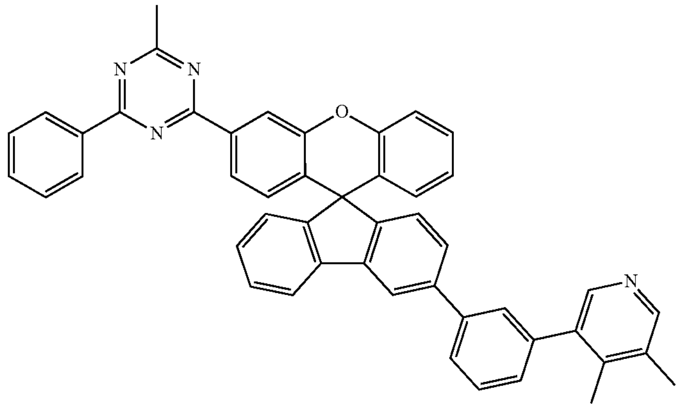
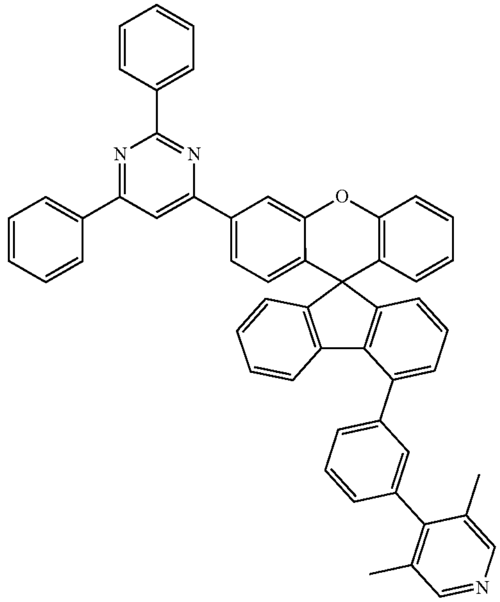
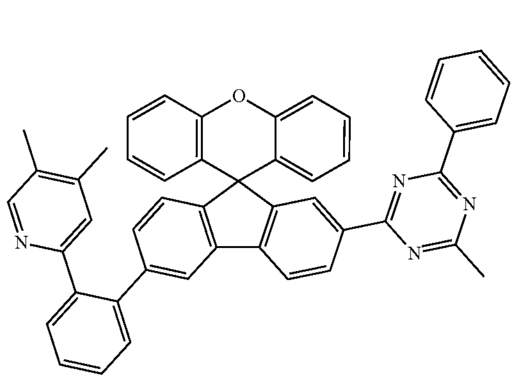

-continued
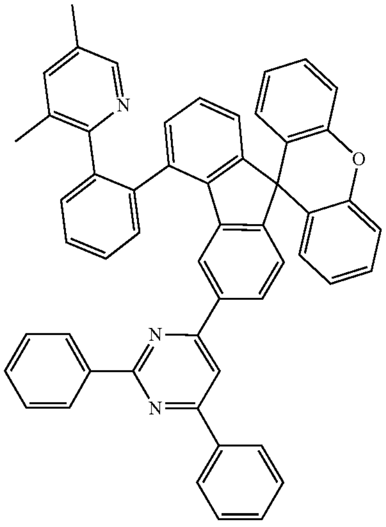
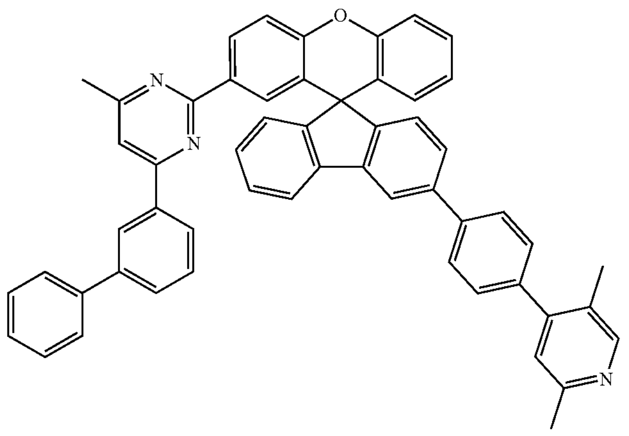
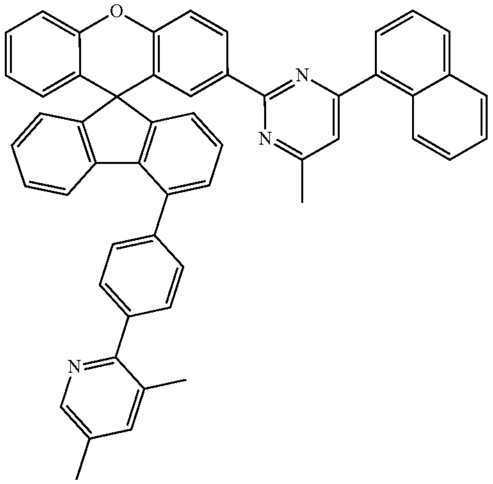
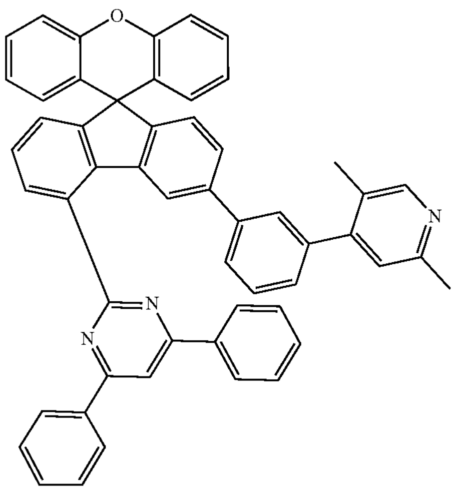
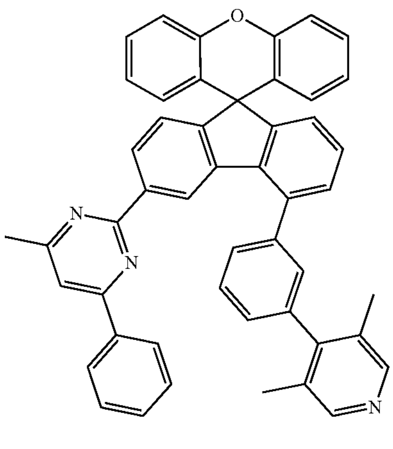
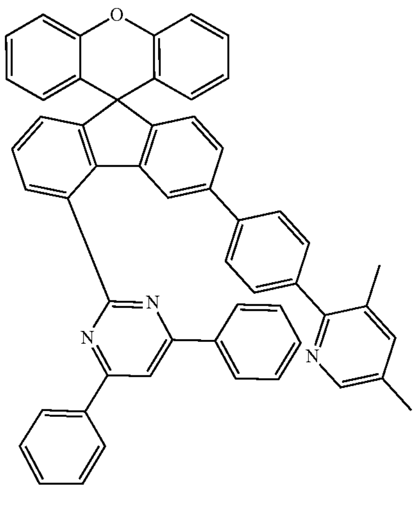

-continued
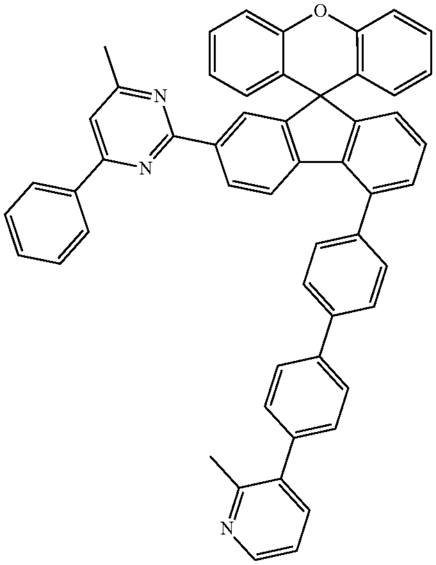
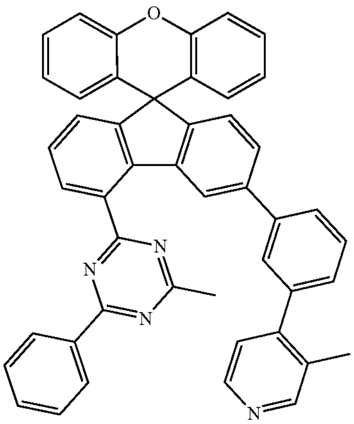
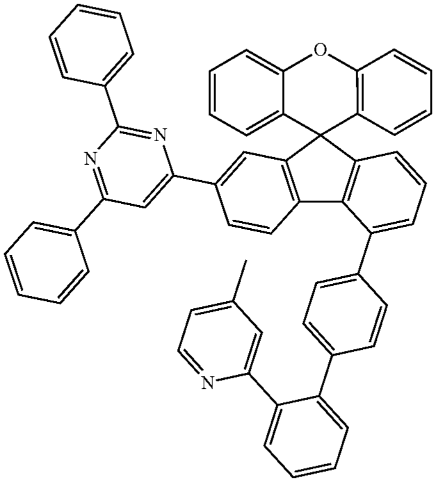 [SMILES: Cc1ccnc(-c2ccccc2-c2ccc(-c3cccc4c3-c3ccc(-c5cc(-c6ccccc6)nc(-c6ccccc6)n5)cc3C43c4ccccc4Oc4ccccc43)cc2)c1]
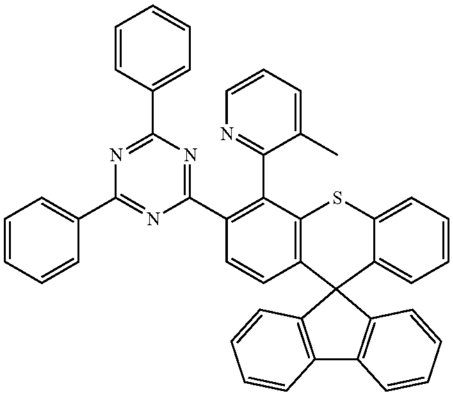
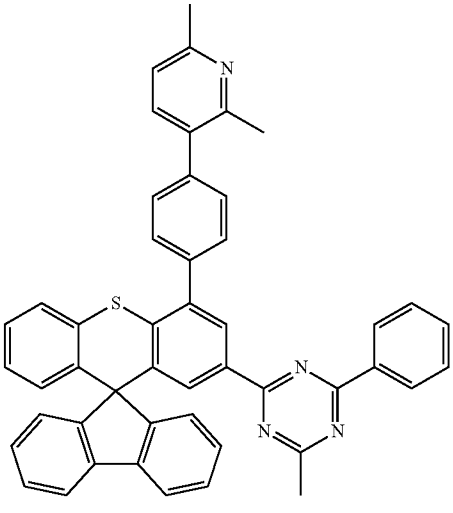

-continued
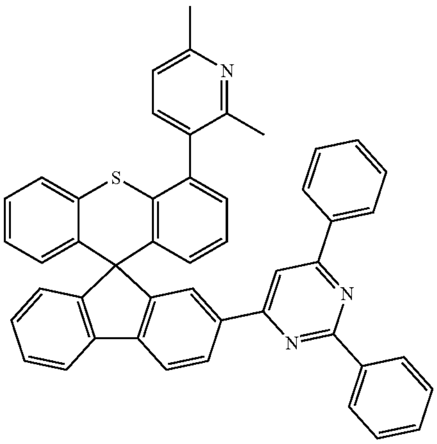
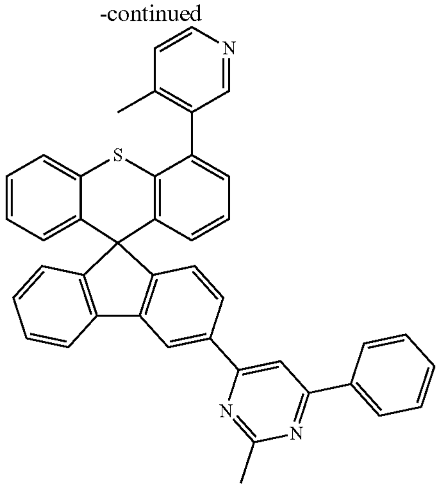
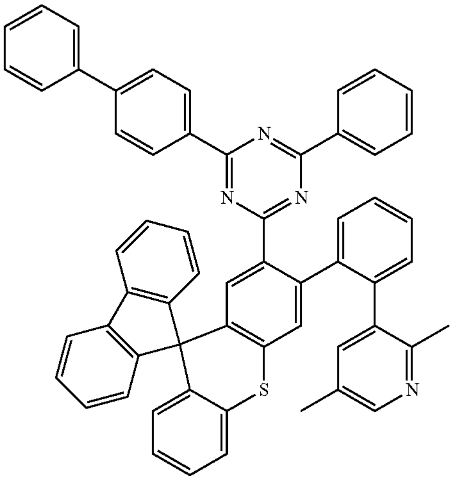
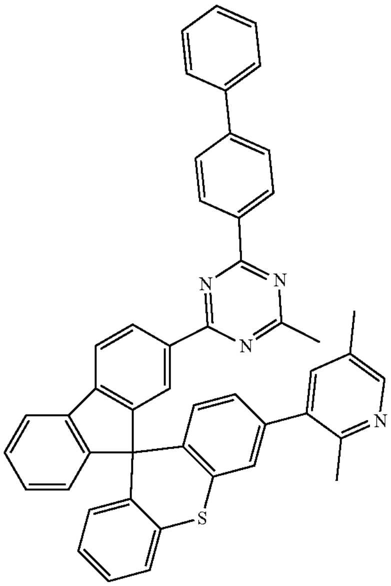
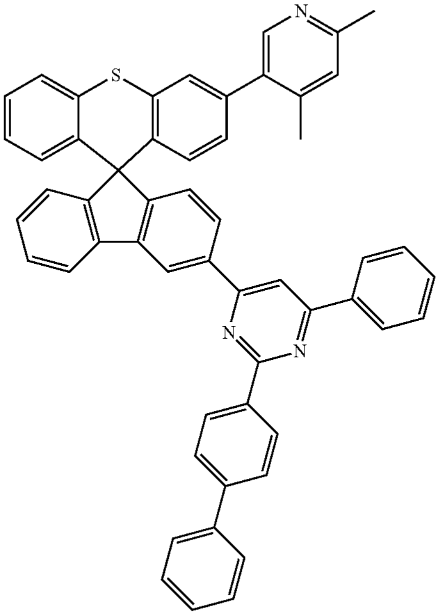
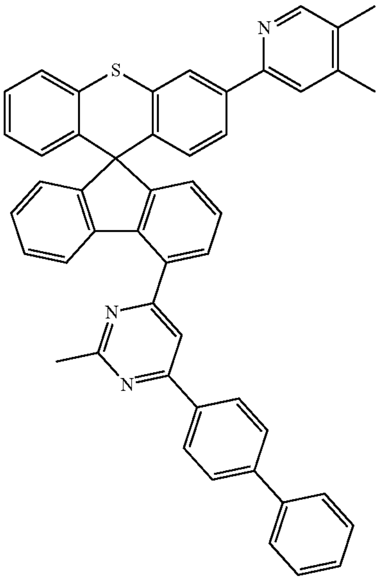

-continued
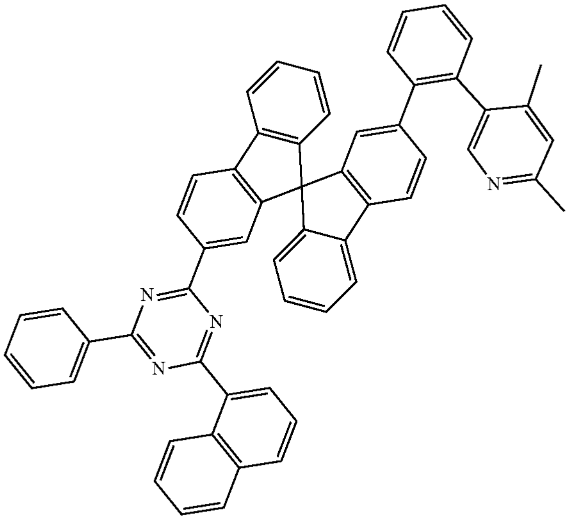
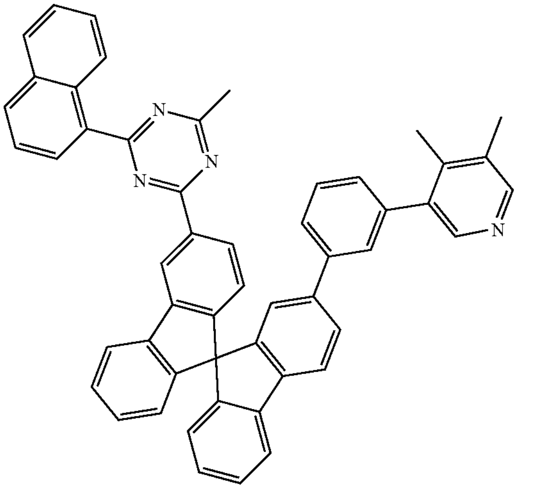
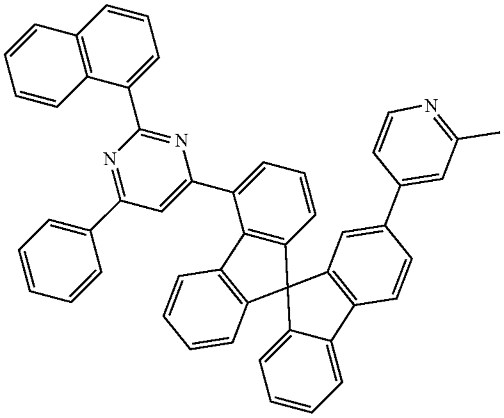
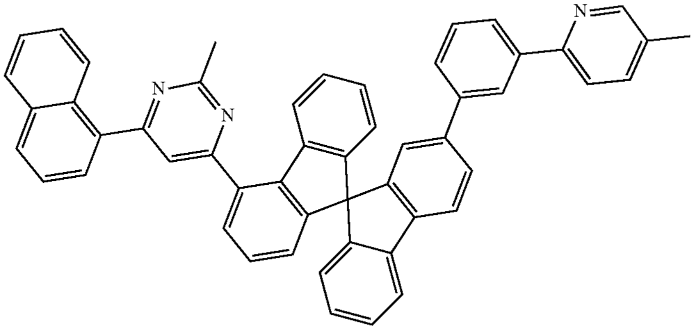
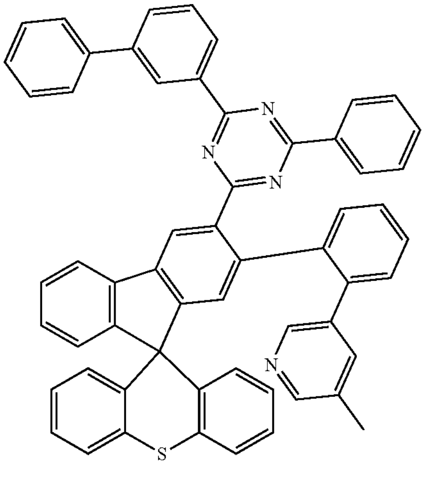

-continued
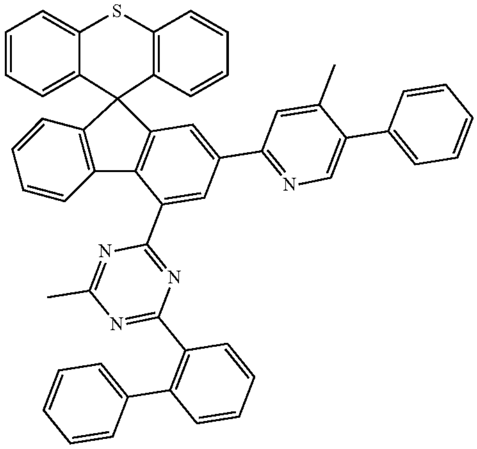
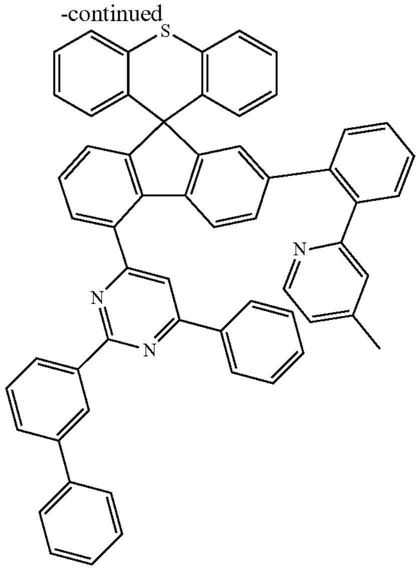
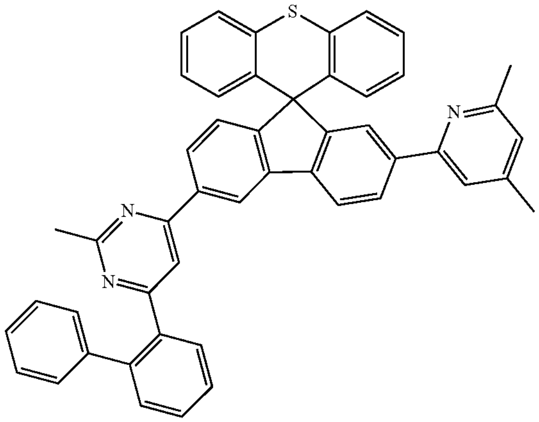
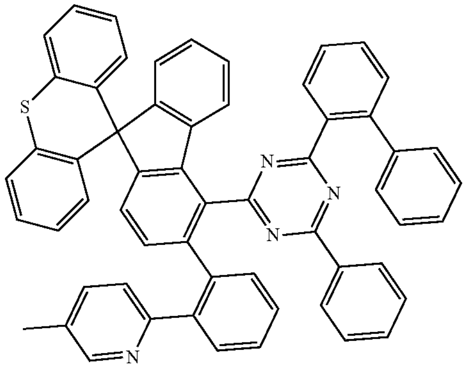
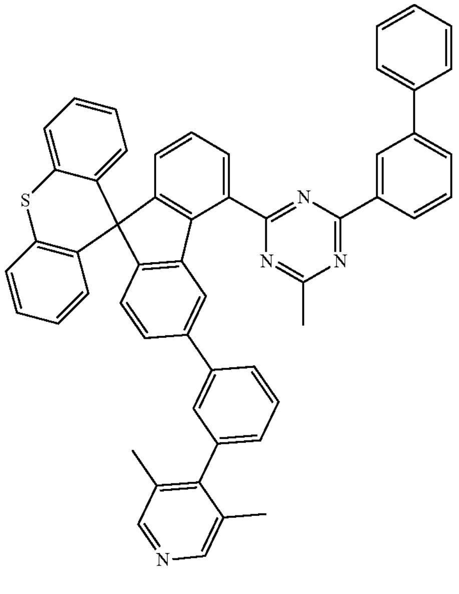
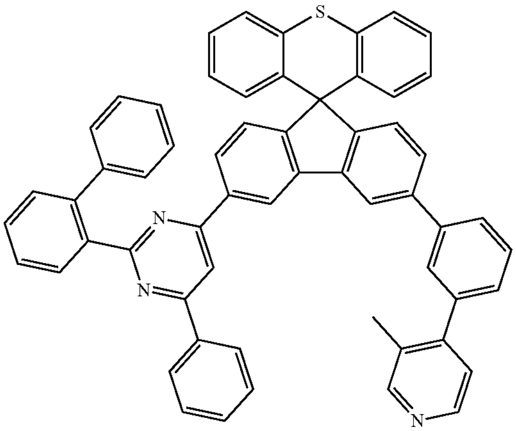

-continued
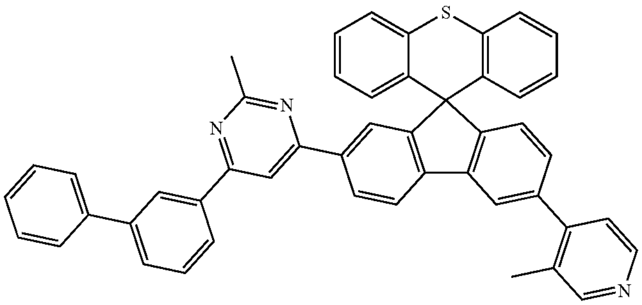
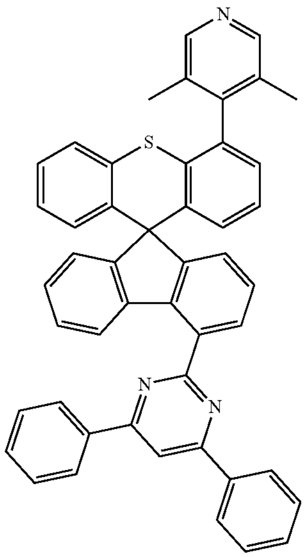
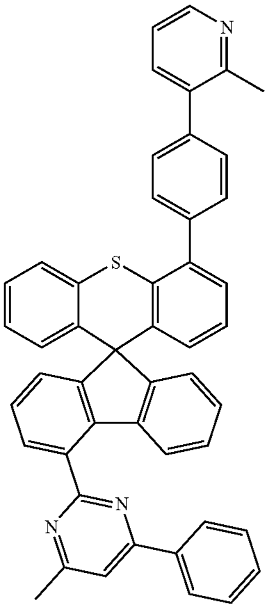
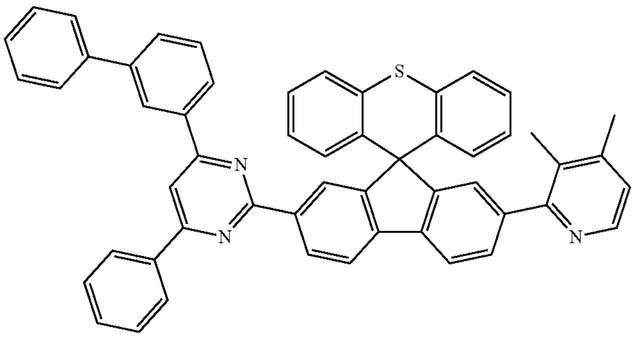

-continued
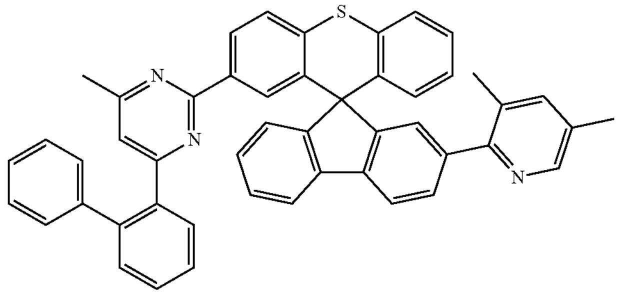
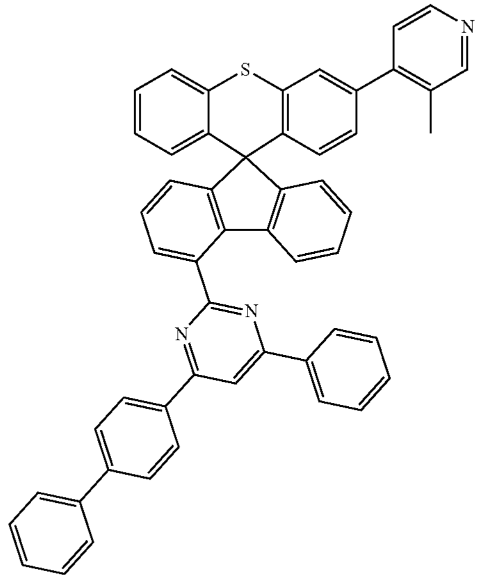
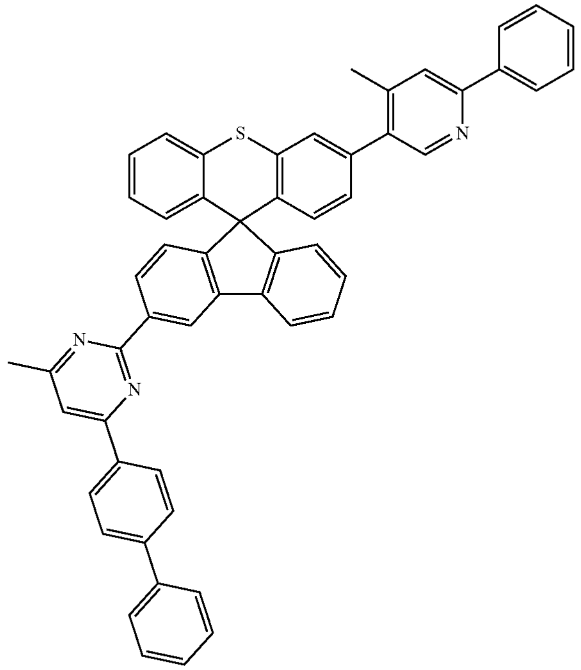
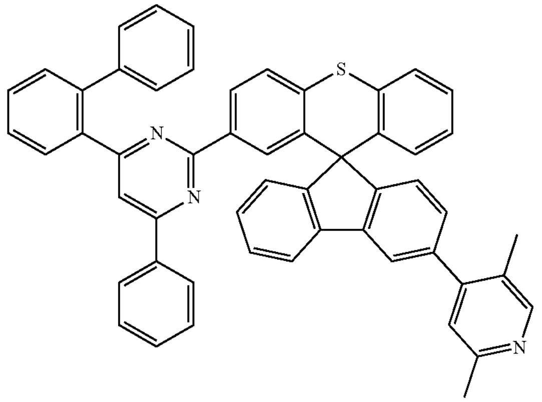
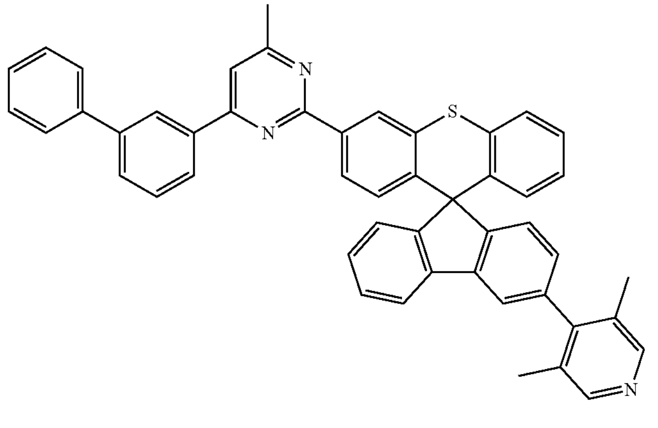

-continued
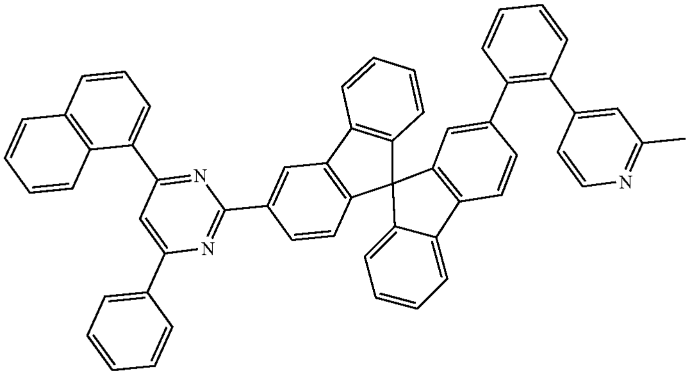
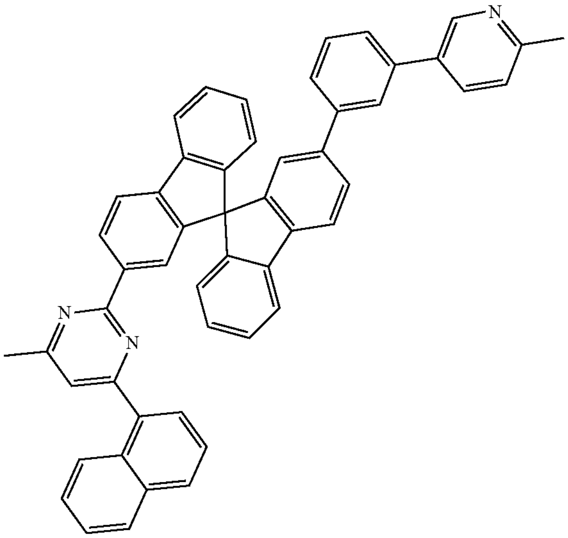
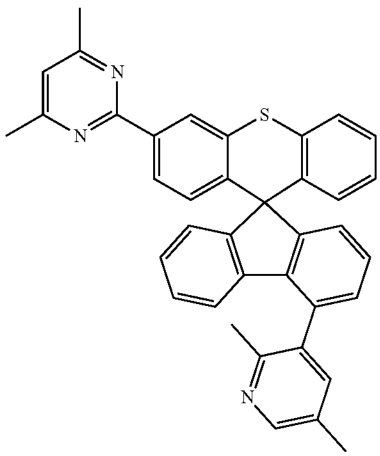
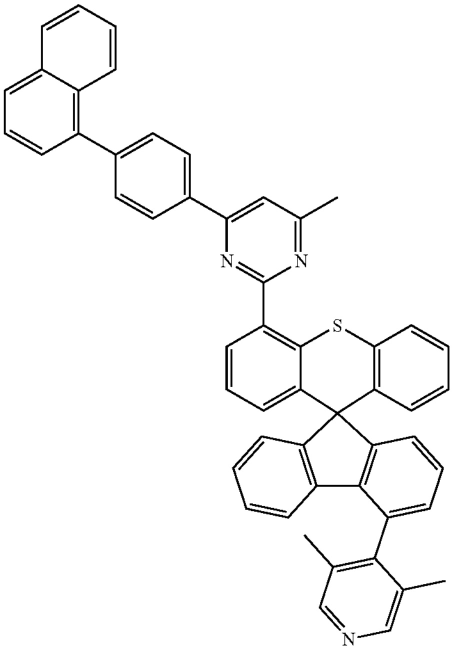
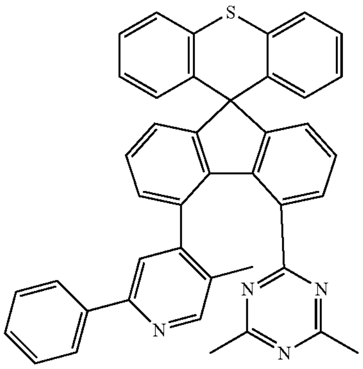

-continued
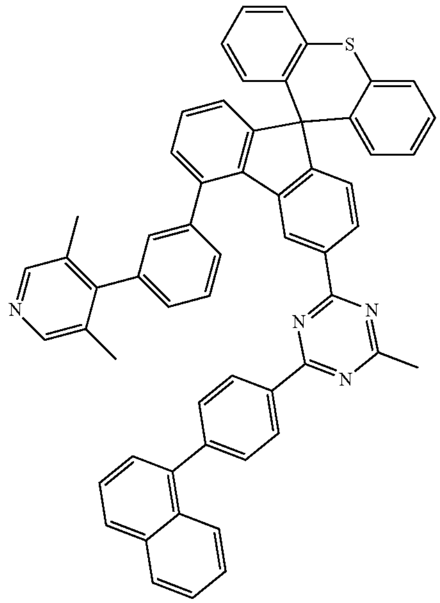
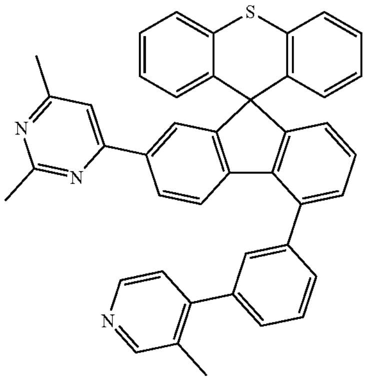
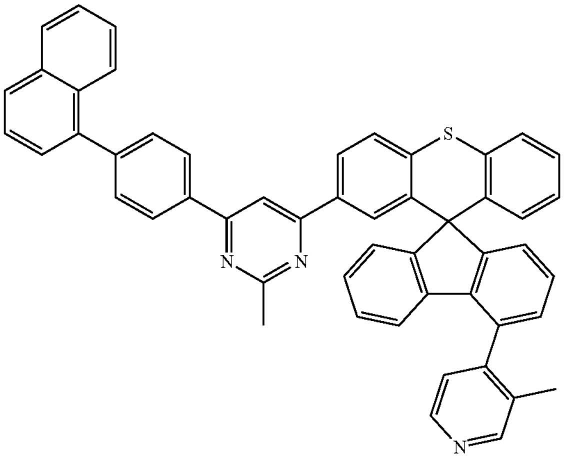
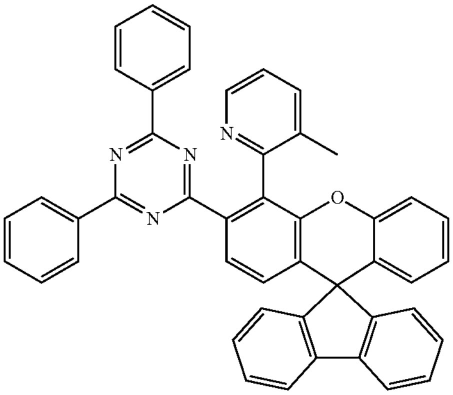

-continued
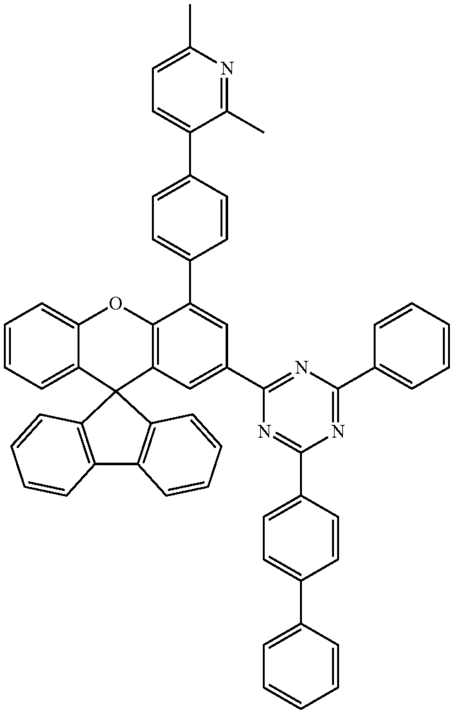
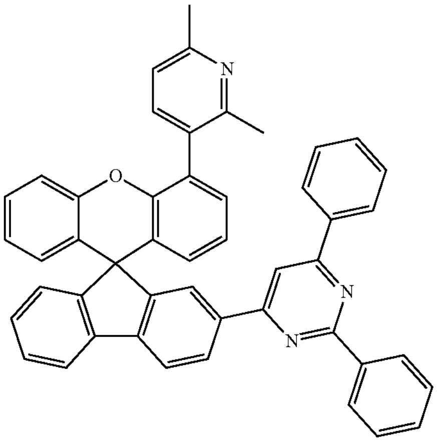
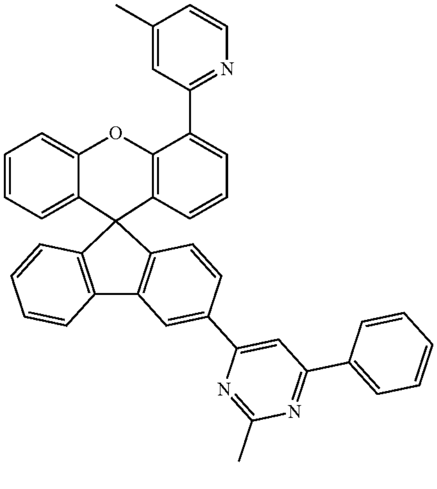
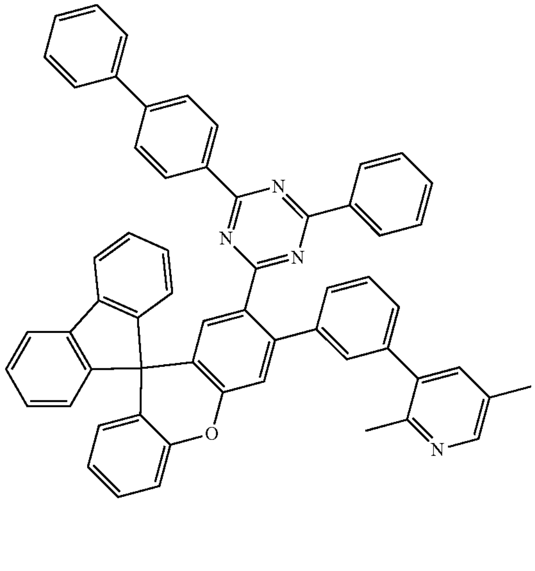

-continued
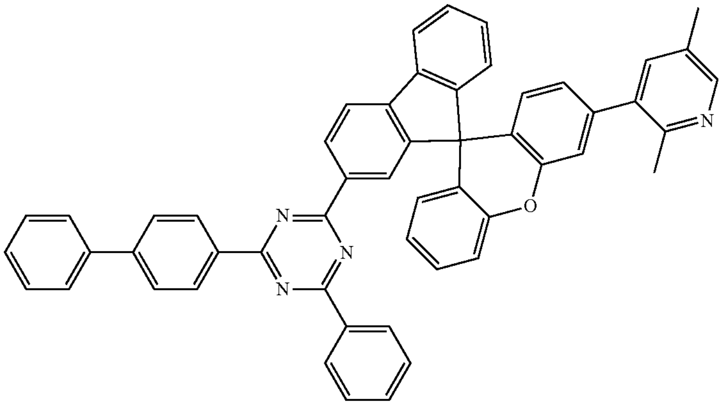
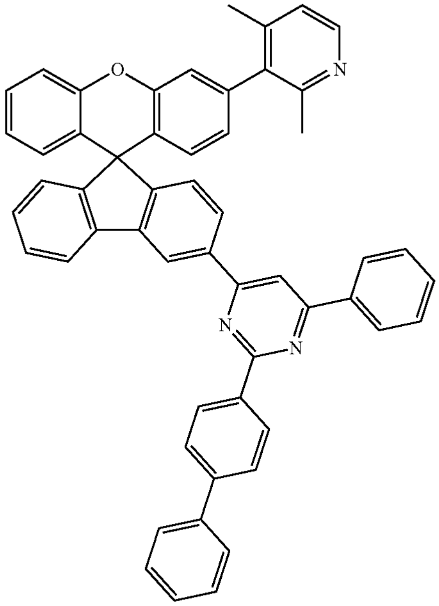
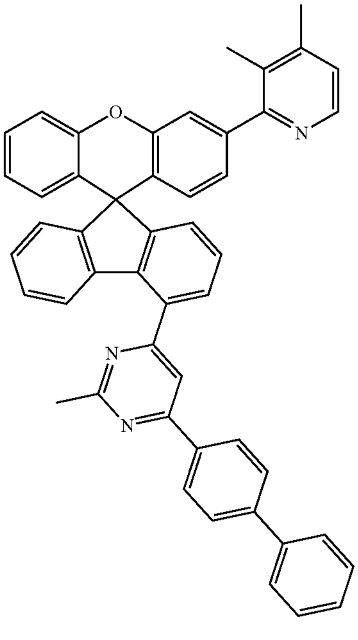
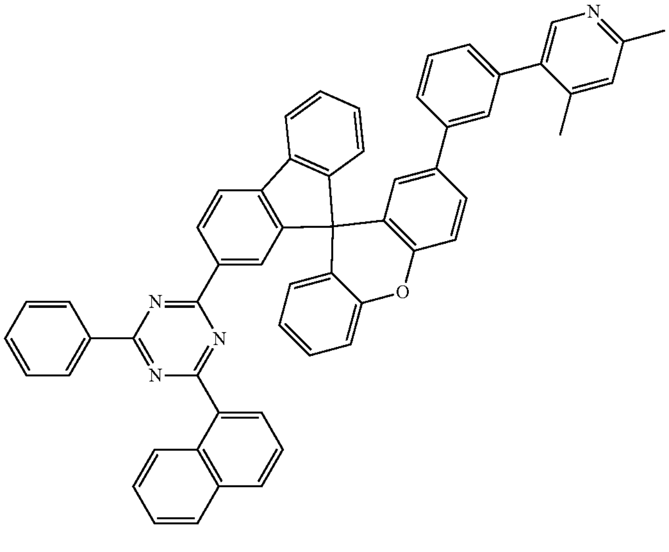

-continued
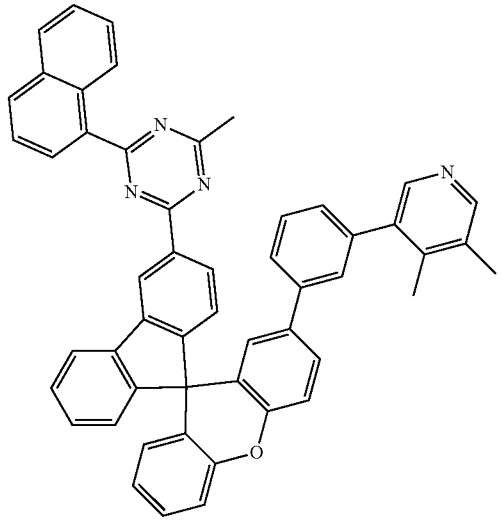
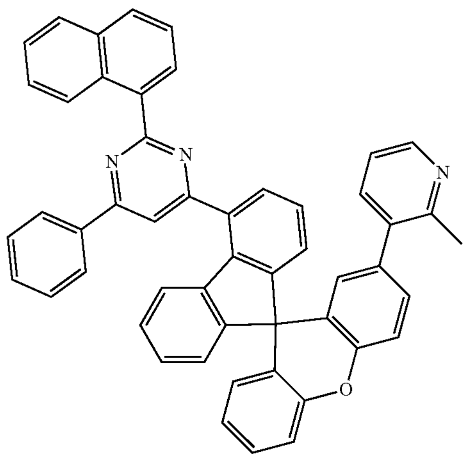
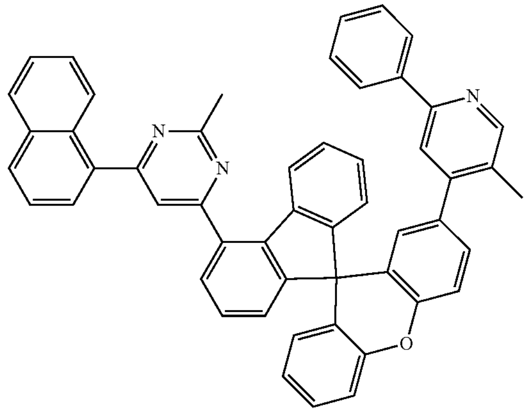
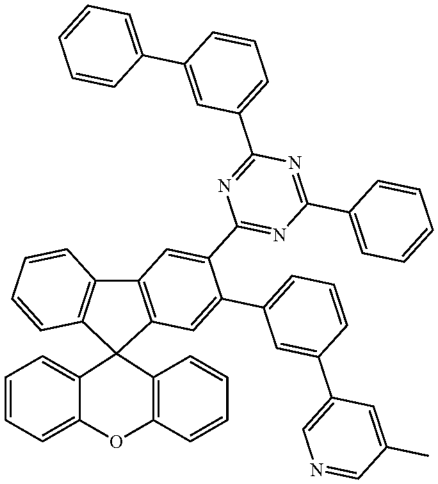
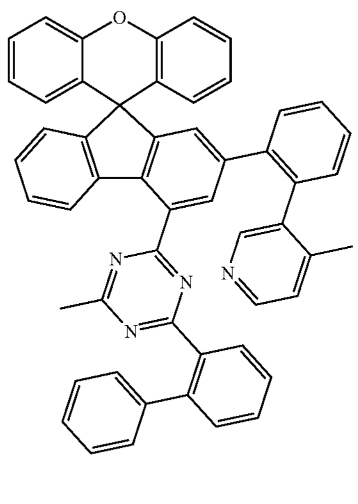
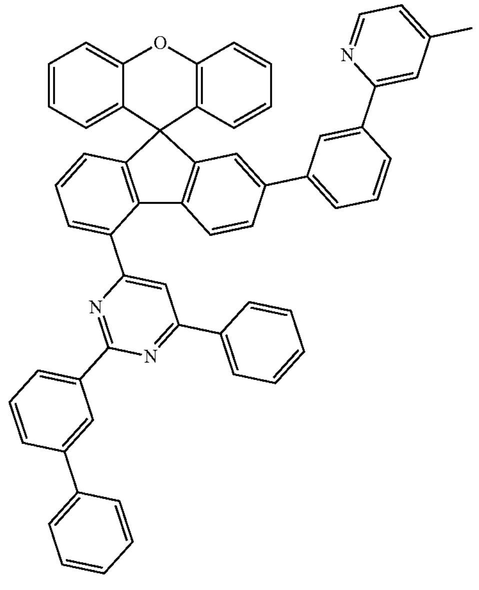

-continued
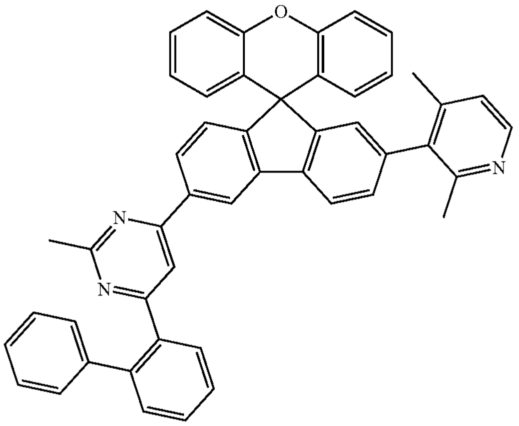
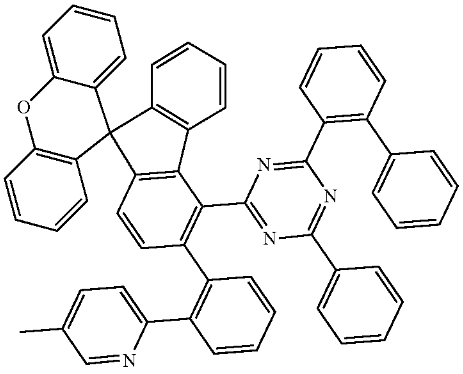
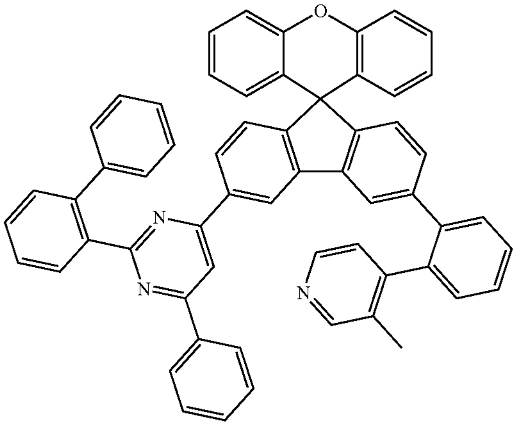
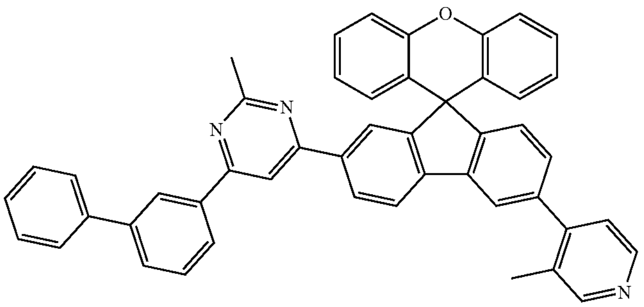
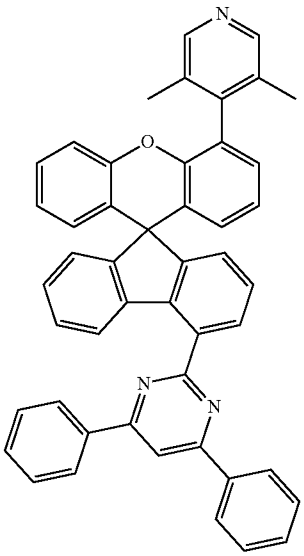
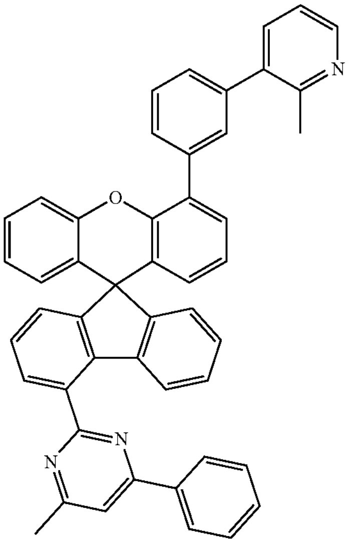

-continued
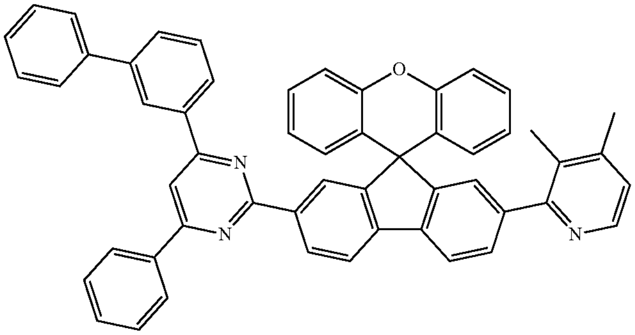
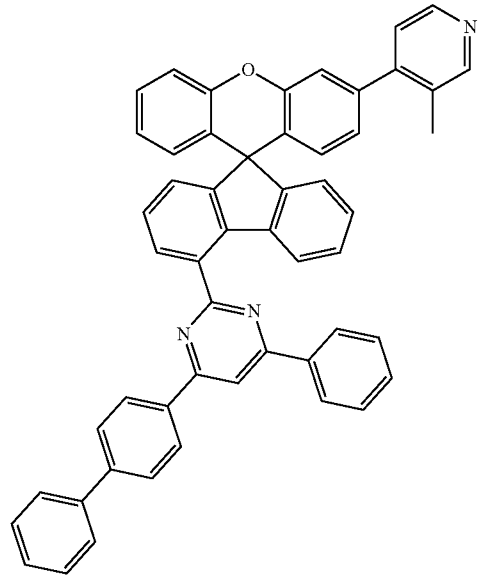
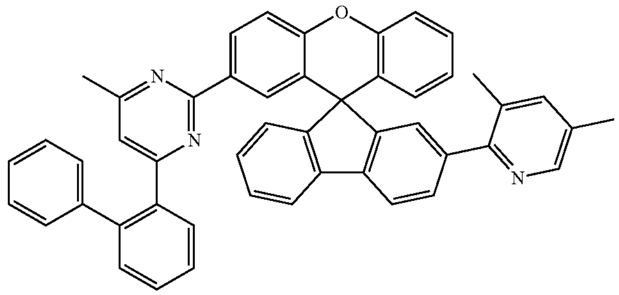
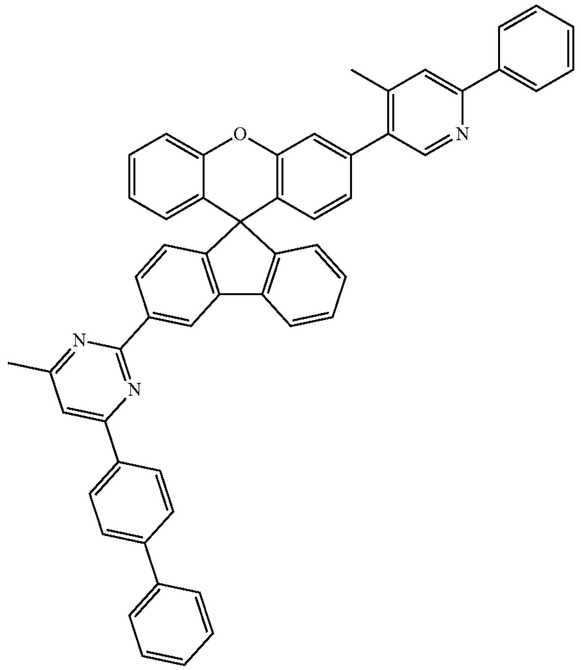
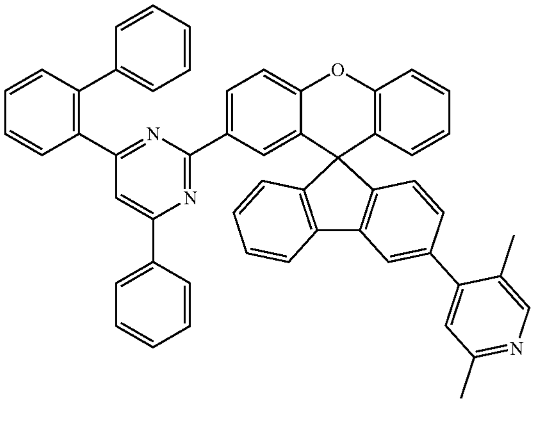

-continued
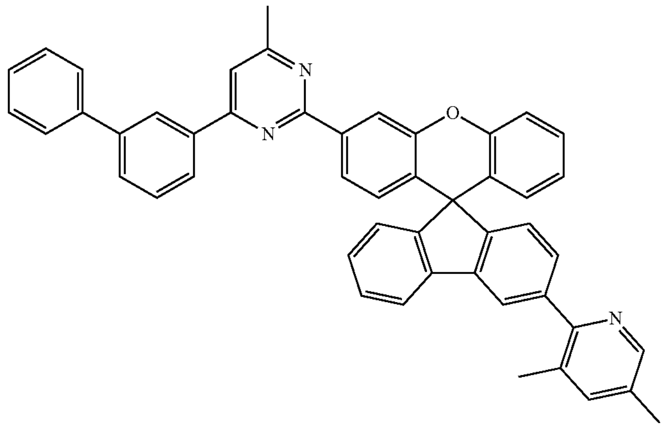
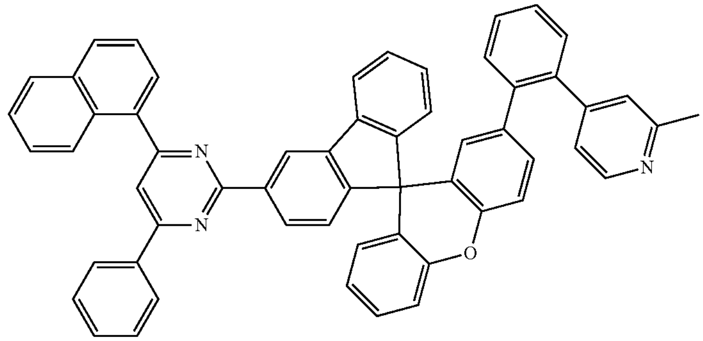
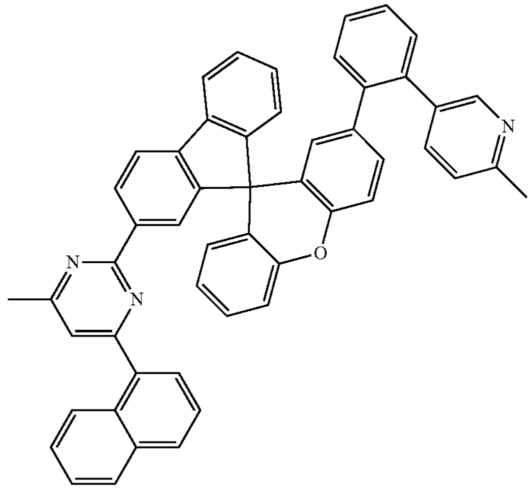
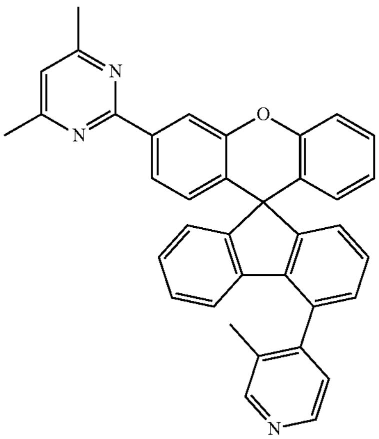

-continued
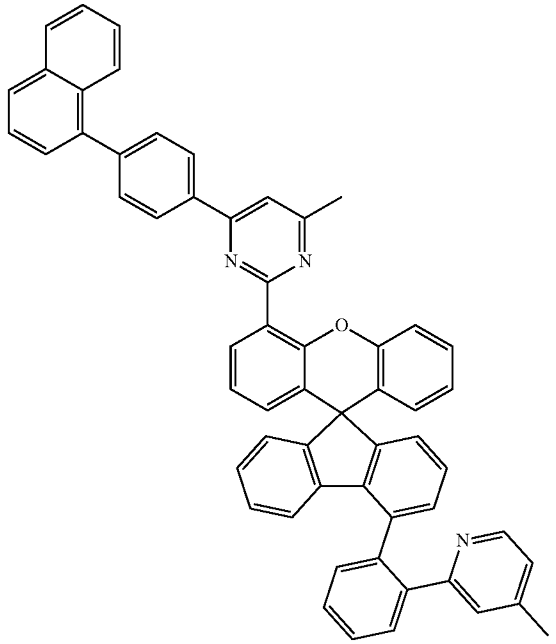
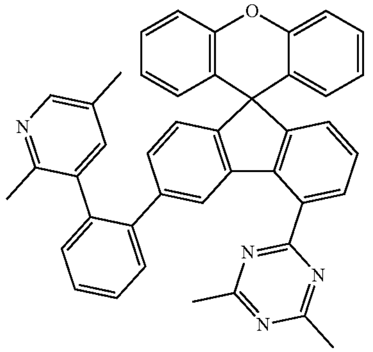
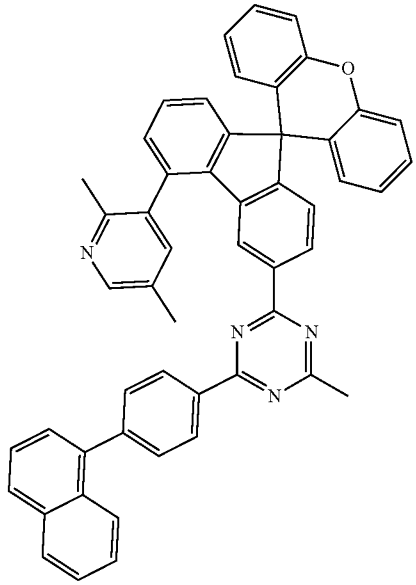
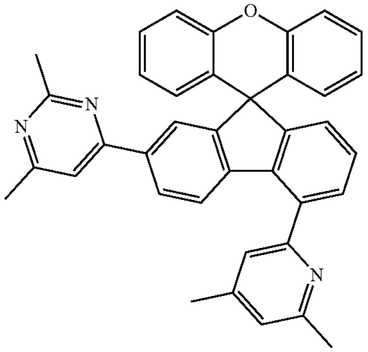
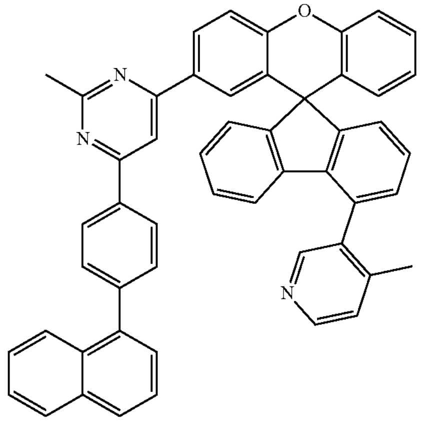
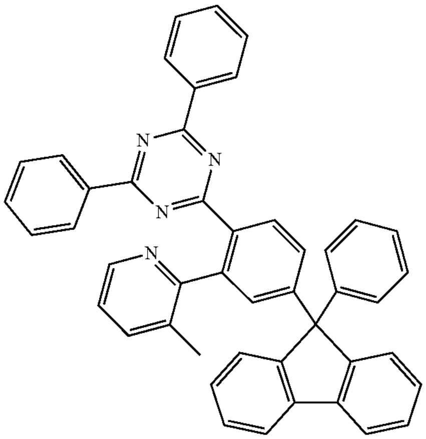

-continued
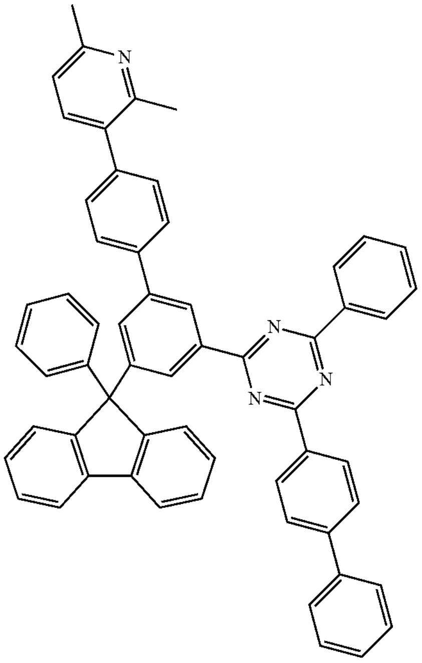
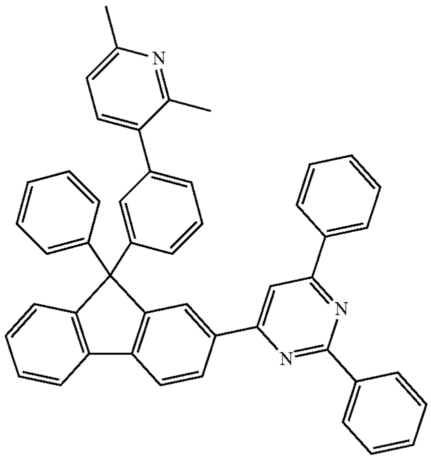
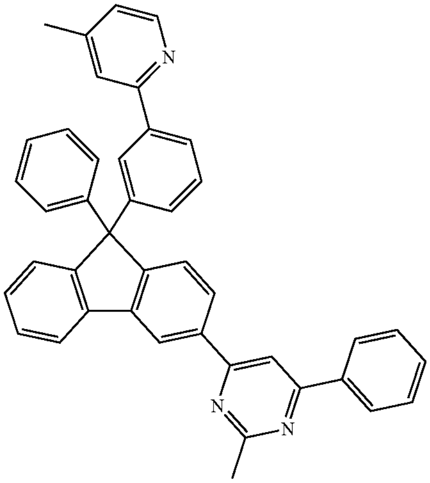
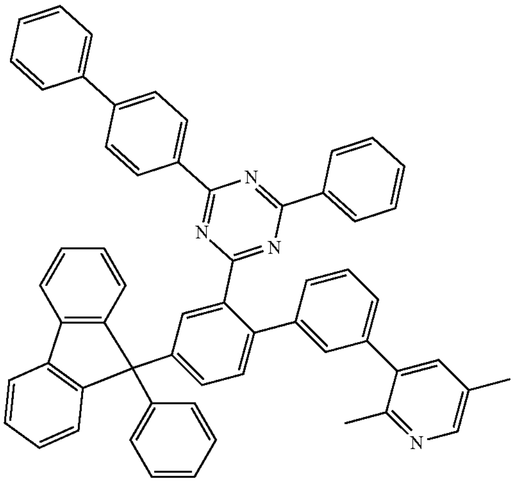
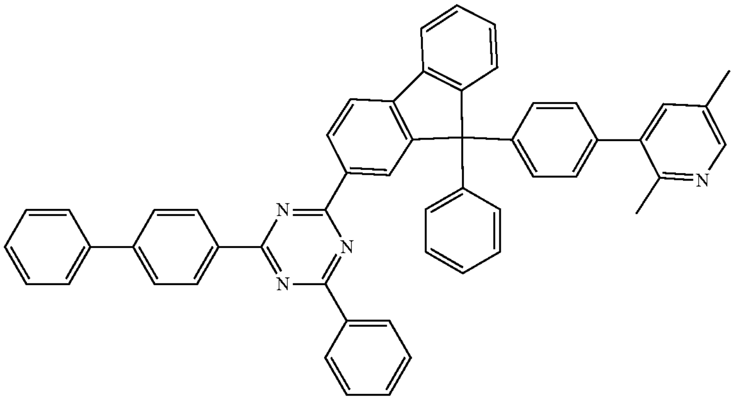

-continued
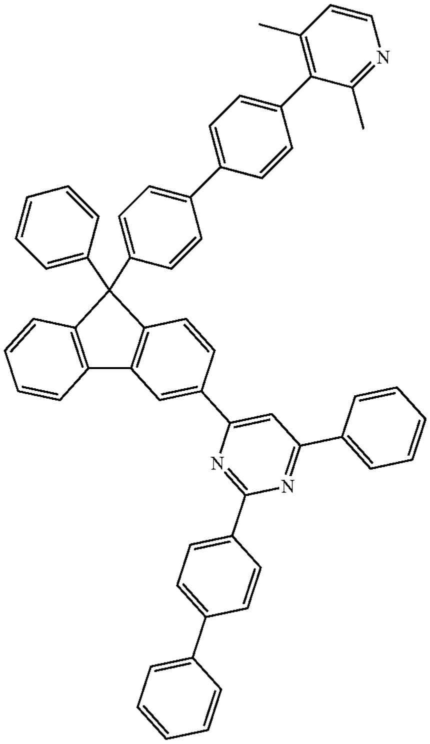
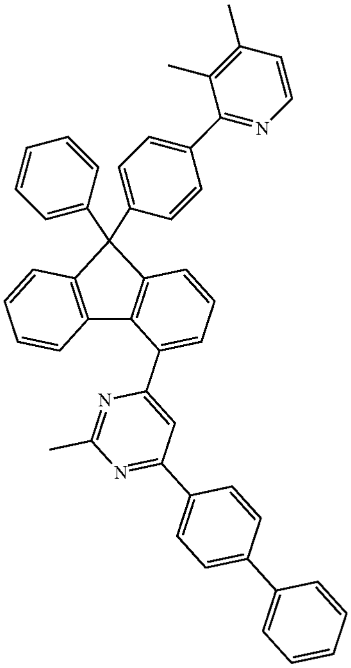
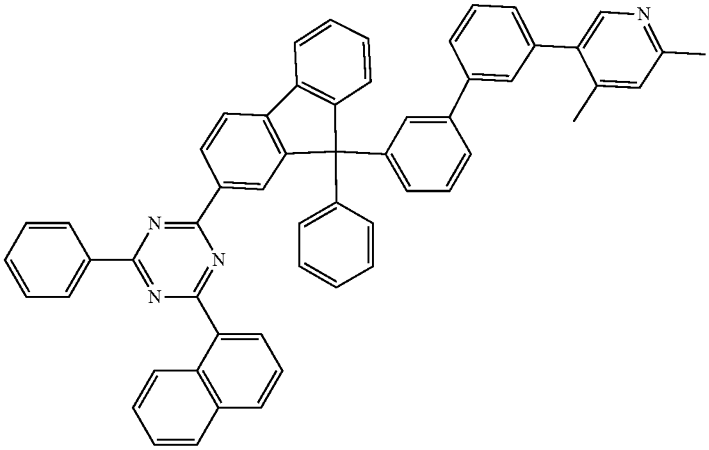
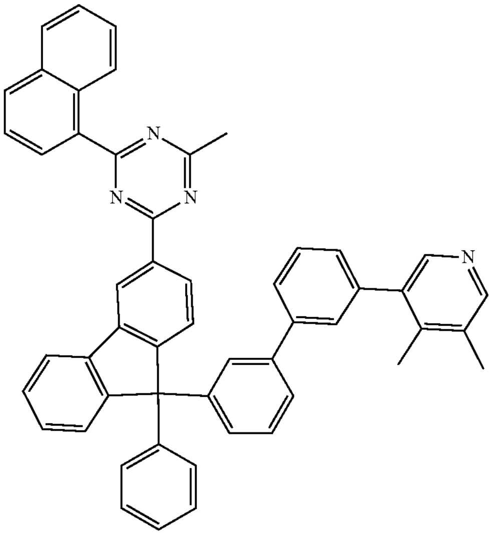
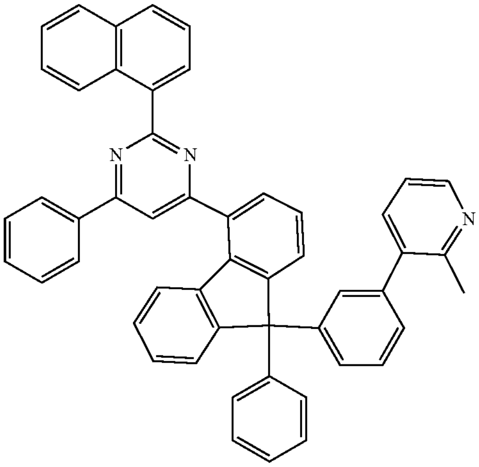

-continued
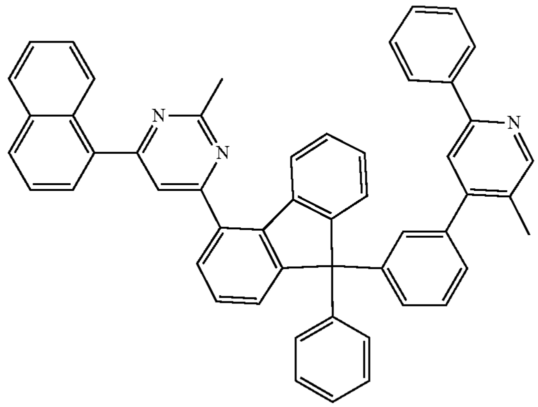
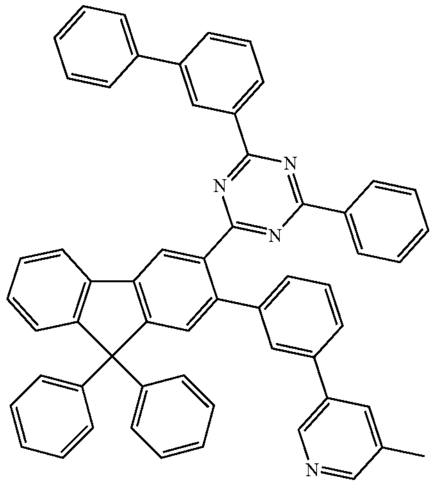
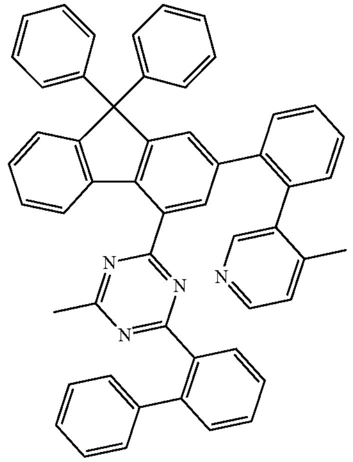
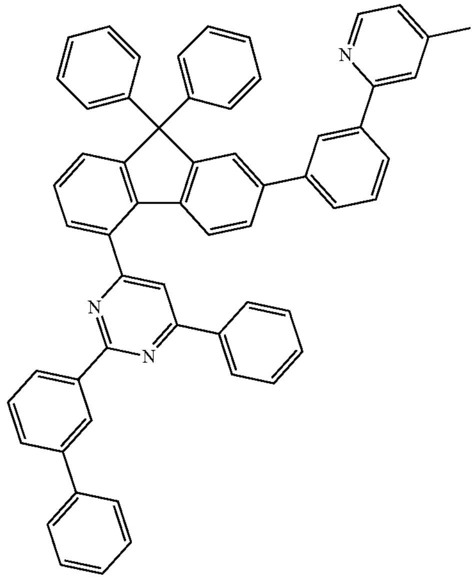
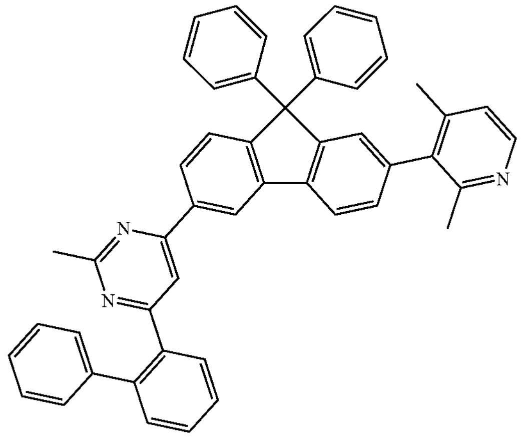
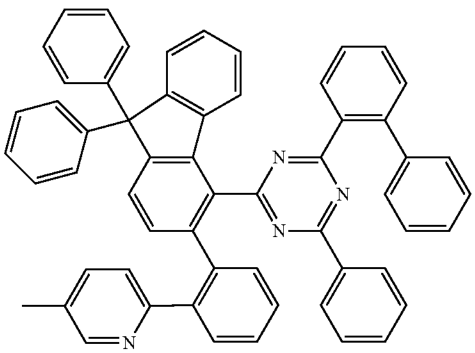

-continued
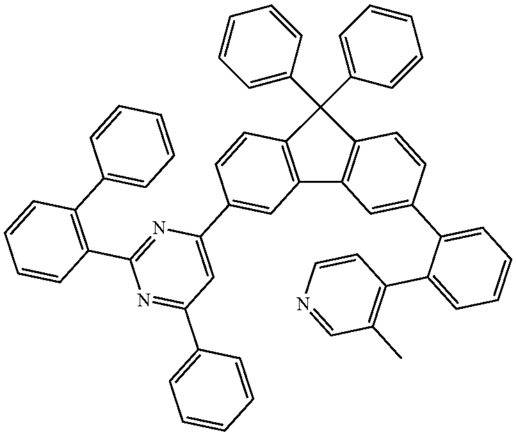
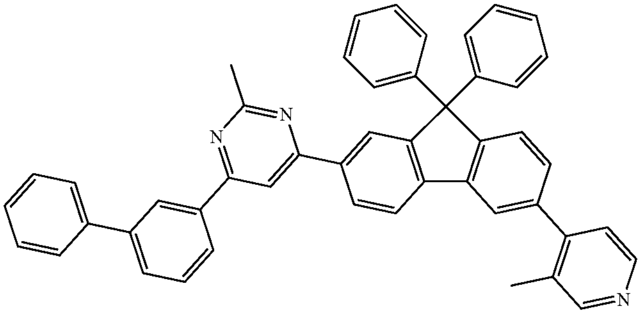
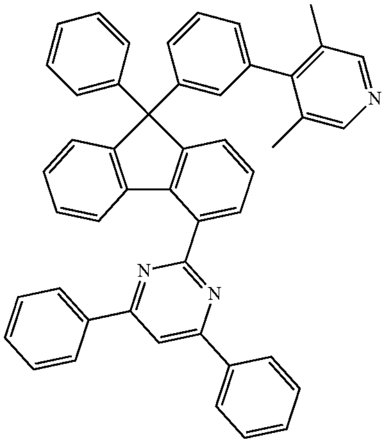
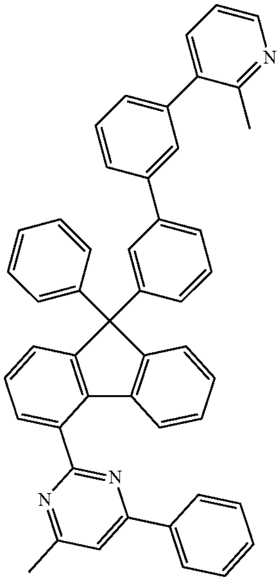
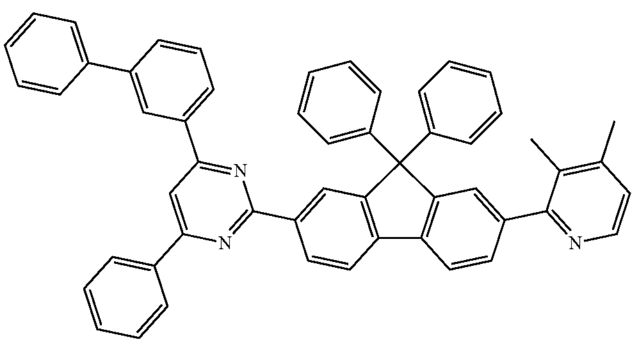

-continued
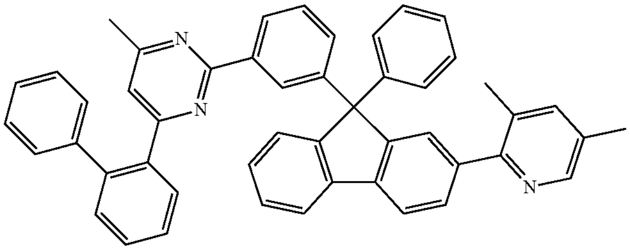
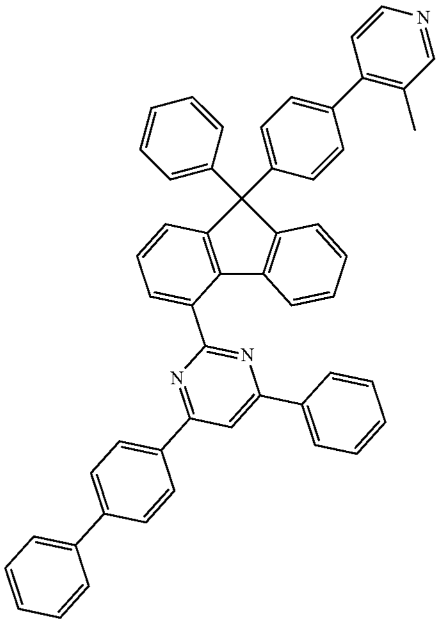
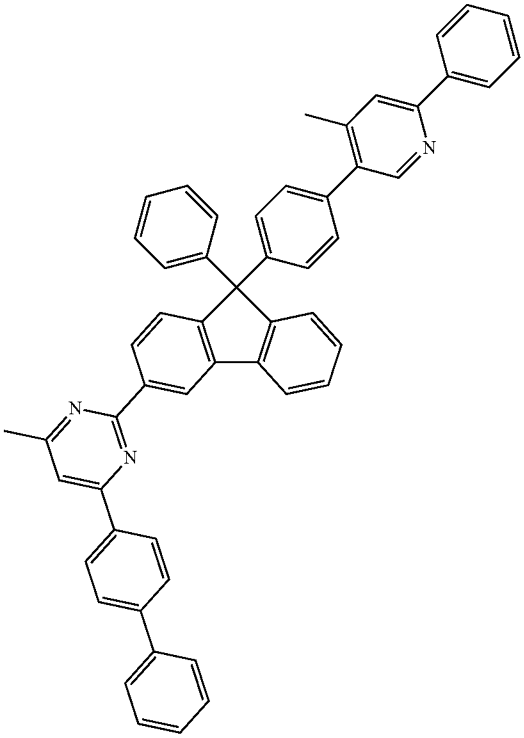
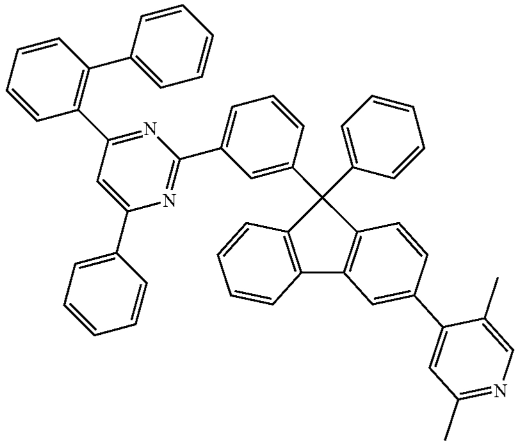

-continued
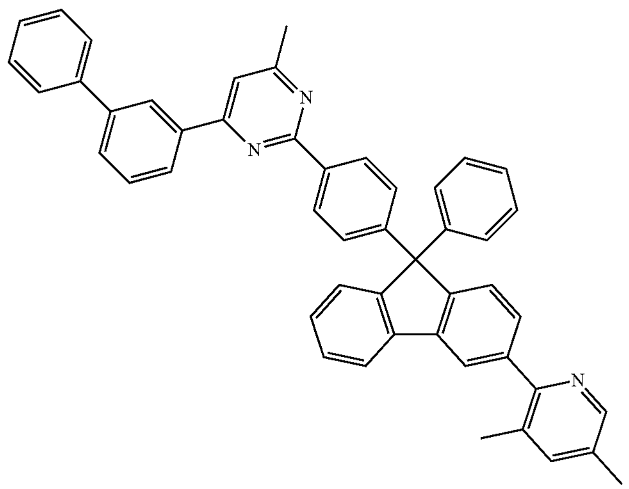
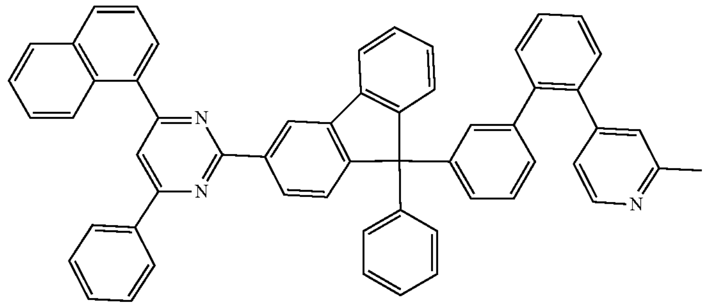
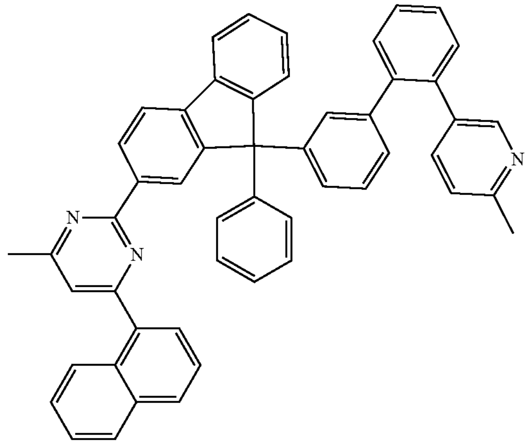
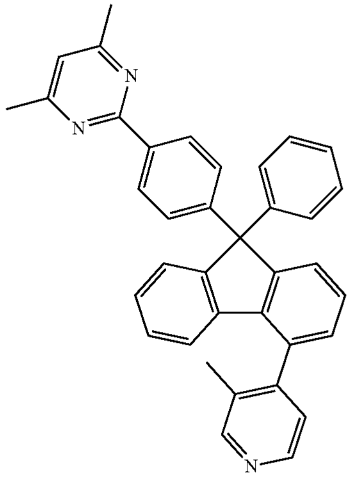

-continued
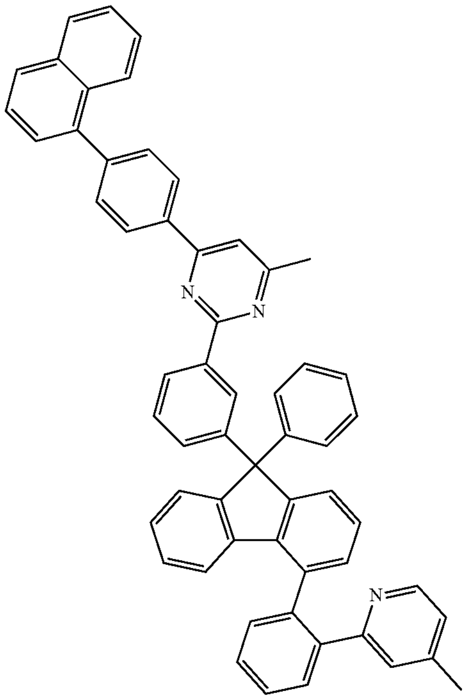
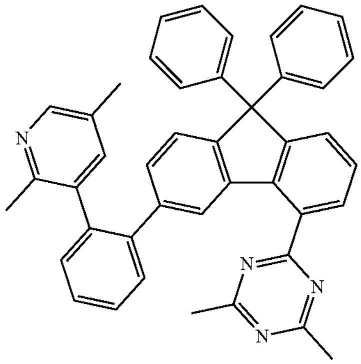
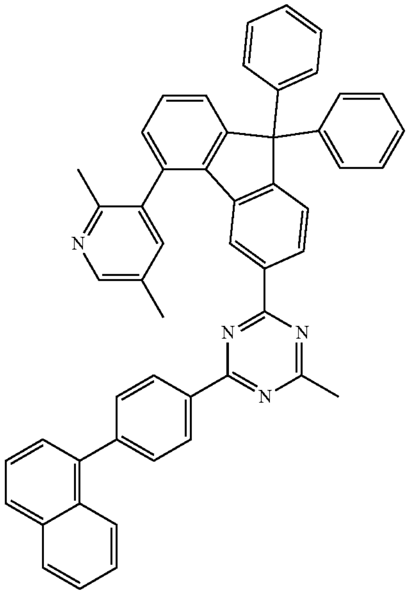
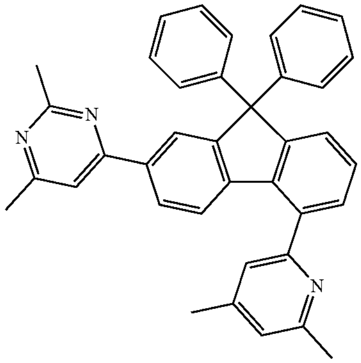
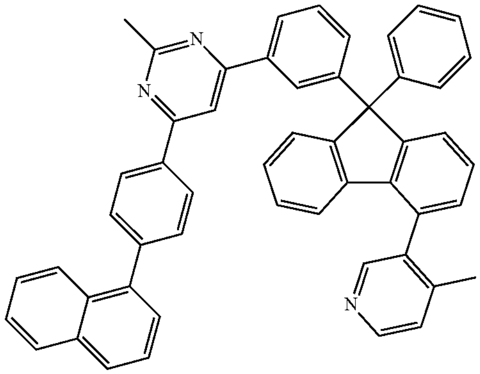
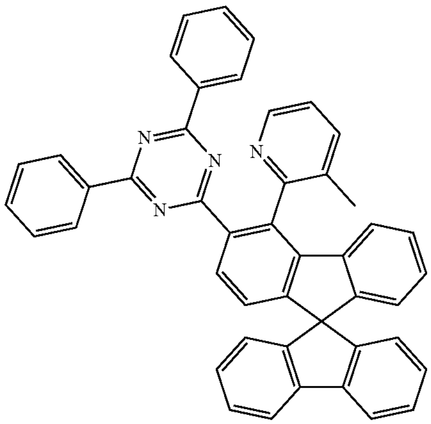

-continued
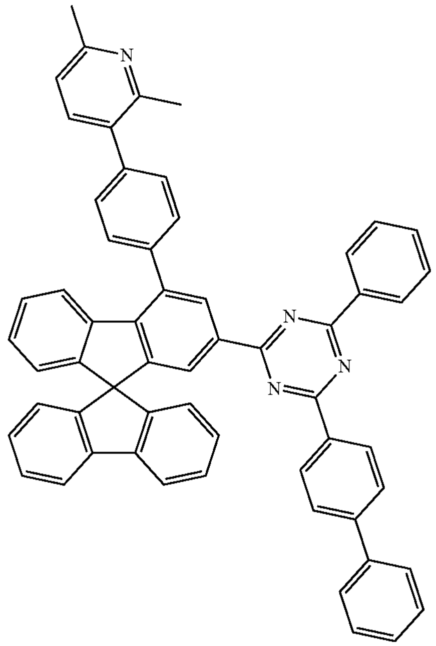
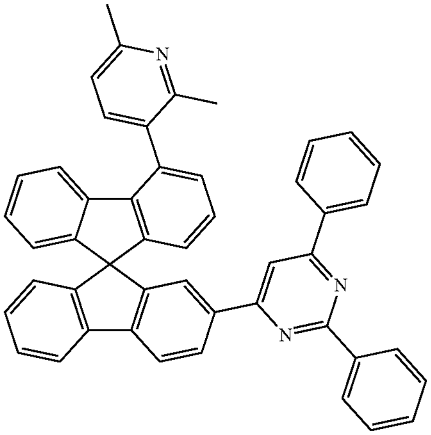
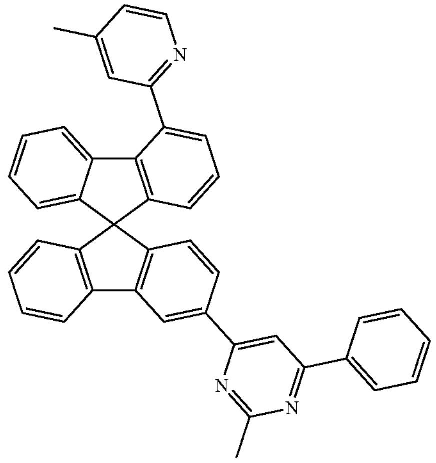
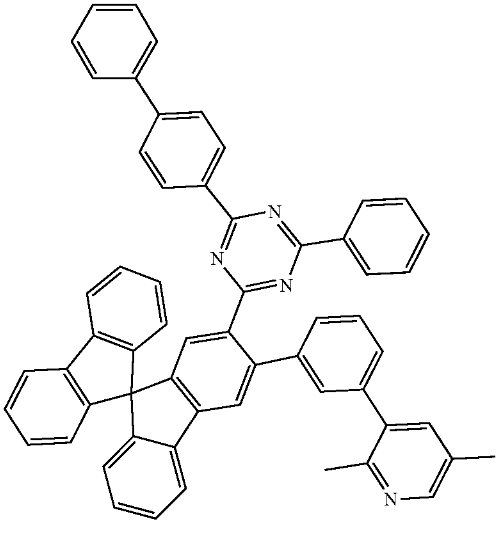

-continued
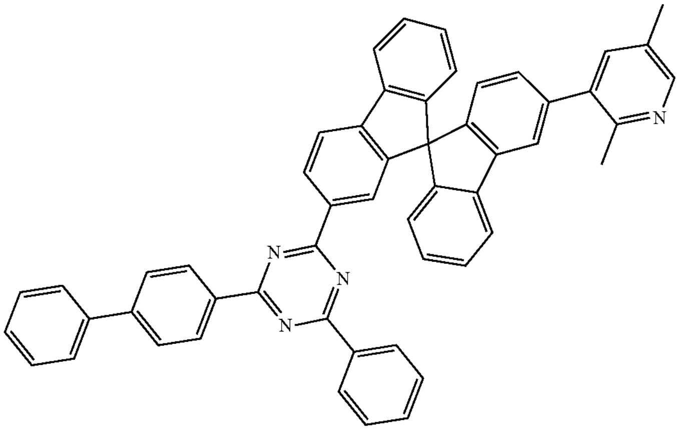
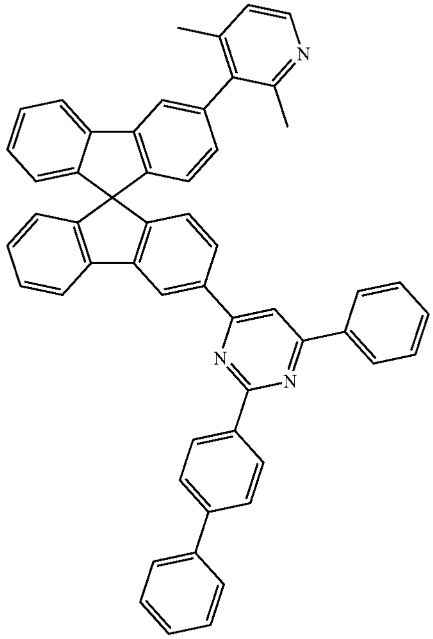
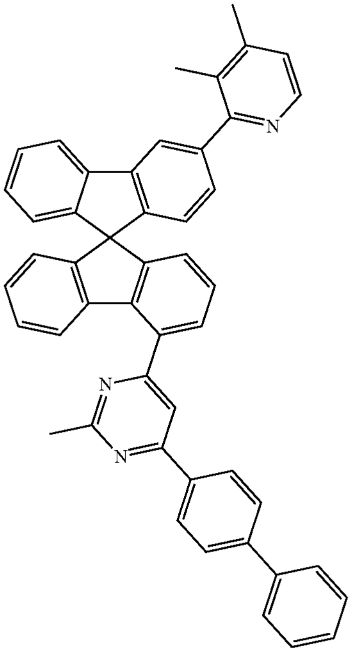
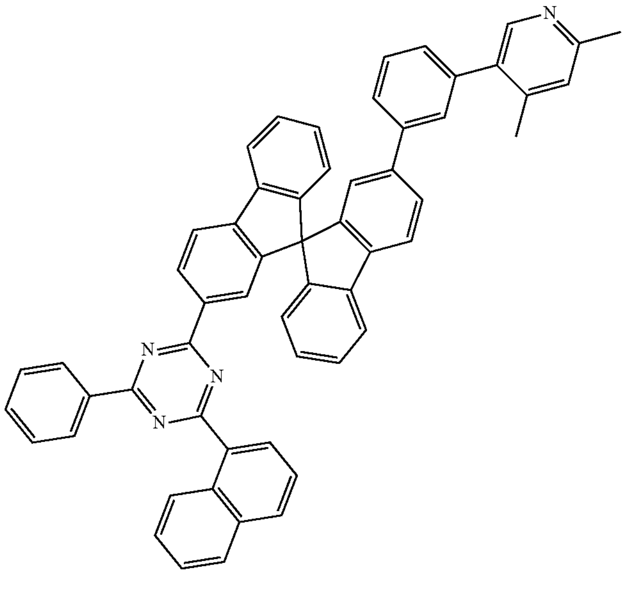

-continued
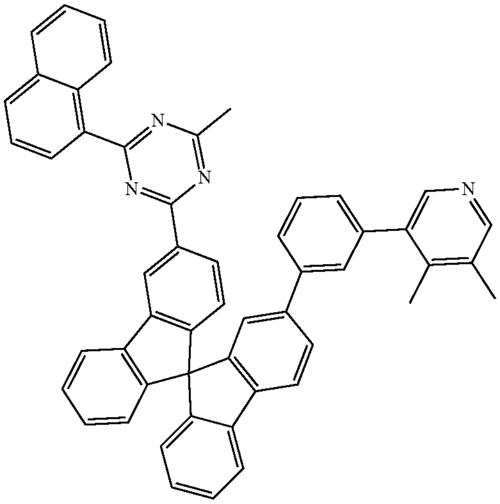
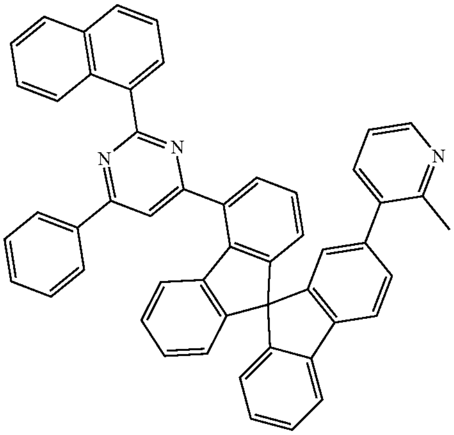
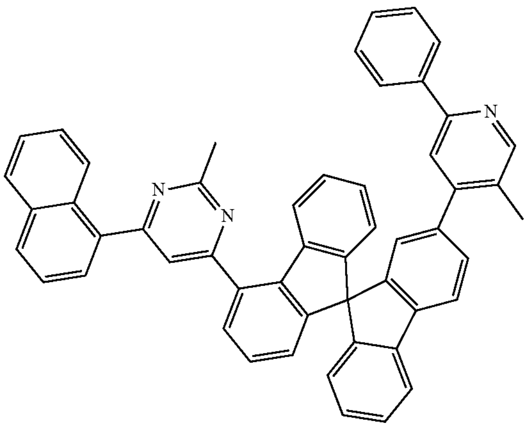
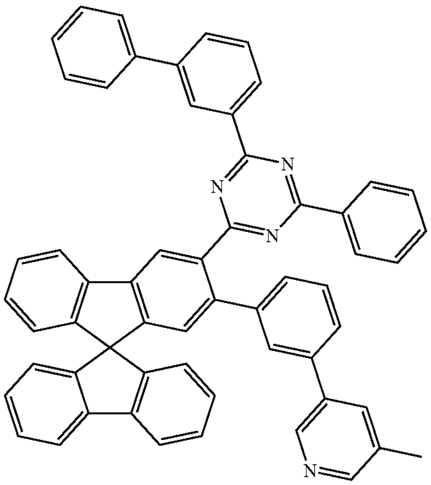
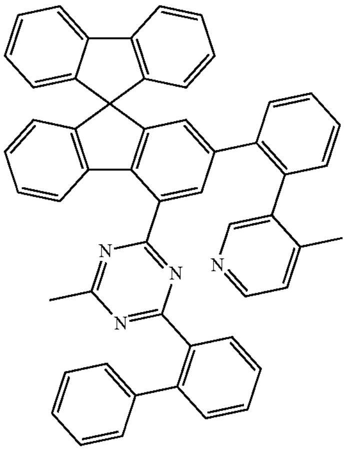
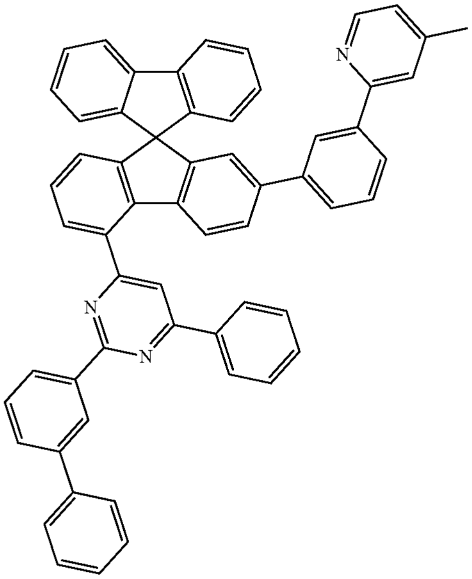

-continued
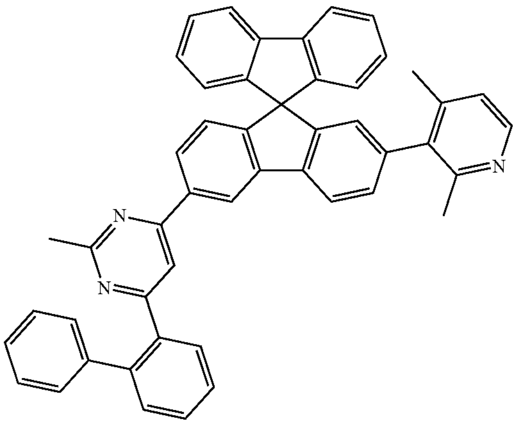
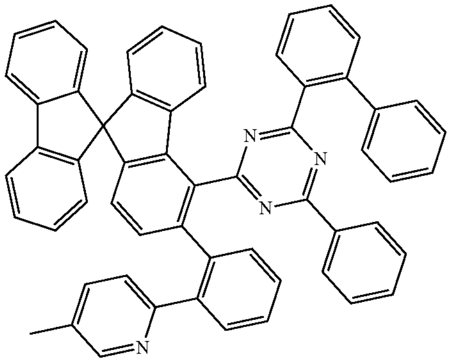
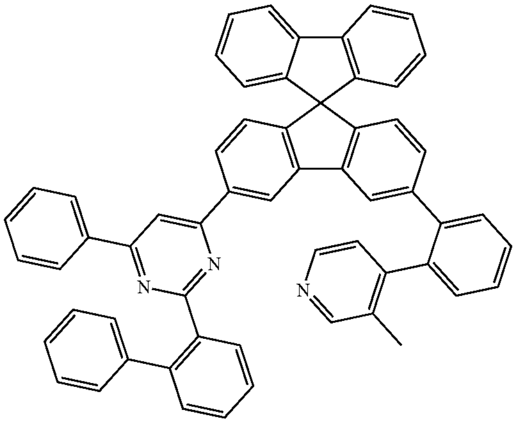
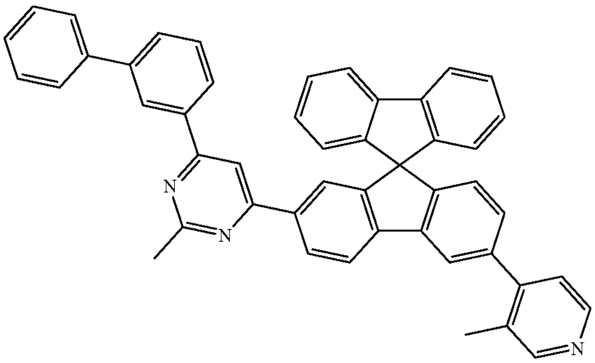
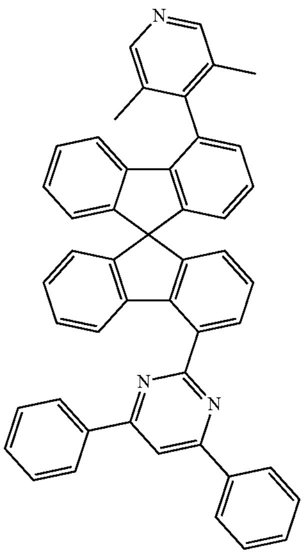
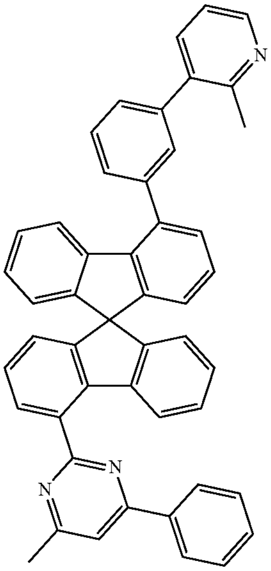

-continued
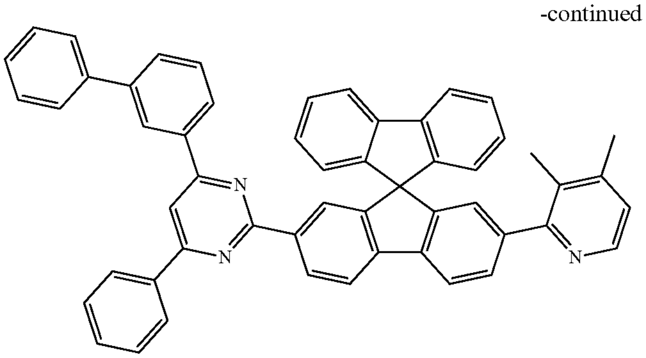
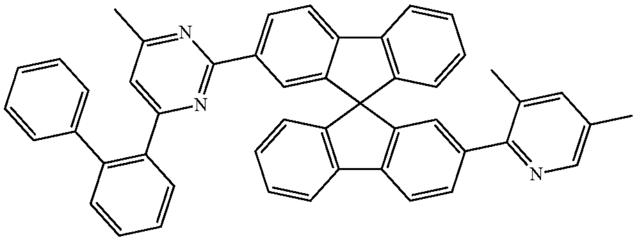
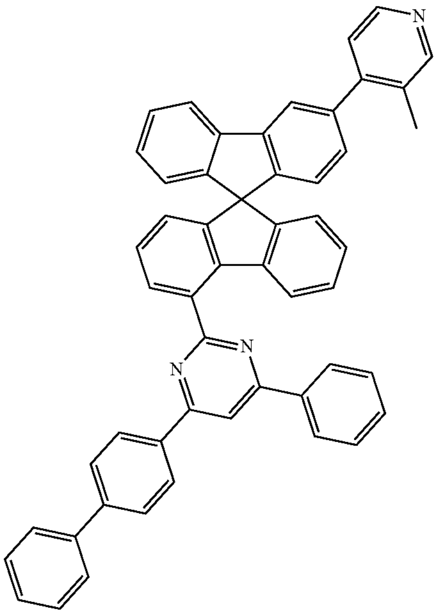
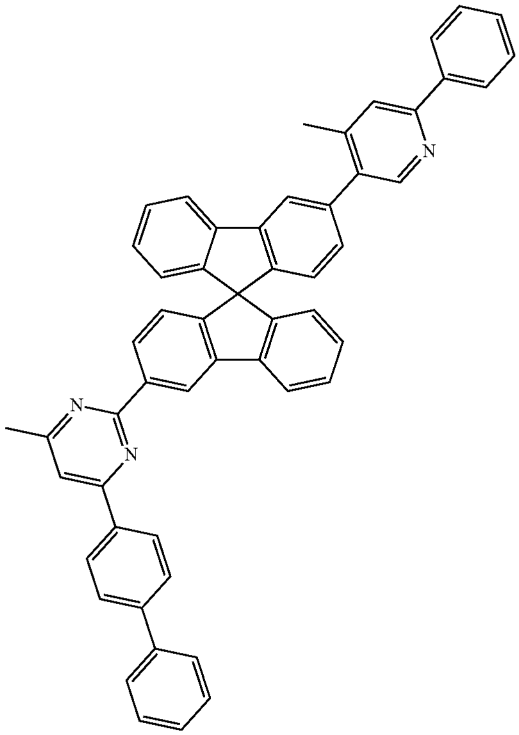

-continued
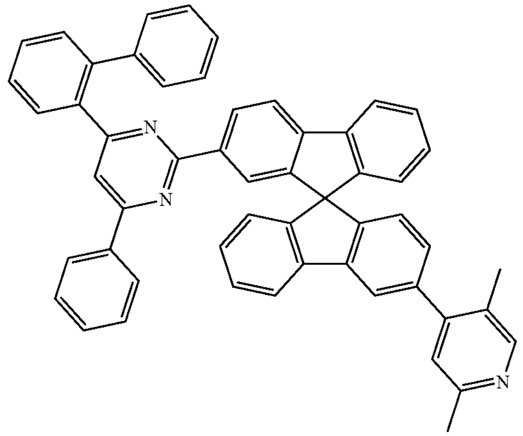
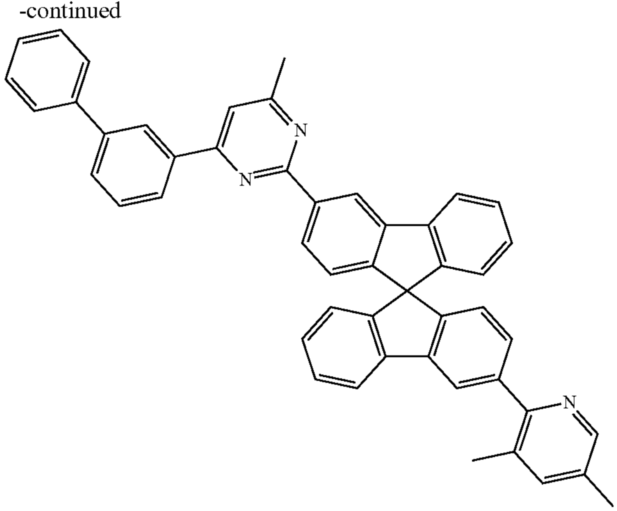
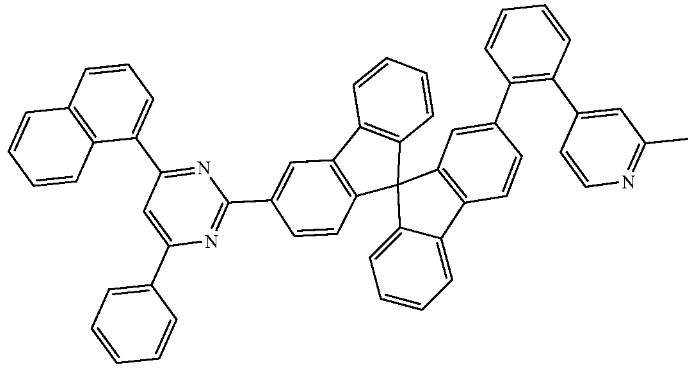
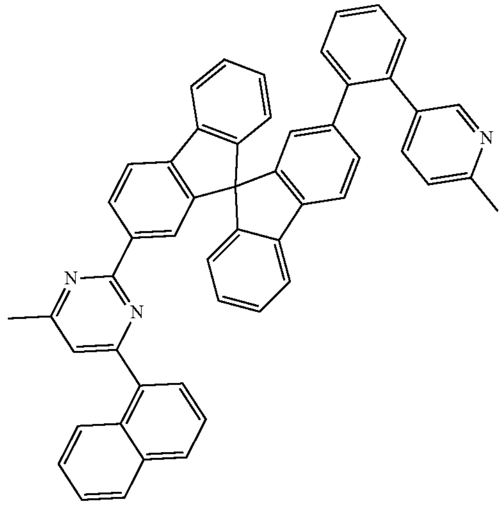
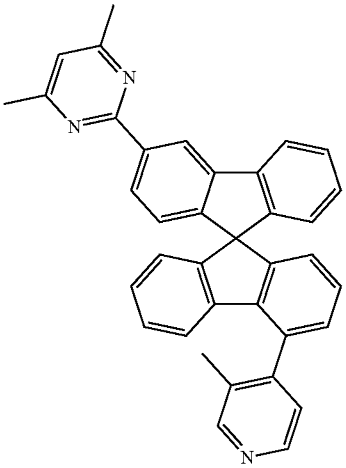

-continued
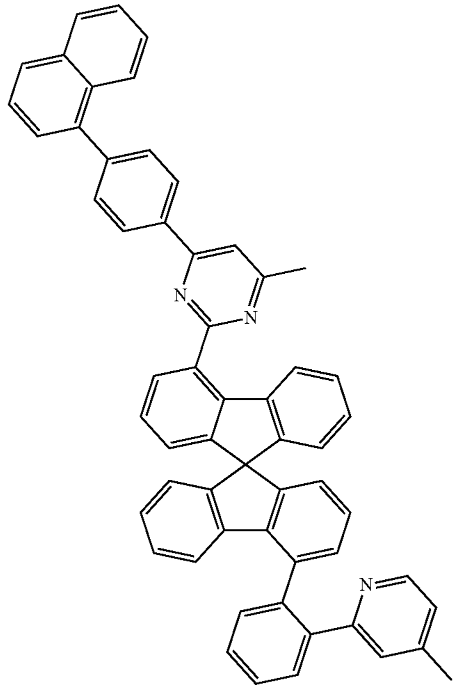
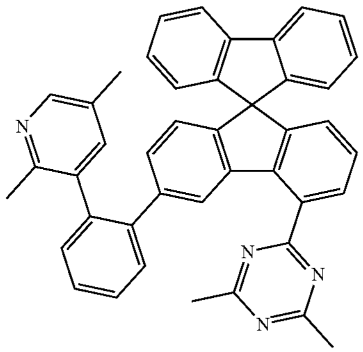
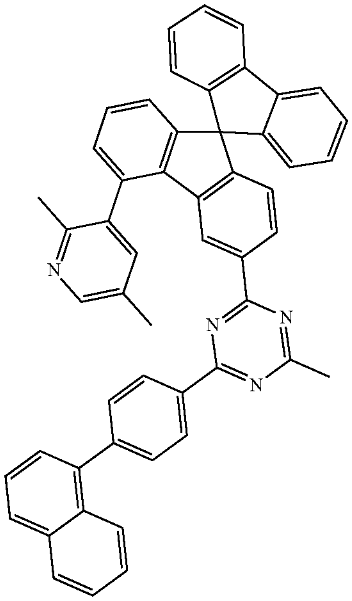
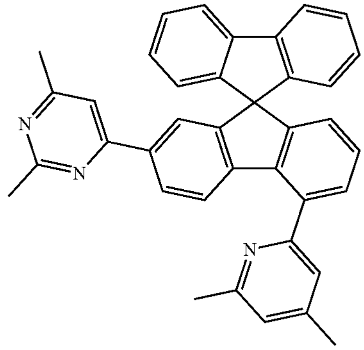
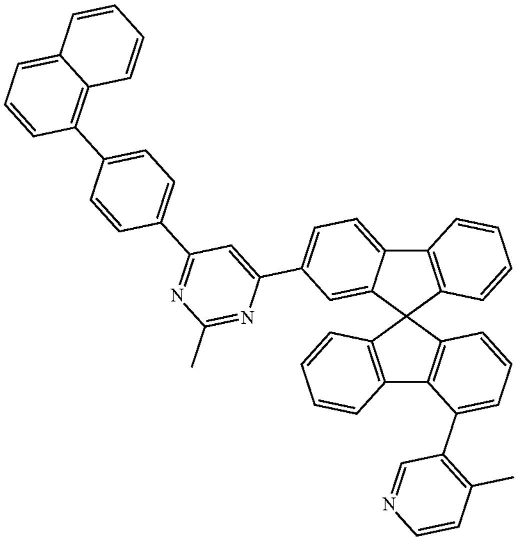

-continued
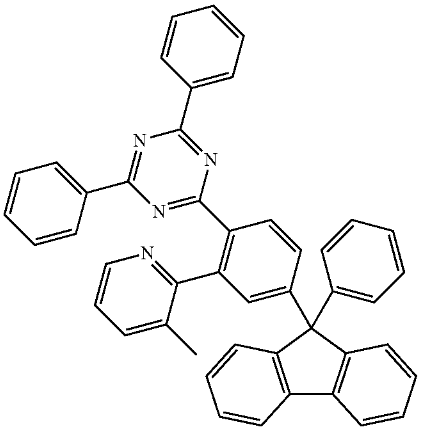
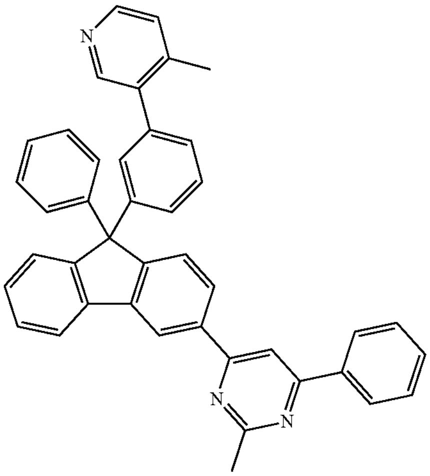
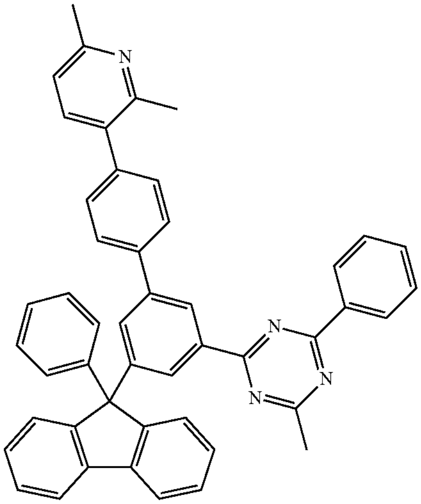
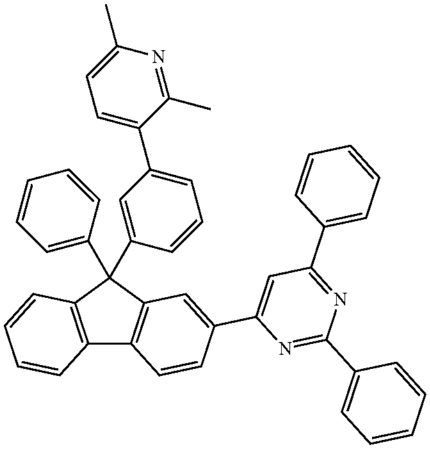
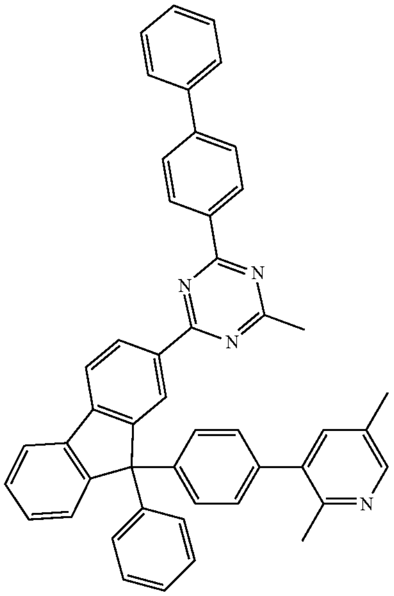

-continued
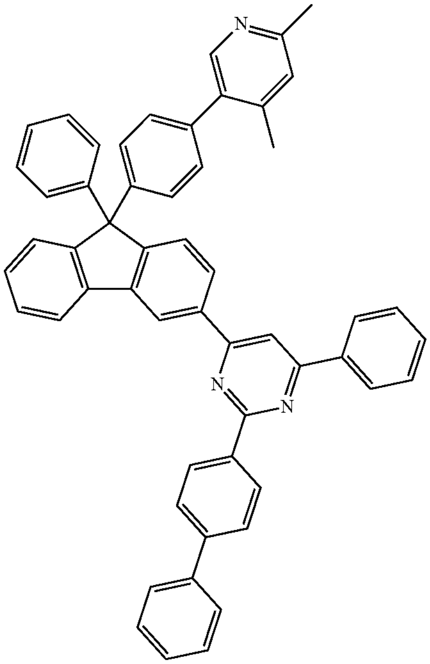
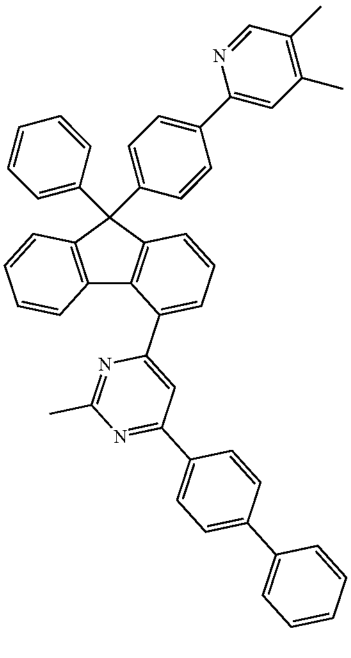
-continued
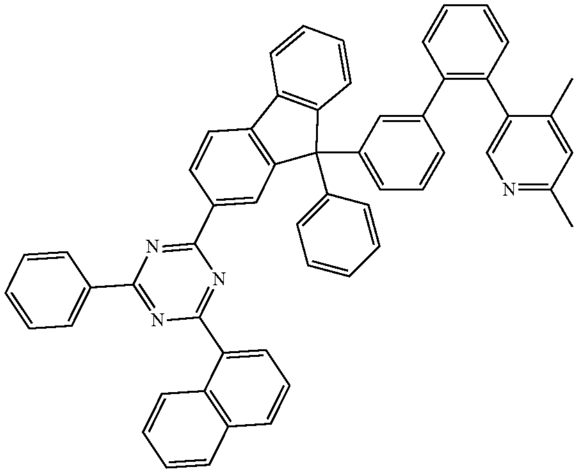
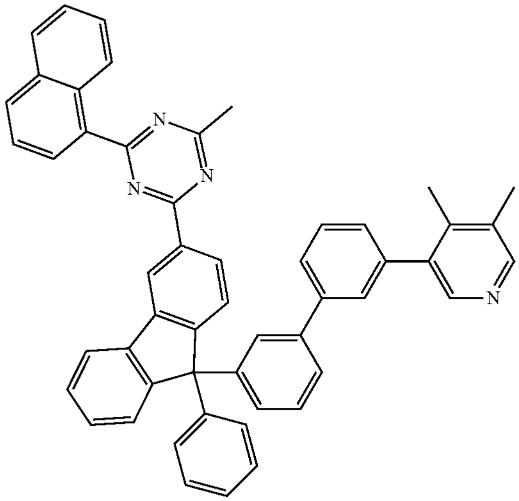
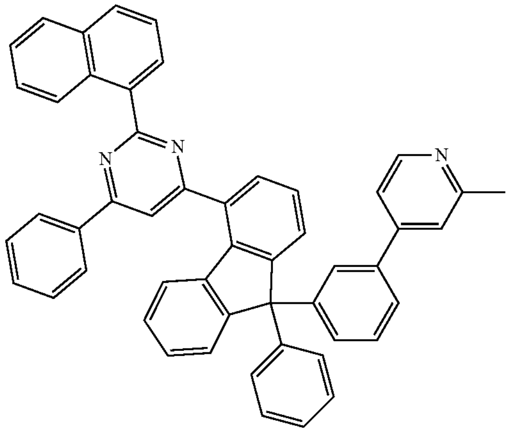
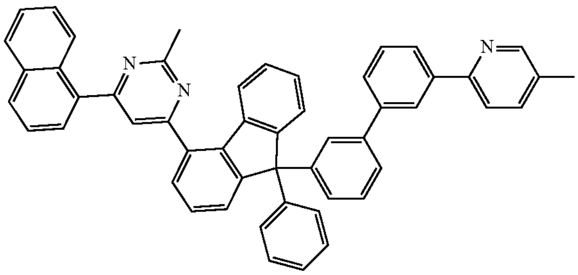

-continued
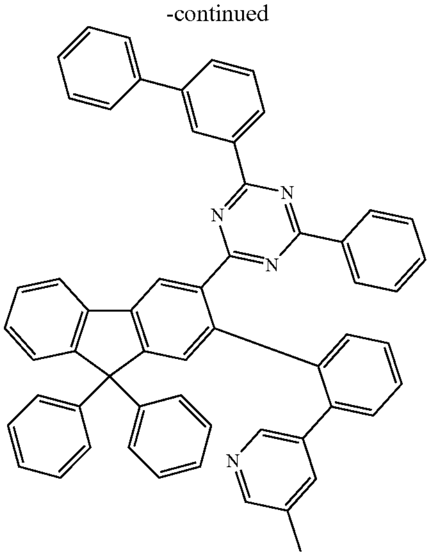
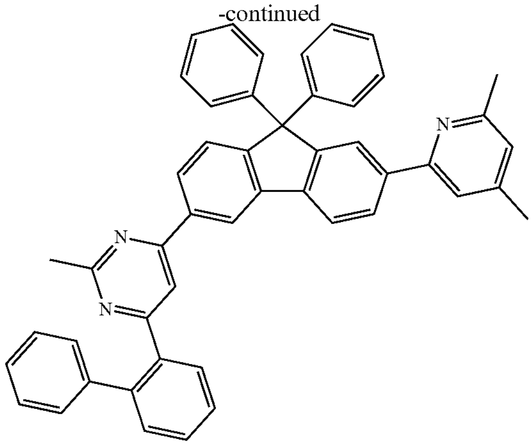
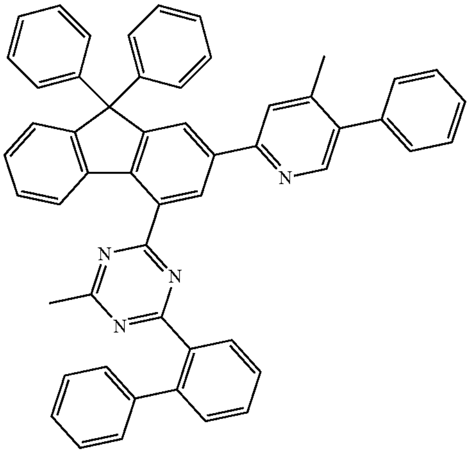
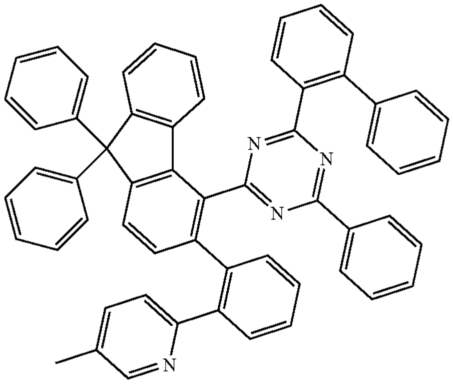
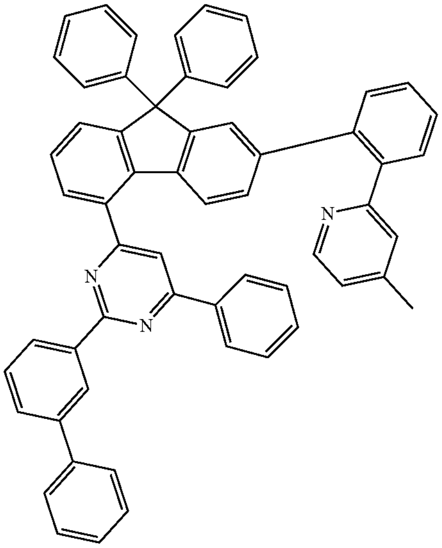
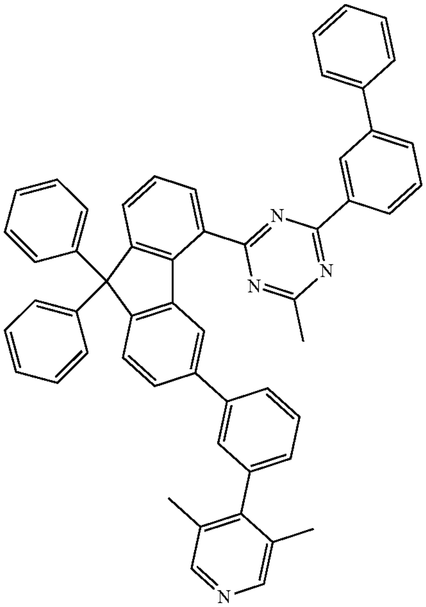

-continued
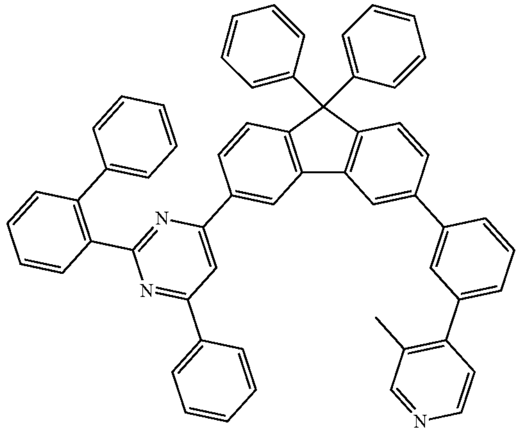
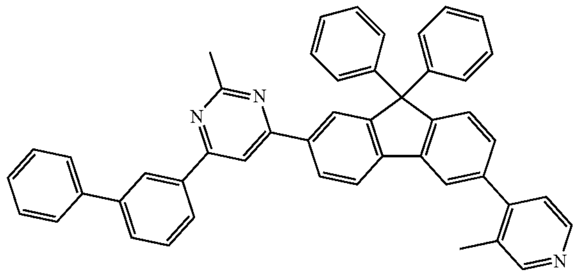
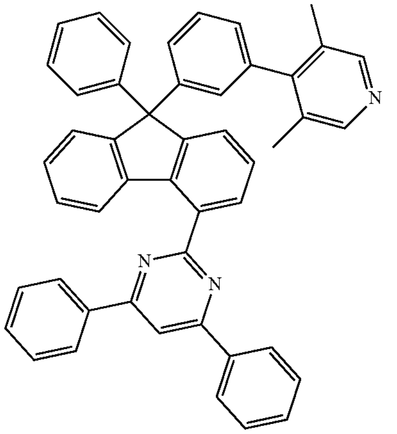
-continued
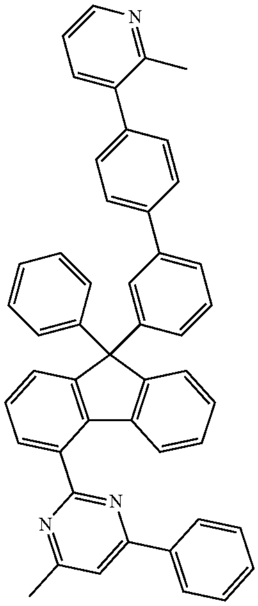
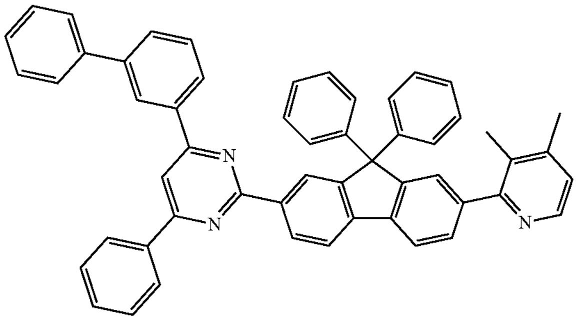
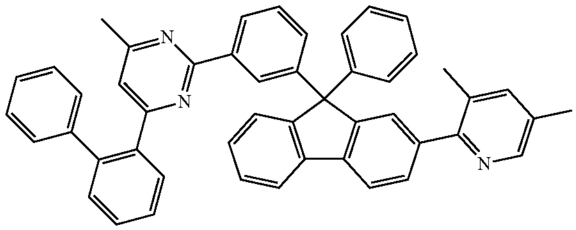

-continued
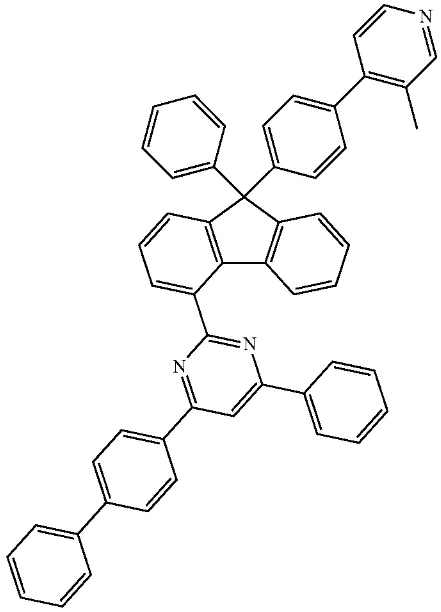
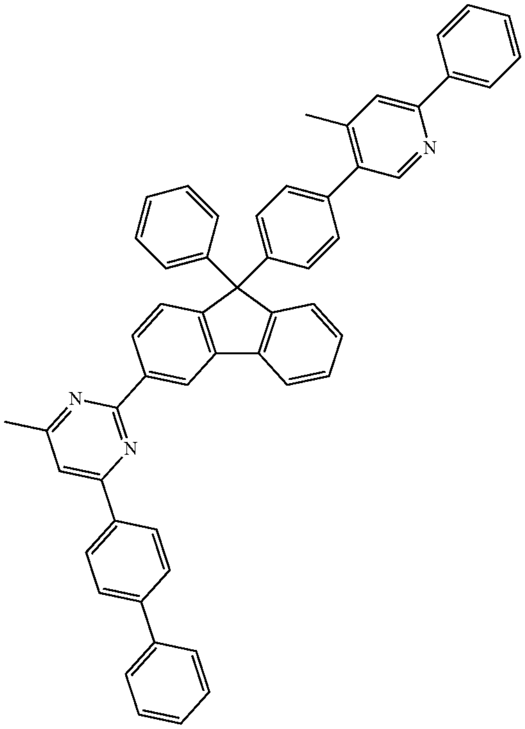
-continued
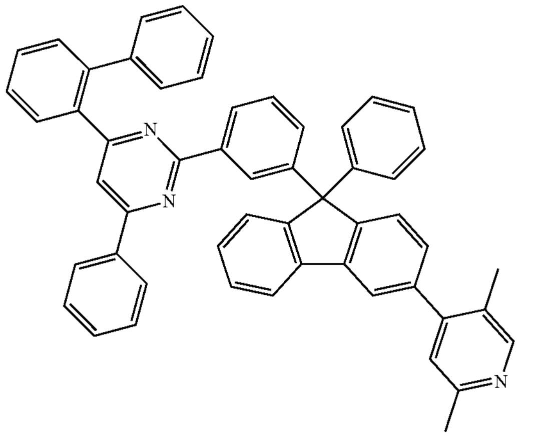
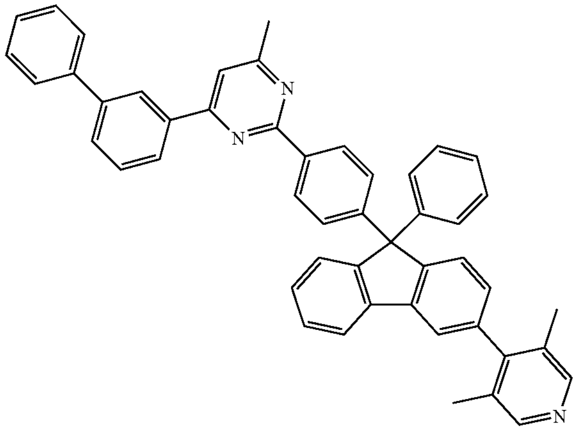
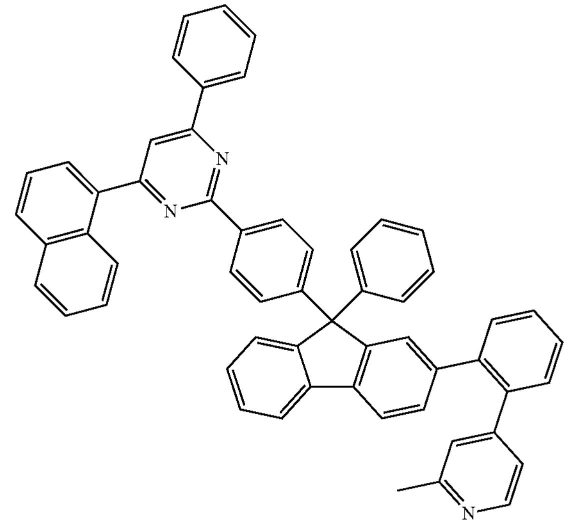
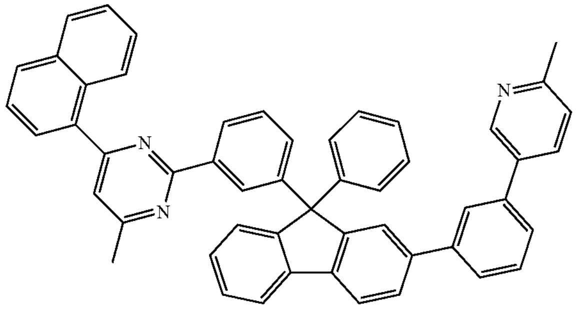

-continued
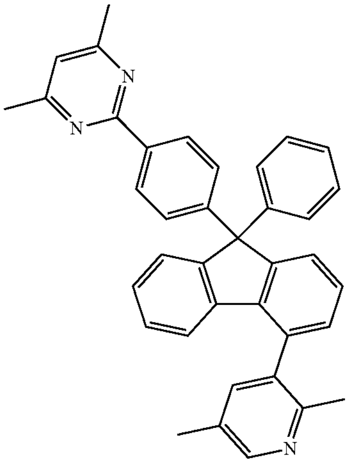
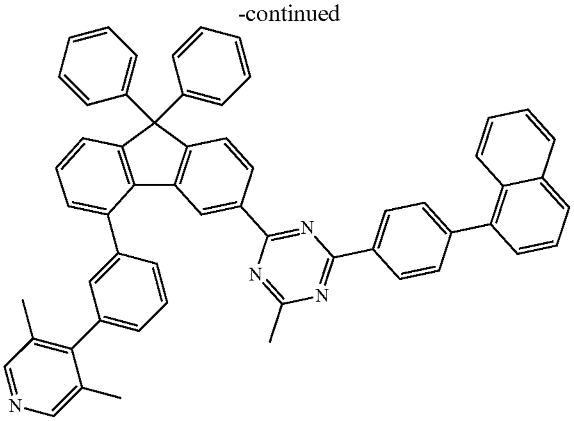
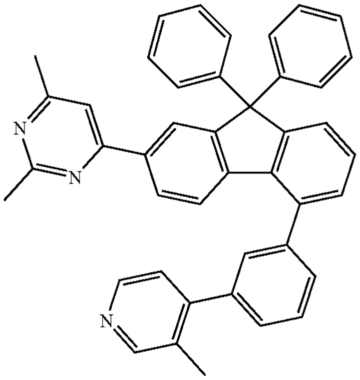
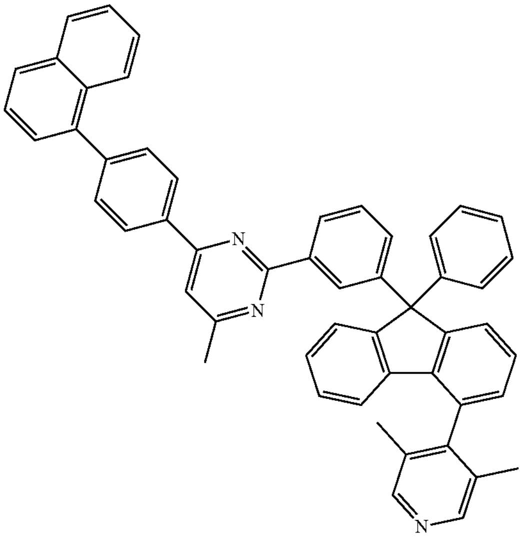
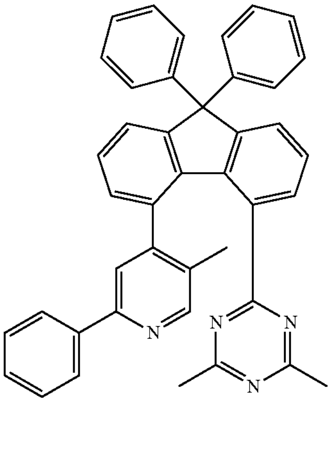
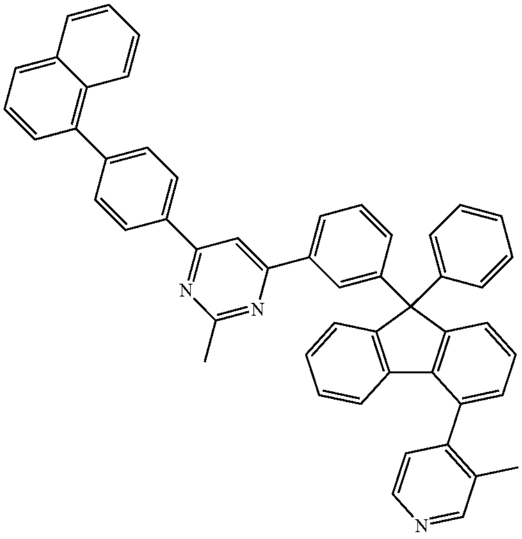

-continued
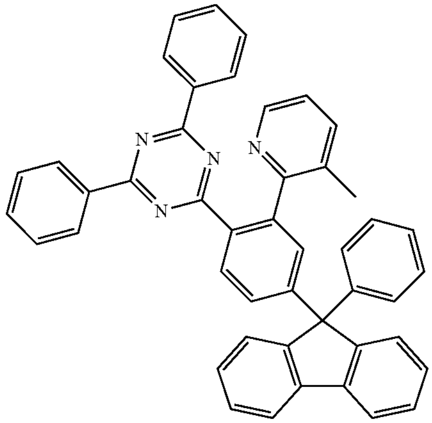
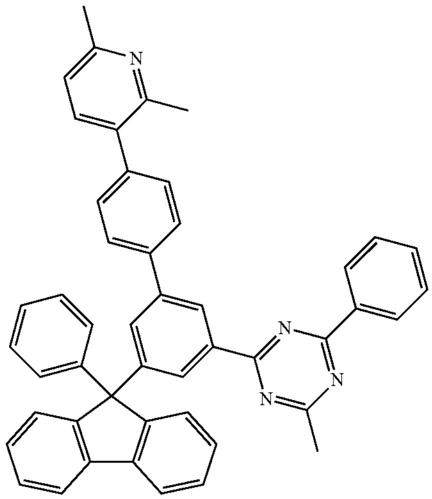
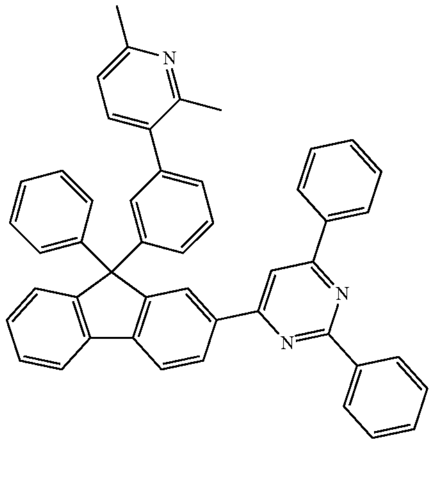
-continued
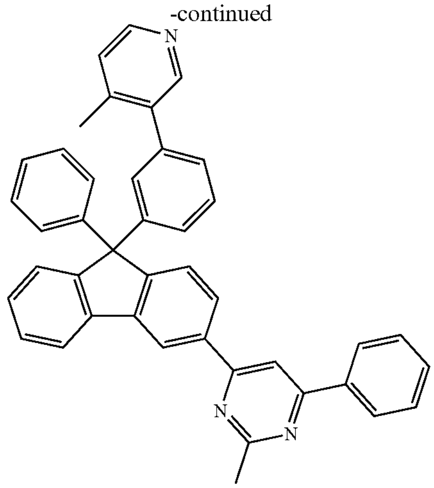
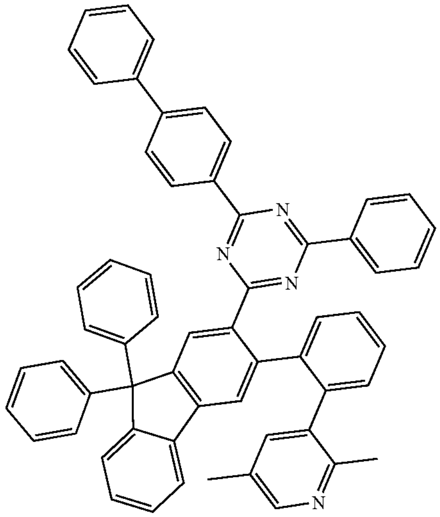
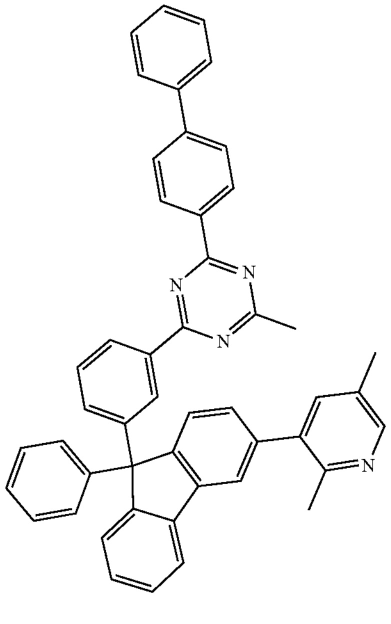

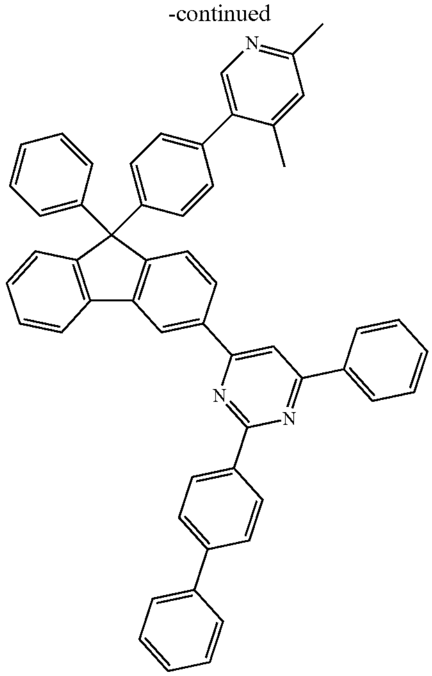
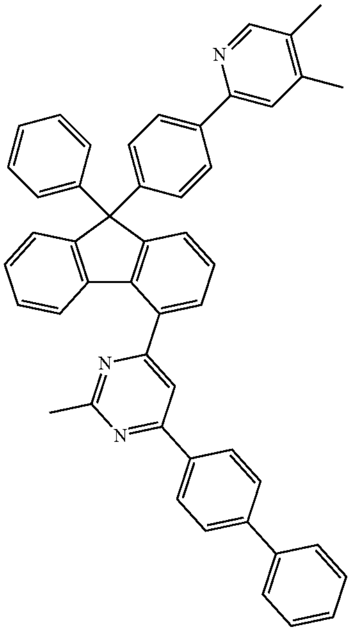
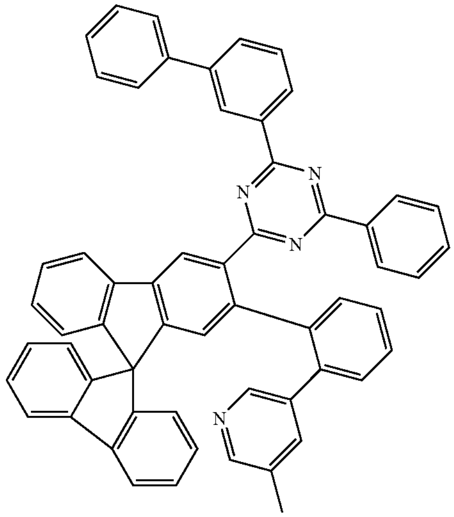
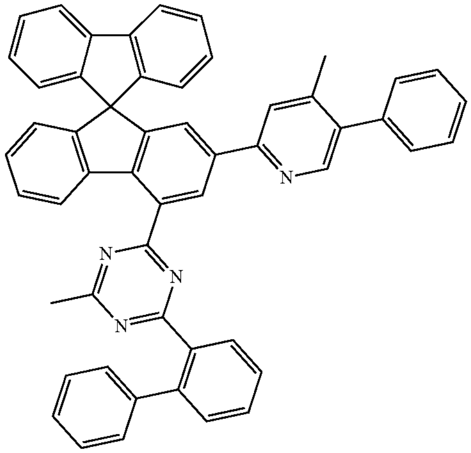
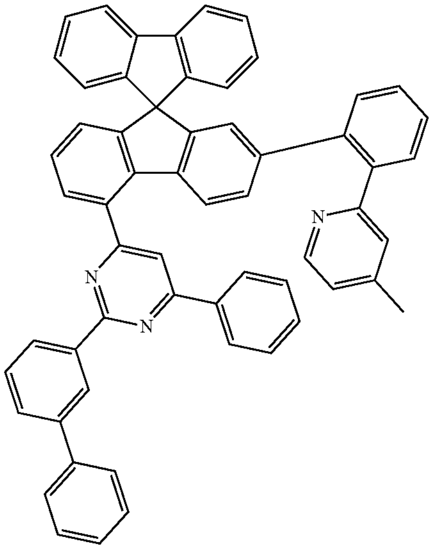

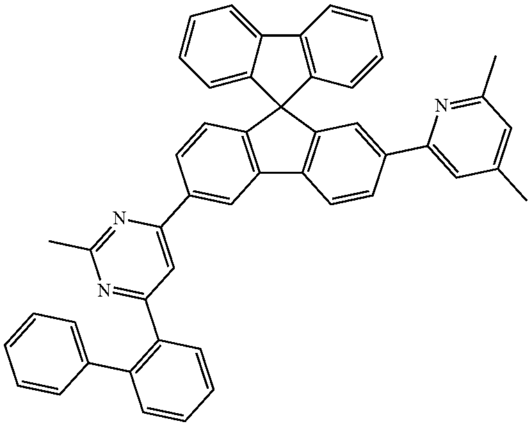
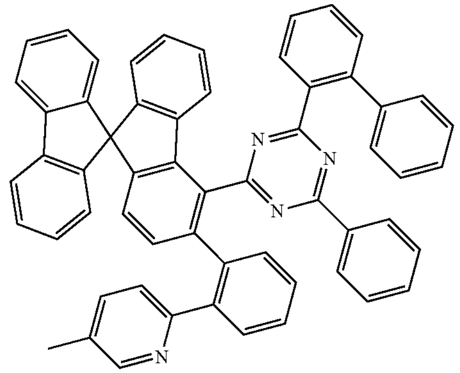
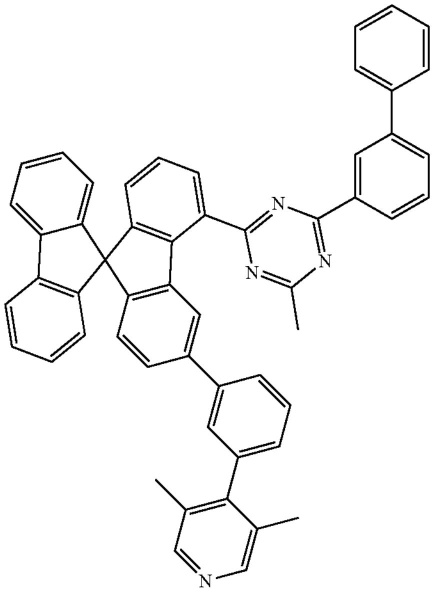
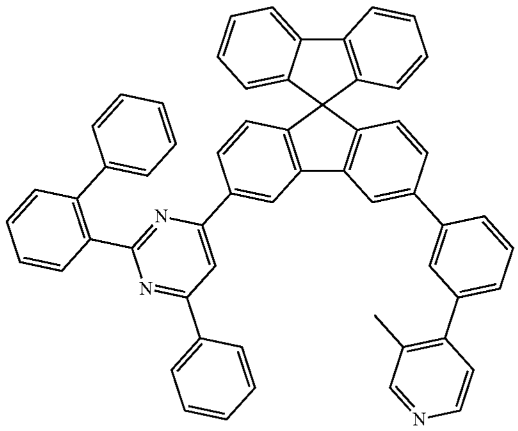
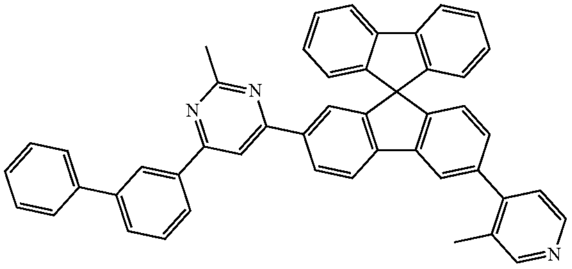
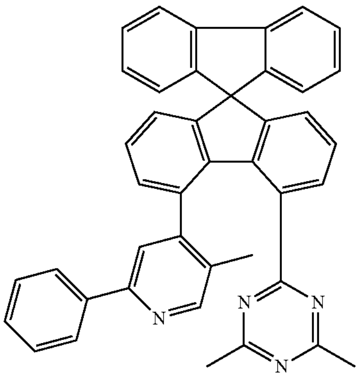
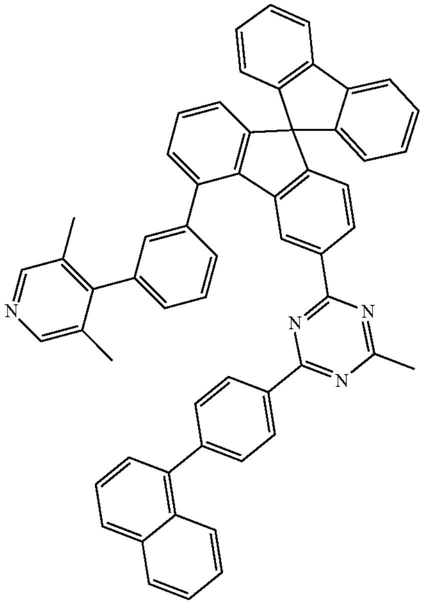

-continued
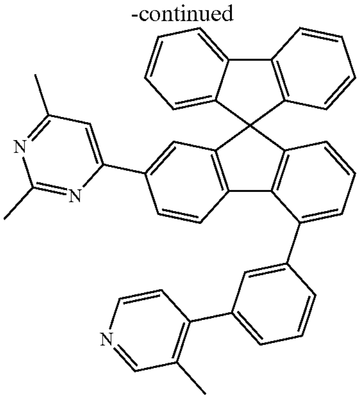
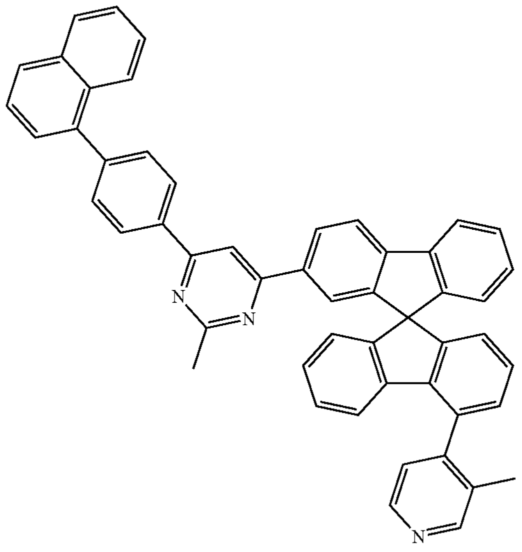
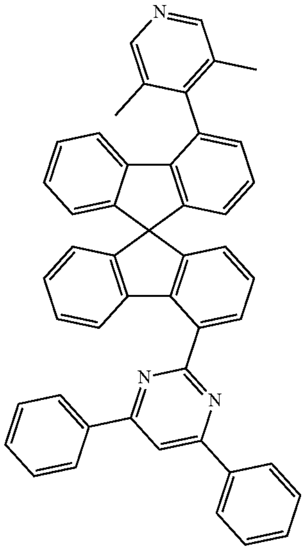
-continued
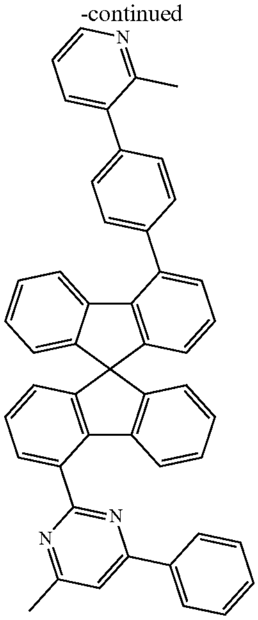
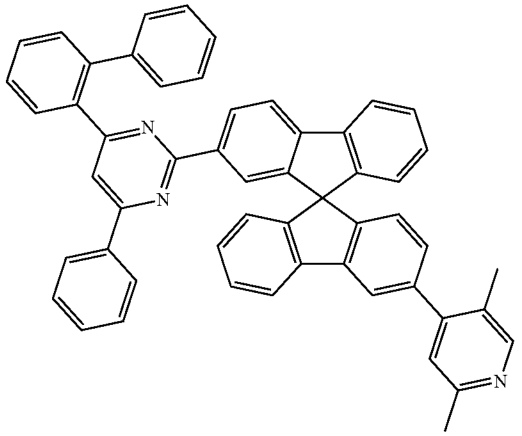
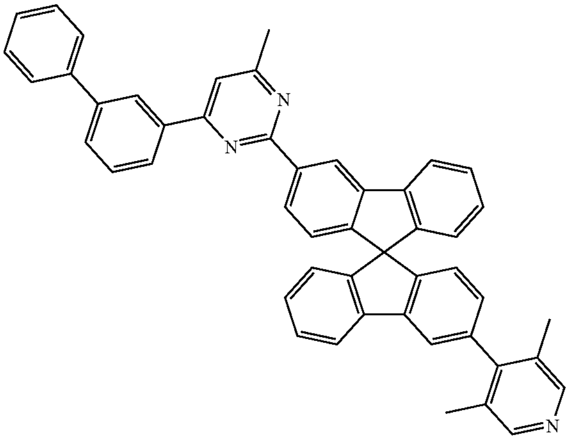

-continued
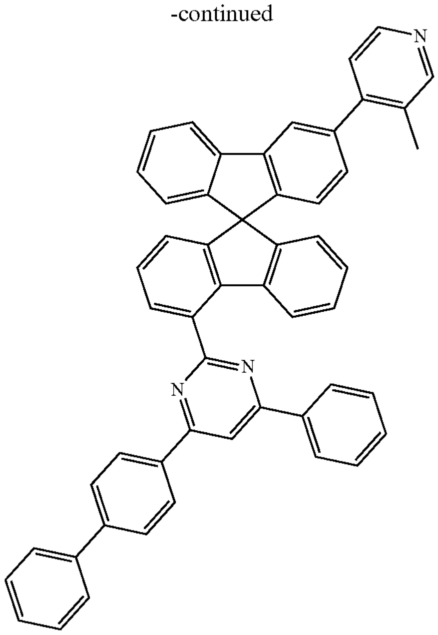
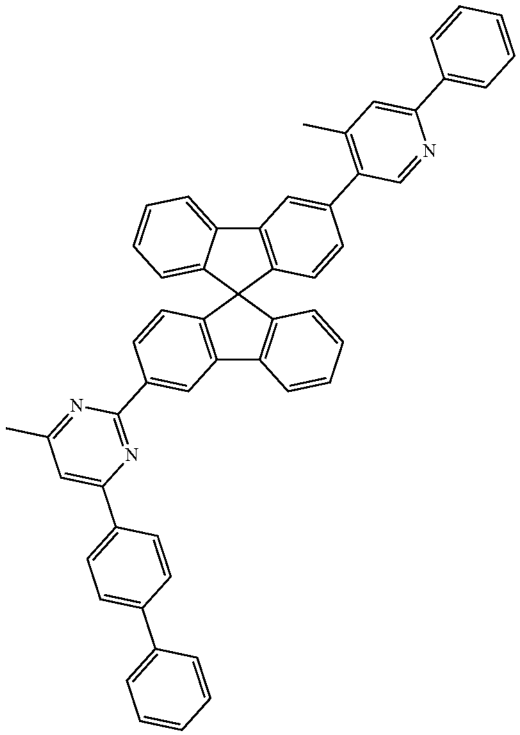
-continued
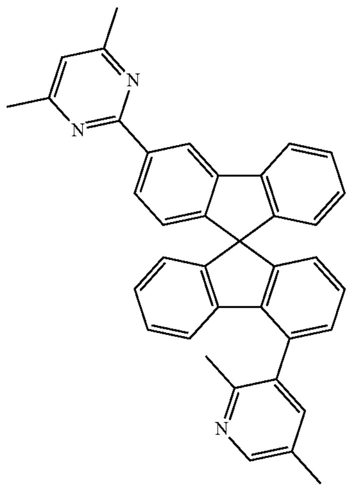
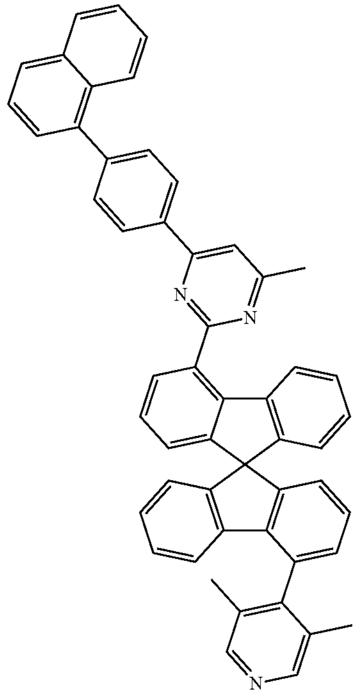
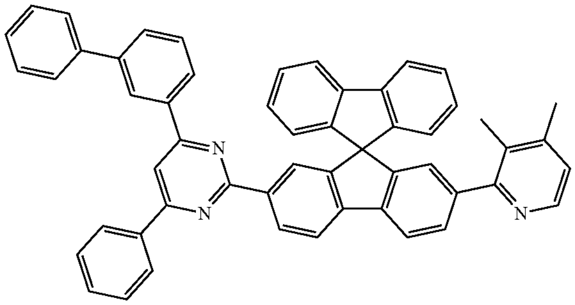
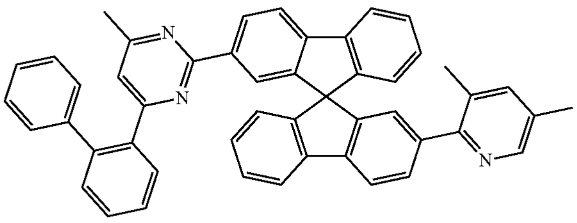

-continued
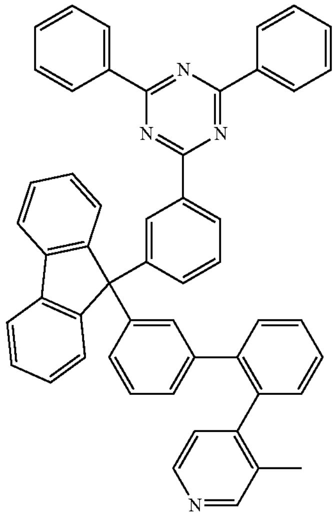
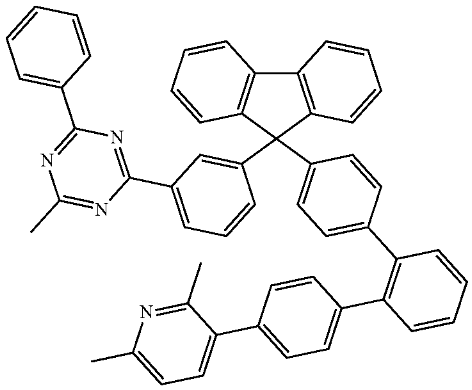
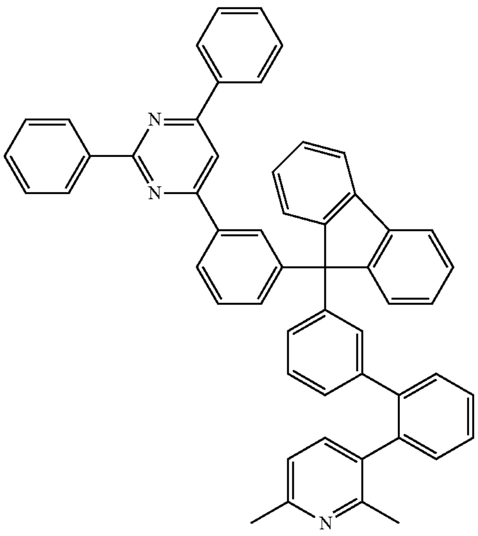
-continued
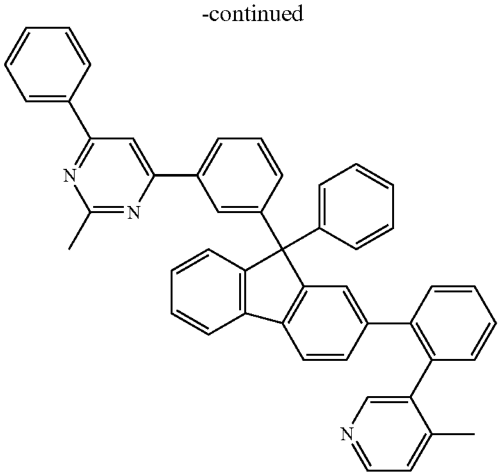
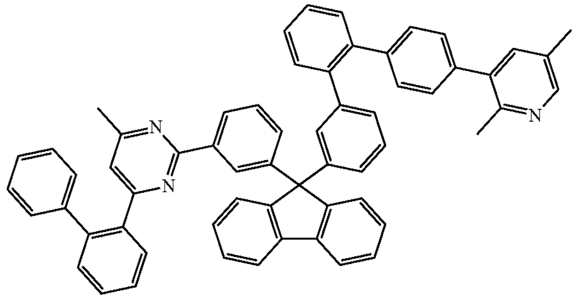
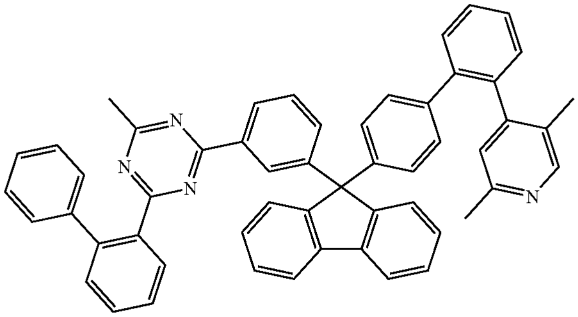
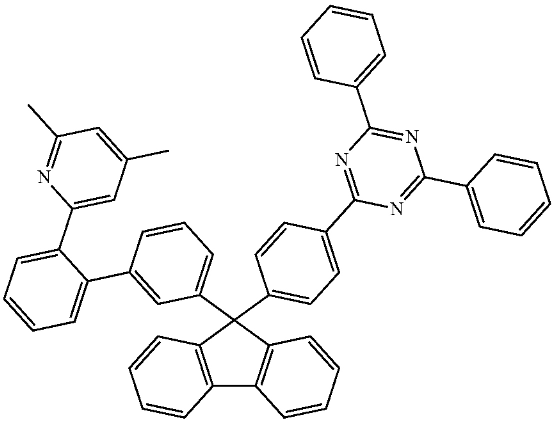

-continued
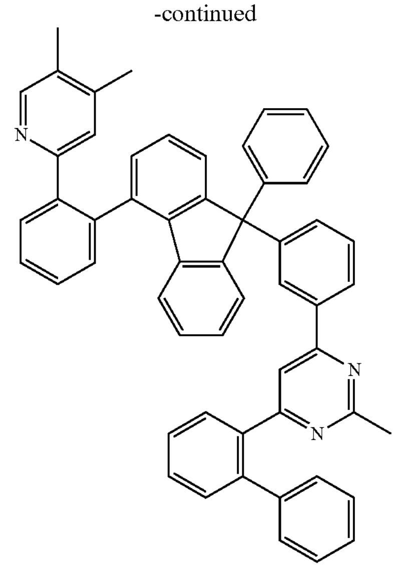
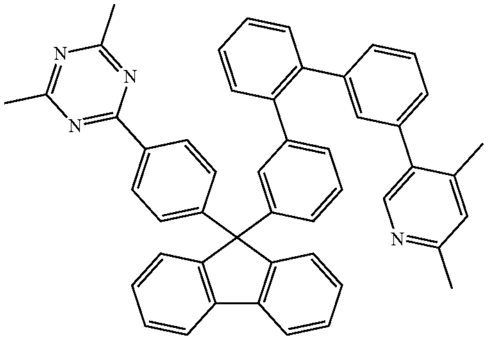
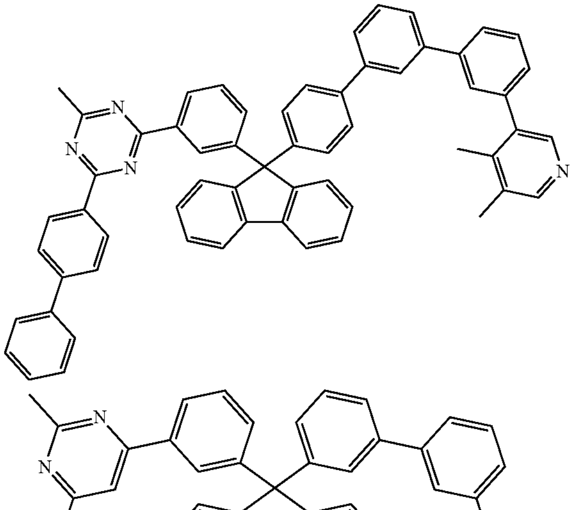
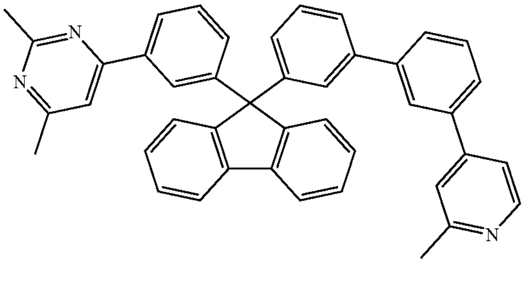
-continued
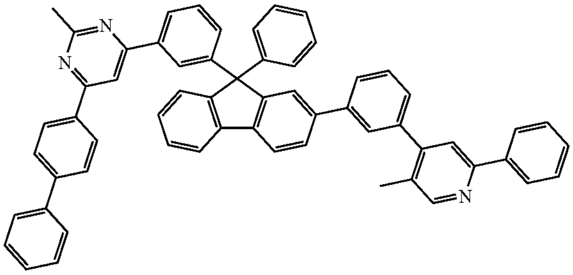
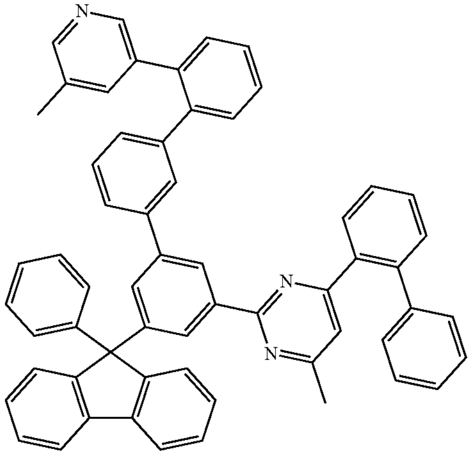
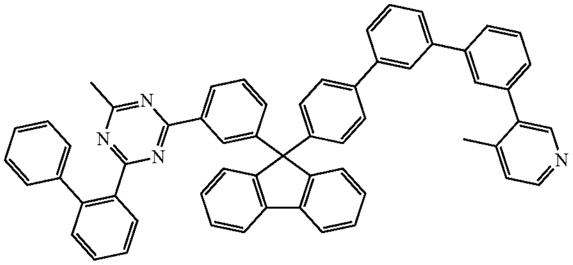
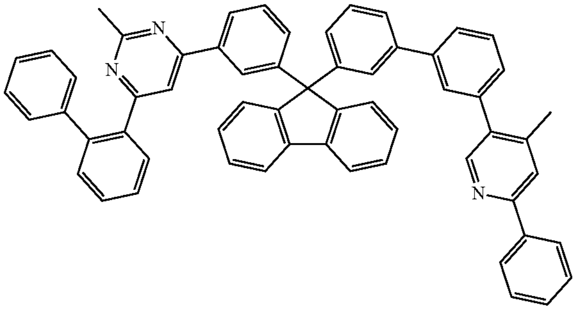
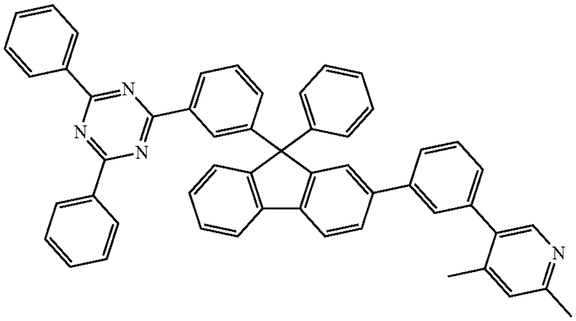

-continued
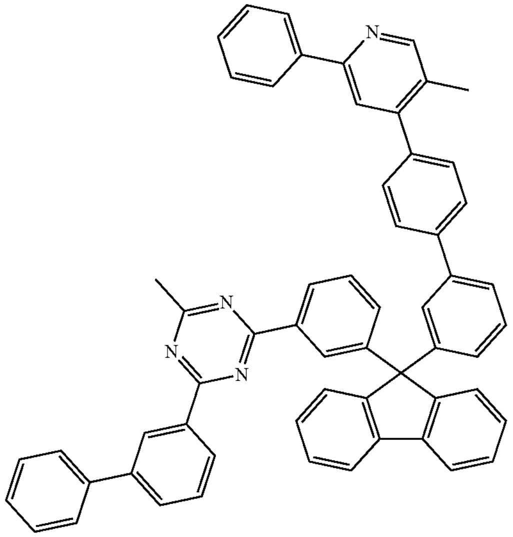
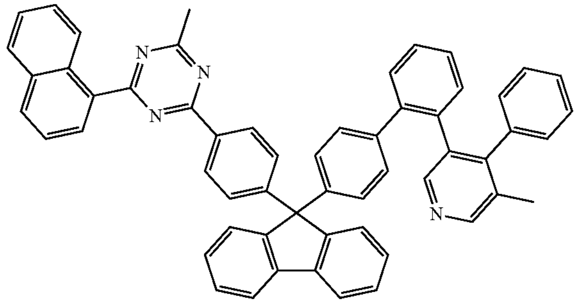
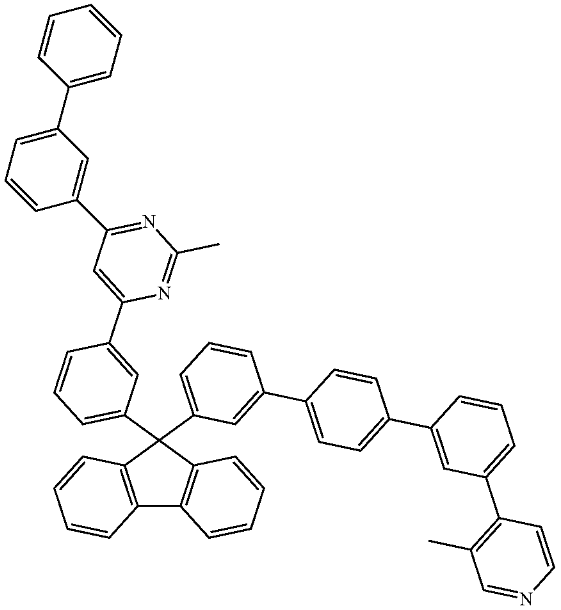
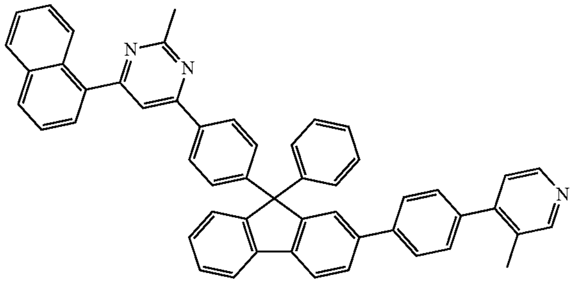
-continued
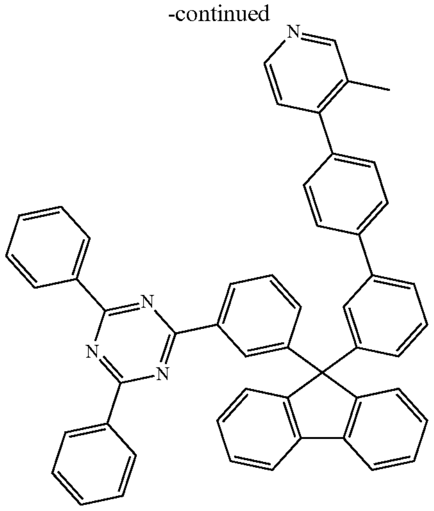
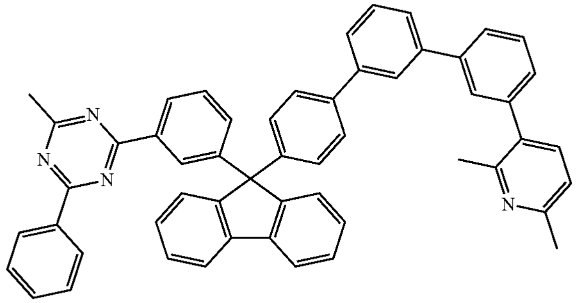
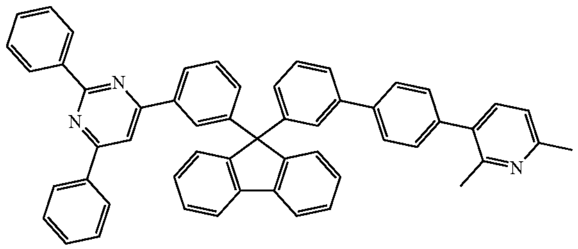
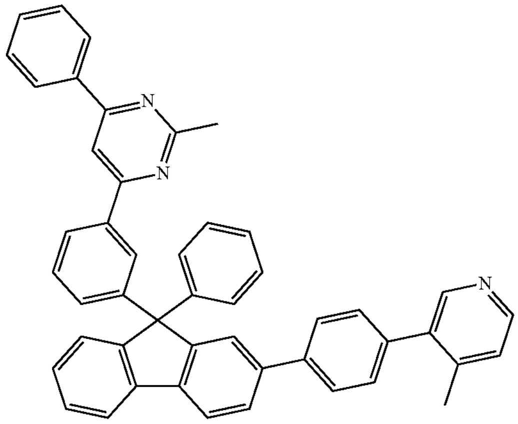

-continued
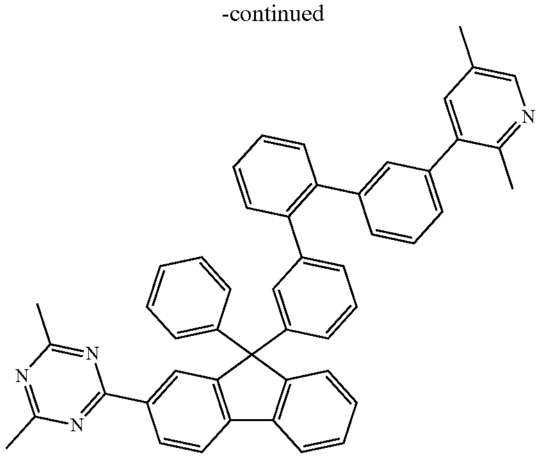
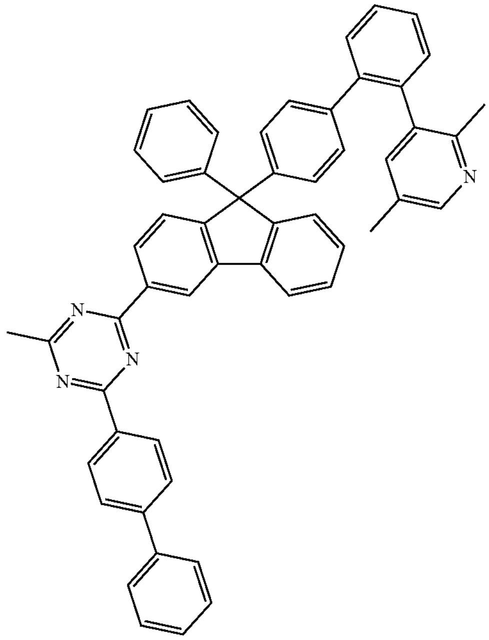
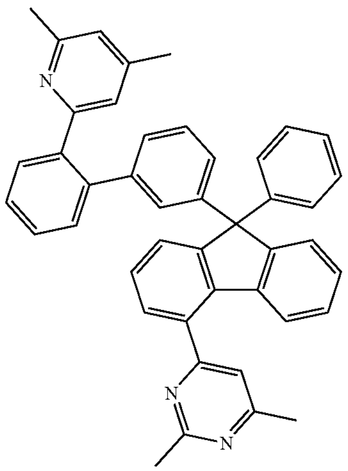
-continued
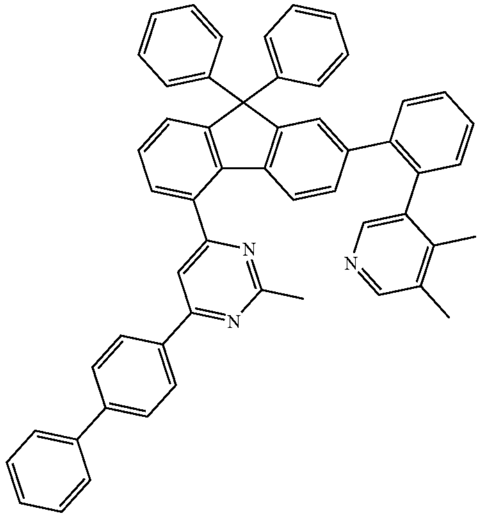
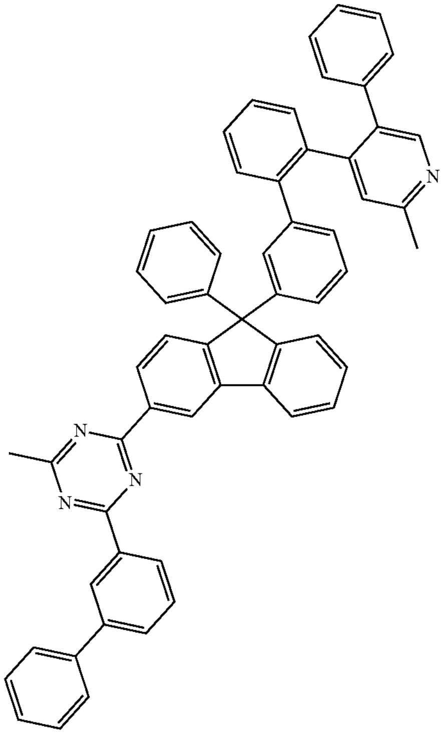
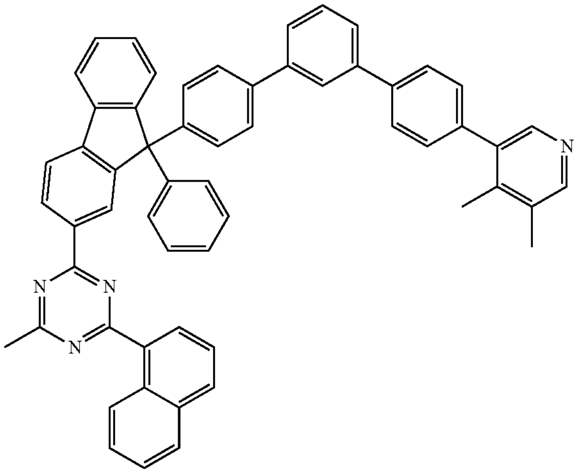

-continued
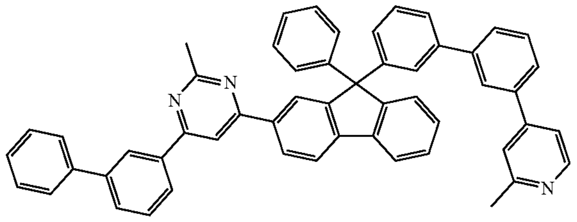
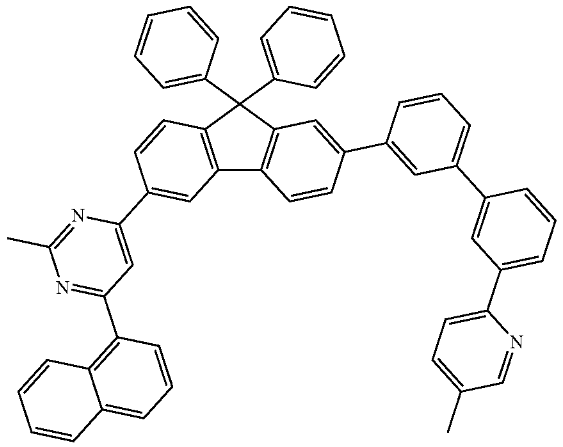
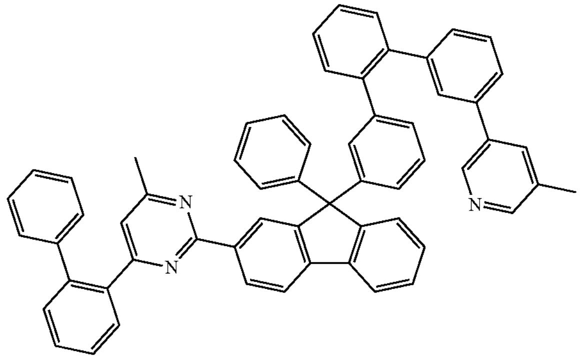
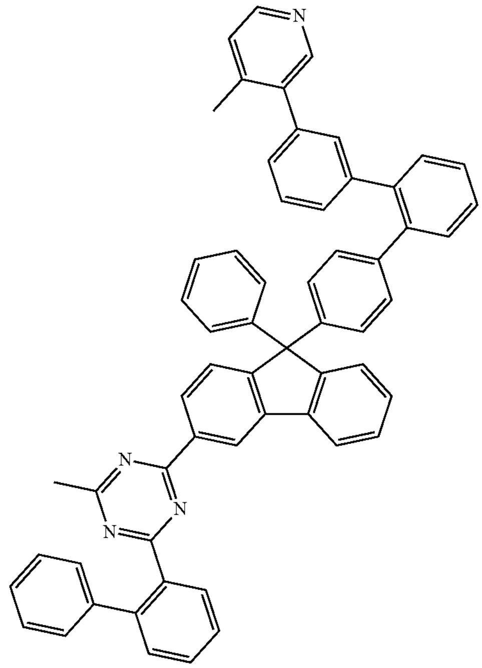
-continued
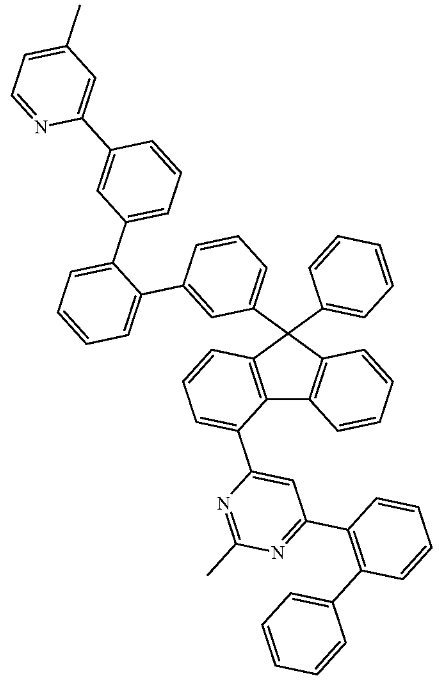
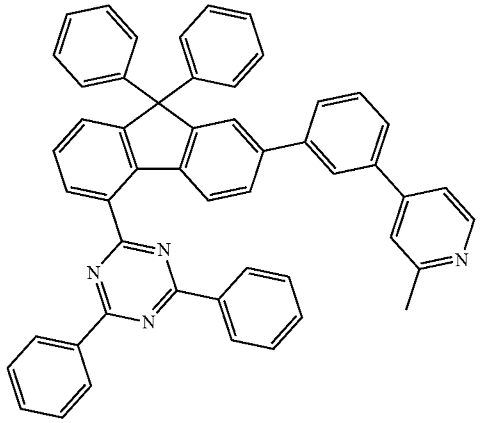
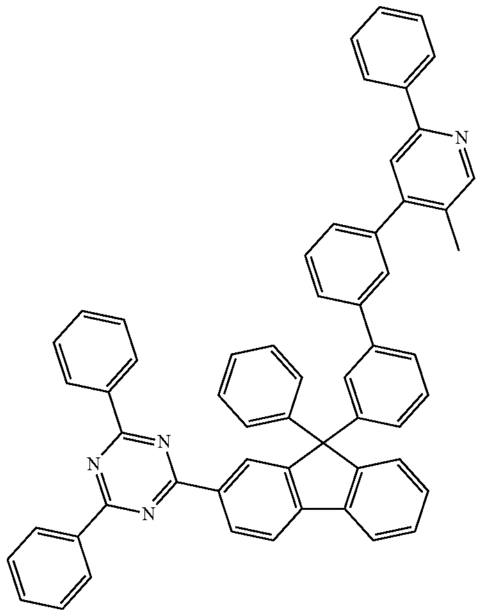

-continued
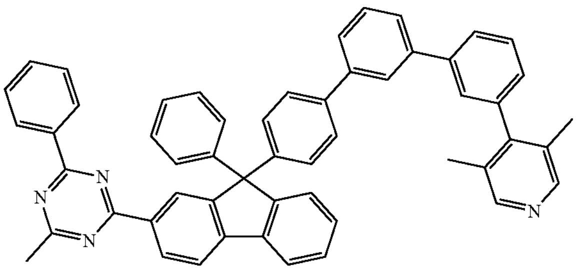
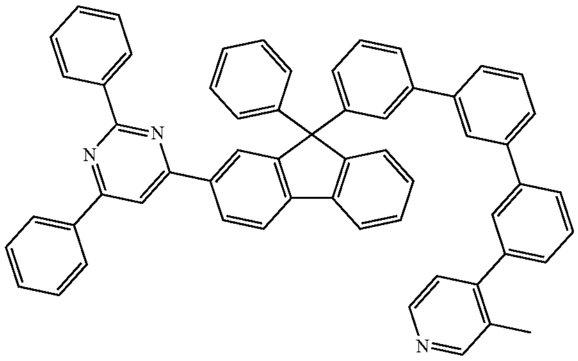
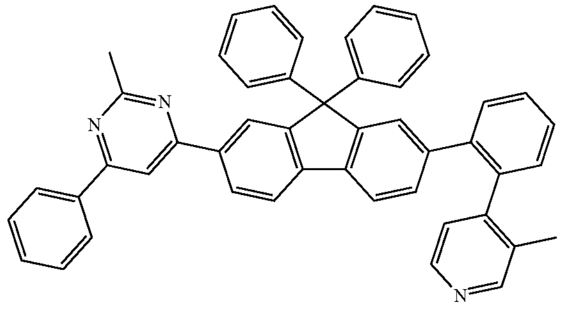
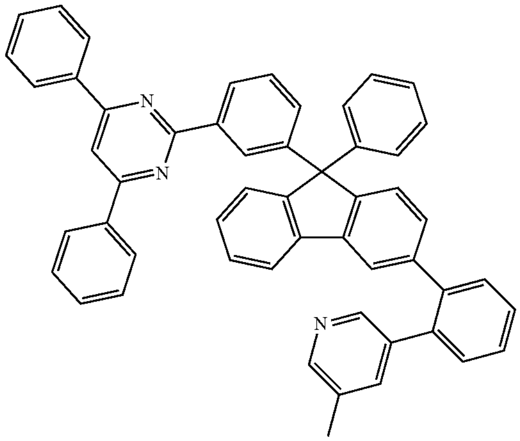
-continued
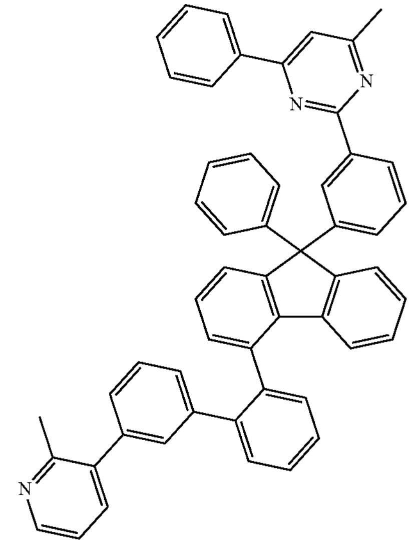
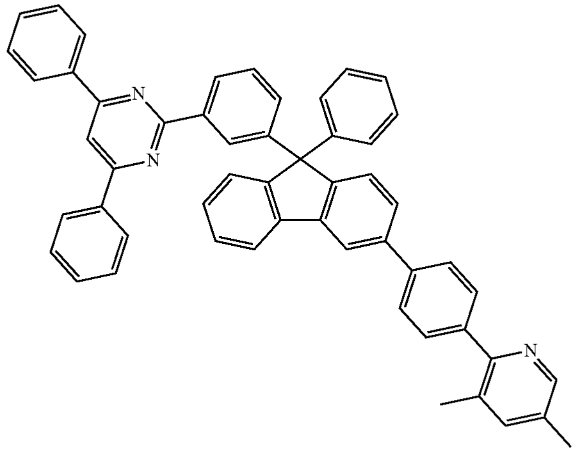
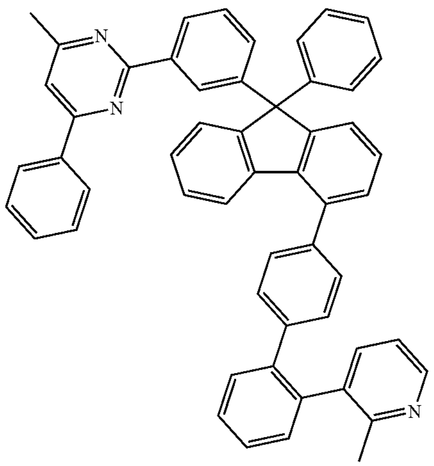

-continued
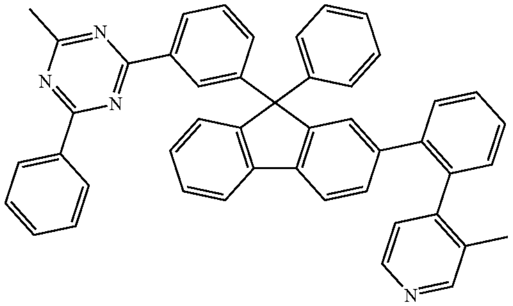
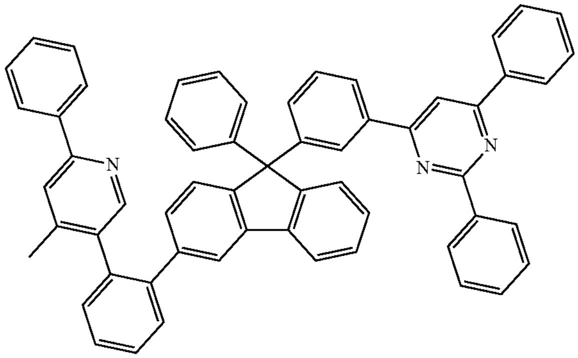
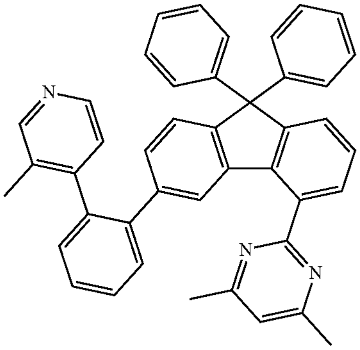
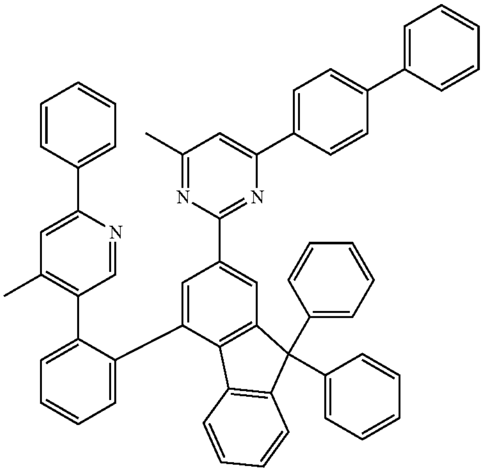
-continued
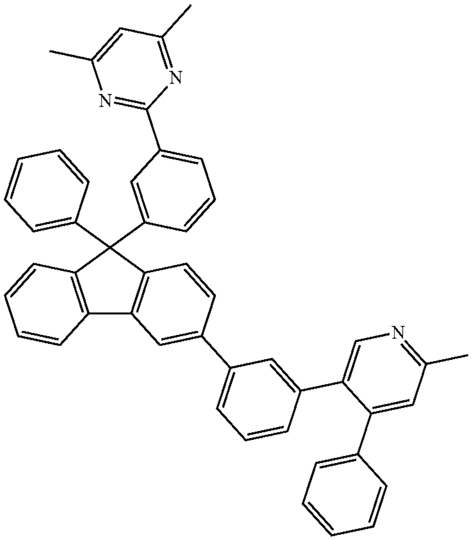
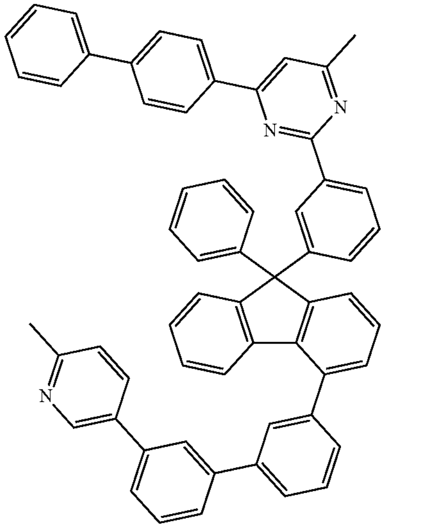
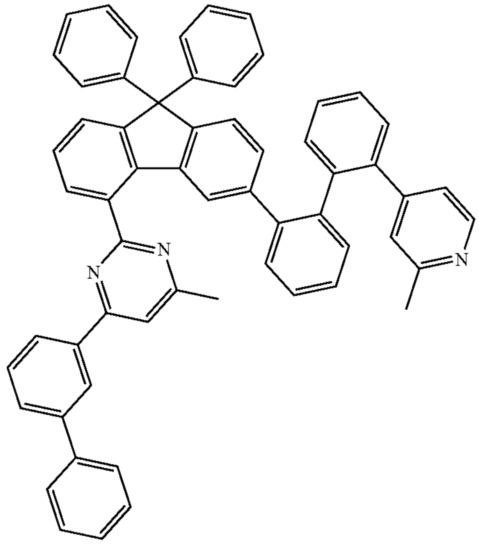

-continued
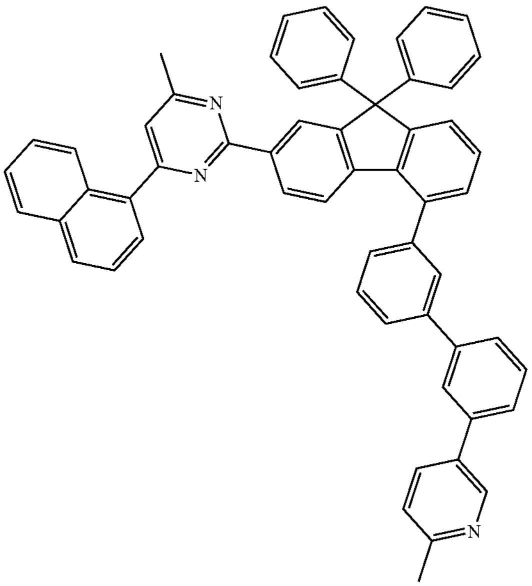
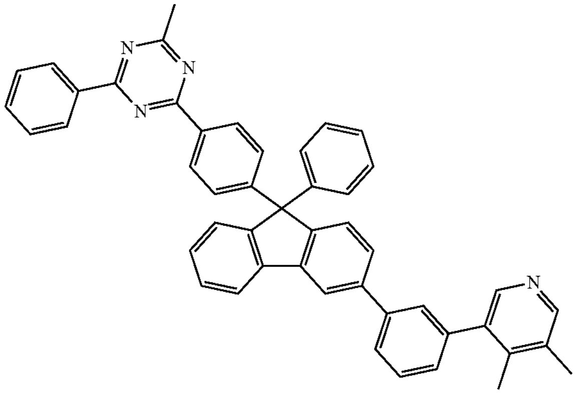
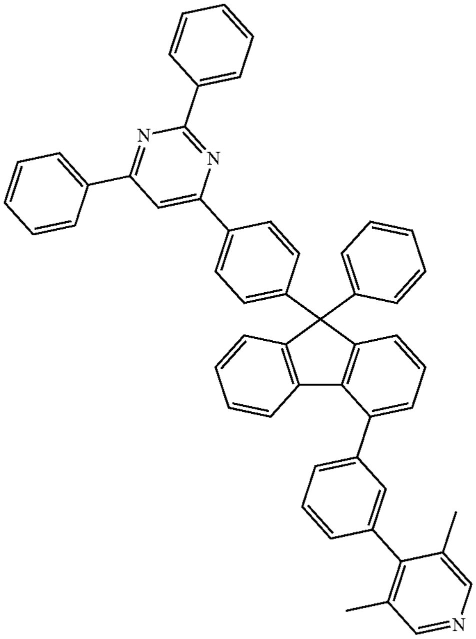
-continued
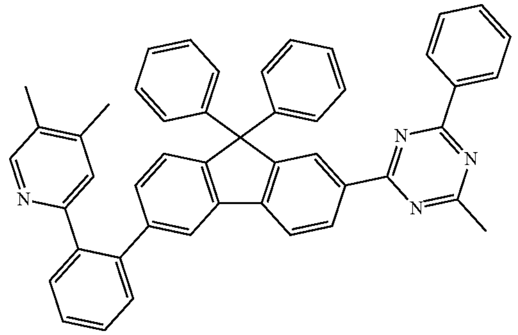
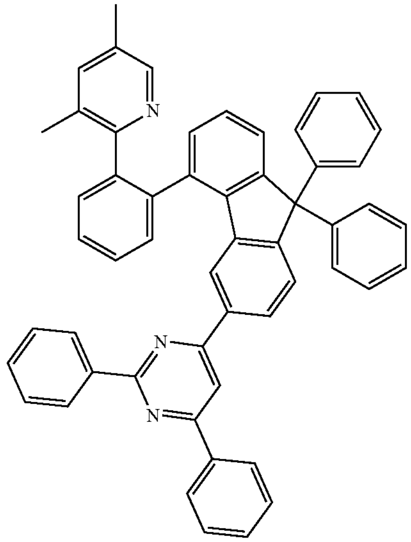
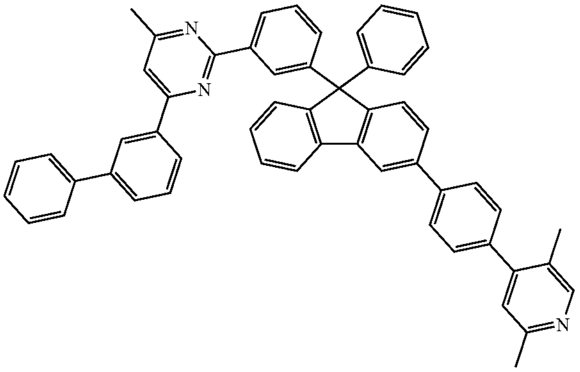

-continued
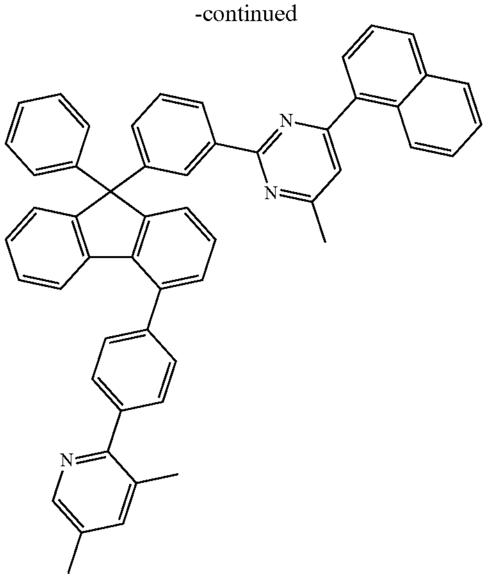
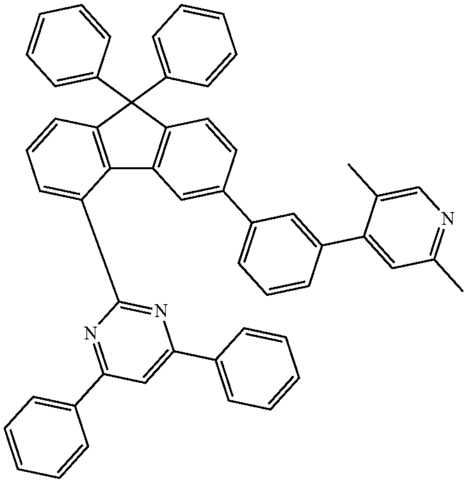
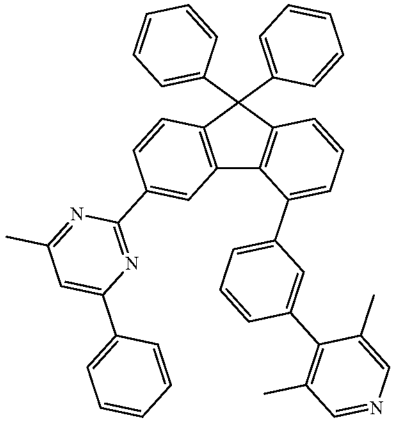
-continued
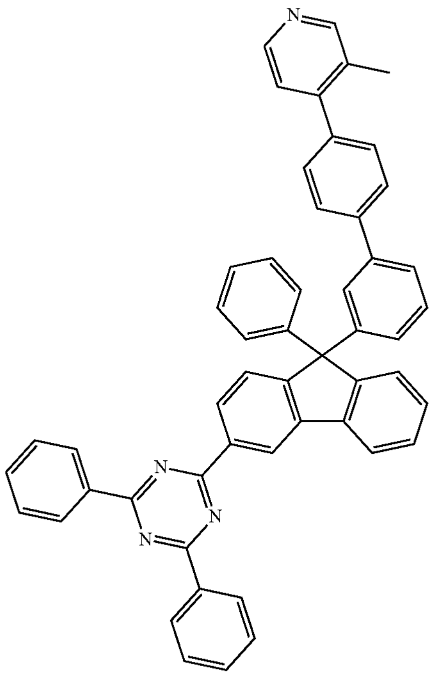
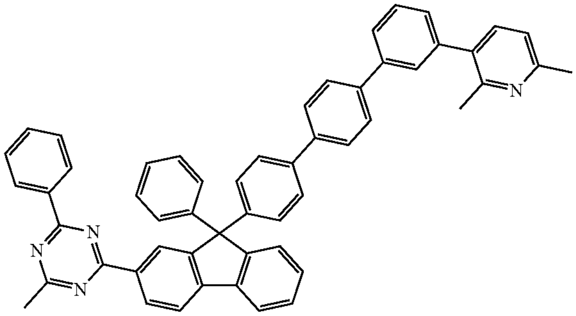
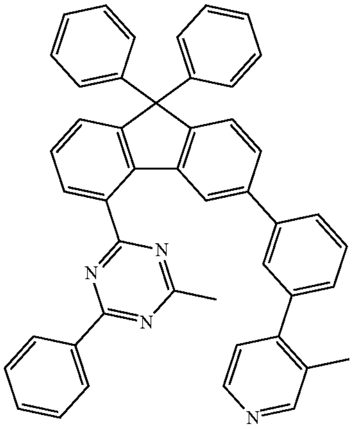

-continued
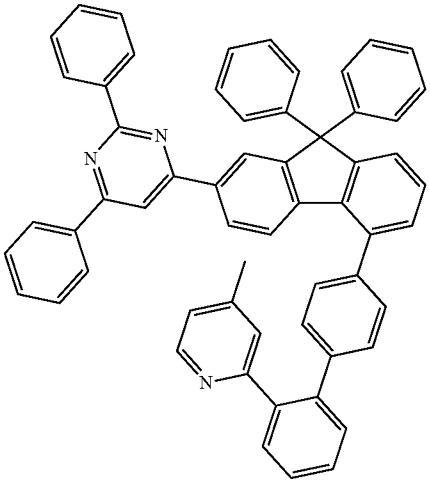
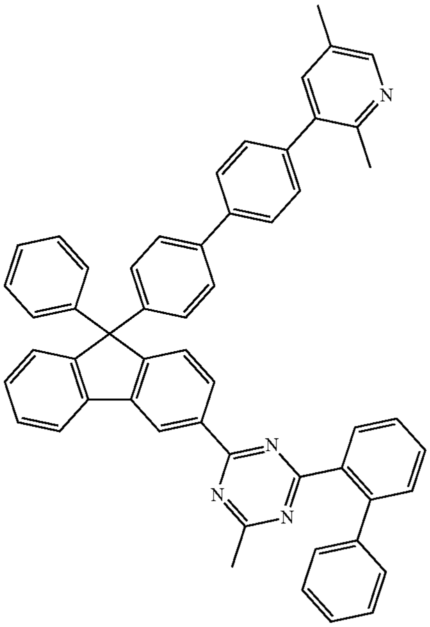
-continued
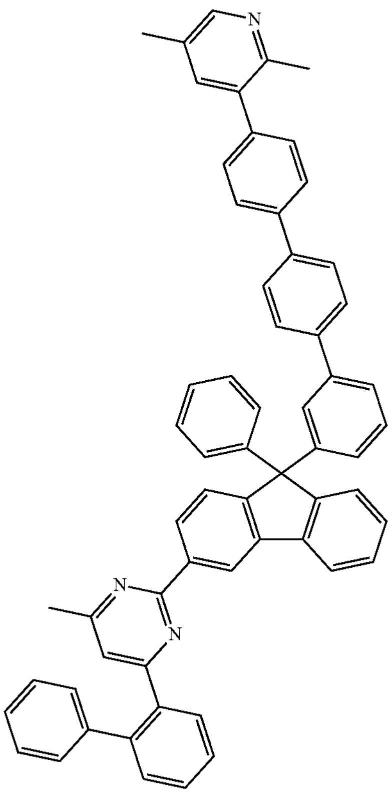
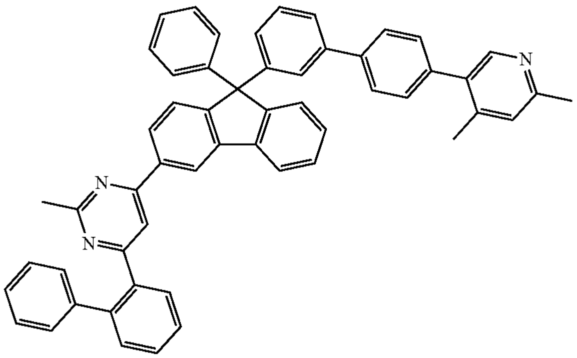
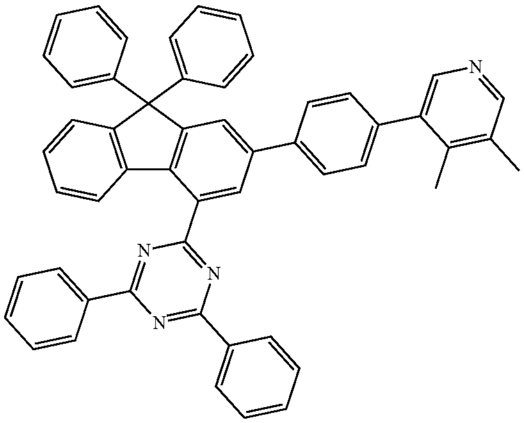

-continued
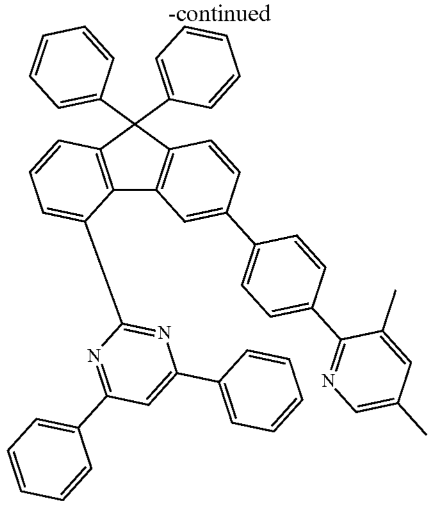
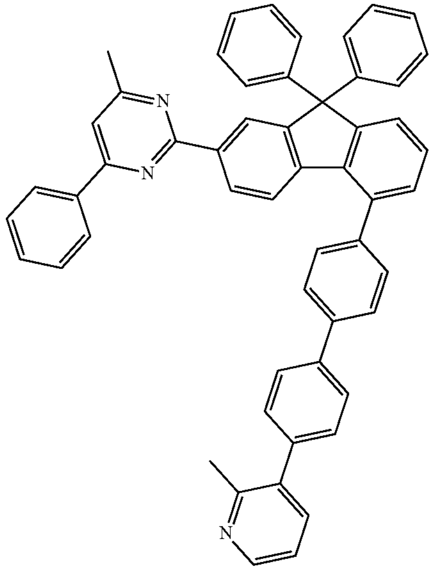
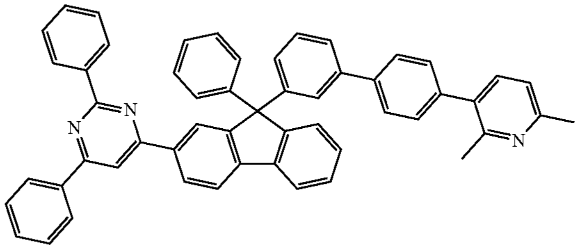
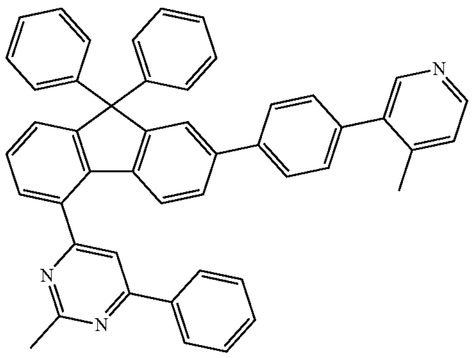
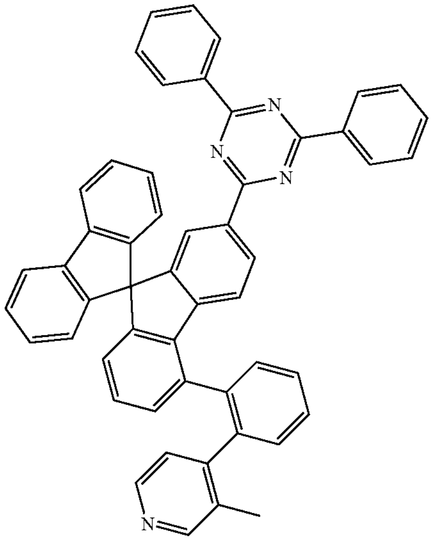
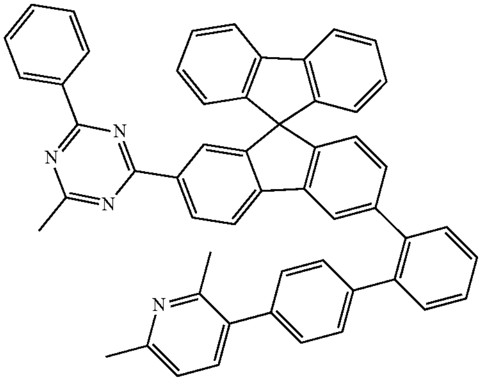
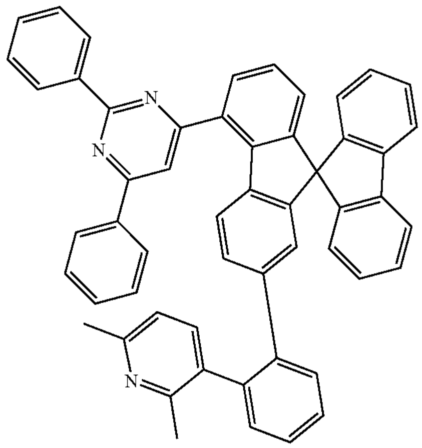

-continued
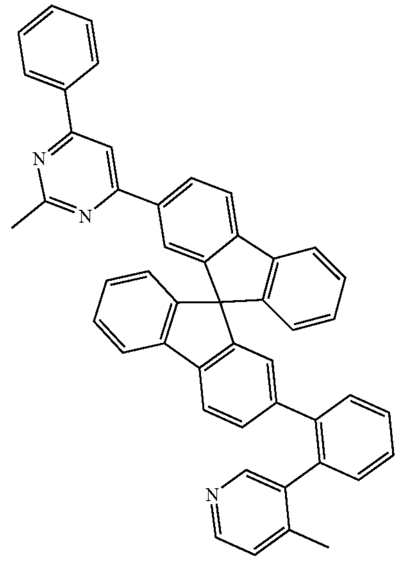
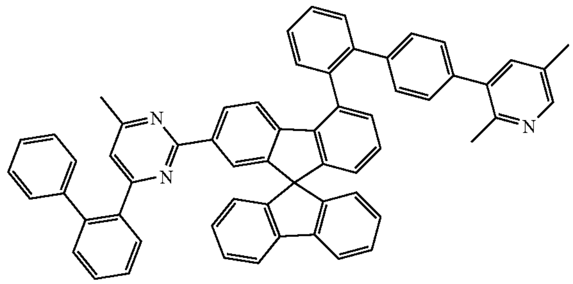
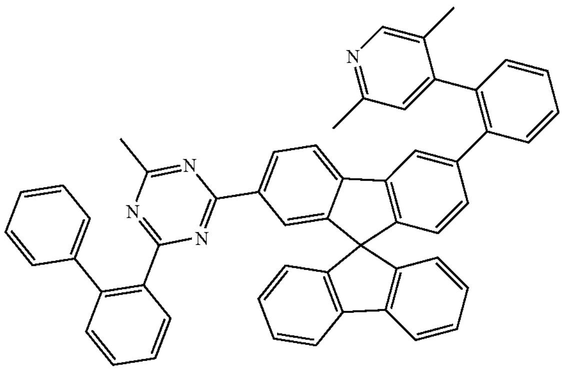
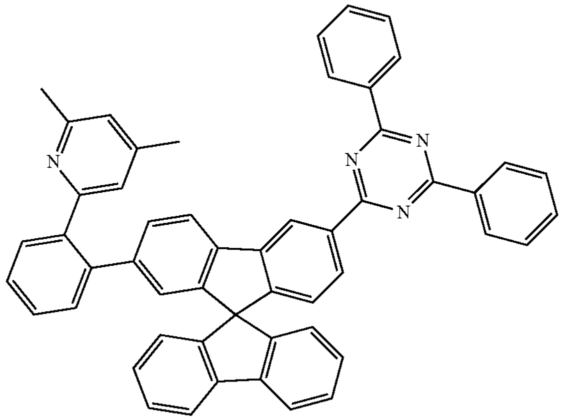
-continued
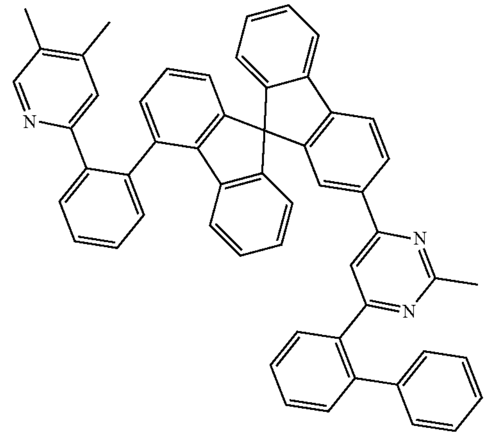 [SMILES: Cc1nc(-c2ccc3c(c2)C2(c4ccccc4-3)c3ccccc3-c3c(-c4ccccc4-c4cc(C)c(C)cn4)cccc32)cc(-c2ccccc2-c2ccccc2)n1]
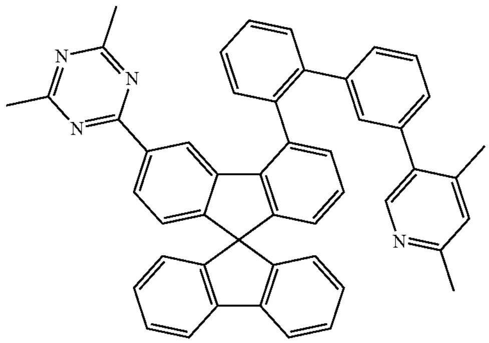
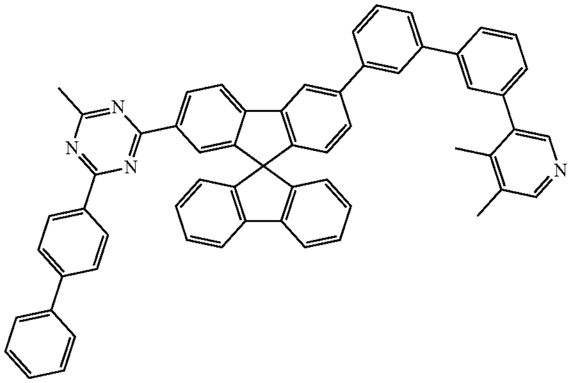
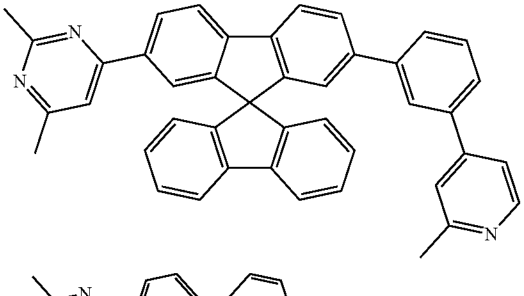
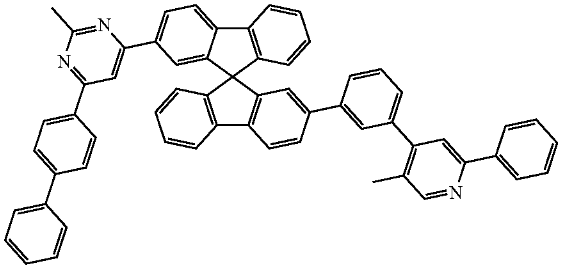

-continued
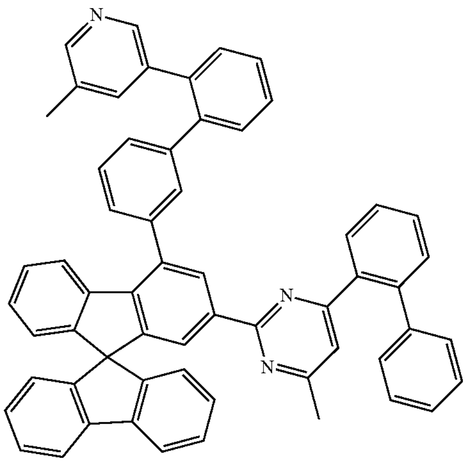
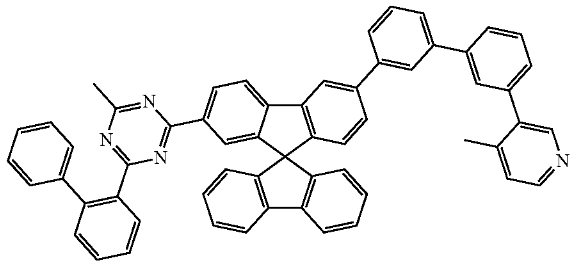
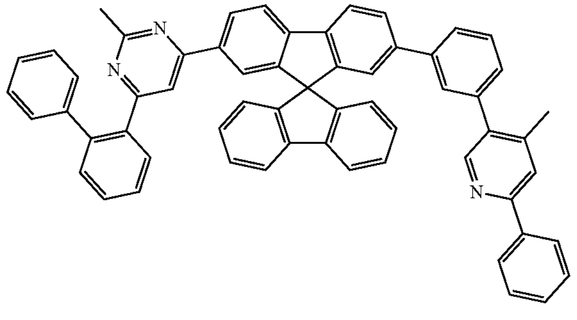
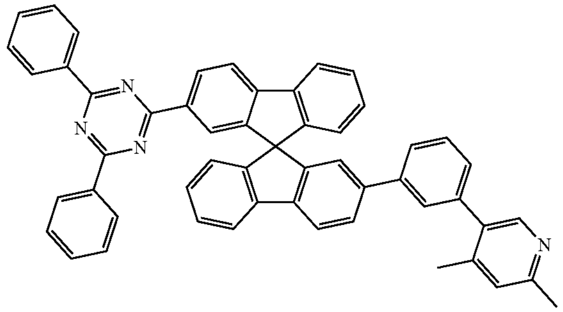
-continued
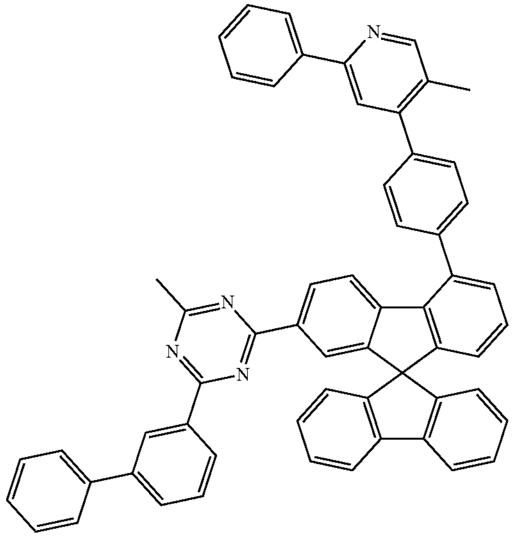
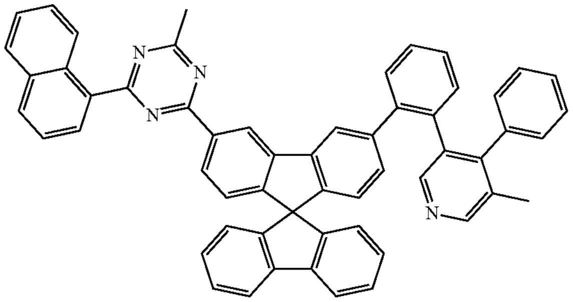
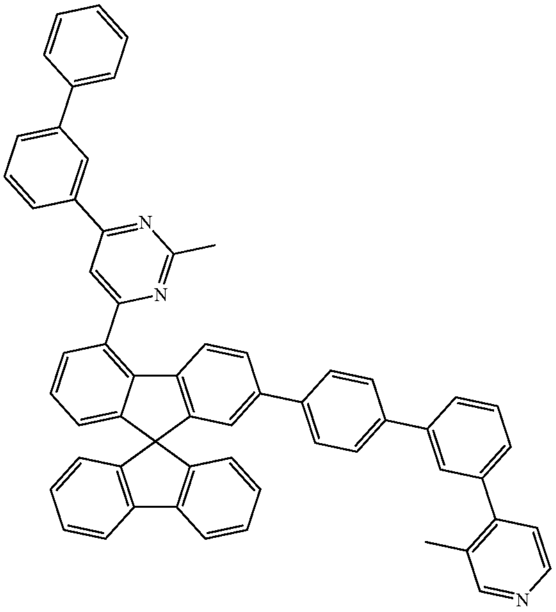
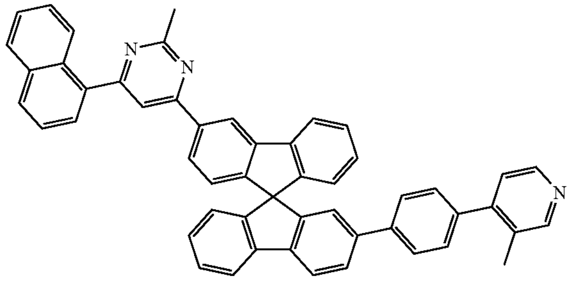

-continued
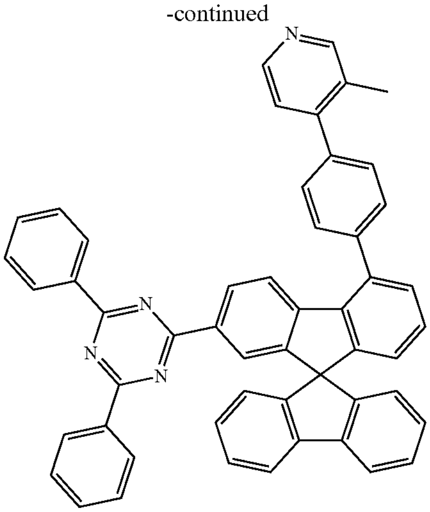
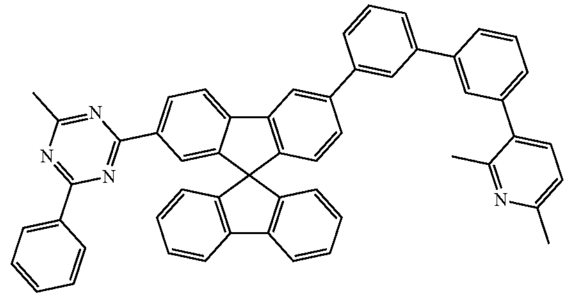
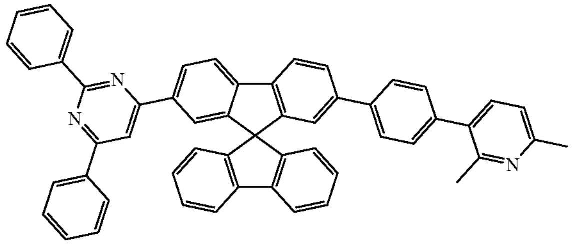
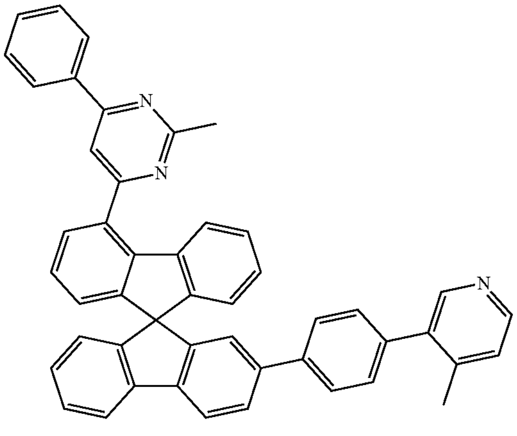
-continued
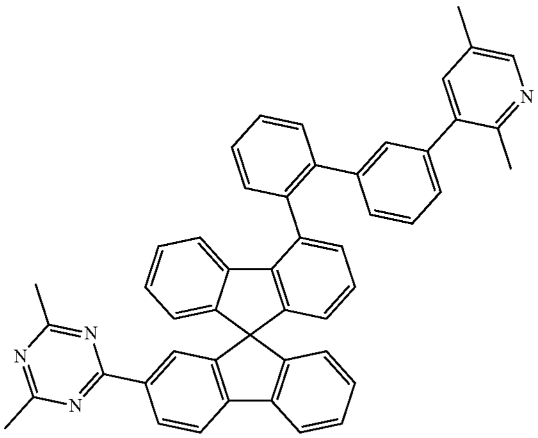
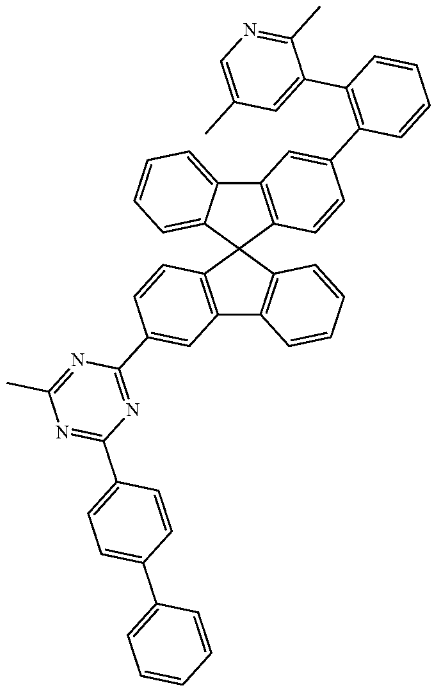
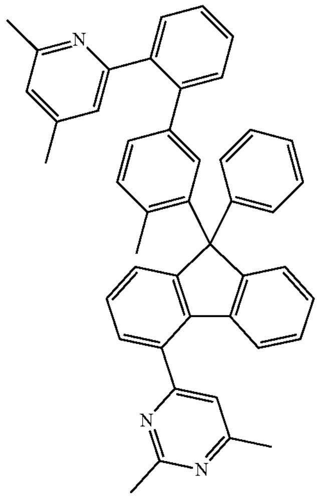

-continued
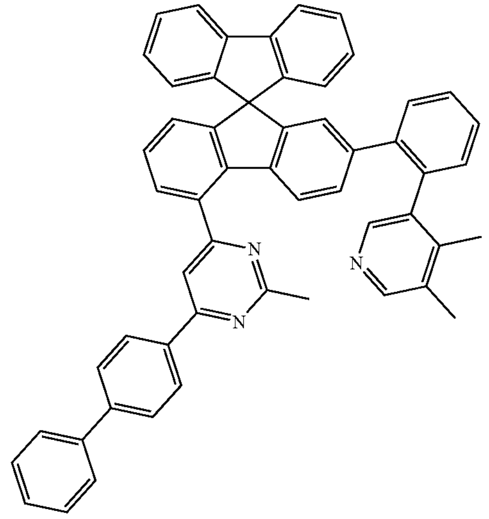
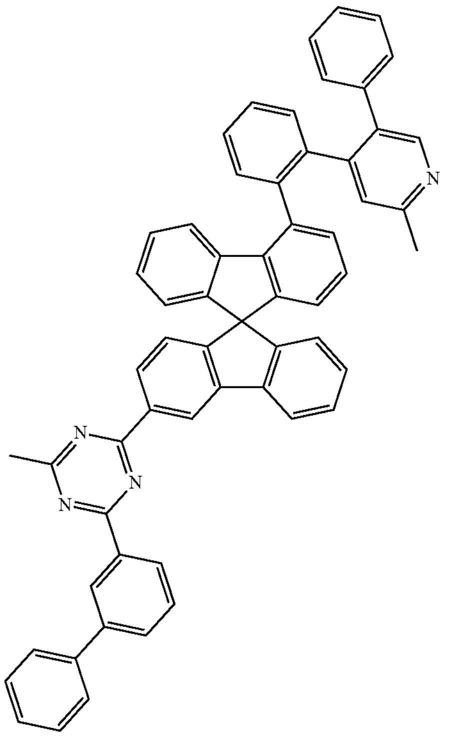
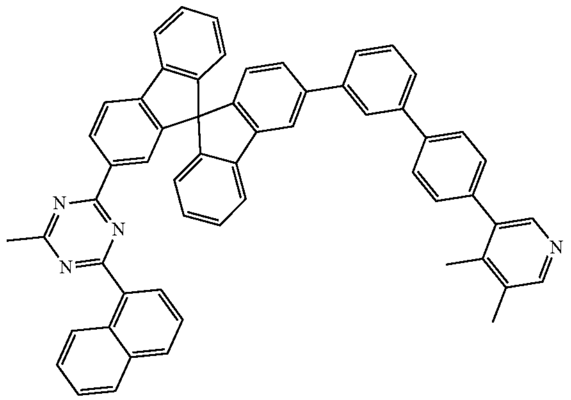
-continued
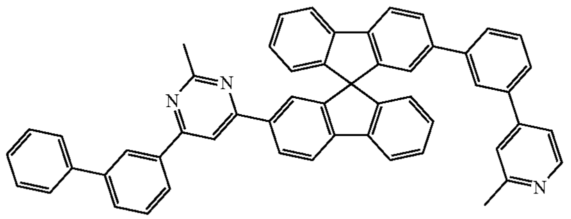
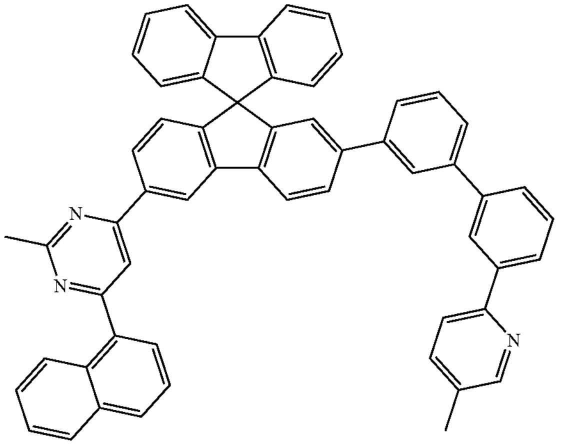
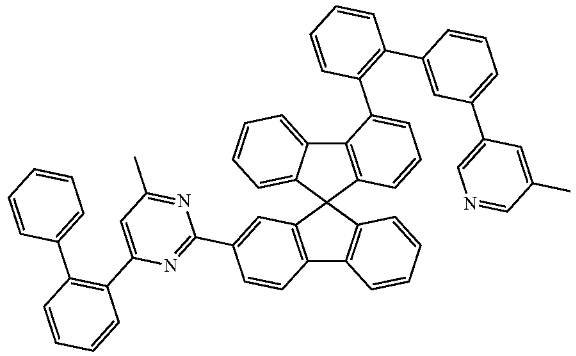
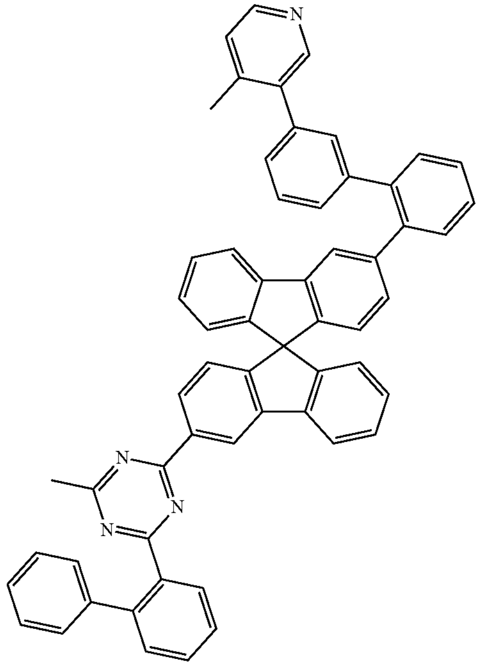

-continued
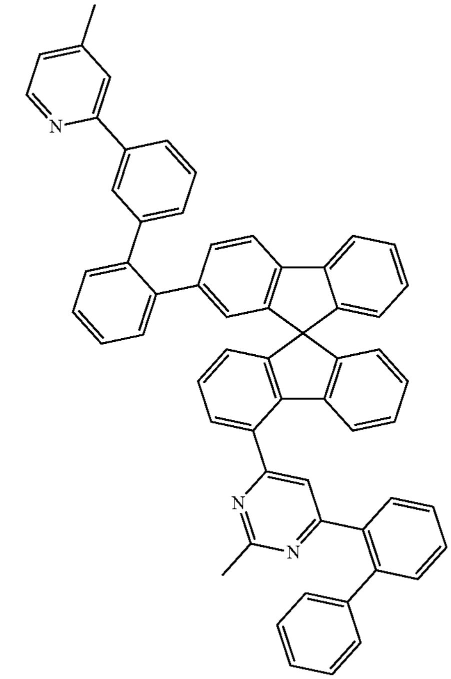
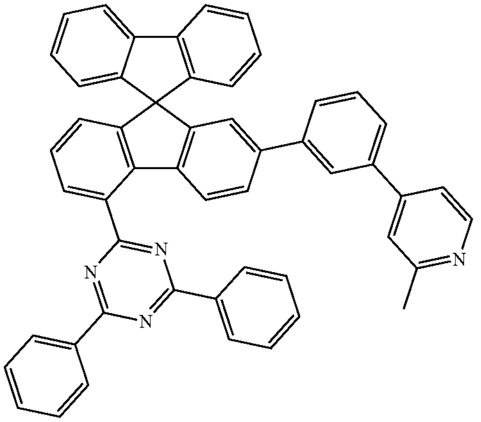
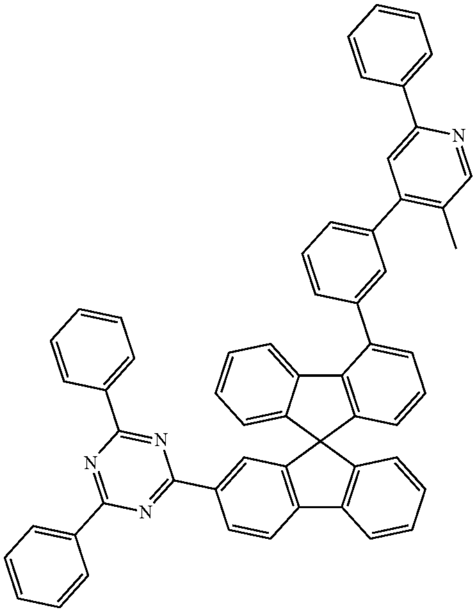
-continued
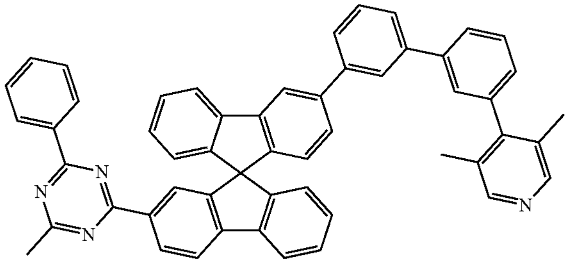
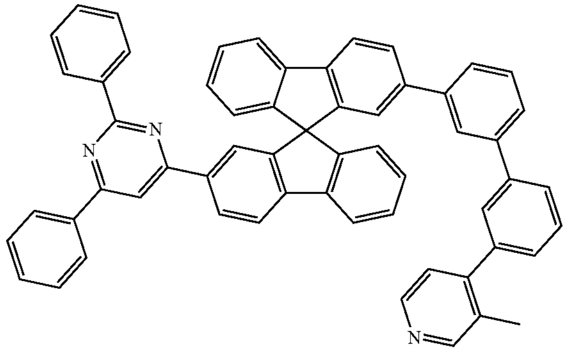
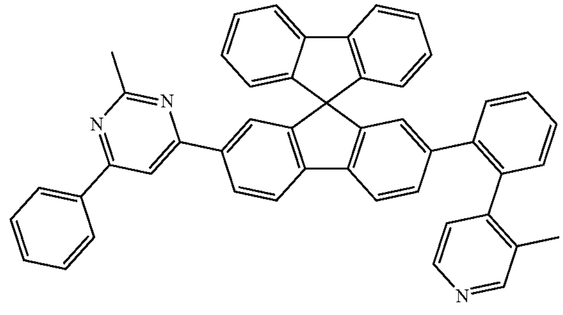
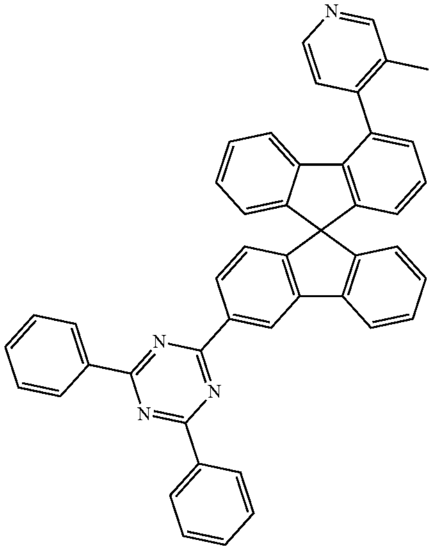

-continued
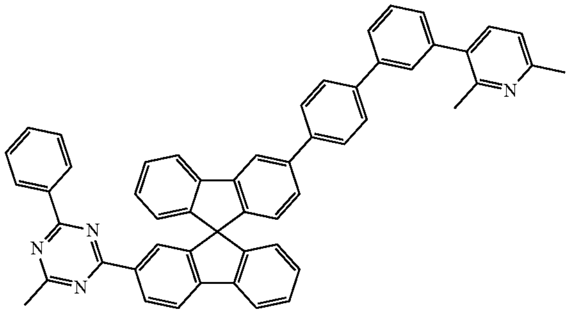
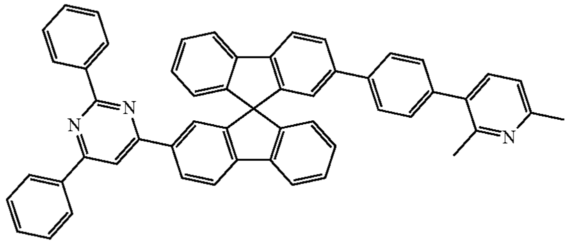
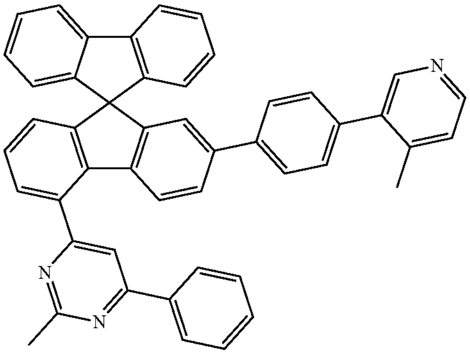
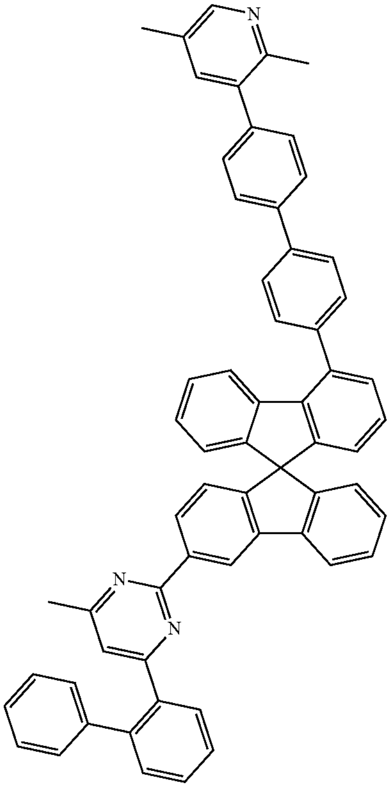
-continued
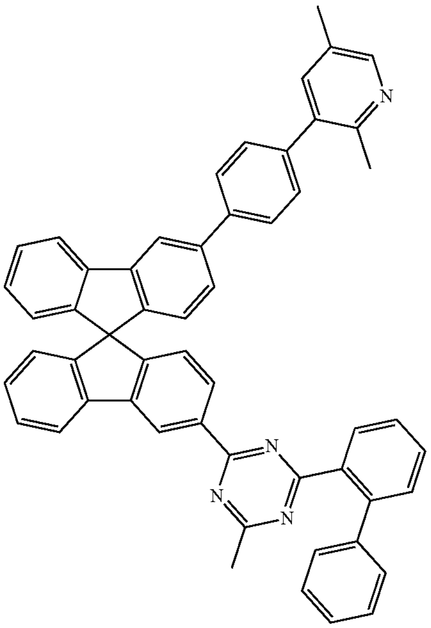
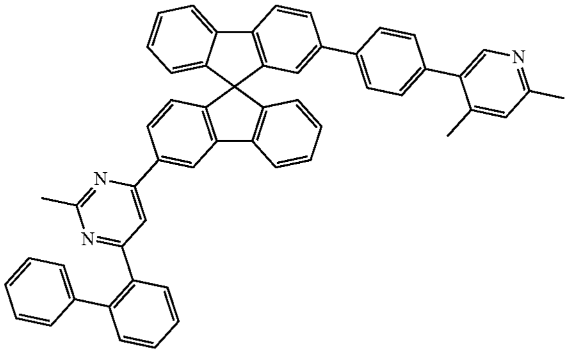
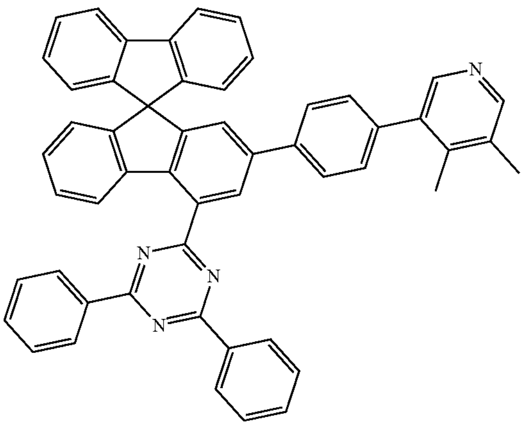

-continued
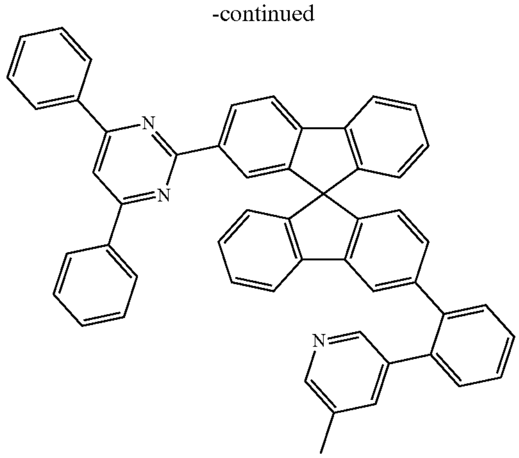
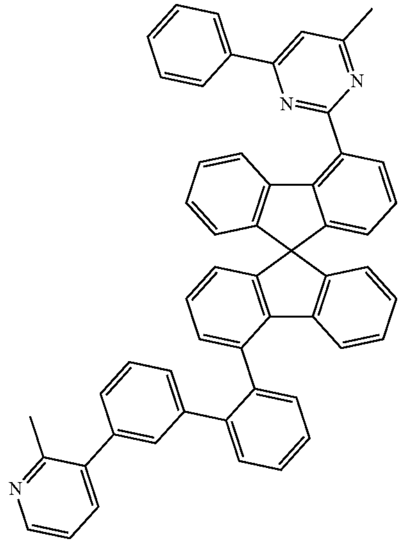
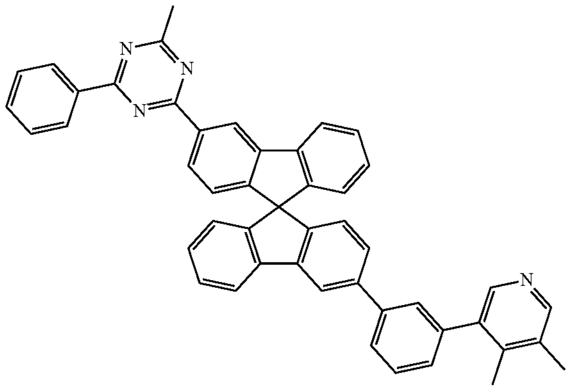
-continued
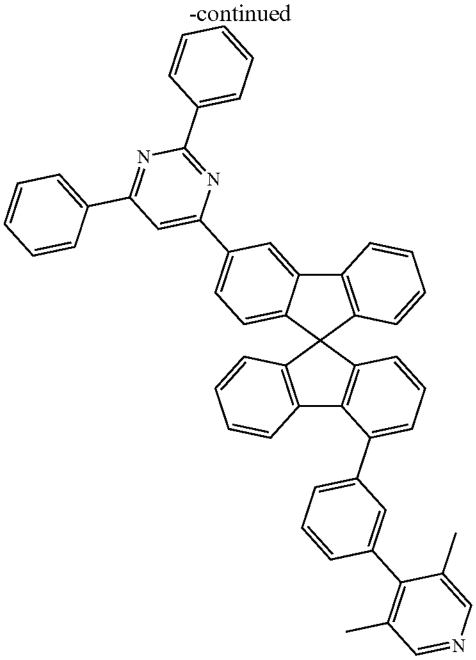
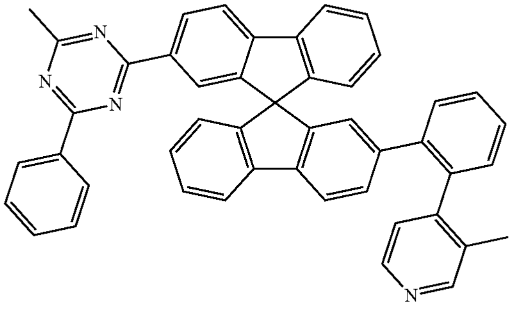
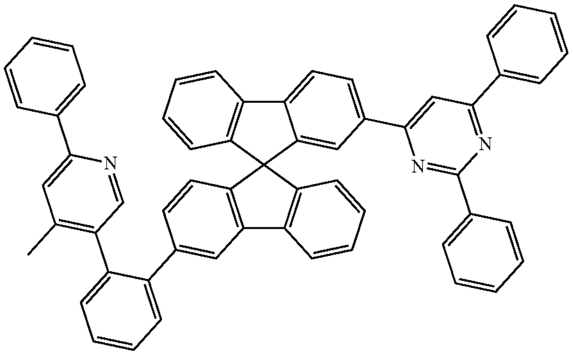
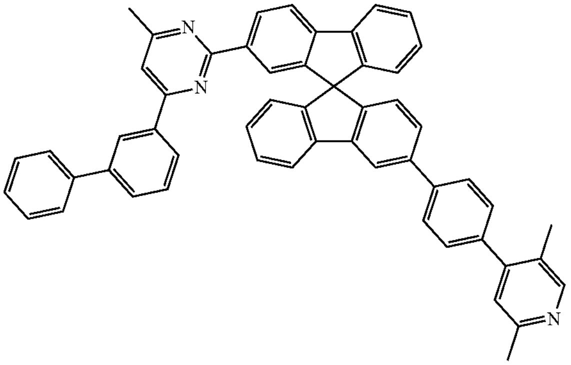

-continued
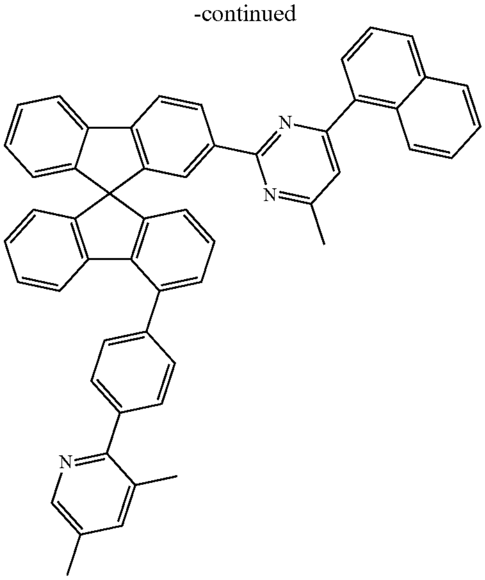
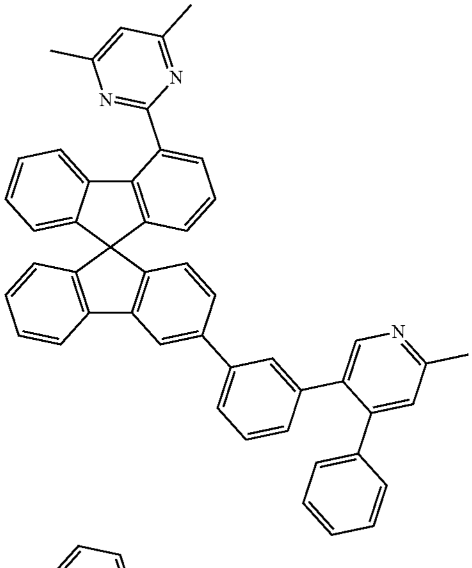
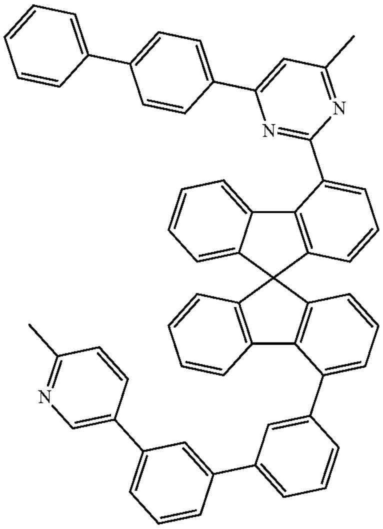
-continued
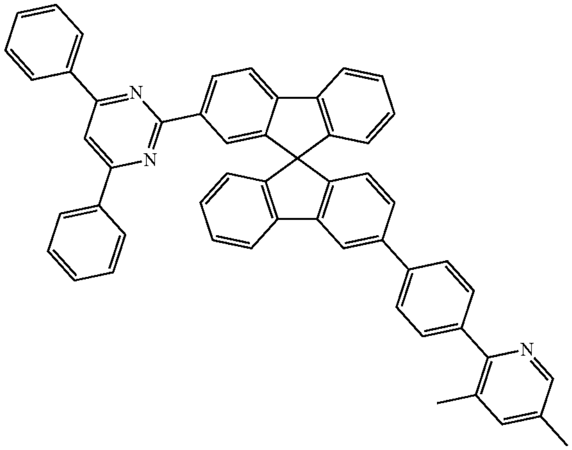
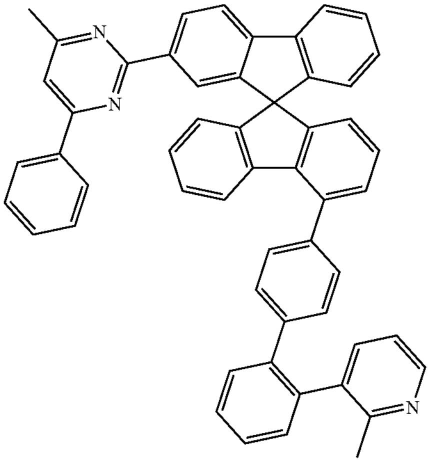
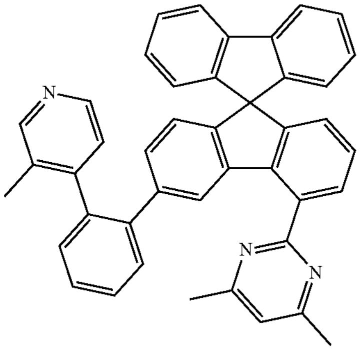

-continued
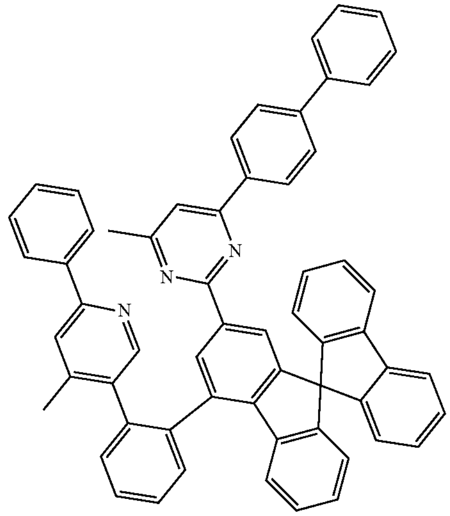
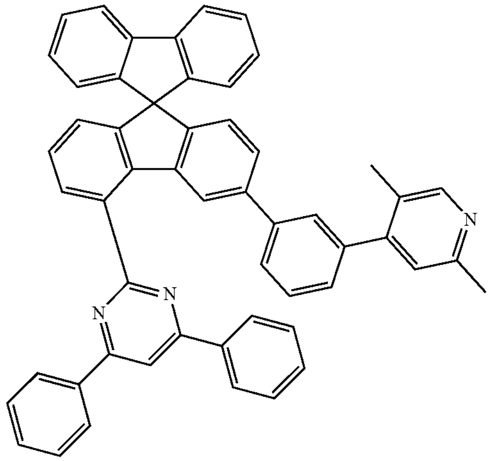
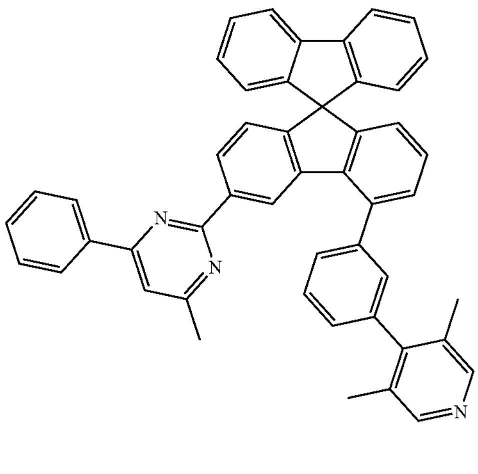
-continued
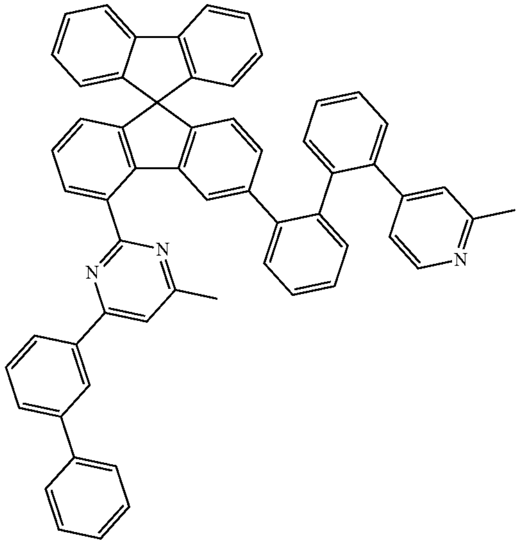
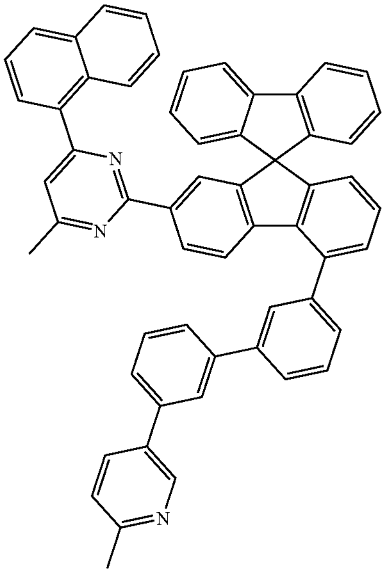
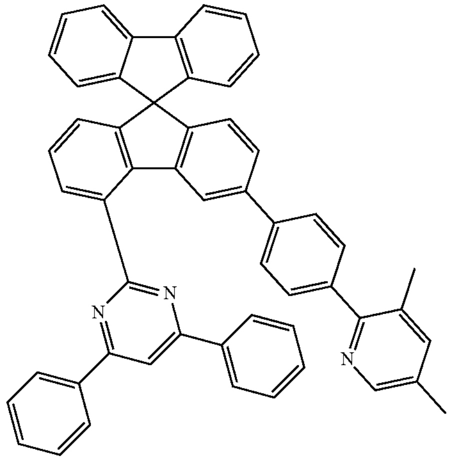

-continued
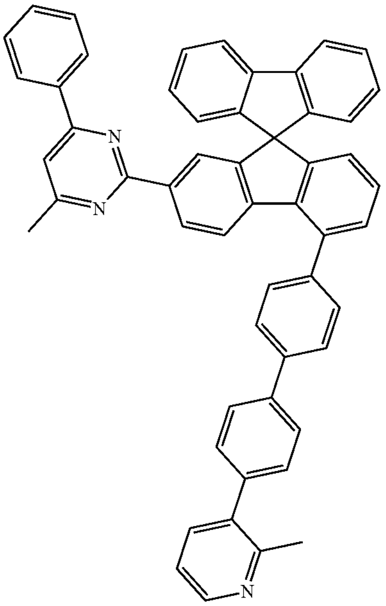
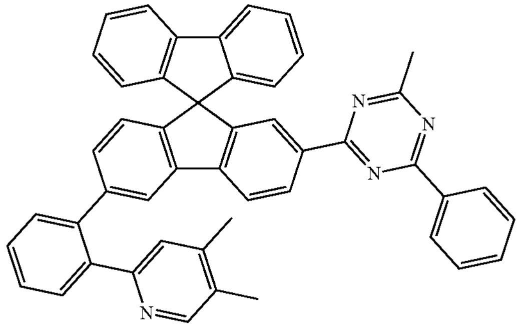
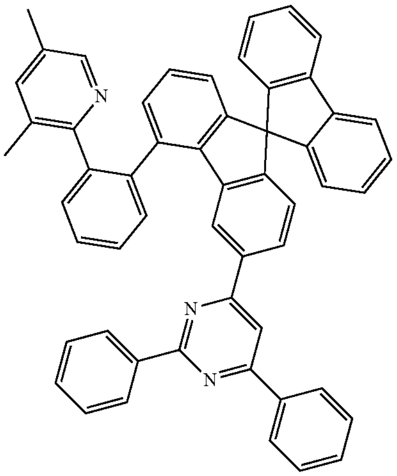
-continued
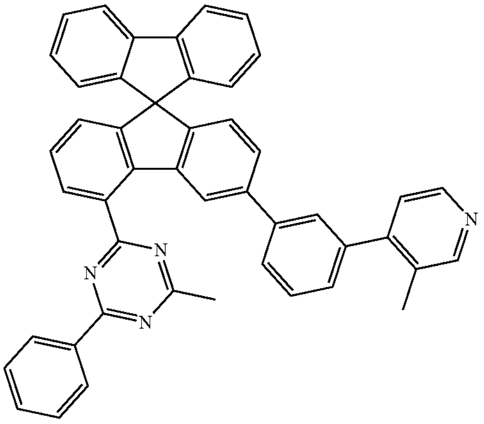
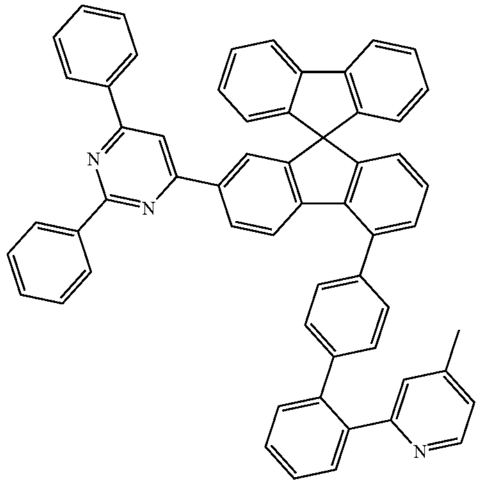
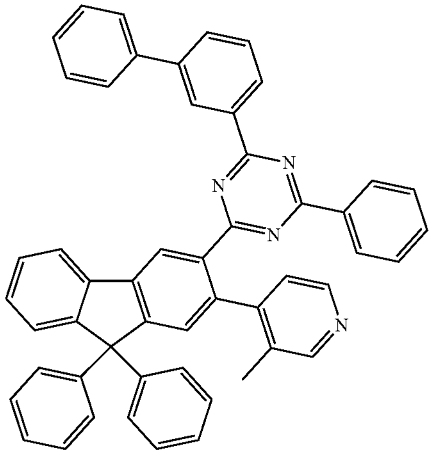

-continued
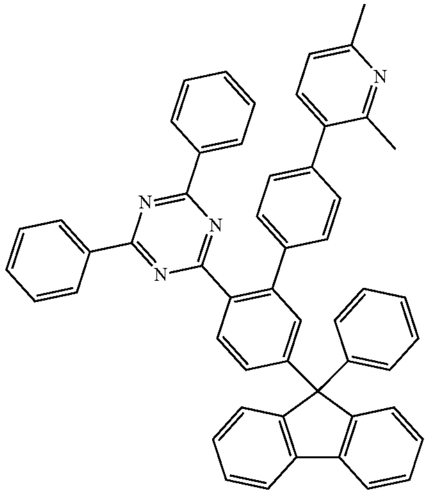
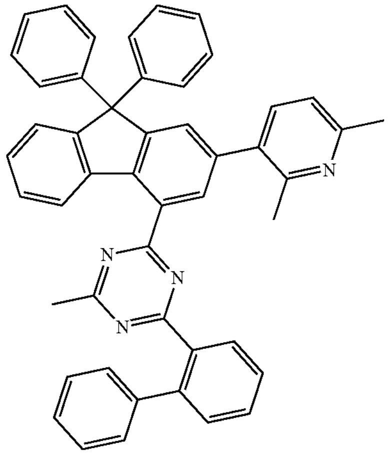
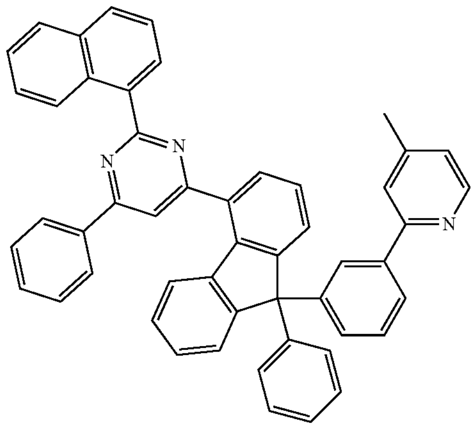
-continued
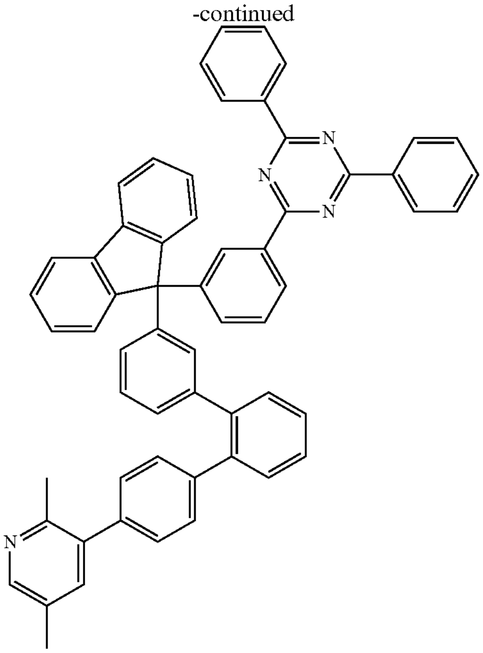
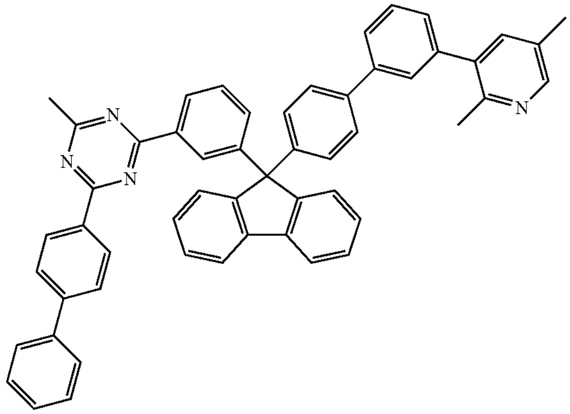
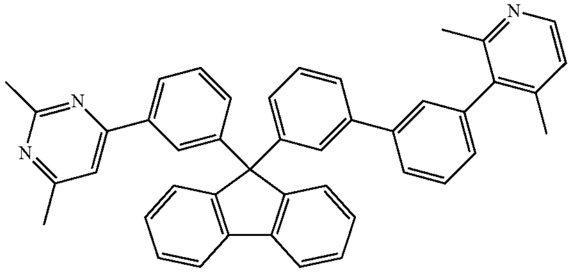
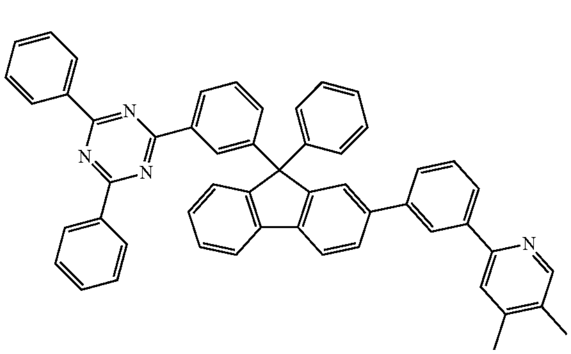

-continued
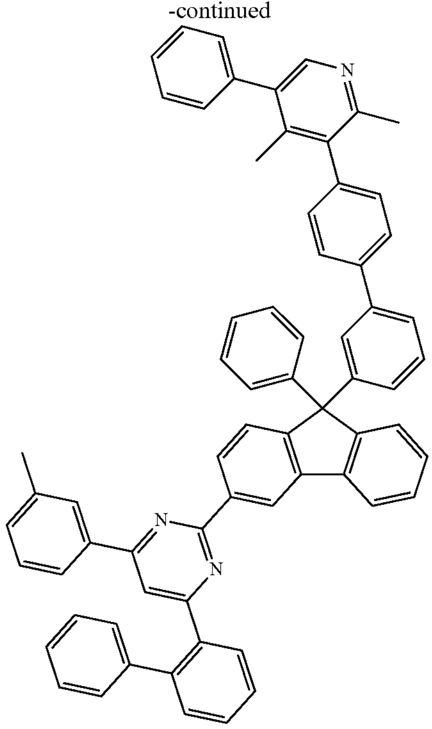
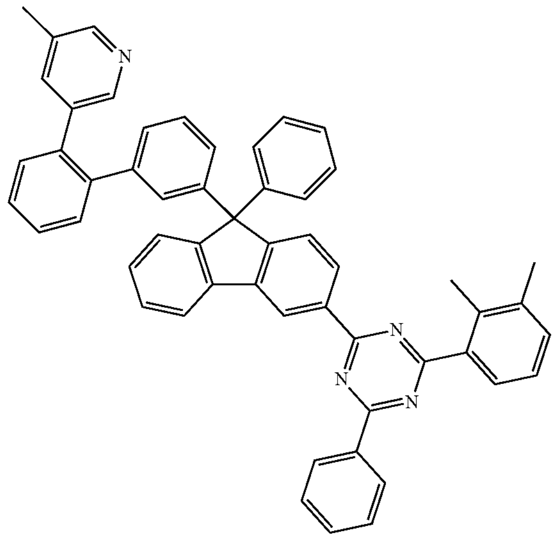
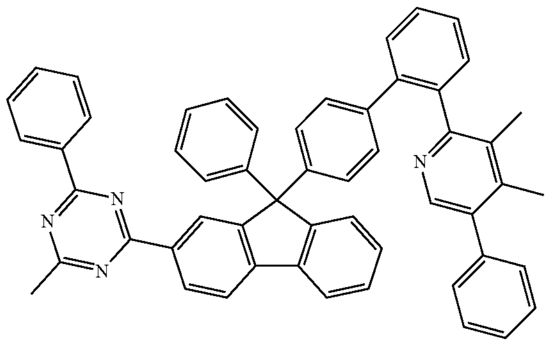
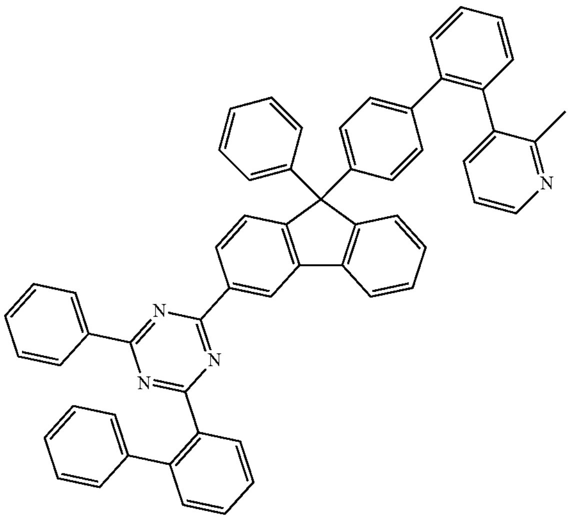
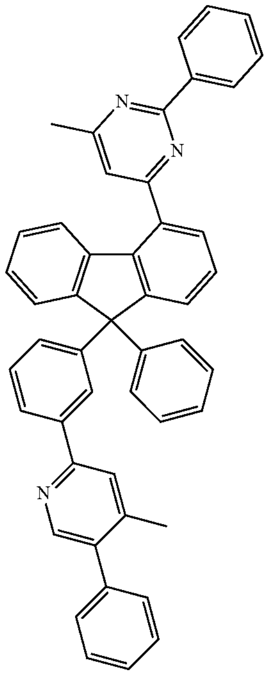

-continued
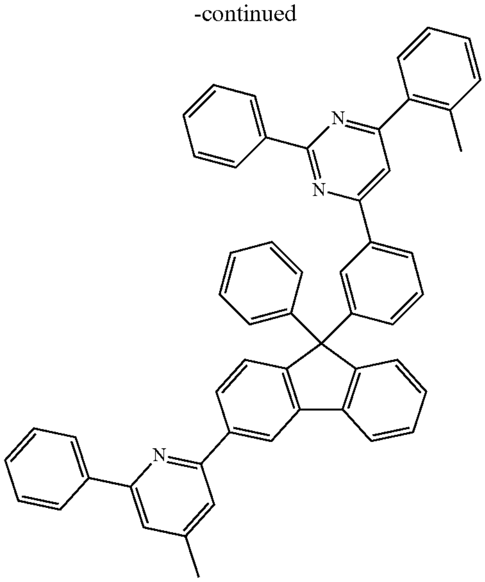
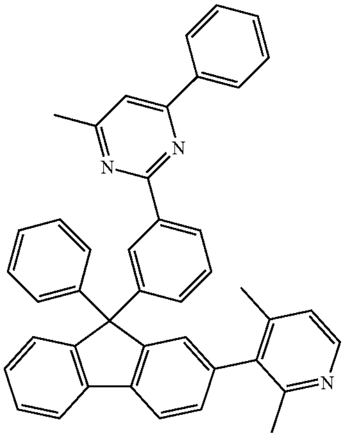
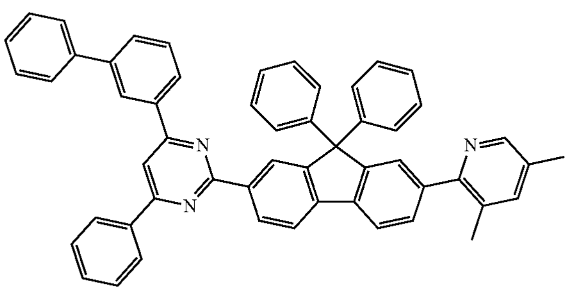
-continued
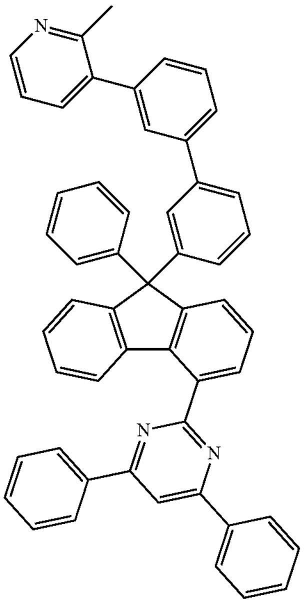
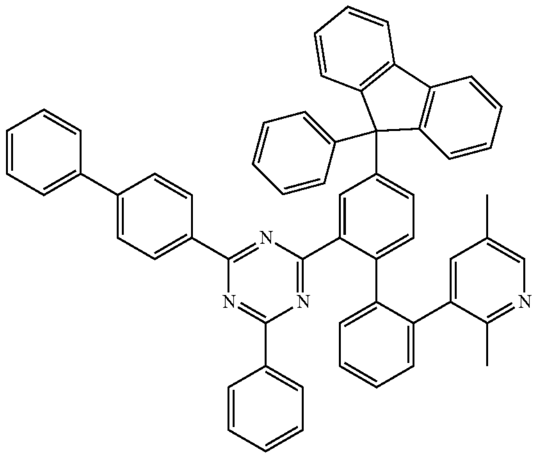
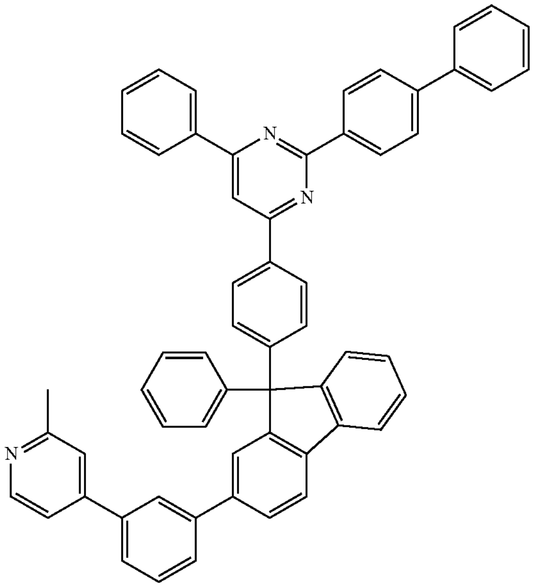

-continued
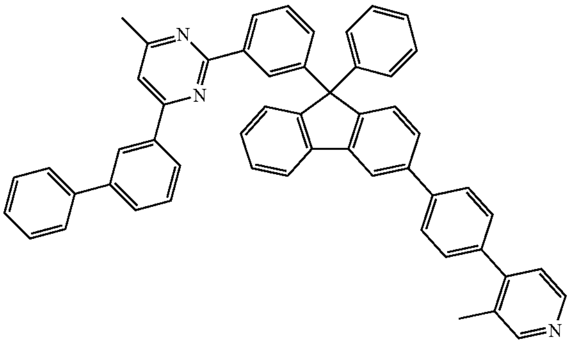
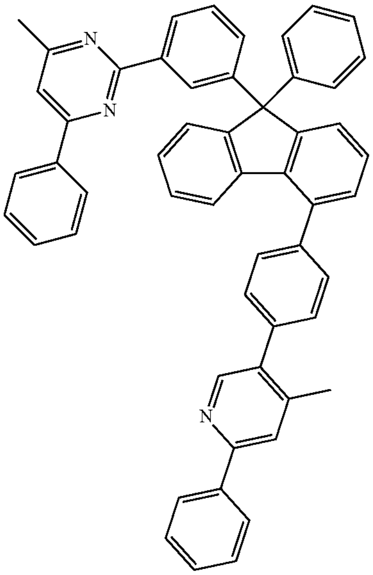
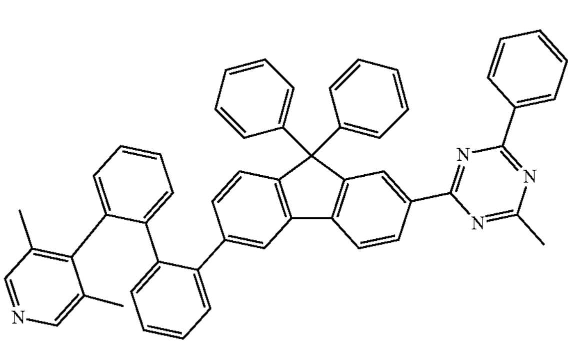
-continued
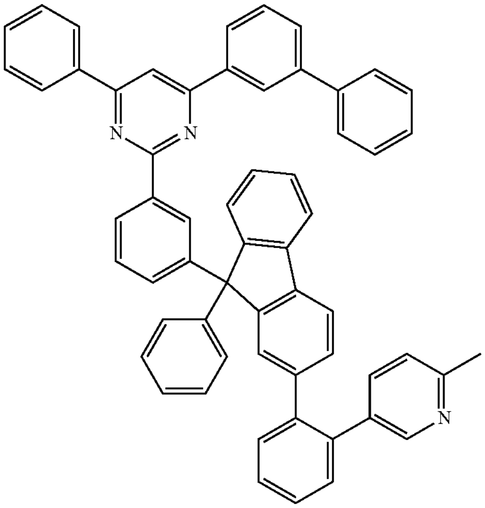
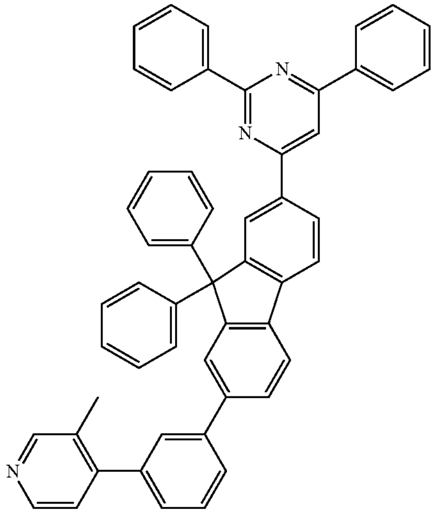
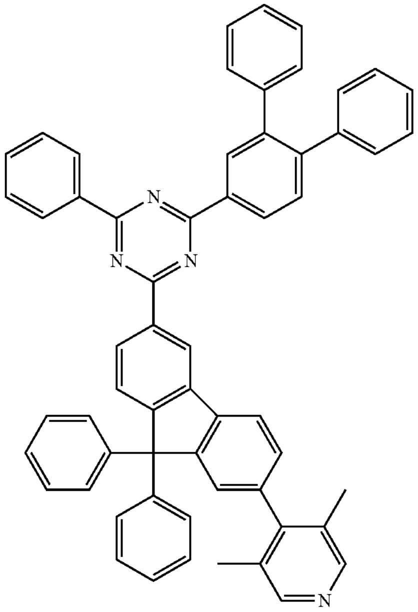

-continued
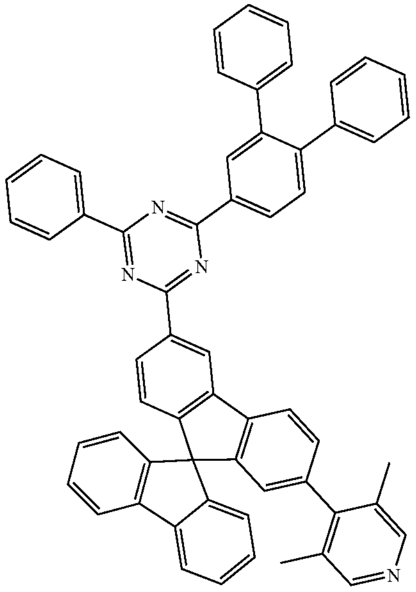
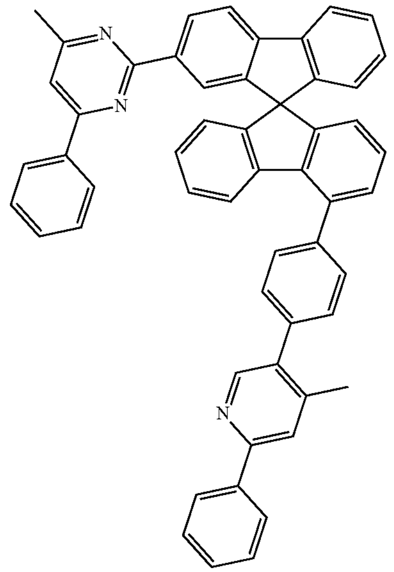
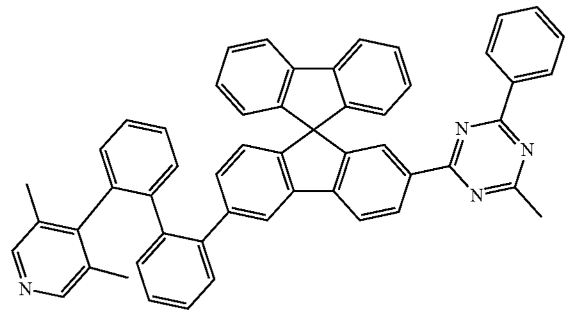
-continued
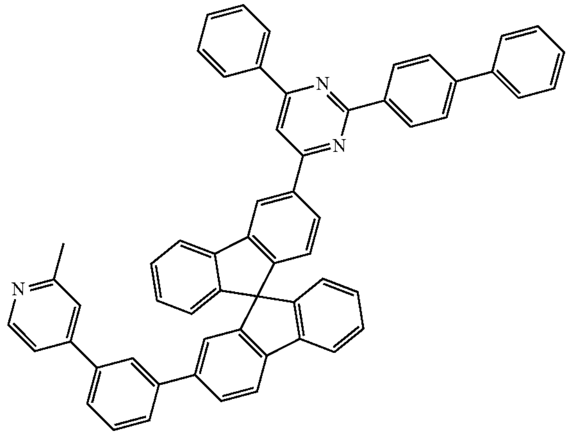
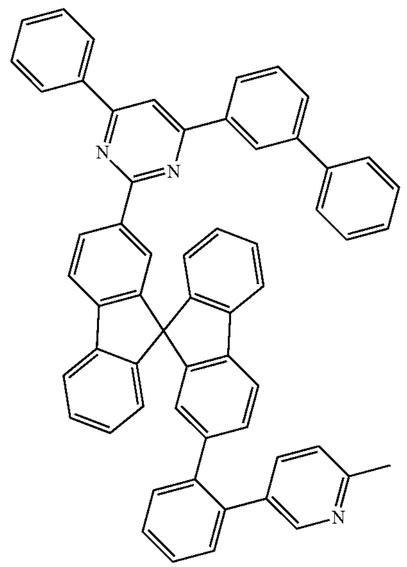
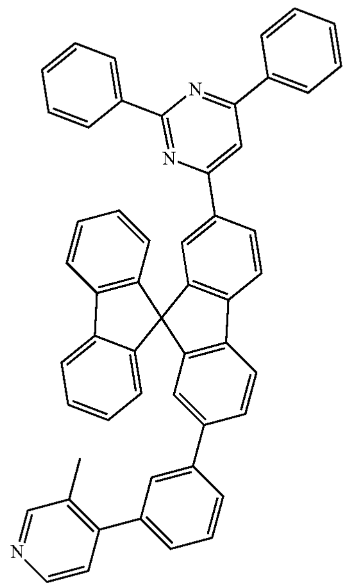

-continued
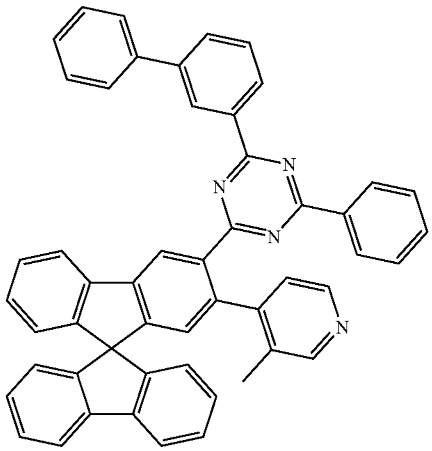
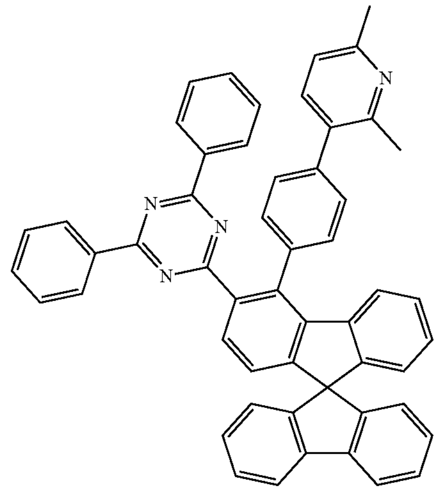
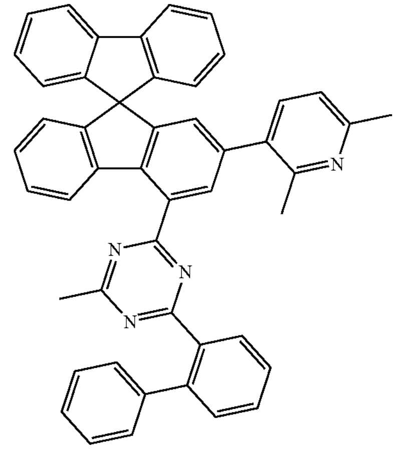
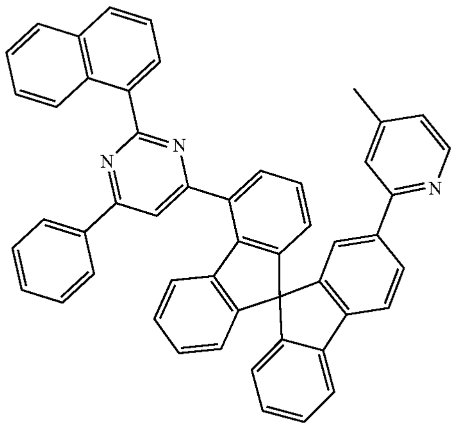
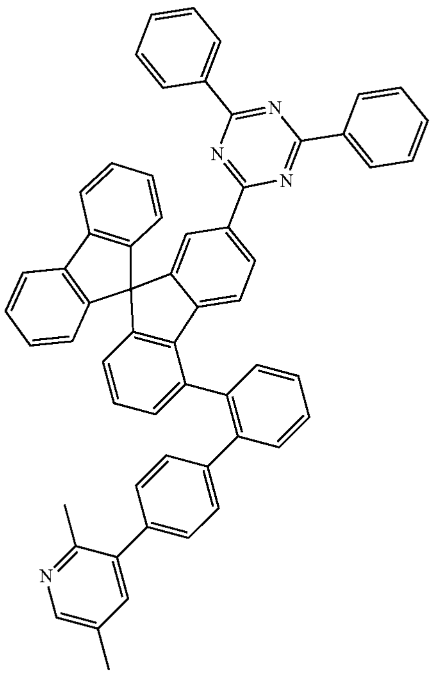
-continued
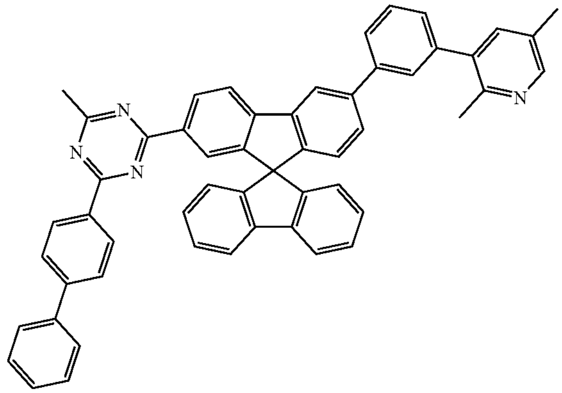

-continued
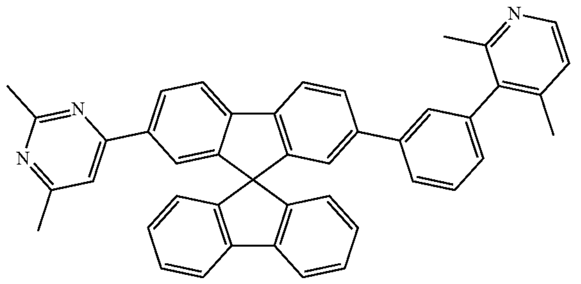
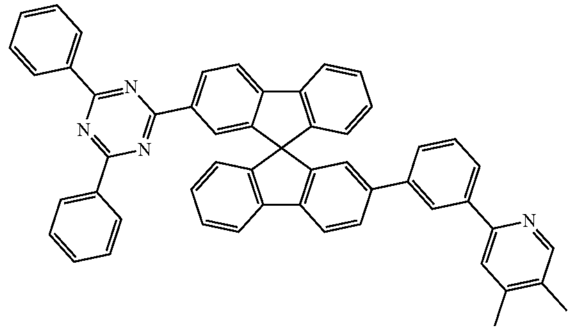
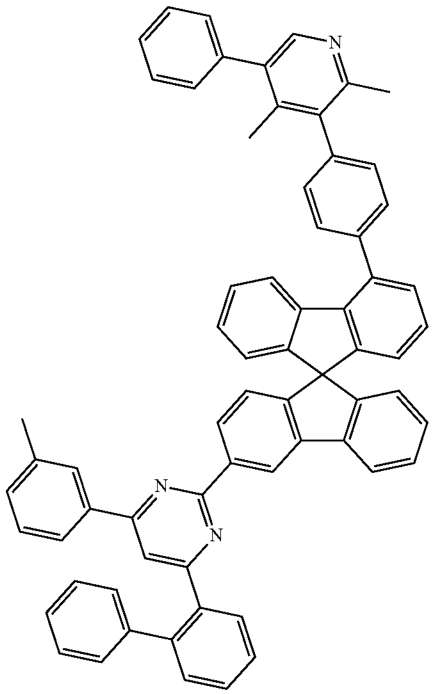
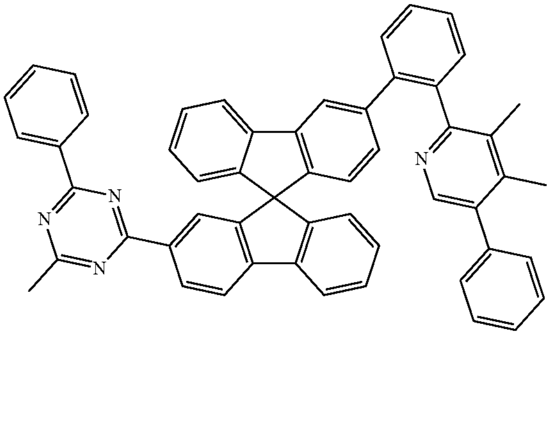
-continued
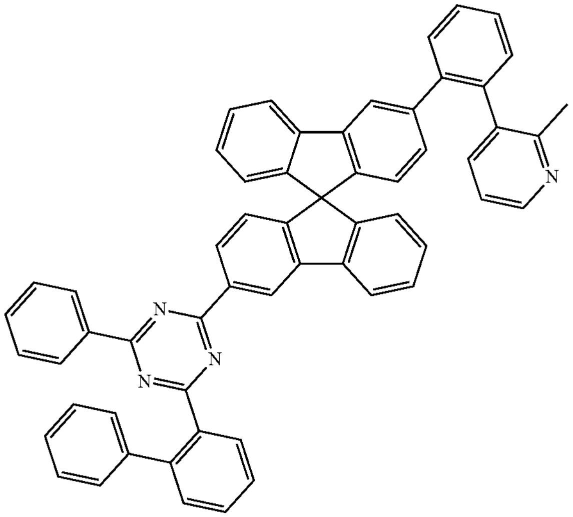
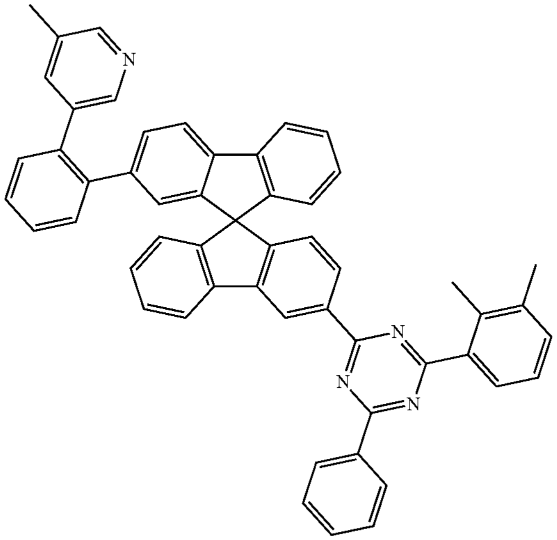
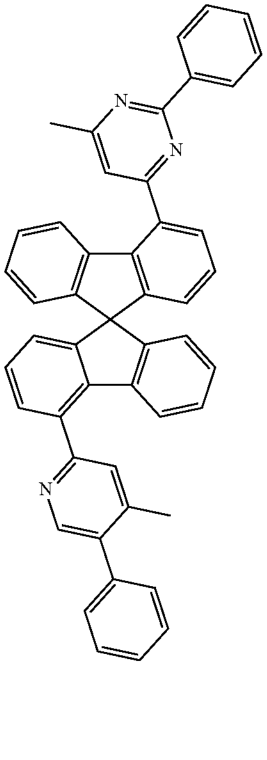

-continued
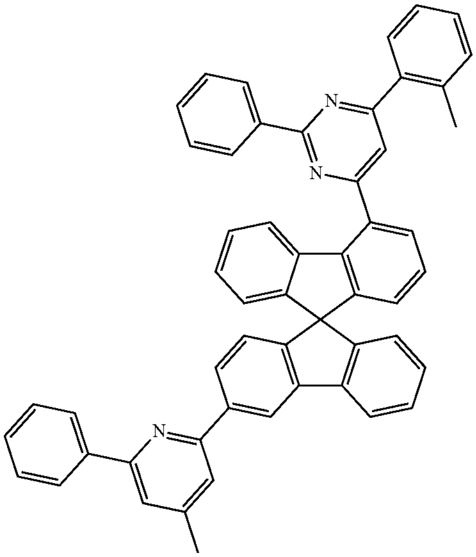
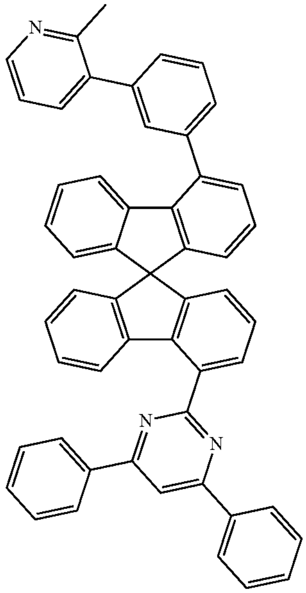
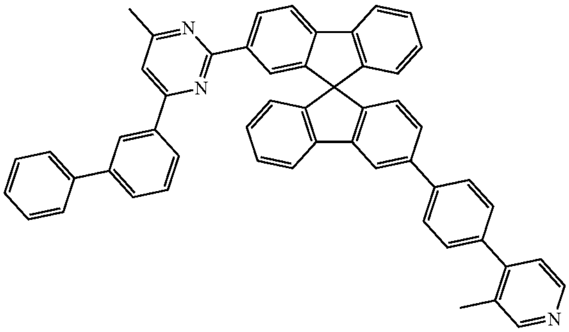
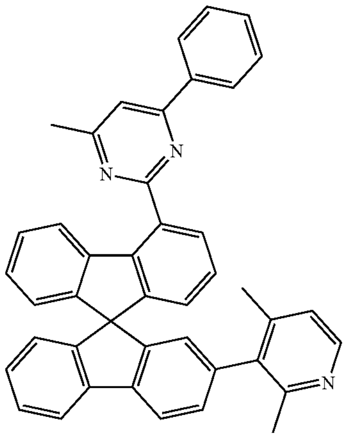
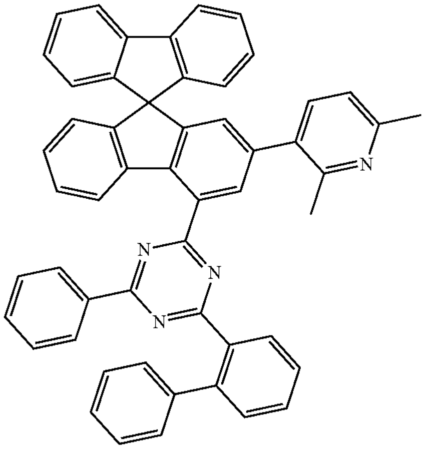
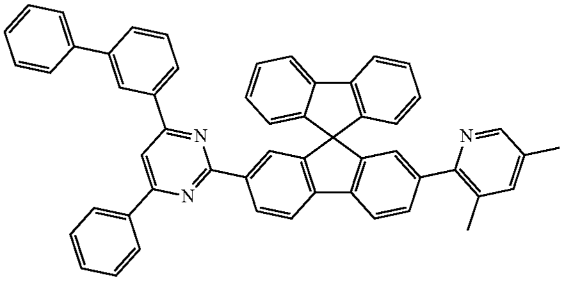

-continued
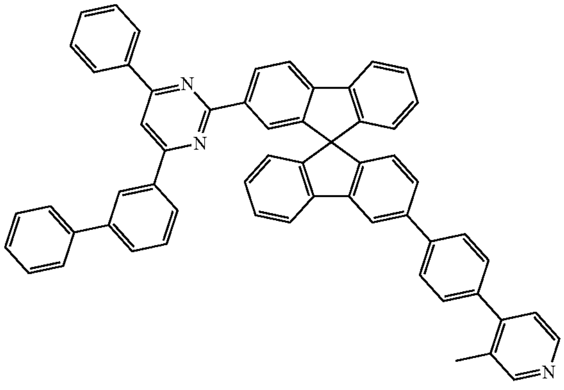
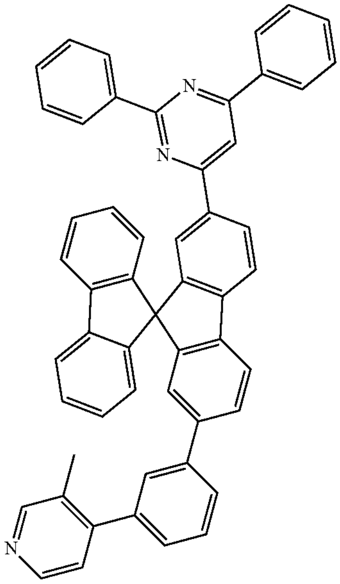
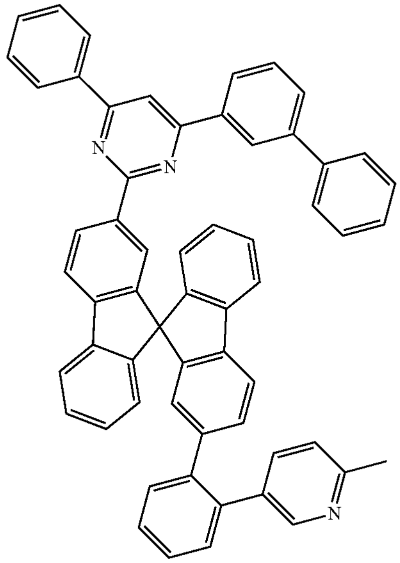
-continued
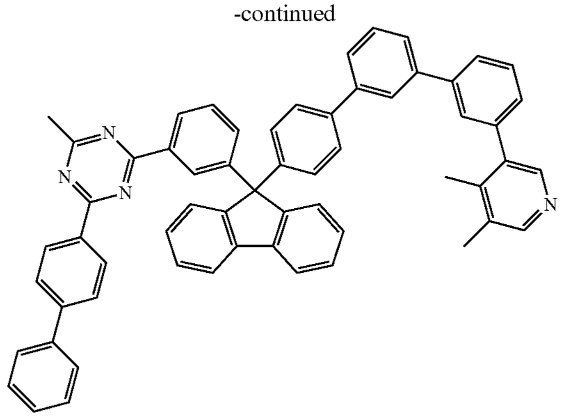
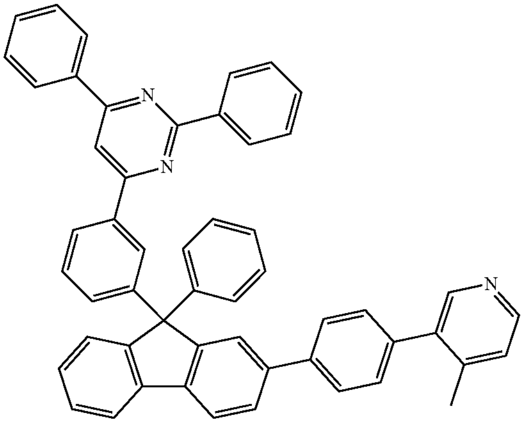
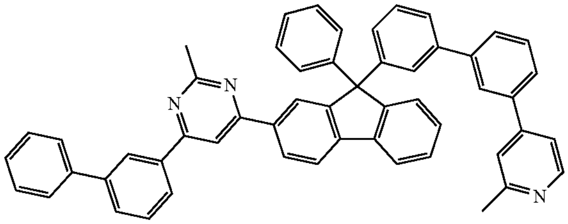
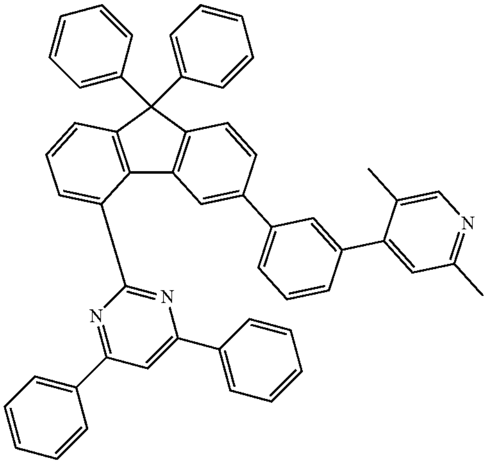

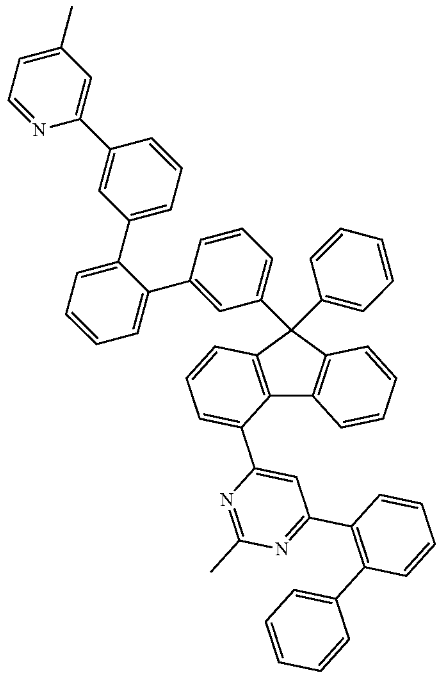
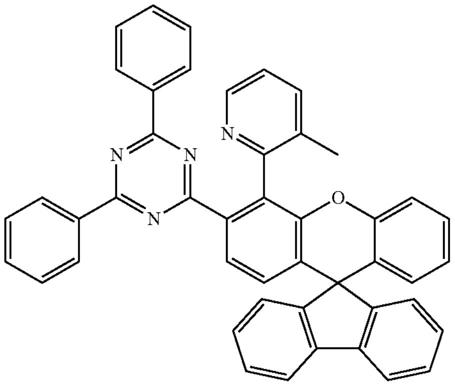
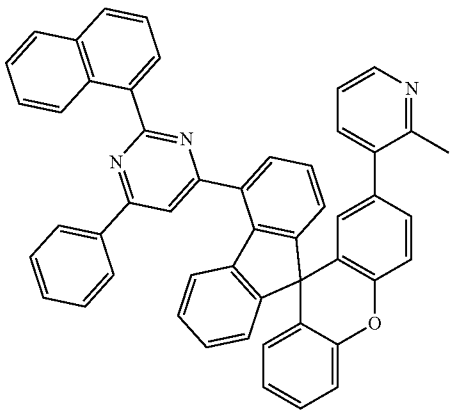
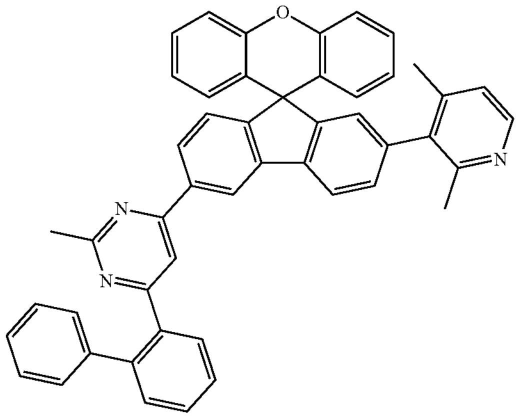
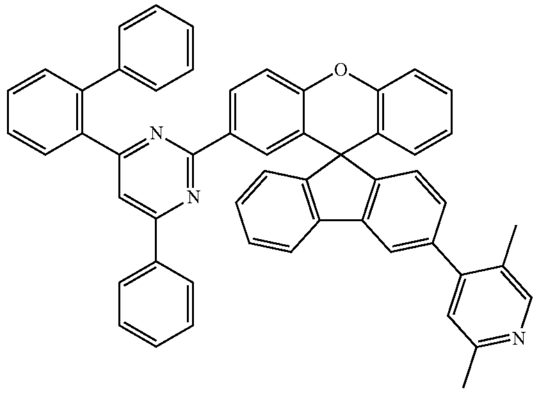
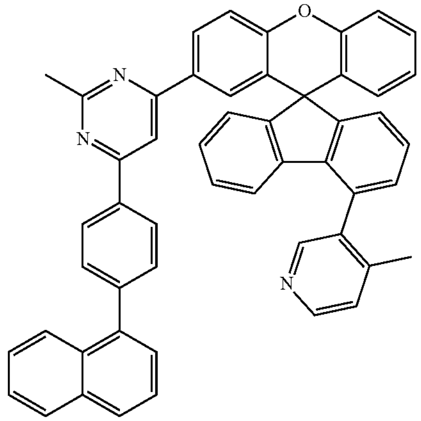
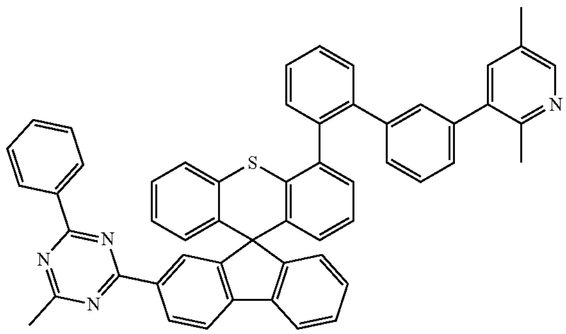

-continued

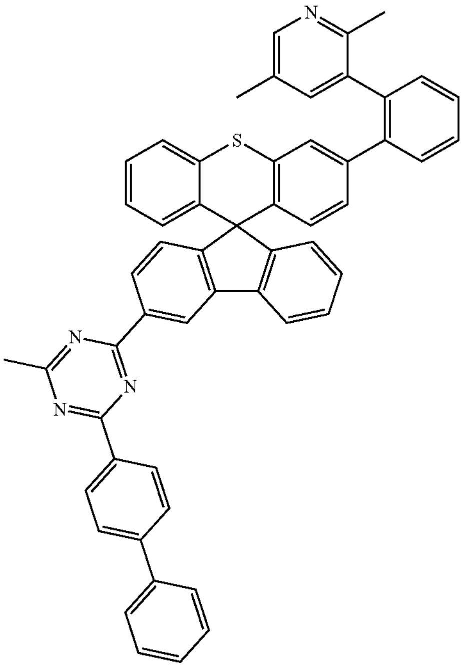

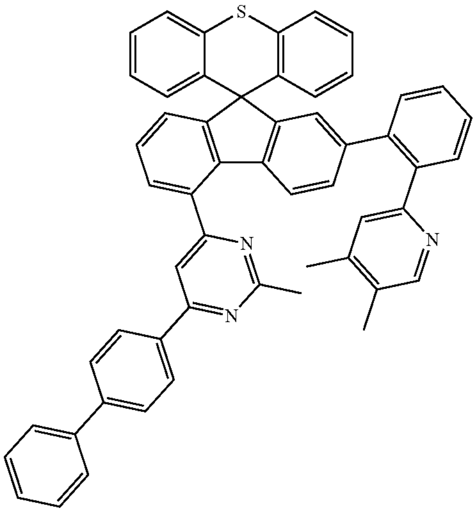

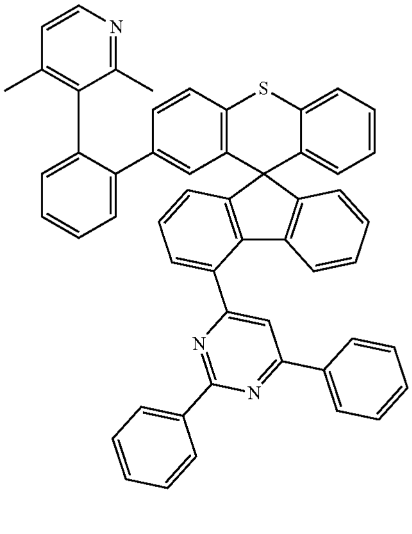

-continued

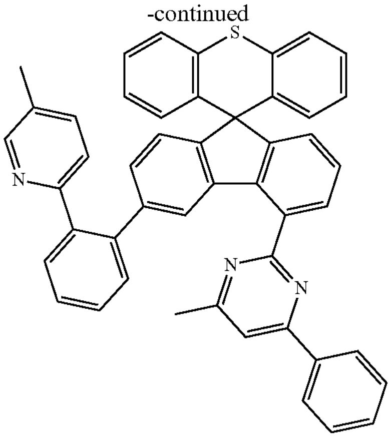

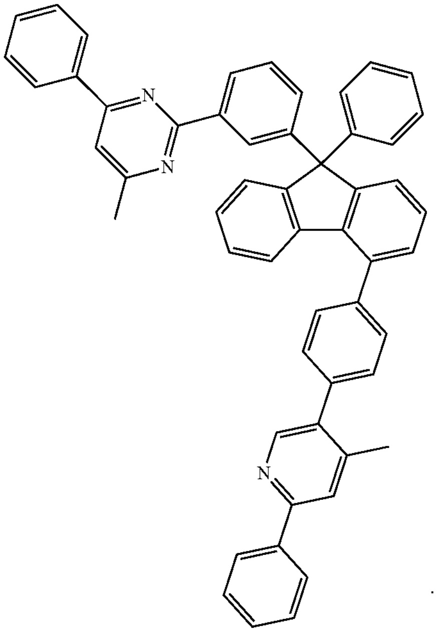

.

7. An organic light emitting device comprising:

a first electrode;

a second electrode provided to face the first electrode; and an organic material layer having one or more layers provided between the first electrode and the second electrode, wherein one or more layers of the organic material layer comprise the heterocyclic compound of claim 1.

8. The organic light emitting device of claim 7, wherein the organic material layer comprises a light emitting layer, and the light emitting layer comprises the heterocyclic compound.

9. The organic light emitting device of claim 7, wherein the organic material layer comprises an electron injection layer, an electron transport layer, an electron injection and transport layer, or a hole blocking layer, and the electron injection layer, the electron transport layer, the electron injection and transport layer, or the hole blocking layer comprises the heterocyclic compound.

10. The organic light emitting device of claim 9, wherein the electron injection layer, the electron transport layer, the electron injection and transport layer, or the hole blocking layer comprises one or two or more n-type dopants selected from alkali metals and alkaline earth metals.

* * * * *